US011473093B2

(12) United States Patent
Leveau et al.

(10) Patent No.: US 11,473,093 B2

(45) Date of Patent: Oct. 18, 2022

(54) ***CUTIBACTERIUM ACNES* RECOMBINANT PHAGES, METHOD OF PRODUCTION AND USES THEREOF**

(71) Applicant: Eligo Bioscience, Paris (FR)

(72) Inventors: Aymeric Leveau, Paris (FR); Inès Canadas Blasco, Paris (FR); Aurélie Mathieu, Paris (FR); Antoine Decrulle, Paris (FR)

(73) Assignee: Eligo Bioscience, Paris (FR)

( * ) Notice: Subject to any disclaimer, the term of this patent is extended or adjusted under 35 U.S.C. 154(b) by 0 days.

(21) Appl. No.: 17/518,960

(22) Filed: Nov. 4, 2021

(65) Prior Publication Data

US 2022/0135987 A1 May 5, 2022

Related U.S. Application Data

(60) Provisional application No. 63/145,969, filed on Feb. 4, 2021, provisional application No. 63/145,967, filed on Feb. 4, 2021, provisional application No. 63/109,834, filed on Nov. 4, 2020, provisional application No. 63/109,832, filed on Nov. 4, 2020.

(51) Int. Cl.

| | |
|---|---|
| ***A61P 17/10*** | (2006.01) |
| ***C12N 15/76*** | (2006.01) |
| ***C12N 15/11*** | (2006.01) |
| ***A61K 39/02*** | (2006.01) |
| ***A61K 39/05*** | (2006.01) |
| ***C12N 9/22*** | (2006.01) |
| *A61K 39/00* | (2006.01) |

(52) U.S. Cl.

CPC .............. *C12N 15/76* (2013.01); *A61K 39/02* (2013.01); *A61K 39/05* (2013.01); *A61P 17/10* (2018.01); *C12N 9/22* (2013.01); *C12N 15/11* (2013.01); *A61K 2039/53* (2013.01); *C12N 2310/20* (2017.05); *C12N 2795/10343* (2013.01); *C12N 2800/101* (2013.01); *C12N 2800/80* (2013.01)

(58) Field of Classification Search

None

See application file for complete search history.

(56) References Cited

U.S. PATENT DOCUMENTS

2021/0252081 A1* 8/2021 Feron et al. ........... C07K 14/33

FOREIGN PATENT DOCUMENTS

| | | | | |
|---|---|---|---|---|
| WO | WO-2007007055 A1 * | 1/2007 | ............. A61K 35/76 |
| WO | 2017/114979 A1 | 7/2017 | |
| WO | 2019/243307 A1 | 12/2019 | |
| WO | 2020181178 A1 | 9/2020 | |
| WO | 2020181180 A1 | 9/2020 | |
| WO | 2020181193 A1 | 9/2020 | |
| WO | 2020181195 A1 | 9/2020 | |
| WO | 2020181202 A1 | 9/2020 | |

OTHER PUBLICATIONS

Farrar et al., Journal of Bacteriology, 2007, 189(11):4161-4167. (Year: 2007).*
Vojdani et al., Journal of Immunology Research, vol. 2020, Article ID 1438957, 16 pages. (Year: 2020).*
Rahman et al., Pak J Med Sci, 2012, 28(1):31-35. (Year: 2012).*
Abudayyeh et al. RNA targeting with CRISPR-Cas13a. Nature. Oct. 12, 2017; 550(7675): 280-284.
Adachi et al. Hair follicle-derived IL-7 and IL-15 mediate skin-resident memory T cell homeostasis and lymphoma. Nat Med. Nov. 2015 ; 21(11): 1272-1279.
Allhorn, M. et al. A novel enzyme with antioxidant capacity produced by the ubiquitous skin colonizer *Propionibacterium acnes.* Sci. Rep. 6, 36412.
Anzalone, A. et al. Search-and-replace genome editing without double-strand breaks or donor DNA. Nature. Dec. 2019 ; 576(7785): 149-157.
Aoki et al., Journal of Medical Microbiology 2019;68:26-30.
Aoki et al., Transferable Multidrug-Resistance Plasmid Carrying a Novel Macrolide-Clindamycin Resistance Gene, erm (50), in *Cutibacterium acnes.* Antimicrob Agents Chemother. Feb. 21, 2020;64(3):e01810-19.
Arazoe et al. Site-specific DNA double-strand break generated by I-SceI endonuclease enhances ectopic homologous recombination in *Pyricularia oryzae.* FEMS Microbiol Lett 352 (2014) 221-229.
Armenteros, et al. SignalP 5.0 improves signal peptide predictions using deep neural networks. Nat Biotechnol 37, 420-423 (2019).
Barnard, E. et al. Strains of the *Propionibacterium acnes* type III lineage are associated with the skin condition progressive macular hypomelanosis. Sci. Rep. 6, 31968.
Barnard, E. et al. The balance of metagenomic elements shapes the skin microbiome in acne and health. Sci. Rep. 6, 39491.
Bay L, et al. 2020. Universal dermal microbiome in human skin. mBio 11:e02945-19.
Brown et al. (2016) The Formulation of Bacteriophage in a Semi Solid Preparation for Control of *Propionibacterium acnes* Growth. PLoS ONE 11(3): e0151184.
Chen et al. Skin microbiota-host interactions. Nature. Jan. 24, 2018; 553(7689): 427-436.
Chen et al. Decoding commensal-host communication through genetic engineering of *Staphylococcus* 5 epidermidis. Jun. 10, 2019. bioRxiv 664656.
Chen et al. Precise and programmable C:G to G:C base editing in genomic DNA. bioRxiv 2020.07.21.213827.

(Continued)

*Primary Examiner* — Nicole Kinsey White

(74) *Attorney, Agent, or Firm* — Arrigo, Lee, Guttman & Mouta-Bellum LLP

(57) ABSTRACT

The invention relates to *C. acnes* strains carrying DNA vectors for the production of recombinant *C. acnes* phages. The invention encompasses a *C. acnes* producer cell carrying DNA vectors, with a template for recombination with *C. acnes* phage genome leading to the insertion of a gene of interest, for the production of recombinant phages that can lead to the transgene expression into *C. acnes* infected by the recombinant phage. The invention encompasses, *C. acnes* strains containing these vectors, *C. acnes* recombinant phages and methods of using these recombinant phages.

4 Claims, 13 Drawing Sheets

Specification includes a Sequence Listing.

(56) References Cited

OTHER PUBLICATIONS

Davidsson S, et al. (2017) Prevalence of Flp Pili-Encoding Plasmids in *Cutibacterium acnes* Isolates Obtained from Prostatic Tissue. Front. Microbiol. 8:2241.
Dréno, et al. (2018), *Cutibacterium acnes* (*Propionibacterium acnes*) and acne vulgaris: a brief look at the latest updates. J Eur Acad Dermatol Venereol, 32: 5-14.
Fitz-Gibbon et al. *Propionibacterium acnes* Strain Populations in the Human Skin Microbiome Associated with Acne. Journal of Investigative Dermatology (2013) 133, 2152-2160.
Fonfara et al. Phylogeny of Cas9 determines functional exchangeability of dual-RNA and Cas9 among orthologous type II CRISPR-Cas systems .Nucleic Acids Research, 2014, vol. 42, No. 4 2577-2590.
Gaudelli et al. Programmable base editing of A•T to G•C in genomic DNA without DNA cleavage. Nature. Nov. 23, 2017; 551(7681): 464-471.
Di Girolamo, et al. Characterization of the housekeeping sortase from the human pathogen *Propionibacterium acnes*: first investigation of a class F sortase. Biochem J Feb. 28, 2019; 476 (4): 665-682.
Grünewald et al. A dual-deaminase CRISPR base editor enables concurrent adenine and cytosine editing. Nat Biotechnol. Jul. 2020 ; 38(7): 861-864.
Karberg, et al. Group II introns as controllable gene targeting vectors for genetic manipulation of bacteria. Nat Biotechnol 19, 1162-1167 (2001).
Kasimatis et al. Analysis of Complete Genomes of *Propionibacterium acnes* Reveals a Novel Plasmid and Increased Pseudogenes in an Acne Associated Strain. Hindawi Publishing Corporation: BioMed Research International. 2013. 1-11.
Komor et al. Programmable editing of a target base in genomic DNA without double-stranded DNA cleavage. Nature. ; 533(7603): 420-424.
Koonin, et al. Diversity, classification and evolution of CRISPR-Cas systems. Current Opinion in Microbiology. vol. 37,2017, pp. 67-78.
Kurt et al. CRISPR C-to-G base editors for inducing targeted DNA transversions in human cells. Nat Biotechnol. Jan. 2021 ; 39(1): 41-46.
Li et al. Targeted, random mutagenesis of plant genes with dual cytosine and adenine base editors. Nature Biotechnology. 38, 875-882 (2020).
Liu et al. The diversity and host interactions of *Propionibacterium acnes* bacteriophages on human skin. The ISME Journal (2015) 9, 2078-2093.
Lood et al. Characterization and genome sequencing of two *Propionibacterium acnes* phages displaying pseudolysogeny. BMC Genomics 2011, 12:198.
McDowell, et al. (2021), Is *Cutibacterium* (previously *Propionibacterium*) *acnes* a potential pathogenic factor in the aetiology of the skin disease progressive macular hypomelanosis?. J Eur Acad Dermatol Venereol, 35: 338-344.
McLaughlin et al. *Propionibacterium acnes* and Acne Vulgaris: New Insights from the Integration of Population Genetic, Multi-Omic, Biochemical and Host-Microbe Studies. Microorganisms 2019, 7(5), 128.
Nagao et al. Stress-induced production of chemokines by hair follicles regulates the trafficking of dendritic cells in skin. Nat Immunol. ; 13(8): 744-752.
Naik et al. Commensal-dendritic-cell interaction specifies a unique protective skin immune signature. Nature. Apr. 2, 2015; 520(7545): 104-108.
Nakatsuji et al. The microbiome extends to subepidermal compartments of normal skin. Nat Commun. 2013 ; 4: 1431.
Nazipi et al. The Skin Bacterium *Propionibacterium acnes* Employs Two Variants of Hyaluronate Lyase with Distinct Properties. Microorganisms 2017, 5, 57.
Oh et al. Biogeography and individuality shape function in the human skin metagenome. Nature. Oct. 2, 2014; 514 (7520): 59-64.
Pasparakis et al. Mechanisms regulating skin immunity and inflammation. Nature Reviews: Immunology. vol. 14. 289-301.
Paus et al. The Hair Follicle and Immune Privilege. JID Symposium Proceedings. 2003. 1087-0024.
Petersen et al. *Propionibacterium acnes* Phylogenetic Type III is Associated with Progressive Macular Hypomelanosis. Eur J Microbiol Immunol (Bp). Feb. 27, 2017;7(1):37-45.
Rouet et al. Expression of a site-specific endonuclease stimulates homologous recombination in mammalian cells. Jun. 1994. Proc. Nati. Acad. Sci. USA. vol. 91, pp. 6064-6068.
Scharschmidt et al. A Wave of Regulatory T Cells into Neonatal Skin Mediates Tolerance to Commensal Microbes. Immunity, vol. 43, Issue 5, 1011-1021.
Scholz et al. The natural history of cutaneous propionibacteria,and reclassification of selected species within the genus *Propionibacterium* to the proposed novel genera *Acidipropionibacterium* gen. nov.,*Cutibacterium* gen. nov. and *Pseudopropionibacterium* gen. nov. International Journal of Systematic and Evolutionary Microbiology (2016), 66, 4422-4432.
Sharon et al. Functional genetic variants revealed by massively parallel precise genome editing. Cell. Oct. 4, 2018; 175(2): 544-557.e16.
Sievers et al. Fast, scalable generation of high-quality protein multiple sequence alignments using Clustal Omega. Molecular Systems Biology 7; 539.
Sörensen et al. Mutagenesis of *Propionibacterium acnes* and analysis of two CAMP factor knock-out mutants. Journal of Microbiological Methods 83 (2010) 211-216.
Wannier et al. Improved bacterial recombineering by parallelized protein discovery. PNAS. Jun. 16, 2020. 117:24. 13689-13698.
Yu. Different *Propionibacterium acnes* Phylotypes Induce Distinct Immune Responses and Express Unique Surface and Secreted Proteomes. Society for Investigative Dermatology. 2016. 2221-2228.
Zhao et al. New base editors change C to A in bacteria and C to G in mammalian cells. Nature Biotechnology. Jul. 20, 2020.
Simon et al., Retrons and their applications in genome engineering, Nucleic Acids Research, 2019, vol. 47, No. 21 11007-11019.
Castillo et al (2019). *Propionibacterium* (*Cutibacterium*) *acnes* Bacteriophage Therapy in Acne: Current Evidence and Future Perspectives. Dermatology and Therapy. 9, 19-31.
Chen et al (2019). Genetic Engineering of Bacteriophages Against Infectious Diseases. Frontiers in Microbiology. 10, 1-12.
Federici et al (2020). Phages and their potential to modulate the microbiome and immunity. Cellular and Molecular Immunology. 18. 889-204.
Marinell et al (2012). *Propionibacterium acnes* Bacteriophages Display Limited Genetic Diversity and Broad Killing Activity against Bacterial Skin Isolates. mBio. 3(5). 1-13.

* cited by examiner

```
                           595                                                   654
PAC7 wt                    tagtggagaaaacaaccaccccggaacgtttaagacaccccctcaaacgaacaaaacagg
PAC7-m28-gp45 plaque n°1   TAGTGGAGAAAACAACCACCCCGGAACGTTTAAGACACCCCCTCAAACGAACAAAACAGG
PAC7-m28-gp45 plaque n°2   TAGTGGAGAAAACAACCACCCCGGAACGTTTAAGACACCCCCTCAAACGAACAAAACAGG
PAC7-m28-gp45 plaque n°3   TAGTGGAGAAAACAACCACCCCGGAACGTTTAAGACACCCCCTCAAACGAACAAAACAGG

                           655                                                   714
PAC7 wt                    gcctagaatcgatcagcagggcaccggtagggtattcctaccccagacgattcaaggcc
PAC7-m28-gp45 plaque n°1   GCCTAGAATCGATCAGCAGGGCACCGGTAGGGTATTCCTACCCCAGACGATTCAAGG
PAC7-m28-gp45 plaque n°2   GCCTAGAATCGATCAGCAGGGCACCGGTAGGGTATTCCTACCCCAGACGATTCAAGG
PAC7-m28-gp45 plaque n°3   GCCTAGAATCGATCAGCAGGGCACCGGTAGGGTATTCCTACCCCAGACGATTCAAGG

                           715                                                   774
PAC7 wt                    attacaggagcaatgagaggctcacagggccatgggagattgggggcgtgatggcaca
PAC7-m28-gp45 plaque n°1
PAC7-m28-gp45 plaque n°2
PAC7-m28-gp45 plaque n°3

                           775                                                   834
PAC7 wt                    caccaaccgcacagccagccaagcccaccggcgctggcgggcaaggctcatcacccaagc
PAC7-m28-gp45 plaque n°1
PAC7-m28-gp45 plaque n°2
PAC7-m28-gp45 plaque n°3

                           835                                                   894
PAC7 wt                    ccgacaacaaggccaaaccgaatgcccactctgcggagtcaccatcacctggaacaccca
PAC7-m28-gp45 plaque n°1               CCAAACCGAATGCCCACTCTGCGGAGTCACCATCACCTGGAACACCCA
PAC7-m28-gp45 plaque n°2               CCAAACCGAATGCCCACTCTGCGGAGTCACCATCACCTGGAACACCCA
PAC7-m28-gp45 plaque n°3               CCAAACCGAATGCCCACTCTGCGGAGTCACCATCACCTGGAACACCCA

                           895                                                   954
PAC7 wt                    cgacctgccaaccagccccgaagccgaccacatcacacccgtcagccggggaggactcaa
PAC7-m28-gp45 plaque n°1   CGACCTGCCAACCAGCCCCGAAGCCGACCACATCACACCCGTCAGCCGGGGAGGACTCAA
PAC7-m28-gp45 plaque n°2   CGACCTGCCAACCAGCCCCGAAGCCGACCACATCACACCCGTCAGCCGGGGAGGACTCAA
PAC7-m28-gp45 plaque n°3   CGACCTGCCAACCAGCCCCGAAGCCGACCACATCACACCCGTCAGCCGGGGAGGACTCAA

                           955           977
PAC7 wt                    caccctcgacaacgggcaaatca (SEQ ID NO: 113)
PAC7-m28-gp45 plaque n°1   CACCCTCGACAACGGGCAAATCA (SEQ ID NO: 78)
PAC7-m28-gp45 plaque n°2   CACCCTCGACAACGGGCAAATCA (SEQ ID NO: 85)
PAC7-m28-gp45 plaque n°3   CACCCTCGACAACGGGCAAATCA (SEQ ID NO: 114)
```

FIGURE 18

*CUTIBACTERIUM ACNES* RECOMBINANT PHAGES, METHOD OF PRODUCTION AND USES THEREOF

CROSS REFERENCE TO RELATED APPLICATIONS

This application claims the benefit of U.S. application 63/109,832 filed Nov. 4, 2020, U.S. application 63/145,967 filed Feb. 4, 2021, U.S. application 63/109,834 filed Nov. 4, 2020, and U.S. application 63/145,969 filed Feb. 4, 2021, all of which are herein incorporated by reference in their entirety.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Nov. 4, 2021, is named EB2020-04c_SequenceListing_ST25.bd and is 530,801 bytes in size.

FIELD OF THE INVENTION

The present invention concerns *Cutibacterium acnes* recombinant phages and production method thereof.

BACKGROUND OF THE INVENTION

The skin is the largest organ of the human body and the biggest interface between our body and our environment. As such it also acts as a barrier protecting us from physical (e.g., UV, wounds), chemical (e.g., acid, base) and microbial (virus, bacteria, fungi) threats. This protection is not only the result of its passive physical isolating nature made from successive layers of dense and interconnected dead cells (stratum corneum) surrounded by a lipidic matrix. It is also thanks to active mechanisms orchestrated by diverse types of skin and immune cells that secrete antimicrobial peptides (AMP), produce cytokines and chemokines to recruit lymphoid immune cells, sense skin injuries and trigger wound healing mechanisms among other processes[1].

Skin is the first organ in contact with microorganisms after our birth, it is populated with a vast amount of immune cells in close contact with a great diversity of microorganisms and thus, the skin immune system needs to develop abilities to recognize beneficial microorganisms from pathogenic ones to avoid constant immune responses and inflammation. Part of this education is happening early in life when specific bacterial species are colonizing the skin and modulate immune responses in order for them to be tolerated[2]. These specific bacterial species are then able to stably colonize the skin establishing communities and becoming commensal strains.

Skin is not physiologically and spatially homogeneous throughout the body: oily (e.g cheek, back), moist (e.g., inguinal crease, interdigital web space, antecubital crease) and dry skin (e.g, volar forearm, hypothenar palm) exist depending on the body sites[3]. These different body sites are associated with different physiological conditions and carry distinct microbiomes, with oily sites being mostly colonized with *Cutibacterium acnes* (formerly known as *Propionibacterium acnes*), whereas *Staphylococcus* and *Corynebacterium* species are more abundant in moist sites [4]. In addition to these physiological characteristics, skin is also heterogeneous in spaces with different appendages: the sweat glands, the hair follicle, the sebaceous gland. The colonization of these appendages is only recently studied but shows differences compared to skin surface (stratum corneum)[4-6].

These skin appendages are specific anatomical places because they do not have stratum corneum. As a consequence, microorganisms inside these appendages are in contact with living keratinocytes and have access to a higher diversity of immune cells due to the dermis proximity. The hair follicle has specific immunological properties. It is able to recruit specific immune cells such as monocyte-derived Langerhans Cells precursors[7] and actively maintain resident memory T cells (TRM)[8] making it a potential essential place for antigen presentation. The hair follicle is also deprived of effector T cells and has a strong immunosuppressive environment making it an immune privileged area[9].

Examples in the published literature indicate that skin-resident bacteria actively engage host immunity through an intact skin barrier, and activate specific immune cells in a species- and strain-dependent manner (Chen et al, Nature 2018; 555(7697):543). For instance, some but not all strains of *S. epidermidis* induce activation of *S. epidermidis*-specific IL-$17^+$$CD8^+$ T cells that protect against cutaneous infection (Naik et al, Nature 2015, 520(7545):104-108).

Due to the absence of stratum corneum, the skin appendages are also more permeable to chemicals as these will only need to cross the tight-junction barrier and not the stratum corneum which normally prevents water exchange, and as a result all water-soluble substances are able to diffuse.

The pilosebaceous subunit comprising the hair follicle and the sebaceous gland is mostly colonized by *C. acnes* that thrive in this sebum rich and anaerobic environment. *Cutibacterium acnes* (formerly *Propionibacterium acnes*) is a gram-positive rod-shaped aerotolerant bacteria, first isolated from skin in 1897. It belongs to the order Actinomycetales, it is part of the Propionibacteriaceae family and it belongs to the genus *Cutibacterium*. This genus includes other human skin species such as *Cutibacterium avidum, Cutibacterium granulosum* and *Cutibacterium humerusii*[10]. *C. acnes* is one of the most prevalent and abundant bacteria on human skin where it can be found both on the skin surface (stratum corneum) and in the hair follicle. Inside the hair follicle, it is in direct contact with a large diversity of living cells such as keratinocytes, stem cells, sebaceous cells and immune cells, unlike on the stratum corneum where it is mostly in contact with the dead corneocyte. *C. acnes* is a commensal bacterium but has also been associated with several skin diseases such as acne vulgaris[11] or progressive macular hypomelanosis[12-14].

In particular, new findings on *C. acnes* reveal that specific phylotypes might play a critical role in acne development[11]. Precisely, the role of *C. acnes* phylotype IA1 in acne is being widely underscored. Fitz-Gibbon and colleagues demonstrated that chromosomal regions, loci 1, 2 and 3, characteristic of ribotypes RT4 and RT5 (classified within the phylogroup IA1), are strongly associated with acne[15]. Since these chromosomal regions are absent in ribotypes that are associated with healthy skin (i.e., RT6), they represent a potential target to eliminate acne-associated *C. acnes* strains.

Being able to edit *Cutibacterium acnes* population by removing specific proinflammatory strains to prevent or cure disease such as acne vulgaris or leverage their privilege location into the pilosebaceous unit to modulate host immune responses or improve wound healing are attractive therapeutic approaches. To implement such approaches, one can either genetically modify *C. acnes* strains in situ or provide in vitro genetically modified *C. acnes*. Because of the large intra-individual and inter-individual microbiome diversity both at the species and at the strain level, it appears difficult to provide a single or cocktail of engineered *C. acnes* strains able to colonize the skin of most patients.

Delivery of DNA in situ to the *C. acnes* population offers a way to circumvent such difficulties by allowing to leverage pre-established strains potentially without disturbing the local microbiome. However, in situ delivery of genetic material to *C. acnes* is a challenging task for several reasons. First, there are so far no genetic elements such as plasmid able to robustly and autonomously replicate inside *C. acnes*. The few described genetic modifications consist in genomic insertion of synthetic DNA through homologous recombination[16-18]. This in vitro process has been shown to be of very low efficiency and rely on the use of an antibiotic selection marker to select such events. Moreover, these genetic modifications have been restricted to a few specific strains (KPA17202, one RT6 *C. acnes*) and might not be generalizable to all *C. acnes* strains. Second, in order to perform in situ genetic modification of *C. acnes* delivery of DNA into *C. acnes* is needed. The only described method for introducing DNA into *C. acnes* is the use of electroporation[19,20], a method that can only be performed in vitro.

The present invention solves both the lack of replicative and stable DNA vectors and their delivery into *C. acnes* using phage-derived particles. The present invention also provides unique and robust tools for *C. acnes* phage genome engineering.

BRIEF SUMMARY OF INVENTION

The invention encompasses *Cutibacterium acnes* phagemids, bacterial cells comprising these phagemids, *Cutibacterium acnes* recombinant phages, methods for making phage-derived particles comprising these phagemids, phage-derived particles comprising these phagemids, and methods for using these phagemids, particles, and cells, particularly in treatments of *Cutibacterium acnes* related disorders and/or diseases.

The invention encompasses a recombinant DNA phagemid vector, phage-derived particles comprising these vectors, and *Cutibacterium acnes* carrying the vector, wherein the vector comprises:

- a phage packaging signal allowing packaging of the DNA vector in a *Cutibacterium acnes* phage capsid; and
- a gene of interest.

In one embodiment, the DNA vector comprises:

- a phage packaging signal allowing packaging of the DNA vector in a *Cutibacterium acnes* phage capsid; wherein the phage packaging signal sequence is at least 80, 83, 85, 87, 90, 93, 95, 97, 98, 99, or 100% identical to the sequence SEQ ID NO: 76; and
- a gene of interest.

In one embodiment, the DNA vector comprises:

- a phage packaging signal allowing packaging of the DNA vector in a *Cutibacterium acnes* phage capsid;
- a gene of interest; and
- a selection marker allowing for selection of the DNA vector in *Cutibacterium acnes*.

In one embodiment, the DNA vector comprises:

- a phage packaging signal allowing packaging of the DNA vector in a *Cutibacterium acnes* phage capsid; wherein the phage packaging signal sequence is at least 80, 83, 85, 87, 90, 93, 95, 97, 98, 99, or 100% identical to the sequence SEQ ID NO: 76;
- a gene of interest; and
- a selection marker allowing for selection of the DNA vector in *Cutibacterium acnes*.

In one embodiment, the DNA vector comprises:

- a phage packaging signal allowing packaging of the DNA vector in a *Cutibacterium acnes* phage capsid;
- a gene of interest;
- an origin of replication allowing replication in *Cutibacterium acnes*; and
- optionally a selection marker allowing for selection of the DNA vector in *Cutibacterium acnes*.

In one embodiment, the DNA vector comprises:

- a phage packaging signal allowing packaging of the DNA vector in a *Cutibacterium acnes* phage capsid; wherein the phage packaging signal sequence is at least 80, 83, 85, 87, 90, 93, 95, 97, 98, 99, or 100% identical to the sequence SEQ ID NO: 76;
- a gene of interest;
- an origin of replication allowing replication in *Cutibacterium acnes*; and
- optionally a selection marker allowing for selection of the DNA vector in *Cutibacterium acnes*.

In one embodiment, the phage packaging signal sequence is at least 80, 83, 85, 87, 90, 93, 95, 97, 98, 99, or 100% identical to a phage packaging signal sequence selected from the group consisting of the sequences SEQ ID NO: 76, SEQ ID NO: 86, SEQ ID NO: 87, SEQ ID NO: 88, SEQ ID NO: 89 and SEQ ID NO: 90.

In one embodiment, the DNA vector further comprises a *C. acnes* phage origin of replication.

In one embodiment, the DNA vector further comprises a *C. acnes* phage origin of replication, wherein the phage origin of replication sequence is at least 75, 77, 80, 83, 85, 87, 90, 93, 95, 97, 98, 99 or 100% identical to the sequence SEQ ID NO: 67.

In one embodiment, the gene of interest is a DNA encoding an antigen.

The invention encompasses a *Cutibacterium acnes* producer cell carrying a recombinant DNA vector for the production of *Cutibacterium acnes* phage-derived particles that contain the recombinant DNA vector.

The DNA vector is typically packaged into proteins produced from a *Cutibacterium acnes* phage genome or a helper phage. The *C. acnes* phage genome can be introduced into the *C. acnes* producer cell, for instance, by transformation or transduction with a *C. acnes* phage whereas the helper phage can be introduced into the *C. acnes* producer cell, for instance, by transformation or conjugation before or after introduction of the DNA vector into the *C. acnes* producer cell (FIG. 1).

The *Cutibacterium acnes* producer cell carrying a recombinant DNA vector typically comprises a *Cutibacterium acnes* phage genome leading to the production of phage-derived particles carrying the DNA vector.

In one embodiment, the *Cutibacterium acnes* phage genome is a non-engineered/wild-type genome.

In another embodiment, the *Cutibacterium acnes* phage genome is engineered.

In one embodiment, the DNA vector comprises an origin of replication able to replicate only in the *Cutibacterium acnes* producer cell and not in the *Cutibacterium acnes* receiver cell.

In one embodiment, the DNA vector comprises:

- a phage packaging signal allowing packaging of the DNA vector in a *Cutibacterium acnes* phage capsid;
- at least one gene of interest;
- an origin of replication allowing replication only in *Cutibacterium acnes* producer cell; and
- optionally a selection marker allowing for selection of the DNA vector in *Cutibacterium acnes*.

In one embodiment, the selection marker is an auxotrophic marker and the *Cutibacterium acnes* producer cell growth is dependent on this auxotrophic marker.

In one embodiment, the selection marker is an antibiotic resistance marker.

In one embodiment, the DNA vector further comprises a CRISPR-Cas system.

In one embodiment, the CRISPR-Cas system targets a *C. acnes* chromosome locus.

Preferably, the targeted locus is not present in the *C. acnes* producer cell. Preferably, the CRISPR array from the CRISPR-Cas system is expressing one or several crRNA targeting the chromosome locus.

In one embodiment, the CRISPR-Cas system targets several *C. acnes* chromosome loci. Preferably, the targeted loci are not present in the *C. acnes* producer cell. Preferably, the CRISPR array from the CRISPR-Cas system is expressing one or several crRNA targeting the chromosome loci.

In one embodiment, the CRISPR-Cas system targets a *C. acnes* plasmid locus.

Preferably, the targeted locus is not present in the *C. acnes* producer cell. Preferably, the CRISPR array from the CRISPR-Cas system is expressing one or several crRNA targeting the plasmid locus.

In one embodiment, the CRISPR-Cas system targets several *C. acnes* plasmid loci. Preferably, the targeted loci are not present in the *C. acnes* producer cell. Preferably, the CRISPR array from the CRISPR-Cas system is expressing one or several crRNA targeting the plasmid loci.

In one embodiment, the CRISPR-Cas system is not expressed in the *C. acnes* producer cell. Preferably the CRISPR-Cas system is repressed in the *C. acnes* producer cell.

In one embodiment, the CRISPR-Cas system targets a proinflammatory sequence related to a host disease.

In one embodiment, the CRISPR-Cas system targets a proinflammatory sequence related to acne vulgaris.

In one embodiment, the DNA vector comprises a CRISPR-Cas system targeting the DNA vector itself.

In one embodiment, the DNA vector comprises a template for homologous recombination in *C. acnes* phages.

In one embodiment, the DNA vector comprises a template for homologous recombination in *C. acnes* chromosome.

In one embodiment, the DNA vector comprises a template for homologous recombination in *C. acnes* endogenous plasmids.

In one embodiment, the DNA vector comprises a template for homologous recombination and a CRISPR-Cas system targeting the DNA vector itself outside of the template region.

In one embodiment, the DNA vector comprises a template for homologous recombination and a CRISPR-Cas system targeting the DNA vector itself outside of the template region wherein the RNA guide (crRNA or sgRNA) from the CRISPR-Cas system is not perfectly matching the DNA target.

In one embodiment, the DNA vector comprises an integrase gene expression cassette and a site specific recombination site allowing for the integration of the DNA vector inside the chromosome.

In one embodiment, the DNA vector comprises a prime editor gene expression cassette and one or multiple pegRNAs.

In one embodiment, the DNA vector comprises a base editor gene expression cassette and one or multiple crRNAs or sgRNAs.

In one embodiment, the selection marker is catA.

In one embodiment, the selection marker is ermE.

In one embodiment, the selection marker is hygB.

The invention encompasses a *C. acnes* phage-derived particle comprising any of the DNA vectors of the invention.

The invention encompasses a *C. acnes*, in particular an engineered *C. acnes*, comprising any of the DNA vectors of the invention.

In a particular embodiment, the engineered *C. acnes* comprises at least one, two, three or more DNA vectors, in particular DNA vectors of the invention.

In a particular embodiment, the engineered *C. acnes* comprises a DNA vector of the invention which comprises a DNA encoding an antigen.

The invention encompasses a *C. acnes* engineered following transduction of any of the vectors of the invention by phage-derived particles.

The invention encompasses an engineered *C. acnes* whose genome is altered following the transduction by a phage-derived particle containing any of the vectors of the invention.

The invention encompasses an engineered *C. acnes* produced by transducing *C. acnes* with any of the vectors of the invention, modifying the *C. acnes* with a gene of interest carried by the vector, and selecting for the modification.

The invention encompasses an engineered *C. acnes* produced by transducing *C. acnes* with any of the vectors of the invention, modifying the *C. acnes* with a gene of interest carried by the vector, selecting for the modification, and curing the engineered *C. acnes* of the vector.

In one embodiment, the engineered *C. acnes* has been modified by a CRISPR-Cas system carried by the vector and transduced by a phage-derived particle containing any vectors from the invention.

In one embodiment, the engineered *C. acnes* has been modified by insertion of an exogenous gene into the *C. acnes* chromosome In one embodiment, the engineered *C. acnes* has been modified by insertion of an exogenous gene into the *C. acnes* plasmid.

In one embodiment, the engineered *C. acnes* has been modified by deletion or mutation of an endogenous genetic sequence in the *C. acnes* chromosome.

In one embodiment, the engineered *C. acnes* has been modified by deletion, insertion or substitution of one or several nucleotides into the *C. acnes* chromosome.

In one embodiment, the engineered *C. acnes* has been modified by deletion, insertion or substitution of one or several nucleotides into the *C. acnes* plasmid.

The invention encompasses a method for producing *C. acnes* phage-derived particles that contain any vectors of the invention, comprising the introduction of any of the DNA vectors of the invention into a *C. acnes* producer cell and contacting the producer cell with *C. acnes* phage genome.

The invention encompasses a method for engineering *C. acnes* comprising the introduction of any of the DNA vectors of the invention into a *C. acnes*. The method can further comprise selecting a modified *C. acnes*. The method can further comprise selecting a modified *C. acnes* that has an insertion of an exogenous gene into the *C. acnes* chromosome or into an endogenous plasmid. The method can further comprise selecting a modified *C. acnes* that has one or several deletions, insertions or substitutions of one or several nucleotides into *C. acnes* chromosome or endogenous plasmids.

The invention encompasses a phage-derived particle produced by any of the methods of the invention.

The invention encompasses methods for treating a *C. acnes*-related disorder or disease. In one embodiment, the method comprises administering a phage-derived particle of the invention or a bacterium producing such a phage-derived particle to a subject. The invention further concerns a phage-derived particle of the invention or a bacterium producing such a phage derived particle for use in a method for treating a *C. acnes*-related disorder or disease.

The invention encompasses methods for modifying *C. acnes* to treat a disorder or disease or skin condition or for cosmetic applications. In one embodiment, the method comprises administering a phage-derived particle of the invention or a bacterium producing such a phage-derived particle to a subject. The invention further concerns a phage-derived particle of the invention or a bacterium producing such a phage-derived particle for use in a method for treating a disorder or disease or skin condition.

In one embodiment, the method is performed ex-situ.

In one embodiment, the method is performed in-situ.

In one embodiment, the method is performed ex-situ with a *C. acnes* strain isolated from the subject.

BRIEF DESCRIPTION OF DRAWINGS

In order to better understand the subject matter that is disclosed herein and to exemplify how it may be carried out in practice, embodiments will be described, by way of non-limiting example, with reference to the accompanying drawings. With specific reference to the drawings, it is stressed that the particulars shown are by way of example and for purposes of illustrative discussion of embodiments of the invention.

FIG. 4A depicts a vector (pEB_HR01) containing a single homology arm (HA) to *C. acnes* chromosome which is conjugated into *C. acnes*. Because the vector is not replicative in *C. acnes*, only *C. acnes* cells that perform a single recombination event stably maintain the antibiotic marker and are able to grow on antibiotic plate. Cells that do not perform the first recombination event or cells that perform the first and the second recombination events are not able to grow on antibiotic plates (erythromycin). FIG. 4B depicts a vector (pEB_HR02) containing two homology arms to *C. acnes* chromosome which is conjugated into *C. acnes*. Selection of the final recombinant is performed using an antibiotic selection (ErmE) and a counter selection (SacB).

FIG. 6A depicts a vector, containing an antibiotic selection marker flanked by two homology arms and a CRISPR-Cas system targeting the vector outside the homology regions, which is conjugated into *C. acnes*. The CRISPR-Cas system cuts the vector leading to linearization of the template and plasmid loss. Thus, only recombinant cells are able to grow in the presence of an antibiotic. FIG. 6B depicts a vector, containing a mutant allele flanked by two homology arms and a CRISPR-Cas system targeting the vector outside the homology regions as well as the non mutated allele of *C. acnes* chromosome, which is conjugated into *C. acnes*. The CRISPR-Cas system cuts the vector leading to linearization of the template and plasmid loss as well as the *C. acnes* chromosome. Thus, only recombinant cells are able to grow in the presence of erythromycin.

FIG. 7A depicts the first step of the method. The first step consists in generating mutant phages (mt PAC7) by having a first phage (wt PAC7) infect a strain containing a plasmid with a recombination template (*C. acnes* pEB-PRECOMB). The recombination template contains a left homology arm (LHA) and a right homology arm (RHA) that are flanking a mutant allele. The two homology arms drive the in vivo recombination between the plasmid (pEB-PRECOMB) and the phage genome. Suspension obtained from infection contains a mix of initial phage (wt PAC7) and the new mutated phage (mt PAC7). FIG. 7B depicts the second step of the method. To select between both phage particles, the suspension is put in contact with a *C. acnes* strain (*C. acnes* pEB-PSCREEN) containing a plasmid expressing CRISPR-Cas system targeting only the wt PAC7 phage and not the mt PAC7. Therefore infection of the *C. acnes* pEB-PSCREEN leads to selective replication of mt PAC7.

ATCC 11828 wt, *C. acnes* ATCC 11828 harbouring pIC238 (Ca0s18233) and *C. acnes* ATCC 11828 harbouring pIC240 (Ca0s18234). Strain *C. acnes* ATCC 11828 is susceptible to both wild-type phage PAC7 and any mutant phage obtained by homologous recombination. Strain Ca0s18233 is resistant to wild-type phage PAC7 and susceptible to mutant phage obtained by homologous recombination with pIC253 template. Strain Ca0s18234 is resistant to wild-type phage PAC7 and resistant to mutant phage obtained by homologous recombination with pIC253.

Figure 10:
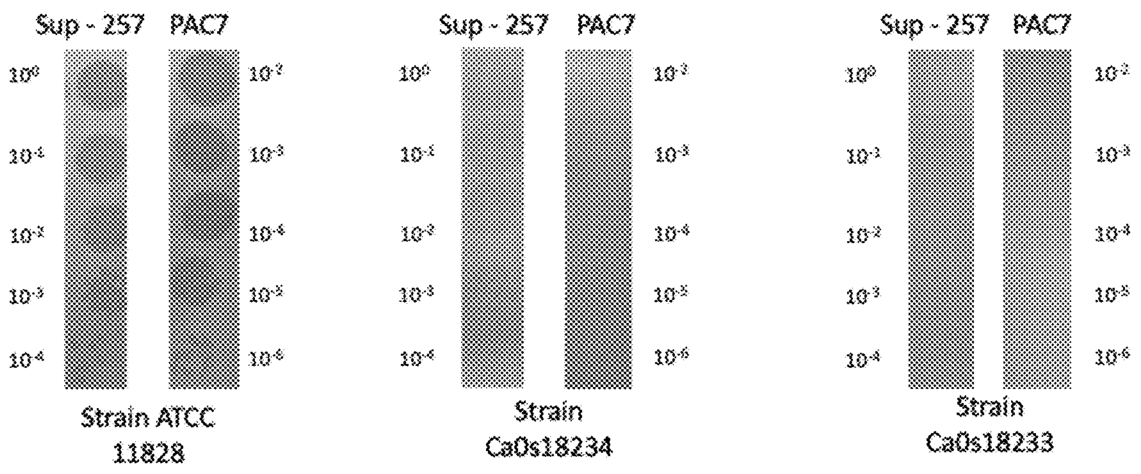

FIG. 10 depicts titration of supernatant obtained after infecting *C. acnes* harbouring editing/targeting vectors pIC257 (Ca0s18208), referred as Sup-257, on *C. acnes* ATCC 11828 wt, *C. acnes* ATCC 11828 harbouring pIC240 (Ca0s18234) and *C. acnes* ATCC 11828 harbouring pIC238 (Ca0s18233). Strain *C. acnes* ATCC 11828 is susceptible to both wild-type phage PAC7 and any mutant phage obtained by homologous recombination. Strain Ca0s18234 is resistant to wild-type phage PAC7 and susceptible to mutant phage obtained by homologous recombination with pIC257. Strain Ca0s18233 is resistant to wild-type phage PAC7 and resistant to mutant phage obtained by homologous recombination with pIC257.

Figure 11:
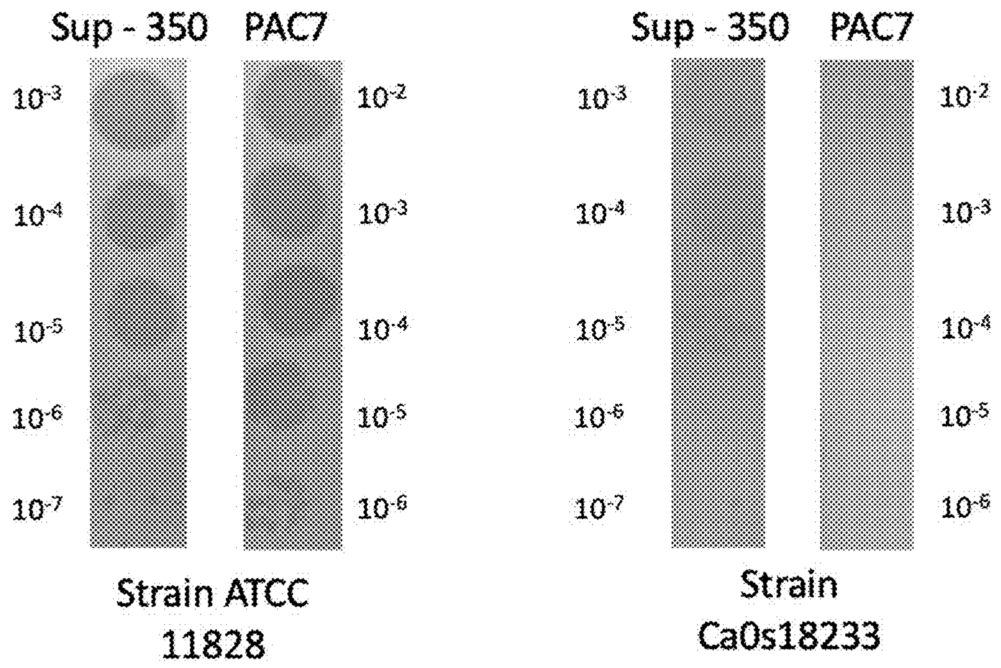

FIG. 11 depicts titration of supernatant obtained after infecting *C. acnes* harbouring editing pIC350 (Ca0s18379), referred as Sup-350, on *C. acnes* ATCC 11828 wt and *C. acnes* ATCC 11828 harbouring pIC238 (Ca0s18233). Strain *C. acnes* ATCC 11828 is susceptible to both wild-type phage PAC7 and mutant phage obtained by homologous recombination with pIC350. Strain Ca0s18233 is resistant to wild-type phage PAC7 and susceptible to mutant phage obtained by homologous recombination with pIC350.

Figure 12:
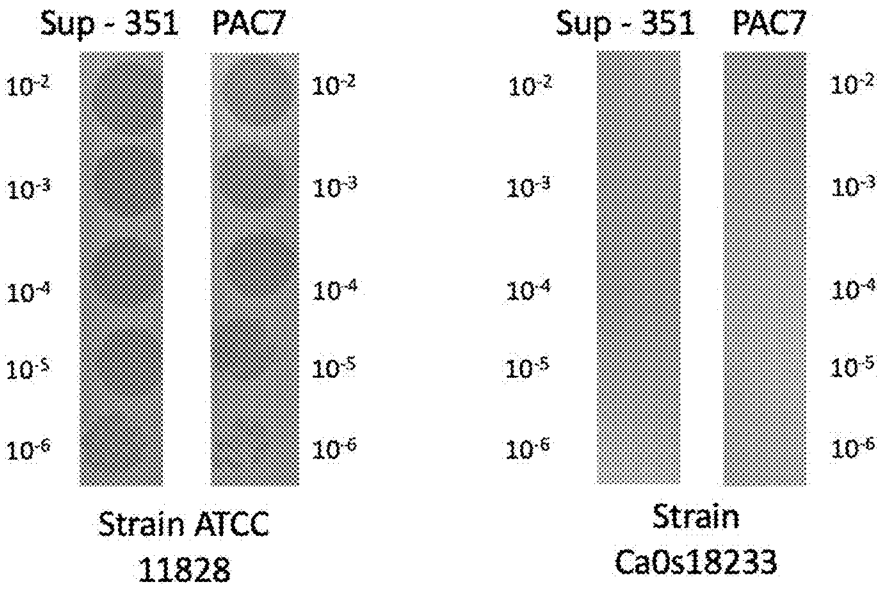

FIG. 12 depicts titration of supernatant obtained after infecting *C. acnes* harbouring editing pIC351 (Ca0s18381), referred as Sup-351, on *C. acnes* ATCC 11828 wt and *C. acnes* ATCC 11828 harbouring pIC238 (Ca0s18233). Strain *C. acnes* ATCC 11828 is susceptible to both wild-type phage PAC7 and mutant phage obtained by homologous recombination with pIC351. Strain Ca0s18233 is resistant to both wild-type phage PAC7 and mutant phage obtained by homologous recombination with pIC351.

Figure 13:
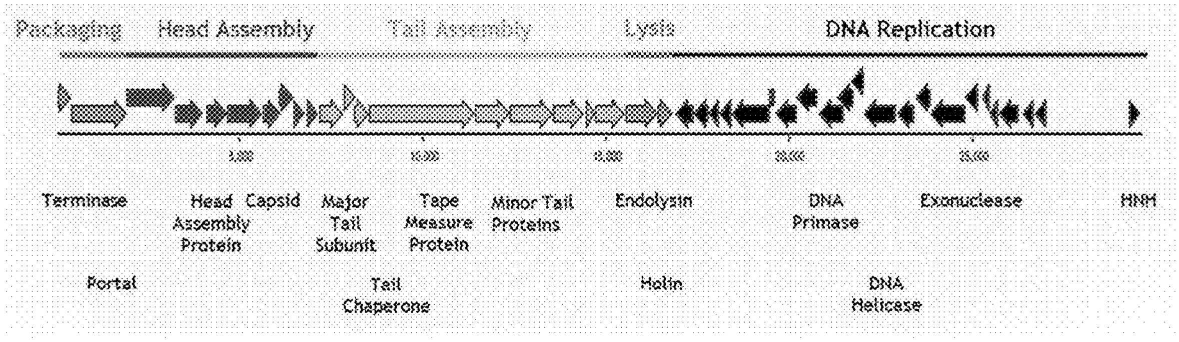

FIG. 13 depicts *C. acnes* phage genome organization. 5 different regions encode different proteins involved in various functions: packaging, head assembly, tail assembly, lysis, DNA replication (Brown et al[28]).

Figure 14A:
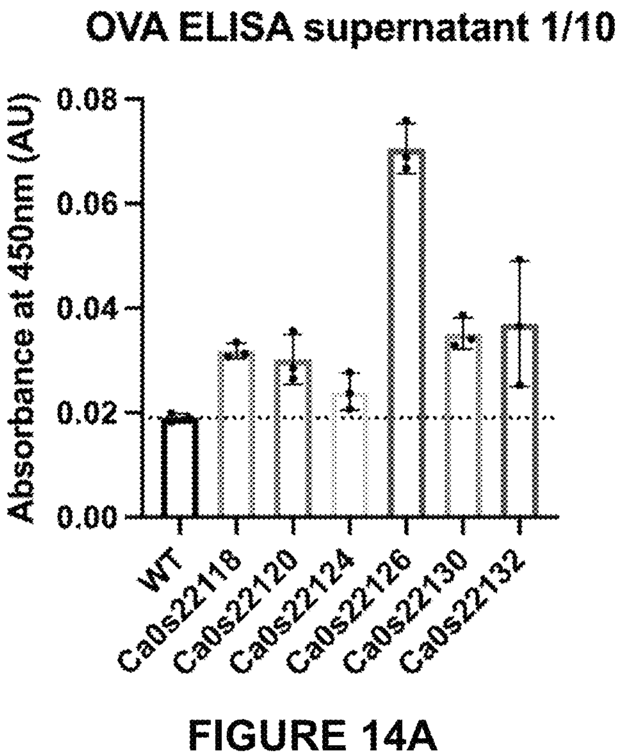
Figure 14B:
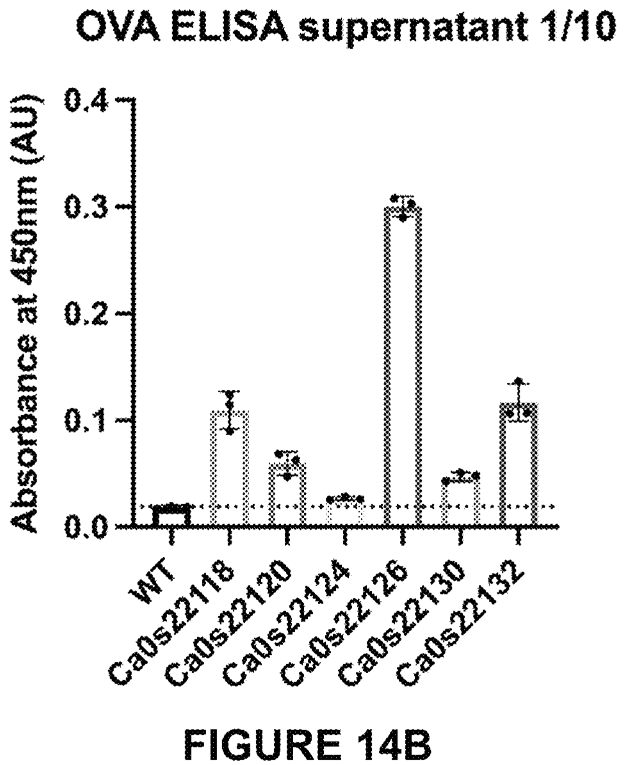

FIG. 14 (A and B) depicts absorbance values from ELISAs for the presence of chicken ovalbumin (OVA) protein in different *C. acnes* culture supernatant diluted 1/10. FIG. 14A and FIG. 14B represent two independent replicas. Bar graphs represent the mean of three technical replicates of the same supernatant culture. *C. acnes* strains ATCC 11828 (WT) was used as negative control.

Figure 15:
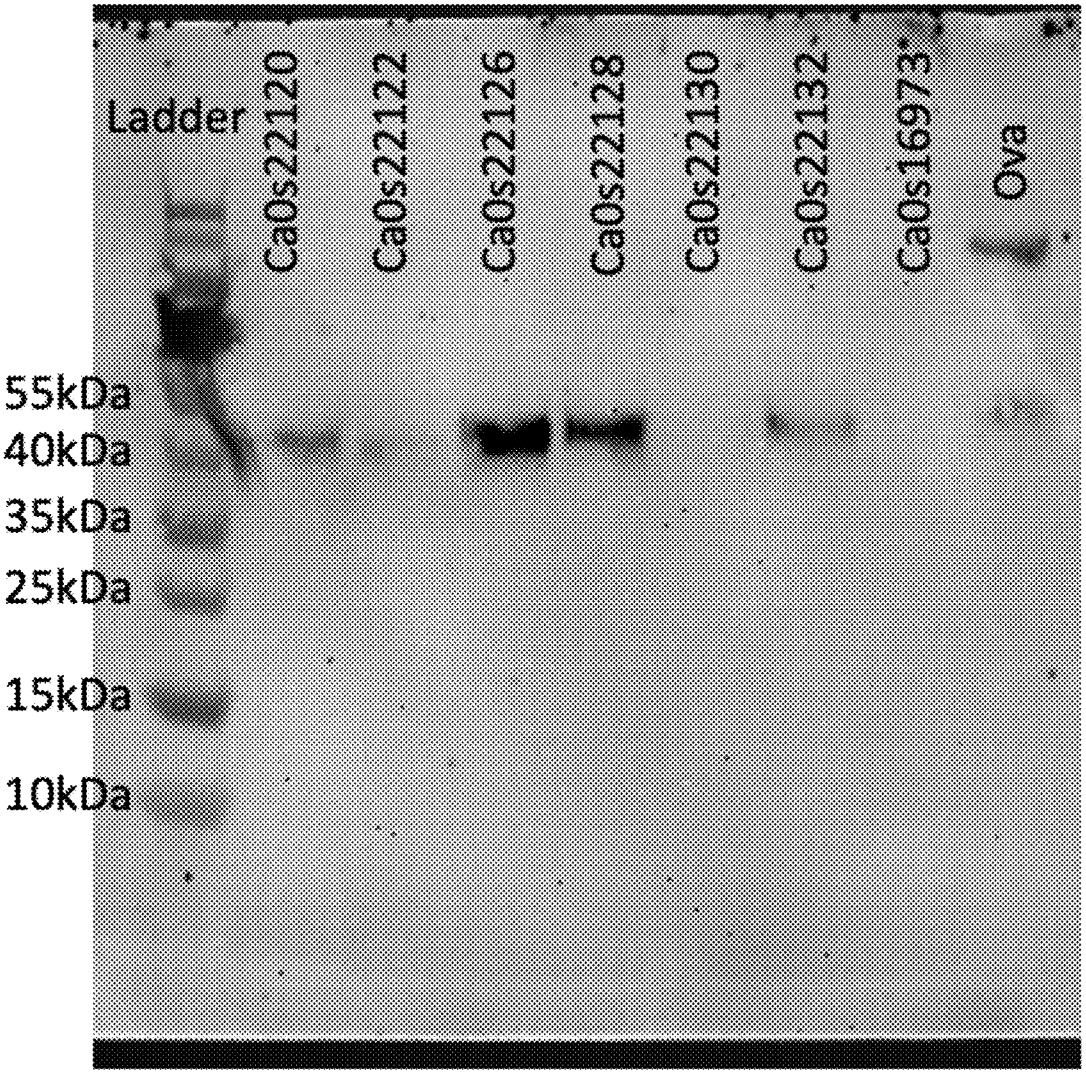

FIG. 15 depicts an ovalbumin specific western blot on culture supernatant from different *C. acnes* strains engineered to secrete ovalbumin. From left to right: (1) Pageruler ladder, (2) supernatant from strain Ca0s22120, (3) supernatant from strain Ca0s22122, (4) supernatant from strain Ca0s22126, (5) supernatant from strain Ca0s22128, (6) supernatant from strain Ca0s22130, (7) supernatant from strain Ca0s22132, (8) supernatant from strain Ca0s16973, (9) ovalbumin.

Figure 16:
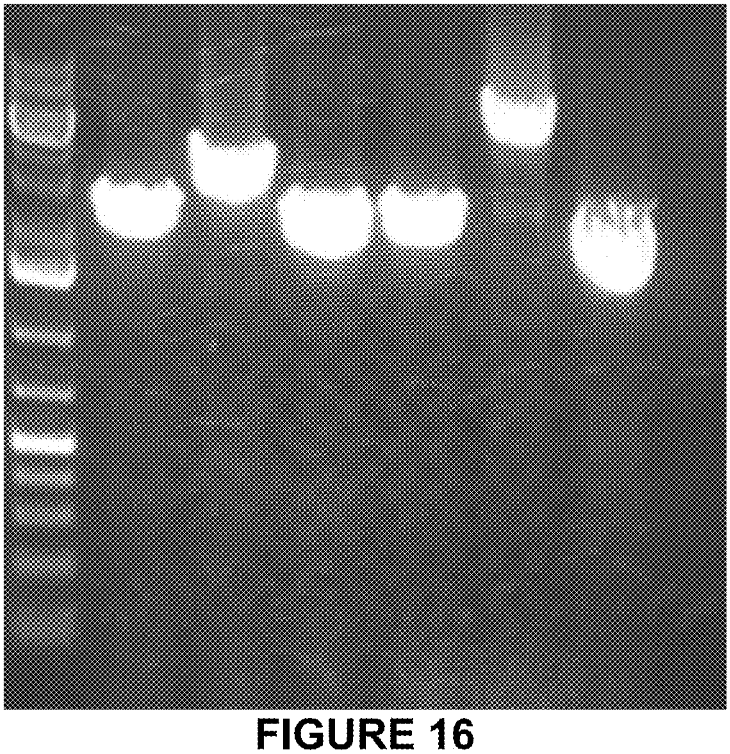

FIG. 16 depicts a gel. First well in the left (1) corresponds to GeneRuler 1 kb DNA Ladder. Other wells correspond to PCR with primers IC443/1C290 performed on plaques. From left to right: (2) Plaque n° 5 from a lawn of the strain Ca0s20472+suspension of infected Ca0s20855, (3) Plaque n° 7 from a lawn of the strain Ca0s20472+suspension of infected Ca0s20855, (4) Plaque n° 1 from a lawn of the strain Ca0s20472+suspension of PAC7, (5) Plaque n° 2 from a lawn of the strain Ca0s20472+suspension of PAC7, (6) Plaque n° 3 from a lawn of the strain Ca0s20472+suspension of infected Ca0s20857, (7) Plaque n° 3 from a lawn of the strain Ca0s20472+suspension of PAC7.

Figure 17:
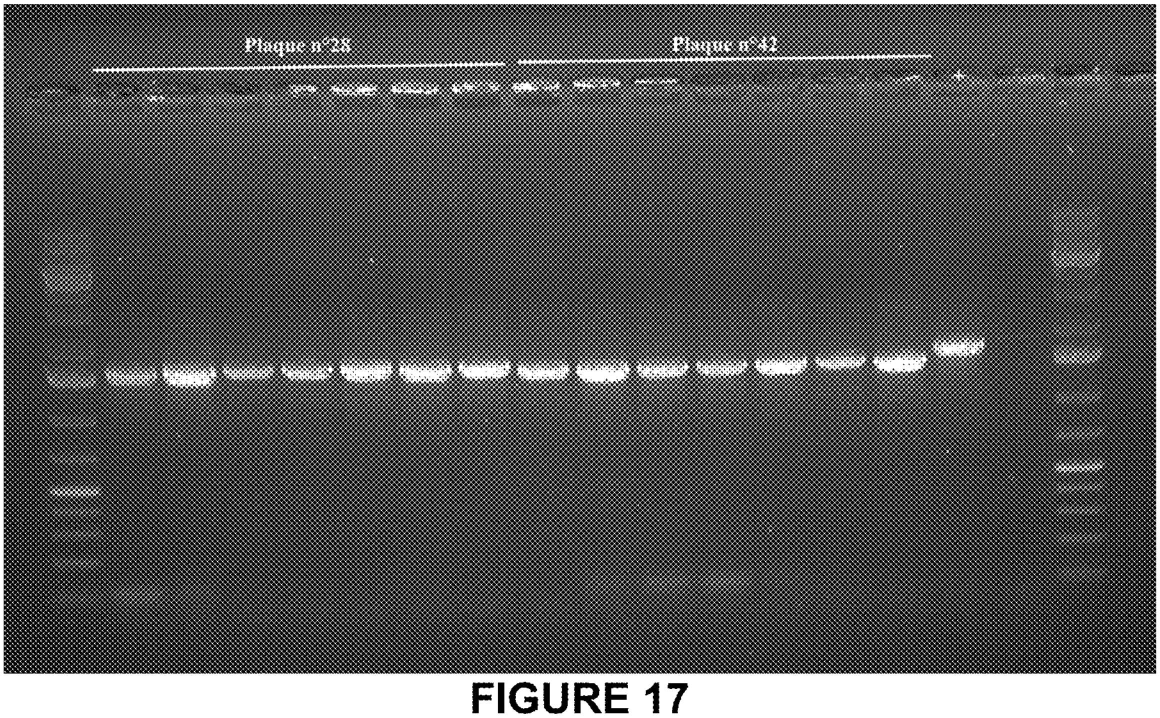

FIG. 17 depicts a gel. First well (1) in the left corresponds to GeneRuler 1 kb DNA Ladder. Other wells correspond to PCR with primers IC619/AL219. From left to right: (well 2-8) 7 plaques isolated from plaque n° 28, (well 9-15) 7 plaques isolated from plaque n° 28, (well 16) PCR on wt PAC7 (positive control), (well 17) negative control on lawn of Ca0s22235.

FIG. 18 depicts a DNA alignment between the PAC7 wt genome (SEQ ID NO: 113) and the sequencing of three different isolated plaques from PAC7-m28-gp45 using primer IC619 (SEQ ID NO: 78; SEQ ID NO: 85; SEQ ID NO: 114). Alignments performed using Clustal Omega (Sievers, F. et al. *Mol Syst Biol* 7, 539-539 (2011)).

DETAILED DESCRIPTION OF INVENTION

The inventors demonstrated, for the first time, the introduction of a recombinant replicative DNA in *C. acnes* by transduction by a phage-derived particle.

The inventors also demonstrated, for the first time, the production of *C. acnes* phage-derived particles from a *C. acnes* strain, carrying a recombinant self-replicative DNA vector.

The invention relates to a *C. acnes* strain carrying a DNA vector comprising a phage packaging signal and a gene of interest, the production of phage-derived particles containing the DNA vector and the use of this phage-derived particles to transduce *C. acnes* in vitro or in situ and the subsequent expression of the gene of interest in the transduced *C. acnes* cell. The invention also relates to the modified *C. acnes* strains obtained by transduction of a DNA vector by the phage-derived particle, the modified *C. acnes* strains containing or not the DNA vector.

*C. acnes* phages are naturally present in the human skin and have been isolated numerous times since the first isolation in 1964. More recently, sequencing of *C. acnes* phages has revealed an unusual high level of nucleotide conservation with ~85% identity. All *C. acnes* phages described so far are siphoviridae with a genome size constraint around 30 kb and a similar genome architecture. Despite their small genetic diversity, most *C. acnes* phages have the capacity to infect several *C. acnes* phylotypes and thus are considered as broad-host range. Their in-situ infectivity and their broad host range make them a relevant platform to be engineered for transgene delivery into the *C. acnes* population.

The inventors show for the first time that phage-derived particles can be produced from the co-occurrence of a wild-type or engineered *C. acnes* phage genome and a recombinant DNA vector with a packaging signal in a *C. acnes* cell ("producer cell"). The phage-derived particles are able to transduce the DNA vector into a "receiver" *C. acnes* cell and express a transgene such as an antibiotic resistance gene allowing the selection of the transductants. This widely expands the possibility to engineer *C. acnes* population directly on the skin, paving the way for many applications (industrial, therapeutic, cosmetic, environmental). The invention encompasses a *C. acnes* "producer" cell carrying DNA vectors, particularly phagemids, and methods for generating phage-derived particles and their use to modify or kill *C. acnes*.

DNA Vectors

The invention encompasses recombinant DNA vectors for use in *Cutibacterium acnes*. Preferably, the DNA vector is a recombinant DNA vector, which is not integrated into the *C. acnes* chromosome. The vector allows transfer to progeny cells. The vector is preferably a phagemid. The DNA vector preferably comprises an origin of replication allowing replication in *C. acnes* and a phage packaging signal.

In various embodiments, the DNA vector comprises any combination of a phage packaging signal, an origin of replication allowing replication in *C. acnes*, a selection marker allowing for selection of the DNA vector in *C. acnes*, a gene of interest, and an origin of replication allowing replication in *C. acnes* producer cell but no replication in *C. acnes* receiver cell.

In one embodiment, the DNA vector comprises a phage packaging signal, an origin of replication allowing replication in *C. acnes*, a first selection marker allowing for selection of the DNA vector in *C. acnes* and a gene of interest.

In one embodiment, the DNA vector comprises a phage packaging signal, an origin of replication allowing replication in *C. acnes* producer cell but no replication in *C. acnes* receiver cell, a first selection marker allowing for selection of the DNA vector in *C. acnes* and a gene of interest.

Preferably, the gene of interest is exogenous to *C. acnes*, that is, one that is not found naturally in *C. acnes*.

In one embodiment, the DNA vector comprises a phage packaging signal, wherein the phage packaging signal sequence is at least 80, 83, 85, 87, 90, 93, 95, 97, 98, 99, or 100% identical to the sequence SEQ ID NO: 76; an origin of replication allowing replication in *C. acnes*; a selection marker allowing for selection of the DNA vector in *C. acnes*; and a gene of interest.

In one embodiment, the DNA vector comprises a phage packaging signal, wherein the phage packaging signal sequence is at least 80, 83, 85, 87, 90, 93, 95, 97, 98, 99, or 100% identical to the sequence SEQ ID NO: 76; an origin of replication allowing replication in *C. acnes* or closely related species; a selection marker allowing for selection of the DNA vector in *C. acnes*; and a gene of interest.

In one embodiment, the DNA vector comprises a phage packaging signal, wherein the phage packaging signal sequence is at least 80, 83, 85, 87, 90, 93, 95, 97, 98, 99, or 100% identical to the sequence SEQ ID NO: 76; an origin of replication allowing replication in *C. acnes* or closely related species; a selection marker allowing for selection of the DNA vector in *C. acnes*; a selection marker allowing for selection in a first bacteria wherein the first bacteria is *E. coli*; an origin of replication allowing replication in a first bacteria wherein the first bacteria is *E. coli*; and a gene of interest.

In one embodiment, the DNA vector can be efficiently introduced into and stably replicated in *C. acnes* producer cell using electroporation, using protoplast electroporation, using chemical transformation, using conjugation, using natural competency or using transduction.

In one embodiment, the DNA vector can be efficiently transformed into and stably replicated in *C. acnes* producer cell using physical methods such as electroporation of *C. acnes* cells or electroporation of *C. acnes* protoplast.

In one embodiment, the *C. acnes* protoplasts are generated using Mutanolysin treatment or Lysozyme treatment, Mutanolysin and Lysozyme treatment, or Mutanolysin and Lysozyme and bead-beating treatment followed by resuspension into hypotonique media.

In one embodiment, the DNA vector can be efficiently transformed into and stably replicated in *C. acnes* producer cell using *C. acnes* protoplast mix with DNA vector or DNA vector+glass beads.

In one embodiment, delivery of the DNA vector into *C. acnes* is by transduction. In one embodiment, the DNA vector comprises one packaging signal selected from the group consisting of the packaging signals of the following *C. acnes* phages: PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74); and PAC263 (typically of sequence SEQ ID NO: 75), and is packaged into proteins expressed from the genome of a *C. acnes* phage selected from the group consisting of the phages PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74); and PAC263 (typically of sequence SEQ ID NO: 75), allowing transduction of the DNA vector into *C. acnes.*

In one embodiment, the DNA vector comprises a packaging signal, the sequence of which is at least 80, 83, 85, 87, 90, 93, 95, 97, 98, 99, or 100% identical to the sequence of any of the above packaging signals.

In one embodiment, the phage packaging signal is of sequence at least 80, 83, 85, 87, 90, 93, 95, 97, 98, 99, or 100% identical to a phage packaging signal sequence selected from the group consisting of: SEQ ID NO: 76, SEQ ID NO: 86, SEQ ID NO: 87, SEQ ID NO: 88, SEQ ID NO: 89 and SEQ ID NO: 90.

In one embodiment, delivery of the DNA vector into *C. acnes* is by conjugation.

In one embodiment, the DNA vector comprises an origin of transfer selected from the group consisting of: oriT_pMRC01 (typically of sequence SEQ ID NO: 1); oriT_RSF1010 (typically of sequence SEQ ID NO: 2); oriT_pRS01 (typically of sequence SEQ ID NO: 3); oriT_pMV158 (typically of sequence SEQ ID NO: 4); oriT_pTF1 (typically of sequence SEQ ID NO: 5); oriT_pSC101 (typically of sequence SEQ ID NO: 6); oriT_pBTK445 (typically of sequence SEQ ID NO: 7); oriT_pBBR1 (typically of sequence SEQ ID NO: 8); oriT_R721 (typically of sequence SEQ ID NO: 9); oriT_pRmeGR4a (typically of sequence SEQ ID NO: 10); oriT_ColE1 (typically of sequence SEQ ID NO: 11); oriT_pTiC58 (typically of sequence SEQ ID NO: 12); oriT_pMdT1 (typically of sequence SEQ ID NO: 13); oriT_R1 (typically of sequence SEQ ID NO: 14); oriT_Tn5520 (typically of sequence SEQ ID NO: 15); oriT_QKH54 (typically of sequence SEQ ID NO: 16); oriT_R64 (typically of sequence SEQ ID NO: 17); oriT_R751 (typically of sequence SEQ ID NO: 18); oriT_RP4 (typically of sequence SEQ ID NO: 19); oriT_pKL1 (typically of sequence SEQ ID NO: 20); oriT_RK2 (typically of sequence SEQ ID NO: 21); oriT_R1162 (typically of sequence SEQ ID NO: 22); oriT_Tn4555 (typically of sequence SEQ ID NO: 23); oriT_pHT (typically of sequence SEQ ID NO: 24); oriT_Tn4399 (typically of sequence SEQ ID NO: 25); oriT_Tn916 (typically of sequence SEQ ID NO: 26); oriT_pST12 (typically of sequence SEQ ID NO: 27); oriT_pCU1 (typically of sequence SEQ ID NO: 28); oriT_pSU233 (typically of sequence SEQ ID NO: 29);

oriT_F (typically of sequence SEQ ID NO: 30); oriT_pMAB01 (typically of sequence SEQ ID NO: 31); oriT_R388 (typically of sequence SEQ ID NO: 32); oriT_pS7a (typically of sequence SEQ ID NO: 33); oriT_pS7b (typically of sequence SEQ ID NO: 34); oriT_R702 (typically of sequence SEQ ID NO: 35); oriT_pMUR274 (typically of sequence SEQ ID NO: 36); oriT_R100 (typically of sequence SEQ ID NO: 37); oriT_pVCR94deltaX (typically of sequence SEQ ID NO: 38); oriT_R46 (typically of sequence SEQ ID NO: 39); oriT_pGO1 (typically of sequence SEQ ID NO: 40); and oriT_pIP501 (typically of sequence SEQ ID NO: 41).

In one embodiment, the DNA vector comprises the origin of transfer oriT_pMRC01 (typically of sequence SEQ ID NO: 1). In one embodiment, the DNA vector comprises the origin of transfer oriT_RSF1010 (typically of sequence SEQ ID NO: 2). In one embodiment, the DNA vector comprises the origin of transfer oriT_pRS01 (typically of sequence SEQ ID NO: 3). In one embodiment, the DNA vector comprises the origin of transfer oriT_pMV158 (typically of sequence SEQ ID NO: 4). In one embodiment, the DNA vector comprises the origin of transfer oriT_pTF1 (typically of sequence SEQ ID NO: 5). In one embodiment, the DNA vector comprises the origin of transfer oriT_pSC101 (typically of sequence SEQ ID NO: 6). In one embodiment, the DNA vector comprises the origin of transfer oriT_pBTK445 (typically of sequence SEQ ID NO: 7). In one embodiment, the DNA vector comprises the origin of transfer oriT_pBBR1 (typically of sequence SEQ ID NO: 8). In one embodiment, the DNA vector comprises the origin of transfer oriT_R721 (typically of sequence SEQ ID NO: 9). In one embodiment, the DNA vector comprises the origin of transfer oriT_pRmeGR4a (typically of sequence SEQ ID NO: 10). In one embodiment, the DNA vector comprises the origin of transfer oriT_ColE1 (typically of sequence SEQ ID NO: 11). In one embodiment, the DNA vector comprises the origin of transfer oriT_pTiC58 (typically of sequence SEQ ID NO: 12). In one embodiment, the DNA vector comprises the origin of transfer oriT_pMdT1 (typically of sequence SEQ ID NO: 13). In one embodiment, the DNA vector comprises the origin of transfer oriT_R1 (typically of sequence SEQ ID NO: 14). In one embodiment, the DNA vector comprises the origin of transfer oriT_Tn5520 (typically of sequence SEQ ID NO: 15). In one embodiment, the DNA vector comprises the origin of transfer oriT_QKH54 (typically of sequence SEQ ID NO: 16). In one embodiment, the DNA vector comprises the origin of transfer oriT_R64 (typically of sequence SEQ ID NO: 17). In one embodiment, the DNA vector comprises the origin of transfer oriT_R751 (typically of sequence SEQ ID NO: 18). In one embodiment, the DNA vector comprises the origin of transfer oriT_RP4 (typically of sequence SEQ ID NO: 19). In one embodiment, the DNA vector comprises the origin of transfer oriT_pKL1 (typically of sequence SEQ ID NO: 20). In one embodiment, the DNA vector comprises the origin of transfer oriT_RK2 (typically of sequence SEQ ID NO: 21). In one embodiment, the DNA vector comprises the origin of transfer oriT_R1162 (typically of sequence SEQ ID NO: 22). In one embodiment, the DNA vector comprises the origin of transfer oriT_Tn4555 (typically of sequence SEQ ID NO: 23). In one embodiment, the DNA vector comprises the origin of transfer oriT_pHT (typically of sequence SEQ ID NO: 24). In one embodiment, the DNA vector comprises the origin of transfer oriT_Tn4399 (typically of sequence SEQ ID NO: 25). In one embodiment, the DNA vector comprises the origin of transfer oriT_Tn916 (typically of sequence SEQ ID NO: 26). In one embodiment, the DNA vector comprises the origin of transfer oriT_pST12 (typically of sequence SEQ ID NO: 27). In one embodiment, the DNA vector comprises the origin of transfer oriT_pCU1 (typically of sequence SEQ ID NO: 28). In one embodiment, the DNA vector comprises the origin of transfer oriT_pSU233 (typically of sequence SEQ ID NO: 29). In one embodiment, the DNA vector comprises the origin of transfer oriT_F (typically of sequence SEQ ID NO: 30). In one embodiment, the DNA vector comprises the origin of transfer oriT_pMAB01 (typically of sequence SEQ ID NO: 31). In one embodiment, the DNA vector comprises the origin of transfer oriT_R388 (typically of sequence SEQ ID NO: 32). In one embodiment, the DNA vector comprises the origin of transfer oriT_pS7a (typically of sequence SEQ ID NO: 33). In one embodiment, the DNA vector comprises the origin of transfer oriT_pS7b (typically of sequence SEQ ID NO: 34). In one embodiment, the DNA vector comprises the origin of transfer oriT_R702 (typically of sequence SEQ ID NO: 35). In one embodiment, the DNA vector comprises the origin of transfer oriT_pMUR274 (typically of sequence SEQ ID NO: 36). In one embodiment, the DNA vector comprises the origin of transfer oriT_R100 (typically of sequence SEQ ID NO: 37). In one embodiment, the DNA vector comprises the origin of transfer oriT_pVCR94deltaX (typically of sequence SEQ ID NO: 38). In one embodiment, the DNA vector comprises the origin of transfer oriT_R46 (typically of sequence SEQ ID NO: 39). In one embodiment, the DNA vector comprises the origin of transfer oriT_pGO1 (typically of sequence SEQ ID NO: 40). In one embodiment, the DNA vector comprises the origin of transfer oriT_pIP501 (typically of sequence SEQ ID NO: 41).

In one embodiment, the DNA vector comprises an origin of transfer (oriT), the sequence of which is at least 80, 83, 85, 87, 90, 93, 95, 97, 98, 99, or 100% identical to the sequence of any of the above oriT.

In one embodiment, a donor bacterium, such as *E. coli*, carry a conjugative plasmid, a conjugative transposon, or an integrative and conjugative element (ICE) selected from the group consisting of pMRC01, RSF1010, pRS01, pMV158, pTF1, pSC101, pBTK445, pBBR1, R721, pRmeGR4a, ColE1, pTiC58, pMdT1, R1, Tn5520, QKH54, R64, R751, RP4, pKL1, RK2, R1162, Tn4555, pHT, Tn4399, Tn916, pST12, pCU1, pSU233, F, pMAB01, R388, pS7a, pS7b, R702, pMUR274, R100, pVCR94deltaX, R46, pGO1 and pIP501; and is used to efficiently transfer the DNA vector into *C. acnes* recipient cells. In one embodiment the DNA vector contains an origin of transfer and the associated relaxase of the conjugative plasmid, conjugative transposon, and integrative and conjugative element (ICE) selected from the group consisting of pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501.

In a preferred embodiment, the DNA vector comprises an origin of transfer and the relaxase of the following conjugative plasmid, conjugative transposon, and integrative and conjugative element (ICE) selected from the group consisting of pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501.

In a preferred embodiment the DNA vector comprises an origin of transfer selected from the group consisting of: oriT_pMRC01 (SEQ ID NO: 1); oriT_RSF1010 (SEQ ID NO: 2); oriT_pRS01 (SEQ ID NO: 3); oriT_pMV158 (SEQ ID NO: 4); oriT_pTF1 (SEQ ID NO: 5); oriT_pSC101 (SEQ ID NO: 6); oriT_pBTK445 (SEQ ID NO: 7); oriT_pBBR1 (SEQ ID NO: 8); oriT_R721 (SEQ ID NO: 9); oriT_pRmeGR4a (SEQ ID NO: 10); oriT_ColE1 (SEQ ID NO: 11); oriT_pTiC58 (SEQ ID NO: 12); oriT_pMdT1 (SEQ ID NO: 13); oriT_R1 (SEQ ID NO: 14); oriT_Tn5520 (SEQ ID NO: 15); oriT_QKH54 (SEQ ID NO: 16); oriT_R64 (SEQ ID NO: 17); oriT_R751 (SEQ ID NO: 18); oriT_RP4 (SEQ ID NO: 19); oriT_pKL1 (SEQ ID NO: 20); oriT_RK2 (SEQ ID NO: 21); oriT_R1162 (SEQ ID NO: 22); oriT_Tn4555 (SEQ ID NO: 23); oriT_pHT (SEQ ID NO: 24); oriT_Tn4399 (SEQ ID NO: 25); oriT_Tn916 (SEQ ID NO: 26); oriT_pST12 (SEQ ID NO: 27); oriT_pCU1 (SEQ ID NO: 28); oriT_pSU233 (SEQ ID NO: 29); oriT_F (SEQ ID NO: 30); oriT_pMAB01 (SEQ ID NO: 31); oriT_R388 (SEQ ID NO: 32); oriT_pS7a (SEQ ID NO: 33); oriT_pS7b (SEQ ID NO: 34); oriT_R702 (SEQ ID NO: 35); oriT_pMUR274 (SEQ ID NO: 36); oriT_R100 (SEQ ID NO: 37); oriT_pVCR94deltaX (SEQ ID NO: 38); oriT_R46 (SEQ ID NO: 39); oriT_pGO1 (SEQ ID NO: 40) and oriT_pIP501 (SEQ ID NO: 41).

In one embodiment, the DNA vector comprises an origin of transfer (oriT) that is at least 80, 83, 85, 87, 90, 93, 95, 97, 98, 99, or 100% identical to any of these ICE.

In one embodiment, the invention encompasses a DNA vector comprising an origin of replication allowing replication in *C. acnes*, an oriT allowing conjugation into *C. acnes*, a selection marker allowing for selection in the transconjugant *C. acnes*, and a selection marker allowing for selection in the donor bacteria. In another embodiment, the invention encompasses a DNA vector comprising an origin of replication allowing replication in *C. acnes* and an oriT allowing conjugation into *C. acnes* as defined above.

In one embodiment, the origin of replication allowing replication in *C. acnes* is selected from the group consisting of: R6K (typically of sequence SEQ ID NO: 42); RK2 (typically of sequence SEQ ID NO: 43); pBBR1 (typically of sequence SEQ ID NO: 44); pRO1600 (typically of sequence SEQ ID NO: 45); RSF1010 (typically of sequence SEQ ID NO: 46); pAMβ1 (typically of sequence SEQ ID NO: 47); pLME106 (typically of sequence SEQ ID NO: 48); pTZC1 (typically of sequence SEQ ID NO: 49); pBC1 (typically of sequence SEQ ID NO: 50); pEP2 (typically of sequence SEQ ID NO: 51); pWVO1 (typically of sequence SEQ ID NO: 52); pAP1 (typically of sequence SEQ ID NO: 53); pWKS1 (typically of sequence SEQ ID NO: 54); pLME108 (typically of sequence SEQ ID NO: 55); pLS1 (typically of sequence SEQ ID NO: 56); pUB6060 (typically of sequence SEQ ID NO: 57); p545 (typically of sequence SEQ ID NO: 58); pJD4 (typically of sequence SEQ ID NO: 59); pIJ101 (typically of sequence SEQ ID NO: 60); pSN22 (typically of sequence SEQ ID NO: 61); pGP01 (typically of sequence SEQ ID NO: 62); pIP501 (typically of sequence SEQ ID NO: 63); pCU1 (typically of sequence SEQ ID NO: 64); and pBAV1K-T5 (typically of sequence SEQ ID NO: 65). In one embodiment, the origin of replication allowing replication in *C. acnes* is R6K (typically of sequence SEQ ID NO: 42). In one embodiment, the origin of replication allowing replication in *C. acnes* is RK2 (typically of sequence SEQ ID NO: 43). In one embodiment, the origin of replication allowing replication in *C. acnes* is pBBR1 (typically of sequence SEQ ID NO: 44). In one embodiment, the origin of replication allowing replication in *C. acnes* is pRO1600 (typically of sequence SEQ ID NO: 45). In one embodiment, the origin of replication allowing replication in *C. acnes* is RSF1010 (typically of sequence SEQ ID NO: 46). In one embodiment, the origin of replication allowing replication in *C. acnes* is pAMβ1 (typically of sequence SEQ ID NO: 47). In one embodiment, the origin of replication allowing replication in *C. acnes* is pLME106 (typically of sequence SEQ ID NO: 48). In one embodiment, the origin of replication allowing replication in *C. acnes* is pTZC1 (typically of sequence SEQ ID NO: 49). In one embodiment, the origin of replication allowing replication in *C. acnes* is pBC1 (typically of sequence SEQ ID NO: 50). In one embodiment, the origin of replication allowing replication in *C. acnes* is pEP2 (typically of sequence SEQ ID NO: 51). In one embodiment, the origin of replication allowing replication in *C. acnes* is pWVO1 (typically of sequence SEQ ID NO: 52). In one embodiment, the origin of replication allowing replication in *C. acnes* is pAP1 (typically of sequence SEQ ID NO: 53). In one embodiment, the origin of replication allowing replication in *C. acnes* is pWKS1 (typically of sequence SEQ ID NO: 54). In one embodiment, the origin of replication allowing replication in *C. acnes* is pLME108 (typically of sequence SEQ ID NO: 55). In one embodiment, the origin of replication allowing replication in *C. acnes* is pLS1 (typically of sequence SEQ ID NO: 56). In one embodiment, the origin of replication allowing replication in *C. acnes* is pUB6060 (typically of sequence SEQ ID NO: 57). In one embodiment, the origin of replication allowing replication in *C. acnes* is p545 (typically of sequence SEQ ID NO: 58). In one embodiment, the origin of replication allowing replication in *C. acnes* is pJD4 (typically of sequence SEQ ID NO: 59). In one embodiment, the origin of replication allowing replication in *C. acnes* is pIJ101 (typically of sequence SEQ ID NO: 60). In one embodiment, the origin of replication allowing replication in *C. acnes* is pSN22 (typically of sequence SEQ ID NO: 61). In one embodiment, the origin of replication allowing replication in *C. acnes* is pGP01 (typically of sequence SEQ ID NO: 62). In one embodiment, the origin of replication allowing replication in *C. acnes* is pIP501 (typically of sequence SEQ ID NO: 63). In one embodiment, the origin of replication allowing replication in *C. acnes* is pCU1 (typically of sequence SEQ ID NO: 64). In one embodiment, the origin of replication allowing replication in *C. acnes* is pBAV1K-T5 (typically of sequence SEQ ID NO: 65).

In one embodiment, the DNA vector comprises an origin of replication allowing replication in *C. acnes*. In one embodiment, the DNA vector comprises an origin of replication selected from the group consisting of: R6K (SEQ ID NO: 42); RK2 (SEQ ID NO: 43); pBBR1 (SEQ ID NO: 44); pRO1600 (SEQ ID NO: 45); RSF1010 (SEQ ID NO: 46); pAMβ1 (SEQ ID NO: 47); pLME106 (SEQ ID NO: 48); pTZC1 (SEQ ID NO: 49); pBC1 (SEQ ID NO: 50); pEP2 (SEQ ID NO: 51); pWVO1 (SEQ ID NO: 52); pAP1 (SEQ ID NO: 53); pWKS1 (SEQ ID NO: 54); pLME108 (SEQ ID NO: 55); pLS1 (SEQ ID NO: 56); pUB6060 (SEQ ID NO: 57); p545 (SEQ ID NO: 58); pJD4 (SEQ ID NO: 59); pIJ101 (SEQ ID NO: 60); pSN22 (SEQ ID NO: 61); pGP01 (SEQ ID NO: 62); pIP501 (SEQ ID NO: 63); pCU1 (SEQ ID NO: 64); and pBAV1K-T5 (SEQ ID NO: 65).

Preferably, the origin of replication is of a sequence at least 80, 83, 85, 87, 90, 93, 95, 97, 98, 99, or 100% identical to the sequence of any of the above origins of replication.

In various embodiments, the selection marker is selected from ermE, catA, hygB, ermX, tetW, erm(50) and other high GC antibiotic resistance genes. In one embodiment, the selection marker is not ermE. In one embodiment, the selection marker is catA. In one embodiment, the selection marker is hygB.

In one embodiment, the DNA vector further comprises a CRISPR-Cas system. Typically, the CRISPR-Cas system comprises a CRISPR array. Typically, the CRISPR-Cas system comprises a RNA guide (crRNA or sgRNA).

In one embodiment, the CRISPR-Cas system targets a *C. acnes* chromosome locus.

Preferably, the targeted locus is not present in the *C. acnes* producer cell. Preferably, the CRISPR array from the CRISPR-Cas system is expressing one or several crRNA targeting the chromosome locus.

In one embodiment, the CRISPR-Cas system targets several *C. acnes* chromosome loci. Preferably, the targeted loci are not present in the *C. acnes* producer cell. Preferably, the CRISPR array from the CRISPR-Cas system is expressing one or several crRNA targeting the chromosome loci.

In one embodiment, the CRISPR-Cas system targets a *C. acnes* plasmid locus.

Preferably, the targeted locus is not present in the *C. acnes* producer cell. Preferably, the CRISPR array from the CRISPR-Cas system is expressing one or several crRNA targeting the plasmid locus.

In one embodiment, the CRISPR-Cas system targets several *C. acnes* plasmid loci. Preferably, the targeted loci are not present in the *C. acnes* producer cell. Preferably, the CRISPR array from the CRISPR-Cas system is expressing one or several crRNA targeting the plasmid loci.

In one embodiment, the CRISPR-Cas system is not expressed in *C. acnes* producer cell. Preferably the CRISPR-Cas system is repressed in *C. acnes* producer cell.

In one embodiment, the CRISPR-Cas system targets a proinflammatory sequence related to a host disease.

In one embodiment, the CRISPR-Cas system targets a proinflammatory sequence related to acne vulgaris.

In one embodiment, the DNA vector comprises a template for homologous recombination and the CRISPR-Cas system is targeting the DNA vector itself.

In one embodiment, the DNA vector comprises a template for homologous recombination in *C. acnes* phages.

In one embodiment, the DNA vector comprises a template for homologous recombination in *C. acnes* chromosome.

In one embodiment, the DNA vector comprises a template for homologous recombination in *C. acnes* endogenous plasmids.

In one embodiment, the DNA vector comprises a template for homologous recombination and a CRISPR-Cas system targeting the DNA vector itself outside of the template region.

In one embodiment, the DNA vector comprises a template for homologous recombination and a CRISPR-Cas system targeting the DNA vector itself outside of the template region wherein the RNA guide (crRNA or sgRNA) from the CRISPR-Cas system is not perfectly matching the DNA target.

In one embodiment, the DNA vector comprises an integrase gene expression cassette and a site specific recombination site allowing for the integration of the DNA vector inside the chromosome.

In one embodiment, the DNA vector comprises a base editor gene expression cassette and one or multiple crRNAs or sgRNAs.

In one embodiment, the base editor is used to inactivate the expression of a gene by editing one or several nucleotides involved in transcription or translation of said gene. More specifically the base editor is targeting one or several nucleotides of a promoter, a RBS or a start codon.

In one embodiment, the base editor is used to introduce a premature stop codon.

In one embodiment, the base editor is used to introduce one or several rare codons.

In another embodiment, the base editor is used to modulate the expression of genes by editing one or several nucleotides involved in transcription or translation of said genes. More specifically the base editor is targeting one or several nucleotides of a promoter, a RBS or a start codon, leading to an increase or decrease in gene expression.

In another embodiment, the base editor is used to revert a mutation that leads to the inactivation, decrease or increase in activity of a gene or pathway.

In another embodiment, the base editor is used to revert a mutation that leads to an increase of pathogenicity.

In one embodiment, the base editor is used to modify the regulation of a gene by editing one or several nucleotides involved in its regulation such as nucleotides of operator sequence, transcription factor binding site, riboswitch, RNAse recognition site, protease cleavage site, methylation site or post translational modification site (phosphorylation, glycosylation, acetylation, pupylation . . . ).

In one embodiment, the DNA vector comprises a prime editor gene expression cassette and one or multiple pegRNAs.

In one embodiment, the prime editor is used to introduce one or several premature stop codon.

In one embodiment, the prime editor is used to introduce one or several rare codons.

In one embodiment, the prime editor is used to introduce or delete a nucleotide inducing a frameshift in the reading frame.

In another embodiment, the prime editor is used to modulate the expression of genes by replacing, deleting or inserting one or several nucleotides involved in transcription or translation of said genes. More specifically the prime editor is replacing, deleting or inserting one or several nucleotides in a promoter, a RBS or a start codon, leading to an increase or decrease in gene expression.

In another embodiment, the prime editor is used to revert a mutation that leads to the inactivation or decrease in activity of a gene or pathway.

In another embodiment, the prime editor is used to revert a mutation that leads to an increase of pathogenicity.

In one embodiment, the vector is a plasmid which comprises an *E. coli* replicon and an *E. coli* resistance marker allowing extraction of the plasmid from *C. acnes* and transformation and replication in *E. coli*.

In one embodiment, the vector is a plasmid which comprises an *E. coli* replicon and an *E. coli* resistance marker allowing extraction of the plasmid from *E. coli* and transformation and replication in *C. acnes*.

In one embodiment, the vector comprises 2 origins or replication, one allowing replication in *C. acnes* or *C. acnes* producer cell only, the second origin of replication allowing replication in another bacteria.

In one embodiment, the vector comprising the template DNA for homologous recombination allows expression of genes increasing recombination rate.

In one embodiment, the template for homologous recombination contains homology arms upstream and downstream of recombination points. These homology arms can be at least 50, 100, 500 or at least 1000 bp in size.

In one embodiment, the gene of interest comprised by the DNA vector can be a transgene that is exogenous to the *C. acnes*. Transgenes include but are not limited to:

- a DNA encoding a fluorescent protein (e.g., UnaG) that leads to fluorescent *C. acnes* cells once a specific substrate is added;
- a DNA encoding an enzymatic reporter (e.g., LacZ) that leads to the production of a chromogenic compound by *C. acnes* colonies;
- a DNA encoding a human protein (e.g., an interleukin);
- a DNA encoding an antigen (e.g. a tumor antigen, a viral antigen, a bacterial antigen, a fungal antigen, a self-antigen, an allergen or a graft-specific antigen);
- a CRISPR-Cas system;
- a prime-editing system; or
- a base-editor system.

In a particular embodiment, the gene of interest encoded by the DNA vector is a DNA encoding an antigen, more particularly a DNA encoding an antigen selected from the group consisting of tumor antigens, viral antigens, bacterial antigens, fungal antigens, self-antigens, allergens and graft-specific antigens, as defined below.

*C. acnes* Strains Comprising DNA Vectors, Engineered *C. acnes* Strains

The invention encompasses *C. acnes* comprising any of the DNA vectors of the invention. The invention further encompasses *C. acnes* produced by any of the methods of the invention. Thus, the invention encompasses *C. acnes* that have been modified following transduction of any of the DNA vectors of the invention by a phage-derived particle, whether retaining the DNA vector or subsequently having that DNA vector removed (i.e., cured) from *C. acnes.*

Thus, the invention encompasses *C. acnes* produced by a method comprising: producing a phage-derived particle from a *C. acnes* producer cell containing a DNA vector of the invention; contacting these phage-derived particles with *C. acnes* receiver cells, leading to transduction of the DNA vector into the *C. acnes* receiver cell and modification of the *C. acnes* receiver cell with a gene of interest carried by the vector (e.g., a CRISPR-Cas system) and/or an exogenous gene inserted into the *C. acnes* chromosome; selecting for the modification; and curing *C. acnes* of the vector.

The invention encompasses an engineered *C. acnes* that has been modified by a CRISPR-Cas system transduced by a phage-derived particle carrying a vector of the invention.

The invention encompasses an engineered *C. acnes* that has been modified by transduction of DNA vector and subsequent insertion of an exogenous gene into the *C. acnes* chromosome.

The invention encompasses an engineered *C. acnes* that has been modified by transduction of DNA vector and subsequent deletion or mutation of an endogenous gene into the *C. acnes* chromosome or *C. acnes* endogenous plasmid.

The invention encompasses *C. acnes* produced by transduction of a DNA vector of the invention.

The invention encompasses an engineered *C. acnes* that has been modified by delivery of a plasmid, in particular by conjugation. In a particular embodiment, said plasmid comprises a CRISPR-Cas system. In another particular embodiment, said plasmid comprises an exogenous gene. In another particular embodiment, said plasmid enables the insertion of an exogenous gene into the *C. acnes* chromosome. In another particular embodiment, said plasmid enables the deletion or mutation of an endogenous gene into the *C. acnes* chromosome or *C. acnes* endogenous plasmid. In a particular embodiment, said plasmid comprises an origin of replication allowing replication in *C. acnes*, as defined above and/or an origin of transfer as defined above.

*Cutibacterium acnes*, previously named *Propionibacterium acnes*, has been historically classified in three major phylotypes based on recA and tly sequencing: IA, IB, II and III. These phylotypes have been further subdivided using different multi-locus sequence typing (MLST) schemes into IA1, IA2, IB, II and III. More recently, Fitz-Gibbon et al (Fitz-Gibbon, S. et al. (2013) J Invest Dermatol 133, 2152-2160) have introduced a new classification based on sequence diversity of 16S rRNA gene (ribotyping) as well as a refined classification of phylotypes: IA-1, IA-2, IB-1, IB-2, IB-3, IC, II, Ill. The present disclosure refers to this classification but concordance between this classification and others is well-known from the skilled person and can be obtained from the following review (Dréno, B. et al. (2018). Journal of the European Academy of Dermatology and Venereology 32, 5-14). In a particular embodiment, *C. acnes* may thus be from a phylotype selected from the group consisting of phylotypes IA-1, IA-2, IB-1, IB-2, IB-3, IC, II and III.

By comparing whole genome sequences of strains isolated from acne and healthy volunteers, Fitz-Gibbon and colleagues could identify acne-associated strains (IA-2 and IB-1) and healthy-associated strains (II) in accordance with previous studies. More interestingly, they found specific loci (locus1, locus 2 and locus 3) present in acne associated strains and absent of neutral and healthy strains. Similar loci were found in a subsequent metagenomic analysis confirming the association between the presence of these loci and acne vulgaris (Barnard, E. et al. (2016) *Scientific Reports* 6, srep39491).

The ability of specific strain phylotypes to induce immune response has been recently investigated (Yu et al. (2016) Journal of Investigative Dermatology 136:2221-2228). Yu et al. demonstrated that the different *C. acnes* phylotypes induced different cytokine profiles when incubated with peripheral blood mononuclear cells (PBMC). More particularly, they showed that acne-associated phylotypes IA-2 p+ (i.e. with a large plasmid associated with acne), IB-1, and IC induced high levels of inflammatory IFN-γ and IL-17 but low levels of IL-10, suggesting that these specific phylotypes could induce both Th1 and Th17 responses. They also showed that phylotypes IB-3, II and III induced lower levels of IL-17 (and of IFN-γ for phylotype III) but higher levels of IL-10, suggesting induction of Treg responses. They further showed that phylotypes IA-1, IA-2 p− (i.e. without the large plasmid associated with acne) and IB-2 induced lower levels of IFN-γ and IL-10 and higher levels of IL-17, suggesting induction of mainly Th17 responses.

Therefore, depending on the particular immune response that is desired when using the engineered *C. acnes* of the invention for a particular indication, the use of a given *C. acnes* phylotype or strain may be advantageous. Accordingly, in a particular embodiment, *C. acnes* is from a phylotype selected from the group consisting of phylotypes IA-2 p+, IB-1 and IC. In another embodiment, *C. acnes* is from a phylotype selected from the group consisting of phylotypes IA-1, IA-2 p- and IB-2. In still another embodiment, *C. acnes* is from a phylotype selected from the group consisting of phylotypes IB-3, II and III.

Furthermore, a previous study showed that it was possible, in *S. epidermidis*, to induce different T cell responses with different strains within the same species by engineering said strains (Chen et al. (2019) "Decoding commensal-host communication through genetic engineering of *Staphylococcus epidermidis*" bioRxiv doi. org/10.1101/664656).

Therefore, in a particular embodiment, the *C. acnes* is a strain inducing, or engineered to induce, a given T cell response. In a particular embodiment, more particularly when the *C. acnes* cell is intended to be used in the prevention and/or treatment of cancer, said *C. acnes* is a strain inducing, or engineered to induce, increased levels of IFN-γ and/or IL-17a. In a particular embodiment, more particularly when the *C. acnes* cell is intended to be used in the prevention and/or treatment of an infection, said *C. acnes* is a strain inducing, or engineered to induce, increased levels of IFN-γ and/or IL-17. In a particular embodiment, more particularly when the *C. acnes* cell is intended to be used in the prevention and/or treatment of an autoimmune disease, said *C. acnes* is a strain inducing, or engineered to induce, increased levels of IL-10. In a particular embodiment, more particularly when the *C. acnes* cell is intended to be used in the prevention and/or treatment of an allergy, such as asthma, said *C. acnes* is a strain inducing, or engineered to induce, increased levels of IFN-g and/or IL-10. In a particular embodiment, more particularly when the *C. acnes* cell is intended to be used in the prevention and/or treatment of a graft rejection, said *C. acnes* is a strain inducing, or engineered to induce, increased levels of IL-10.

*C. acnes* comprising a recombinant self-replicative DNA vector of the invention (or comprising a plasmid, in particular a conjugative plasmid as defined above) can be generated for the expression of molecules of interest and modulation of *C. acnes*-host interaction. The molecule of interest can be carried on a self-replicative DNA vector in the *C. acnes* (or on a plasmid, in particular a conjugative plasmid) or can be inserted into the chromosome of the *C. acnes* through the action of the self-replicative DNA vector (or of the plasmid, in particular the conjugative plasmid, as defined above).

In one embodiment, the DNA vector is used for *C. acnes* chromosome engineering.

In one embodiment, the DNA vector is used for *C. acnes* plasmid engineering.

In one embodiment, the DNA vector is used for *C. acnes* phage engineering.

In one embodiment, the DNA vector (or the plasmid, in particular the conjugative plasmid, as defined above) is used for the expression of molecules of interest and modulation of *C. acnes*-host interaction. In one embodiment, the DNA vector (or the plasmid, in particular the conjugative plasmid, as defined above) is used for the expression of transgenes in *C. acnes*. A transgene can be cloned into the recombinant autonomously-replicating DNA vector (or in the plasmid, in particular the conjugative plasmid) under the control of a given promoter (constitutive or inducible) and followed by a given terminator. The transfer of this vector into *C. acnes* allows the expression of the transgene. The transgene can be, for example, a CRISPR-Cas system or can encode a human protein, such as an interleukin. In one embodiment the DNA vector (or the plasmid, in particular the conjugative plasmid) encodes several transgenes under the control of a single promoter or under the control of different promoters. The promoters can be endogenous or exogenous, inducible or constitutive.

In one embodiment, the DNA vector (or the plasmid, in particular the conjugative plasmid) is used for the modification of *C. acnes* genome. In one embodiment, the transfer of the vector (or of the plasmid, in particular the conjugative plasmid) into *C. acnes* allows the expression of a CRISPR/Cas system that cleaves the *C. acnes* genome (plasmid or chromosome) at a specific site, leading to modification of the *C. acnes* genome. In one embodiment, the vector (or the plasmid, in particular the conjugative plasmid) further comprises a gene of interest and homology with the site of cleavage to facilitate integration of the gene of interest into the *C. acnes* genome.

Delivery of DNA Vectors into *C. acnes* Strains

In one embodiment, delivery of any DNA vector of the invention into *C. acnes* producer cell is performed by contacting *C. acnes* with any DNA vector of the invention.

In one embodiment, delivery of any DNA vector of the invention into *C. acnes* producer cell is performed by transfection (e.g., electroporation) into *C. acnes* cells, where it stably replicates. In one embodiment the DNA vector transfected is purified from dam(−) *E. coli* cells such as ET12567 and electroporated into *C. acnes* cells made competent at 24° C.

In one embodiment, delivery of any DNA vector of the invention into *C. acnes* producer cell is performed by transfection (e.g., electroporation) into *C. acnes* protoplasts. In one embodiment *C. acnes* protoplasts are generated using Mutanolysin treatment or Lysozyme treatment, Mutanolysin and Lysozyme treatment, or Mutanolysin and Lysozyme and bead-beating treatment followed by resuspension into hypotonique media.

In one embodiment, delivery of any DNA vector of the invention into a *C. acnes* producer cell is performed by mixing *C. acnes* protoplasts with the DNA vector. In one embodiment glass beads are added with the DNA vector and bead beating is performed to introduce the DNA into *C. acnes* protoplasts.

In one embodiment, delivery of DNA vectors of the invention into *C. acnes* is by transduction. In one embodiment, the DNA vector comprises one packaging signal of a *C. acnes* phage selected from the group consisting of the phages PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74) and PAC263 (typically of sequence SEQ ID NO: 75); and is packaged into proteins expressed from the genome of a *C. acnes* phage selected from the group consisting of the phages PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74) and PAC263 (typically of sequence SEQ ID NO: 75), allowing transduction of the DNA vector into *C. acnes*.

In one embodiment, delivery of any DNA vector of the invention into a *C. acnes* producer cell is by conjugation. In one embodiment, the DNA vector comprises an origin of transfer. In one embodiment, a donor bacterium, such as *E. coli*, is used to efficiently transfer the DNA vector into *C. acnes* recipient cells, where it stably replicates. In one embodiment, the DNA vector comprises an origin of transfer selected from the group consisting of: oriT_pMRC01 (typically of sequence SEQ ID NO: 1); oriT_RSF1010 (typically of sequence SEQ ID NO: 2); oriT_pRS01 (typically of sequence SEQ ID NO: 3); oriT_pMV158 (typically of sequence SEQ ID NO: 4); oriT_pTF1 (typically of sequence SEQ ID NO: 5); oriT_pSC101 (typically of sequence SEQ ID NO: 6); oriT_pBTK445 (typically of sequence SEQ ID NO: 7); oriT_pBBR1 (typically of sequence SEQ ID NO: 8); oriT_R721 (typically of sequence SEQ ID NO: 9); oriT_pRmeGR4a (typically of sequence SEQ ID NO: 10); oriT_ColE1 (typically of sequence SEQ ID NO: 11); oriT_p-

TiC58 (typically of sequence SEQ ID NO: 12); oriT_pMdT1 (typically of sequence SEQ ID NO: 13); oriT_R1 (typically of sequence SEQ ID NO: 14); oriT_Tn5520 (typically of sequence SEQ ID NO: 15); oriT_QKH54 (typically of sequence SEQ ID NO: 16); oriT_R64 (typically of sequence SEQ ID NO: 17); oriT_R751 (typically of sequence SEQ ID NO: 18); oriT_RP4 (typically of sequence SEQ ID NO: 19); oriT_pKL1 (typically of sequence SEQ ID NO: 20); oriT_RK2 (typically of sequence SEQ ID NO: 21); oriT_R1162 (typically of sequence SEQ ID NO: 22); oriT_Tn4555 (typically of sequence SEQ ID NO: 23); oriT_pHT (typically of sequence SEQ ID NO: 24); oriT_Tn4399 (typically of sequence SEQ ID NO: 25); oriT_Tn916 (typically of sequence SEQ ID NO: 26); oriT_pST12 (typically of sequence SEQ ID NO: 27); oriT_pCU1 (typically of sequence SEQ ID NO: 28); oriT_pSU233 (typically of sequence SEQ ID NO: 29); oriT_F (typically of sequence SEQ ID NO: 30); oriT_pMAB01 (typically of sequence SEQ ID NO: 31); oriT_R388 (typically of sequence SEQ ID NO: 32); oriT_pS7a (typically of sequence SEQ ID NO: 33); oriT_pS7b (typically of sequence SEQ ID NO: 34); oriT_R702 (typically of sequence SEQ ID NO: 35); oriT_pMUR274 (typically of sequence SEQ ID NO: 36); oriT_R100 (typically of sequence SEQ ID NO: 37); oriT_pVCR94deltaX (typically of sequence SEQ ID NO: 38); oriT_R46 (typically of sequence SEQ ID NO: 39); oriT_pGO1 (typically of sequence SEQ ID NO: 40) and oriT_pIP501 (typically of sequence SEQ ID NO: 41). In one embodiment, a donor bacterium, such as *E. coli*, carries a conjugative plasmid, a conjugative transposon or an integrative and conjugative element (ICE) selected from the group consisting of: pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501, and is used to efficiently transfer the DNA vector into *C. acnes* recipient cells. In one embodiment the DNA vector contains an origin of transfer and the associated relaxase of a conjugative plasmid, conjugative transposon or integrative and conjugative element (ICE) selected from the group consisting of: pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501.

In a preferred embodiment the DNA vector comprises the origin of transfer oriT_pMRC01 (typically of sequence SEQ ID NO: 1). In a preferred embodiment, the DNA vector comprises the origin of transfer oriT_RSF1010 (typically of sequence SEQ ID NO: 2). In a preferred embodiment, the DNA vector comprises the origin of transfer oriT_pRS01 (typically of sequence SEQ ID NO: 3). In a preferred embodiment, the DNA vector comprises the origin of transfer oriT_pMV158 (typically of sequence SEQ ID NO: 4). In a preferred embodiment, the DNA vector comprises the origin of transfer oriT_pTF1 (typically of sequence SEQ ID NO: 5). In a preferred embodiment, the DNA vector comprises the origin of transfer oriT_pSC101 (typically of sequence SEQ ID NO: 6). In a preferred embodiment, the DNA vector comprises the origin of transfer oriT_pBTK445 (typically of sequence SEQ ID NO: 7). In a preferred embodiment, the DNA vector comprises the origin of transfer oriT_pBBR1 (typically of sequence SEQ ID NO: 8). In a preferred embodiment, the DNA vector comprises the origin of transfer oriT_R721 (typically of sequence SEQ ID NO: 9). In a preferred embodiment, the DNA vector comprises the origin of transfer oriT_pRmeGR4a (typically of sequence SEQ ID NO: 10). In a preferred embodiment, the DNA vector comprises the origin of transfer oriT_ColE1 (typically of sequence SEQ ID NO: 11). In a preferred embodiment, the DNA vector comprises the origin of transfer oriT_pTiC58 (typically of sequence SEQ ID NO: 12). In a preferred embodiment, the DNA vector comprises the origin of transfer oriT_pMdT1 (typically of sequence SEQ ID NO: 13). In a preferred embodiment, the DNA vector comprises the origin of transfer oriT_R1 (typically of sequence SEQ ID NO: 14). In a preferred embodiment, the DNA vector comprises the origin of transfer oriT_Tn5520 (typically of sequence SEQ ID NO: 15). In a preferred embodiment, the DNA vector comprises the origin of transfer oriT_QKH54 (typically of sequence SEQ ID NO: 16). In a preferred embodiment, the DNA vector comprises the origin of transfer oriT_R64 (typically of sequence SEQ ID NO: 17). In a preferred embodiment, the DNA vector comprises the origin of transfer oriT_R751 (typically of sequence SEQ ID NO: 18). In a preferred embodiment, the DNA vector comprises the origin of transfer oriT_RP4 (typically of sequence SEQ ID NO: 19). In a preferred embodiment, the DNA vector comprises the origin of transfer oriT_pKL1 (typically of sequence SEQ ID NO: 20). In a preferred embodiment, the DNA vector comprises the origin of transfer oriT_RK2 (typically of sequence SEQ ID NO: 21). In a preferred embodiment, the DNA vector comprises the origin of transfer oriT_R1162 (typically of sequence SEQ ID NO: 22). In a preferred embodiment, the DNA vector comprises the origin of transfer oriT_Tn4555 (typically of sequence SEQ ID NO: 23). In a preferred embodiment, the DNA vector comprises the origin of transfer oriT_pHT (typically of sequence SEQ ID NO: 24). In a preferred embodiment, the DNA vector comprises the origin of transfer oriT_Tn4399 (typically of sequence SEQ ID NO: 25). In a preferred embodiment, the DNA vector comprises the origin of transfer oriT_Tn916 (typically of sequence SEQ ID NO: 26). In a preferred embodiment, the DNA vector comprises the origin of transfer oriT_pST12 (typically of sequence SEQ ID NO: 27). In a preferred embodiment, the DNA vector comprises the origin of transfer oriT_pCU1 (typically of sequence SEQ ID NO: 28). In a preferred embodiment, the DNA vector comprises the origin of transfer oriT_pSU233 (typically of sequence SEQ ID NO: 29). In a preferred embodiment, the DNA vector comprises the origin of transfer oriT_F (typically of sequence SEQ ID NO: 30). In a preferred embodiment, the DNA vector comprises the origin of transfer oriT_pMAB01 (typically of sequence SEQ ID NO: 31). In a preferred embodiment, the DNA vector comprises the origin of transfer oriT_R388 (typically of sequence SEQ ID NO: 32). In a preferred embodiment, the DNA vector comprises the origin of transfer oriT_pS7a (typically of sequence SEQ ID NO: 33). In a preferred embodiment, the DNA vector comprises the origin of transfer oriT_pS7b (typically of sequence SEQ ID NO: 34). In a preferred embodiment, the DNA vector comprises the origin of transfer oriT_R702 (typically of sequence SEQ ID NO: 35). In a preferred embodiment, the DNA vector comprises the origin of transfer oriT_pMUR274 (typically of sequence SEQ ID NO: 36). In a preferred embodiment, the DNA vector comprises the origin of transfer oriT_R100 (typically of sequence SEQ ID NO: 37). In a preferred embodiment, the DNA vector comprises the origin of transfer oriT_pVCR94deltaX (typically of sequence SEQ ID NO:

38). In a preferred embodiment, the DNA vector comprises the origin of transfer oriT_R46 (typically of sequence SEQ ID NO: 39). In a preferred embodiment, the DNA vector comprises the origin of transfer oriT_pGO1 (typically of sequence SEQ ID NO: 40). In a preferred embodiment, the DNA vector comprises the origin of transfer oriT_pIP501 (typically of sequence SEQ ID NO: 41).

In one embodiment, a donor bacterium is selected from selected from the group consisting of: *Escherichia coli, Pseudomonas aeruginosa, Lactococcus lactis, Lactobacillus casei, Lactobacillus fermentum, Lactobacillus rhamnosus, Propionibacterium freudenreichii, Lactobacillus brevis, Staphylococcus epidermidis, Staphylococcus aureus, Cutibacterium granulosum, Cutibacterium humerusii, Enterococcus faecalis* and *Bacillus subtilis*, carrying a conjugative plasmid, a conjugative transposon or an integrative and conjugative element (ICE).

In one embodiment the conjugation is performed growing at high density the donor bacteria, such as *E. coli*, harboring the mobilizable DNA vector and the conjugative machinery (ICE, plasmid, conjugative transposon). Donor cells are pelleted by centrifugation, and washed to remove antibiotics added during growth to maintain mobilizable and conjugative DNA vectors. Donor cells are then mixed in presence of *C. acnes* cells. The mixture donor cells—*C. acnes* is spotted onto Brucella agar plates and allowed to mate at 37° C. under anaerobic conditions. After mating, cells are harvested from the mating plate, re-suspended in BHI broth and plated onto Brucella agar plates that are supplemented with:

- a compound killing donor cells but not *C. acnes*, or
- an antibiotic selecting the mobilizable DNA vector.

After several days of incubation, *C. acnes* colonies are streaked on Brucella agar plates supplemented with the appropriate selection and the presence of the conjugated plasmid is confirmed via specific PCRs. The identity of *C. acnes* as well as the absence of donor cells is also confirmed by PCR analyses.

In one embodiment the conjugation is performed according to the following protocol: 2 mL of overnight cultures of *E. coli* donor cells harboring a mobilizable DNA vector and a conjugative machinery (ICE, plasmid, conjugative transposon) is grown in LB broth and pelleted at 6,000×g for 1 min. Supernatants are discarded and pellets are washed with 500 μL of pre-sterilized LB medium, centrifuged again using the same conditions. Pellet is then re-suspended in 200 μL of exponentially growing (OD600=0.5) *C. acnes* receptor BHI culture concentrated 10×. The mixture *E. coli-C. acnes* is spotted (50 μL/spot) onto Brucella agar plates and allowed to mate at 37° C. under anaerobic conditions for 24 hours. After that time, cells are harvested from the mating plate, re-suspended in 300 μL of BHI broth and plated onto Brucella agar plates that had been supplemented with 50 μg/mL polymyxin B and 5 μg/mL erythromycin or 3.5 μg/mL chloramphenicol depending on the selection marker present in the mobilizable DNA vector. After 7 days, *C. acnes* cells that grow in the presence of selection are streaked on Brucella agar plates supplemented with the appropriate selection and the presence of the conjugated plasmid confirmed via specific PCRs. The identity of *C. acnes* as well as the absence of *E. coli* donor strain are also confirmed by PCR analyses.

Methods to Modify Endogenous *C. acnes* Plasmids

Naturally occurring *C. acnes* plasmids have been described[21,22] and some of them are able to be transferred from one *C. acnes* to another by conjugation[20]. Being able to modify such plasmids is of interest to study their effect notably their pro-inflammatory role in acne vulgaris or to use them for further genetic manipulation of *C. acnes*. The inventors have developed methods to modify *C. acnes* plasmids.

In one embodiment, the method comprises, in a first step, introducing into *C. acnes* a replicative vector comprising:

- a selection marker for *C. acnes* as defined above,
- an origin of replication for *C. acnes* as defined above,
- a phage packaging signal as defined above, and
- a template for homologous recombination with the *C. acnes* endogenous plasmid.

In one embodiment, the method comprises, in a first step, introducing into *C. acnes* a replicative vector comprising:

- a selection marker for *C. acnes* as defined above,
- an origin of replication for *C. acnes* as defined above,
- a phage packaging signal as defined above,
- a CRISPR-Cas system, and
- a template for homologous recombination in the *C. acnes* endogenous plasmid.

Introduction can be achieved with electroporation, electroporation of protoplast, conjugation, chemical transformation, or transduction. *C. acnes* recombinants are then preferably grown in presence of an antibiotic.

Recombinants are then typically infected with *C. acnes* phage to produce phage-derived particles carrying the DNA vectors.

Phage-derived particles are then typically mixed with *C. acnes* receiver cells containing an endogenous plasmid such as pIMPLE-HL096PA1. *C. acnes* transductants are then typically selected on the appropriate antibiotic.

In a second step, *C. acnes* transductants are grown in the presence of an antibiotic A to a high density to increase chances of a homologous recombination event occurring. Homologous recombination typically leads to introduction of a selection marker, giving resistance to an antibiotic B. In the dense culture, *C. acnes* strains carrying wild-type endogenous plasmid and recombinant endogenous plasmid carrying a resistance marker are typically present. The high-density culture is then preferably washed and typically put in the presence of a receiver *C. acnes* strain that is resistant to a third antibiotic C. Selection of transconjugant with antibiotics C and B typically leads to selection of receiver cells with the recombinant plasmid.

Other modifications enabled by the methods of the invention include the insertion of an *E. coli* replicon and an *E. coli* resistant marker on the plasmid allowing extraction of the plasmid from *C. acnes* and transformation and replication in *E. coli.*

Additionally, the plasmid carrying the template DNA for homologous recombination preferably allows the expression of genes that increase recombination rate.

The template for homologous recombination typically contains homology arms upstream and downstream recombination points. These homology arms are preferably 50, 100, 500, 1000 bp long or more.

*C. acnes* Genome Engineering and Engineered *C. acnes* Strains

The invention encompasses methods of *C. acnes* genome engineering and engineered *C. acnes* strains that have been engineered by any of the methods of the invention. An "engineered strain" is a strain that has been obtained by any of the methods of the invention to contain an alteration either found or not found in nature. For example, the engineered *C. acnes* strain can comprise any of the vectors or DNAs of the invention.

The invention encompasses methods for delivering DNA of interest into *C. acnes* strains by conjugation. The invention also encompasses methods for delivering DNA of interest into *C. acnes* strains via phage-derived particles. The invention encompasses methods to engineer the *C. acnes* chromosome with replicative and non-replicative vector methods.

In one embodiment, delivery of the DNA vector into *C. acnes* is by transduction. In one embodiment, the DNA vector comprises a phage packaging signal (cos) originating from *C. acnes* phages. In one embodiment, phage-derived particles containing the DNA vector can be generated and can allow the DNA vector to be transduced into *C. acnes* cells.

In one embodiment, the invention encompasses replicative and non-replicative vector methods using a vector comprising at least a recombination template with one or two homology arms.

To engineer the *C. acnes* genome, the inventors have developed methods using replicative and non-replicative vectors.

Non-Replicative Vector Methods

In one embodiment, non replicative vector methods use a vector comprising at least:

- a phage packaging signal, as defined above;
- a selection marker for *C. acnes*, as defined above;
- a recombination template with one or two homology arms;
- an origin of replication allowing replication only in *Cutibacterium acnes* producer cell; and
- optionally a counter selection marker such as SacB.

Non-replicative vector methods use vectors that carry a *C. acnes* replicon that replicate only in a *C. acnes* producer cell but not in other *C. acnes* cells. Thus, such vectors are able to replicate in *C. acnes* producer cell, get packaged into phage capsid upon contacting with phage genome leading to a phage-derived particle, and get transduced by the phage-derived particle into *C. acnes* receiver cell where they do not replicate.

Figure 4A:
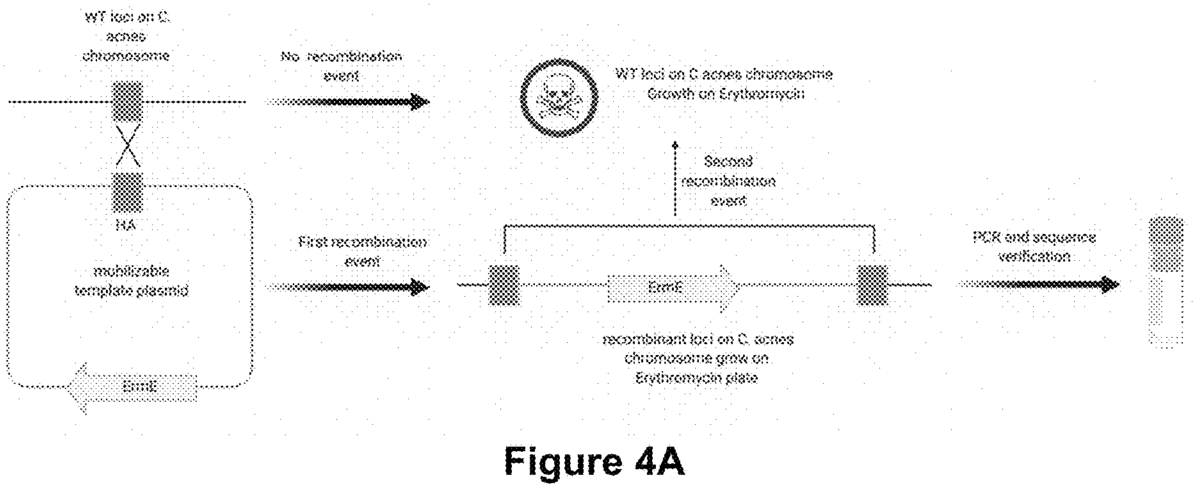
FIGS. 4A and 4B depict a method for *C. acnes* genome engineering using non-replicative vector carrying recombination template.
Figure 4B:
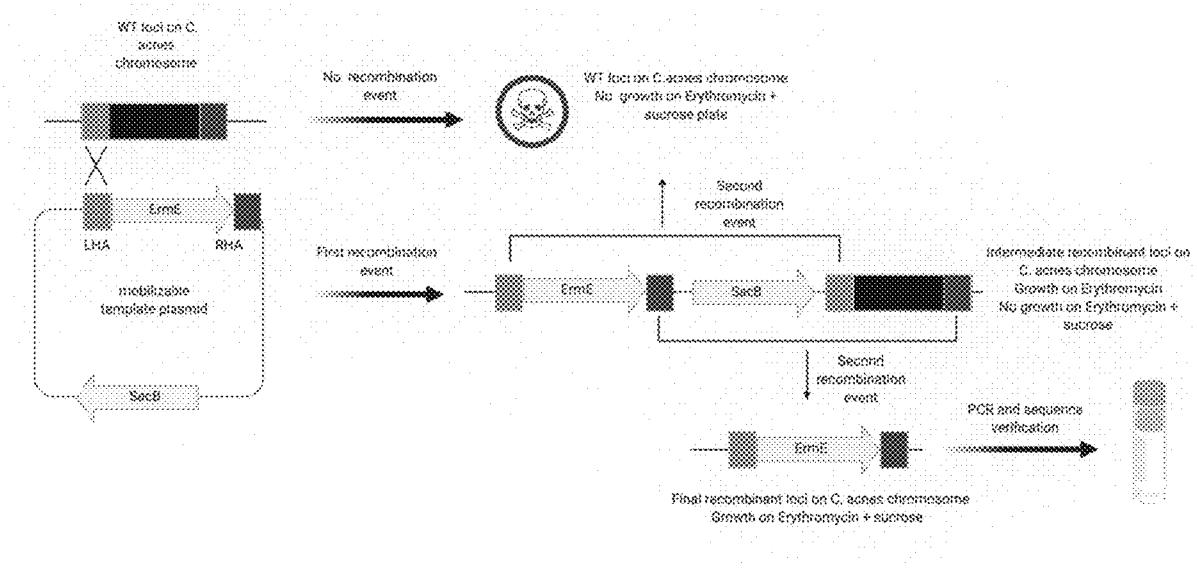

The methods comprise introducing into a *C. acnes* producer cell a plasmid containing a template for homologous DNA recombination inside the genome. The template can contain one (FIG. 4A) or two homologous regions (FIG. 4B) leading to homologous recombination.

In one embodiment, the method comprises a *C. acnes* producer cell, carrying a plasmid containing a template for homologous DNA recombination inside the chromosome where the homologous DNA is not present in the *C. acnes* producer cell, a phage packaging signal (cos) originating from *C. acnes* phages, a selection marker for *C. acnes*, as defined above, and an origin of replication for *C. acnes* producer cell but not replicating in *C. acnes* receiver cell. The template can contain one (FIG. 4A) or two homologous regions (FIG. 4B), leading to homologous recombination. The producer cell is typically infected by a *C. acnes* phage leading to production of phage-derived particles containing the DNA vector with homology arm(s). Phage-derived particles are preferably mixed with *C. acnes* receiver cells (e.g., ATCC 11828). Transductants can be selected on antibiotic plates, streaked on antibiotic plates and plasmid integration screened by PCR. Because the plasmid is not replicative in *C. acnes*, only recombinant cells that stably maintain the antibiotic marker are able to grow on antibiotic plates.

In the case where there are two homology arms present on the template DNA, a first recombination event (also called cross-over) typically leads to the full integration of the plasmid. This is typically followed by a second recombination event that removes the plasmid backbone and leads to either the modification of the chromosome or to the reconstitution of the wild-type locus.

In one embodiment, the *C. acnes* producer cell carries a vector containing a left homology arm (LHA) and a right homology arm (RHA) flanking a *C. acnes* selection marker, for example, ermE (pEB_HR02). The two homology arms typically do not match the *C. acnes* producer cell chromosome. In one embodiment, the vector also contains a phage packaging signal (cos) originating from *C. acnes* phages, a selection marker for *C. acnes* and an origin of replication for *C. acnes* producer cell but not replicating in *C. acnes* receiver cell. In one embodiment the DNA vector also contains a *C. acnes* counter-selection marker, such as sacB, on the plasmid backbone allowing selection of the second recombination event. The *C. acnes* producer cell carrying pEB_HR02 is typically infected by a phage leading to production of phage-derived particles comprising pEB_HR02. The phage-derived particles are typically put in presence of *C. acnes* receiver cells (e.g., ATCC 11828). Transductants are typically selected on plates supplemented with the antibiotic (e.g., erythromycin), streaked onto plates supplemented with the antibiotic (e.g., erythromycin) and integration of the plasmid confirmed by PCR. Because the plasmid is not replicative in *C. acnes* receiver cell, *C. acnes* clones able to grow in the presence of the antibiotic (e.g., erythromycin), have undergone a single homologous recombination event, which has led to the integration of the full plasmid. To select for final recombinant loci, cells are typically exposed to the counter-selection (e.g., sucrose) and the antibiotic (e.g., erythromycin), which leads to cell death due to sacB activity (the full plasmid remains integrated in the chromosome). Survivors are typically screened by PCR for successful final recombinant loci presence. In one embodiment the DNA vector contains only one homology arm (pEB_HR01). In one embodiment, both pEB_HR01 and pEB_HR02 phage-derived particles are applied on the skin and no antibiotic selection is applied.

In one embodiment, the *C. acnes* producer cell carries a plasmid (vector) containing a left homology arm (LHA) and a right homology arm (RHA) flanking *C. acnes* selection marker ErmE (pEB_HR02). The vector also preferably contains an *E. coli* origin of replication, an *E. coli* selection marker, an oriT and relaxase from a conjugative plasmid and a *C. acnes* counter-selection marker, such as sacB. pEB_HR02 can be transformed into an *E. coli* donor strain (e.g. Ec0s2862). Transformants are typically selected, grown and mixed with *C. acnes* receiver cells (e.g., ATCC 11828). Transconjugants are typically selected on plates supplemented with the antibiotic (e.g., erythromycin), streaked onto plates supplemented with the antibiotic (e.g., erythromycin) and integration of the plasmid confirmed by PCR. Because the plasmid is not replicative in *C. acnes* receiver cell, *C. acnes* clones able to grow in the presence of the antibiotic (e.g., erythromycin), have undergone a single homologous recombination event, which has led to the integration of the full plasmid. To select for final recombinant loci, cells are typically exposed to the counter-selection (e.g., sucrose) and the antibiotic (e.g., erythromycin), which leads to cell death due to sacB activity (the full plasmid remains integrated in the chromosome). Survivors are typically screened by PCR for successful final recombinant loci presence Replicative CRISPR-Cas System Selection Vector Methods The invention encompasses replicative vectors comprising an origin of replication for *C. acnes.*

In one embodiment, a replicative CRISPR-Cas selection vector method uses vector comprising at least:

- a phage packaging signal (cos) originating from *C. acnes* phages, as defined above;

a selection marker for *C. acnes*, as defined above;
an origin of replication for *C. acnes;*
a recombination template with two homology arms; and
a CRISPR-Cas system for expression in *C. acnes.*

In one embodiment, a replicative CRISPR-Cas selection vector method uses a vector comprising at least:

a selection marker for *E. coli*, as defined above;
an origin of replication for *E. coli;*
a selection marker for *C. acnes*, as defined above;
a recombination template with two homology arms;
an origin of replication for *C. acnes*; and
a CRISPR-Cas system that is expressed in *C. acnes.*

Thus, such vectors are able to replicate in *E. coli* and are able to replicate in *C. acnes*. They also carry a CRISPR-Cas system able to induce double stranded breaks at the wild-type loci where recombination is wanted, leading to death of *C. acnes* receiver cell.

Figure 5:
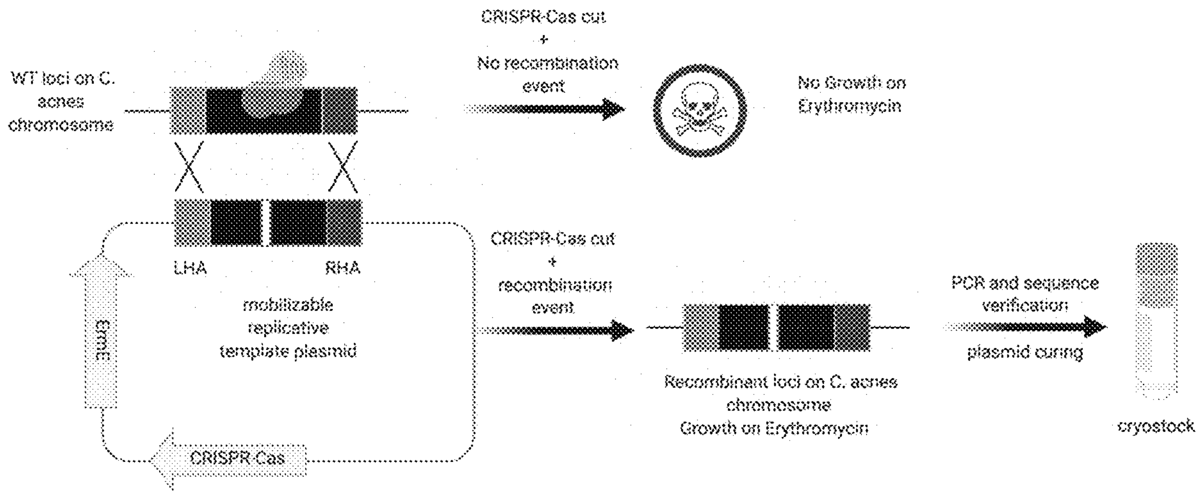
FIG. 5 depicts a method for *C. acnes* genome engineering using a replicative CRISPR-Cas system selection vector carrying a recombination template. A replicative CRISPR-Cas system selection vector containing a template for homologous DNA recombination with the chromosome is conjugated into *C. acnes*. The template contains two homology arms (LHA and RHA) leading to homologous recombination in *C. acnes* chromosome and removal of the target sequence of the CRISPR-Cas system. Thus, only recombinants *C. acnes* are able to grow in the presence of erythromycin when selected for the presence of the vector expressing CRISPR-Cas system.

In one embodiment, the method comprises the use of a *C. acnes* producer cell, for example strain ATCC 6919, carrying a replicative CRISPR-Cas system selection vector containing a template for homologous DNA recombination inside the chromosome and a phage packaging signal (cos) originating from *C. acnes* phages. In one embodiment, the template contains two homologous regions (FIG. 5), leading to homologous recombination. The producer cell preferably does not contain the wild-type loci targeted by the CRISPR-Cas system. The *C. acnes* producer cell is typically infected by a *C. acnes* phage leading to production of phage-derived particles carrying the DNA vector. Phage-derived particles are typically put in contact with *C. acnes* receiver cell. After transduction into *C. acnes* receiver cell, cells that have recombined with the DNA template vector are not targeted by the CRISPR-Cas system because, for example, they do not have the associated PAM sequence anymore. Plating on antibiotic-containing media, e.g. erythromycin plates, typically ensures that the cells that survive have been transduced and still carry the DNA vector (e.g. plasmid) expressing the CRISPR-Cas system. Single colonies are typically streaked on antibiotic-containing media, e.g. erythromycin plates, and recombinant loci are typically confirmed by PCR and sequencing.

In one embodiment, a step of plasmid curing is performed to eliminate the plasmid.

In one embodiment, the *C. acnes* producer cell contains the DNA target of the CRISPR-Cas system, but the CRISPR-Cas system is not expressed in the *C. acnes* producer cell but is expressed in *C. acnes* receiver cell. More preferably the CRISPR-Cas system is repressed in the *C. acnes* producer cell but not in *C. acnes* receiver cell.

Such methods can be used for scarless editing such as substitution, deletion or insertion because there is no need to introduce a selection marker to select for recombinants, the selection being done by CRISPR-Cas killing.

Self-Targeted Replicative Vector Methods

In one embodiment, the invention encompasses self-targeted replicative vector methods. In one embodiment, the invention encompasses the use of a CRISPR-Cas system to program cutting of the DNA vector (e.g. plasmid) in one or several target sequences, leading to linearization of the recombination template that have been shown to increase recombination efficiency[9]. To be able to clone a self-targeting vector, an inducible CRISPR-Cas system can be used, for example, using an inducible promoter upstream of the gene encoding the Cas nuclease. By combining this inducible promoter with a riboswitch, even tighter inhibition of CRISPR-Cas system expression can be assured. Another strategy to generate self-targeting CRISPR-Cas system relies on promoters that are repressed in the *C. acnes* producer cell and not in *C. acnes* receiver cell. In this way, the CRISPR-Cas system will only be active once transduced in a *C. acnes* receiver cell.

Figure 6A:
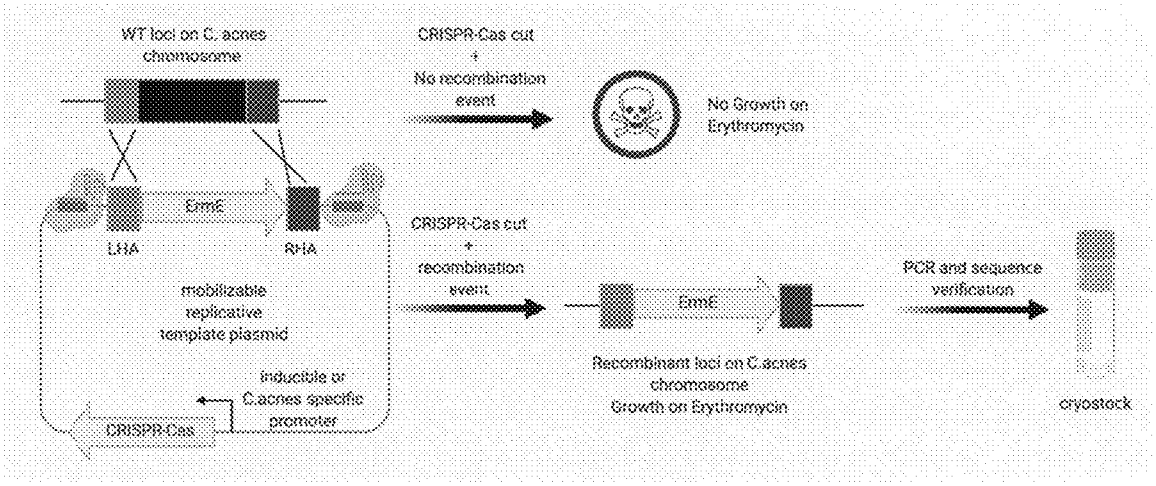
FIGS. 6A and 6B depict a method for *C. acnes* genome engineering using self-targeted replicative vector carrying a CRISPR-Cas system and a recombination template.
Figure 6B:
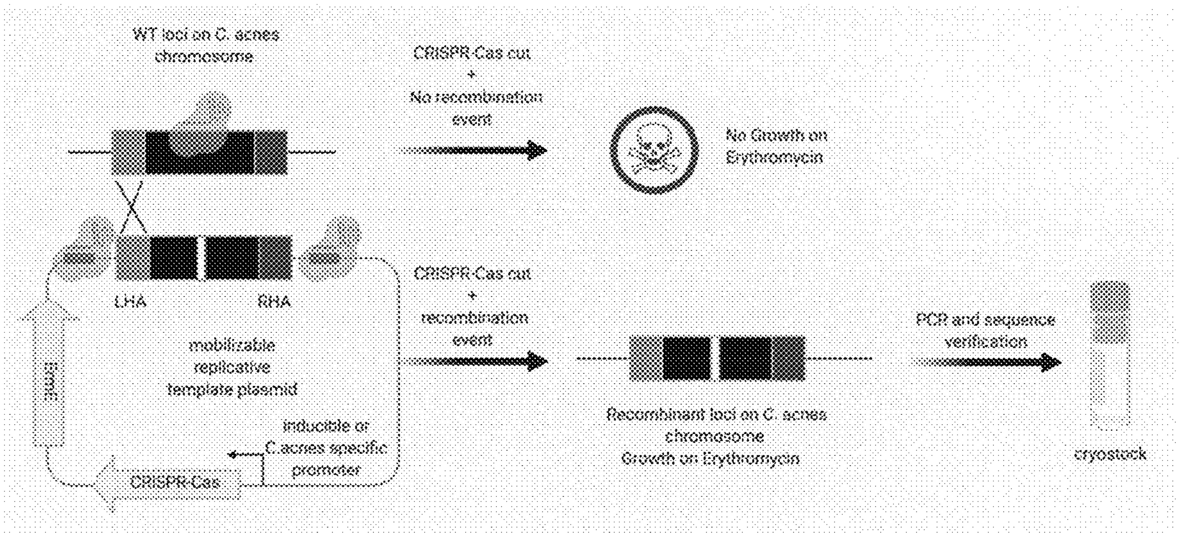

Using such strategy, for example, a gene replacement can be performed using an antibiotic marker flanked by homology arms (FIG. 6A) or by performing scarless recombination using the CRISPR-Cas system ability to kill the bacteria when targeting *C. acnes* chromosome (FIG. 6B).

After introduction and selection of the DNA vector (e.g. plasmid), a homologous event typically takes place leading to removal of a PAM sequence.

Additionally, the DNA vector (e.g. plasmid) carrying the template DNA for homologous recombination typically allows expression of genes increasing recombination rate.

In one embodiment, the DNA vector comprises a template for homologous recombination and a CRISPR-Cas system targeting the DNA vector itself outside of the template region wherein the RNA guide (crRNA or sgRNA) from the CRISPR-Cas system is not perfectly matching the DNA target.

In one embodiment, the invention encompasses replicative vector methods using a vector comprising at least:

a phage packaging signal (cos) originating from *C. acnes* phages, as defined above;
a selection marker for *C. acnes*, as defined above;
an origin of replication for *C. acnes*, as defined above; and
a CRISPR-Cas system for expression in *C. acnes.*

In one embodiment, vectors carry a CRISPR-Cas system able to induce double stranded break leading to death of most *C. acnes* receiver cells except *C. acnes* receiver cells that by spontaneous mutation or recombination do not carry anymore the CRISPR-Cas system target sequence.

*C. acnes* Phage Genome Engineering

The invention encompasses methods for *C. acnes* phage genome engineering and engineered *C. acnes* phage that have been engineered by any of the methods of the invention. An "engineered or recombinant phage" is a phage that has been obtained by any of the methods of the invention to contain an alteration either found or not found in nature. For example, an engineered *C. acnes* phage genome carries a substitution, a deletion or an insertion of one or several nucleotides. In another example the *C. acnes* phage genome carries one or several transgenes expressed upon phage infection.

In one embodiment, the *C. acnes* phage contains one or several genetic modifications into the *C. acnes* phage genome.

In one embodiment, the *C. acnes* phage genome modifications are insertion, deletion or substitution of one or several nucleotides into the *C. acnes* phage genome.

In one embodiment, the *C. acnes* phage genome modification is silent.

In one embodiment, the *C. acnes* phage genome modification is not silent.

In one embodiment, the *C. acnes* phage genome modifications do not impair *C. acnes* phage production.

In one embodiment, the *C. acnes* phage genome modification modifies the phage host range.

In one embodiment, the *C. acnes* phage genome modification leads to inhibition of its packaging into the phage capsid without interfering with the production of the capsid itself. More preferably the genome modification is a modification of the phage packaging sequence. Even more preferably the modification is a deletion of the phage packaging sequence.

In one embodiment, the deleted phage packaging sequence is a cos site from a *C. acnes* phage wherein the cos site sequence is at least 80, 83, 85, 87, 90, 93, 95, 96, 97, 98, 99 or 100% identical to the sequence SEQ ID NO: 66.

In one embodiment, the deleted phage packaging sequence is a cos site from a *C. acnes* phage wherein the cos site sequence is at least 80, 83, 85, 87, 90, 93, 95, 96, 97, 98, 99 or 100% identical to one or more sequence(s) selected from the group consisting of the sequences SEQ ID NO: 76, SEQ ID NO: 86, SEQ ID NO: 87, SEQ ID NO: 88, SEQ ID NO: 89 and SEQ ID NO: 90.

In one embodiment, the *C. acnes* phage modifications are inside coding sequences.

In one embodiment, the *C. acnes* phage modifications are inside regulatory elements such as promoters, transcriptional terminators, origins of replication, RBSs, riboswitch.

In one embodiment, the *C. acnes* phage modifications are inside non-coding sequences and non-regulatory sequences.

In one embodiment, the *C. acnes* phage modifications are insertion of one or several transgenes into the *C. acnes* phage genome.

In one embodiment, the *C. acnes* phage modifications are insertion of one or several transgenes into the *C. acnes* phage genome wherein the insertion does not remove any nucleotide originally present in the phage genome.

In one embodiment, the *C. acnes* phage modifications are insertion of one or several transgenes into the *C. acnes* phage genome wherein the insertion are in intergenic regions.

In one embodiment, the *C. acnes* phage modifications are insertion of one or several transgenes into the *C. acnes* phage genome wherein the insertion replaces one or several nucleotides.

In one embodiment, the *C. acnes* phage modifications are insertion of one or several transgenes into the *C. acnes* phage genome wherein the transgene replaces one or several genes inside a transcriptional unit containing one or several genes without perturbating upstream and downstream genes.

In one embodiment, the *C. acnes* phage modifications are insertion of one or several transgenes into the *C. acnes* phage genome wherein the transgene replaces the holin gene.

In one embodiment, the *C. acnes* phage modifications are insertion of one or several transgenes into the *C. acnes* phage genome wherein the transgene replaces the endolysin gene.

In one embodiment, the *C. acnes* phage modifications are insertion of one or several transgenes into the *C. acnes* phage genome wherein the transgene replaces the holin and the endolysin genes.

In one embodiment, the *C. acnes* phage modifications are insertion of one or several transgenes into the *C. acnes* phage genome wherein the holin and endolysin genes are previously modified to be inactive.

In one embodiment, the *C. acnes* phage modifications are insertion of one or several transgenes into the *C. acnes* phage genome wherein the transgene is a selection marker in *C. acnes*, as defined above.

In one embodiment, the *C. acnes* phage modifications are insertion of an origin of replication allowing replication in *C. acnes*.

In one embodiment, the *C. acnes* phage modifications are insertion of:

- an origin of replication allowing replication in *C. acnes*, as defined above, and
- a selection marker in *C. acnes*, as defined above.

In one embodiment, the *C. acnes* phage modifications are insertion of one or several transgenes into the *C. acnes* phage genome wherein each transgene contains a promoter, one or several coding sequence and a transcriptional terminator.

In one embodiment, the *C. acnes* phage modifications are insertion of one or several transgenes into the *C. acnes* phage genome wherein each transgene contain a promoter, one or several coding sequence with their ribosome binding sites and a transcriptional terminator and where the promoter is inducible.

In one embodiment, the *C. acnes* phage modifications are insertion of one or several transgenes into the *C. acnes* phage genome wherein each transgene contain a promoter, one or several coding sequence with their ribosome binding sites and a transcriptional terminator and where the promoter is active in specific *C. acnes* strains and inactive or less active in other *C. acnes* strains.

To engineer the *C. acnes* phage genome, the inventors have developed methods to generate recombinant *C. acnes* phages:

- using in vitro or in vivo DNA assembly of the recombinant phage genome, and introduction of the recombinant phage genome into rebooting bacteria such as, but not limited to, *C. acnes*, allowing production of recombinant phage; and/or
- using recombination in *C. acnes* and selection of recombinant phage using replicative CRISPR-Cas system selection vector.

Recombinant *C. acnes* Phage Engineering by Genome Assembly and Rebooting Methods The invention encompasses methods for producing engineered phages using DNA assembly to generate a modified phage genome and subsequent generation of phage containing the assembled modified phage genome.

In one embodiment, DNA fragments are assembled into a recombinant *C. acnes* phage genome and introduced into rebooting bacteria to produce recombinant *C. acnes* phages.

In one embodiment, DNA fragments are assembled into a recombinant *C. acnes* phage genome and transformed into rebooting bacteria to produce recombinant *C. acnes* phages.

In one embodiment, the rebooting bacteria is from the family Propionibacteriaceae. Preferably the rebooting bacteria is *P. freudenreichii*, even more preferably the rebooting bacteria is *C. acnes*.

In one embodiment, DNA fragments are assembled into a recombinant *C. acnes* phage genome inside a vector and introduced into rebooting bacteria to produce recombinant *C. acnes* phages.

In one embodiment, DNA fragments are assembled into a recombinant *C. acnes* phage genome inside a vector and introduced into a bacteria such as *E. coli* that conjugate the vector carrying the recombinant *C. acnes* phage genome into *C. acnes* into which recombinant phages are produced and then amplified on *C. acnes*.

In one embodiment, DNA fragments are assembled into a recombinant *C. acnes* phage genome inside a vector and transformed into a bacteria such as *E. coli* that conjugate the vector carrying the recombinant *C. acnes* phage genome into *C. acnes* into which recombinant phages are produced and then amplified on *C. acnes*.

In one embodiment, DNA fragments are assembled into a recombinant *C. acnes* phage genome inside a vector, wherein the vector contains:

- An origin of replication allowing replication in *E. coli*, as defined above;
- A selection marker for *E. coli*, as defined above;

An oriT from conjugative plasmid, as defined above;

optionally a relaxase from conjugative plasmid; and optionally an origin of replication allowing replication in *C. acnes*, as defined above, and transformed into an *E. coli* carrying a conjugative vector. The vector containing the recombinant *C. acnes* phage genome is then typically conjugated into *C. acnes*.

In one embodiment, the vector into which the DNA fragments are assembled into a recombinant *C. acnes* phage genome is a Bacterial Artificial Chromosome (BAC).

In one embodiment, DNA fragments are assembled into a recombinant *C. acnes* phage genome in vitro using one or a combination of the following techniques:

Gibson assembly,

PCR assembly,

Golden Gate assembly and derivatives (MOCLO, GoldenBraid . . . ),

GeneArt® Seamless assembly,

SLIC assembly,

CPEC assembly,

SLiCE assembly.

In one embodiment, DNA fragments are generated by one of the following methods or a combination of the following methods:

PCR on *C. acnes* phage genome,

Digestion of *C. acnes* phage genome,

DNA synthesis (chemical or enzymatic),

Oligo assembly.

In one embodiment, DNA fragments are assembled into a recombinant *C. acnes* phage genome in vivo using Transformation Associated Recombination (TAR) in yeast.

In one embodiment, the DNA fragments are assembled, in vitro or in vivo, into a recombinant phage genome inside a cloning vector such as a Bacterial Artificial Chromosome (BAC), a Yeast Artificial Chromosome (YAC), a P1-derived artificial chromosome, a plasmid or any combination. The recombinant phage genome is then typically extracted from the cloning vector, optionally circularized and introduced into a rebooting bacterial strain.

In one embodiment, the recombinant *C. acnes* phage genome is introduced into *C. acnes* by transformation. More preferably the recombinant *C. acnes* phage genome is introduced into *C. acnes* by electroporation.

In one embodiment the recombinant *C. acnes* phage genome is introduced into *C. acnes* L-form or *C. acnes* protoplast.

*C. acnes* Phage Engineering by Recombination Methods

The invention encompasses methods for producing engineered phages comprising introducing modification into *C. acnes* phage genome using recombination between a DNA template and a *C. acnes* phage genome, and generation of phages containing the modified phage genome.

In one embodiment a *C. acnes* phage genome is introduced into a *C. acnes* strain containing a DNA template, and recombination events between the phage genome and the DNA template lead to modification of some of the phage genomes that are then packaged into *C. acnes* phages.

In one embodiment an engineered *C. acnes* phage is produced after introduction of a *C. acnes* phage genome into a *C. acnes* cell which comprises a replicative vector containing:

a selection marker for *C. acnes*, as defined above, an origin of replication for *C. acnes*, as defined above, a recombination template with one or two homology arms, and optionally a recombination machinery.

In one embodiment an engineered *C. acnes* phage is produced after introduction of a *C. acnes* phage genome into a *C. acnes* with a replicative vector containing:

a selection marker for a donor bacteria such as *E. coli*, as defined above, an origin of replication for a donor bacteria such as *E. coli*, as defined above, a selection marker for *C. acnes*, as defined above, an oriT from conjugative plasmid, as defined above, optionally a relaxase from conjugative plasmid, an origin of replication for *C. acnes*, as defined above, a recombination template with one or two homology arms, and optionally a recombination machinery.

In one embodiment the *C. acnes* phage genome is introduced into *C. acnes* by electroporation.

In one embodiment the *C. acnes* phage genome is introduced into *C. acnes* through infection by the phage.

In one embodiment the DNA templates for homologous recombination are linear double stranded DNA (dsDNA) or single stranded DNA (ssDNA) introduced by electroporation.

In one embodiment the DNA templates for homologous recombination are oligonucleotides.

In one embodiment both the phage genome and the DNA template are transformed into *C. acnes*. Preferably the transformation method is electroporation.

Recombinant Phage CRISPR-Cas System Selection Methods

The invention encompasses recombinant phage CRISPR-Cas system selection methods. The invention encompasses a *C. acnes* cell, carrying a CRISPR-Cas system expressed in *C. acnes* and engineered to target a wild-type phage or a previously modified phage genome but not the newly generated recombinant *C. acnes* phage.

In one embodiment, the engineered CRISPR-Cas system is an endogenous CRISPR-Cas system.

In another embodiment, the CRISPR-Cas system is an exogenous CRISPR-Cas system.

In one embodiment the CRISPR-Cas system is an exogenous CRISPR-Cas system integrated on the *C. acnes* chromosome.

In one embodiment the CRISPR-Cas system is an exogenous CRISPR-Cas system on a replicative vector.

In one embodiment, the invention encompasses replicative CRISPR-Cas system selection vector comprising at least:

a selection marker for *C. acnes*, as defined above, an origin of replication for *C. acnes*, as defined above, and an exogenous CRISPR-Cas system that is expressed in *C. acnes* and targets the wild-type *C. acnes* phage genome or a previously modified phage genome but not the newly generated recombinant *C. acnes* phage genome.

In one embodiment, the invention encompasses replicative CRISPR-Cas system selection vector comprising at least:

a selection marker for a donor bacteria such as *E. coli*, as defined above, an origin of replication for a donor bacteria such as *E. coli*, as defined above, a selection marker for *C. acnes*, as defined above, an oriT from conjugative plasmid, as defined above, optionally a relaxase from conjugative plasmid, an origin of replication for *C. acnes*, as defined above, and an exogenous CRISPR-Cas system that is expressed in *C. acnes* and targets the wild-type *C. acnes* phage genome or a previously modified phage genome but not the newly generated recombinant *C. acnes* phage genome.

In one embodiment, the method comprises conjugating into *C. acnes*, for example strain ATCC 6919, a replicative CRISPR-Cas system selection vector containing:

- a selection marker for a donor bacteria such as *E. coli*, as defined above,
- an origin of replication for a donor bacteria such as *E. coli*, as defined above,
- a selection marker for *C. acnes*, as defined above,
- an oriT from conjugative plasmid, as defined above,
- optionally a relaxase from conjugative plasmid,
- an origin of replication for *C. acnes*, as defined above, and
- an exogenous CRISPR-Cas system that is expressed in *C. acnes* and targets the wild-type *C. acnes* phage genome or a previously modified phage genome but not the newly generated recombinant *C. acnes* phage genome.

After conjugation into *C. acnes*, transconjugants are typically selected on appropriate antibiotic. After optional confirmation by PCR of the presence of the replicative CRISPR-Cas system selection vector in *C. acnes*, single colony is typically grown in a dense culture in presence of the appropriate antibiotic, is preferably mixed with a *C. acnes* phage suspension containing a mix of wild-type phage, or previously produced recombinant phage, and newly produced recombinant phage, and is typically poured as a top agar lawn. Optionally a first amplification of the recombinant *C. acnes* phage can be performed on the *C. acnes* carrying the replicative CRISPR-Cas system selection vector, phage suspension can typically be obtained and mixed with a new culture of *C. acnes* carrying the replicative CRISPR-Cas system selection vector for a top agar.

Newly generated recombinant phages typically bind, inject their recombinant phage genome, replicate and generate new recombinant particles leading to plaque formation, whereas wild-type or previously generated recombinant phages inject their phage genome which is recognized and cut by the CRISPR-Cas system leading to abortion of the phage replication cycle, thus leading to no plaques being produced. Single plaques are typically picked, isolated, and confirmed to be recombinant and carrying the expected genetic modification. Finally, the isolated plaque is typically reamplified into a *C. acnes* indicator strain or into the *C. acnes* carrying the replicative CRISPR-Cas system selection vector and the pure phage suspension is preferably stored.

In one embodiment, the recombinant DNA phage is not targeted by the CRISPR-Cas system because, for example, it does not have the associated PAM sequence.

Methods to Produce Recombinant Phages in *C. acnes*

The invention encompasses methods to produce phage-derived particles in *C. acnes*. *C. acnes* phages that have been described so far are all genetically extremely conserved and are not able to stably replicate as a plasmid state, nor integrate in the chromosome of their host[1]. As a consequence, they are difficult to engineer because they lead to the death of the cell they infect. To address this issue, the inventors have developed a two-step method to engineer *C. acnes* phages.

In the first step, an *E. coli* donor strain carrying a conjugative vector is transformed with a mobilizable replicative vector (e.g., pEB-PRECOMB) comprising:

- a selection marker for *E. coli*, as defined above,
- an origin of replication for *E. coli*, as defined above,
- a selection marker for *C. acnes*, as defined above,
- a relaxase and oriT from conjugative plasmid, and
- a recombination template with one or two homology arms.

Figure 7A:
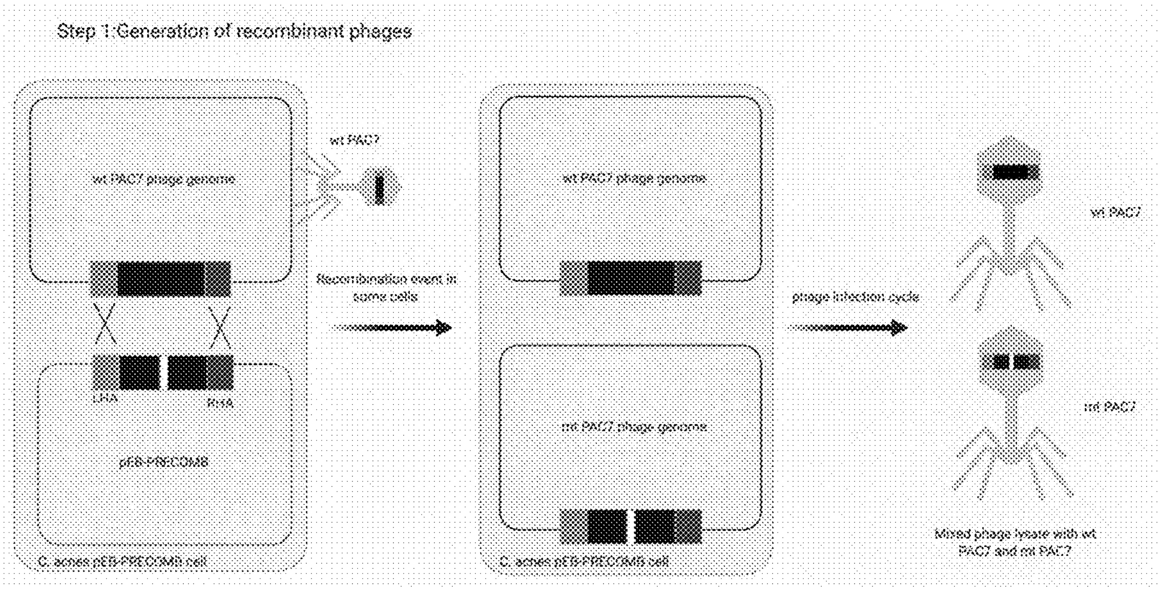
FIGS. 7A and 7B depict a two-step method for engineering and selection of *C. acnes* phages using CRISPR-Cas system.

Conjugation between *E. coli* donor cells (*E. coli* pEB-PRECOMB) and *C. acnes* receiver cells (for example *C. acnes* ATCC 6919) is performed. *C. acnes* transconjugants (*C. acnes* pEB-PRECOMB) are typically selected on the appropriate antibiotic, grown and infected by *C. acnes* phages (e.g., PAC7). After phage infection, a recombination event takes place, which leads to a phage lysate containing both wild-type *C. acnes* phage (e.g., wt PAC7) or parent *C. acnes* phage (i.e. a phage from which the desired recombinant phage originates) and recombinant phages (e.g., mt PAC7) (FIG. 7A).

In the second step, a replicative plasmid (e.g., pEB-PSCREEN) is used, comprising:

- a selection marker for *E. coli*, as defined above,
- an origin of replication for *E. coli*, as defined above,
- a selection marker for *C. acnes*, as defined above, and
- a relaxase and oriT from a conjugative vector, as defined above, and
- a CRISPR-Cas system for expression in *C. acnes* and targeting the wild-type phage (e.g., PAC7).

Figure 7B:
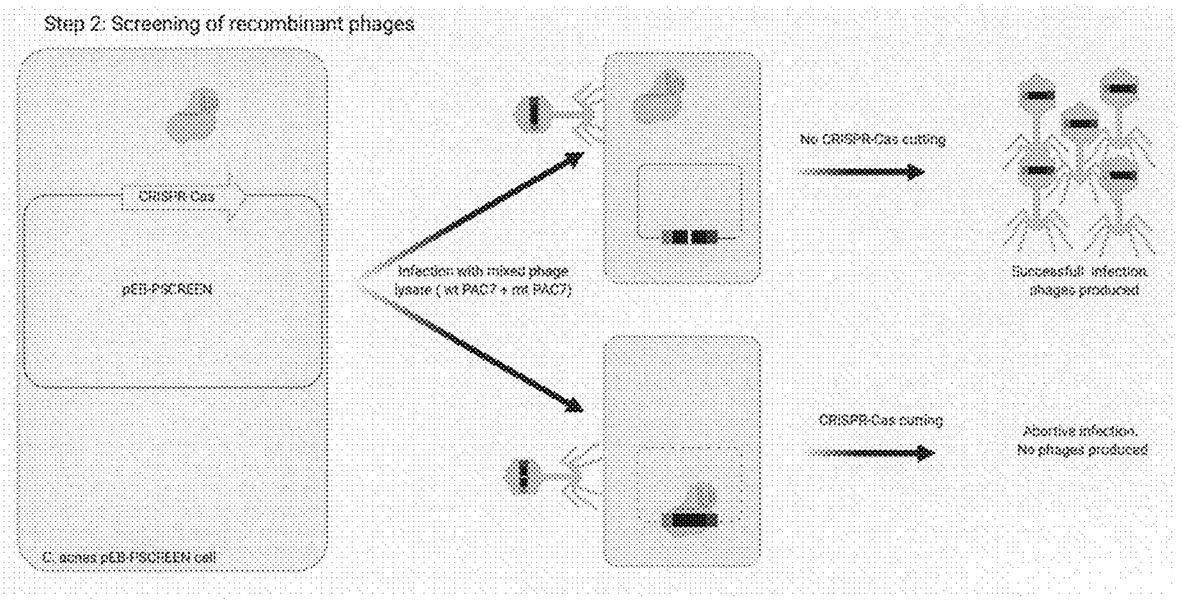

In one embodiment, said replicative plasmid is transformed into an *E. coli* donor strain carrying a conjugative plasmid (e.g. leading to the production of *E. coli* donor strain pEB-PSCREEN). Conjugation is performed between the *E. coli* donor strain pEB-PSCREEN and *C. acnes* receiver cells (for example *C. acnes* ATCC 6919). Transconjugant *C. acnes* pEB-PSCREEN cells are typically selected on antibiotic plates, grown to a dense culture and mixed with the phage lysate containing both wild-type phage (e.g., wt PAC7) and mutant phage (e.g., mt PAC7) (FIG. 7B). Wild-type phage genomes are typically cut by the CRISPR-Cas nuclease and are not able to replicate and form plaques, whereas recombinant mt phage genomes are not recognized by the CRISPR-Cas system and successfully replicate, which leads to plaque formation. Single plaques are typically isolated, screened by PCR and sequence verified. If confirmed by sequencing, the recombinant phages are typically amplified on wild-type *C. acnes* strain or on *C. acnes* strain with the CRISPR-Cas system vector targeting wild-type phage.

The recombination event can lead to substitution, deletion, or insertion that leads, therefore, to the removal of the PAM sequence or any part of the sequence necessary for CRISPR-Cas targeting. Insertion can lead to the introduction of a fluorescent or enzymatic reporter that helps to isolate recombinant plaques.

The template for homologous recombination typically contains homology arms upstream and downstream recombination points. These homology arms are typically at least 50, 100, 500, 1000 or at least 5000 bp in size.

Examples of applications of the engineering of *C. acnes* phages include, but are not limited to:

- expression of therapeutic proteins that are produced during phage infection and released when cells are lysed,
- expression of therapeutic proteins that are produced, secreted or exported to surface during phage infection,
- display of specific proteins, such as antigens, on the capsid of the phage,
- modification of the host range of the phage, and
- obtaining of a strictly lytic phage variant.

Additionally, the vector (e.g. plasmid) carrying the template DNA for homologous recombination typically allows expression of genes that increase recombination rate.

Additionally, the vector (e.g. plasmid) carrying the template DNA for homologous recombination is typically carrying an inducible endonuclease, such as but not limited to CRISPR-Cas, that leads to the linearization of the vector during infection of the phage. This linearization of the template vector typically leads to an increase in recombination rate.

Expression of Proteins by Engineered *C. acnes* Phage

The invention encompasses the expression of proteins by engineered *C. acnes* phage. By incorporating an expression cassette into the phage, the protein can be expressed by the infected *C. acnes*. The promoter within the expression cassette can be inducible or constitutive, allowing inducible or constitutive expression of proteins by engineered *C. acnes* phage.

In one embodiment, the phage is used for the expression of molecules of interest and/or modulation of *C. acnes*-host interaction. In one embodiment, the phage genome is used for the expression of transgenes in *C. acnes*. A transgene can be cloned into the recombinant autonomously-replicating phage vector under the control of a given promoter (constitutive or inducible) and followed by a given terminator. The injection of this phage genome into *C. acnes* allows the expression of the transgene. The transgene can be, for example, a CRISPR-Cas system, a base editing or prime editing expression cassette, or can encode a human protein, such as an interleukin, or can encode an antigen, such as a tumor antigen, a viral antigen, a bacterial antigen, a fungal antigen, a self-antigen, an allergen or a graft-specific antigen, as defined below.

Expression of Proteins by Engineered *C. acnes* Strains

The invention encompasses the expression of proteins by engineered *C. acnes* strains. By incorporating an expression cassette into the DNA vector, the protein can be expressed by the transduced *C. acnes*. The promoter within the expression cassette can be inducible or constitutive, allowing inducible or constitutive expression of proteins by engineered *C. acnes* strains. Expression of several proteins can be performed as single transcriptional unit (operon) or as separated transcriptional units. In a particular embodiment, said protein is an antigen, such as a tumor antigen, a viral antigen, a bacterial antigen, a fungal antigen, a self-antigen, an allergen or a graft-specific antigen, as defined below.

*C. acnes* Phage

The invention encompasses the *C. acnes* phage and related engineered phages, methods for producing these phages, and methods for using these phages to transduce *C. acnes.*

In a particular embodiment, the engineered *C. acnes* phage of the invention is incapable of self-reproduction.

In the context of the present invention, the terms "self-reproduction" and "self-replication" are used indifferently, and refer to the capability of having a progeny, in particular of producing new phages.

By "phage incapable of self-reproduction" is meant herein that at least one, several or all functional gene(s) necessary to produce said phage (also called herein "essential gene(s)") is(are) absent from said engineered phage (and from said phage genome included in said engineered phage).

In a preferred embodiment, said at least one, several or all functional gene(s) necessary to produce said engineered phage is(are) present in a producer cell, preferably in a plasmid, in a phagemid, in the chromosome or in a helper phage present in the producer cell, enabling the production of said engineered phage in said producer cell. In such an embodiment, said engineered *C. acnes* phage incapable of self-reproduction is also called conditionally replicative *C. acnes* phage.

In the context of the invention, said functional gene necessary to produce an engineered phage may be absent through (i) the absence of the corresponding gene or (ii) the presence of the corresponding gene but in a non-functional form.

In an embodiment, the sequence of said gene necessary to produce said engineered phage is absent from said engineered phage. In a preferred embodiment, the sequence of said gene necessary to produce said engineered phage has been replaced by a nucleic acid sequence of interest.

Alternatively, said gene necessary to produce said engineered phage is present in said engineered phage in a non-functional form, for example in a mutant non-functional form, or in a non-expressible form, for example with deleted or mutated non-functional regulators. In a preferred embodiment, said gene necessary to produce said engineered phage is present in said engineered phage in a mutated form which renders it non-functional in the receiver cell, while remaining functional in the producer cell.

In the context of the invention, genes necessary to produce said engineered phage encompass any coding or non-coding nucleic acid required for the production of said engineered phage.

Examples of genes necessary to produce said engineered phage include genes encoding phage structural proteins; phage genes involved in the control of genetic expression; phage genes involved in transcription and/or translation regulation; phage genes involved in phage DNA replication; phage genes involved in production of phage proteins; phage genes involved in phage proteins folding; phage genes involved in phage DNA packaging; and phage genes encoding proteins involved in bacterial cell lysis.

In one embodiment, the engineered *C. acnes* phage comprises an essential gene, as defined above, the expression of which is controlled by a *C. acnes* phage promoter. It can be expressed constitutively or under an inducible system, such as an inducible promoter or a riboswitch. When said essential gene is under an inducible system, said engineered *C. acnes* phage is also considered as a conditionally replicative phage.

In one embodiment the conditionally replicative phage does not or cannot kill a non-engineered *C. acnes* production strain, in particular which does not comprise said essential gene(s) absent from said conditionally replicative phage.

In one embodiment the conditionally replicative phage is carrying a CRISPR-Cas system.

In one embodiment the conditionally replicative phage comprises a transgene.

Phage-Derived Particles in *C. acnes*

The invention encompasses phage-derived particles comprising any DNA vector of the invention and the methods for the production of these phage-derived particles.

In one embodiment a *C. acnes* strain carrying any DNA vector of the invention is contacted with a *C. acnes* phage leading to introduction of the phage genome into the *C. acnes* strain and the expression of the phage proteins necessary for the assembly of a phage capsid and the packaging of the DNA vector inside the phage capsid.

In one embodiment a *C. acnes* strain carrying any DNA vector comprising a selection marker for *C. acnes* as defined above, a *C. acnes* phage packaging signal (cos site) as defined above and an origin of replication for *C. acnes*, as defined above, is contacted with a *C. acnes* phage leading to introduction of the phage genome into the *C. acnes* strain and the expression of the phage proteins necessary for the assembly of a phage capsid and the packaging of the DNA vector inside the phage capsid.

In one embodiment, the phage genome is a wild type phage genome.

In one embodiment, the *C. acnes* phage is PAC7 (typically of sequence SEQ ID NO: 68).

In one embodiment, the phage genome is an engineered phage genome.

The phage-derived particles can be purified by methods known in the art. The invention encompasses purified phage-derived particles comprising a DNA vector of the invention. In one embodiment, the purified phage-derived particles are in an isolated composition or pharmaceutical composition. The composition can comprise at least $10^4$, $10^5$, $10^6$, $10^7$, $10^8$, $10^9$, $10^{10}$, $10^{11}$, $10^{12}$, $10^{13}$, $10^{14}$, or more purified phage-derived particles.

Sequence Specific Killing of *C. acnes* by Phage-Derived Particles

In one embodiment, the invention comprises specific killing of *C. acnes* by phage-derived particles carrying CRISPR-Cas system.

Phage-derived particles carrying a vector (e.g. plasmid) encoding CRISPR-Cas system have been recently used to perform in situ sequence specific killing of bacteria[10,11]. The inventors have developed a method to produce such phage-derived particles to target *C. acnes*, which is encompassed by the invention.

In said method, a *C. acnes* producer strain comprising a DNA vector of the invention is contacted with a *C. acnes* phage, such as PAC7 (typically of sequence SEQ ID NO: 68) to produce a high titer phage suspension.

In one embodiment, the *C. acnes* comprises a DNA vector comprising:

- a selection marker for *C. acnes*, as defined above,
- a *C. acnes* phage packaging signal (cos site), as defined above,
- an origin of replication for *C. acnes*, as defined above and
- a CRISPR-Cas system targeting a specific *C. acnes* receiver cell chromosomal locus (pTarget).

High titer *C. acnes* phage suspensions are typically added to *C. acnes*. The suspensions typically contain a mix of wild-type phages and phage-derived particles carrying the plasmid. Contacting of *C. acnes* cells carrying the locus targeted by the pTarget CRISPR-Cas system is typically performed with phage-derived particles containing pTarget. This can be performed in vivo or in vitro. Sequence specific killing is typically observed for lysate containing phage-derived particles comprising pTarget.

In one embodiment, the phage-derived particles comprising the pTarget vector (e.g. plasmid) are not mixed with phage and allow sequence specific killing of cells carrying the DNA targeted by the CRISPR-Cas system.

*C. acnes* Plasmid Curing

Naturally occurring *C. acnes* plasmids have been described and some of them have been associated with pro-inflammatory phenotypes[15,23] and acne vulgaris[16-18]. Being able to cure such plasmids is of interest to study their effect, notably, their pro-inflammatory role in acne vulgaris. The inventors have developed a method to cure *C. acnes* plasmid.

In a first step, a *C. acnes* producer cell carrying a DNA vector comprising:

- a *C. acnes* phage packaging signal as defined above,
- optionally a selection marker for *C. acnes*, as defined above,
- an origin of replication that allows replication only in *C. acnes* producer cell, as defined above, and
- a transgene, such as a CRISPR-Cas system targeting a genetic sequence of an endogenous plasmid to be cured in a target *C. acnes* receiver cell, the sequence being preferably in a conserved region such as the origin of replication or in loci associated with acne vulgaris, is infected by a *C. acnes* phage leading to production of phage-derived particles carrying the DNA vector.

Contacting *C. acnes* phage-derived particles with *C. acnes* receiver cell carrying the endogenous plasmid to be cured, such as pIMPLE-HL096PA1 is performed. This can be performed in vivo or in vitro.

In some embodiments, *C. acnes* transductants can be selected on the appropriate antibiotic. Single colonies are typically streaked on plates with media containing the antibiotic and the presence of the plasmid is typically screened by PCR. Single colonies where no positive PCR for the plasmid pIMPLE-HL096PA1 is obtained, are then cured from the vector (e.g. plasmid) comprising the CRISPR-Cas system, and typically cryostocked.

Treatment Methods

The invention encompasses methods to treat a *C. acnes* related disorder or disease.

The invention encompasses the use of engineered *C. acnes* strains as defined above, phage-derived particles as defined above and engineered phages as defined above, and/or bacteria producing them for the treatment and/or prevention of a wide range of skin diseases and disorders.

The invention encompasses methods to treat a decrease in sebum production, follicular hyperkeratinization, colonization of skin bacteria, and inflammation using engineered *C. acnes* strains as defined above, phage-derived particles as defined above and engineered phages as defined above, and/or bacteria producing them.

The invention encompasses the use of engineered *C. acnes* strains as defined above in cosmetics and other compositions.

In one embodiment, the invention encompasses expression of therapeutic molecules by engineered *C. acnes*.

In one embodiment, the invention encompasses expression of non-therapeutic molecules by engineered *C. acnes*.

*Cutibacterium acnes* is one of the most prevalent and abundant bacteria on human skin, where it can be found both on the skin surface (stratum corneum) and in the hair follicle[12]. Inside the hair follicle, it is in direct contact with a large diversity of living cells such as keratinocytes, stem cells, sebaceous cells and immune cells. This is not the case on the stratum corneum, where it is mostly in contact with the dead corneocyte[13]. Thus, it appears interesting to use *C. acnes* as a bacterial chassis for the production and delivery of therapeutic molecules in situ inside and outside the hair follicle.

Phage-derived particles as defined above and engineered phages as defined above, and/or bacteria producing them, can be delivered to the skin by dermal or other appropriate administration method to a subject.

The subject according to the invention is an animal, preferably a mammal, even more preferably a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, or non-mammals such as poultry, that are in need of treatment.

The human subject according to the invention may be a human at the prenatal stage, a new-born, a child, an infant, an adolescent or an adult at any age.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with engineered *C. acnes* strains as defined above, phage-derived particles as defined above, engineered phages as defined above, and/or bacteria producing them (e.g., *E. coli* or *C. acnes*) according to the invention, is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is of about 1 week. Alternatively, the treatment may last as long as the infection, disorder and/or disease persists.

The form of the pharmaceutical or veterinary compositions, the route of administration and the dose of administration of engineered *C. acnes* strains as defined above, phage-derived particles as defined above, engineered phages as defined above, and/or bacteria producing them (e.g., *E. coli* or *C. acnes*) according to the invention, can be adjusted by the man skilled in the art according to the type and severity of the disease, disorder and/or infection (e.g. depending on the bacteria species involved in the disease, disorder and/or infection and its localization in the patient's or subject's body), and to the patient or subject, in particular its age, weight, sex, and general physical condition.

Particularly, the amount of engineered *C. acnes* strains as defined above, phage-derived particles as defined above, engineered phages as defined above, and/or bacteria producing them (e.g., *E. coli* or *C. acnes*) according to the invention, to be administered has to be determined by standard procedure well known by those of ordinary skills in the art. Physiological data of the patient or subject (e.g. age, size, and weight) and the routes of administration have to be taken into account to determine the appropriate dosage, so as a therapeutically effective amount will be administered to the patient or subject.

For example, the total amount of phage-derived particles as defined above and/or engineered phages as defined above according to the invention, for each administration is comprised between $10^4$ and $10^{15}$ particles.

Preferably, total amount of an engineered bacteria producing phage-derived particles as defined above and/or engineered phages as defined above (e.g., *E. coli* or *C. acnes*) according to the invention, or engineered *C. acnes* strains as defined above, for each administration is comprised between $10^4$ and $10^{15}$ bacteria.

The invention encompasses plasmids for the expression of toxins such as nuclease, more preferably CRISPR-Cas systems to kill transduced *C. acnes* population.

The invention encompasses plasmids for the expression of CRISPR-Cas systems where the CRISPR-Cas system is targeted towards sequences present only in specific strains and not present in others allowing strain specific killing among the *C. acnes* population.

The invention encompasses modifications of *C. acnes* chromosome or *C. acnes* endogenous plasmid. Modifications such as deletion, substitution and/or insertion leading to alteration in the *C. acnes*-host relation are for example contemplated.

The invention encompasses vectors, e.g. plasmids, for the expression of therapeutic molecules containing one or several genes involved in the production of the therapeutic molecule.

In the case where the therapeutic molecule is not freely diffusing from *C. acnes* cells, such as in the case of a therapeutic protein, a fusion with a signal peptide allowing secretion or export on the cell membrane or wall of *C. acnes* cells is preferably encoded on the vector, e.g. plasmid. Examples of secretion systems or signal peptides include: TAT, SEC and type VII/WXG100 secretion systems. More specifically, the signal peptide can be extracted from proteins selected from the group consisting of the proteins PPA0532 (typically referenced as Q6AAD1 in the UniprotKB database as of Nov. 4, 2020); PPA0533 (typically referenced as Q6AAD0 in the UniprotKB database as of Nov. 4, 2020); PPA0534 (typically referenced as Q6AAC9 in the UniprotKB database as of Nov. 4, 2020); PPA0598 (typically referenced as Q6AA63 in the UniprotKB database as of Nov. 4, 2020); PPA0644 (typically referenced as Q6AA16 in the UniprotKB database as of Nov. 4, 2020); PPA0687 (typically referenced as Q6A9X2 in the UniprotKB database as of Nov. 4, 2020); PPA0721 (typically referenced as Q6A9T8 in the UniprotKB database as of Nov. 4, 2020); PPA0816 (typically referenced as Q6A9J4 in the UniprotKB database as of Nov. 4, 2020); PPA1310 (typically referenced as Q6A856 in the UniprotKB database as of Nov. 4, 2020); PPA1498 (typically referenced as Q6A7M0 in the UniprotKB database as of Nov. 4, 2020); PPA1662 (typically referenced as Q6A771 in the UniprotKB database as of Nov. 4, 2020); PPA1715 (typically referenced as Q6A720 in the UniprotKB database as of Nov. 4, 2020); PPA1939 (typically referenced as Q6A6F6 in the UniprotKB database as of Nov. 4, 2020); PPA2097 (typically referenced as Q6A608 in the UniprotKB database as of Nov. 4, 2020); PPA2105 (typically referenced as Q6A601 in the UniprotKB database as of Nov. 4, 2020); PPA2106 (typically referenced as Q6A600 in the UniprotKB database as of Nov. 4, 2020); PPA2142 (typically referenced as Q6A5W4 in the UniprotKB database as of Nov. 4, 2020); PPA2164 (typically referenced as Q6A5U3 in the UniprotKB database as of Nov. 4, 2020); PPA2175 (typically referenced as Q6A5T2 in the UniprotKB database as of Nov. 4, 2020); PPA2152 (typically referenced as Q6A5V4 in the UniprotKB database as of Nov. 4, 2020); PPA1340 (typically referenced as Q6A826 in the UniprotKB database as of Nov. 4, 2020) and PPA2239 (typically referenced as Q6A5M0 in the UniprotKB database as of Nov. 4, 2020).

In the case where secretion is not wanted or functional, a lysing module can be added to the vector, e.g. plasmid, in order to lyse the cell and release the therapeutic molecule.

In a particular embodiment, said therapeutic molecule may be displayed on the cell membrane or wall of *C. acnes* cells. To be displayed, a protein of interest typically requires a N-terminal secretion signal peptide such as the ones described above as well as a C-terminal LPXTG motif allowing the class F sortase from *C. acnes* (Girolamo, S. D. et al. Biochem J 476, 665-682 (2019) to covalently link the protein of interest to the cell wall. Additionally a PT rich region might be integrated upstream of the LPXTG motif. Alternatively a more classical cell wall sorting sequence (CWSS) combining a LPxTG motif followed by hydrophobic amino acids and a positively charged C-terminus can be used.

In order to control expression of the therapeutic molecule, one or several of the genes, as an operon or as single isolated genes, can be put under the control of an inducible system, such as an inducible promoter, a riboswitch, a RNA-based induction system or a combination thereof. Several promoters of several transcriptional strengths might be tested and combined with different RBS strengths to optimize for in situ production of the therapeutic molecule. An RBS library approach might be used to select the best RBS variant for in vitro or in situ expression.

Examples of therapeutic molecules include but are not limited to antibodies, antibody-based drugs, Fc fusion proteins, anticoagulants, blood factors, bone morphogenetic proteins, engineered protein scaffolds, enzymes, growth factors, hormones, interferons, interleukins, and thrombolytics. Other examples include those that bind non-covalently to target (e.g., monoclonal antibodies), those that affect covalent bonds (e.g., enzymes), and those that exert activity without specific interactions (e.g., serum albumin).

Also contemplated herein are therapeutic molecules (e.g., recombinant therapeutic proteins) used to treat, for example, cancers, immune disorders, infections and/or other diseases. Engineered proteins, including bispecific mAbs and multi-specific fusion proteins, and proteins with optimized pharmacokinetics are also contemplated by the present disclosure.

In some embodiments, the therapeutic protein is Etanercept, Bevacizumab, Rituximab, Adalimumab, Infliximab, Trastuzumab, Insulin glargine, Epoetin alfa, Pegfilgrastim, Ranibizumab, Darbepoetin alfa, Interferon beta-Ia, Interferon beta-Ia. Insulin aspart, Rhu insulin, Octocog alfa, Insulin lispro, Cetuximab, Peginterferon alfa-2a, Interferon beta-Ib, Eptacog alfa, Insulin aspart, OnabotulinumtoxinA, Epoetin beta, Rec antihemophilic factor, Filgrastin, Insulin detemir, Natalizumab, Insulin (humulin) or Palivizumab.

Examples of antibodies, antibody fragments, and/or Fc fusion proteins that may be expressed in the context of the present disclosure include, without limitation, Abagovomab, Abciximab, Actoxumab, Adalimumab, Adecatumumab, Afelimomab, Afutuzumab, Alacizumab pegol, ALD, Alemtuzumab, Alirocumab, Altumomab pentetate, Amatuximab, Anatumomab mafenatox, Anifrolumab, Anrukinzumab, Apolizumab, Arcitumomab, Aselizumab, Atinumab, Atlizumab (or tocilizumab), Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, Cedelizumab, Certolizumab pegol, Cetuximab, Citatuzumab bogatox, Cixutumumab, Clazakizumab, Clenoliximab, Clivatuzumab tetraxetan, Conatumumab, Concizumab, Crenezumab, Dacetuzumab, Daclizumab, Dalotuzumab, Daratumumab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Eldelumab, Elotuzumab, Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab, Farletuzumab, Fasinumab, FBTA, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lambrolizumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Margetuximab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN, Ticilimumab (or tremelimumab), Tildrakizumab, Tigatuzumab, TNX-, Tocilizumab (or atlizumab), Toralizumab, Tositumomab, Tovetumab, Tralokinumab, Trastuzumab, TRBS, Tregalizumab, Tremelimumab, Tucotuzumab celmoleukin, Tuvirumab, Ublituximab, Urelumab, Urtoxazumab, Ustekinumab, Vantictumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab and Zolimomab aritox.

Other examples of Fc fusion proteins that may be expressed in the context of the present disclosure include, without limitation, Etanercept, Alefacept, Abatacept, Rilonacept, Romiplostim, Belatacept and Aflibercept.

Examples of anticoagulants and/or blood factors that may be expressed in the context of the present disclosure include, without limitation, Protein C, Protein S, and antithrombin, Factors I-VIII, prothrombinase, prothrombin, thrombin von Willebrand Factor (vWF), fibrinogen, fibrin and fibrinopeptides.

Examples of bone morphogenetic proteins (BMPs) that may be expressed in the context of the present disclosure include, without limitation, BMP1-BMP7, BMP8a, BMP8b, BMP 10, and BMP15.

Examples of enzymes that may be expressed in the context of the present disclosure include, without limitation, any of the enzymes assigned an Enzyme Commission Number (EC) number (e.g., EC1-EC6) by the International Union of Biochemistry and Molecular Biology (IUBMB) (Webb, Edwin C. Enzyme nomenclature 1992: recommendations of the Nomenclature Committee of the International Union of Biochemistry and Molecular Biology on the nomenclature and classification of enzymes. San Diego: Published for the International Union of Biochemistry and Molecular Biology by Academic Press. ISBN 0-12-227164-5 (1992), incorporated by reference herein). Other examples include: styrene monooxygenase (StyAB), toluene dioxygenase (TODC1C2AB), luciferase and lactase. In some embodiments, the enzyme is toluene dioxygenase. In some embodiments, the enzyme is styrene monoxygenase.

Examples of growth factors that may be expressed in the context of the present disclosure include, without limitation, Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha(TGF-a), Transforming growth factor beta(TGF-P), Tumor necrosis factor-alpha(TNF-), Vascular endothelial growth factor (VEGF), placental growth factor (P1GF), Foetal Bovine Somatotrophin (FBS) and IL-1-IL7.

Examples of peptide hormones that may be expressed in the context of the present disclosure include, without limitation, Amylin (or Islet Amyloid Polypeptide), Antimullerian hormone (or Miillerian inhibiting factor or hormone), Adiponectin, Adrenocorticotropic hormone (or corticotropin), Angiotensinogen and angiotensin, Antidiuretic hormone (or vasopressin, arginine vasopressin), Atrial-natriuretic peptide (or atriopeptin), Brain natriuretic peptide, Calcitonin, Cholecystokinin, Corticotropin-releasing hormone, Enkephalin, Endothelin, Erythropoietin, Follicle-stimulating hormone, Galanin, Gastrin, Ghrelin, Glucagon, Gonadotropin-releasing hormone, Growth hormone-releasing hormone, Human chorionic gonadotropin, Human placental lactogen, Growth hormone, Inhibin, Insulin, Insulin-like growth factor (or somatomedin), Leptin, Lipotropin, Luteinizing hormone, Melanocyte stimulating hormone, Motilin, Orexin, Oxytocin, Pancreatic polypeptide, Parathyroid hormone, Prolactin, Prolactin releasing hormone, Relaxin, Renin, Secretin, Somatostatin, Thrombopoietin, Thyroid-stimulating hormone (or thyrotropin), and Thyrotropin-releasing hormone.

Examples of interferons (IFNs) that may be expressed in the context of the present disclosure include, without limitation, IFN-α, IFN-β, IFN-ω and IFN-γ.

Examples of interleukins that may be expressed in the context of the present disclosure include, without limitation, interleukin 1-17. In some embodiments, the interleukin is Interleukin-4, Interleukin-6, Interleukin-10, Interleukin-11 or Interleukin-13.

Other examples of therapeutic proteins that may be expressed in the context of the ipresent disclosure include, without limitation, Insulin (blood glucose regulator), Pramlintide acetate (glucose control), Growth hormone GH (growth failure), Pegvisoman (growth hormone receptor antagonist), Mecasermin (IGFI, growth failure), Factor VIII (coagulation factor), Factor IX (coagulation factor, Protein C concentrate (anti-coagulation), al-proteinase inhibitor (anti-trypsin inhibitor), Erythropoietin (stimulates erythropoiesis), Filgrastim (granulocyte colony-stimulating factor, G-CSF; stimulates neutrophil proliferation), Sargramostim[36, 37] (granulocytemacrophage colony-stimulating factor, GM-CSF), Oprelvekin (interleukin II, IL11), Human follicle-stimulating hormone (FSH), Human chorionic gonadotropin (HCG), Lutropin-a (human luteinizing hormone), Interleukin 2 (IL2), Interleukin-1 Receptor Agonist, Denileukin diftitox (fusion of IL2 and Diphtheria toxin), Interferon alfacon 1 (consensus interferon), Interferon-2a (IFNa2a), Interferon-2b (IFNa2b), Interferon-n3 (IFNan3), Interferon-pia (rIFN-β), Interferon-β Ib (rIFN-β), Interferon-yIb (IFNy, Salmon calcitonin (32-amino acid linear polypeptide hormone), Teriparatide (part of human parathyroid hormone 1-34 residues), Exenatide (Incretin mimetic with actions similar to glucagon-like peptide 1), Octreotide (octapeptide that mimics natural somatostatin), Dibotermin-a (recombinant human bone morphogenic protein 2), Recombinant human bone morphogenic protein 7, Histrelin acetate (gonadotropin-releasing hormone; GnRH), Palifermin (Keratinocyte growth factor, KGF), Becaplermin (platelet-derived growth factor, PDGF), Nesiritide (recombinant human B-type natriuretic peptide), Lepirudin (recombinant variant of hirudin, another variant is Bivalirudin), Anakinra (interleukin 1 (11_1) receptor antagonist), Enfuviritide (an HIV-1 gp41-derived peptide), β-Glucocerebrosidase (hydrolyzes to glucose and ceramide), Alglucosidase-a (degrades glycogen), Laronidase (digests glycosaminoglycans within lysosomes), Idursulfase (cleaves O-sulfate preventing GAGs accumulation), Galsulfase (cleave terminal sulphate from GAGs), Agalsidase-β (human α-galactosidase A, hydrolyzes glycosphingolipids), Lactase (digest lactose), Pancreatic enzymes (lipase, amylase, protease; digest food), Adenosine deaminase (metabolizes adenosine), Tissue plasminogen activator (tPA, serine protease involved in the breakdown of blood clots), Factor Vila (serine protease, causes blood to clot), Drotrecogin-a (serine protease, human activated protein C), Trypsin (serine protease, hydrolyzes proteins), Botulinum toxin type A (protease, inactivates SNAP-25 which is involved in synaptic vesicle fusion), Botulinum toxin type B (protease that inactivates SNAP-25 which is involved in synaptic vesicle fusion), Collagenase (endopeptidase, digest native collagen), Human deoxyribonuclease I (endonuclease, DNase I, cleaves DNA), Hyaluronidase (hydrolyzes hyaluronan), Papain (cysteine protease, hydrolyzes proteins), L-Asparaginase (catalyzes the conversion of L-asparagine to aspartic acid and ammonia), Rasburicase (urate oxidase, catalyzes the conversion of uric acid to allantoin), Streptokinase (Anistreplase is anisoylated plasminogen streptokinase activator complex (APS AC)), and Antithrombin III (serine protease inhibitor).

Other examples of therapeutic proteins that may be expressed in the context of the present disclosure include antigens, as defined below.

The invention further encompasses engineered *C. acnes* comprising vectors (e.g. plasmids) for the expression of antigens, such as a tumor antigen, a viral antigen, a bacterial antigen, a fungal antigen, a self-antigen, an allergen or a graft-specific antigen.

As used herein, an "antigen" refers to a molecule containing one or more epitopes (e.g., linear, conformational or both) that elicit an immunological response. The antigen may be of any type. In particular, it can be a protein, a polypeptide or a peptide, a carbohydrate, a lipid, a nucleic acid, such as DNA or RNA. In a particular embodiment, it is a protein, a polypeptide or a peptide. As intended herein, "protein" will be understood to encompass protein, polypeptide and peptide. Furthermore, for purposes of the present invention, an "antigen" encompasses a protein which includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts which produce the antigens.

In a particular embodiment, said antigen induces the activation or enhancement of an immune response, in particular specific to said antigen. In an alternative embodiment, said antigen results in tolerization or suppression of an immune response, in particular towards said antigen.

In a particular embodiment, said antigen decreases the subject inflammatory response.

In a particular embodiment, said antigen is a tumor antigen.

By "tumor antigen" is meant herein an antigenic substance produced in tumor cells. Tumor antigens can be, for example, peptide-containing tumor antigens, such as a polypeptide tumor antigen or glycoprotein tumor antigens. A tumor antigen can also be, for example, a saccharide-containing tumor antigen, such as a glycolipid tumor antigen or a ganglioside tumor antigen.

Tumor antigens include, but are not limited to, (a) polypeptide-containing tumor antigens, including polypeptides (which can range, for example, from about 8 to about 20 amino acids in length, although lengths outside this range are also common), lipopolypeptides and glycoproteins, and (b) saccharide-containing tumor antigens, including polysaccharides, mucins, gangliosides, glycolipids and glycoproteins. Moreover, tumor antigens can be (a) full length molecules associated with cancer cells, (b) homologs and modified forms of the same, including molecules with deleted, added and/or substituted portions, and (c) fragments of the same. Tumor antigens include, for example, class I-restricted antigens recognized by CD8+ lymphocytes or class II-restricted antigens recognized by CD4+ lymphocytes.

Numerous tumor antigens are known in the art, including: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CD 4 (associated with, e.g., melanoma), MUM 1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkin's lymphoma), BCR-abl (associated with, e.g., chronic myelogenous leukemia), triosephosphate isomerase, IA 0205, CDC-27, and LDLR-FUT, (c) overexpressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), SA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-I/Melan A, gpIOO, MC1R, melanocyte-stimulating hormone receptor, tyrosinase, tyrosinase related protein-1/TRPI and tyrosinase related protein-2/TRP2 (associated with, e.g., melanoma), (e) prostate associated antigens such as PAP, PSA, PSMA, PSH-P1, PSM-P1, PSM-P2 (associated with e.g., prostate cancer), (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Lex (associated with, e.g., breast and colorectal cancer) as well as various mucins; glycoproteins may be coupled to a carrier protein (e.g., MUC-1 may be coupled to LH); (ii) lipopolypeptides (e.g., MUC-1 linked to a lipid moiety); (iii) polysaccharides (e.g., Globo H synthetic hexasaccharide), which may be coupled to a carrier protein (e.g., to KLH), (iv) gangliosides such as GM2, GM 12, GD2, GD3 (associated with, e.g., brain, lung cancer, melanoma), which also may be coupled to carrier proteins (e.g., KLH).

Other tumor antigens include pi 5, Hom/Me1-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23HI, TAG-72-4, CA 19-9, CA 72-4, CAM 17.1, NuMa, K-ras, p 16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV 18, NB/70K, NY-CO-1, RCAS1, SDCCAG16, TA-90 (Mac-2 binding protein\cyclophilin C-associated protein), TAAL6, TAG72, TLP, TPS, and the like.

In another embodiment, said antigen is a viral antigen.

By "viral antigen" is meant herein a protein encoded by a viral genome.

In certain embodiments, viral antigens preferably include epitopes which are exposed on the surface of the virus during at least one stage of its life cycle. Viral antigens are preferably conserved across multiple serotypes or isolates. Viral antigens suitable for use in the context of the invention include, but are not limited to, antigens derived from one or more of the viruses set forth below as well as the specific antigens examples identified below.

Orthomyxovirus: Viral antigens include, but are not limited to, those derived from an Orthomyxovirus, such as Influenza A, B and C. In certain embodiments, orthomyxovirus antigens are selected from one or more of the viral proteins, including hemagglutinin (HA), neuraminidase (NA), nucleoprotein (NP), matrix protein (MI), membrane protein (M2), one or more of the transcriptase components (PB1, PB2 and PA). In certain embodiments the viral antigen include HA and NA. In certain embodiments, the influenza antigens are derived from interpandemic (annual) flu strains, while in other embodiments, the influenza antigens are derived from strains with the potential to cause a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens include, but are not limited to, those derived from Paramyxoviridae viruses, such as Pneumoviruses (RSV), Paramyxoviruses (PIV), Metapneumovirus and Morbilliviruses (Measles).

Pneumovirus: Viral antigens include, but are not limited to, those derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. In certain embodiments, pneumovirus antigens are selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. In other embodiments, pneumovirus antigens include F, G and M.

Paramyxovirus: Viral antigens include, but are not limited to, those derived from a Paramyxovirus, such as Parainfluenza virus types 1-4 (PIV), Mumps, Sendai viruses, Simian virus 5, Bovine parainfluenza virus, Nipahvirus, Henipavirus and Newcastle disease virus. In certain embodiments, the Paramyxovirus is PIV or Mumps. In certain embodiments, paramyxovirus antigens are selected from one or more of the following proteins: Hemagglutinin-Neuraminidase (HN), Fusion proteins F1 and F2, Nucleoprotein (NP), Phosphoprotein (P), Large protein (L), and Matrix protein (M). In other embodiments, paramyxovirus proteins include HN, F1 and F2. In other embodiments, the Paramyxovirus is Nipahvirus or Henipavirus and the antigens are selected from one or more of the following proteins: Fusion (F) protein, Glycoprotein (G) protein, Matrix (M) protein, Nucleocapsid (N) protein, Large (L) protein and Phosphoprotein (P).

Poxviridae: Viral antigens include, but are not limited to, those derived from Orthopoxvirus such as Variola vera, including but not limited to, Variola major and Variola minor.

Metapneumovirus: Viral antigens include, but are not limited to, Metapneumovirus, such as human metapneumovirus (hMPV) and avian metapneumoviruses (aMPV). In certain embodiments, metapneumovirus antigens are selected from one or more of the following proteins, including surface proteins Fusion (F), Glycoprotein (G) and Small Hydrophobic protein (SH), matrix proteins M and M2, nucleocapsid proteins N, P and L. In other embodiments, metapneumovirus antigens include F, G and M.

Morbillivirus: Viral antigens include, but are not limited to, those derived from a Morbillivirus, such as Measles. In certain embodiments, morbillivirus antigens are selected from one or more of the following proteins: hemagglutinin (H), Glycoprotein (G), Fusion factor (F), Large protein (L), Nucleoprotein (NP), Polymerase phosphoprotein (P), and Matrix (M).

Picornavirus: Viral antigens include, but are not limited to, those derived from Picornaviruses, such as Enteroviruses, Rhinoviruses, Heparnavirus, Cardioviruses and Aphthoviruses. In certain embodiments, the antigens are derived from Enteroviruses, while in other embodiments the enterovirus is Poliovirus. In still other embodiments, the antigens are derived from Rhinoviruses.

Enterovirus: Viral antigens include, but are not limited to, those derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. In certain embodiments, the antigens are derived from Enteroviruses, while in other embodiments the enterovirus is Poliovirus. In certain embodiments, the enterovirus antigens are selected from one or more of the following Capsid proteins VP0, VP1, VP2, VP3 and VP4.

Bunyavirus: Viral antigens include, but are not limited to, those derived from an Orthobunyavirus, such as California encephalitis virus, a Phlebovirus, such as Rift Valley Fever virus, or a Nairovirus, such as Crimean-Congo hemorrhagic fever virus. Rhinovirus: Viral antigens include, but are not limited to, those derived from rhinovirus. In certain embodiments, the rhinovirus antigens are selected from one or more of the following Capsid proteins: VPO, VP1, VP2, VP2 and VP4.

Heparnavirus: Viral antigens include, but are not limited to, those derived from a Heparnavirus, such as, by way of example only, Hepatitis A virus (HAV).

Togavirus: Viral antigens include, but are not limited to, those derived from a Togavirus, such as a Rubivirus, an Alphavirus, or an Arterivirus. In certain embodiments, the antigens are derived from Rubivirus, such as by way of example only, Rubella virus. In certain embodiments, the togavirus antigens are selected from E1, E2, E3, C, NSP-1, NSPO-2, NSP-3 or NSP-4. In certain embodiments, the togavirus antigens are selected from E1, E2 or E3.

Flavivirus: Viral antigens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus. In certain embodiments, the flavivirus antigens are selected from PrM, M, C, E, NS-1, NS-2a, NS2b, NS3, NS4a, NS4b, and NS5. In certain embodiments, the flavivirus antigens are selected from PrM, M and E.

Pestivirus: Viral antigens include, but are not limited to, those derived from a Pestivirus, such as Bovine viral diarrhea (BVDV), Classical swine fever (CSFV) or Border disease (BDV).

Hepadnavirus: Viral antigens include, but are not limited to, those derived from a Hepadnavirus, such as Hepatitis B virus. In certain embodiments, the hepadnavirus antigens are selected from surface antigens (L, M and S), core antigens (HBc, HBe).

Hepatitis C virus: Viral antigens include, but are not limited to, those derived from a Hepatitis C virus (HCV). In certain embodiments, the HCV antigens are selected from one or more of E1, E2, E1/E2, NS345 polyprotein, NS 345-core polyprotein, core, and/or peptides from the non-structural regions. In certain embodiments, the Hepatitis C virus antigens include one or more of the following: HCV E1 and or E2 proteins, E1/E2 heterodimer complexes, core proteins and non-structural proteins, or fragments of these antigens, wherein the non-structural proteins can optionally be modified to remove enzymatic activity but retain immunogenicity.

Rhabdovirus: Viral antigens include, but are not limited to, those derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS).

Caliciviridae; Viral antigens include, but are not limited to, those derived from Caliciviridae, such as Norwalk virus, and Norwalk-like Viruses, such as Hawaii Virus and Snow Mountain Virus.

Coronavirus: Viral antigens include, but are not limited to, those derived from a Coronavirus, SARS, Human respiratory coronavirus, Avian infectious bronchitis (IBV), Mouse hepatitis virus (MHV), and Porcine transmissible gastroenteritis virus (TGEV). In certain embodiments, the coronavirus antigens are selected from spike (S), envelope (E), matrix (M), nucleocapsid (N), and Hemagglutinin-esterase glycoprotein (HE). In certain embodiments, the coronavirus antigen is derived from a SARS virus. In certain embodiments, the coronavirus is derived from a SARS viral antigen as described in WO 04/92360.

Retrovirus: Viral antigens include, but are not limited to, those derived from a Retrovirus, such as an Oncovirus, a Lentivirus or a Spumavirus. In certain embodiments, the oncovirus antigens are derived from HTLV-1, HTLV-2 or HTLV-5. In certain embodiments, the lentivirus antigens are derived from HIV-1 or HIV-2. In certain embodiments, the antigens are derived from HIV-1 subtypes (or clades), including, but not limited to, HIV-1 subtypes (or clades) A, B, C, D, F, G, H, J. K, O. In other embodiments, the antigens are derived from HIV-1 circulating recombinant forms (CRFs), including, but not limited to, A/B, A/E, A/G, A/G/I, etc. In certain embodiments, the retrovirus antigens are selected from gag, pol, env, tax, tat, rex, rev, nef, vif, vpu, and vpr. In certain embodiments, the HIV antigens are selected from gag (p24gag and p55gag), env (gp160 and gp41), pol, tat, nef, rev vpu, miniproteins, (preferably p55 gag and gp140v delete). In certain embodiments, the HIV antigens are derived from one or more of the following strains: HIVIIIb, HIVSF2, HIVLAV, HIVLAI, HIVMN, HIV-1CM235, HIV-1US4, HIV-1 SF162, HIV-1TV1, HIV-1MJ4. In certain embodiments, the antigens are derived from endogenous human retroviruses, including, but not limited to, HERV-K ("old" HERV-K and "new" HERV-K).

Reovirus: Viral antigens include, but are not limited to, those derived from a Reovirus, such as an Orthoreovirus, a Rotavirus, an Orbivirus, or a Coltivirus. In certain embodiments, the reovirus antigens are selected from structural proteins λ1, λ2, λ3, μ1, μ2, σ1, σ2, or σ3, or nonstructural proteins σNS, μNS, or ols. In certain embodiments, the reovirus antigens are derived from a Rotavirus. In certain embodiments, the rotavirus antigens are selected from VP1, VP2, VP3, VP4 (or the cleaved product VP5 and VP8), NSP 1, VP6, NSP3, NSP2, VP7, NSP4, or NSP5. In certain embodiments, the rotavirus antigens include VP4 (or the cleaved product VP5 and VP8), and VP7.

Parvovirus: Viral antigens include, but are not limited to, those derived from a Parvovirus, such as Parvovirus B19. In certain embodiments, the Parvovirus antigens are selected from VP-1, VP-2, VP-3, NS-1 and NS-2. In certain embodiments, the Parvovirus antigen is capsid protein VP1 or VP-2.

Delta hepatitis virus (HDV): Viral antigens include, but are not limited to, those derived from HDV, particularly δ-antigen from HDV.

Hepatitis E virus (HEV): Viral antigens include, but are not limited to, those derived from HEV.

Hepatitis G virus (HGV): Viral antigens include, but are not limited to, those derived from HGV.

Human Herpesvirus: Viral antigens include, but are not limited to, those derived from a Human Herpesvirus, such as, by way of example only, Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). In certain embodiments, the Human Herpesvirus antigens are selected from immediate early proteins (a), early proteins (β), and late proteins (γ). In certain embodiments, the HSV antigens are derived from HSV-1 or HSV-2 strains. In certain embodiments, the HSV antigens are selected from glycoproteins gB, gC, gD and gH, fusion protein (gB), or immune escape proteins (gC, gE, or gI). In certain embodiments, the VZV antigens are selected from core, nucleocapsid, tegument, or envelope proteins. A live attenuated VZV vaccine is commercially available. In certain embodiments, the EBV antigens are selected from early antigen (EA) proteins, viral capsid antigen (VCA), and glycoproteins of the membrane antigen (MA). In certain embodiments, the CMV antigens are selected from capsid proteins, envelope glycoproteins (such as gB and gH), and tegument proteins. In other embodiments, CMV antigens may be selected from one or more of the following proteins: pp65, 1E1, gB, gD, gH, gL, gM, gN, gO, UL128, UL129, gUL130, UL150, UL131, UL33, UL78, US27, US28, RL5A, RL6, RL10, RL11, RL12, RL13, UL1, UL2, UL4, UL5, UL6, UL7, UL8, UL9, UL10, UL11, UL14, UL15A, UL16, UL17, UL18, UL22A, UL38, UL40, UL41A, UL42, UL116, UL119, UL120, UL121, UL124, UL132, UL147A, UL148, UL142, UL144, UL141, UL140, UL135, UL136, UL138, UL139, UL133, UL135, UL148A, UL148B, UL148C, UL148D, US2, US3, US6, US7, US8, US9, US10, US11, US12, US13, US14, US15, US16, US17, US18, US19, US20, US21, US29, US30 and US34A. CMV antigens may also be fusions of one or more CMV proteins, such as, by way of example only, pp65/IEI (Reap et al., Vaccine (2007) 25:7441-7449).

Papovaviruses: Antigens include, but are not limited to, those derived from Papovaviruses, such as Papillomaviruses and Polyomaviruses. In certain embodiments, the Papillomaviruses include HPV serotypes 1, 2, 4, 5, 6, 8, 11, 13, 16, 18, 31, 33, 35, 39, 41, 42, 47, 51, 57, 58, 63 and 65. In certain embodiments, the HPV antigens are derived from serotypes 6, 11, 16 or 18. In certain embodiments, the HPV antigens are selected from capsid proteins (L1) and (L2), or E1-E7, or fusions thereof. In certain embodiments, the HPV antigens are formulated into virus-like particles (VLPs). In certain embodiments, the Polyomavirus viruses include BK virus and JK virus. In certain embodiments, the Polyomavirus antigens are selected from VP1, VP2 or VP3.

Adenovirus: Antigens include those derived from Adenovirus. In certain embodiments, the Adenovirus antigens are derived from Adenovirus serotype 36 (Ad-36). In certain embodiments, the antigen is derived from a protein or peptide sequence encoding an Ad-36 coat protein or fragment thereof (WO 2007/120362).

In another embodiment, said antigen is a bacterial antigen.

Examples of bacterial antigens suitable for use in the context of the invention include, but are not limited to, proteins, polysaccharides and lipopolysaccharides, which are derived from a bacteria. In certain embodiments, the bacterial antigens include epitopes which are exposed on the surface of the bacteria during at least one stage of its life cycle. Bacterial antigens are preferably conserved across multiple serotypes. In certain embodiments, the bacterial antigens include antigens derived from one or more of the bacteria set forth below as well as the specific antigens examples identified below:

*Neisseria meningitidis*: *N. meningitidis* antigens include, but are not limited to, proteins, saccharides (including a polysaccharide, or lipooligosaccharide), derived from *N. meningitidis* serogroup such as A, C, W135, Y, X or B. A useful combination of *N. meningitidis* protein antigens includes one, two or three of a NHBA, a fHbp, and/or a NadA immunogen.

*Streptococcus pneumoniae*: *Streptococcus pneumoniae* antigens include, but are not limited to, a saccharide (including a polysaccharide or an oligosaccharide) and/or protein from *Streptococcus pneumoniae*. In certain embodiments saccharide antigens are selected from one or more of the following pneumococcal serotypes 1, 2, 3, 4, 5, 6A, 6B, 7F, 8, 9N, 9V, 10A, 11A, 12F, 14, 15B, 17F, 18C, 19A, 19F, 20, 22F, 23F, and/or 33F. A vaccine or immunogenic composition may include multiple serotypes e.g. 2, 3, 4, 5, 6, 7, 8, 9, 10, 11, 12, 13, 14, 15, 16, 17, 18, 19, 20, 21, 22, 23 or more serotypes. 7-valent, 9-valent, 10-valent, 11-valent and 13-valent conjugate combinations are already known in the art, as is a 23-valent unconjugated combination. For example, an 10-valent combination may include saccharide from serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; r 22F and 15B; A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F. etc. In certain embodiments, protein antigens may be selected from a protein identified in WO98/18931, WO98/18930, U.S. Pat. Nos. 6,699,703, 6,800,744, WO97/43303, WO97/37026, WO 02/079241, WO 02/34773, WO 00/06737, WO 00/06738, WO 00/58475, WO 2003/082183, WO 00/37105, WO 02/22167, WO 02/22168, WO 2003/104272, WO 02/08426, WO 01/12219, WO 99/53940, WO 01/81380, WO 2004/092209, WO 00/76540, WO 2007/116322, LeMieux et al., Infect. Imm. (2006) 74:2453-2456, Hoskins et al., J. Bacteriol. (2001) 183:5709-5717, Adamou et al., Infect. Immun. (2001) 69(2):949-958, Briles et al., J. Infect. Dis. (2000) 182:1694-1701, Talkington et al., Microb. Pathog. (1996) 21(1):17-22, Bethe et al., FEMS Microbiol. Lett. (2001) 205(1):99-104, Brown et al., Infect. Immun. (2001) 69:6702-6706, Whalen et al., FEMS Immunol. Med. Microbiol. (2005) 43:73-80, Jomaa et al., Vaccine (2006) 24(24):5133-5139. In other embodiments, *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, SpIC1, Sp130, Sp125, Sp133, pneumococcal pilus subunits.

*Streptococcus pyogenes* (Group A *Streptococcus*): Group A *Streptococcus* antigens include, but are not limited to, a protein identified in WO 02/34771 or WO 2005/032582 (including GAS 40), fusions of fragments of GAS M proteins (including those described in WO 02/094851, and Dale, Vaccine (1999) 17:193-200, and Dale, Vaccine 14(10): 944-948), fibronectin binding protein (Sfbl), Streptococcal heme-associated protein (Shp), and Streptolysin S (SagA).

*Moraxella catarrhalis: Moraxella* antigens include, but are not limited to, antigens identified in WO 02/18595 and WO 99/58562, outer membrane protein antigens (HMW-OMP), C-antigen, and/or LPS.

*Bordetella pertussis*: Pertussis antigens include, but are not limited to, pertussis toxoid (PT) and filamentous haemagglutinin (FHA) from *B. pertussis*, optionally also combination with pertactin and/or agglutinogens 2 and 3.

*Burkholderia: Burkholderia* antigens include, but are not limited to *Burkholderia mallei, Burkholderia pseudomallei* and *Burkholderia cepacia.*

*Staphylococcus aureus: S. aureus* antigens include, but are not limited to, a polysaccharide and/or protein from *S. aureus. S. aureus* polysaccharides include, but are not limited to, type 5 and type 8 capsular polysaccharides (CP5 and CP8) optionally conjugated to nontoxic recombinant *Pseudomonas aeruginosa* exotoxin A, such as StaphVAX™, type 336 polysaccharides (336PS), polysaccharide intercellular adhesions (PIA, also known as PNAG). *S. aureus* proteins include, but are not limited to, antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin). In certain embodiments, *S. aureus* antigens may be selected from a protein identified in WO 02/094868, WO 2008/019162, WO 02/059148, WO 02/102829, WO 03/011899, WO 2005/079315, WO 02/077183, WO 99/27109, WO 01/70955, WO 00/12689, WO 00/12131, WO 2006/032475, WO 2006/032472, WO 2006/032500, WO 2007/113222, WO 2007/113223, WO 2007/113224. In other embodiments, *S. aureus* antigens may be selected from IsdA, IsdB, IsdC, SdrC, SdrD, SdrE, ClfA, ClfB, SasF, SasD, SasH (AdsA), Spa, EsaC, EsxA, EsxB, Emp, HlaH35L, CP5, CP8, PNAG, 336PS.

*Staphylococcus epidermis: S. epidermidis* antigens include, but are not limited to, slime-associated antigen (SAA).

*Clostridium tetani* (Tetanus): Tetanus antigens include, but are not limited to, tetanus toxoid (TT).

*Clostridium perfringens*: Antigens include, but are not limited to, Epsilon toxin from *Clostridium perfringens.*

*Clostridium botulinum* (Botulism): Botulism antigens include, but are not limited to, those derived from *C. botulinum.*

*Corynebacterium diphtheriae* (Diphtheria): Diphtheria antigens include, but are not limited to, diphtheria toxin, preferably detoxified, such as CRM 197. In certain embodiments, the diphtheria toxoids are used as carrier proteins.

*Haemophilus influenzae* B (Hib): Hib antigens include, but are not limited to, a Hib saccharide antigen. The Hib antigens may be conjugated.

*Pseudomonas aeruginosa: Pseudomonas* antigens include, but are not limited to, endotoxin A, Wzz protein, *P. aeruginosa* LPS, LPS isolated from PAO1 (O5 serotype), and/or Outer Membrane Proteins, including Outer Membrane Proteins F (OprF).

*Brucella*: Bacterial antigens derived from *Brucella*, including but not limited to, *B. abortus, B. canis, B. melitensis, B. neotomae, B. ovis, B. suis* and *B. pinnipediae.*

*Francisella*: Bacterial antigens derived from *Francisella*, including but not limited to, *F. novicida, F. philomiragia* and *F. tularensis.*

*Streptococcus agalactiae* (Group B *Streptococcus*): Group B *Streptococcus* antigens include, but are not limited to, a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neiserria gonorrhoeae: Gonorrhoeae* antigens include, but are not limited to, Por (or porin) protein, such as PorB (see Zhu et al., Vaccine (2004) 22:660-669), a transferrin binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al, J Infectious Disease (2000) 182:848-855), also see, e.g., WO99/24578, WO99/36544, WO99/57280, WO02/079243).

*Chlamydia trachomatis: Chlamydia trachomatis* antigens include, but are not limited to, antigens derived from serotypes A, B, Ba and C (agents of trachoma, a cause of blindness), serotypes L1, L2 & L3 (associated with Lymphogranuloma venereum), and serotypes, D-K. In certain embodiments, *Chlamydia trachomatis* antigens include, but are not limited to, an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include, but are not limited to, TmpA antigen.

*Haemophilus ducreyi* (causing chancroid): *Ducreyi* antigens include, but are not limited to, outer membrane protein (DsrA).

*Enterococcus faecalis* or *Enterococcus faecium*: Antigens include, but are not limited to, a trisaccharide repeat or other *Enterococcus* derived antigens.

*Helicobacter pylori: H. pylori* antigens include, but are not limited to, CagA, VacA, NAP, HopX, HopY and/or urease antigen.

*Staphylococcus saprophyticus*: Antigens include, but are not limited to, the 160 kDa hemagglutinin of *S. saprophyticus* antigen.

*Yersinia enterocolitica*: Antigens include, but are not limited to, LPS.

*E. coli: E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC antigens include, but are not limited to, accessory colonization factor (orf3526), orf353, bacterial Ig-like domain (group 1) protein (orf405), orf1364, NodT-family outer-membrane-factor-lipoprotein efflux transporter (orf1767), gspK (orf3515), gspJ (orf3516), tonB-dependent siderophore receptor (orf3597), fimbrial protein (orf3613), upec-948, upec-1232, A chain precursor of the type-1 fimbrial protein (upec-1875), yap H homolog (upec-2820), and hemolysin A (recp-3768).

*Bacillus anthracis* (anthrax): *B. anthracis* antigens include, but are not limited to, A-components (lethal factor (LF) and edema factor (EF)), both of which can share a common B-component known as protective antigen (PA). In certain embodiments, *B. anthracis* antigens are optionally detoxified.

*Yersinia pestis* (plague): Plague antigens include, but are not limited to, F1 capsular antigen, LPS, *Yersinia pestis* V antigen.

*Mycobacterium tuberculosis*: Tuberculosis antigens include, but are not limited to, lipoproteins, LPS, BCG antigens, a fusion protein of antigen 85B (Ag85B), ESAT-6, *Mycobacterium tuberculosis* (Mtb) isocitrate dehydrogenase associated antigens, and MPT51 antigens.

*Rickettsia*: Antigens include, but are not limited to, outer membrane proteins, including the outer membrane protein A and/or B (OmpB), LPS, and surface protein antigen (SPA).

*Listeria monocytogenes*: Bacterial antigens include, but are not limited to, those derived from *Listeria monocytogenes.*

*Chlamydia pneumoniae*: Antigens include, but are not limited to, those identified in WO 02/02606.

*Vibrio cholerae*: Antigens include, but are not limited to, proteinase antigens, LPS, particularly lipopolysaccharides of *Vibrio cholerae* II, O1 Inaba O-specific polysaccharides, *V. cholera* O139, antigens of IEM108 vaccine and Zonula occludens toxin (Zot).

*Salmonella typhi* (typhoid fever): Antigens include, but are not limited to, capsular polysaccharides preferably conjugates (Vi, i.e. vax-TyVi).

*Borrelia burgdorferi* (Lyme disease): Antigens include, but are not limited to, lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein), VIsE Antigenic Variation Protein.

*Porphyromonas gingivalis*: Antigens include, but are not limited to, *P. gingivalis* outer membrane protein (OMP).

*Klebsiella*: Antigens include, but are not limited to, an OMP, including OMP A, or a polysaccharide optionally conjugated to tetanus toxoid.

Other bacterial antigens used in the context of the invention include, but are not limited to, capsular antigens, polysaccharide antigens, or protein antigens of any of the above. In certain embodiments, the bacterial antigens used in the context of the invention are derived from gram-negative bacteria, while in other embodiments they are derived from gram-positive bacteria. In certain embodiments, the bacterial antigens used in the context of the invention are derived from aerobic bacteria, while in other embodiments they are derived from anaerobic bacteria.

In another embodiment, said antigen is a fungal antigen.

Examples of fungal antigens used in the context of the invention include, but are not limited to, those derived from one or more of the fungi set forth below.

Fungal antigens may be derived from Dermatophytes, including: *Epidermophyton floccosum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleinii, Trichophyton tonsurans, Trichophyton verrucosum, T. verrucosum* var. *album*, var. *discoides*, var. *ochraceum, Trichophyton violaceum*, and/or *Trichophyton faviforme.*

Fungal antigens may also be derived from *Aspergillus fumigatus, Aspergillus flavus, Aspergillus niger, Aspergillus nidulans, Aspergillus terreus, Aspergillus sydowii, Aspergillus flavarus, Aspergillus glaucus, Blastoschizomyces capitatus, Candida albicans, Candida enolase, Candida tropicalis, Candida glabrata, Candida krusei, Candida parapsilosis, Candida stellatoidea, Candida krusei, Candida parakwsei, Candida lusitaniae, Candida pseudotropicalis, Candida guilliermondii, Cladosporium carrionii, Coccidioides immitis, Blastomyces dermatitidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis Pythium insidiosum, Pityrosporum ovale, Saccharomyces cerevisiae, Saccharomyces boulardii, Saccharomyces pombe, Scedosporium apiospermum, Sporothrix schenckii, Trichosporon Beigelii, Toxoplasma Gondii, Penicillium Mameffei, Malassezia* Spp., *Fonsecaea* Spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monilinia* spp, *Rhizoctonia* spp, *Paecilomyces* spp, *Pithomyces* spp, and *Cladosporium* spp.

For example, the fungal antigen may elicit an immune response against a *Candida* fungus such as *C. albicans.*

In another embodiment, said antigen is a self-antigen.

In the context of the invention, the term "self-antigen" refers to an immunogenic antigen or epitope which is native to the subject and which may be involved in the pathogenesis of an autoimmune disease.

In some embodiments, the self-antigen is a central nervous system (CNS) antigen. In some embodiments, the self-antigen is a multiple sclerosis-associated antigen, a diabetes mellitus-associated antigen, a rheumatoid arthritis associated antigen, a myocarditis associated self-antigen, or a thyroiditis associated antigen.

Exemplary self-antigens are disclosed, for example, in US Patent Application Publication 2016/0022788, which is incorporated herein by reference in its entirety.

In some embodiments, the self-antigen is a multiple sclerosis-associated antigen. In some embodiments, the self-antigen is an antigenic peptide of or derived from myelin oligodendrocyte glycoprotein (MOG), myelin basic protein (MBP), myelin associated glycoprotein (MAG), alphaB-crystallin, S100beta, or proteolipid protein (PLP).

In some embodiments, the self-antigen is a diabetes mellitus-associated antigen. In some embodiments, the self-antigen is selected from insulin, chromogranin A, glutamic acid decarboxylase (GAD1; GAD67), glutamate decarboxylase 2 (GAD2; GAD65) and islet-specific glucose-6-phosphatase catalytic subunit-related protein and combinations thereof. Antigenic fragments and antigenic derivatives of these antigens are also contemplated. In some embodiments, the antigen can be proinsulin.

In some embodiments, the self-antigen is a rheumatoid arthritis associated antigen. In some embodiments, the rheumatoid arthritis associated self-antigen can be the peptide (Q/R)(K/R)RAA. In some embodiments, the arthritis associated self-antigen can be type II collagen or a fragment thereof.

In some embodiments, the self-antigen is a myocarditis associated self-antigen. In some embodiments, the myocarditis associated self-antigen is myosin or an antigenic fragment or antigenic derivative. In some embodiments, the antigen can be a peptide contained in human myosin. In some embodiments, the antigen can be a peptide contained within a-myosin.

In some embodiments, the self-antigen is a thyroiditis associated antigen. In some embodiments, the self-antigen is selected from thyroid peroxidase (TPO), thyroglobulin, or Pendrin.

In another embodiment, said antigen is an allergen.

An "allergen" is defined as a substance, usually a protein, which elicits the production of IgE antibodies in predisposed individuals. Similar definitions are presented in the following references: Clin. Exp. Allergy, No. 26, pp. 494-516 (1996); Mol. Biol. of Allergy and Immunology, ed. R. Bush, Immunology and Allergy Clinics of North American Series (August 1996). In a particular embodiment, the antigen is a protein allergen, i.e. any amino acid chain likely to trigger an allergic response, including short peptides of about 6 to 20 amino acids, polypeptides, or full proteins.

Non limitative examples of allergens include pollen allergens (such as tree-, herb, weed-, and grass pollen allergens), insect allergens (such as inhalant, saliva and venom allergens, e.g., cockroach and midges allergens, hymenoptera venom allergens), mite allergens, animal hair and dandruff allergens (from e.g. dog, cat, horse, rat, mouse etc.), and food allergens.

For instance, the protein allergen may be selected from the group consisting of a protein allergen of the genus *Dermatophagoides*; a protein allergen of the genus *Fells*; a protein allergen of the genus *Ambrosia*; a protein allergen of the genus *Lolium*; a protein allergen of the genus *Cryptomeria*; a protein allergen of the genus *Alternaria*; a protein allergen of the genus Alder, a protein allergen of the genus *Betula*; a protein allergen of the genus of *Blomia*; a protein allergen of the genus *Quercus*; a protein allergen of the genus *Olea*; a protein allergen of the genus *Artemisia*; a protein allergen of the genus *Plantago*; a protein allergen of the genus *Parietaria*; a protein allergen of the genus *Canine*; a protein allergen of the genus *Blattella*; a protein allergen of the genus *Apis*; a protein allergen of the genus *Cupressus*; a protein allergen of the genus *Thuya*; a protein allergen of the genus *Chamaecyparis*; a protein allergen of the genus *Periplaneta*; a protein allergen of the genus *Agropyron*; a protein allergen of the genus *Secale*; a protein allergen of the genus *Triticum*; a protein allergen of the genus *Cynorhodon*; a protein allergen of the genus *Juniperus*; a protein allergen of the genus *Dactylis*; a protein allergen of the genus *Festuca*; a protein allergen of the genus *Poa*; a protein allergen of the genus *Avena*; a protein allergen of the genus *Holcus*; a protein allergen of the genus *Anthoxanthum*; a protein allergen of the genus *Arrhenatherum*; a protein allergen of the genus *Agrostis*; a protein allergen of the genus *Phleum*; a protein allergen of the genus *Phalaris*; a protein allergen of the genus *Paspalum*; and a protein allergen of the genus Sorghum.

Examples of various known protein allergens derived from some of the above-identified genus include: *Betula* (*verrucosa*) Bet v I; Bet v II; *Blomia* Blo t I; Blo t III; Blo t V; Blo t XII; *Cynorhodon* Cyn d I; *Dermatophagoides* (*pteronyssinus* or *farinae*) Der p I; Der p II; Der p III; Der p VII; Der f I; Der f II; Der f III; Der f VII; *Felis* (*domesticus*) Fel d I; *Ambrosia* (*artemiisfolia*) Amb a 1.1; Amb a 1.2; Amb a 1.3; Amb a 1.4; Amb a II; *Lollium* (*perenne*) Lol p I; Lot p II; Lol p III; Lot p IV; Lol p IX (Lol p V or Lol p Ib); *Cryptomeria* (*japonica*) Cry j 1; Cry j 11; *Canis* (*familiaris*) Can f 1; Can f II; *Juniperus* (*sabinoides* or *virginiana*) Jun s 1; Jun v 1; *Juniperus* (*ashei*) Jun a 1; Jun a II; *Dactylis* (*glomerata*) Dac g 1; Dac g V; Poa (*pretensis*) Poa p 1; Phl p I; Phl p V; Phl p VI and *Sorghum* (*halepensis*) Sor h I.

Food allergens may originate from milk and milk products, eggs, legumes (peanuts and soy), tree nuts, cereals (such as wheat), brassicaceae (such as mustard), crustaceans, fish, and mollusks. In particular, food allergens may be ovalbumin or gluten.

The invention also encompasses vaccine and/or immunogenic and/or immunotherapeutic compositions comprising a DNA vector, as defined above, comprising a nucleic acid encoding an antigen, such as a tumor antigen, a viral antigen, a bacterial antigen, a fungal antigen, a self-antigen, an allergen or a graft-specific antigen, as defined above, or an engineered *C. acnes* comprising said DNA vector; and optionally an adjuvant.

Any conventional or exploratory, synthetic or biological adjuvant for vaccination, including heat-labile enterotoxin (LT), cholera-toxin (CT), cholera toxin B subunit (CTB), polymerised liposomes, mutant toxins, probiotic bacteria, oligonucleotides, RNA, siRNA, DNA, lipids can be used.

The invention also encompasses methods to prevent and/or a treat cancer in a subject in need thereof, comprising administering to said subject a therapeutically or prophylactically efficient amount of a DNA vector comprising a nucleic acid encoding a tumor antigen, as defined above, or of an engineered *C. acnes* comprising said DNA vector. The invention also concerns a DNA vector comprising a nucleic acid encoding a tumor antigen, as defined above, or an engineered *C. acnes* comprising said DNA vector for use in a method to prevent and/or treat cancer in a subject.

As used herein, the term "cancer" means a type of hyperproliferative disease that includes a malignancy characterized by deregulated or uncontrolled cell growth. Cancers of virtually every tissue are known. Examples of cancer include, but are not limited to, carcinoma, lymphoma, blastema, sarcoma, and leukemia or lymphoid malignancies. More particular examples of such cancers are noted below and include squamous cell cancer (e.g., epithelial squamous cell cancer), lung cancer (including small-cell lung cancer, non-small cell lung cancer, adenocarcinoma of the lung and squamous carcinoma of the lung), cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer, uterine carcinoma, salivary gland carcinoma, kidney or renal cancer, prostate cancer, thyroid cancer, hepatic carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

The term "cancer," is encompassed within the scope of the broader term "abnormal cellular proliferation", which can also be referred to as "excessive cellular proliferation or "cellular proliferative disease". Examples of diseases associated abnormal cellular proliferation include metastatic tumors, malignant tumors, benign tumors, cancers, precancers, hyperplasias, warts, and polyps, as well as non-cancerous conditions such as benign melanomas, benign chondroma, benign prostatic hyperplasia, moles, dysplastic nevi, dysplasia, hyperplasias, and other cellular growths occurring within the epidermal layers. Classes of precancers include acquired small or microscopic precancers, acquired large lesions with nuclear atypia, precursor lesions occurring with inherited hyperplastic syndromes that progress to cancer, and acquired diffuse hyperplasias and diffuse metaplasias. Examples of small or microscopic precancers include HGSIL (high grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma.

The invention also encompasses methods to prevent and/or treat a viral infection in a subject in need thereof, comprising administering to said subject a therapeutically or prophylactically efficient amount of a DNA vector comprising a nucleic acid encoding a viral antigen, as defined above, or of an engineered *C. acnes* comprising said DNA vector. The invention also concerns a DNA vector comprising a nucleic acid encoding a viral antigen, as defined above, or an engineered *C. acnes* comprising said DNA vector for use in a method to prevent and/or treat a viral infection in a subject.

In said embodiment, said antigen preferably induces the activation or enhancement of an immune response, in particular specific to said antigen.

Particular examples of viral infections include, but are not limited to, cytomegalovirus (CMV) pneumonia, enteritis and retinitis; Epstein-Barr virus (EBV) lymphoproliferative disease; chicken pox/shingles (caused by varicella zoster virus, VZV); HSV-1 and -2 mucositis; HSV-6 encephalitis, BK-virus hemorrhagic cystitis; viral influenza; pneumonia from respiratory syncytial virus (RSV); AIDS (caused by HIV); and hepatitis A, B or C. Additional examples of viral infections include infections caused by Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arenaviridae (hemorrhagic fever viruses); Reoviridae (e.g., reoviruses, orbiviruses and rotaviruses); Bimaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C)); Norwalk and related viruses, and astroviruses.

The invention also encompasses methods to prevent and/or treat a bacterial infection in a subject in need thereof, comprising administering to said subject a therapeutically or prophylactically efficient amount of a DNA vector comprising a nucleic acid encoding a bacterial antigen, as defined above, or of an engineered *C. acnes* comprising said DNA vector. The invention also concerns a DNA vector comprising a nucleic acid encoding a bacterial antigen, as defined above, or an engineered *C. acnes* comprising said DNA vector for use in a method to prevent and/or treat a bacterial infection in a subject.

In said embodiment, said antigen preferably induces the activation or enhancement of an immune response, in particular specific to said antigen.

Examples of bacterial infections include, but are not limited to, infections caused by *Helicobacter pyloris, Borrelia burgdorferi, Legionella pneumophila, Mycobacteria* sp. (such as *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix*

*rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira*, and *Actinomyces israelii.*

The invention also encompasses methods to prevent and/or treat a fungal infection in a subject in need thereof, comprising administering to said subject a therapeutically or prophylactically efficient amount of a DNA vector comprising a nucleic acid encoding a fungal antigen, as defined above, or of an engineered *C. acnes* comprising said DNA vector. The invention also concerns a DNA vector comprising a nucleic acid encoding a fungal antigen, as defined above, or an engineered *C. acnes* comprising said DNA vector for use in a method to prevent and/or treat a fungal infection in a subject.

In said embodiment, said antigen preferably induces the activation or enhancement of an immune response, in particular specific to said antigen.

Examples of fungal infections include but are not limited to: aspergillosis; thrush (caused by *Candida albicans*); cryptococcosis (caused by *Cryptococcus*); and histoplasmosis. Thus, examples of fungal infections include, but are not limited to, infections caused by *Cryptococcus neoformans, Histoplasma capsulatum, Coccidioides immitis, Blastomyces dermatitidis, Chlamydia trachomatis*, or *Candida albicans.*

The invention also encompasses methods to prevent and/or treat an auto-immune disease in a subject in need thereof, comprising administering to said subject a therapeutically or prophylactically efficient amount of a DNA vector comprising a nucleic acid encoding a self-antigen, as defined above, or of an engineered *C. acnes* comprising said DNA vector. The invention also concerns a DNA vector comprising a nucleic acid encoding a self-antigen, as defined above, or an engineered *C. acnes* comprising said DNA vector for use in a method to prevent and/or treat an auto-immune disease in a subject.

In said embodiment, said antigen preferably results in tolerization or suppression of an immune response, in particular towards said antigen.

Autoimmune diseases include, but are not limited to, multiple sclerosis, rheumatoid arthritis, myasthenia gravis, psoriasis, systemic lupus erythematosus, autoimmune thyroiditis (Hashimoto's thyroiditis), Graves' disease, inflammatory bowel disease, autoimmune uveoretinitis, myocarditis, polymyositis, and certain types of diabetes, including Type 1 diabetes.

The invention also encompasses methods to prevent and/or treat allergy, such as asthma in a subject in need thereof, comprising administering to said subject a therapeutically or prophylactically efficient amount of a DNA vector comprising a nucleic acid encoding an allergen, as defined above, or of an engineered *C. acnes* comprising said DNA vector. The invention also concerns a DNA vector comprising a nucleic acid encoding an allergen, as defined above, or an engineered *C. acnes* comprising said DNA vector for use in a method to prevent and/or treat allergy, such as asthma in a subject.

In said embodiment, said antigen preferably results in tolerization or suppression of an immune response, in particular towards said antigen.

In the context of the disclosure allergy relates to asthma or to the allergies due to the above-defined allergens.

The invention also encompasses methods to prevent and/or treat graft rejection in a subject in need thereof, comprising administering to said subject a therapeutically or prophylactically efficient amount of a DNA vector comprising a nucleic acid encoding a graft-specific antigen, as defined above, or of an engineered *C. acnes* comprising said DNA vector. The invention also concerns a DNA vector comprising a nucleic acid encoding a graft-specific antigen, as defined above, or an engineered *C. acnes* comprising said DNA vector for use in a method to prevent and/or treat graft rejection in a subject.

In said embodiment, said antigen preferably results in tolerization or suppression of an immune response, in particular towards said antigen.

Unless defined otherwise, all technical and scientific terms used herein have the same meaning as commonly understood by one of ordinary skill in the art to which this invention belongs.

All publications mentioned herein are incorporated herein by reference. It is understood that the present disclosure supersedes any disclosure of an incorporated publication to the extent there is a contradiction.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

Definitions

«Delivery Vehicle»

As used herein, the term «delivery vehicle» refers to any mean that allows the transfer of a payload into a bacterium.

There are several types of delivery vehicle encompassed by the present invention including, without limitation, bacteriophage scaffold, virus scaffold, chemical based delivery vehicle (e.g., cyclodextrin, calcium phosphate, cationic polymers, cationic liposomes), protein-based or peptide-based delivery vehicle, lipid-based delivery vehicle, nanoparticle-based delivery vehicles, non-chemical-based delivery vehicles (e.g., transformation, electroporation, sonoporation, optical transfection), particle-based delivery vehicles (e.g., gene gun, magnetofection, impalefection, particle bombardment, cell-penetrating peptides) or donor bacteria (conjugation).

Any combination of delivery vehicles is also encompassed by the present invention.

The delivery vehicle can refer to a bacteriophage derived scaffold and can be obtained from a natural, evolved or engineered capsid.

In some embodiment, the delivery vehicle is the payload as bacteria are naturally competent to take up a payload from the environment on their own.

«Conjugation»

Conjugation is a process by which a donor bacteria actively transfers DNA to a recipient bacteria. DNA transfer involves recognition of an origin of transfer (oriT) by a protein known as the relaxase which nicks and covalently binds to the oriT DNA. The relaxase and single stranded DNA are then typically injected into a recipient cell through a type IV secretion system. During conjugation of a plasmid or ICE (Integrative and Conjugative Elements), transfer of the relaxase is coupled with rolling circle replication of the plasmid or ICE. Once in the recipient, the relaxase will recircularize the transferred strand at the oriT.—Smillie et al, Microbiology and Molecular Biology Rev, 2010, P. 434-452.

Examples of conjugative plasmids are F, R388, RP4, RK2, R6K. Plasmids of the following groups are frequently conjugative and carry a type IV secretion system: IncA, IncB/O (Ind O), IncC, IncD, IncE, IncFI, IncF2, IncG, IncHM, IncHI2, Inch, IncI2, IncJ, IncK, IncUM, IncN, IncP, IncQl, IncQ2, IncR, IncS, IncT, IncU, IncV, IncW, IncXI, IncX2, IncY, IncZ, ColE1, CoIE2, CoIE3, p15A, pSC101, IncP-2, IncP-5, IncP-7, IncP-8, IncP-9, Ind, Inc4, Inc7, Inc8, Inc9, Inc1 1, Inc13, Ind 4 or Ind 8.

List of type IV secretion systems can be found in public databases such as AtlasT4SS.

Conjugation is not limited to plasmids but can also occur from the chromosome of bacteria when an oriT is present. This can happen naturally through the recombination of conjugative plasmids in the chromosome or artificially by introducing an oriT at a position of interest in the chromosome. A particular class of conjugative elements are known as Integrative and Conjugative Elements (ICEs). These are not maintained in a circular plasmidic form but integrate in the host chromosome. Upon transfer, the ICE excises from the chromosome and is then transferred in a manner akin to a conjugative plasmid. Once in a recipient cell, the ICE integrates in the recipient's chromosome. Lists of ICE elements can be found in public databases such as ICEberg.

ICEs or plasmids which carry both an origin of transfer and the type IV secretion system genes are commonly referred to as mobile elements, while ICEs or plasmids that only carry the oriT can be referred to as mobilisable plasmids. Mobilisable elements can only be transferred from the donor cell to a recipient cell if a type IV secretion system is expressed in trans, either by another plasmid or from the chromosome of the host cell.

«Payload»

As used herein, the term «payload» refers to any nucleic acid sequence or amino acid sequence, or a combination of both (such as, without limitation, peptide nucleic acid or peptide-oligonucleotide conjugate) transferred into a bacterium with a delivery vehicle.

The term «payload» may also refer to a plasmid, a vector or a cargo.

The payload can be a phagemid or phasmid obtained from natural, evolved or engineered bacteriophage genome. The payload can also be composed only in part of phagemid or phasmid obtained from natural, evolved or engineered bacteriophage genome.

In some embodiment, the payload is the delivery vehicle as bacteria are naturally competent to take up a payload from the environment on their own.

«Nucleic Acid»

As used herein, the term "nucleic acid" refers to a sequence of at least two nucleotides covalently linked together which can be single-stranded or double-stranded or contains portion of both single-stranded and double-stranded sequence. Nucleic acids of the present invention can be naturally occurring, recombinant or synthetic. The nucleic acid can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases, including uracil, adenine, thymine, cytosine, guanine, inosine, xanthine, hypoxanthine, isocytosine, 5-hydroxymethylcytosine and isoguanine. Other examples of modified bases that can be used in the present invention are detailed in Chemical Reviews 2016, 116 (20) 12655-12687. The term "nucleic acid" also encompasses any nucleic acid analogs which may contain other backbones comprising, without limitation, phosphoramide, phosphorothioate, phosphorodithioate, O-methylphophoroamidite linkage and/or deoxyribonucleotides and ribonucleotides nucleic acids. Any combination of the above features of a nucleic acid is also encompassed by the present invention.

«Vector»

As used herein, the term "vector" refers to any construct of sequences that are capable of expression of a polypeptide in a given host cell. If a vector is used then the choice of vector is dependent upon the method that will be used to transform host bacteria as is well known to those skilled in the art. Vectors can include, without limitation, plasmid vectors and recombinant phage vectors, or any other vector known in that art suitable for delivering a polypeptide of the invention to target bacteria. The skilled artisan is well aware of the genetic elements that must be present on the vector in order to successfully transform, select and propagate host cells comprising any of the isolated nucleotides or nucleic acid sequences of the invention.

«Phagemid»

As used herein the term "phagemid" or "phasmid" are equivalent and refer to a recombinant DNA vector comprising at least one sequence of a bacteriophage genome. A phagemid of the disclosure comprises a phage packaging site and optionally an origin of replication (ori), in particular a bacterial and/or phage origin of replication. In one embodiment, the phagemid of the disclosure does not comprise a bacterial origin of replication and thus cannot replicate by itself once injected into a bacterium. Alternatively, the phagemid comprises a plasmid origin of replication, in particular a bacterial and/or phage origin of replication.

«Packaged Phagemid»

As used herein, the term "packaged phagemid" or "phage-derived particle" refers to a phagemid which is encapsidated in a bacteriophage scaffold, bacterial virus particle or capsid. Particularly, it refers to a bacteriophage scaffold, bacterial virus particle or capsid devoid of a bacteriophage genome. The packaged phagemid or phage-derived particle may be produced with a helper phage strategy, well known from the man skilled in the art. The helper phage comprises all the genes coding for the structural and functional proteins that are indispensable for the phagemid according to the invention to be encapsidated. The packaged phagemid or phage-derived particle may be produced with a satellite virus strategy, also known from the man skilled in the art. Satellite virus are subviral agent and are composed of nucleic acid that depends on the co-infection of a host cell with a helper virus for all the morphogenetic functions, whereas for all its episomal functions (integration and immunity, multicopy plasmid replication) the satellite is completely autonomous from the helper. In one embodiment, the satellite genes can encode proteins that promote capsid size reduction of the helper phage, as described for the P4 Sid protein that controls the P2 capsid size to fit its smaller genome.

«Peptide»

As used herein, the term "peptide" refers both to a short chain of at least 2 amino acids linked between each other and to a part of, a subset of, or a fragment of a protein which part, subset or fragment being not expressed independently from the rest of the protein. In some instances, a peptide is a protein. In some other instances, a peptide is not a protein and peptide only refers to a part, a subset or a fragment of a protein. Preferably, the peptide is from 4, 5, 6, 7, 8, 9, 10, 11, 12, 13, 14, 15 amino acids to 4, 5, 6, 7, 8, 9, 10, 11, 12, 13, 14, 15, 20, 25, 30, 40, 50, 100, 200 amino acids in size.

"Engineered"

As used herein, the term "engineered" means that the bacterial cells, phages, phage-derived particles, phagemids or vectors of the invention have been modified by molecular biology techniques. As will be understood by the skilled person, engineering of bacterial cells, phages, phage-derived particles, phagemids or vectors implies a deliberate action to introduce or modify a nucleic acid sequence and does not cover introduction or modification of a nucleic acid sequence through natural evolution of the bacterial cell, phage, phage-derived particle, phagemid or vector.

"Percent of Identity"

As used herein, the percent identity is calculated in relation to polymers (e.g., polynucleotide or polypeptide) whose sequences have been aligned. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4: 11-17 (1988)) which has been incorporated into the ALIGN program (version 2.0), using a PAM 120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using a BLOSUM62 matrix, a BLOSUM30 matrix or a PAM250 matrix, and a gap weight of 16, 14, 12, 10, 8, 6, or 4 and a length weight of 1, 2, 3, 4, 5, or 6. In a specific embodiment the BLOSUM30 matrix is used with gap open penalty of 12 and gap extension penalty of 4.

CRISPR-Cas System

A CRISPR-Cas system refers to DNA encoding two distinct elements, i.e. i) an endonuclease, in this case the CRISPR associated nuclease (Cas or "CRISPR associated protein") and ii) a guide RNA. Depending on the type of CRISPR system, the guide RNA may be in the form of a chimeric RNA which consists of the combination of a CRISPR (crRNA) bacterial RNA and a tracrRNA (trans-activating RNA CRISPR) (Jinek et al., Science 2012). The guide RNA combines the targeting specificity of the crRNA corresponding to the "spacing sequences" that serve as guides to the Cas proteins, and the conformational properties of the tracrRNA in a single transcript. When the guide RNA and the Cas protein are expressed simultaneously in the cell, the target genomic sequence can be permanently interrupted (and causing disappearance of the targeted and surrounding sequences and/or cell death, depending on the location) or modified. The modification may be guided by a repair matrix.

The CRISPR-Cas system includes two main classes depending on the nuclease mechanism of action:

- Class 1 is made of multi-subunit effector complexes and includes type I, Ill and IV
- Class 2 is made of single-unit effector modules, like Cas9 nuclease, and includes type II (II-A, II-B, II-C, II-C variant), V (V-A, V-B, V-C, V-D, V-E, V-U1, V-U2, V-U3, V-U4, V-U5) and VI (VI-A, VI-B1, VI-B2, V1-C, V1-D)

The sequence of interest according to the present invention comprises a nucleic acid sequence encoding Cas protein. A variety of CRISPR enzymes are available for use as a sequence of interest on the plasmid according to the present invention. In some embodiments, the CRISPR enzyme is a Type 11 CRISPR enzyme, a Type 11-A or Type 11-B CRISPR enzyme. In another embodiment, the CRISPR enzyme is a Type 1 CRISPR enzyme or a Type III CRISPR enzyme. In some embodiments, the CRISPR enzyme catalyzes DNA cleavage. In some other embodiments, the CRISPR enzyme catalyzes RNA cleavage. In one embodiment, the CRISPR enzymes may be coupled to a guide RNA or single guide RNA (sgRNA). In certain embodiments, the guide RNA or sgRNA targets a gene selected from the group consisting of an antibiotic resistance gene, virulence protein or factor gene, toxin protein or factor gene, a bacterial receptor gene, a membrane protein gene, a structural protein gene, a secreted protein gene, a gene expressing resistance to a drug in general and a gene causing a deleterious effect to the host.

The sequence of interest may comprise a nucleic acid sequence encoding a guide RNA or sgRNA to guide the Cas protein endogenous to the targeted bacteria, alone or in combination with a Cas protein and/or a guide RNA encoded by the payload.

Non-limiting examples of Cas proteins as part of a multi-subunit effector or as a single-unit effector include Cas1, Cas1B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csyl, Csy2, Csy3, Csf1, Csf2, Csf3, Csf4, Csm1, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, homologues thereof, orthologues thereof, variants thereof, or modified versions thereof. In some embodiments, the CRISPR enzyme cleaves both strands of the target nucleic acid at the Protospacer Adjacent Motif (PAM) site.

In a particular embodiment, the CRISPR enzyme is any Cas9 protein, for instance any naturally-occurring bacterial Cas9 as well as any variants, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA (s).

The sequence encoding Cas9 (the entire protein or a fragment thereof) as used in the context of the invention can be obtained from any known Cas9 protein (Fonfara et al., 2014; Koonin et al., 2017). Examples of Cas9 proteins useful in the present invention include, but are not limited to, Cas9 proteins of *Streptococcus pyogenes* (SpCas9), *Streptococcus thermophiles* (St1Cas9, St3Cas9), *Streptococcus mutans, Staphylococcus aureus* (SaCas9), *Campylobacter jejuni* (CjCas9), *Francisella novicida* (FnCas9) and *Neisseria meningitides* (NmCas9).

The sequence encoding Cpf1 (Cas12a) (the entire protein or a fragment thereof) as used in the context of the invention can be obtained from any known Cpf1 (Cas12a) protein (Koonin et al., 2017). Examples of Cpf1(Cas12a) proteins useful in the present invention include, but are not limited to, Cpf1(Cas12a) proteins of *Acidaminococcus* sp, *Lachnospiraceae bacteriu* and *Francisella novicida*.

The sequence encoding Cas13a (the entire protein or a fragment thereof) as used in the context of the invention can be obtained from any known Cas13a (C2c2) protein (Abudayyeh et al., 2017). Examples of Cas13a (C2c2) proteins useful in the present invention include, but are not limited to, Cas13a (C2c2) proteins of *Leptotrichia wadei* (LwaCas13a).

The sequence encoding Cas13d (the entire protein or a fragment thereof) as used in the context of the invention can be obtained from any known Cas13d protein (Yan et al., 2018). Examples of Cas13d proteins useful in the present invention include, but are not limited to, Cas13d proteins of *Eubacterium siraeum* and *Ruminococcus* sp.

In a particular embodiment, the nucleic sequence of interest is a CRISPR/Cas9 system for the reduction of gene expression or inactivation a gene selected from the group consisting of an antibiotic resistance gene, virulence factor or protein gene, toxin factor or protein gene, a gene expressing a bacterial receptor, a membrane protein, a structural protein, a secreted protein, a gene expressing resistance to a drug in general and a gene causing a deleterious effect to the host.

In one embodiment, the CRISPR-Cas system is used to target and inactivate a virulence factor. A virulence factor can be any substance produced by a pathogen that alters host-pathogen interaction by increasing the degree of damage done to the host. Virulence factors are used by pathogens in many ways, including, for example, in cell adhesion or colonization of a niche in the host, to evade the host's immune response, to facilitate entry to and egress from host cells, to obtain nutrition from the host, or to inhibit other physiological processes in the host. Virulence factors can include enzymes, endotoxins, adhesion factors, motility factors, factors involved in complement evasion, scavenging factors and factors that promote biofilm formation. For example, such targeted virulence factor gene can be *E. coli* virulence factor gene such as, without limitation, EHEC-HlyA, Sb(1 (VT1), Stx2 (VT2), Stx2a (VT2a), Stx2b (VT2b), Stx2c (VT2c), Stx2d (VT2d), Stx2e (VT2e) and Stx2f (VT2f), Stx2h (VT2h), stx2k, fimA, fimF, fimH, neuC, kpsE, sfa, foc, iroN, aer, iha, papC, papGI, papGII, papGIII, hlyC, cnf1, hra, sat, ireA, usp ompT, ibeA, malX, fyuA, irp2, traT, afaD, ipaH, eltB, estA, bfpA, eaeA, espA, aaiC, aatA, TEM, CTX, SHV, csgA, csgB, csgC, csgD, csgE, csgF, csgG, csgH, T1SS, T2SS, T3SS, T4SS, T5SS, T6SS (secretion systems). For example, such targeted virulence factor gene can be *Shigella dysenteriae* virulence factor gene such as, without limitation, stx1 and stx2. For example, such targeted virulence factor gene can be *Yersinia pestis* virulence factor gene such as, without limitation, yscF (plasmid-borne (pCDI) T3SS external needle subunit). For example, such targeted virulence factor gene can be *Francisella tularensis* virulence factor gene such as, without limitation, fslA. For example, such targeted virulence factor gene can be *Bacillus anthracis* virulence factor gene such as, without limitation, pag (Anthrax toxin, cell-binding protective antigen). For example, such targeted virulence factor gene can be *Vibrio cholera* virulence factor gene such as, without limitation, ctxA and ctxB (cholera toxin), tcpA (toxin co-regulated pilus), and toxT (master virulence regulator). For example, such targeted virulence factor gene can be *Pseudomonas aeruginosa* virulence factor genes such as, without limitation, pyoverdine (e.g., sigma factor pvdS, biosynthetic genes pvdL, pvdl, pvdJ, pvdH, pvdA, pvdF, pvdQ, pvdN, pvdM, pvdO, pvdP, transporter genes pvdE, pvdR, pvdT, opmQ), siderophore pyochelin (e.g., pchD, pchC, pchB, pchA, pchE, pchF and pchG, and toxins (e.g., exoU, exoS and exoT). For example, such targeted virulence factor gene can be *Klebsiella pneumoniae* virulence factor genes such as, without limitation, fimA (adherence, type I fimbriae major subunit), and cps (capsular polysaccharide). For example, such targeted virulence factor gene can be *Acinetobacter baumannii* virulence factor genes such as, without limitation, ptk (capsule polymerization) and epsA (assembly). For example, such targeted virulence factor gene can be *Salmonella enterica Typhi* virulence factor genes such as, without limitation, MIA (invasion, SPI-1 regulator), ssrB (SPI-2 regulator), and those associated with bile tolerance, including efflux pump genes acrA, acrB and toIC. For example, such targeted virulence factor gene can be *Fusobacterium nucleatum* virulence factor genes such as, without limitation, FadA and TIGIT. For example, such targeted virulence factor gene can be *Bacteroides fragilis* virulence factor genes such as, without limitation, bft. For example, such targeted virulence factor gene can be *Cutibacterium acnes* porphyrins genes, CAMP-factors (CAMP1, CAMP2, CAMP3, CAMP4), Hyaluronate lyase (HYL-IB/II, HYL-IA), Lipases (GehA, GehB), Haemolysins, Sialidases, Endoglycoceramidases, Endo-β-N-acetylglucosaminidase, Dermatan sulphate adhesin (DsA1, DsA2), Proline-Threonine Repeats (PTRs) or any virulence factors included on the acne associated genomic loci 1, 2, 3(plasmid), 4 such as a tight adhesion locus (tad), Streptolysin S-associated genes (sag), nonribosomal peptide synthetases (NRPS) as described in Tomida et al.

In another embodiment, the CRISPR/Cas9 system is used to target and inactivate an antibiotic resistance gene such as, without limitation, GyrB, ParE, ParY, AAC(1), AAC(2'), AAC(3), AAC(6'), ANT(2"), ANT(3"), ANT(4'), ANT(6), ANT(9), APH(2"), APH(3"), APH(3'), APH(4), APH(6), APH(7"), APH(9), ArmA, RmtA, RmtB, RmtC, Sgm, AER, BLA1, CTX-M, KPC, SHV, TEM, BlaB, CcrA, IMP, NDM, VIM, ACT, AmpC, CMY, LAT, PDC, OXA β-lactamase, mecA, Omp36, OmpF, PIB, bla (blal, blaR1) and mec (mecl, mecR1) operons, Chloramphenicol acetyltransferase (CAT), Chloramphenicol phosphotransferase, Ethambutol-resistant arabinosyltransferase (EmbB), MupA, MupB, Integral membrane protein MprF, Cfr 23S rRNA methyltransferase, Rifampin ADP-ribosyltransferase (Arr), Rifampin glycosyltransferase, Rifampin monooxygenase, Rifampin phosphotransferase, DnaA, RbpA, Rifampin-resistant beta-subunit of RNA polymerase (RpoB), Erm 23S rRNA methyltransferases, Lsa, MsrA, Vga, VgaB, Streptogramin Vgb lyase, Vat acetyltransferase, Fluoroquinolone acetyltransferase, Fluoroquinolone-resistant DNA topoisomerases, Fluoroquinolone-resistant GyrA, GyrB, ParC, Quinolone resistance protein (Qnr), FomA, FomB, FosC, FosA, FosB, FosX, VanA, VanB, VanD, VanR, VanS, Lincosamide nucleotidyltransferase (Lin), EreA, EreB, GimA, Mgt, Ole, Macrolide phosphotransferases (MPH), MefA, MefE, Mel, Streptothricin acetyltransferase (sat), Sul1, Sul2, Sul3, sulfonamide-resistant FoIP, Tetracycline inactivation enzyme TetX, TetA, TetB, TetC, Tet30, Tet31, TetM, TetO, TetQ, Tet32, Tet36, MacAB-ToIC, MsbA, MsrA, VgaB, EmrD, EmrAB-ToIC, NorB, GepA, MepA, AdeABC, AcrD, MexAB-OprM, mtrCDE, EmrE, adeR, acrR, baeSR, mexR, phoPQ, mtrR, or any antibiotic resistance gene described in the Comprehensive Antibiotic Resistance Database (CARD card. mcmaster. cal).

In another embodiment, the CRISPR/Cas9 system is used to target and inactivate a bacterial toxin gene. Bacterial toxin can be classified as either exotoxins or endotoxins. Exotoxins are generated and actively secreted; endotoxins remain part of the bacteria. The response to a bacterial toxin can involve severe inflammation and can lead to sepsis. Such toxin can be for example Botulinum neurotoxin, Tetanus toxin, Staphylococus toxins, Diphteria toxin, Anthrax toxin, Alpha toxin, Pertussis toxin, Shiga toxin, Heat-stable enterotoxin (*E. coli* ST), colibactin, BFT (*B. fragilis* toxin) or any toxin described in Henkel et al., (Toxins from Bacteria in EXS. 2010; 100: 1-29).

Base Editing

Base editing (BE) refers to the ability to substitute a specific nucleotide base pair on a DNA or RNA molecule by another. Until recently, the only way to perform a specific substitution on DNA in vivo was using recombination of a template DNA, carrying the specific base pair change, with the locus of interest. Base editing technology relies on completely different strategies. There is no exchange of DNA, instead an enzymatic reaction converts a nucleotide to another one leading to a mismatch at the level of dsDNA that is then corrected by the cell machinery.

One of the main challenges for base editing is how to restrict activity of the enzyme performing the nucleotide conversion to the target nucleotide, for example a SNP involved in pathogenicity. This spatial restriction has been achieved recently repurposing the CRISPR-Cas system. Indeed, fusing catalytically impaired or inactive Cas nuclease to base modification enzymes that are active only on single stranded DNA, it's possible to achieve high efficiency base editing. This is possible thanks to the CRISPR-Cas ability to generate locally ssDNA bubble in an 'R loop' when the complex is annealed to its DNA target strand by RNA-DNA base pairing.

So far there are seven types of DNA base editors described:

- Cytosine Base Editor (CBE) that convert C:G into T:A (Komor, A et al. Programmable editing of a target base in genomic DNA without double-stranded DNA cleavage. Nature 533:420-4. (2016).
- Adenine Base Editor (ABE) that convert A:T into G:C (Programmable base editing of A·T to G·C in genomic DNA without DNA cleavage. Nature 551(7681) 464-471 (2017).
- Cytosine Guanine Base Editor (CGBE) that convert C:G into G:C Chen, L et al. Precise and programmable C:G to G:C base editing in genomic DNA. Biorxiv (2020); Kurt, I et al. CRISPR C-to-G base editors for inducing targeted DNA transversions in human cells. Nature Biotechnology (2020).
- Cytosine Adenine Base Editor (CABE) that convert C:G into A:T Zhao, D et al. New base editors change C to A in bacteria and C to G in mammalian cells. Nature Biotechnology (2020).
- Adenine Cytosine Base Editor (ACBE) that convert A:T into C:G (Liu, D et al. A:T to C:G base editors and uses thereof. Patent application WO2020181180 (2020).
- Adenine Thymine Base Editor (ATBE) that convert A:T into T:A (Liu, D et al. A:T to C:G base editors and uses thereof. Patent application WO2020181180 (2020).
- Thymine Adenine Base Editor (TABE) that convert T:A into A:T (Liu, D et al. T:A TO A:T base editing through adenosine methylation. Patent application WO2020181193 (2020); Liu, D et al. T:A TO A:T base editing through thymine alkylation. Patent application WO2020181178 (2020); Liu, D et al. T:A TO A:T base editing through adenine excision. Patent application WO2020181195 (2020).

Base editors differ in the base modification enzymes. CBE rely on ssDNA cytidine deaminase among which: APOBEC1, rAPOBEC1, APOBEC1 mutant or evolved version (evoAPOBEC1), and APOBEC homologs (APOBEC3A (eA3A), Anc689), Cytidine deaminase 1 (CDA1), evoCDA1, FERNY, evoFERNY. ABE rely on deoxyadenosine deaminase activity of a tandem fusion TadA-TadA* where TadA* is an evolved version of TadA, an *E. coli* tRNA adenosine deaminase enzyme, able to convert adenosine into Inosine on ssDNA. TadA* include TadA-8a-e and TadA-7.10.

Except from base modification enzyme there has been also modifications implemented to base editor to increase editing efficacy, precision and modularity:

- the addition of one or two uracil DNA glycosylase inhibitor domain (UGI) to prevent base excision repair mechanism to revert base edition
- the addition of Mu-GAM that decrease insertion-deletion rate by inhibiting Non-homologuous end joining mechanism in the cell (NHEJ)
- the use of nickase active Cas9 (nCas9 D10A) that, by creating nicks on the non-edited strand favor its repair and consequently the fixation of the edited base
- the use of divers Cas proteins from for example different organisms, mutants with different PAM motifs or different fidelity or different family (e.g. Cas12a)

Non-limiting examples of DNA based editor proteins include BE1, BE2, BE3, BE4, BE4-GAM, HF-BE3, Sniper-BE3, Target-AID, Target-AID-NG, ABE, EE-BE3, YE1-BE3, YE2-BE3, YEE-BE3, BE-PLUS, SaBE3, SaBE4, SaBE4-GAM, Sa(KKH)-BE3, VQR-BE3, VRER-BE3, EQR-BE3, xBE3, Cas12a-BE, Ea3A-BE3, A3A-BE3, TAM, CRISPR-X, ABE7.9, ABE7.10, ABE7.10*, xABE, ABESa, VQR-ABE, VRER-ABE, Sa(KKH)-ABE, ABE8e, SpRY-ABE, SpRY-CBE, SpG-CBE4, SpG-ABE, SpRY-CBE4, SpCas9-NG-ABE, SpCas9-NG-CBE4, enAsBE1.1, enAsBE1.2, enAsBE1.3, enAsBE1.4, AsBE1.1, AsBE1.4, CRISPR-Abest, CRISPR-Cbest, eA3A-BE3, AncBE4.

Cytosine Guanine Base Editors (CGBE) consist of a nickase CRISPR fused to:

- A cytosine deaminase (rAPOBEC) and base excision repair proteins (e.g. rXRCC1). (Precise and programmable C:G to G:C base editing in genomic DNA. Biorxiv (2020).
- A rat APOBEC1 variant (R33A) protein and an *E. coli*-derived uracil DNA N-glycosylase (eUNG). (Kurt, I et al. CRISPR C-to-G base editors for inducing targeted DNA transversions in human cells. Nature Biotechnology (2020).
- Cytosine Adenine Base Editors (CABE) consist of a Cas9 nickase, a cytidine deaminase (e.g. AID), and a uracil-DNA glycosylase (Ung). Zhao, D et al. New base editors change C to A in bacteria and C to G in mammalian cells. Nature Biotechnology (2020).
- ACBE include a nucleic acid programmable DNA-binding protein and an adenine oxidase. Liu, D et al. A:T to C:G base editors and uses thereof. Patent application WO2020181180 (2020).
- ATBE consist of a Cas9 nickase and one or more adenosine deaminase or an oxidase domain. Liu, D et al. A:T to T:A base editing through adenine deamination and oxidation. Patent application WO2020181202 (2020).
- TABE consist of a Cas9 nickase and an adenosine methyltransferase, a thymine alkyltransferase, or an adenosine deaminase domain. (Liu, D et al. T:A TO A:T base editing through adenosine methylation. Patent application WO2020181193 (2020); Liu, D et al. T:A TO A:T base editing through thymine alkylation. Patent application WO2020181178 (2020); Liu, D et al. T:A TO A:T base editing through adenine excision. Patent application WO2020181195 (2020).

Base editor molecules can also consist of two or more of the above listed editor enzymes fused to a Cas protein (e.g. combination of an ABE and CBE). These biomolecules are named dual base editors and enable the editing of two different bases. (Grunewald, J et al. A dual-deaminase CRISPR base editor enables concurrent adenine and cytosine editing, Nature Biotechnology (2020); Li, C et al. Targeted, random mutagenesis of plant genes with dual cytosine and adenine base editors, Nature Biotechnology (2020).

In one embodiment, the base editor is used to inactivate the expression of a gene by editing one or several nucleotides involved in transcription or translation. More specifically the base editor is targeting one or several nucleotides of a promoter, a RBS, a start codon.

In one embodiment, the base editor is used to introduce a premature stop codon.

In one embodiment, the base editor is used to introduce one or several rare codons.

In another embodiment, the base editor is used to modulate the expression of genes by editing one or several nucleotides involved in transcription or translation. More specifically the base editor is targeting one or several nucleotides of a promoter, a RBS, a start codon. leading to an increase or decrease of gene expression.

In another embodiment, the base editor is used to revert a mutation that leads to the inactivation, decrease or increase in activity of a gene or pathway.

In another embodiment, the base editor is used to revert a mutation that leads to an increase of pathogenicity.

In one embodiment, the base editor is used to modify the regulation of a gene by editing one or several nucleotides involved in its regulation such as nucleotides of operator sequence, transcription factor binding site, riboswitch, RNAse recognition site, protease cleavage site, methylation site, post translational modification site (phosphorylation, glycosylation, acetylation, pupylation . . . ).

RNA Based Editing

RNA base editing is based on the same principle as DNA base editing: an enzyme catalysing the conversion of a RNA base into another has to be brought close to the target base to perform its conversion locally. So far the only enzyme used for RNA editing is an adenosine deaminase from ADAR family that converts Adenosine into Inosine in dsRNA structure. Several seminal studies used this specificity for dsRNA and fused the ADAR deaminase domain (ADARDD) to an antisense oligo in order to program local RNA base editing. More recently the ability of some CRISPR-Cas systems to bind RNA molecules was repurposed into RNA editing. Using catalytically dead Cas13b enzyme (dPspCas13b) fused to an hyperactive mutant of ADAR2 deaminase domain (ADAR2DD-E488Q for REPAIRv1 and ADAR2DD-E488Q-T375G for REPAIRv2) Cox et al improved specificity and efficiency compare to previous RNA editing strategies.

Non-limiting examples of RNA based editor proteins include REPAIRv1, REPAIRv2

In one embodiment, the RNA base editor is used to inactivate the expression of a gene by editing one or several nucleotides involved in translation. More specifically the base editor is targeting one or several nucleotides of a 5'UTR, a RBS, a start codon.

In one embodiment, the RNA base editor is used to introduce a premature stop codon.

In one embodiment, the RNA base editor is used to introduce one or several rare codons.

In another embodiment, the RNA base editor is used to modulate the expression of genes by editing one or several nucleotides involved in translation. More specifically the base editor is targeting one or several nucleotides of a 5'UTR, a RBS, a start codon leading to an increase or decrease of gene expression.

In another embodiment, the RNA base editor is used to revert a mutation that leads to the inactivation or a decrease in activity of a gene or pathway.

In another embodiment, the base editor is used to revert a mutation that leads to an increase of pathogenicity.

Prime Editing

Prime editors (PE), as described in Anzalone et al. (Anzalone, A. V. et al. Search-and-replace genome editing without double-strand breaks or donor DNA. Nature 576, 149-157 (2019) which is hereby incorporated by reference, consist of a nCas9 fused to a reverse transcriptase used in combination with a prime editing RNA (pegRNA; a guide RNA that includes a template region for reverse transcription).

Prime Editing allows introduction of insertions, deletions (indels) and 12 base-to-base conversions. Prime editing relies on the ability of a reverse transcriptase (RT), fused to a Cas nickase variant, to convert RNA sequence brought by a prime editing guide RNA (pegRNA) into DNA at the nick site generated by the Cas protein. The DNA flap generated from this process is then included or not in the targeted DNA sequence.

Prime editing systems include:

a Cas nickase variant such as Cas9-H840A fused to a reverse transcriptase domain such as M-MLV RT or its mutant version (M-MLV RT(D200N), M-MLV RT(D200N/L603VV), M-MLV RT(D200N/L603W/T330P/T306K/W313F)

a prime editing guide RNA (pegRNA)

To favor editing the prime editing system can include the expression of an additional sgRNA targeting the Cas nickase activity towards the non-edited DNA strand ideally only after the resolution of the edited strand flap by designing the sgRNA to anneal with the edited strand but not with the original strand.

Non-limiting examples of prime editing systems include PE1, PE1-M1, PE1-M2, PE1-M3, PE1-M6, PE1-M15, PE1-M3inv, PE2, PE3, PE3b, Cas9 Retron preciSe Parallel Editing via homologY ('CRISPEY'), a retron RNA fused to the sgRNA and expressed together with Cas9 and the retron proteins including at least the reverse transcriptase (Sharon, E. et al. Functional Genetic Variants Revealed by Massively Parallel Precise Genome Editing. Cell 175, 544-557.e16 (2018).), The SCRIBE strategy: a retron system expressed in combination with a recombinase promoting the recombination of single stranded DNA, also known as single stranded annealing proteins (SSAPs)12. Such recombinases include but are not limited to phage recombinases such as lambda red, recET, Sak, Sak4, and newly described SSAPs described in Wannier et al (Wannier, T. M. et al. Improved bacterial recombineering by parallelized protein discovery. Biorxiv 2020.01.14.906594 (2020) doi:10.1101/2020.01.14.906594.), the targetron system based on group II introns described in Karberg et al. (Karberg, M. et al. Group II introns as controllable gene targeting vectors for genetic manipulation of bacteria. Nat Biotechnol 19, 1162-7 (2001) and which has been adapted to many bacterial species, Other retron based gene targeting approaches, as described in Simon et al (Simon, A. J., Ellington, A. D. & Finkelstein, I.

J. Retrons and their applications in genome engineering. Nucleic Acids Res 47, 11007-11019 (2019)).

In one embodiment, the prime editing system is used to inactivate the expression of a gene by replacing, deleting, inserting one or several nucleotides involved in transcription or translation. More specifically the prime editing system is replacing, deleting, inserting one or several nucleotides in a promoter, a RBS, a coding sequence.

In one embodiment, the prime editing system is used to introduce one or several premature stop codon.

In one embodiment, the prime editing system is used to introduce one or several rare codons.

In one embodiment, the prime editing system is used to introduce, delete a nucleotide inducing a frameshift in the reading frame.

In another embodiment, the prime editing system is used to modulate the expression of genes by replacing, deleting, inserting one or several nucleotides involved in transcription or translation. More specifically the prime editing system is replacing, deleting, inserting one or several nucleotides in a promoter, a RBS, a start codon. leading to an increase or decrease of gene expression.

In another embodiment, the prime editing system is used to revert a mutation that leads to the inactivation or a decrease in activity of a gene or pathway.

In another embodiment, the prime editing system is used to revert a mutation that leads to an increase of pathogenicity.

The invention encompasses the following embodiments:

1. A recombinant *C. acnes* phage.

2. The recombinant *C. acnes* phage of embodiment 1, comprising at least one transgene.

3. The recombinant *C. acnes* phage of embodiment 2, wherein said transgene is a CRISPR-Cas system or part of a CRISPR-Cas system.

4. The recombinant *C. acnes* phage of embodiment 1, wherein the host range is different from the host range of the corresponding wild type *C. acnes* phage.

5. The recombinant *C. acnes* phage of embodiment 1, comprising an engineered capsid.

6. The recombinant *C. acnes* phage of embodiment 5, wherein an antigen is displayed at the surface of the engineered capsid.

7. A *C. acnes* cell carrying a recombinant DNA vector comprising:
- a DNA template for homologous recombination with a *C. acnes* phage genome
- an origin of replication allowing replication in *C. acnes*; and
- optionally a first selection marker allowing for selection of the DNA vector in *C. acnes;*

8. The *C. acnes* cell of embodiment 7, wherein the *C. acnes* phage genome is introduced into said cell 9. The *C. acnes* cell of embodiment 7, wherein the *C. acnes* phage genome recombines with the DNA vector leading to production of recombinant phages.

10. A *C. acnes* cell carrying a DNA vector for the selective production of recombinant *C. acnes* phage comprising:
- an origin of replication allowing replication in *C. acnes;*
- a CRISPR-Cas system expressed in said *C. acnes* cell but not targeting the newly generated recombinant *C. acnes* phage genome, and
- optionally a first selection marker allowing for selection of the DNA vector in *C. acnes*.

11. A method for producing a phage lysate containing wild-type or parent *C. acnes* phages and recombinant *C. acnes* phages wherein a wild-type or parent *C. acnes* phage genome is introduced into *C. acnes* cell of embodiment 7.

12. A method for selecting recombinant *C. acnes* phages wherein a phage lysate containing wild-type or parent *C. acnes* phages and recombinant *C. acnes* phages is mixed with the *C. acnes* cell of embodiment 10, leading to selective production of recombinant *C. acnes* phages.

13. A method to treat *C. acnes* related disorder or disease comprising administering to a subject a recombinant *C. acnes* phage of anyone of embodiments 1-6 or a recombinant *C. acnes* phage obtained by the methods of embodiments 11-12.

14. A recombinant DNA vector comprising:
- an origin of replication allowing replication in *C. acnes;*
- optionally a first selection marker allowing for selection of the DNA vector in *C. acnes*; and
- a gene of interest.

15. The DNA vector of embodiment 14 further comprising an oriT allowing conjugation into *C. acnes*; an origin of replication allowing replication in a donor bacteria and a second selection marker allowing for selection in a donor bacteria.

16. The DNA vector of embodiment 14 or 15, wherein the origin of replication allowing replication in *C. acnes* is R6K (typically of sequence SEQ ID NO: 42).

17. The DNA vector of embodiment 14 or 15, wherein the origin of replication allowing replication in *C. acnes* is RK2 (typically of sequence SEQ ID NO: 43).

18. The DNA vector of embodiment 14 or 15, wherein the origin of replication allowing replication in *C. acnes* is pBBR1 (typically of sequence SEQ ID NO: 44).

19. The DNA vector of embodiment 14 or 15, wherein the origin of replication allowing replication in *C. acnes* is pRO1600 (typically of sequence SEQ ID NO: 45).

20. The DNA vector of embodiment 14 or 15, wherein the origin of replication allowing replication in *C. acnes* is RSF1010 (typically of sequence SEQ ID NO: 46).

21. The DNA vector of embodiment 14 or 15, wherein the origin of replication allowing replication in *C. acnes* is pAMβ1 (typically of sequence SEQ ID NO: 47).

22. The DNA vector of embodiment 14 or 15, wherein the origin of replication allowing replication in *C. acnes* is pLME106 (typically of sequence SEQ ID NO: 48).

23. The DNA vector of embodiment 14 or 15, wherein the origin of replication allowing replication in *C. acnes* is pTZC1 (typically of sequence SEQ ID NO: 49).

24. The DNA vector of embodiment 14 or 15, wherein the origin of replication allowing replication in *C. acnes* is pBC1 (typically of sequence SEQ ID NO: 50).

25. The DNA vector of embodiment 14 or 15, wherein the origin of replication allowing replication in *C. acnes* is pEP2 (typically of sequence SEQ ID NO: 51).

26. The DNA vector of embodiment 14 or 15, wherein the origin of replication allowing replication in *C. acnes* is pWVO1 (typically of sequence SEQ ID NO: 52).

27. The DNA vector of embodiment 14 or 15, wherein the origin of replication allowing replication in *C. acnes* is pAP1 (typically of sequence SEQ ID NO: 53).

28. The DNA vector of embodiment 14 or 15, wherein the origin of replication allowing replication in *C. acnes* is pWKS1 (typically of sequence SEQ ID NO: 54).

29. The DNA vector of embodiment 14 or 15, wherein the origin of replication allowing replication in *C. acnes* is pLME108 (typically of sequence SEQ ID NO: 55).

30. The DNA vector of embodiment 14 or 15, wherein the origin of replication allowing replication in *C. acnes* is pLS1 (typically of sequence SEQ ID NO: 56).

31. The DNA vector of embodiment 14 or 15, wherein the origin of replication allowing replication in *C. acnes* is pUB6060 (typically of sequence SEQ ID NO: 57).

32. The DNA vector of embodiment 14 or 15, wherein the origin of replication allowing replication in *C. acnes* is p545 (typically of sequence SEQ ID NO: 58).

33. The DNA vector of embodiment 14 or 15, wherein the origin of replication allowing replication in *C. acnes* is pJD4 (typically of sequence SEQ ID NO: 59).

34. The DNA vector of embodiment 14 or 15, wherein the origin of replication allowing replication in *C. acnes* is pIJ101 (typically of sequence SEQ ID NO: 60).

35. The DNA vector of embodiment 14 or 15, wherein the origin of replication allowing replication in *C. acnes* is pSN22 (typically of sequence SEQ ID NO: 61).

36. The DNA vector of embodiment 14 or 15, wherein the origin of replication allowing replication in *C. acnes* is pGP01 (typically of sequence SEQ ID NO: 62).

37. The DNA vector of embodiment 14 or 15, wherein the origin of replication allowing replication in *C. acnes* is pIP501 (typically of sequence SEQ ID NO: 63).

38. The DNA vector of embodiment 14 or 15, wherein the origin of replication allowing replication in *C. acnes* is pCU1 (typically of sequence SEQ ID NO: 64).

39. The DNA vector of embodiment 14 or 15, wherein the origin of replication allowing replication in *C. acnes* is pBAV1K-T5 (typically of sequence SEQ ID NO: 65).

40. The DNA vector of any one of embodiments 15 to 39, wherein the oriT is oriT_pMRC01 (typically of sequence SEQ ID NO: 1).

41. The DNA vector of any one of embodiments 15 to 39, wherein the oriT is oriT_RSF1010 (typically of sequence SEQ ID NO: 2).

42. The DNA vector of any one of embodiments 15 to 39, wherein the oriT is oriT_pRS01 (typically of sequence SEQ ID NO: 3).

43. The DNA vector of any one of embodiments 15 to 39, wherein the oriT is oriT_pMV158 (typically of sequence SEQ ID NO: 4).

44. The DNA vector of any one of embodiments 15 to 39, wherein the oriT is oriT_pTF1 (typically of sequence SEQ ID NO: 5).

45. The DNA vector of any one of embodiments 15 to 39, wherein the oriT is oriT_pSC101 (typically of sequence SEQ ID NO: 6).

46. The DNA vector of any one of embodiments 15 to 39, wherein the oriT is oriT_pBTK445 (typically of sequence SEQ ID NO: 7).

47. The DNA vector of any one of embodiments 15 to 39, wherein the oriT is oriT_pBBR1 (typically of sequence SEQ ID NO: 8).

48. The DNA vector of any one of embodiments 15 to 39, wherein the oriT is oriT_R721 (typically of sequence SEQ ID NO: 9).

49. The DNA vector of any one of embodiments 15 to 39, wherein the oriT is oriT_pRmeGR4a (typically of sequence SEQ ID NO: 10).

50. The DNA vector of any one of embodiments 15 to 39, wherein the oriT is oriT_ColE1 (typically of sequence SEQ ID NO: 11).

51. The DNA vector of any one of embodiments 15 to 39, wherein the oriT is oriT_pTiC58 (typically of sequence SEQ ID NO: 12).

52. The DNA vector of any one of embodiments 15 to 39, wherein the oriT is oriT_pMdT1 (typically of sequence SEQ ID NO: 13).

53. The DNA vector of any one of embodiments 15 to 39, wherein the oriT is oriT_R1 (typically of sequence SEQ ID NO: 14).

54. The DNA vector of any one of embodiments 15 to 39, wherein the oriT is oriT_Tn5520 (typically of sequence SEQ ID NO: 15).

55. The DNA vector of any one of embodiments 15 to 39, wherein the oriT is oriT_QKH54 (typically of sequence SEQ ID NO: 16).

56. The DNA vector of any one of embodiments 15 to 39, wherein the oriT is oriT_R64 (typically of sequence SEQ ID NO: 17).

57. The DNA vector of any one of embodiments 15 to 39, wherein the oriT is oriT_R751 (typically of sequence SEQ ID NO: 18).

58. The DNA vector of any one of embodiments 15 to 39, wherein the oriT is oriT_RP4 (typically of sequence SEQ ID NO: 19).

59. The DNA vector of any one of embodiments 15 to 39, wherein the oriT is oriT_pKL1 (typically of sequence SEQ ID NO: 20).

60. The DNA vector of any one of embodiments 15 to 39, wherein the oriT is oriT_RK2 (typically of sequence SEQ ID NO: 21).

61. The DNA vector of any one of embodiments 15 to 39, wherein the oriT is oriT_R1162 (typically of sequence SEQ ID NO: 22).

62. The DNA vector of any one of embodiments 15 to 39, wherein the oriT is oriT_Tn4555 (typically of sequence SEQ ID NO: 23).

63. The DNA vector of any one of embodiments 15 to 39, wherein the oriT is oriT_pHT (typically of sequence SEQ ID NO: 24).

64. The DNA vector of any one of embodiments 15 to 39, wherein the oriT is oriT_Tn4399 (typically of sequence SEQ ID NO: 25).

65. The DNA vector of any one of embodiments 15 to 39, wherein the oriT is oriT_Tn916 (typically of sequence SEQ ID NO: 26).

66. The DNA vector of any one of embodiments 15 to 39, wherein the oriT is oriT_pST12 (typically of sequence SEQ ID NO: 27).

67. The DNA vector of any one of embodiments 15 to 39, wherein the oriT is oriT_pCU1 (typically of sequence SEQ ID NO: 28).

68. The DNA vector of any one of embodiments 15 to 39, wherein the oriT is oriT_pSU233 (typically of sequence SEQ ID NO: 29).

69. The DNA vector of any one of embodiments 15 to 39, wherein the oriT is oriT_F (typically of sequence SEQ ID NO: 30).

70. The DNA vector of any one of embodiments 15 to 39, wherein the oriT is oriT_pMAB01 (typically of sequence SEQ ID NO: 31).

71. The DNA vector of any one of embodiments 15 to 39, wherein the oriT is oriT_R388 (typically of sequence SEQ ID NO: 32).

72. The DNA vector of any one of embodiments 15 to 39, wherein the oriT is oriT_pS7a (typically of sequence SEQ ID NO: 33).

73. The DNA vector of any one of embodiments 15 to 39, wherein the oriT is oriT_pS7b (typically of sequence SEQ ID NO: 34).

74. The DNA vector of any one of embodiments 15 to 39, wherein the oriT is oriT_R702 (typically of sequence SEQ ID NO: 35).

75. The DNA vector of any one of embodiments 15 to 39, wherein the oriT is oriT_pMUR274 (typically of sequence SEQ ID NO: 36).

76. The DNA vector of any one of embodiments 15 to 39, wherein the oriT is oriT_R100 (typically of sequence SEQ ID NO: 37).

77. The DNA vector of any one of embodiments 15 to 39, wherein the oriT is oriT_pVCR94deltaX (typically of sequence SEQ ID NO: 38).

78. The DNA vector of any one of embodiments 15 to 39, wherein the oriT is oriT_R46 (typically of sequence SEQ ID NO: 39).

79. The DNA vector of any one of embodiments 15 to 39, wherein the oriT is oriT_pGO1 (typically of sequence SEQ ID NO: 40).

80. The DNA vector of any one of embodiments 15 to 39, wherein the oriT is oriT_pIP501 (typically of sequence SEQ ID NO: 41).

81. The DNA vector of any one of embodiments 14 to 80, further comprising:

a relaxase gene;

a selection marker allowing for selection in the transconjugant *C. acnes*; and a selection marker allowing for selection in the donor bacteria wherein the donor bacteria is an *E. coli* strain carrying a conjugative plasmid, conjugative transposon, or integrative and conjugative element (ICE), expressing a conjugative machinery.

82. The DNA vector of embodiment 81, wherein the donor bacteria is an *E. coli* strain carrying the conjugative plasmid, conjugative transposon or ICE pMRC01.

83. The DNA vector of embodiment 81, wherein the donor bacteria is an *E. coli* strain carrying the conjugative plasmid, conjugative transposon or ICE RSF1010.

84. The DNA vector of embodiment 81, wherein the donor bacteria is an *E. coli* strain carrying the conjugative plasmid, conjugative transposon or ICE pRS01.

85. The DNA vector of embodiment 81, wherein the donor bacteria is an *E. coli* strain carrying the conjugative plasmid, conjugative transposon or ICE pMV158.

86. The DNA vector of embodiment 81, wherein the donor bacteria is an *E. coli* strain carrying the conjugative plasmid, conjugative transposon or ICE pTF1.

87. The DNA vector of embodiment 81, wherein the donor bacteria is an *E. coli* strain carrying the conjugative plasmid, conjugative transposon or ICE pSC101.

88. The DNA vector of embodiment 81, wherein the donor bacteria is an *E. coli* strain carrying the conjugative plasmid, conjugative transposon or ICE pBTK445.

89. The DNA vector of embodiment 81, wherein the donor bacteria is an *E. coli* strain carrying the conjugative plasmid, conjugative transposon or ICE pBBR1.

90. The DNA vector of embodiment 81, wherein the donor bacteria is an *E. coli* strain carrying the conjugative plasmid, conjugative transposon or ICE R721.

91. The DNA vector of embodiment 81, wherein the donor bacteria is an *E. coli* strain carrying the conjugative plasmid, conjugative transposon or ICE pRmeGR4a.

92. The DNA vector of embodiment 81, wherein the donor bacteria is an *E. coli* strain carrying the conjugative plasmid, conjugative transposon or ICE ColE1.

93. The DNA vector of embodiment 81, wherein the donor bacteria is an *E. coli* strain carrying the conjugative plasmid, conjugative transposon or ICE pTiC58.

94. The DNA vector of embodiment 81, wherein the donor bacteria is an *E. coli* strain carrying the conjugative plasmid, conjugative transposon or ICE pMdT1.

95. The DNA vector of embodiment 81, wherein the donor bacteria is an *E. coli* strain carrying the conjugative plasmid, conjugative transposon or ICE R1.

96. The DNA vector of embodiment 81, wherein the donor bacteria is an *E. coli* strain carrying the conjugative plasmid, conjugative transposon or ICE Tn5520.

97. The DNA vector of embodiment 81, wherein the donor bacteria is an *E. coli* strain carrying the conjugative plasmid, conjugative transposon or ICE QKH54.

98. The DNA vector of embodiment 81, wherein the donor bacteria is an *E. coli* strain carrying the conjugative plasmid, conjugative transposon or ICE R64.

99. The DNA vector of embodiment 81, wherein the donor bacteria is an *E. coli* strain carrying the conjugative plasmid, conjugative transposon or ICE R751.

100. The DNA vector of embodiment 81, wherein the donor bacteria is an *E. coli* strain carrying the conjugative plasmid, conjugative transposon or ICE RP4.

101. The DNA vector of embodiment 81, wherein the donor bacteria is an *E. coli* strain carrying the conjugative plasmid, conjugative transposon or ICE pKL1.

102. The DNA vector of embodiment 81, wherein the donor bacteria is an *E. coli* strain carrying the conjugative plasmid, conjugative transposon or ICE RK2.

103. The DNA vector of embodiment 81, wherein the donor bacteria is an *E. coli* strain carrying the conjugative plasmid, conjugative transposon or ICE R1162.

104. The DNA vector of embodiment 81, wherein the donor bacteria is an *E. coli* strain carrying the conjugative plasmid, conjugative transposon or ICE Tn4555.

105. The DNA vector of embodiment 81, wherein the donor bacteria is an *E. coli* strain carrying the conjugative plasmid, conjugative transposon or ICE pHT.

106. The DNA vector of embodiment 81, wherein the donor bacteria is an *E. coli* strain carrying the conjugative plasmid, conjugative transposon or ICE Tn4399.

107. The DNA vector of embodiment 81, wherein the donor bacteria is an *E. coli* strain carrying the conjugative plasmid, conjugative transposon or ICE Tn916.

108. The DNA vector of embodiment 81, wherein the donor bacteria is an *E. coli* strain carrying the conjugative plasmid, conjugative transposon or ICE pST12.

109. The DNA vector of embodiment 81, wherein the donor bacteria is an *E. coli* strain carrying the conjugative plasmid, conjugative transposon or ICE pCU1.

110. The DNA vector of embodiment 81, wherein the donor bacteria is an *E. coli* strain carrying the conjugative plasmid, conjugative transposon or ICE pSU233.

111. The DNA vector of embodiment 81, wherein the donor bacteria is an *E. coli* strain carrying the conjugative plasmid, conjugative transposon or ICE F.

112. The DNA vector of embodiment 81, wherein the donor bacteria is an *E. coli* strain carrying the conjugative plasmid, conjugative transposon or ICE pMAB01.

113. The DNA vector of embodiment 81, wherein the donor bacteria is an *E. coli* strain carrying the conjugative plasmid, conjugative transposon or ICE R388.

114. The DNA vector of embodiment 81, wherein the donor bacteria is an *E. coli* strain carrying the conjugative plasmid, conjugative transposon or ICE pS7a.

115. The DNA vector of embodiment 81, wherein the donor bacteria is an *E. coli* strain carrying the conjugative plasmid, conjugative transposon or ICE pS7b.

116. The DNA vector of embodiment 81, wherein the donor bacteria is an *E. coli* strain carrying the conjugative plasmid, conjugative transposon or ICE R702.

117. The DNA vector of embodiment 81, wherein the donor bacteria is an *E. coli* strain carrying the conjugative plasmid, conjugative transposon or ICE pMUR274.

118. The DNA vector of embodiment 81, wherein the donor bacteria is an *E. coli* strain carrying the conjugative plasmid, conjugative transposon or ICE R100.

119. The DNA vector of embodiment 81, wherein the donor bacteria is an *E. coli* strain carrying the conjugative plasmid, conjugative transposon or ICE pVCR94deltaX.

120. The DNA vector of embodiment 81, wherein the donor bacteria is an *E. coli* strain carrying the conjugative plasmid, conjugative transposon or ICE R46.

121. The DNA vector of embodiment 81, wherein the donor bacteria is an *E. coli* strain carrying the conjugative plasmid, conjugative transposon or ICE pGO1.

122. The DNA vector of embodiment 81, wherein the donor bacteria is an *E. coli* strain carrying the conjugative plasmid, conjugative transposon or ICE pIP501.

123. An engineered *C. acnes* comprising any of the DNA vectors of any one of embodiments 14 to 122.

124. An engineered *C. acnes* produced by contacting *C. acnes* with any of the vectors of any one of embodiments 14 to 122.

125. A method for engineering a *C. acnes* comprising introducing the DNA vector of any one of embodiments 14 to 122 into a *C. acnes.*

126. A recombinant *C. acnes* phage.

127. The recombinant *C. acnes* phage according to embodiment 126 comprising at least one transgene.

128. The recombinant *C. acnes* phage according to embodiment 127 wherein said transgene is a CRISPR-Cas system or part of a CRISPR-Cas system.

129. The recombinant *C. acnes* phage according to embodiment 127 wherein said transgene is a DNA encoding an antigen.

130. The recombinant *C. acnes* phage according to any one of embodiments 126 to 129, wherein the host range of the recombinant phage is different from the host range of the corresponding wild type *C. acnes* phage.

131. The recombinant *C. acnes* phage according to any one of embodiments 126 to 130 comprising an engineered capsid.

132. The recombinant *C. acnes* phage according to embodiment 131 wherein an antigen is displayed at the surface of the engineered capsid.

133. A *C. acnes* cell carrying a recombinant DNA vector comprising:

a DNA template for homologous recombination with a *C. acnes* phage genome, an origin of replication allowing replication in *C. acnes*, and optionally a first selection marker allowing for selection of the DNA vector in *C. acnes.*

134. The *C. acnes* cell according to embodiment 133, wherein the *C. acnes* phage genome is introduced into said cell.

135. The *C. acnes* cell according to embodiment 133, wherein the *C. acnes* phage genome recombines with the DNA vector leading to production of recombinant phages.

136. A *C. acnes* cell comprising a recombinant DNA vector which comprises a DNA encoding an antigen.

137. A *C. acnes* cell carrying a DNA vector for the selective production of recombinant *C. acnes* phage comprising:

an origin of replication allowing replication in *C. acnes,* a CRISPR-Cas system expressed in said *C. acnes* cell but not targeting the newly generated recombinant *C. acnes* phage genome, and optionally a first selection marker allowing for selection of the DNA vector in *C. acnes.*

138. A method for producing a phage lysate containing wild-type or parent *C. acnes* phages and recombinant *C. acnes* phages wherein a wild-type or parent *C. acnes* phage genome is introduced into a *C. acnes* cell of embodiment 133.

139. A method for selecting recombinant *C. acnes* phages wherein a phage lysate containing wild-type or parent *C. acnes* phages and recombinant *C. acnes* phages is mixed with the *C. acnes* cell of embodiment 137, leading to selective production of recombinant *C. acnes* phages.

140. A method to treat *C. acnes* related disorder or disease comprising administering to a subject a recombinant *C. acnes* phage of anyone of embodiments 126 to 131 or a recombinant *C. acnes* phage obtained by the methods of embodiments 138 or 139.

141. A vaccine and/or immunogenic composition comprising a *C. acnes* cell of embodiment 136 comprising a DNA vector comprising a nucleic acid encoding an antigen.

142. A method to prevent and/or treat cancer in a subject in need thereof, comprising administering to said subject a therapeutically or prophylactically efficient amount of a *C. acnes* cell of embodiment 136 comprising a DNA vector comprising a nucleic acid encoding a tumor antigen.

143. A method to prevent and/or treat a viral infection in a subject in need thereof, comprising administering to said subject a therapeutically or prophylactically efficient amount of a *C. acnes* cell of embodiment 136 comprising a DNA vector comprising a nucleic acid encoding a viral antigen.

144. A method to prevent and/or treat a bacterial infection in a subject in need thereof, comprising administering to said subject a therapeutically or prophylactically efficient amount of a *C. acnes* cell of embodiment 136 comprising a DNA vector comprising a nucleic acid encoding a bacterial antigen.

145. A method to prevent and/or treat a fungal infection in a subject in need thereof, comprising administering to said subject a therapeutically or prophylactically efficient amount of a *C. acnes* cell of embodiment 136 comprising a DNA vector comprising a nucleic acid encoding a fungal antigen.

146. A method to prevent and/or treat an autoimmune disease in a subject in need thereof, comprising administering to said subject a therapeutically or prophylactically efficient amount of a *C. acnes* cell of embodiment 136 comprising a DNA vector comprising a nucleic acid encoding a self-antigen.

147. A method to prevent and/or treat allergy in a subject in need thereof, comprising administering to said subject a therapeutically or prophylactically efficient amount of a *C. acnes* cell of embodiment 136 comprising a DNA vector comprising a nucleic acid encoding an allergen.

148. A method to prevent and/or treat graft rejection in a subject in need thereof, comprising administering to said subject a therapeutically or prophylactically efficient amount of *C. acnes* cell of embodiment 136 comprising a DNA vector comprising a nucleic acid encoding a graft-specific antigen.

149. A recombinant *C. acnes* phage of anyone of embodiments 126 to 131 or a recombinant *C. acnes* phage obtained by the methods of embodiment 138 or 139 for use in a method to treat *C. acnes* related disorder or disease.

150. A *C. acnes* cell of embodiment 136 comprising a DNA vector comprising a nucleic acid encoding a tumor antigen for use in a method to prevent and/or treat cancer in a subject.

151. A *C. acnes* cell of embodiment 136 comprising a DNA vector comprising a nucleic acid encoding a viral antigen for use in a method to prevent and/or treat a viral infection in a subject.

152. A *C. acnes* cell of embodiment 136 comprising a DNA vector comprising a nucleic acid encoding a bacterial antigen for use in a method to prevent and/or treat a bacterial infection in a subject.

153. A *C. acnes* cell of embodiment 136 comprising a DNA vector comprising a nucleic acid encoding a fungal antigen for use in a method to prevent and/or treat a fungal infection in a subject.

154. A *C. acnes* cell of embodiment 136 comprising a DNA vector comprising a nucleic acid encoding a self-antigen for use in a method to prevent and/or treat an autoimmune disease in a subject.

155. A *C. acnes* cell of embodiment 136 comprising a DNA vector comprising a nucleic acid encoding an allergen for use in a method to prevent and/or treat allergy in a subject.

156. A *C. acnes* cell of embodiment 136 comprising a DNA vector comprising a nucleic acid encoding a graft-specific antigen for use in a method to prevent and/or treat graft rejection in a subject.

EXAMPLES

Example 1. Phage-Derived Particles for Delivery of DNA Payload into *C. acnes*

*C. acnes* phage-derived particles containing a synthetic DNA payload and able to inject it inside *C. acne* were developed. It is demonstrated for the first time the stable and autonomous replication of a recombinant DNA vector that allows for transgene expression. These phage-derived particles are produced upon the co-occurrence of a *C. acnes* phage genome and a DNA payload inside a *C. acnes* producer cell. The DNA payload is introduced into the *C. acnes* producer cell by different methods such as electroporation, electroporation of protoplast, conjugation, chemical transformation, transduction into the *C. acnes* producer cell. Such phage-derived particles open possibilities to deliver DNA encoding a therapeutic molecule into all *C. acnes* strains in situ with high efficiency and specificity, allowing, for example, sequence specific killing due to CRISPR-Cas expression or modulation of the immune system by secretion of immunomodulators.

Being able to edit *Cutibacterium acnes* population by removing specific proinflammatory strains to prevent or cure disease such as acne vulgaris or leverage their privilege location into the pilosebaceous unit to modulate the immune system or improve wound healing are attractive therapeutic approaches. To implement such approaches, one can either genetically modify *C. acnes* strains in situ or provide in vitro genetically modified *C. acnes*. Because of the large intra and inter-individual microbiome diversity both at the species and strain level, it appears difficult to provide a single or cocktail of engineered *C. acnes* strains able to colonize the skin of most patients.

Delivery of DNA in situ to the *C. acnes* population offers a way to circumvent such difficulties by allowing to leverage pre-establish strains potentially without disturbing the local microbiome. However, in situ delivery of genetic material to *C. acnes* is a challenging task for several reasons. First, there are so far no genetic elements such as plasmid able to robustly and autonomously replicate inside *C. acnes*. The few described genetic modifications consist in genomic insertion of synthetic DNA through homologous recombination[26]. This in vitro process has been shown to be very low efficiency and rely on the use of an antibiotic selection marker to select such events. Moreover, these genetic modifications have been restricted to a few specific strains (KPA17202) and might not be generalizable to all *C. acnes* strains. Second, in order to perform in situ genetic modification of *C. acnes* delivery of DNA is needed. The only described method for introducing DNA into *C. acnes* is the use of electroporation[26,27] a method that can only be performed in vitro.

The present invention solves both delivery and maintenance of synthetic DNA inside *C. acnes* population in situ. Phage-derived particles composed of a synthetic DNA vector/payload packaged inside the phage capsid at the expense of the phage genome are used. By hijacking the phage-capsid, it was taken advantage of the ability of the phage to transduce DNA into the bacterial host. These phage-derived particles, when put in the presence of the natural bacterial host of the phage, are able to bind to the bacteria and inject the DNA vector/payload inside the bacterial cytoplasm where it can replicate and lead to expression of a protein of interest.

*C. acnes* phage are naturally present on the skin where they infect and replicate using *C. acnes* as a host. *C. acnes* phages have a broad host range, meaning that they can infect most of the *C. acnes* strain diversity isolated so far. This makes the capsid of these phages a really efficient vehicle to deliver DNA in situ into all *C. acnes* strains regardless of their genetic diversity. To develop phage-derived particles from *C. acnes* phages, several phages from the skin of volunteer individuals were first isolated by sampling nose microcomedones using Biore Deep Cleansing Pore Strips (Kao Brands Company), following manufacturer's instructions. After being removed from the nose, microcomedones were collected, homogenized in sterile water and spread onto an RCM agar plate. After incubation under anaerobic conditions at 37° C. for 7 days, plaques could be observed on the lawn of *C. acnes* growth. Plaques were then isolated and the phages amplified on an indicator strain. Phage DNA was extracted using the Promega wizard DNA clean-up System and sent for library preparation by mechanical random fragmentation and sequenced with an Illumina MiSeq platform. Sequencing reads were assembled using Spades. As expected from previous publications, isolated phages were genetically similar to other sequenced phages.

Figure 1:
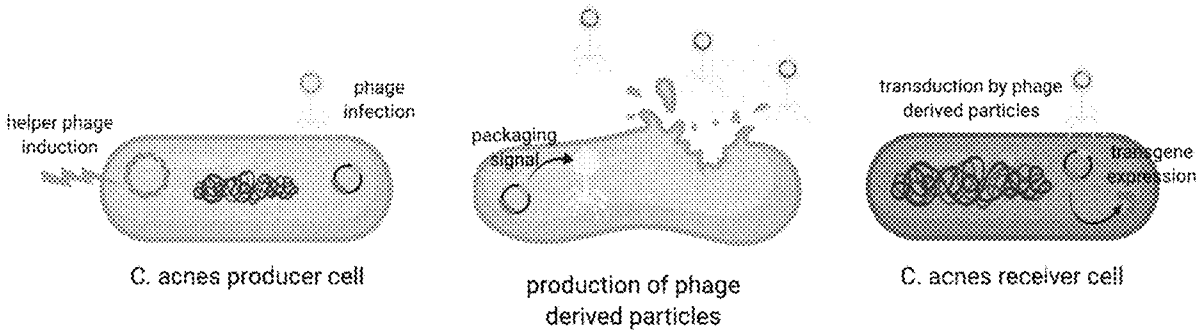
FIG. 1 depicts a *C. acnes* producer cell carrying a DNA vector with a packaging signal and a transgene which is infected by a *C. acnes* phage; phage-derived particles carrying the DNA vector are then produced and upon binding to *C. acnes* receiver cell transduce the DNA vector that replicates and leads to transgene expression. Alternatively, the *C. acnes* producer is not infected by a phage but carries also a helper phage that is induced to trigger phage-derived particle production.
Figure 2:
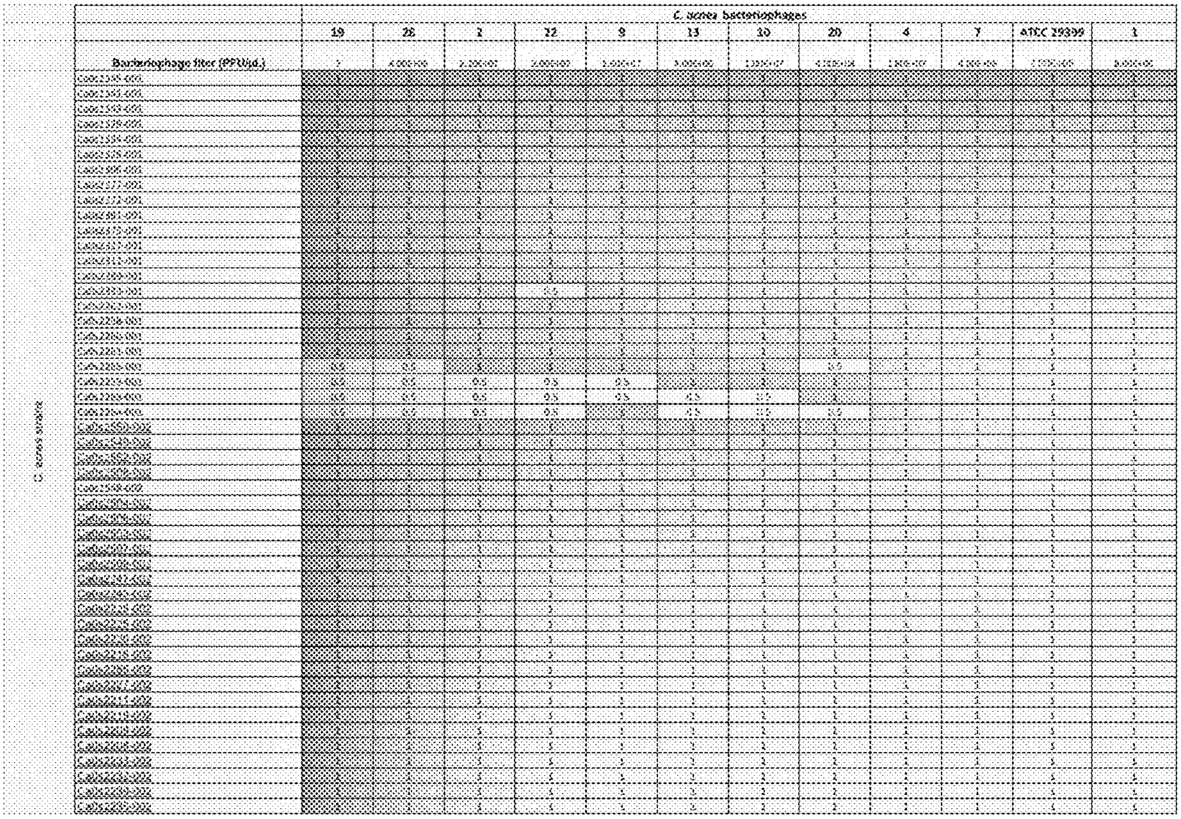
FIG. 2 depicts host range determination of isolated *C. acnes* bacteriophages. 1 indicates strain infection with full spot lysis; 0.5 indicates lower efficiency in strain infection with single plaques observed instead of full spot lysis.

A host-range determination was performed with the different isolated phages against a collection of *C. acnes* strains, covering the known phylogenetic diversity. All phages were able to infect most of the *C. acnes* strains showing, as previously reported, a broad host-range (FIG. 2). PAC7 phage was selected for further experiments.

Genome of phage PAC7 was purified, mechanically sheared to allow for random DNA fragmentation and a PCR-free library preparation was performed prior to paired-end sequencing using illumina Mi-seq. DNA reads were assembled using Spades, a single contig was obtained and annotated. After annotation, cohesive-ends were identified and DNA fragments of different sizes, containing cohesive ends, were cloned in order to identify the packaging sequence (called cos site for phages with cohesive ends) that allow recognition by the small terminase and packaging of the phage genome into the phage capsid. Potential packaging signals from PAC7 were cloned into the pIC086 vector in two different orientations. The pIC086 vector contains:

an origin of replication allowing replication into *C. acnes*, and a selection marker functional in *C. acnes* (here giving resistance to erythromycin).

Cos containing vectors (cosmids) were cloned into the *E. coli* DH10B cloning strain, sequence verified. The DNA vectors (Table 1) were introduced into the *C. acnes* strain ATCC 11828, and recombinants were selected on agar plates with erythromycin.

To produce phage-derived particles, a liquid culture of the different *C. acnes* strains carrying the DNA vector (Table 2) were grown and infected by PAC7. A strain containing a plasmid without cos PAC7 (Ca0s16973) was used as control. After infection, the supernatant was filtered and collected. Because both phage genomes and DNA vectors contain a packaging signal, they compete for packaging into the capsid, giving rise to a phage/phage-derived particle mixture.

Figure 8:
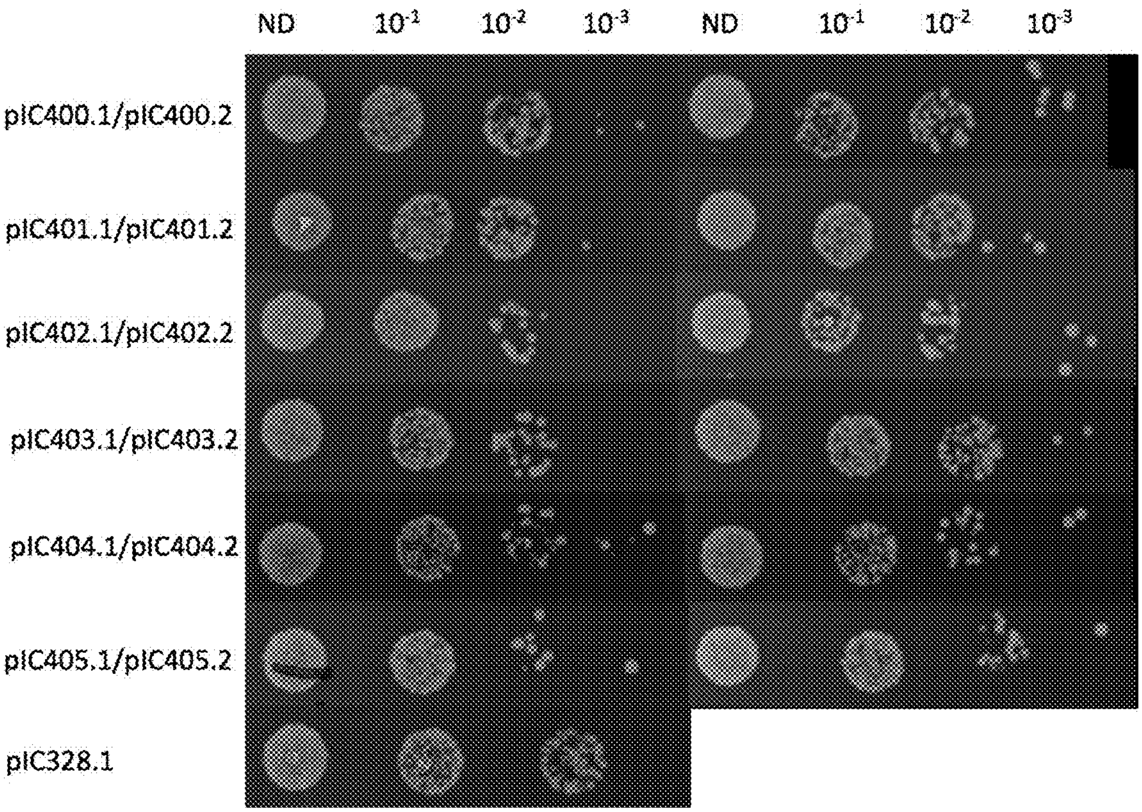
FIG. 8 depicts *C. acnes* transductants of phage-derived particles carrying DNA vector with phage packaging signal (cos) of different sizes. Each suspension of phage-derived particles, also containing phages, was mixed with *C. acnes* ATCC 11828 pseudolysogene, the mixture was incubated for 1 hour at room temperature, diluted and 4 μL of each dilution was plated on Brucella plates in presence of erythromycin (5 μg/m L). For each phage-derived particle containing a same DNA vector, two suspensions from independent productions were used (e.g. pIC400.1 and pIC400.2).

To quantify the number of phages and phage-derived particles in the suspension, phage and phage-derived particles titration was performed. Titration of phage-derived particles was first performed with *C. acnes* ATCC 6919, showing high efficiency killing due to phage infection but no transductants could be observed. In these conditions, transductants are co-infected with the phage, leading to death of transduced cells and to the underestimation of phage-derived particle titers. To circumvent this, it was decided to perform titration with a *C. acnes* ATCC 11828 pseudolysogene strain. Indeed, *C. acnes* phages are not strictly temperate nor strictly lytic phages in laboratory conditions. They are able to inject their genome into cells and stay dormant in the cell without integrating into the genome. These cells carrying the phage in pseudolysogeny state are immune to phage killing. Using a pseudolysogene culture for phage/phage-derived particles titration, a higher amount of transductants were observed. However due to some residual killing of *C. acnes* by phages, a large variability in phage-derived particle titers can be observed in different productions from infection of the same producer cell (FIG. 8). The concentration of phage was determined by plaque assay and showed a high concentration of phage for all phage/phage-derived particle suspension with a titer of approximately $10^7$ PFU/μL for each suspension (Table 3). Several colonies were confirmed to be *C. acnes* harbouring the cosmid by PCR. Phage suspension from infection of Ca0s16973 carrying pIC086 plasmid without cos did not show any transductant, confirming that packaging, and thus, the production of phagemid particles, was specific to cos carrying plasmids.

Titration of the phage-derived particles carrying the DNA vectors comprising phage packaging signal of different sizes shows (FIG. 8) no significant difference in number of transductants. The phage-derived particles titer was similar between all the different cosmids indicating that they are all functional and allow packaging of the DNA vector inside the phage capsid to produce phage-derived particles.

The results show, for the first time:

transduction by a phage-derived particle of a synthetic DNA vector in *C. acnes* replication of the DNA vector in *C. acnes* expression of a transgene (erythromycin resistance gene) carried by the replicative DNA vector.

This is a key milestone for the development of in situ DNA delivery, genetic modification and transgene expression in *C. acnes.*

Materials and Methods:

Cosmids construction: Cos fragments were extracted by PCR on diluted phage PAC7 suspension, gel purified and cloned using SapI golden gate reaction and the pIC086 vector.

Introduction of cosmids in *C. acnes* can be performed by methods such as electroporation, protoplast electroporation, chemical transformation, using conjugation, natural competency, transduction.

*C. acnes* conjugation: 2 mL of overnight cultures of *E. coli* donor harboring the different mobilizable shuttle plasmids, grown in LB broth (Fisher Scientific), were pelleted in a benchtop centrifuged at 6,000×g for 1 min. Supernatants were discarded and pellets were washed with 500 μL of pre-sterilized LB medium and centrifuged again using the same conditions. Each pellet was then re-suspended in 200 μL of exponentially growing ($OD_{600}$=0.5) *C. acnes* receptor BHI culture concentrated 10× (BHI broth, Oxoid). The mixture *E. coli*-*C. acnes* was spotted (50 μL/spot) onto Brucella agar plates (Sigma-Aldrich) and allowed to mate at 37° C. under anaerobic conditions for 24 hours. After that time, cells were harvested from the mating plate, re-suspended in 300 μL of BHI broth and plated onto Brucella agar plates that had been supplemented with 50 μg/mL polymyxin B (Sigma-Aldrich) and 5 μg/mL erythromycin (Sigma-Aldrich) or 5 μg/mL chloramphenicol (Sigma-Aldrich). After 7 days, *C. acnes* cells that grew in the presence of selection were streaked on Brucella agar plates supplemented with the appropriate selection and the presence of the conjugated plasmid was confirmed via specific PCRs. The identity of *C. acnes* as well as the absence of *E. coli* donor strain were also confirmed by PCR analyses.

Phage/phage-derived particles production: Overnight cultures of *C. acnes* ATCC 11828 harbouring the different vectors (two clones per construct) were set in 10 mL BHI cultures supplemented with 5 μg/mL erythromycin. Production from phagemid pIC328 was used as a positive control. After overnight culture, once the OD600 had reached 0.8-1, 15 mL of each culture were taken and spin down at 3,000×g for 5 min. The supernatant was discarded and the pellet was re-suspended in 200 μL of PAC7 phage suspension and left on the bench at room temperature for 30 min so phages infect the cells. After one hour, 15 mL of BHI medium were added to each culture and allowed to grow/infect overnight under anaerobic conditions at 37° C. After overnight incubation, cultures were very clear, indicating that infection had taken place. Cultures were spun down at 3,000×g for 5 min, and the supernatant was filtered through a 0.45 μm filter.

Phage titration: Serial dilutions of the phage/packaged phagemid mixture were made in $MgSO_4$ 5 mM and 4 μL of each dilution were spotted onto Brucella plates containing a top layer of agarose 4.5 g/L and the strain ATCC 11828. After overnight incubation under anaerobic conditions at 37° C., lysis plaques were counted.

Phage-derived particles titration: 90 μL of an overnight culture ($OD_{600}$ approx 0.8-1, concentrated ×10) of *C. acnes* ATCC 11828 pseudolysogene cells were mixed with 10 uL of Phage/Phage-derived particles from non-diluted to dilution $10^{-4}$ (dilution in $MgSO_4$ 5 mM). A control of cells with no phage was included in the assay. The cultures were incubated at room temperature for 1 hour. After this first incubation period, the cultures (bacteria+phages/phage-derived particles at different dilutions) were serially diluted up to $10^{-7}$ in BHI and incubated for 3-4 hours under anaerobic conditions at 37° C. After incubation, 4 μL of each dilution were spotted onto Brucella plates in the presence and absence of erythromycin (5 μg/mL). After 5 days of incubation at 37° C. under anaerobic conditions, colonies on BHI plates and BHI+erythromycin 5 μg/mL plates were scanned (FIG. 8).

Pseudolysogene production: strains were freshly made prior to the transduction test. PAC7 phage was added to a suspension of *C. acnes* ATCC 11828 cells and plated onto BHI agar plates. After 3 to 4 incubation days, cells growing on plates were recovered and either plated again to have more cells or used for titration. If successive growth on plates is needed, *C. acnes* phages are added to the culture in order to maintain strains in the pseudolysogene state.

Figure 3:
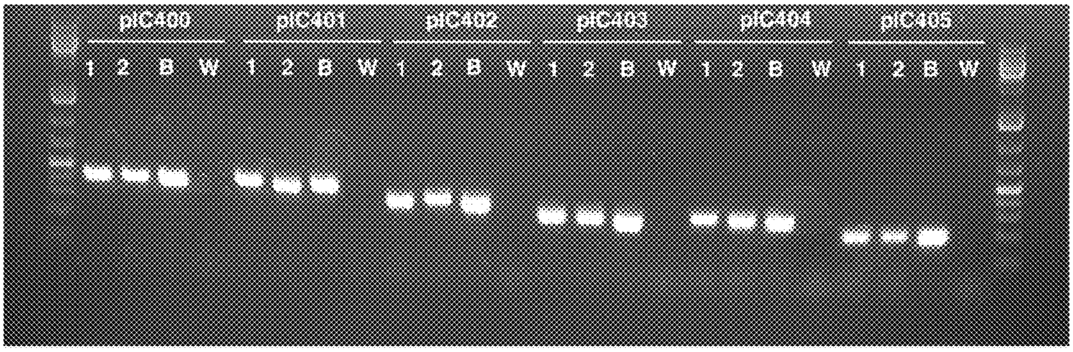
FIG. 3 depicts a gel. Individual colonies from phage-derived particles titration were streaked and a PCR on an individual colony was performed with primers IC208 (SEQ ID NO: 99)/IC310 (SEQ ID NO: 100) to confirm the presence of the phagemid. 1 and 2 refer to transductants coming from the independent production and titration of phage-derived particles carrying the same phagemid. B and W are respectively PCR on the phagemid extraction (positive control) and the ATCC 11828 strain (negative control). Presence of the plasmid after restreak confirms that transductants carry the replicative phagemid.

Confirmation of the phagemid transduction into *C. acnes* cells: colonies observed on BHI plates supplemented with erythromycin were re-isolated on BHI+erythromycin plates. Individual erythromycin resistant colonies obtained after streaking were then tested by PCR to confirm the presence of the phagemid (FIG. 3).

PCR verification of the transductant: colony PCR to check the presence of the phagemid was performed with primers IC208/1C310. A PCR performed with primers AD1261/AD1262 was also included to confirm *C. acnes* identity.

TABLE 1

Mobilizable DNA vectors including packaging signal of PAC7 phage

| DNA vector Name | Cos region | Primers for cloning | Mobilisable vector |
|---|---|---|---|
| pIC328 | PAC7 Cos region 1 in orientation 1 (383 bp) | AD1542/ AD1541 | pIC086 |
| pIC400 | PAC7 Cos region 1 in orientation 1 (317 bp) | IC511/ AD1542 | pIC086 |
| pIC401 | PAC7 Cos region 1 in orientation 2 (317 bp) | AD1541/ IC512 | pIC086 |
| pIC402 | PAC7 Cos region 2 in orientation 1 (217 bp) | IC511/ IC512 | pIC086 |
| pIC403 | PAC7 Cos region 2 in orientation 2 (167 bp) | IC513/ IC512 | pIC086 |
| pIC404 | PAC7 Cos region 3 in orientation 1 (167 bp) | IC511/ IC514 | pIC086 |
| pIC405 | PAC7 Cos region 3 in orientation 2 (83 bp) | IC513/ IC514 | pIC086 |

TABLE 2

List of *C. acnes* strains generated

| name | Strain description | plasmid |
|---|---|---|
| Ca0s16973 | *Cutibacterium acnes* ATCC 11828 | pIC086 |
| Ca0s18253 | *Cutibacterium acnes* ATCC 11828 | pIC328 |
| Ca0s19443 | *Cutibacterium acnes* ATCC 11828 | pIC400 |
| Ca0s19444 | *Cutibacterium acnes* ATCC 11828 | pIC401 |
| Ca0s19445 | *Cutibacterium acnes* ATCC 11828 | pIC402 |
| Ca0s19446 | *Cutibacterium acnes* ATCC 11828 | pIC403 |
| Ca0s19447 | *Cutibacterium acnes* ATCC 11828 | pIC404 |
| Ca0s19448 | *Cutibacterium acnes* ATCC 11828 | pIC405 |

TABLE 3

Results of phage titration

| strain infected | DNA payload | Phage used for infection | Phage titer (PFU/μL) on *C. acnes* ATCC 11828 indicator strain |
|---|---|---|---|
| Ca0s16973 | pIC086 | PAC7 | ~1E+8 |
| Ca0s18253 | pIC328 | PAC7 | ~1E+7 |
| Ca0s19443 | pIC400 | PAC7 | ~1E+7 |
| Ca0s19444 | pIC401 | PAC7 | ~1E+7 |

TABLE 3-continued

Results of phage titration

| strain infected | DNA payload | Phage used for infection | Phage titer (PFU/μL) on *C. acnes* ATCC 11828 indicator strain |
|---|---|---|---|
| Ca0s19445 | pIC402 | PAC7 | ~1E+7 |
| Ca0s19446 | pIC403 | PAC7 | ~1E+7 |
| Ca0s19447 | pIC404 | PAC7 | ~1E+7 |
| Ca0s19448 | pIC405 | PAC7 | ~1E+7 |

TABLE 4

Primers sequences

| Primers name | Primers sequence |
|---|---|
| AD1541 | GTTCCAGCTCTTCCGAGGACCACATCACACCCGTC (SEQ ID NO: 91) |
| AD1542 | GTTCCAGCTCTTCCTGCCCACTCCTCATCAGACAC (SEQ ID NO: 92) |
| IC511 | GTTCCAGCTCTTCCGAGAGGCAACAGAACACAACCAAA (SEQ ID NO: 93) |
| IC512 | GTTCCAGCTCTTCCTGCGACTATCAGGAAGCTCAGGC (SEQ ID NO: 94) |
| IC513 | GTTCCAGCTCTTCCGAGAAAACCCGCCAACCCCCACC (SEQ ID NO: 95) |
| IC514 | GTTCCAGCTCTTCCTGCACAAAAGGGAGGTATTTCACT (SEQ ID NO: 96) |
| AD1261 | CAGCGGCGCTGCTAAGAACTT (SEQ ID NO: 97) |
| AD1262 | CCGGCTGGCAAATGAGGCAT (SEQ ID NO: 98) |
| IC208 | GCTTCCTTAGCTTGCGAAATCTCGA (SEQ ID NO: 99) |
| IC310 | GTTCGGCTAAACCCAAAAGTAAAAAC (SEQ ID NO: 100) |

Example 2. Engineering and Selection of *C. acnes* Phages Using CRISPR-Cas System Single nucleotide modifications (SNM) were performed at various loci of the *C. acnes* phage PAC7 using CRISPR via two different strategies. In one strategy, a single vector containing both the editing template and the CRISPR system targeting the unmodified (not engineered or wt phage), allows to generate and amplify selectively the recombinant phage compared to the WT. However a step of isolation of the mutant phages is necessary. In the second strategy, two vectors, one harbouring the editing template and another harbouring the CRISPR system targeting the wt phage, are necessary to obtain and select mutant phages. In this document, both examples are included and explained separately:

Single Vector Strategy:

Using DNA sequences and associated annotations, the putative endolysin gene (SEQ ID NO: 77) and cos sequences (SEQ ID NO: 66) were identified and it was decided to attempt a SNM in such loci. In the case of the endolysin locus, the single base change leads to the same protein as the original or wt sequence after translation—a so-called synonymous mutation. In both cases, the editing template was designed so that after a second homologous recombination event, which results in the intended modification of the phage genome, the PAM sequence necessary for the CRISPR system to perform a double strand break, is removed. In such scenario, only the unmodified phage—and not the mutant phage—is targeted by the CRISPR system, providing the selection necessary for mutant-wt discrimination.

A CRISPR vector, named pIC104, was selected to further introduce the elements necessary to engineer PAC 7. pIC104 is an *E. coli*-*C. acnes* shuttle plasmid that includes:

- an origin of replication allowing replication into *C. acnes*
- a selection marker functional in *C. acnes* (here giving resistance to erythromycin)
- a relaxase and associated origin of transfer (oriT) to conjugate the DNA payload into *C. acnes*
- an origin and selection marker allowing replication in *E. coli.*
- the elements necessary for CRISPR targeting, including the gene encoding SpCas9, previously codon-optimised for *C. acnes* expression and the sgRNA.

Introduction of the target/seed sequences into pIC104 led to the vectors pIC238 and pIC240 in the case in which the endolysin (SEQ ID NO: 79) and the cos site (SEQ ID NO: 80) are targeted, respectively. Introduction of the editing template (SEQ ID NO: 81 for endolysin, SEQ ID NO: 82 for cos) into pIC238 and pIC240 led to vectors pIC253 and pIC257, respectively. Vectors (editing/targeting vectors) were cloned into the *E. coli* DH10B cloning strain, sequence verified and transformed into the *E. coli* donor strain harbouring conjugation machinery. These vectors were finally conjugated into *C. acnes* strain ATCC 11828 and transformants were selected on agar plates supplemented with erythromycin. The following strains were generated Ca0s18233 (*C. acnes* ATCC 11828 harbouring pIC238); Ca0s240 (*C. acnes* ATCC 11828 harbouring pIC240); Ca0s18206 (*C. acnes* ATCC 11828 harbouring pIC253), and; Ca0s18208 (*C. acnes* ATCC 11828 harbouring pIC257).

To produce engineered phages, a liquid culture of the different *C. acnes* strains carrying the DNA vector pIC253 (Ca0s18206) or pIC257 (Ca0s18208) were grown and infected by phage PAC7. After infection, the supernatant was filtered and collected. Here, it is referred to these supernatants as Sup-253 and Sup-257 to those obtained after infecting with phage PAC7 the strains Ca0s18206 and Ca0s18208, respectively. Theoretically, the unmodified phage has been targeted by the CRISPR system and the supernatant contains a high fraction of the engineered phage, the efficiency of the wt phage targeting being dependent on the efficiency of the CRISPR system and seed sequence used.

Figure 9:
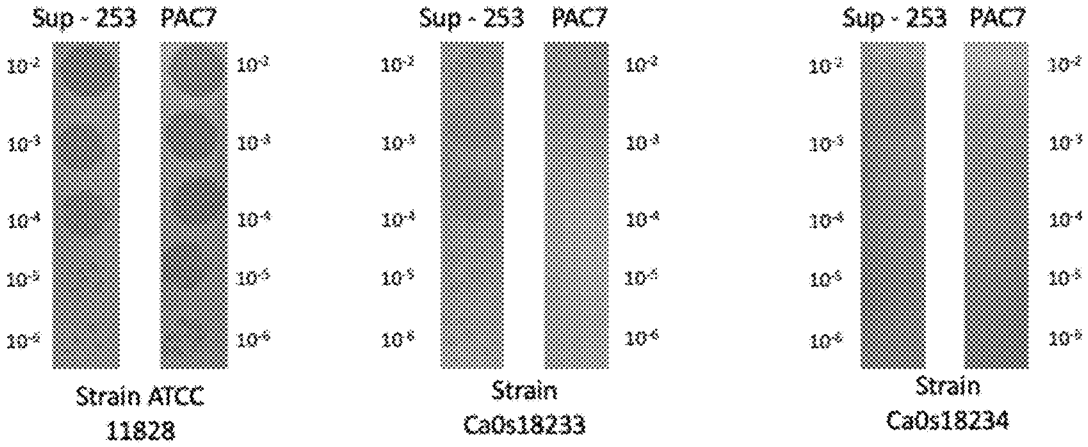
FIG. 9 depicts titration of supernatants obtained after infecting *C. acnes* harbouring editing/targeting vectors pIC253 (Ca0s18206), referred as Sup-253, on *C. acnes*

To demonstrate and quantify the presence of mutant and wt phage in the suspension, a phage titration was performed. Titration was performed with *C. acnes* ATCC 11828 and *C. acnes* ATCC 11828 harbouring pIC238 (Ca0s18233) and pIC240 (Ca0s18234) in the case of the phage modified in the endolysin or cos loci, respectively (FIG. 9 and FIG. 10). As mentioned above, these vectors contain the CRISPR system that selects for the intended modifications for each locus. If the mutant phage has been obtained and replicate, plaques corresponding to recombinant phage when titrating on *C. acnes* ATCC 11828 harbouring the targeting vectors should be observed. Titration of the supernatant obtained after infecting the strain containing the editing template for the endolysin locus in the strain harbouring the targeting vector for the cos locus—and vice versa—serves as a control in this experiment (any phage obtained in this supernatant should be targeted by *C. acnes* harbouring a vector that targets the wt cos locus in the same manner as a wt phage is targeted).

Individual plaques obtained after titration of supernatants on *C. acnes* ATCC 11828 were screened by PCR using primers IC443/IC444 and IC446/AD1289 in the case of Sup-253 and Sup-257, respectively, and the identity of the phage mutant confirmed by genome sequencing. Sequencing results of isolated plaques obtained after re-infection of *C. acnes* ATCC 11828 with previously isolated and sequenced plaques further confirmed the identity of the engineered phage.

Two-Vector Strategy:

Using DNA sequences and associated annotations, the putative endolysin gene (SEQ ID NO: 77) was identified and it was decided to attempt a SNM in such loci. The single base change leads to the same protein as the original or wt sequence after translation—a so-called synonymous mutation. The editing template or homology arms were designed so that after a second homologous recombination event, which results in the intended modification of the phage genome, the PAM sequence necessary for the CRISPR system to perform a double strand break, is removed. In such scenario, only the unmodified phage—and not the mutant phage—is targeted by the CRISPR system, providing the selection necessary for mutant-wt discrimination.

A shuttle mobilisable vector, named pIC086, was selected to further introduce the editing template. pIC086 is an *E. coli*-*C. acnes* shuttle plasmid that includes:

- an origin of replication allowing replication into *C. acnes*
- a selection marker functional in *C. acnes* (here giving resistance to erythromycin)
- a relaxase and associated origin of transfer (oriT) to conjugate the DNA payload into *C. acnes*
- an origin and selection marker allowing replication in *E. coli.*

A CRISPR vector, named pIC104, was selected to further introduce the elements necessary to engineer PAC 7. pIC104 is an *E. coli*-*C. acnes* shuttle plasmid that includes:

- An origin of replication allowing replication into *C. acnes*
- a selection marker functional in *C. acnes* (here giving resistance to erythromycin)
- a relaxase and associated origin of transfer (oriT) to conjugate the DNA payload into *C. acnes*
- an origin and selection marker allowing replication in *E. coli.*
- the elements necessary for CRISPR targeting, including the gene encoding SpCas9, previously codon-optimised for *C. acnes* expression and the sgRNA.

Introduction of the editing template into pIC086 led to the vector pIC350. Introduction of the target/seed sequence into pIC104 led to the vector pIC238. A vector containing the editing template for a different locus (vector pIC351) was also included as control. Targeting and editing vectors were cloned into the *E. coli* DH10B cloning strain, sequence verified and transformed into the *E. coli* donor strain harbouring a conjugation machinery. These vectors were finally conjugated into *C. acnes* strain ATCC 11828 and transformants were selected on agar plates supplemented with erythromycin. The following strains were generated Ca0s18233 (*C. acnes* ATCC 11828 harbouring pIC238); Ca0s18379 (*C. acnes* ATCC 11828 harbouring pIC350), and; Ca0s18381 (*C. acnes* ATCC 11828 harbouring pIC351).

To produce engineered phages, a liquid culture of the different *C. acnes* strains carrying the DNA vectors pIC350 (Ca0s18379) and pIC351 (control for editing template; strain Ca0s18381) were grown and infected by phage PAC7.

After infection, the supernatant was filtered and collected. Here, it is referred to these supernatants as Sup-350 and Sup-351 to those obtained after infecting with phage PAC7 the strains Ca0s18379 and Ca0s18381, respectively. Theoretically, if homologous recombination has taken place, the suspension contains a mixture of wt and engineered phage.

To select and quantify the presence of mutant and wt phage in the suspension, a phage titration was performed. Titration was performed with *C. acnes* ATCC 11828 and *C. acnes* ATCC 11828 harbouring pIC238 (Ca0s18233) (FIG. 11). The vector pIC238 contains the CRISPR system that selects for the intended modifications. If the mutant phage has been obtained, phage titer on Sup-350 should differ when titrated on *C. acnes* ATCC 11828 and *C. acnes* ATCC 11828 harbouring the targeting vector pIC238 (Ca0s18233). *C. acnes* ATCC 11828 is susceptible to both wt phage PAC7 and the engineered phage, whereas *C. acnes* harbouring pIC238 is only susceptible to the engineered phage. Titration of Sup-351 (control for editing template) on *C. acnes* ATCC 11828 and *C. acnes* harbouring pIC238 (Ca0s18233) should be the same, since both strains are susceptible to both, the wt phage PAC7 and the engineered phage (FIG. 12).

Individual plaques obtained after titration of supernatants on *C. acnes* ATCC 11828 were screened by PCR using primers 10443/10444 and IC446/AD1289 and the identity of the phage mutant confirmed by genome sequencing. Sequencing results of isolated plaques obtained after re-infection of *C. acnes* ATCC 11828 with previously isolated and sequenced plaques further confirmed the identity of the engineered phage.

It has been demonstrated, for the first time, that recombinant *C. acnes* phages could be efficiently produced, using in vivo recombination (recombineering) in *C. acnes* between a DNA template carried by a DNA vector and a *C. acnes* phage genome. These recombinant particles can be directly amplified selectively compared to wt particles if the DNA vector contains a CRISPR-Cas system targeting the wt phage genome but not the recombinant phage genome (1 vector strategy). Otherwise the few recombinant particles, obtained using a DNA vector that do not contain CRISPR-Cas system targeting wt phage genome, can be selected using a second infection with a *C. acnes* strain carrying a CRISPR-Cas system targeting wt phage genome but not recombinant phage genome (2 vector strategy). This demonstration was performed using single nucleotide modifications however insertion, deletion, replacement of one or several nucleotides including introduction of transgene without perturbing the phage production open the possibility to use *C. acnes* recombinant phage has a tool to for example express therapeutic proteins in vivo or to modify *C. acnes* phage host range.

Materials and Methods:

*C. acnes* conjugation: 2 mL of overnight cultures of *E. coli* harboring the different mobilizable shuttle plasmids, grown in LB broth (Fisher Scientific), were pelleted in a benchtop centrifuged at 6,000×g for 1 min. Supernatants were discarded and pellets were washed with 500 μL of pre-sterilized LB medium and centrifuged again using the same conditions. Each pellet was then re-suspended in 200 μL of exponentially growing ($OD_{600}$=0.5) *C. acnes* receptor BHI culture concentrated 10× (BHI broth, Oxoid). The mixture *E. coli*-*C. acnes* was spotted (50 μL/spot) onto Brucella agar plates (Sigma-Aldrich) and allowed to mate at 37° C. under anaerobic conditions for 24 hours. After that time, cells were harvested from the mating plate, re-suspended in 300 μL of BHI broth and plated onto Brucella agar plates that had been supplemented with 50 μg/mL polymyxin B (Sigma-Aldrich) and 5 μg/mL erythromycin (Sigma-Aldrich) or 5 μg/mL chloramphenicol (Sigma-Aldrich). After 7 days, *C. acnes* cells that grew in the presence of selection were streaked on Brucella agar plates supplemented with the appropriate selection and the presence of the conjugated plasmid was confirmed via specific PCRs. The identity of *C. acnes* as well as the absence of *E. coli* donor strain were also confirmed by PCR analyses.

Phage production: a liquid culture (BHI+erythromycin 5 μg/m L) of *C. acnes* ATCC 11828 or *C. acnes* carrying a DNA vector were grown to the exponential phase, centrifuged and resuspended (approx. $10^8$-$10^9$ cells) in 100 μL of *C. acnes* phage PAC7 suspension (approx. $10^5$ PFU/μL). The mixture was then incubated for 30-60 min at RT so that infection took place. After incubation, the mixture was diluted in 5 mL BHI supplemented with 5 μg/mL erythromycin and incubated overnight at 37° C. under anaerobic conditions. After overnight incubation, cultures were centrifuged and filtered through a 0.2 μm membrane filter.

Phage titration: phage suspensions were serially diluted in MgSO4 5 mM and spotted (4p1/spot) on a BHI double-layer plates containing *C. acnes* ATCC 11828 wt or *C. acnes* ATCC 11828 harbouring a targeting vector (Ca0s18233 and Ca0s18234). After 2 days of incubation under anaerobic conditions at 37° C., lysis plaques were counted.

PCR screening of phage mutants: PCR on individual plaques was performed with primers IC443/IC444 and IC446/AD1289 for SNM obtained in the endolysin and cos loci, respectively.

TABLE 5

Mobilizable targeting, editing and targeting/editing DNA vectors:

| DNA vector Name | Description | Target/ seed sequences | Editing template sequence |
|---|---|---|---|
| pIC238 | Mobilisable targeting vector with CRISPR system targeting the endolysin gene | SEQ ID NO: 79 | — |
| pIC240 | Mobilisable targeting vector with CRISPR system targeting the cos locus | SEQ ID NO: 80 | — |
| pIC253 | Mobilisable targeting and editing vector with CRISPR system targeting the endolysin gene and editing template to introduce a SNM in the endolysin gene | SEQ ID NO: 79 | SEQ ID NO: 81 |
| pIC257 | Mobilisable targeting and editing vector with CRISPR system targeting the cos locus and editing template to introduce a SNM in the cos locus | SEQ ID NO: 80 | SEQ ID NO: 82 |
| pIC350 | Mobilisable editing vector to introduce a SNM in the endolysin gene | — | SEQ ID NO: 81 |
| pIC351 | Mobilisable editing vector to introduce a SNM in the endonuclease locus. Used as control. | — | SEQ ID NO: 83 |

TABLE 6

List of *C. acnes* strains generated:

| Name | Strain description | Plasmid |
|---|---|---|
| Ca0s18233 | *Cutibacterium acnes* ATCC 11828 | pIC238 |
| Ca0s18234 | *Cutibacterium acnes* ATCC 11828 | pIC240 |
| Ca0s18206 | *Cutibacterium acnes* ATCC 11828 | pIC253 |
| Ca0s18208 | *Cutibacterium acnes* ATCC 11828 | pIC257 |
| Ca0s18379 | *Cutibacterium acnes* ATCC 11828 | pIC350 |
| Ca0s18381 | *Cutibacterium acnes* ATCC 11828 | pIC351 |

TABLE 7

| Primer sequences | |
|---|---|
| Primers name | Primers sequence |
| IC443 | CCAGGGTGTGAAACCGTCGCCTCTA (SEQ ID NO: 101) |
| IC444 | CGCAAACACCCCGTTTACCGGCCTT (SEQ ID NO: 102) |
| IC446 | AGGGTATTCCTACCCCCAGACGATT (SEQ ID NO: 103) |
| AD1289 | CCAATCATCCAACACCTGCTGC (SEQ ID NO: 104) |

Example 3. Introduction and Expression of Transgene into *C. acnes* Phages Using CRISPR-Cas System Introduction of a transgene expression cassette is performed at various loci of the *C. acnes* phage using in vivo homologous recombination in a first *C. acnes* strain followed by selection of the *C. acnes* recombinant phage, containing the transgene expression cassette, in a second *C. acnes* strain carrying a vector expressing a CRISPR-Cas system targeting WT phage but not the recombinant phage. Upon infection transgene expression can be observed.

One of the challenges in engineering bacteriophage is being able to perform genetic modifications without affecting the production of functional particles. This appears to be particularly difficult because bacteriophage genomes have few non-coding regions and their genetic program is tightly regulated to maximize progeny production. As an example of such genetic constraints, most of the bacteriophages organize their genetic information as long operon whose transcription is dependent on anti-termination mechanism or the expression of specific RNA polymerase or sigma factor. Another example of the high compaction of genetic information is the presence of numerous overlapping coding sequences. Indeed a lot of genes have their ribosome binding site and their start codon inside the gene upstream. Finally because of their small size, typically only a small fraction of genes are not essential to the phage life-cycle.

For all these reasons it is difficult to introduce transgene without perturbing the production of phage thus only specific genes and specific intergenic region can be used to introduce transgenes.

The genetic architecture of *C. acnes* phages is highly conserved and five different regions with different functions have been identified: Packaging, head assembly, tail assembly, lysis, DNA replication (FIG. 13).

Several candidates loci for insertion of transgene (Table 8) were selected. These loci have been chosen for several reasons.

Locus 1 for example is at the end of a potential operon (table 8 locus 1) and thus introduction of the transgene will supposedly have no impact on upstream genes.

Locus 2 is between the end of the region encoding tail assembly and upstream the lysis region. Introduction of a transgene here should not impact the tail assembly and if it happens to impact downstream lysis gene, consisting of a holin and an endolysin, recombinant particles by lysing *C. acnes* cells using for example chloroform treatment could still be produced.

Locus 3 is downstream of the HNH endonuclease gene and no gene is present downstream limiting potential interference of the transgene insertion.

TABLE 8

| Locus number | Description | Location in PAC7 phage genome (SEQ ID NO: 105) |
|---|---|---|
| 1 | Downstream of holin (gp21) and upstream of gp22 | 16709-16793 |
| 2 | Downstream of tail protein (gp19) and upstream of amidase (gp20) | 15390-15478 |
| 3 | Downstream endonuclease (gp45) | 29705-29755 |

Transgene can be inserted or replace one or several genes. The transgene can be with its own promoter and terminator, as a translational unit (RBS-CDS) or as a single coding sequence.

To determine which loci in the *C. acnes* phage genome allow for transgene insertion, production of phage and the expression of the transgene during infection a transcriptional unit (promoter RBS CDS terminator) or a translational unit (RBS-CDS) driving the expression of a reporter gene, here the oxygen independent and bilirubin dependent fluorescent gene UnaG (SEQ ID NO: 84) codon optimized for *C. acnes* expression, is inserted.

Introduction of the transgene will be performed using in vivo recombination.

Plasmids with 1 kb homologies upstream and downstream to the phage genome insertion site and the transgene in-between is cloned into an *E. coli*-*C. acnes* shuttle mobilisable vector (table 9) that includes:

- An origin of replication allowing replication into *C. acnes*
- a selection marker functional in *C. acnes* (here giving resistance to erythromycin)
- a relaxase and associated origin of transfer (oriT) to conjugate the DNA payload into *C. acnes*
- an origin and selection marker allowing replication in *E. coli*.

TABLE 9

| Plasmid containing DNA template for homologous recombination with phage genome at different loci | |
|---|---|
| Plasmid name | Description |
| pIC86-UnaGPAC7locus1 | Locus 1 upstream homology arm-UnaG transcriptional unit-Locus 1 downstream homology arm |
| pIC86-UnaGPAC7locus2 | Locus 2 upstream homology arm-UnaG transcriptional unit-Locus 2 downstream homology arm |
| pIC86-UnaGPAC7locus3 | Locus 3 upstream homology arm-UnaG transcriptional unit-Locus 3 downstream homology arm |

A CRISPR vector, will be constructed to select recombinant *C. acnes* phage with transgene. pIC104 is an *E. coli*-*C. acnes* shuttle plasmid that includes:

- an origin of replication allowing replication into *C. acnes*
- a selection marker functional in *C. acnes* (here giving resistance to erythromycin)
- a relaxase and associated origin of transfer (oriT) to conjugate the DNA payload into *C. acnes*
- an origin and selection marker allowing replication in *E. coli*.

the elements necessary for CRISPR targeting, including the gene encoding SpCas9, codon-optimised for *C. acnes* expression and the sgRNA scaffold.

Several sgRNA targets candidates targeting the WT phage at the locus of transgene insertion are cloned into pIC104 (Table 10).

Recombinant plaques are then isolated and reamplified on the *C. acnes* ATCC 11828 or *C. acnes* 11828 carrying the corresponding pIC104 derivative.

Expected number of total plaques and fluorescent plaques observed are summarized in the following table (Table 11).

TABLE 11

Expected outcome of phage titration of different suspension on different *C. acnes* strains

| Strain used for recombinant phage production | Phage plaques/ fluorescent phage plaques on strain ATCC 11828 | Phage plaques/fluorescent phage plaques on strain ATCC 11828 pIC104-PAC7locus1 | Phage plaques/fluorescent phage plaques on strain ATCC 11828 pIC104-PAC7locus2 | Phage plaques/fluorescent phage plaques on strain ATCC 11828 pIC104-PAC7locus3 |
|---|---|---|---|---|
| pIC86-UnaGPAC7locus1 | ~$10^7$ plaques No fluorescent plaques | <$10^7$ plaques Only fluorescent plaques | No plaques or few plaques Not fluorescent | No plaques or few plaques Not fluorescent |
| pIC86-UnaGPAC7locus2 | ~$10^7$ plaques No fluorescent plaques | No plaques or few plaques Not fluorescent | <$10^7$ plaques Only fluorescent plaques | No plaques or few plaques Not fluorescent |
| pIC86-UnaGPAC7locus3 | ~$10^7$ plaques No fluorescent plaques | No plaques or few plaques Not fluorescent | No plaques or few plaques Not fluorescent | <$10^7$ plaques Only fluorescent plaques |

TABLE 10

| Plasmid name | Description |
|---|---|
| pIC104-PAC7locus1 | pIC104 with sgRNA targeting locus 1 |
| pIC104-PAC7locus2 | pIC104 with sgRNA targeting locus 2 |
| pIC104-PAC7locus3 | pIC104 with sgRNA targeting locus 3 |

Targeting and editing vectors is cloned into the *E. coli* DH10B cloning strain, sequence verified and transformed into the *E. coli* donor strain harboring the conjugation machinery. These vectors are finally conjugated into *C. acnes* strain ATCC 11828 and transformants are selected on agar plates supplemented with erythromycin.

To produce engineered phages, a liquid culture of the different *C. acnes* strains carrying respectively pIC86-UnaGPAC7locus1, pIC86-UnaGPAC7locus2, pIC86-UnaGPAC7locus3 is grown and infected by phage PAC7. After infection, the supernatant is filtered and collected. Theoretically, if homologous recombination has taken place, the suspension contains a mixture of wt and engineered phage.

To select and quantify the presence of mutant and WT phage in the suspensions, a phage titration is performed. Titration is performed with *C. acnes* ATCC 11828 and *C. acnes* ATCC 11828 carrying respectively pIC104-PAC7locus1, pIC104-PAC7locus2, pIC104-PAC7locus3. *C. acnes* ATCC 11828 is susceptible to both wt phage PAC7 and the engineered phage, whereas *C. acnes* harbouring the corresponding pIC104 derivative is only susceptible to the phage engineered at the corresponding locus. A titration is also performed on a pIC104 derivative targeting a locus non engineered as a control for the CRISPR-Cas specificity. Titration is performed by spot assay on BHI erythromycin (5 μg/mL) supplemented with Bilirubin (20 μM). Bilirubin is necessary for UnaG fluorescence.

Individual plaques obtained after titration of supernatants on *C. acnes* ATCC 11828 and *C. acnes* carrying pIC104 derivatives are screened for fluorescence under blue light. Plaques that show fluorescence are screened by PCR to check the presence of the transgene. Finally sequencing of the insertion locus is performed.

Locus for which transgene is inserted and fluorescence can be observed are suitable for transgene expression.

Based on the screening of locus, several potential therapeutic proteins to be expressed by a recombinant phage are inserted among which IL-10 and anti-TNFalpha.

In conclusion, ability to engineer *C. acnes* phages allows the combination of two functions:

transgene expression in situ killing of a fraction of the *C. acnes* population in situ.

This can offer beneficial outcome for disease or conditions were *C. acnes* colonization is to high and/or leading to inflammatory response by for example expressing an anti-inflammatory protein such as IL-10 while killing *C. acnes* cell leading to inflammation.

Materials and Methods:

*C. acnes* conjugation: 2 mL of overnight cultures of *coli* donor strain harboring the conjugation machinery and the different mobilizable shuttle plasmids and a conjugative plasmid or ICE, grown in LB broth (Fisher Scientific), were pelleted in a benchtop centrifuged at 6,000×g for 1 min. Supernatants were discarded and pellets were washed with 500 μL of pre-sterilized LB medium and centrifuged again using the same conditions. Each pellet was then re-suspended in 200 μL of exponentially growing ($OD_{600}$=0.5) *C. acnes* receptor BHI culture concentrated 10× (BHI broth, Oxoid). The mixture *E. coli*-*C. acnes* was spotted (50 μL/spot) onto Brucella agar plates (Sigma-Aldrich) and allowed to mate at 37° C. under anaerobic conditions for 24 hours. After that time, cells were harvested from the mating plate, re-suspended in 300 μL of BHI broth and plated onto Brucella agar plates that had been supplemented with 50 μg/mL polymyxin B (Sigma-Aldrich) and 5 μg/mL erythromycin (Sigma-Aldrich) or 3.5 μg/mL chloramphenicol (Sigma-Aldrich). After 7 days, *C. acnes* cells that grew in the presence of selection were streaked on Brucella agar plates supplemented with the appropriate selection and the presence of the conjugated plasmid was confirmed via specific PCRs. The identity of *C. acnes* as well as the absence of *E. coli* donor strain were also confirmed by PCR analyses.

Phage production: a liquid culture (BHI+erythromycin 5 μg/mL) of *C. acnes* ATCC 11828 or *C. acnes* carrying a DNA vector were grown to the exponential phase, centrifuged and resuspended (approx. $10^5$-$10^9$ cells) in 100 μL of *C. acnes* phage PAC7 suspension (approx. $10^5$ PFU/pL). The mixture was then incubated for 30-60 min at RT so that infection took place. After incubation, the mixture was diluted in 5 mL BHI supplemented with 5 μg/mL erythromycin and incubated overnight at 37° C. under anaerobic conditions. After overnight incubation, cultures were centrifuged and filtered through a 0.2 μm membrane filter.

Phage titration: phage suspensions were serially diluted in $MgSO_4$ 5 mM and spotted (4p1/spot) on a BHI double-layer plates containing *C. acnes* ATCC 11828 wt or *C. acnes* ATCC 11828 harbouring a targeting vector. After 2 days of incubation under anaerobic conditions at 37° C., lysis plaques were counted.

PCR screening of phage mutants: PCR on individual plaques was performed with primers matching on one side the transgene and on the other side the WT phage.

Example 4

Effects of genetically modified *C. acnes* strains are tested in vitro for their effects on immune cells, in particular for their ability to induce specific cytokines or immune profiles, according to previously described protocols.

In particular, the protocol disclosed in Yu et al. (2016) Journal of Investigative Dermatology 136:2221-2228, with optional modifications and/or adaptations if needed, is implemented on said strains.

Example 5: Secretion of Antigens by Engineered *C. acnes* Strains

The pilosebaceous unit (PSU) is a complex skin appendage containing a diverse set of cells such as immune cells, sebaceous cells and stem cells. It's also a highly vascularized area making it an entry point for systemic delivery of molecules. The PSU microbiota is dominated by *C. acnes*, therefore the ability to engineer *C. acnes* to secrete recombinant proteins in situ is of great interest to both modulate the activity of the cells present as well as for the delivery of molecules in the blood. The present example demonstrates the use of DNA vectors that once introduced into *C. acnes* led to the secretion of recombinant proteins, here the chicken ovalbumin antigen protein. This invention opens possibilities to use engineered *C. acnes* strains secreting specific proteins of interest such as antigens as skin probiotics. Alternatively engineered phages or phage-derived particles can be used to deliver DNA vectors, encoding for the secretion of protein of interest, in the *C. acnes* population already present in the PSU.

*C. acnes* is one of the, if not the, most abundant and prevalent bacterial commensal of the human skin. It resides mostly in the PSU even if it can also be isolated from the skin surface. Specific strains belonging to specific phylotypes have been associated with acne vulgaris disease and are considered to be "pro-inflammatory". In order to characterize the difference between the different *C. acnes* phylotypes, a few studies have been characterizing the secretome in order to identify potential proteins specific to the pro-inflammatory phenotypes. Using a subset of the identified secreted proteins, the present inventors were able to identify putative secretion signal peptides (Table 12) using signalP (Armenteros, J. et al. SignalP 5.0 improves signal peptide predictions using deep neural networks. Nat Biotechnol 37, 420-423 (2019)).

To test ability of these secretion signal peptides to drive secretion of a recombinant protein in *C. acnes*, the present inventors built several replicative plasmids comprising:

- a promoter driving the expression of the recombinant protein,
- a signal peptides addressing the proteins to secretion systems fused to the N-terminal of a chicken ovalbumin CDS codon optimized for *C. acnes,*
- an erythromycin selection marker for *C. acnes,*
- an origin of replication functional in *C. acnes.*

The different DNA vectors (Table 13) were introduced into *C. acnes* ATCC 11828 (Table 14). Introduction into *C. acnes* cells can be performed by different methods such as electroporation, electroporation of protoplast, conjugation, chemical transformation, transduction into the *C. acnes*. Presence of the DNA vectors into *C. acnes* was confirmed, after streaking on selective plates, by colony PCR. Secretion of chicken ovalbumin protein in the different *C. acnes* culture supernatants was monitored using ELISA (FIG. 14) and Western Blot (FIG. 15). As shown in FIG. 14, both replicas of ELISA experiment show a significantly higher absorbance for most engineered *C. acnes* strains, except Ca0s22124, compared to wild-type *C. acnes* (*C. acnes* ATCC 11828). Strain Ca0s22126 was repeatedly giving the highest signal indicating higher level of secreted ovalbumin in culture supernatant. Secretion was further confirmed by Western blot (FIG. 15). A single band just above 40 kDa was observed for culture supernatant from strains Ca0s22120, Ca0s22122, Ca0s22126, Ca0s22128 and Ca0s22132. This band corresponds to ovalbumin size (43 kDa) and to the faint band from the ovalbumin control well. No band was observed for control strain Ca0s16973 that carries the empty plasmid used for cloning the different secretion plasmids. More intense band was found for Ca0s22126 confirming the results of the ELISA.

In conclusion, the present inventors describe for the first time the use of endogenous *C. acnes* secretion peptide for the secretion of recombinant protein by *C. acnes* using replicative DNA plasmids.

Materials and Methods:

Plasmids construction: Synthetic DNA fragments were ordered and assembled using Sapl golden gate cloning in the pIC47 plasmid (pIC086).

Conjugation: As described in Materials and methods of Example 1.

ELISA: The different *C. acnes* strains were streaked from cryostock into BHI+erythromycin plate, except for the control strain without plasm id that was streaked on BHI without antibiotic, and plates were incubated at 37° C. in anaerobic conditions for 4-7 days. When fully grown, 10 mL cultures of BHI+5 μg/mL erythromycin were inoculated with an inoculum from the corresponding streak and incubated one overnight at 37° C. in anaerobic conditions. After incubation, $OD_{600nm}$ was measured to control for difference in growth. 1 mL of culture was dispensed into a 1.5 mL tube and centrifuged 6 min at 6000 g. 10 μL of the supernatant was transferred to a high-binding 96 well-plate (Greiner 655061) prefiled with 90 μL of 1×PBS. Incubation of the covered plate during 2 hours at 37° C. was performed. After incubation, samples were discarded from the plate, 100 μL of PBS+5% bovine serum albumin (BSA) was added and the covered plate was incubated for 1 hour at 37° C. Three consecutive washing steps with 100 μL of PBS+0.05% Tween 20 were performed prior to the addition of 100 μL of primary antibody solution (Anti-OVA innovagen PA-0323-

100 diluted 1/1000 in PBS 1X+1% BSA+0.05% Tween 20). The covered plate was incubated at RT for 1 hour. Following incubation, three consecutive washing steps with 100 μL of PBS+0.05% Tween 20 were performed prior to the addition of 100 μL of secondary antibody solution (Anti-rabbit I nvitrogen A16035 antibody diluted 1/5000 in PBS 1X+1% BSA+0.05% Tween 20) and incubation at RT for 1 hour. After incubation, samples were discarded from the plate and final three consecutive washing steps with 100 μL of PBS+0.05% Tween 20 were performed. 100 μL of TMB-ELISA substrate (Thermo Scientific 34028) was added to each well and incubation was performed under light protection for 10 to 12 min at RT. 100 μL of 1 M sulfuric acid was added to each well to stop the reaction. Absorbance measurement at 450 nm was performed using an infinite reader (Tecan).

Western blot: The different *C. acnes* strains were streaked from cryostock into BHI+erythromycin plate, except for the control strain without plasmid that was streaked on BHI without antibiotic, and plates were incubated at 37° C. in anaerobic conditions for 4-7 days. When fully grown, 10 mL cultures of BHI+5 μg/mL erythromycin were inoculated with an inoculum from the corresponding streak and incubated one overnight at 37° C. in anaerobic conditions. After incubation, $OD_{60}0$ was measured to control for difference in growth. 1 mL of culture was dispensed into a 1.5 mL tube and centrifuged 6 min at 6000 g. Filtration of the supernatant using 0.2 μm filter. 30 μL of the filtered supernatant was supplemented with 7.5 μL of LDS sample buffer (B0008 Invitrogen™) and 3 μL of Bolt™ antioxidant (BT0005 Invitrogen™) before boiling at 100° C. for 10 min. 30 μL of the mixture was loaded into a Bolt™ 4 to 12% Bis-Tris gel (NW04120 Invitrogen™). After migration, transfer on nitrocellulose membrane was performed. After the transfer, the membrane was: soaked first in 5% skim milk solution in PBS+0.05% Tween 20 for 1 h, then soaked in 20 mL 5% skim milk solution in PBS+0.05% Tween 20 containing the primary antibody (Anti-OVA innovagen PA-0323-100) diluted 1:1000 overnight at 4° C., washed three times with PBS+Tween 0.05%, soaked 1 h in 20 mL 5% skim milk solution in PBS+0.05% Tween 20 containing the secondary antibody (Anti-rabbit Invitrogen A16035 antibody) diluted 1:5000, washed three times with PBS+Tween 0.05%. Final step of revelation was performed using chemiluminescent substrate (34580 Thermofisher). Imaging was done using iBright CL1000 (Invitrogen™)

TABLE 12

Secreted proteins used to extract secretion signals

| Protein id | SignalP 5.0 prediction |
|---|---|
| YP_056615.1 | Prediction: Signal peptide (Sec/SPI) Cleavage site between pos. 23 and 24: GAA-TP. Probability: 0.4339 |
| YP_056817.1 | Prediction: Lipoprotein signal peptide (Sec/SPII) Cleavage site between pos. 20 and 21: LSA-CG. Probability: 0.9859 |
| YP_055402.1 | Prediction: Signal peptide (Sec/SPI) Cleavage site between pos. 28 and 29: AHA-VE. Probability: 0.9710 |
| YP_056047 | Prediction: Signal peptide (Sec/SPI) Cleavage site between pos. 28 and 29: AHA-AP. Probability: 0.8551 |

TABLE 13

DNA vectors encoding secretion of ovalbumin

| DNA vector Name | Promoter | signal peptide from | protein |
|---|---|---|---|
| p2152 | P138 | YP_056047 | chicken ovalbumin |
| p2154 | P138 | YP_055402.1 | chicken ovalbumin |
| p2156 | P138 | YP_056817.1 | chicken ovalbumin |
| p2158 | P138 | YP_056615.1 | chicken ovalbumin |
| p2160 | ProxP | YP_056047 | chicken ovalbumin |
| p2162 | ProxP | YP_055402.1 | chicken ovalbumin |
| p2164 | ProxP | YP_056817.1 | chicken ovalbumin |
| p2166 | ProxP | YP_056615.1 | chicken ovalbumin |

TABLE 14

List of *C. acnes* strains generated

| name | Strain description | plasmid |
|---|---|---|
| Ca0s22118 | *Cutibacterium acnes* ATCC 11828 | p2152 |
| Ca0s22120 | *Cutibacterium acnes* ATCC 11828 | p2154 |
| Ca0s22122 | *Cutibacterium acnes* ATCC 11828 | p2156 |
| Ca0s22124 | *Cutibacterium acnes* ATCC 11828 | p2158 |
| Ca0s22126 | *Cutibacterium acnes* ATCC 11828 | p2160 |
| Ca0s22128 | *Cutibacterium acnes* ATCC 11828 | p2162 |
| Ca0s22130 | *Cutibacterium acnes* ATCC 11828 | p2164 |
| Ca0s22132 | *Cutibacterium acnes* ATCC 11828 | p2166 |
| Ca0s16973 | *Cutibacterium acnes* ATCC 11828 | p1047 (pIC86) |

Example 6: Introduction of Recombinant DNA into *C. acnes* Phages Using CRISPR-Cas System Inventors demonstrated the successful introduction of several recombinant DNA fragments inside *C. acnes* phage genome. Introduction of fragments as large as 3.3 kb could be performed without abolishing the ability of the engineered *C. acnes* phage to produce plaques. Engineered *C. acnes* phages were produced by first infecting different *C. acnes* strains (Ca0s20855, Ca0s20857, Ca0s20859) with wild-type PAC7. Each of these strains (table 15) contains a DNA vector carrying a template for homologous recombination with the recombinant DNA to be inserted flanked by homology regions present upstream and downstream of the phage insertion locus (FIG. 7A). The selected locus was locus 1 as described in Table 8.

Once the first infection performed, the phage suspension, containing both WT phage (PAC7) and potential mutant phages, was mixed with the screening strain Ca0s20472 in a top assay. After incubation, plaques could be observed for all three suspensions. Mutant phage plaques were discriminated from wild-type phage plaques using PCR from each individual plaques. Once identified, putative mutant plaques were peaked and isolated by streaking on a new top with Ca0s20472. New PCR on isolated plaques, with primers IC443 (SEQ ID NO: 101)/10290 (SEQ ID NO: 106), were performed to confirm the presence of a recombinant insert in the phage locus 1 (FIG. 16). Plaques coming from infection with PAC7 gave a band at the size corresponding to wt PAC7 (2.4 kb) whereas plaques coming from the infection of Ca0s20855 and Ca0s20859 gave a band at higher size, respectively 3.3 kb and 5.4 kb. Sequencing of the PCR product was performed and confirmed the introduction of the recombinant DNA in the locus 1 of the phage genome. Therefore, inventors demonstrated for the first time the introduction of a recombinant DNA into *C. acnes* phage genome.

Materials and Methods:

Phage production: 20 mL of dense liquid culture (BHI+ erythromycin 5 μg/mL) of *C. acnes* carrying a DNA vector were grown to the exponential phase, centrifuged and resuspended (approx. $10^8$-$10^9$ cells) in 200 μL of *C. acnes* phage PAC7 suspension (approx. $10^7$ PFU/μL). The mixture was then incubated for 30-60 min at RT so that infection took place. After incubation, 20 mL of BHI was added to the mixture and incubated overnight at 37° C. under anaerobic conditions. After overnight incubation, cultures were centrifuged and filtered through a 0.2 μm membrane filter.

Top assay: 100 μL of phage suspension was mixed with dense culture of Ca0s20472 in a final mixture of 2 mL of 0.45% BHI agar. All mixture was poured on Brucella plates supplemented with 5 μg/mL erythromycin.

TABLE 15

List of *C. acnes* strains

| name | Strain description | plasmid |
|---|---|---|
| Ca0s20855 | *Cutibacterium acnes* ATCC 11828 with template for homologous recombination to introduce 908 bp in locus 1 (SEQ ID NO: 112) | p1717 |
| Ca0s20857 | *Cutibacterium acnes* ATCC 11828 with template for homologous recombination to introduce 2863 bp in locus 1 | p1719 |
| Ca0s20859 | *Cutibacterium acnes* ATCC 11828 with template for homologous recombination to introduce 3315 bp in locus 1 | p1721 |
| Ca0s20472 | *Cutibacterium acnes* ATCC 11828 containing a CRISPR-Cas system targeting wt PAC7 phage genome at locus 1 | p1683 |

Example 7: Production/Generation of Conditionally-Replicative Phage

Phage therapy using cocktails of naturally occurring or engineered phages appears to be an attractive alternative to antibiotics for the killing of pathogenic bacteria or as a way to modulate microbiota by specific removal of strains or species. One peculiar feature of phages as a drug is their ability to replicate. Indeed after each infection of the target bacteria by one phage, as much as hundreds of particles might be produced. This replication implies that the activity of the phage drug substance is actually not controlled solely by the dose given but also by how much replication of the phage might happen. Amount of phage replication might depend on the accessibility and the load of the target bacterial population as well as the identity of the target population. Indeed different strains might lead to different burst size, meaning a different number of phage progeniture from the infection by one phage. These uncontrolled pharmacodynamics aspects might be a negligible drawback when phages are used to eradicate a population of pathogenic strains but this may be problematic if it is intended to use phages for precise regulation of a given bacterial population among a given microbiota.

Inventors herein demonstrate how to select conditionally replicative *C. acnes* phages; these phages are able to replicate in a specific engineered host production strain but not in the target bacterial population. This invention paves the way for the use of conditionally-replicative phages as an alternative to classical phage therapy.

For a phage to successfully produce more copies of itself it needs to go through several steps:

1) Binding to a bacterial host and injection of its genome into the cytoplasm,
2) Replication of its genome,
3) Expression of the different genes necessary for the production of the new capsids,
4) Packaging of the newly replicated genomes into the capsids, and
5) Release of the particles thanks to the active lysis of the host bacterial cell.

Completion of all these steps, in a manner that maximizes the number of phage particles produced, requires the coordinated expression of dozens of genes. For example, expression of genes involved in lysis such as holin and endolysin is programmed so that lysis occurs only once most of the phage particles assembly is done. In order to generate a conditionally-replicative phage, the inventors propose to delete or inactivate, in the phage genome, one or several genes that are essential for a complete phage replication cycle and to provide them in trans.

As a proof of concept, inventors were able to produce conditionally-replicative *C. acnes* phages with a deletion in an essential endonuclease gene (gp45, SEQ ID NO: 107).

First, a *C. acnes* strain (Ca0s22235) containing a plasmid (p2192) expressing spCas9, a sgRNA targeting the wt PAC7 phage in the region of the essential endonuclease gene (SEQ ID NO: 108), and a cassette expressing the essential endonuclease using P138 promoter was generated. A suspension of PAC7 phage was mixed with the strain Ca0s22235 in a top assay. After incubation plaques were obtained and screened by PCR for deletion using primers IC446 (SEQ ID NO: 103)/AL97 (SEQ ID NO: 109). 2 plaques (n° 28 and n° 42) showed shorter band size compared to wt PAC7 indicating potential deletion in the endonuclease locus. Plaques were peaked and re-isolated separately with selective strain Ca0s22235. After incubation, plaques were picked for PCR using IC619 (SEQ ID NO: 110)/AL219 (SEQ ID NO: 111). PCR confirmed the presence of a deletion in the essential endonuclease gene with smaller band size for plaques n° 28 (PAC7-m28-gp45) and n° 42 compared to wt PAC7 plaques (FIG. 17). Sequencing of the PCR product showed partial deletion of the first 25 amino acids of the endonuclease for phage PAC7-m28-gp45 (FIG. 18). Streaking of the isolated plaques in presence of *C. acnes* ATCC 11828 strain led to no plaques for phage PAC7-m28-gp45 whereas plaques could be observed for phage isolated from plaque n° 42. This indicates that phage PAC7-m28-gp45 can produce plaques in strain Ca0s22235 that express in trans the essential endonuclease whereas it cannot produce plaques in the strain ATCC 11828 (which does not carry the essential endonuclease gene). Thus phage PAC7-m28-gp45 is a conditionally-replicative phage that can only replicate in a strain expressing in trans the endonuclease.

To conclude, inventors demonstrated production of the first *C. acnes* conditionally-replicative phage. This phage containing a deletion in the endonuclease gp45 was only able to replicate in an engineered strain expressing the endonuclease in trans.

TABLE 16

List of *C. acnes* strains

| name | Strain | plasmid | Description |
|---|---|---|---|
| Ca0s22235 | *Cutibacterium acnes* ATCC 11828 | p2192 | p2192 carry a CRISPR-Cas system targeting wt PAC7 phage genome in the endonuclease region |

Materials and Methods:

Phage production: 20 mL of dense liquid culture (BHI+ erythromycin 5 μg/mL) of

*C. acnes* carrying a DNA vector were grown to the exponential phase, centrifuged and resuspended (approx. $10^8$-$10^9$ cells) in 200 μL of *C. acnes* phage PAC7 suspension (approx. $10^7$ PFU/μL). The mixture was then incubated for 30-60 min at RT so that infection took place. After incubation, 20 mL of BHI was added to the mixture and incubated overnight at 37° C. under anaerobic conditions. After overnight incubation, cultures were centrifuged and filtered through a 0.2 μm membrane filter.

Top assay: 50 μl of phage suspension was mixed with 50 μl of Ca0s22235 high cell density culture, in a final mixture of 2 ml of 0.45% BHI agar. Mixture was poured BHI agar plate supplemented with 5 ug/ml erythromycin. Top plate was incubated at 37° C. in anaerobic conditions.

REFERENCES

1. Pasparakis, M., Haase, I. & Nestle, F. O. Mechanisms regulating skin immunity and inflammation. *Nature Reviews Immunology* 14, 289-301 (2014).
2. Scharschmidt, T. C. et al. A Wave of Regulatory T Cells into Neonatal Skin Mediates Tolerance to Commensal Microbes. *Immunity* 43, 1011-1021 (2015).
3. Oh, J. et al. Biogeography and individuality shape function in the human skin metagenome. *Nature* 514, 59-64 (2014).
4. Oh, J. et al. Biogeography and individuality shape function in the human skin metagenome. *Nature* 514, 59-64 (2014).
5. Nakatsuji, T. et al. The microbiome extends to subepidermal compartments of normal skin. *Nat Commun* 4, 1431 (2013).
6. Bay, L. et al. Universal Dermal Microbiome in Human Skin. *Mbio* 11, (2020).
7. Nagao, K. et al. Stress-induced production of chemokines by hair follicles regulates the trafficking of dendritic cells in skin. *Nat Immunol* 13, 744-752 (2012).
8. Adachi, T. et al. Hair follicle—derived IL-7 and IL-15 mediate skin-resident memory T cell homeostasis and lymphoma. *Nat Med* 21, 1272-1279 (2015).
9. Paus, R., Ito, N., Takigawa, M. & Ito, T. The Hair Follicle and Immune Privilege. *J Invest Derm Symp P* 8, 188-194 (2003).
10. Scholz, C. F. & Kilian, M. The natural history of cutaneous propionibacteria, and reclassification of selected species within the genus *Propionibacterium* to the proposed novel genera Acidipropionibacterium gen. nov., Cutibacterium gen. nov. and Pseudopropionibacterium gen. nov. *International Journal of Systematic and Evolutionary Microbiology* 66, 4422-4432 (2016).
11. McLaughlin, J. et al. *Propionibacterium acnes* and Acne Vulgaris: New Insights from the Integration of Population Genetic, Multi-Omic, Biochemical and Host-Microbe Studies. *Microorganisms* 7, 128 (2019).
12. Barnard, E. et al. Strains of the *Propionibacterium acnes* type III lineage are associated with the skin condition progressive macular hypomelanosis. *Scientific reports* 6, 31968 (2016).
13. Petersen, R. L. W., Scholz, C. F. P., Jensen, A., Bruggemann, H. & Lomholt, H. B. *Propionibacterium acnes* phylogenetic type III is associated with progressive macular hypomelanosis. *European J Microbiol Immunol* 7, 37-45 (2017).
14. McDowell, A., McLaughlin, J. & Layton, A. M. Is Cutibacterium (previously *Propionibacterium*) *acnes* a potential pathogenic factor in the aetiology of the skin disease progressive macular hypomelanosis? *J European Acad Dermatology Venereol Jeadv* (2020) doi:10.1111/jdv.16789.
15. Fitz-Gibbon, S. et al. *Propionibacterium acnes* Strain Populations in the Human Skin Microbiome Associated with Acne. *J Invest Dermatol* 133, 2152-2160 (2013).
16. Sörensen, M. et al. Mutagenesis of *Propionibacterium acnes* and analysis of two CAMP factor knock-out mutants. *Journal of Microbiological Methods* 83, 211-216 (2010).
17. Allhorn, M., Arve, S., Bruggemann, H. & Lood, R. A novel enzyme with antioxidant capacity produced by the ubiquitous skin colonizer *Propionibacterium acnes. Sci Rep-uk* 6, 36412 (2016).
18. Nazipi, S., Stødkilde, K., Scavenius, C. & Bruggemann, H. The Skin Bacterium *Propionibacterium acnes* Employs Two Variants of Hyaluronate Lyase with Distinct Properties. Microorg 5, 57 (2017).
19. Kasimatis, G., Fitz-Gibbon, S., Tomida, S., Wong, M. & Li, H. Analysis of Complete Genomes of *Propionibacterium acnes* Reveals a Novel Plasmid and Increased Pseudogenes in an Acne Associated Strain. *BioMed Research International* 2013, 1-11 (2013).
20. Davidsson, S. et al. Prevalence of Flp Pili-Encoding Plasmids in *Cutibacterium acnes* Isolates Obtained from Prostatic Tissue. *Frontiers in microbiology* 8,2241 (2017).
21. Aoki, S., Nakase, K., Hayashi, N. & Noguchi, N. Transconjugation of erm(X) conferring high-level resistance of clindamycin for *Cutibacterium acnes. Journal of Medical Microbiology* (2018) doi:10.1099/jmm.0.000875.
22. Aoki, S. et al. Transferable Multidrug-Resistance Plasmid Carrying a Novel Macrolide-Clindamycin Resistance Gene, erm (50), in *Cutibacterium acnes. Antimicrob Agents Ch* 64, (2019).
23. Barnard, E., Shi, B., Kang, D., Craft, N. & Li, H. The balance of metagenomic elements shapes the skin microbiome in acne and health. *Scientific Reports* 6, srep39491 (2016).
24. Rouet, P., Smih, F. & Jasin, M. Expression of a site-specific endonuclease stimulates homologous recombination in mammalian cells. *Proc National Acad Sci* 91, 6064-6068 (1994).
25. Arazoe, T. et al. Site-specific DNA double-strand break generated by I-Scel endonuclease enhances ectopic homologous recombination in *Pyricularia oryzae. Fems Microbiol Lett* 352, 221-229 (2014).
26. Liu, J. et al. The diversity and host interactions of *Propionibacterium acnes* bacteriophages on human skin. *The ISME Journal* 9, 2078 (2015).
27. Lood, R. & Collin, M. Characterization and genome sequencing of two *Propionibacterium acnes* phages displaying pseudolysogeny. *BMC Genomics* 12, 198 (2011).
28. Brown, T., Petrovski, S., Dyson, Z., Seviour, R., Tucci, J. The Formulation of Bacteriophage in a Semi Solid Preparation for Control of *Propionibacterium acnes* Growth. *PloS one* 11(3), e0151184. (2016)

We claim:

1. A recombinant *C. acnes* phage, comprising at least one transgene, said transgene being a CRISPR-Cas system or part of a CRISPR-Cas system.

2. The recombinant *C. acnes* phage according to claim 1, comprising an engineered capsid.

3. The recombinant *C. acnes* phage according to claim 2, wherein an antigen is displayed at the surface of the engineered capsid.

4. A method to treat *C. acnes* related disorder or disease comprising administering to a subject the recombinant *C. acnes* phage of claim 1.

* * * * *

SEQUENCE LISTING

<160> NUMBER OF SEQ ID NOS: 114

<210> SEQ ID NO 1
<211> LENGTH: 38
<212> TYPE: DNA
<213> ORGANISM: Artificial Sequence
<220> FEATURE:
<223> OTHER INFORMATION: oriT_pMRC01

<400> SEQUENCE: 1
acaccaccca attttggagt ggtgtgtaag tgcgcatt 38

<210> SEQ ID NO 2
<211> LENGTH: 38
<212> TYPE: DNA
<213> ORGANISM: Artificial Sequence
<220> FEATURE:
<223> OTHER INFORMATION: oriT_RSF1010

<400> SEQUENCE: 2
ccagtttctc gaagagaaac cggtaagtgc gccctccc 38

<210> SEQ ID NO 3
<211> LENGTH: 40
<212> TYPE: DNA
<213> ORGANISM: Artificial Sequence
<220> FEATURE:
<223> OTHER INFORMATION: oriT_pRS01

<400> SEQUENCE: 3
tccgtaagat gctatcatct tactatgctt gcaaaaggtc 40

<210> SEQ ID NO 4
<211> LENGTH: 41
<212> TYPE: DNA
<213> ORGANISM: Artificial Sequence
<220> FEATURE:
<223> OTHER INFORMATION: oriT_pMV158

<400> SEQUENCE: 4
cactttatga atataaagta tagtgtgtta tactttacat g 41

<210> SEQ ID NO 5
<211> LENGTH: 42
<212> TYPE: DNA
<213> ORGANISM: Artificial Sequence
<220> FEATURE:
<223> OTHER INFORMATION: oriT_pTF1

<400> SEQUENCE: 5
gcacgggtaa tctcgaagag attactctaa gtgcgccctt gc 42

<210> SEQ ID NO 6
<211> LENGTH: 45
<212> TYPE: DNA
<213> ORGANISM: Artificial Sequence
<220> FEATURE:
<223> OTHER INFORMATION: oriT_pSC101

<400> SEQUENCE: 6
gggcgcacgt ttctgaacga agtgaagaaa gtctaagtgc gccct 45

<210> SEQ ID NO 7
<211> LENGTH: 51
<212> TYPE: DNA
<213> ORGANISM: Artificial Sequence
<220> FEATURE:
<223> OTHER INFORMATION: oriT_pBTK445

<400> SEQUENCE: 7
agcctttaaa gcgaaaatag ggtactccat gctcgctata tcatcctgac a 51

<210> SEQ ID NO 8
<211> LENGTH: 52
<212> TYPE: DNA
<213> ORGANISM: Artificial Sequence
<220> FEATURE:
<223> OTHER INFORMATION: oriT_pBBR1

<400> SEQUENCE: 8
ggtcacgact ttgcgaagca aagtctagtg agtatactca agcattgagt gg 52

<210> SEQ ID NO 9
<211> LENGTH: 53
<212> TYPE: DNA
<213> ORGANISM: Artificial Sequence
<220> FEATURE:
<223> OTHER INFORMATION: oriT_R721

<400> SEQUENCE: 9
cacacgattg taacatgacc ggaacggtct tgtgtacaat cggtatcgtg cct 53

<210> SEQ ID NO 10
<211> LENGTH: 59
<212> TYPE: DNA
<213> ORGANISM: Artificial Sequence
<220> FEATURE:
<223> OTHER INFORMATION: oriT_pRmeGR4a

<400> SEQUENCE: 10
gcaggaaaac ggcgtagcac atttttccgt atcctgcccc tccacattgt aaggggatt 59

<210> SEQ ID NO 11
<211> LENGTH: 60
<212> TYPE: DNA
<213> ORGANISM: Artificial Sequence
<220> FEATURE:
<223> OTHER INFORMATION: oriT_ColE1

<400> SEQUENCE: 11
gggtgtcggg gcgcagccct gacccagtca cgtagcgata gcggagtgta tactggctta 60

<210> SEQ ID NO 12
<211> LENGTH: 61
<212> TYPE: DNA
<213> ORGANISM: Artificial Sequence
<220> FEATURE:
<223> OTHER INFORMATION: oriT_pTiC58

<400> SEQUENCE: 12
ggatccaagg gcgcaattat acgtcgctga cgcgacgcct tgcgtagggg gccaaacagg 60
g 61

<210> SEQ ID NO 13
<211> LENGTH: 64
<212> TYPE: DNA
<213> ORGANISM: Artificial Sequence
<220> FEATURE:
<223> OTHER INFORMATION: oriT_pMdT1

<400> SEQUENCE: 13
aggtttcggg gcgcagccct gaaccagtca cctagcgcta gcggagtgta tactggctta 60
gtat 64

<210> SEQ ID NO 14
<211> LENGTH: 71
<212> TYPE: DNA
<213> ORGANISM: Artificial Sequence
<220> FEATURE:
<223> OTHER INFORMATION: oriT_R1

<400> SEQUENCE: 14
agcaaatcag caaaaacttg tttttgcgtg ggtgtggtg cttttggtgg tgagaaccac 60
caacctgttg a 71

<210> SEQ ID NO 15
<211> LENGTH: 71
<212> TYPE: DNA
<213> ORGANISM: Artificial Sequence
<220> FEATURE:
<223> OTHER INFORMATION: oriT_Tn5520

<400> SEQUENCE: 15
cttattgggg aattttcagc gatacggagt attgcggctc ggaaaattcc ctaataagct 60
acggtatttt c 71

<210> SEQ ID NO 16
<211> LENGTH: 90
<212> TYPE: DNA
<213> ORGANISM: Artificial Sequence
<220> FEATURE:
<223> OTHER INFORMATION: oriT_QKH54

<400> SEQUENCE: 16
gtgaagatag ttaaccggct tgccggttag ctaacttcac ctatcttgcc cggctcttcg 60
agccgtttaa cgccaggtga gtatcgcata 90

<210> SEQ ID NO 17
<211> LENGTH: 92
<212> TYPE: DNA
<213> ORGANISM: Artificial Sequence
<220> FEATURE:
<223> OTHER INFORMATION: oriT_R64

<400> SEQUENCE: 17
ggggtgtcgg ggcgaagccc tgaccagatg gcaattgtaa tagcgtcgcg tgtgacggta 60
ttacaattgc acatcctgtc ccgtttttcg gg 92

<210> SEQ ID NO 18
<211> LENGTH: 99
<212> TYPE: DNA
<213> ORGANISM: Artificial Sequence
<220> FEATURE:
<223> OTHER INFORMATION: oriT_R751

<400> SEQUENCE: 18
gaataaggga cagtgaagat agataaccgg ctcgccggtt agctaacttc acacatcctg 60
cccgccttac ggcgttaata acaccaagga aagtctaca 99

<210> SEQ ID NO 19
<211> LENGTH: 814
<212> TYPE: DNA
<213> ORGANISM: Artificial Sequence
<220> FEATURE:
<223> OTHER INFORMATION: oriT_RP4

<400> SEQUENCE: 19
cgacaggctc atgccggccg ccgccgcctt ttcctcaatc gctcttcgtt cgtctggaag 60
gcagtacacc ttgataggtg ggctgccctt cctggttggc ttggtttcat cagccatccg 120
cttgccctca tctgttacgc cggcggtagc cggccagcct cgcagagcag gattcccgtt 180
gagcaccgcc aggtgcgaat aagggacagt gaagaaggaa cacccgctcg cgggtgggcc 240
tacttcacct atcctgcccg gctgacgccg ttggatacac caaggaaagt ctacacgaac 300
cctttggcaa aatcctgtat atcgtgcgaa aaaggatgga tataccgaaa aaatcgctat 360
aatgaccccg aagcagggtt atgcagcgga aaagcgctgc ttccctgctg ttttgtggaa 420
tatctaccga ctggaaacag gcaaatgcag gaaattactg aactgagggg acaggcgaga 480
gacgatgcca aagagctaca ccgacgagct ggccgagtgg gttgaatccc gcgcggccaa 540
gaagcgccgg cgtgatgagg ctgcggttgc gttcctggcg gtgagggcgg atgtcgaggc 600
ggcgttagcg tccggctatg cgctcgtcac catttgggag cacatgcggg aaacggggaa 660
ggtcaagttc tcctacgaga cgttccgctc gcacgccagg cggcacatca aggccaagcc 720
cgccgatgtg cccgcaccgc aggccaaggc tgcggaaccc gcgccggcac ccaagacgcc 780
ggagccacgg cggccgaagc aggggggcaa ggct 814

<210> SEQ ID NO 20
<211> LENGTH: 100
<212> TYPE: DNA
<213> ORGANISM: Artificial Sequence
<220> FEATURE:
<223> OTHER INFORMATION: oriT_pKL1

<400> SEQUENCE: 20
cggggtgtcg ggtgaagcc ctgaccaagt ggtaatcgta tcggcgtgca tgcgcggtta 60
tacgattaca catcctgtcc cgatttctga ggcgttttaa 100

<210> SEQ ID NO 21
<211> LENGTH: 112
<212> TYPE: DNA
<213> ORGANISM: Artificial Sequence
<220> FEATURE:
<223> OTHER INFORMATION: oriT_RK2

<400> SEQUENCE: 21
ccggccagcc tcgcagagca ggattcccgt tgagcaccgc caggtgcgaa taagggacag 60
tgaagaagga acacccgctc gcgggtgggc ctacttcacc tatcctgccc gg 112

<210> SEQ ID NO 22
<211> LENGTH: 160
<212> TYPE: DNA
<213> ORGANISM: Artificial Sequence
<220> FEATURE:
<223> OTHER INFORMATION: oriT_R1162

<400> SEQUENCE: 22
ggccagtttc tcgaagagaa accggtaaat gcgccctccc ctacaaagta gggtcgggat 60
tgccgccgct gtgcctccat gatagcctac gagacagcac attaacaatg ggtgtcaag 120 atggttaagg ggagcaacaa ggcggcggat cggctggcca 160

<210> SEQ ID NO 23

```
<211> LENGTH: 174
<212> TYPE: DNA
<213> ORGANISM: Artificial Sequence
<220> FEATURE:
<223> OTHER INFORMATION: oriT_Tn4555

<400> SEQUENCE: 23

ccctcgggag agcccacaac tacgtaagcg gagcgtgtag ttatagtggg ctatatcaat      60

ggcaagccat tgtctgcaaa ctccagccta cggcttccgc tctcctccgt cagggaggtt    120

tttcatcatc gttgccgatt ggagatgcac cgaccagcac aaggtctaaa tcgt          174

<210> SEQ ID NO 24
<211> LENGTH: 192
<212> TYPE: DNA
<213> ORGANISM: Artificial Sequence
<220> FEATURE:
<223> OTHER INFORMATION: oriT_pHT

<400> SEQUENCE: 24

ccaaagaatt aatgcaaaga gcataaggga aaactaatag caccttccta aaggaaggtg      60

gctaagttgg ctgtgccaac tggttttctt tcaaaatcac ttcatatttt ttgctatcac    120

aaaaaaatcc attttcgacc tattttcggt cataatatag tacctacttt tggtcatagt    180

ttcgtccgta gt                                                        192

<210> SEQ ID NO 25
<211> LENGTH: 199
<212> TYPE: DNA
<213> ORGANISM: Artificial Sequence
<220> FEATURE:
<223> OTHER INFORMATION: oriT_Tn4399

<400> SEQUENCE: 25

taaggtgatt atgttgtttt tcttcatctg ttctatctgt tttttagtga ataatccgat      60

tgatgtaatc tgaaaagtcc gtgaccatcg ggagccgttc ccctcatctt tttgaggggc    120

aagtggtcgg ggaatgtaat acgccgacat taacttgcta tcctaaaaaa gatgtgattt    180

acggcttaga tgccgaatc                                                 199

<210> SEQ ID NO 26
<211> LENGTH: 216
<212> TYPE: DNA
<213> ORGANISM: Artificial Sequence
<220> FEATURE:
<223> OTHER INFORMATION: oriT_Tn916

<400> SEQUENCE: 26

aagcggaagt cgcaggtgtg gactgatctt gctggctggt gtggcaatag ccacgccagc      60

acttaacccc ccgtatctaa caggggggta caaatcgaca ggaaacagtc aaaaaaacat    120

tagaaaatcc tttggttaca agggatttac aaaatttcag cgtatgtcaa atgggcttta    180

aaagttgaca tacggccttt ttgattggag ggattt                              216

<210> SEQ ID NO 27
<211> LENGTH: 242
<212> TYPE: DNA
<213> ORGANISM: Artificial Sequence
<220> FEATURE:
<223> OTHER INFORMATION: oriT_pST12

<400> SEQUENCE: 27

ttgtgtgatt atatcgcgta ccacttttcg actgttttac cgccggtatt ctgccgtctg      60
```

acgctttgac gggtatttct gcctgacaat actgtcactg ccaaaaaact gccgtgcctt 120
tgtcggtaat tcgagcttgc tgacaggaca ggatgtgcaa ttgttatacc gcgcatacat 180
gcacgctatt acaattaccc tggtcagggc ttcgccccga caccccatgt cagatacgga 240
gc 242

<210> SEQ ID NO 28
<211> LENGTH: 268
<212> TYPE: DNA
<213> ORGANISM: Artificial Sequence
<220> FEATURE:
<223> OTHER INFORMATION: oriT_pCU1

<400> SEQUENCE: 28
gtattaccaa agtaataaag caaactcatt ataaaacaat gagttattag gtgtttttaa 60
tacctaatta ttaccgaata ttgacgctat ttattttttt attttttaaa tcagtgtgat 120
agcgtgattt atgccgctgc gttaggtgta tagcaggtta agggataaaa aatcatcttt 180
tttggtagga gcgatctacg taggttaagg actaactgac taaaaagcgt tcaatattcc 240
gtattcatgc ttgcatgaat accagtac 268

<210> SEQ ID NO 29
<211> LENGTH: 279
<212> TYPE: DNA
<213> ORGANISM: Artificial Sequence
<220> FEATURE:
<223> OTHER INFORMATION: oriT_pSU233
<220> FEATURE:
<221> NAME/KEY: misc_feature
<222> LOCATION: (199)..(199)
<223> OTHER INFORMATION: n is a, c, g, or t

<400> SEQUENCE: 29
cgctagcagc gcccctgacg gtatcctata aaaaaacaca ccgcgccgct agcagcaccc 60
ctaatataaa ataatgtttt ttataaaaat agtcagtacc acccctacaa agcggtgtcg 120
gcgcgttgct gtagctgcgt taacgacgct gctttaaata aatcagattt aaacaatata 180
aatccacaaa tacaactcna tgatattaaa gataaatcag caaaaacttg tttttgcgtg 240
gggtgtggtg cttttggtgg tgagaaccac caacctgtt 279

<210> SEQ ID NO 30
<211> LENGTH: 290
<212> TYPE: DNA
<213> ORGANISM: Artificial Sequence
<220> FEATURE:
<223> OTHER INFORMATION: oriT_F

<400> SEQUENCE: 30
cgcaccgcta gcagcgcccc tagcggtatc ctataaaaaa acacaccgcg ccgctagcag 60 caccccctaat ataaaataat gtttttttata aaaatagtca gtaccacccc tacaaaacgg 120
tgtcggcgcg ttgttgtagc cgcgccgaca ccgctttttt aaatatcata aagagagtaa 180
gagaaactaa tttttcataa cactctattt ataaagaaaa atcagcaaaa acttgttttt 240
gcgtggggtg tggtgctttt ggtggtgaga accaccaacc tgttgagcct 290

<210> SEQ ID NO 31
<211> LENGTH: 304
<212> TYPE: DNA
<213> ORGANISM: Artificial Sequence
<220> FEATURE:

<223> OTHER INFORMATION: oriT_pMAB01

<400> SEQUENCE: 31
tgcctcgcag agcaggatga cccgttgagc gcccccggcg cgaataaggg acagtgaaga 60
tagataaccg gctcgccggt tagctaactt cacacatcct gcccgcctta cggcgttaat 120
aacaccaagg aaagtctaca ccagccatta cgatttatcc gcaactatcg cgctatcagg 180
ccgcaaaagc agcaacggat atagcgaaaa ccgccacaat ggcccataat gccgctatcg 240
aagcgtgcca atgcacgccg atagcggact ttttgcgttt ccgtagcgcc gcttagtagc 300
gtta 304

<210> SEQ ID NO 32
<211> LENGTH: 402
<212> TYPE: DNA
<213> ORGANISM: Artificial Sequence
<220> FEATURE:
<223> OTHER INFORMATION: oriT_R388

<400> SEQUENCE: 32
ccgcctcgtc ctccaaaagt gcctgctttt ccgggcttag ccgtacttgg atggggtcgc 60
ctagtgccat gtcctctccc gtagtgttac tgtagtggtt caatcctagc atttacaagg 120
ggttgcggca atattgtagt ggcataacac tacacaggtt ttcgtccttg gcgtggaagt 180
cattgtaaat caatgactta cgcgcaccga aaggtgcgta ttgtctatag cccagattta 240
aggataccaa cccggctttt aaggacggaa accatgcgat aacgccagcg tgaccctaaa 300
gagggtcaaa actgctccca atgcgctatg cgcattgggt tatcgtgcag caatgatgca 360
actataatgc tatgatggtg ctacaatgat gcagaaaatg ag 402

<210> SEQ ID NO 33
<211> LENGTH: 456
<212> TYPE: DNA
<213> ORGANISM: Artificial Sequence
<220> FEATURE:
<223> OTHER INFORMATION: oriT_pS7a

<400> SEQUENCE: 33
ggatgatcaa acaaaatacg agagattttt tgttcgttca tccatggttt tagaaaaaag 60
agggacgatt tcggaagaag aaaatcgtct cttttttttc ttctttttgt atgacaaaaa 120
gaaagatctt ttgcccattt ttattttta taaaatgggc aggtggcgtt tgcgtaaagc 180
aaatcgacac aatccaaagg ggataaaagg ggaaagtgaa acttcccccct tttcaagcca 240 cattgtaata caagaacgaa gtgctttgta ttacaatgtg atagcttgca gtatttatgg 300
ttttatatgg tctattttgt tgtgaggatt gtaaccgaat agggcgcaat acttattaca 360
aaatcaatga caaagggcga ttgagaaatg agcgctgggg cattttatct ttgaggaagt 420
tcttgatgga tcagaaaaat gtatcacaaa tttaaa 456

<210> SEQ ID NO 34
<211> LENGTH: 456
<212> TYPE: DNA
<213> ORGANISM: Artificial Sequence
<220> FEATURE:
<223> OTHER INFORMATION: oriT_pS7b

<400> SEQUENCE: 34
tggatgatca aacaaaatac gagagatttt ttgttcgttc atccatggtt ttagaaaaaa 60
gagggacgat ttcggaagaa gaaaatcgtc tctttttttt cttctttttg tatgacaaaa 120
agaaagatct tttgcccatt tttatttttt ataaaatggg caggtggcgt ttgcgtaaag 180
caaatcgaca caatccaaag gggataaaag gggaaagtga aacttccccc ttttcaagcc 240
acattgtaat acaagaacga agtgctttgt attacaatgt gatagcttgc agtatttatg 300
gttttatatt tcctattttg ttgtgaggat tgtaaccgaa tagggcgcaa tgcttattac 360
aaaatcaatg acaaagggcg agtgaggaat gagcgctgag gcattttatc tttgaggaag 420
ttcttgatgg atcagaaaaa tgtatcacaa atttaa 456

<210> SEQ ID NO 35
<211> LENGTH: 697
<212> TYPE: DNA
<213> ORGANISM: Artificial Sequence
<220> FEATURE:
<223> OTHER INFORMATION: oriT_R702

<400> SEQUENCE: 35
ccctgcttcg gggtcattat agcgattttt tcggtatatc catccttttt cgcacgatat 60
acaggatttt gccaaagggt tcgtgtagac tttccttggt gtatccaacg gcgtcagccg 120
ggcaggatag gtgaagtagg cccacccgcg agcgggtgtt ccttcttcac tgtcccttat 180
tcgcacctgg cggtgctcaa cgggaatcct gctctgcgag gctggccggc taccgccggc 240
gtaacagatg agggcaagcg gatggctgat gaaaccaagc caaccaggaa gggcagccca 300
cctatcaagg tgtactgcct tccagacgaa cgacgagcga ttgaggaaaa ggcggcggcg 360
gccggcatga gcctgtcggc ctacctgctg gccgtcggcc agggctacaa aatcacgggc 420
gtcgtggact atgagcacgt ccgcgagctg gcccgcatca atggcgacct gggccgcctg 480
ggcggcctgc tgaaactctg gctcaccgac gacccgcgca cggcgcggtt cggtgatgcc 540
acgatcctcg ccctgctggc gaagatcgaa gagaagcagg acgagcttgg caaggtcatg 600
atgggcgtgg tccgcccgag ggcagagcca tgactttttt agccgctaaa acggccgggg 660
ggtgcgcgtg attgccaagc acgtccccat gcgctcc 697

<210> SEQ ID NO 36
<211> LENGTH: 475
<212> TYPE: DNA
<213> ORGANISM: Artificial Sequence
<220> FEATURE:
<223> OTHER INFORMATION: oriT_pMUR274

<400> SEQUENCE: 36
actccgatac gttgccctcc gaacggtatt caaggtcgat tttttgcgct tcggtcactc 60
ttaaactgat agatggcata ggtttccttt gtgtaatacc gatgtaatac atacaaatct 120
agcatagatg cggcttaatt ccacatatgt aatacgttgt gtattacata ttaaaacaca 180
aattagaata atttgttttg ttttcaagca tttacgatga aaatcgtaat tgcgtatggt 240
gtatagccgt taagggatac cataccacgc cttttttaag ggagaaaccg gtgttacgtg 300
caagtgaatc gctcaaaaag cgttcacatt cacacctttc atgcttgcat gaaaggaaac 360
ggacgggaat tagacaaaaa taagacacga tgagtaagtt attgagacaa gaaaaggaca 420
caaataagac attttttaga aaaaaacatt gacttgagac tagaaatgga caata 475

<210> SEQ ID NO 37
<211> LENGTH: 550
<212> TYPE: DNA
<213> ORGANISM: Artificial Sequence
<220> FEATURE:

<223> OTHER INFORMATION: oriT_R100

<400> SEQUENCE: 37
ttactctggc cataagataa aacctttcat tattaagcaa cgaacttttc actataaata 60
tgcatatagt gtttacaagt aagaaagaca ctcctagcag cgcctctagg atcatcctat 120
aaaaaaatgc gatccggcgc taggggcgtc cctaatatat atcaatgttt ttcgtgaaaa 180
ttgtcagtac tgatcctaat aagagtcgct atagggtcgt aacaggatcg ccaacgactc 240
tctatttaat aattcagaat tattaaatat aaatagcgtt tgttaattac atgatttaaa 300
acgtaaatca gcaaaaactt gtttttgcgt agtgtgtggt gcttttggtg gtgagaacca 360
ccaacctgtt gagccttttt gtggagtggg ttaaattatt tacggataaa gtcaccagag 420
gtggaaaaat gaaaaaatgg atgttagcaa tctgcctgat gtttataaat gggatctgcg 480
aagccgccga ttgctttgat cttgcaggtc gggattacaa aatagacccg gatttactaa 540
gaatgatatc 550

<210> SEQ ID NO 38
<211> LENGTH: 551
<212> TYPE: DNA
<213> ORGANISM: Artificial Sequence
<220> FEATURE:
<223> OTHER INFORMATION: oriT_pVCR94deltaX

<400> SEQUENCE: 38
gagcagagct atgtgtgaca agaagtatag agattacgag gtagccatca tggtcgatgt 60
gaaccctttc gacagggtta tgaatgaatt gaaaagtcgt ggccgcaaga acgctcacat 120
cctgagcatc ctccaattcg actggcctgc atcggaggcc atcatcgaga agctgagctg 180
ctacatcaca gacgggatta aggctaatca ggagcctgtg atttacccga tcattgaaga 240
agctctgcat cgctacagcc agctcgtgtt tcatgagcag agagagaaat atgaagaccc 300
ggccagaatt ggggcatttc tggaaaccct gatcaccgaa acctgccggg cgttggaagt 360
gcaaattgtc gatagtggcg gtgattcatg gtctgtcgat tcaggagagt cgttctcact 420
gtggctttct tcccatccag gagaactatc cattaacccg cagccccatg aggatgagac 480
ctctttgcgt ggcttgctgt atgagctcat cacctgtgag agcgtgaaaa ctgttttaag 540
gagaaccgac t 551

<210> SEQ ID NO 39
<211> LENGTH: 650
<212> TYPE: DNA
<213> ORGANISM: Artificial Sequence
<220> FEATURE:
<223> OTHER INFORMATION: oriT_R46

<400> SEQUENCE: 39
agcgccgcag ataatctgac cgattacctc ctgaaaccag gtctatatag gccaaaaagt 60
tcatctgata cttttgcggt tattattggc attcagtcct cacattgtgc atttcttaaa 120
caaaagattg ggatctaaca agctgaaatc ttagtattac caaagtaata aagcaaactc 180
attataaaac aatgagttat taggtgtttt taatacctaa ttattaccga atattgacgc 240
tatttatttt tttatttttt aaatcagtgt gatagcgtga tttatgccgc tgcgttaggt 300
gtatagcagg ttaagggata aaaaatcatc ttttttggta ggagcgatct acgtaggtta 360
aggactaact gactaaaaag cgttcaatat tccgtattca tgcttgcatg aataccagta 420
caacactatt acaacaaaag tacatcaaaa ttacatcaaa agtacatcac ttgaaggttg 480
acagtacaac agaattacat cattatctgg tactgaggta gccagtacaa caaaagtaca 540
tcaaaaatac atcataaata catcagaaat acatcaaaat tacatcattc taaatgaggg 600
tactatgaag cccaaaagta tcagggcggc acttcagttg atgttgccgg 650

<210> SEQ ID NO 40
<211> LENGTH: 36
<212> TYPE: DNA
<213> ORGANISM: Artificial Sequence
<220> FEATURE:
<223> OTHER INFORMATION: oriT_pGO1

<400> SEQUENCE: 40
cacgcgaacg gaacgttcgc ataagtgcgc ccttac 36

<210> SEQ ID NO 41
<211> LENGTH: 38
<212> TYPE: DNA
<213> ORGANISM: Artificial Sequence
<220> FEATURE:
<223> OTHER INFORMATION: oriT_pIP501

<400> SEQUENCE: 41
atacgaagta acgaagttac tgcgtataag tgcgccct 38

<210> SEQ ID NO 42
<211> LENGTH: 392
<212> TYPE: DNA
<213> ORGANISM: Artificial Sequence
<220> FEATURE:
<223> OTHER INFORMATION: R6K

<400> SEQUENCE: 42
gatctgaaga tcagcagttc aacctgttga tagtacgtac taagctctca tgtttcacgt 60
actaagctct catgtttaac gtactaagct ctcatgttta acgaactaaa ccctcatggc 120
taacgtacta agctctcatg gctaacgtac taagctctca tgtttcacgt actaagctct 180
catgtttgaa caataaaatt aatataaatc agcaacttaa atagcctcta aggttttaag 240
ttttataaga aaaaaaagaa tatataaggc ttttaaagcc tttaaggttt aacggttgtg 300
gacaacaagc cagggatgta acgcactgag aagcccttag agcctctcaa agcaattttg 360
agtgacacag gaacacttaa cggctgacat gg 392

<210> SEQ ID NO 43
<211> LENGTH: 2222
<212> TYPE: DNA
<213> ORGANISM: Artificial Sequence
<220> FEATURE:
<223> OTHER INFORMATION: RK2

<400> SEQUENCE: 43
gcgatgcagg tggctgctga acccccagcc ggaactgacc ccacaaggcc ctagcgtttg 60
caatgcacca ggtcatcatt gacccaggcg tgttccacca ggccgctgcc tcgcaactct 120
tcgcaggctt cgccgacctg ctcgcgccac ttcttcacgc gggtggaatc cgatccgcac 180
atgaggcgga aggtttccag cttgagcggg tacggctccc ggtgcgagct gaaatagtcg 240
aacatccgtc gggccgtcgg cgacagcttg cggtacttct cccatatgaa tttcgtgtag 300
tggtcgccag caaacagcac gacgatttcc tcgtcgatca ggacctggca acgggacgtt 360
ttcttgccac ggtccaggac gcggaagcgg tgcagcagcg acaccgattc caggtgccca 420

-continued

```
acgcggtcgg acgtgaagcc catcgccgtc gcctgtaggc gcgacaggca ttcctcggcc    480

ttcgtgtaat accggccatt gatcgaccag cccaggtcct ggcaaagctc gtagaacgtg    540

aaggtgatcg gctcgccgat aggggtgcgc ttcgcgtact ccaacacctg ctgccacacc    600

agttcgtcat cgtcggcccg cagctcgacg ccggtgtagg tgatcttcac gtccttgttg    660

acgtggaaaa tgaccttgtt ttgcagcgcc tcgcgcggga ttttcttgtt gcgcgtggtg    720

aacagggcag agcgggccgt gtcgtttggc atcgctcgca tcgtgtccgg ccacggcgca    780

atatcgaaca aggaaagctg catttccttg atctgctgct tcgtgtgttt cagcaacgcg    840

gcctgcttgg cttcgctgac ctgttttgcc aggtcctcgc cggcggtttt tcgcttcttg    900

gtcgtcatag ttcctcgcgt gtcgatggtc atcgacttcg ccaaacctgc cgcctcctgt    960

tcgagacgac gcgaacgctc cacggcggcc gatggcgcgg gcagggcagg gggagccagt   1020

tgcacgctgt cgcgctcgat cttggccgta gcttgctgga ctatcgagcc gacggactgg   1080

aaggtttcgc ggggcgcacg catgacggtg cggcttgcga tggtttcggc atcctcggcg   1140

gaaaaccccg cgtcgatcag ttcttgcctg tatgccttcc ggtcaaacgt ccgattcatt   1200

caccctcctt gcgggattgc cccggaatta attccccgga tcgatccgtc gatcttgatc   1260

ccctgcgcca tcagatcctt ggcggcaaga aagccatcca gtttactttg cagggcttcc   1320

caaccttacc agagggcgcc ccagctggca attccggttc gcttgctgtc cataaaaccg   1380

cccagtctag ctatcgccat gtaagcccac tgcaagctac ctgctttctc tttgcgcttg   1440

cgttttccct tgtccagata gcccagtagc tgacattcat ccggggtcag caccgtttct   1500

gcggactggc tttctacgtg gctgccattt ttggggtgag gccgttcgcg gccgaggggc   1560

gcagcccctg gggggatggg aggcccgcgt tagcgggccg ggagggttcg agaagggggg   1620

gcaccccccct tcggcgtgcg cggtcacgcg cacagggcgc agccctggtt aaaaacaagg   1680

tttataaata ttggtttaaa agcaggttaa aagacaggtt agcggtggcc gaaaaacggg   1740

cggaaaccct tgcaaatgct ggattttctg cctgtggaca gcccctcaaa tgtcaatagg   1800

tgcgcccctc atctgtcagc actctgcccc tcaagtgtca aggatcgcgc cctcatctg   1860

tcagtagtcg cgcccctcaa gtgtcaatac cgcagggcac ttatccccag gcttgtccac   1920

atcatctgtg ggaaactcgc gtaaaatcag gcgttttcgc cgatttgcga ggctggccag   1980

ctccacgtcg ccggccgaaa tcgagcctgc ccctcatctg tcaacgccgc gccgggtgag   2040

tcggcccctc aagtgtcaac gtccgcccct catctgtcag tgagggccaa gttttccgcg   2100

aggtatccac aacgccggcg gccctacatg gctctgctgt agtgagtggg ttgcgctccg   2160

gcagcggtcc tgatcccccg cagaaaaaaa ggatctcaag aagatccttt gatcttttct   2220

ac                                                                  2222
```

<210> SEQ ID NO 44
<211> LENGTH: 1522
<212> TYPE: DNA
<213> ORGANISM: Artificial Sequence
<220> FEATURE:
<223> OTHER INFORMATION: pBBR1

<400> SEQUENCE: 44

```
ctaccggcgc ggcagcgtta cccgtgtcgg cggctccaac ggctcgccat cgtccagaaa     60

acacggctca tcgggcatcg gcaggcgctg ctgcccgcgc cgttcccatt cctccgtttc    120

ggtcaaggct ggcaggtctg gttccatgcc cggaatgccg ggctggctgg gcggctcctc    180

gccggggccg gtcggtagtt gctgctcgcc cggatacagg gtcgggatgc ggcgcaggtc    240
```

```
gccatgcccc aacagcgatt cgtcctggtc gtcgtgatca accaccacgg cggcactgaa    300

caccgacagg cgcaactggt cgcggggctg gccccacgcc acgcggtcat tgaccacgta    360

ggccgacacg gtgccggggc cgttgagctt cacgacggag atccagcgct cggccaccaa    420

gtccttgact gcgtattgga ccgtccgcaa agaacgtccg atgagcttgg aaagtgtctt    480

ctggctgacc accacggcgt tctggtggcc catctgcgcc acgaggtgat gcagcagcat    540

tgccgccgtg ggtttcctcg caataagccc ggcccacgcc tcatgcgctt tgcgttccgt    600

ttgcacccag tgaccgggct tgttcttggc ttgaatgccg atttctctgg actgcgtggc    660

catgcttatc tccatgcggt aggggtgccg cacggttgcg gcaccatgcg caatcagctg    720

caacttttcg gcagcgcgac aacaattatg cgttgcgtaa aagtggcagt caattacaga    780

ttttctttaa cctacgcaat gagctattgc ggggggtgcc gcaatgagct gttgcgtacc    840

cccctttttt aagttgttga tttttaagtc tttcgcattt cgccctatat ctagttcttt    900

ggtgcccaaa gaagggcacc cctgcggggt tcccccacgc cttcggcgcg gctcccctc     960

cggcaaaaag tggcccctcc ggggcttgtt gatcgactgc gcggccttcg gccttgccca   1020

aggtggcgct gccccccttgg aacccccgca ctcgccgccg tgaggctcgg ggggcaggcg   1080

ggcgggcttc gcccttcgac tgccccccact cgcataggct tgggtcgttc caggcgcgtc   1140

aaggccaagc cgctgcgcgg tcgctgcgcg agccttgacc cgccttccac ttggtgtcca   1200

accggcaagc gaagcgcgca ggccgcaggc cggaggcttt tccccagaga aaattaaaaa   1260

aattgatggg gcaaggccgc aggccgcgca gttggagccg gtgggtatgt ggtcgaaggc   1320

tgggtagccg gtgggcaatc cctgtggtca agctcgtggg caggcgcagc ctgtccatca   1380

gcttgtccag cagggttgtc cacgggccga gcgaagcgag ccagccggtg gccgctcgcg   1440

gccatcgtcc acatatccac gggctggcaa gggagcgcag cgaccgcgca gggcgaagcc   1500

cggagagcaa gcccgtaggg gg                                             1522
```

<210> SEQ ID NO 45
<211> LENGTH: 1969
<212> TYPE: DNA
<213> ORGANISM: Artificial Sequence
<220> FEATURE:
<223> OTHER INFORMATION: pRO1600

<400> SEQUENCE: 45

```
gataatctca tgaccaaaat cccttaacgt gagttttcgt tccactgagc gtcagacccc     60

gtagaaaaga tcaaaggatc ttcttgagat cctttttttc tgcgcgtaat ctgctgcttg    120

caaacaaaaa aaccaccgct accagcggtg gtttgtttgc cggatcaaga gctaccaact    180

ctttttccga aggtaactgg cttcagcaga gcgcagatac caaatactgt tcttctagtg    240

tagccgtagt taggccacca cttcaagaac tctgtagcac cgcctacata cctcgctctg    300

ctaatcctgt taccagtggc tgctgccagt ggcgataagt cgtgtcttac cgggttggac    360

tcaagacgat agttaccgga taaggcgcag cggtcgggct gaacgggggg ttcgtgcaca    420

cagcccagct tggagcgaac gacctacacc gaactgagat acctacagcg tgagctatga    480

gaaagcgcca cgcttcccga agggagaaag gcggacaggc atccggtaag cggcagggtc    540

ggaacaggag agcgcacgag ggagcttcca gggggaaacg cctggtatct ttatagtcct    600

gtcgggtttc gccacctctg acttgagcgt cgatttttgt gatgctcgtc aggggggcgg    660

agcctatgga aaaacgccag caacgcggcc gtgaaaggca ggccggtccg tggtggccac    720
```

-continued ggcctctagg ccagatccag cggcatctgg gttagtcgag cgcgggccgc ttcccatgtc 780
tcaccagggc gagcctgttt cgcgatctca gcatctgaaa tcttcccggc cttgcgcttc 840
gctggggcct tacccaccgc cttggcgggc ttcttcggtc caaaactgaa caacagatgt 900
gtgaccttgc gcccggtctt tcgctgcgcc cactccacct gtagcgggct gtgctcgttg 960
atctgcgtca cggctggatc aagcactcgc aacttgaagt ccttgatcga gggataccgg 1020
ccttccagtt gaaaccactt tcgcagctgg tcaatttcta tttcgcgctg gccgatgctg 1080
tcccattgca tgagcagctc gtaaagcctg atcgcgtggg tgctgtccat cttggccacg 1140
tcagccaagg cgtatttggt gaactgtttg gtgagttccg tcaggtacgg cagcatgtct 1200
ttggtgaacc tgagttctac acggccctca ccctcccggt agatgattgt ttgcacccag 1260
ccggtaatca tcacactcgg tcttttcccc ttgccattgg gctcttgggt taaccggact 1320
tcccgccgtt tcaggcgcag ggccgcttct ttgagctggt tgtaggaaga ttcgataggg 1380
acacccgcca tcgtcgctat gtcctccgcc gtcactgaat acatcacttc atcggtgaca 1440
ggctcgctcc tcttcacctg gctaatacag gccagaacga tccgctgttc ctgaacactg 1500
aggcgatacg cggcctcgac cagggcattg cttttgtaaa ccattggggg tgaggccacg 1560
ttcgacattc cttgtgtata aggggacact gtatctgcgt cccacaatac aacaaatccg 1620
tccctttaca acaacaaatc cgtcccttct taacaacaaa tccgtccctt aatggcaaca 1680
aatccgtccc tttttaaact ctacaggcca cggattacgt ggcctgtaga cgtcctaaaa 1740
ggtttaaaag ggaaaaggaa gaaaagggtg gaaacgcaaa aaacgcacca ctacgtggcc 1800
ccgttggggc cgcatttgtg cccctgaagg ggcgggggag gcgtctgggc aatccccgtt 1860
ttaccagtcc cctatcgccg cctgagaggg cgcaggaagc gagtaatcag ggtatcgagg 1920
cggattcacc cttggcgtcc aaccagcggc accagcggcg cctgagagg 1969

<210> SEQ ID NO 46
<211> LENGTH: 3674
<212> TYPE: DNA
<213> ORGANISM: Artificial Sequence
<220> FEATURE:
<223> OTHER INFORMATION: RSF1010

<400> SEQUENCE: 46
tcagcctgcc gccttgggcc gggtgatgtc gtacttgccc gccgcgaact cggttaccgt 60
ccagcccagc gcgaccagct ccggcaacgc ctcgcgcacc cgctggcggc gcttgcgcat 120
ggtcgaacca ctggcctctg acggccagac atagccgcac aaggtatcta tggaagcctt 180
gccggttttg ccggggtcga tccagccaca cagccgctgg tgcagcaggc gggcggtttc 240
gctgtccagc gcccgcacct cgtccatgct gatgcgcaca tgctggccgc cacccatgac 300
ggcctgcgcg atcaaggggt tcagggccac gtacaggcgc ccgtccgcct cgtcgctggc 360
gtactccgac agcagccgaa acccctgccg cttgcggcca ttctgggcga tgatggatac 420
cttccaaagg cgctcgatgc agtcctgtat gtgcttgagc gccccaccac tatcgacctc 480
tgccccgatt tcctttgcca gcgcccgata gctacctttg accacatggc attcagcggt 540
gacggcctcc cacttgggtt ccaggaacag ccggagctgc cgtccgcctt cggtcttggg 600
ttccgggcca agcactaggc cattaggccc agccatggcc accagccctt gcaggatgcg 660
cagatcatca gcgcccagcg gctccgggcc gctgaactcg atccgcttgc cgtcgccgta 720
gtcatacgtc acgtccagct tgctgcgctt gcgctcgccc cgcttgaggg cacggaacag 780
gccgggggcc agacagtgcg ccgggtcgtg ccggacgtgg ctgaggctgt gcttgttctt 840

```
aggcttcacc acggggcacc cccttgctct tgcgctgcct ctccagcacg gcgggcttga    900
gcaccccgcc gtcatgccgc ctgaaccacc gatcagcgaa cggtgcgcca tagttggcct    960
tgctcacacc gaagcggacg aagaaccggc gctggtcgtc gtccacaccc cattcctcgg   1020
cctcggcgct ggtcatgctc gacaggtagg actgccagcg gatgttatcg accagtaccg   1080
agctgccccg gctggcctgc tgctggtcgc ctgcgcccat catggccgcg cccttgctgg   1140
catggtgcag gaacacgata gagcacccgg tatcggcggc gatggcctcc atgcgaccga   1200
tgacctgggc catggggccg ctggcgtttt cttcctcgat gtggaaccgg cgcagcgtgt   1260
ccagcaccat caggcggcgg ccctcggcgg cgcgcttgag gccgtcgaac cactccgggg   1320
ccatgatgtt gggcaggctg ccgatcagcg gctggatcag caggccgtca gccacggctt   1380
gccgttcctc ggcgctgagg tgcgccccaa gggcgtgcag gcggtgatga atggcggtgg   1440
gcgggtcttc ggcgggcagg tagatcaccg ggccggtggg cagttcgccc acctccagca   1500
gatccggccc gcctgcaatc tgtgcggcca gttgcagggc cagcatggat ttaccggcac   1560
caccgggcga caccagcgcc ccgaccgtac cggccaccat gttgggcaaa acgtagtcca   1620
gcggtggcgg cgctgctgcg aacgcctcca gaatattgat aggcttatgg gtagccattg   1680
attgcctcct ttgcaggcag ttggtggtta ggcgctggcg gggtcactac ccccgccctg   1740
cgccgctctg agttcttcca ggcactcgcg cagcgcctcg tattcgtcgt cggtcagcca   1800
gaacttgcgc tgacgcatcc ctttggcctt catgcgctcg gcatatcgcg cttggcgtac   1860
agcgtcaggg ctggccagca ggtcgccggt ctgcttgtcc ttttggtctt tcatatcagt   1920
caccgagaaa cttgccgggg ccgaaaggct tgtcttcgcg gaacaaggac aaggtgcagc   1980
cgtcaaggtt aaggctggcc atatcagcga ctgaaaagcg gccagcctcg gccttgtttg   2040
acgtataacc aaagccaccg ggcaaccaat agcccttgtc acttttgatc aggtagaccg   2100
accctgaagc gctttttcg tattccataa aaccccttc tgtgcgtgag tactcatagt    2160
ataacaggcg tgagtaccaa cgcaagcact acatgctgaa atctggcccg cccctgtcca   2220
tgcctcgctg gcggggtgcc ggtgcccgtg ccagctcggc ccgcgcaagc tggacgctgg   2280
gcagacccat gaccttgctg acggtgcgct cgatgtaatc cgcttcgtgg ccgggcttgc   2340
gctctgccag cgctgggctg gcctcggcca tggccttgcc gatttcctcg gcactgcggc   2400
cccggctggc cagcttctgc gcggcgataa agtcgcactt gctgaggtca tcaccgaagc   2460
gcttgaccag cccggccatc tcgctgcggt actcgtccag cgccgtgcgc cggtggcggc   2520
taagctgccg ctcgggcagt tcgaggctgg ccagcctgcg ggccttctcc tgctgccgct   2580
gggcctgctc gatctgctgg ccagcctgct gcaccagcgc cgggccagcg gtggcggtct   2640
tgcccttgga ttcacgcagc agcacccacg gctgataacc ggcgcgggtg gtgtgcttgt   2700
ccttgcggtt ggtgaagccc gccaagcggc catagtggcg gctgtcggcg ctggccgggt   2760
cggcgtcgta ctcgctggcc agcgtccggg caatctgccc ccgaagttca ccgcctgcgg   2820
cgtcggccac cttgacccat gcctgatagt tcttcgggct ggtttccact accagggcag   2880
gctcccggcc ctcggctttc atgtcatcca ggtcaaactc gctgaggtcg tccaccagca   2940
ccagaccatg ccgctcctgc tcggcgggcc tgatatacac gtcattgccc tgggcattca   3000
tccgcttgag ccatggcgtg ttctggagca cttcggcggc tgaccattcc cggttcatca   3060
tctggccggt ggtggcgtcc ctgacgccga tatcgaagcg ctcacagccc atggccttga   3120
gctgtcggcc tatggcctgc aaagtcctgt cgttcttcat cgggccacca agcgattccc   3180
```

```
acacattata cgagccggaa gcataaagtg taaagcctag atccgaagga tgagccgggc   3240
tgaatgatcg accgagacag gccctgcggg gctgcacacg cgcccccacc cttcgggtag   3300
ggggaaaggc cgctaaagcg gctaaaagcg ctccagcgta tttctgcggg gtttggtgtg   3360
gggtttagcg ggctttgccc gcctttcccc ctgccgcgca gcggtggggc ggtgtgtagc   3420
ctagcgcagc gaatagacca gctatccggc ctctggccgg gcatattggg caagggcagc   3480
agcgccccac aagggcgctg ataaccgcgc ctagtggatt attcttagat aatcatggat   3540
ggatttttcc aacaccccgc cagcccccgc ccctgctggg tttgcaggtt tgggggcgtg   3600
acagttattg caggggttcg tgacagttat tgcagggggg cgtgacagtt attgcagggg   3660
ttcgtgacag ttag                                                     3674
```

<210> SEQ ID NO 47
<211> LENGTH: 2982
<212> TYPE: DNA
<213> ORGANISM: Artificial Sequence
<220> FEATURE:
<223> OTHER INFORMATION: pAMbeta1

<400> SEQUENCE: 47

```
attctcccaa gaattagaaa tgagtagatc aaattattca cgaatagaat caggaaaatc     60
agatccaacc ataaaaacac tagaacaaat tgcaaagtta actaactcaa cgctagtagt    120
ggattttaat cccaaatgag ccaacagaac cagagccaga aacagaatca gaacaagtaa    180
cattggattt agaaatggaa gaagaaaaaa gcaatgactt cgtgtgaata atgcacgaaa    240
tcgttgctta ttttttttaa aagcggtata ctagatataa cgaaacaacg aactgaatag    300
aaacgaaaaa agagccatga cacatttata aaatgtttga cgacatttta taaatgcata    360
gcccgataag attgccaaac caacgcttat cagttagtca gatgaactct tccctcgtaa    420
gaagttattt aattaacttt gtttgaagac ggtatataac cgtactatca ttatataggg    480
aaatcagaga gttttcaagt atctaagcta ctgaatttaa gaattgttaa gcaatcaatc    540
ggaaatcgtt tgattgcttt ttttgtattc atttatagaa ggtggagttt gtatgaatca    600
tgatgaatgt aaaacttata taaaaaatag tttattggag ataagaaaat tagcaaatat    660
ctatacacta gaaacgttta agaaagagtt agaaaagaga aatatctact tagaaacaaa    720
atcagataag tatttttctt cggagggga agattatata tataagttaa tagaaaataa    780
caaaataatt tattcgatta gtggaaaaaa attgacttat aaaggaaaaa aatctttttc    840
aaaacatgca atattgaaac agttgaatga aaaagcaaac caagttaatt aaacaaccta    900
ttttatagga tttataggaa aggagaacag ctgaatgaat atcccttttg ttgtagaaac    960
tgtgcttcat gacggcttgt taaagtacaa atttaaaaat agtaaaattc gctcaatcac   1020
taccaagcca ggtaaaagca aaggggctat ttttgcgtat cgctcaaaat caagcatgat   1080
tggcggtcgt ggtgttgttc tgacttccga ggaagcgatt caagaaaatc aagatacatt   1140
tacacattgg acacccaacg tttatcgtta tggaacgtat gcagacgaaa accgttcata   1200
cacgaaagga cattctgaaa acaatttaag acaaatcaat accttcttta ttgattttga   1260
tattcacacg gcaaaagaaa ctatttcagc aagcgatatt ttaacaaccg ctattgattt   1320
aggttttatg cctactatga ttatcaaatc tgataaaggt tatcaagcat attttgtttt   1380
agaaacgcca gtctatgtga cttcaaaatc agaatttaaa tctgtcaaag cagccaaaat   1440
aatttcgcaa aatatccgag aatattttgg aaagtctttg ccagttgatc taacgtgtaa   1500
tcattttggt attgctcgca taccaagaac ggacaatgta gaattttttg atcctaatta   1560
```

ccgttattct ttcaaagaat ggcaagattg gtctttcaaa caaacagata ataagggctt 1620
tactcgttca agtctaacgg ttttaagcgg tacagaaggc aaaaaacaag tagatgaacc 1680
ctggtttaat ctcttattgc acgaaacgaa attttcagga gaaaagggtt taatagggcg 1740
taataacgtc atgtttaccc tctctttagc ctactttagt tcaggctatt caatcgaaac 1800
gtgcgaatat aatatgtttg agtttaataa tcgattagat caacccttag aagaaaaaga 1860
agtaatcaaa attgttagaa gtgcctattc agaaaactat caaggggcta atagggaata 1920
cattaccatt ctttgcaaag cttgggtatc aagtgattta accagtaaag atttatttgt 1980
ccgtcaaggg tggtttaaat tcaagaaaaa aagaagcgaa cgtcaacgtg ttcatttgtc 2040
agaatggaaa gaagatttaa tggcttatat tagcgaaaaa agcgatgtat acaagcctta 2100
tttagtgacg accaaaaaag agattagaga agtgctaggc attcctgaac ggacattaga 2160
taaattgctg aaggtactga aggcgaatca ggaaattttc tttaagatta aaccaggaag 2220
aaatggtggc attcaacttg ctagtgttaa atcattgttg ctatcgatca ttaaagtaaa 2280
aaaagaagaa aaagaaagct atataaaggc gctgacaaat tcttttgact tagagcatac 2340
attcattcaa gagactttaa acaagctagc agaacgccct aaaacggaca cacaactcga 2400
tttgtttagc tatgatacag gctgaaaata aaacccgcac tatgccatta catttatatc 2460
tatgatacgt gtttgttttt tctttgctgt ttagcgaatg attagcagaa atatacagag 2520
taagatttta attaattatt agggggagaa ggagagagta gcccgaaaac ttttagttgg 2580
cttggactga acgaagtgag ggaaaggcta ctaaaacgtc gaggggcagt gagagcgaag 2640
cgaacacttg atttttaat tttctatctt ttataggtca ttagagtata cttatttgtc 2700
ctataaacta tttagcagca taatagattt attgaatagg tcatttaagt tgagcatatt 2760
agaggaggaa aatcttggag aaatatttga agaacccgat tacatggatt ggattagttc 2820
ttgtggttac gtggttttta actaaaagta gtgaattttt gatttttggt gtgtgtgtct 2880
tgttgttagt atttgctagt caaagtgatt aaatagaatt ctcatgtttg acagcttatc 2940
atcggagctc cgatgataag ctgtcaaaca tgagaattcc cg 2982

<210> SEQ ID NO 48
<211> LENGTH: 4154
<212> TYPE: DNA
<213> ORGANISM: Artificial Sequence
<220> FEATURE:
<223> OTHER INFORMATION: pLME106

<400> SEQUENCE: 48
gatccggcgg aacttcacgt cctggcggtg gagttggcgg gcgcgttcca gccgttcctc 60
cagcacggtg atccgggcct ccagacgctc acgctcaccc tgctccaggt gccgggtcac 120
cgtcaccgtc cgcaccggcc gggcctcggc ctgggcggcc cggcgttcct cactggcccg 180
cttccggcaa tcgtcggaac accacacccg gggccgaccc cgcccaccgt gggcctccac 240
cggcgccccg cagtggggac acgcccgcag cgccgacgca tcctcatcca aggccatcac 300
cgggtcggaa tccatacccg aaaccatatc gtccggacga tgaactgcgc cagacagcta 360
agaatgcacg aggtgtgtct ccgattctca ggaaacgctc agcattttcc gagacgttcg 420
gcgcacgcac acaccccccac aagaaccgac ccgcccagca tccgccgaca cgtcgatccg 480
cacccgcgat gggctggccg aggccgacta cgaccgctag tcagcacctg cgctgatcta 540
ccgtcgccct gaccgactct cccgtcggga ttgtcgccgg ccgctgccag catggacctg 600

-continued

```
cggccccgcc ccctcgccct gcaactcgag ggaggcgggg ccgtccaccc cccacaccac    660
cccgacaccg tgatgcgccc atgtcgccta acgggttgcc cgacctcccc gacatcaaga    720
aaacctgaca ccgtcgccgc aagcgctaca ctgactacta gtagtcagga ggtgcgtgat    780
gaccatcgcc acatcggtga aactctccga agagaccggc cgcaaactcg atgaactagc    840
ccgggccacc gggcgatcca agtcctacta cctgcgcgag gccatcgagg accacatcga    900
ccagatggtc cacgactacg ccatcgcccg actcgccgac gacgtgcgag ccggccgggc    960
cgccacctac agcgccgacg aagtggacca gatccttggc ctggacgatt gagtacaccg   1020
accccgccgt caaagcactg cgcaaactcg accgagccca ggcccgccgc atcaccgcct   1080
acatacgtga gctcaccggc ctggacgatc cccaccaacg cgggaaaggc ctcaccgggc   1140
ccctggccgg actctggcgc taccgcgtcg gggactaccg gatcatctgc gacctgaacg   1200
ccgaccgcct ggccatcatc gccctgacca tcgagcaccg atcccaggcc taccgctgac   1260
acgcaacccc gcaccctcgg ccaagacgtc acacaccacc cgccccaccg agcactgagg   1320
atgtcaactc gcccgagccg gcctgccggc cgtcttacgg gttgtcttgg cgggcggggt   1380
gtctttgccc tggcccagca gccccacgat ctcccgcagc gtgtcggcgg tggcggcgtc   1440
ccgggccgcc tgacgctccg cctccgccct ggcctgctcg gctgcctgcg cccgatcctc   1500
cgcggcggcg gcctgctccc tcgcctcggc cagctcgccg gtcagggcct cgacccgggc   1560
ctgcacctgc cccaggcgcg cctccgcctc ctgctgcacc tgctcggccc gggcctccgc   1620
ctggtcccgg gccgcctcgg cctcggcccg gtgctgatcc gccagggccg cctcggccac   1680
cgcttcggcc tgcccatcca ccgcctgctc ggcccgagcc ccgaactcct cgcgggccgc   1740
atcactcgcc tgacgccacg ccgccgccca caccagaccc aacggctccg acagatccgg   1800
cggggccggc gtctggaccg acgccgagac gtcgcgcagg aaccccgccg cagcgtcggt   1860
ggagcacccc gcctccgcct tcaacgaccg caccgtcacc cgccgacccg caccgctcaa   1920
ccgcgcatag gccgccgcca accttgaccc attcgactcc atgacccacc ctcccattct   1980
gtaccctgta cctgttccta ggtacgttcc taatgtacct caccggatgc agaacccgca   2040
accccccctca cactccccct gcacggggcc cgccccctgc acccccgctg ccgcgcccgc   2100
tcctgcgtcg cggccttgcc cctgcccaac gccgggccgg cgggcagccc accagaggct   2160
ctgtgagacg tcggcgcccc cgtccaccta ccctaaagac caaccggccg tggaaacgtc   2220
tgtgaggagc cttgtaggag ttcccaggac aagccagcaa ggccgggcct gacggcccgg   2280
aaaggaagtc gctgcgctcc tacgaagaag cccctctggg gacccccaga ccccggaact   2340
atctgatttg gtttagcggc gtacttccgt cataccggaa tttatggcat gctgtggtca   2400
tggcgacgac gacggtcgat gagcagtggg agcaggtgtg gctgccccgc tggcccctgg   2460
cctccgacga cctggcagcg ggcatctacc ggatggcccg cccctcggcg ctgggggtcc   2520
gatacatcga ggtcaacccc caagccatca gcaacctcct cgtggtcgac tgcgaccacc   2580
ccgacgctgc catgcgcgcc gtctgggacc gccacgactg gctgcccaac gccatcgtcg   2640
agaaccccga caacggccac gcccacgccg tgtgggccct ggaagcagcc atcccgcgca   2700
ccgagtacgc ccaccgcaag cccatcgcct acgccgccgc cgtcaccgag ggcctgcgcc   2760
gatccgtcga cggagacgcc tcctacgccg gcctgatcac caagaacccc gaacaccccg   2820
cctggaacac cacctggtgc accgaccacc tctaccggct ggccgagctc gacacccacc   2880
tggatgccgc cggcctcatg cccgccccct cctggcgacg cacccgccgg cgcaaccccg   2940
tcggcctggg ccgcaactgc gccatcttcg agaccgcccg cacctgggcc taccgcgacg   3000
```

cccgccgcat ccgacaacgc cacgaatacc cgaccgccga ggactcggcc gacctgcacg 3060
ccgtcatcgc ctccaccgtc gaggcgctca acgccggcta cagcgaaccc ctgccggccc 3120
gcgaggccgc cggcatcgcc gccagcatcc accgatggat cacccaccgt ttctacggct 3180
ggatcgactc ccacaccgtc aacgaggcca ctttctccac catccagagc tacagaggac 3240
acaagggagc cggcaaggct cgtcctcgtg cccgccgtgc tgcttctatc accgattggg 3300
aggcatgatg gctgacgtcc agcaccgcgt gaagcgtcgg ggcacggccc gcgaggccgc 3360
agaacgtgta ggggcctcca tccgaaccgc ccagcggtgg acctccatcc cccgtgagga 3420
atggatcact cagaaggccg tcgagcgtga ggagatccgg gcctacaagt acgacgaggg 3480
gcacacgtgg ggcgagacct cgcgccactt cgggatcgcg aagaccaccg cccaggagcg 3540
ggcccggcgg gctcgaaggg agcgggcggc cgaagcggag aaggctgccg aggaggccga 3600
ggccgcgctg cgtccgacac tcttcgaggg ccaggagcaa ggttctgcat gagcaacccc 3660
gagtcctcgg gtagaccgtc tggcccgacg ttaagcatgg ctgaagcggc ccgtgcctgt 3720
ggggtttcag tgtccacggt gaggcgtcac cgtgatgccc tggtggccca cggtgctacc 3780
cgtcatgacg cgtcatgggt gataccccta tcagcgttga tttcatgcgg tttgatgccc 3840
cgggtgacac cccctgatgc cccgtcaccc aataacgtgg cgcctgccat gacgtcccac 3900
ggtgacgccc ccctgacggg ggaagtccaa gagctgcgcg agcgactggc caacgctgag 3960
catcgagccg agctagcagt agaggttggg gacgacgtct cggcgactcc ggagaacacc 4020
aagtcagggt ctcatgagtg tgcgatagct tgagctgtct accaatctgg atatagctat 4080
atcggtcgtt tgtgtctgat tcgccagtga gccaacggcg gggcgacac gcggtggcga 4140 aaccccctgg caga 4154

<210> SEQ ID NO 49
<211> LENGTH: 22046
<212> TYPE: DNA
<213> ORGANISM: Artificial Sequence
<220> FEATURE:
<223> OTHER INFORMATION: pTZC1

<400> SEQUENCE: 49
gcgagcacac ttccctcacg ctgactcgtc actccgacac gctcgctcgt gtccgtgaac 60
tggcgggcga cggcccgcca gtcacccgga tcgatgaccg ccgcattagt cgaaacccac 120
acgccatcct gggtcgcatc gggccgcgtg atgtacgcca gcgccttcgc cggcgtcgtc 180
ttgatctgcc ccatcttcac aacagccatc actccgcccc cgcttccgtt gcggcgtcga 240
tggcccgttg gacttgtccc agcagctccc gcgtggcacg catctgctca accgtcacca 300
catcatcagt gttcacctgc cgagcgatct ggttgatgtt gttcccgatc ctcgacaact 360
cggcgcgcag cggagccgga tcgaacgcca cgcgacgcac gacgatcttc ccctcagtga 420
gagcgcgccg cgcatagtcg gcgaacgtcc tcgcctccgc aagttccata cgccgttcca 480
cccgcttcca ttcagcatca ctgagccaca agcccttgaa gacccctcgc gaccgcttcg 540
cgccctgctc agccatgcat ccactcctac cgggtttggg cagagcccat agtgcccagg 600
gggccacgca actgtgtaac agttgctatg cttgctaccc cgtcagggtc agtctacaac 660
ctacggtcta catggcgcta gaatgagaaa cggatcgtcc ggctaaccgg acgatccgag 720
atcggaaggg ccgcccaggg gcggcccacg atgatccttg tacggggtgt cccgcgctgc 780
ccgcgcggga caccctaggg gtcgccgtcg gcggccccgc accaagatga aggagggcgt 840

-continued

```
atggccacca agtccgaccc cgatctaatc gacgacctgc tgcgccaaga cgaggcggag    900
ctgcgggcga agaagaagcg gctgcgcgcc tttcagacgg ctctggatga gcttcggcac    960
gccagcgagg cagtggccac ggccggtgcc gccctcatcg ctgccggcga tgtctcccgc   1020
gccgaggcga gcaaggtctt caagctctcc aagggagaac gcgccgccgc gttccctacc   1080
cggcctcgct cagagtcgag cgtcgcggat gcggtcgatg agccgccgaa ccccgtagac   1140
gatccatccg atgagtcgga tgaacagcac accgatctgg gtcagtagcc acaccgcgac   1200
gtggaagatc gcgctcagtc cgtacatcgc gatgatgagg atgagcgcga gcacggcgat   1260
cacgccggcg atcatcaacc acgcgagccc catcgctcat cctcccttca actctcggtg   1320
tctccatggt gccacttcgg gatgactctt gtcccgatgc catcaggatg gtgcgctcca   1380
ggtcgccgtc aagggcgctg cgcgtcgctg cgcgatgccg caagcggcac ccttgaccgc   1440
gaccctccac acaccgattg gcagttatcg gaacgaaggg gcgctctggg ctcggacgag   1500
ggctcggcgt accgacgacg tgctcacacc gagcacggtg gcgatatgcg cgttgctctg   1560
accctgcgcc ttcatgcgca aggcggcgtc ggtccgctcc ggacccatga cggtgggacg   1620
gccaccgact ctgccctggg cccgcgcgta ggccaggccc cgccgggtgt tctcccggat   1680
cgtgtccacg cgcagctggg cgaacacggc catgatcccc acaatggcct ggcccatcgg   1740
gctcgacgtg tcgatgctca acgccggctc cgtcaggctc ctgatactca ctccctgccc   1800
gatcaggtca tggacgatct cgatggccat gacctcgctt ccggccagcc ggtccagcgc   1860
ccggaacacc agcgtgtcgc ccggacgcag atagtcgcgg cacgccaacc actgcggccg   1920
gtcggccgca cggctggact cgccgtggtc cacgaacaca cgctcggccc cggccgcgcg   1980
cagctcggcc tcctgcgcgg ccgggttctg ctcgcgcgtg gacacgcgcg cgtacccgac   2040
gatggtcatc ttctccccccg ccccacaggg ccgcctcggt gcggctcgtc gtcgccgcgc   2100
tccgctcgac gacgttccac ctcccgctcg atgcgctcgt gcaggccgct gcgggtactc   2160
tcccgccggg ctaggccgcg aatgctcgcc gcccacgcct tggtgcgcgt cttcacgtcg   2220
tcgagctgac tggccgtcag accgtagacg cgcacctctt cgggctggat gcgctccacg   2280
ttgtcgaggt tctgggcgaa ccgtcctagg tcgaagccgg catcagcgtt gcgggccaag   2340
ttcagcagtt ccttgtcgct gtacctgccg gaacgccgga tcgcgtccac atcgagatag   2400
tcgcgggtct cggcccgcga gaacagggca cccaccttgt tccctaccgc gtcctcgatg   2460
gcaagcacgg gcccgacctc cagccgcacg ggcgggtgag cccgccagtc cacgcccagg   2520
tccatgtcgg tactgcgccc ttgcgcactg acgatggtga gctgggcgaa cgtgtcctgg   2580
cggcggcggg tctccacggt gtagccggcc gcacgcagcg cggcgataat ccggtcgagc   2640
gacgtgccga atcgggcctg ggcctgctgg acggtgaaca ggtccacgtc ctctgtgggc   2700
cggtcgatca gcccatgctc acggatcgcg cccgagccgg ccagggcgaa gccggcatcg   2760
tcgccgacgg cctccagggc caggcgcgtg atgcgccgct gctcctcctg gtcaccgctc   2820
acacgggcac ccgaagccgg gggaaccgtc cctcccacaa gacgcggacg tgcgggtcca   2880
tgttcaggat cggccacgtc tcgatgagcc gatctcggtt catcaagcgg ccctgctcgt   2940
caaccgtccc ctcggcgagc agcgcctggt aggccatacg acgccaaccc aggttcgaca   3000
cgtccacacc gagccgatca gcctgccagc gcacagagtg aggcaggtcg atgggcccgt   3060
catagggccc acgcagctcg tcgagcgaag cgggcgcgtc atagggcttg acatcgcgga   3120
accgcacacg agtcgctgcc acctcagcca tggcccgcct ccttccatct catcccagtt   3180
tacccggcca ggtcgaaaac ggtctatcac tggtttcggt ttcggtgggg gttttgaccg   3240
```

```
cccttccacc gccaacctac gcggattgtg aatgtgatcg ctatatgtcg tggattcttg    3300

atcactctat ggcgtgctgg tctggtggac cgggaagaca ttgctcttcg catggcaaac    3360

ggtgccgtct ttaggatttc tctgcgccag gatccggaag ggatggcact tcttctcctg    3420

ccgacatcgg tcggagcggc tgatggtatc gcgatcagct tgcctttagc accccacggc    3480

cgtaaacagt gtggcccact gccccgcgtc caactgtttc ggcagtgcgt gtgccggaac    3540

accggcctca cgcaagacct gggcacaccg tcgcgcacgc cgacgcccca caacccggga    3600

cacgatgtcg gcgacgccac ggcccttgcc ggtgaacacg tcatggacga aggacgcgta    3660

ccgcgcacgc tccgaccagt ccacgagagg ttcctcccgg cgacgtatca ccaggacacc    3720

ggcgtcgacg gtggggcggg gacggaaatg cgtggacggc acccgcccgt actgttcgaa    3780

gtcgacccac ggccaccact gggcagtcat catcgtggca ccaccgacac cggcgcggcg    3840

gcgcgcgacc tcccactgca ccaggagcac cgcgtgggtc caccccggtg agtgaaggac    3900

gtgccgcagg atcgcggtgg tcaggtggaa cggcaggttc cccaccagga cgtgcgggcc    3960

gtccggaagc acaaaatcaa ggacatcctg ctcgtacagg tggacctccg ggcgcagccg    4020

cttctccaac caccggacag aggccgggtc gatctcgacg gcggtcaacg atccaccggc    4080

agccaagaca cgatcctgaa ggggaaaggt cagcgccccg tgtcccgggc cgatctcgat    4140

gaccgggacg gaggcgttga cggggacgag gtcgacgatc cgtctgatcg tcgcctcatt    4200

gacgaggtag ttctggccgt tctcgtgacg gcccttgttc ggcctgtagg taggcatgga    4260

aagacactcc gcagcagata tcgtgctccg ggcatgccga aaaggccgcc cggctggaca    4320

agctgagcgg tgggtgtctc tacctccgtg gaacgtcccc cgttagcgca cacacccacc    4380

ggcggctccg gggttccgga gccgaccgaa ggtggtgaaa attgcattca ttgcacccat    4440

ggggtgaacc ataccacagc acgcggatgc ctgacctgcc ctgtcccggt catccaaaac    4500

tgtcatgtgg acctgacccg gtcggtctgc cgactggtgc tggatacgcc gccggggtca    4560

gattggtggg tgagtaccta cgcctccacg gaggtacggc agcaagcaac gtgcatgcgc    4620

tggcagaaac aattctgtct gatgttctcc ctcggctcgg gctaggtaat gagtagtagt    4680

acaaaactgt actgccgtt ctctcttgta ttgaaatgct aaaggtttac aagacatcta    4740

cggcgaacgc actgaaacag ggcgctcctg cgagaatcga cccgaaaact gtctcgtata    4800

cctgtctcac cgtaatgtgt tccaccttct tccaatctgg ggtttggtga ggcatgatgg    4860

tggtcatgag actgttgggc tacacccggg tgtccaccgt cggtcaggat ccgactcttc    4920

aacacgacgc cttggtcacc gccggggttc aggaccgtga tgtcttcagc gatgtcacct    4980

ccggggcgaa aaacgccact gagcgtccgg ggatgaagaa gctcctcgcc tacgctcaac    5040

ccggtgacac ggtggtggtg tggcgcatcg accggctggg ccgtccccta ctcgatgtac    5100

tcaacacggt gaacctgtta cgcgaacgag acgtgaaaat caagtccgtc tccgacggca    5160

tcgacccgga gacctcctcg ggccggttga tgctcggcat gctgggcacc ctggctgagt    5220

acgaacgaga actgatcacc gaacgcgtca cgccggcat cgccgcagca agtccaacg    5280

gcacccgctt cggccgacca cctgtggatc cagaggtggt cgaccgcaaa ctcgccatcg    5340

tcgccgagga acgagccaaa ggccgcagtg ccgaagacgc cgcgagcatg gtcggctggt    5400

cacgggcgac actgtaccgc catctgcagg gcgccaaacg acgacagtca gcactgcccg    5460

cctgacacga acacaatgac cagcgcgtga ggtgacggtg atggacgaga tgcaacgctg    5520

ggagatcctc cggctccaca tcgaagacga catcaccctg accgacctgg cacaggccac    5580
```

-continued

```
cgacatcagc acccgaaccc tatcccggtg ggtagcccga taccgcgccg acggaatccg   5640
cgggctacgc aacaccacac gatccgacgc cggagcccat cgcatatccg cggaactcgt   5700
cgcctacatc gaacaccttg gtctcaccaa gccacgccca tcgatcgccg ccctgcatcg   5760
cctcgtgagc tgtcgagcac aacaactatc gctgaaacca cccagctacg ccaccgtgcg   5820
cagcatcatc caagcccttg acccggcgat ggtcaccctc gcattggagg gcccgacgtc   5880
ctaccgagat cgacacgaac tggtctaccg gcaccgggct gaacacccca acgccatctg   5940
gcaggccgat cacacccaac tcgacatcct catccagaac ccggacggca ccccgactcg   6000
cccctggctc accatcatca tcgacgacta ctcccgggca gtgtgcggct acatggtcac   6060
caccaccgca ccctcggcaa tgaacaccgc cctggcacta cgccaggcga tctggcgaaa   6120
aacagacccc acctgggcga tgtgcggtat tcccgacgtc ctctacgtcg atcacggctc   6180
cgacttcacc agtggccata tcacgtacac cacgacagca ctgaagatcc ggatcatcca   6240
ctcgaccatc gcccgtccgc agggccgcgg caagatcgag cggttcttca gcaccgtcaa   6300
caccgaactt ctcaccaccc tgcccggcca cctcgccccc ggcgtccgca acccacaccc   6360
cgtactagac ctgacgagcc tggataccgc cgtcggcgag ttcatcagca gctacaacca   6420
gcgcacgcat tcttcaatca acaccagccc gaaagccgcg tggatcgggc aggggtggat   6480
ccccagaatg ccggagaacc ttgaagaact cgacggactc ctgctgcggg tctccaccca   6540
ccgccgagtc cagcgagacg gcatccactt ccaaggccag cgctacatca gcccgaccct   6600
ggcacctttt gtcggccatg acgtcaccat ccgctacgac ccgcgggatc tctccgagat   6660
ccgggtctac gaccacgaca cgttgctgtg cgtcgctgtc gatgaagacc accccaacca   6720
gcgctacagc ctggccgata tccaggccgc tcgtcgacgc cgacggcgtc aactacgtgc   6780
cgggatcaac gagcgcatcc ccatccacga gccacgccca tcagaccttg cccctgtgaa   6840
ccccgatgtg agcgccgaag cgccacggcc gcgtggtcgt acgtctcgcc tgcggaccta   6900
tgaagaggac ctgtcaccat gaaccgcgac ttcatcgtca ccaaagagca ccgccgcttc   6960
gtcgagttcg ccaacgcgat ccgcaaagac gccaccatcg gcatctgcca cggtgatgca   7020
ggagtcggca aaacacagtc cgccagacgc tatgcccact gggatgctct gggctcgttc   7080
attgacgact ggggtccacg cagtgaatct gacctggcca tctacgcgac ggctcatcgg   7140
gcgcgcaccg tgttctacac ccctgaggtg caaccgaagt accggacgtt gatccgtgac   7200
atcgaatttt accggggcaa actcgacgtc tgcatcatgg agcatctgat ggccaccgga   7260
cagcgggaca ggctccacat gcgcagatcc agtggcgaga agctcaccca actgatcatt   7320
attgatgagg cagaacgtct gcctcccacc gccctggaga tgctgcgcga catccacgat   7380
cgtgacggtg tggcgatcat gttcatcggc atgcccggta ttgaccagcg cttccggcac   7440
taccctcagt tgttcagccg gctggggttc tcgcatcgct accgtgccct gggcaaagac   7500
gagctgctgt tcgtgctgaa ccggcactgg aggcgcctgg gtagagaatt gaacccggag   7560
gatttcacgg atgcgcaggc catcgccgcg atcgagcggc tgacccgcgg caatttccgt   7620
gtggtggagc gattgttccc acagatcaag cgagtgttga agatcaacga gttggagacc   7680
atcaccgacg atgtgattga agctgccgcc agcaccctgg tactcggcca ctgaccaggt   7740
cagtacgaca catagtgatc aaaaaagcag gccacatagc gatcacattc acagcggatc   7800
acacgacata ccgccaaccg gtgcaaaaac gatcgttttt gagacgcacc gcgagagcgg   7860
agccgttagc cgctcccgga gcgtccacaa cgcgtctcaa aaccggtcgt gtcgcaccct   7920
ggttttacgc ccgggcagtc tgcttatgtg tgataaagaa gcaatagaag tgcaaaaaat   7980
```

```
tttgccgttc ctatccgaca cttggccatt gtgtcggata ggtcgggcgg ttattcgggc   8040
aagtcaatct tgccgacaaa gctgtaataa atctcaatgt cctgcctgcg ggtgccgttc   8100
tcatcatagc tgcactcatg caccacaatt ttctcgatca tttcccgcaa gagagtgggg   8160
gtcagttctt caaaggcaag gtgcttgcgg acaatgccca taaatttctc ggcgttgacg   8220
gtagttgcct gtgacttgtc cagttcggct tgcagggcgg cggctctctt tttcagctcc   8280
gcttgctcgg cttcgtagtc agccgacagt tccatgaaac gctcatcgct gattttgccg   8340
tttacattgt cctcatacag ccgcttgata atgcggctga tttcagaaat gcgttcctgc   8400
gcctgttcaa gctgcttgat ggctgcggcg gtctttcgct tgccgccgat ctcgttctgc   8460
tggacaaaat gtaatccgca ggattaggag atagaagttc cgttactttg ggacgcacta   8520
cctctctgtg aaattcatta gattcgtcac ccattgcatt atcccaaaat tgtgcgttct   8580
cctcccagat ttttttactt tcctctgttc ccatgttctc tcccactccc caaatttgct   8640
tttttgcttc cattaaatct tccttactat attccattgt taccctccat aacttctgat   8700
tgttgccgtc ttgacgatta tgtatcttta cattaccttc tgaaacatat ggcgcacctt   8760
gtccaggcgg ctgtttggac ggcggggctg gatgaccggc tgaccgacag cggcctgata   8820
tcctttcagc tctgtaaggc atacgctccg cccgttggtg taaaaggcca gatcagtacg   8880
gtatgcctgt atacagcggg cgggaatctc gccagtaaag acaacttcat cctttttac    8940
ctgggccgtt tcgatggtgg cacagtattt cggtgcatca tgataagccc tggaaaggta   9000
ttcctggggc gcatagagga tgaaggagag ataaggttcc agcagctgcg tccccgattc   9060
cttcaatgcc tgttccaata caatcggggc caatgagcgg aagtccgccg gcgtgctgac   9120
cggactgtaa taaagcccgt attcaaagca aatcttacag tccgttacgt tccagccgaa   9180
caagccctgc tccagcccgt aacggatacc atccctgaca gcgttttgaa aactctggtt   9240
caagtatccc agcgaaaccc ggctctcgta ttgtacaccg gagccaagcg agagtggtgt   9300
aacagacagt cctatggatg cccaaaacgg gttgggcggc acctcgatat ggatggtgtg   9360
gctggctgct ttgagcggcc gctccatata aatgacggag ggttccttta ccactgtttc   9420
aagcttgtat tttccgaca  gcaaagcgga aacaacctcc aactgcaccc ggcccaaaaa   9480
agaaagaatg atctcatggg tgatggaatc cacttcgcaa cgcaaaagcg ggtcagtatc   9540
cgcaagttgc gtaagagcgt ccagcagccg ttctctttgc gctgccgttt tcggcgcaat   9600
cgtcgtccgc agcatgggga gggggtcctc gcgccacctt ttacgaggga gccgggtttg   9660
gtcccctaat acatcgttta acctcacgct gtcgctggga aggataacaa tttcaccctg   9720
ataagcggtg tctgtccgaa caatttcccc tttggatgga atacgcatct ctgtgatttt   9780
cagcttttct ctcccggcca gggccaccgt atcccgcagg cgcagcgttc cgctgtataa   9840
ccgtagatag acacgccgct ggccgcaatc ggtgtactca accttgaaaa cgctgccgca   9900
tagggcggcg ccccctgtt  ccccaatcgg ttggaacagc cctgtcaccg catccatcaa   9960
cggttgaatg ccaaggccat ttttggcgct gccatgatag actgggaaca gggaggcgtc  10020
ttgaacccgc tgctgttcct cccgcgcaag tttttcccgg ctgattggtt ctcctgcgat  10080
atacttttcc aataattcat cgttattttc gatgaccgca tcccatgctt ctatgtcggt  10140
attttcctcc aggactattt ccggggacag cgacaccgtc tgcttgatga taatatcggc  10200
ggagagctta tcccgaacag actgaaccac gctctgcaaa tcaacgccag cctggtcgat  10260
cttgttgata aagataacgg tgggaatgtt cattttccgc agggcatgga acagaatacg  10320
```

-continued

```
ggtctgggcc tgcacgccat ctttagcgga gatcaccaag atggccccat ctaaaacagc  10380
caaagagcgg tacacctccg ccaaaaaatc catgtggccg ggcgtatcca caatgttaac  10440
tttacatctg tgccactgga aggaagtgac tgccgcttga atggtaatcc cacgctgccg  10500
ctccaaaaac atggtgtccg tcctcgttgt cccttttttcg acgctccccg gttctgaaat  10560
ggctccgctg gcatatagca ggctctccgt caaggtcgtc tttccagcgt ctacatgggc  10620
aagaattcca atattgatta ttttcatgtg attgtcctcc ctttacagcc ccaaagggca  10680
taaaaatccc cagcagtaaa atacttttac cactggggat tataagttgc ggacatacac  10740
atatacagca tacacctgtt tgtgattgct gtttttgggg atatgtcaaa attgataagg  10800
caaaagtatt cttaaattgg gtacaaaaaa ctaagcccct acaaaaggag ctatcataat  10860
cctttgttcc cactatttga ttatagtttt atttaagaat accttgccgc atatttttta  10920
ctccttttct ggattaaatc attgtatcac atcagtttta ggaaagcaag tacctaaaag  10980
aaatttttct tcccctttata tgtaacaatc ataccggctt cctagcgttc agaatgtttt  11040
ctgctgtctg ctgtggtgtt tggttggaat tgtccaacca aaagccgatc cgtggtgttg  11100
tctgcatttt actaaataca aattcaatgt atacagaaag atataaggag tgggagggat  11160
tccgccgtag ttggcattgt aggaaaatcc aaaagtttag atttcccac aatgcttatc  11220
ttttggtctt tggttcggaa tagtgtagtg ctggcggtct atctcttgtt ttcggttgct  11280
tgcttcctta ccgtacatga gcattcgcgc agtgcattcc cgaccacgtc cggcacggca  11340
cctcgaccgt ctgcgccgcg ctgaacattg cgacccgctt cgacaaactc gccatcacgt  11400
accgcgccgg cgtcaccctc tgcgccatcc tcacctgggt ccgactattg ggagacacga  11460
cctaggagaa gaccggctcc cacatccgct accgcttcgt gggaggccgt ggcccggctc  11520
ccgccgggca tgaagaaggg tccgctgaag gtttggttga cctcctacgg cagcagctca  11580
gccagttctc gcagctgctc aaggatccgc tcggcctggt cgggagcgac attcttgtcc  11640
agctgcttga gctgacgctg catcttctcg atgactgcgt cggaaccagc ggactcgctg  11700
tggagcttca ggaagtgtac ccaagcacgc gtctcgatac cgaggatggg cacacgcatc  11760
gtcgactcaa cgaacgaatc catgaggggg cgacaccgag gcagtcgtcc gaagttgcca  11820
ccgccatcgt tcaccggatg caccgtcacg cggtcagcct tcgacgggta cggcgtcgcg  11880
tcggccgggt actccagctc cgcactgcca tcggtctcct tgatgttggt ccaccagtag  11940
tcgcgccact cggcggcgta cttggcggac tcgacccacg gctcggccac caccggcacg  12000
ccgctgacgg cgctgtcgag gtgccacggc acgcagcaca ccaggtccca gtcggtgcag  12060
gcatcggggg agacctggta ccgcagcgaa gggaccttct ccttggccag catccaccag  12120
cccttgagct cgatgccgat cgcgatgggc tcaccctcgg ttccacgatt caccagacgc  12180
acgtcgggga aggcctgcgc cgaccgctcg aaccggtagg tcgaccactc ggagtccggg  12240
tcccagatct gccgaaggct gttcagcgtg cgcacgacct ccagctcgat gcccgagccc  12300
aagaagctgt tgaggctgaa caggtcggtg gcgttgaccc cgctgatctc gttcttcgac  12360
tcgaactcgc ccggaagggc ttggagggcc gcggagaccc ccttctggag cttggtatgc  12420
ggatcgttgg gatccagcac cgggcgggca ggacccgcac ccacctgggc gctcgtcgcc  12480
actgcatcaa ccgacattgc tctcctcctc ggggttggcg tcgaagaggg ccacgagctc  12540
gtcgttggtc tcggcctcct cggcggcgac gtcaagccgc tcgtgcgcaa gctccgcgaa  12600
gtaggggtca cgctcggcaa ggaaagcctg ccgacgcagg gccaccgcag ccacggagcc  12660
cgtgccaagc ccgccgaagg gctcccatac gacgtcgccc tccttcgtga cggcgtgcac  12720
```

```
caggcgctcc atgagctcca gtggcttctg gttcagatgg gtcgtgctgg ccttcgtggg  12780
cttgtacacg cgcggcgccg accgacgcat cgagcccttc atacgctcgc cgtcgtgcag  12840
cggggggcgg ctccacacgt tggtcaggcc atggacgtgg tgccactggt ggcgcatccg  12900
gtcccactgc ttcgcggtga ccgacgtcac accgtcgagc gagaagtacg ggcggccgct  12960
ctccaggccg tgctgattgc agtacgcggc catggcggcc acggcgactc ccggcggcca  13020
gtaccagagc cagtcgttcg tcaggtactt gcgcgtggcg gcgttcttca cgccgcaggc  13080
ctcattggcc aggtacatcg gcagaccaga gcggcgccac tcgtgccgca gccactgctg  13140
ggcatcgaga atgcccgcgt cggtcgccgc ctcgaagcgg cgctggtaga ggacgcagac  13200
ctccgtgacg acggggaagc ggcggatggt gttgccgttg acgttgcccg cgatgtggct  13260
cagacccttg tcccagacca cggtctggac gtagtcccag ccctgacgct tcaactcagg  13320
atgcaccgtg gcccagccca cctccgtacc ccagaaccac agcgccgtgc ccggggcggc  13380
agccttcgtc cactgctcga tgtgcggggc gtaccagtca acgagccctt cctcgtcggt  13440
ggtgtccccg taaaaaccgc ggacgccgta ggcgccgtcg ctgatgatgc acgtcggcga  13500
cggccaggac gcgtaggcgt ccgccacatc cccacgtgc aggtcgtagg gcctcttctt  13560
ctcggccatg ctcccagcct ctcataatcg atggttactg gtcattcgcc cggtccaggt  13620
acgtcaggcc ggcgcggcgt agcgcgtcgg ccggcgtgcc gccgctccag tcgggggcgg  13680
tcccggtcat cggcaggggc gtggccgacc gggctgtgtt ctccagctcg tcggccagtt  13740
cgtcccactc gggcacgtcg aggacctggt tgaccgagac ctcgacgacg acgctcaccc  13800
cgcgctcggc cagcagccgg cccacggtct ccttgtacgc ctcggcgtag tcggcctggt  13860
cctgctccca ccgggcctct acagcgtcag cggcgcgccg cgcctcgatg agggtggccg  13920
ccagcggatg ggcactctcg gctgctcgct cctccacggc cttgatgatc tttccggcct  13980
cctcatacat cgcggtcacc cggtcggggt cactgtccca ctcgggtccc ccgagctggg  14040
gcatgtcggc ctggagcgcg gccagccggt cgcgctcctc ggccgtggcc acggcctccc  14100
agagtgcatc ggccgccgcg tcgacgcggc ggccgagttc ttcggccgcg tcctcgtaga  14160
gctggtagag cccgaagtcc tcgaagacgg cctccacgtc gagcgcgagg cgcaccggct  14220
cggtgcgcca ggccagcagg tcccgatcat cggtgccggc tgtcccctcg acgacctggc  14280
ggatgagggc ggcctcccac gatccgggcc ggccggccag cagctcgtcg acgctgccga  14340
tgttcgcggc cacggccgtg agcacgtggc acgcgatccc cgcgaagtcg tccggctccg  14400
tgtgctcgct tggggtgccc gctccgacga cgcgacgccg gcgcgccgcg tcggtcaggg  14460
ccgtgatcgc ctgggcgatc gggtccggga ctgtctcggt catgtctggc tccttcagtg  14520
ggtggtgatg ccgggcttgg ggcctggcgt cacggcgtcg aggtcgggga acgggcggcc  14580
gtcgttgtac tcggcttcca gccgggcgac tttctcgttg acggcttctt ggacgaactg  14640
ccagtagggg cggatgccga gcttcgcctg cgtgtagaac cacgctcccc tggcacgccg  14700
gccttcctcg atggtgtgct tgaagctggt gcgcgtccat ccttcgccgg tcccggtctt  14760
tttcgcggcc tcgtgccggg cctcgtcaac gttgggcggc tgcgccgcct cgacggcctg  14820
gggcacgagg gggttgctca ggttggtggt gcgccgctcg ggccgcttgc tcatttgatc  14880
gctcctttag tgatggtgtc gaggtgctgg cggtagaggt cggccagctc ggcggcgtcc  14940
ttgccgcccc actggtccag gccggtggca gcctccagcg cgtcggcgat gacggcgcgc  15000
ttcgggatgg gcggatcaag gatggtcagg ccctcgatct tctccaggtc ttccagagcg  15060
```

-continued

```
cttcgcgcgc cgatggtttg cgcctcgtac tggttgacga tcaccccggc cacggccaac  15120
tgcgggttgt agtacttgcg cacgatggcg atcgtctgaa gcagccgacc gagcccggcg  15180
atcgagtaga ccttggcctg ggtgacgatg gccacccgct cggcggccac taggccgttg  15240
agggtgaggt gatccagcga tggcgggcag tcgatgagca ccaggtcgta gcggtccgcg  15300
acgctggcca cggcctcgct cagccggtgc tcgacgccgg gggtctgcgt ggtcagcagt  15360
tcgttgcgaa cgctggtcag cgcctcgttg ggcggcgtcg gggccacgtc gaggccatcc  15420
cacacgccgg ggacgatgac gctctccagc gtctcggtac tgcgttcact cagcgcgtcg  15480
gccacgccga cgtcctcggg cgtgggcgtg tctttcgcgg ccgacatggt ggcgttaccc  15540
tgcgggtcga ggtcgatcag gagggtccgc cggccctcgg tgacggcggc gcgcgcgaag  15600
ttgacggcgg tggtcgtctt cccgacaccg cccttctggt tgctgattgc gagggtcatg  15660
ctcatgctgt tggttccgtt cgtgcgattg gtgcggttcg tggtgttagt gccattcgtt  15720
ctgttcgcac taactagtgt agtcgcttcc cgcctcgctg tcacggcgtc gaggacagtc  15780
gggagatcaa gtccggccgg aggccggcgc accgtggggg ctccggccgg acttgttctc  15840
actgttcatt ctattcgttc ctttcgttct aatggtgcga atcgcaccat tagaactagt  15900
cggtgatggc ttcgatgatc cggtgcgcgg cggccagcac acggctggcg ctcttgcgga  15960
tgaggtcggc gtctcccttg gaccatccgg cgacgtagcc gacgctgtag gcgctggtgt  16020
cgagtccaac gatgccggcg accacgtggg cgacgctttc ggcctcgacc tcgcattgtc  16080
cccggtgctc gtggtactcg gtgggggtga tgtcggcgtg catgagcgcg tgggcggcct  16140
cgtgaagggt cgtcttggcg gcttgggcgg gggagatatc ggccgcgatc acgattcgct  16200
tgtcgtcgtg gctggtgtag ccgttgagtc cggccccgag ctggtcgtgc tcgatggtcc  16260
agccctggcc ggtgagccag tcggtcacgg cctcggcgat gccggcgggg tcgtcgccgc  16320
tgagctggtg ggcgtcggcg gggttctcgg ggatcggctc ggctccctcg atggggtcgg  16380
tctgggcgag gtcgaagacg gacacgggga agaatcgcgt gcggcgtcgc tcggtctcct  16440
ctccggtggt ctcgtcctcg atcgtttcgg tgacctcgcg gccgccgaag attctgattc  16500
cgcgctcacc tttgcggacc tgccggccga gcttctgcca ggtgcggtac cccgcgacct  16560
gcgtcgcgtt ctcgcgctgg gcgaggatca ggagcaagtt gttcaggctg tagcggtgga  16620
acttcccggc gaaggcgagg aactgggccc atgcttccga ggtggccagg gcctcaacct  16680
gctgggcgat ggtctcgtgc agttcggccg cttcggtgcg gcgctgctcg gggtcttgt  16740
gggtcttgat cttccgggcc atgatgttgg ttcctttcgt gtgattggtg cggttcgtgc  16800
gaactgcctg tcttccctca cgttttttg ccattgaagg cactggaagt gccgccaggg  16860
agggagcccg gagtgcaagg gaccgtggaa taccggactg agcgcagcga gggaggatat  16920
gccgcgaaag cccttgcgcg tagggcggac gaccgtatgc tgccgaaggc ttcaatggca  16980
aaaacgtgcg ccgtaggcgc atgctgccgg ccgcgcagcg gccgtcctta tgatgacggt  17040
ccgccagggc cgcctgggga gggtcggcct gggggccggc tcgttgtggt cggctgtcca  17100
cctgtgggcg ggccagccgg tcgggagctg ggccgtccac aggtgcgtca ggcggtcccc  17160
tctacggagc ggccctgtgg ggcgttctgc gggccgtgac cccctccgc gtgtggttgc  17220
ctgggtgggg ttgagttcgg ccgtttcggg gcgttgtatg gcgtcgtttt tcgtggtcga  17280
tcatggctgc cgcctgtgga cggcccttcg gcccgcccac agttgccttc gaaaccgggt  17340
ggccgggttc cggcgtggtt gggacgaggg ttgcccccgg cggtcaggcg gcagtgacga  17400
ggctctgatg aaggtggtcg agtgctccgg cggcgatcgc ttcgcgggcc gctcgatggt  17460
```

```
cagcgcggcc gtctggtcgg cgcgggtagg gggggtagat gtcccagggt cggccgaacg  17520
tgagcgcaat ctgtcccgtg ggctggtggc gtcgtttgtg gcggcctggt gtggtcatcc  17580
attccagttc ggcctgccac cattcccaca gatcgcgctc ggccttgtag cggccttctc  17640
gtgcgtcgag acgcccctcg acgccgagcc gtcgggccgc gaggtcgcgc agctcgggcc  17700
gggttcgccg ccagccggtg ggcgtggcca cgatgagacc ggcgtaggcg agtcggtcga  17760
gtagggggt gatctccgta gtggtgacct gggggtgatt gagcctggcg tagaggtttc  17820
ctgcggcgag gcccagggcg tgggggttgg tgaaggtgtc gtggcgggcg aggtctaggc  17880
ggtgggtgag ttcgtccagg aggaggtttc tccatcggct gcccgcccct gcggggcgtg  17940
cagccccttg tgaccgggca tggtctgcat ccatgtggat agcggtctgg ggctcgattg  18000
tccaggtggt ggcgtgcctg ccggtgcccg cctgggcctg gctgatccac ccgtcgccgg  18060
ccaggcgcag gagggcggtg cgggcggtct ctcggccgat gccggcgagc agggcgaggc  18120
ggcgcacgtc tgcttcgacg gctgcgctga cggcttggag ggcgagcagg cacagggcgt  18180
cgagcacgcg ccggtcggcc ggccctcctc cgcgtgtcca gcgccctggt gccgcatcgg  18240
cgcggcgctg cacctggtcg acggtggcgg cgatcgcttc ggctcggggg tcgaaggtgg  18300
gatcgtcgcc tgcctggcgc gcgtgggtgg ccacgaacct gacggcggcc tgccacactc  18360
ggccgagcgc ggcttcgctg ctttgggctc cgtgtgtggg gcgcgcctgg cgtgcacggc  18420
ctccgtggcg tgcgcgctgg gtgcgggcgt gctccatgcc gggtgccgtg gacacgaggg  18480
cggccgcgtc gcggtagtgc cagtgggcgg cggctgcacc gagcaggatc acgtagagga  18540
cgcgggaggc gtcctcactg gcggcggcgt cttcgtcgac ggcagcgcgg ctcttggcgg  18600
gcatggcacg gcggggtccg ggcagccacg gccgcccgtc ctcgtcgacg ggcacgcgca  18660
gctcggctgc gtgggggagc gaggtcaccg tggccacgtc gccgaactcc tcattgagtc  18720
gggtcgccag ggccacgagc tgggctggtg tggtggtcgg gtgtgtgagg gtggcgagat  18780
ttccggcgat cacgcgggat gctccaccgt ggcggtgggg cgtgccgggg gggcgcaagc  18840
atccggtggt cgggttgagc aggggagtgg ggtccaggct ggtggcgaga ccctggaggg  18900
agtgcgtcag gtggtgcacg agctgcgggt cggccgtctc ggccagggcg atccacacgt  18960
ggcggccgcc ggtggggccg gactcgcaga tgacgtgctc gatgccggcc tggtcgagca  19020
ccgtggcgat cgccgtggca tcccgctctg cttgggcggc tccgccctcg tgggcgtcga  19080
ggtcgaggcc gatgtagcgg tagcggcgct gcgcgtccgt caggtacatg gcccacgggc  19140
cggccggggc cggccccgcg acgggcacct gcgtcgggta ggcgttcacc tggtcgccgc  19200
tggcggcgcg cacctgcggg cgcgggctca acgtgcgtgt gagacgccac gccgcgccga  19260
tatgcgtagc gtcacggtta tcggcatctg ttgctatcat gtacgtgttc cttccgggga  19320
aagacgcaac gatccctcct tcggttggtg ggcccctgcc aagggcccta ggtgtttggg  19380
tgttgcatcg ggtgccgact gccaaaccgg cttccgtact tggttcgctt gatctggttg  19440
tgttggggaa ctcagcagat caggcgctta ctcttctgac ccccgccctg ccaagggcgg  19500
gggtctgttc atgtctatgc ggtgcccgta gggtcctcct cgatgctcag ttccggttgg  19560
gtgctatctg gggttggaag ctcccatccc tgtggccagc cgtccgggcc tgggacacca  19620
gagcggatcg cagcttcaag gactgcccac tggggggcac ccttggcgcg cgcgtaggcg  19680
tcgagcttgg ccttgacgtc cggcgcaacg aagatgtgaa gcgctacggt aggcgctcca  19740
cggtcgcgac ggaatcggct ggtcatgaca gtcatcatat aagggcggct gtacatgtac  19800
```

-continued

```
acgggccgac acgccggcgt gtcgcgactt cttttcagat atcagagtcc tcgggcgacg  19860
gcggcggctg cgcgcagcca tgcgcgttgt gtgctggggc gcaggctgtc ccattggagg  19920
atgccgtcca cgatggcggg gtcgtggggg atcgtgacga cttcgcgggc gaggtcctgg  19980
tagccggtga cgatgttggt gatgtcggtc ttgctggcgc gcgggtcggc ttgggtgacc  20040
acggcgacgg cgttgtccgc gagctggcgt gagtgttggt cgcggccgcg cagcgcgtcg  20100
aggaggagcg cgccggcttc ggcgtggtct gcgcgggtgg tggtgggcac gacgatctgg  20160
tcggcgtgtt cgatggcttc cagccacaca ggatcggatt cgtcgttgcc ggtgtcgatg  20220
aagatgaggc ggtagtactt gccgacgacg ttccagatga ggtcgacgtc gtgaggggtg  20280
acgcgctggt cggcggcgag ctggatgggc tggctgcgca gcacgtcgaa ccggtcggcg  20340
gtctggtggt gaacgtagtg cgccagatcg gccgactggg ctccggtgcc caacagtcgt  20400
tcggtttggg gaaggaggtc gaggacggtg gcctcgtggg gtccctgttc ggtccgccat  20460
cccagggtgc ccctggtttg gttggcgtcc caggcgacca cgcccgcgcc gccataacgc  20520
gcgaacacag cactgagtag caccgtggtg ggggttttgc ctgccccgcc cttcccgttg  20580
gccacgatga tcgtcctggg gccgggccag tgctgggaga cggcgtgcac gtcgtcccgt  20640
tccgcgcgct cctgctggct cgggttcatg cgcagcccga gccgggtggc aacgccgcgc  20700
cagccctgcg tggcgggctg ctcgatctcg gtggctttga ggaatgaatg gcggctctgg  20760
acctcgcgcc tgctgggcag gtgcgcgatg gggctgtcgg ccgagcgtgg gagagtgtgt  20820
gcctgggtgt gagggctgtc ctggcgtggg gttgggctgt catagaccgg ggccgccgtg  20880
gcggccgcgg cctcggcggg atcgtggagt tcgccgtcgg gggtgacgat gacggtccac  20940
acgccgtcgg ggtcggaggc ggtgagcgtg gcgctttcgc cggcggtggc tgcgcgctcc  21000
tgggcgatcg cgacgacctg ggcgcgggcg tcttcgaggc tggtggcggt gatcttctgc  21060
ggcgtgccgt cgatcgtgac gatggcgctg ccgtcgcggg ctgtggtggc ctctatgtcc  21120
atggggatgc tccttcgttc agctttgggt ggcctgggtc tgcatggctg tgatcgccca  21180
ctggccgttc tcttgggtcg cggtgaccca tgcgtcccag gccacgtcgt cgggggcgtc  21240
tgagccgtct cggggcgtgg tcttgacgag gtagtggacg atccggtgcg cgtcgccgtc  21300
ttggtcgggg tcgagtcctt cctcgacaat ctcgcggatg gtgacggtgg tgtaggagtc  21360
atgctgcgcg gcctgtgtga actgggcctg gcccttcgcg gtgtcggggt cgtagtcggc  21420
ggccgcttgg cgtagcgcgt cggttaggta gatcgccgcc cgttgggtgg cgtaggcgct  21480
ggtcttgtcg accgtggtgt cccaggtggc ggccgtggcc acgtaggcgc ggatgacggc  21540
ctcggggtcg gtgcggtcga cggtgctggg gttgggcagg tcggcgagcc aggtgggctt  21600
gcccccgggg atgggtgtgc cgtcgggtgc ctgcccgatt gtggggctgg tcgtggccgg  21660
cgtgctggtg gcgctcgtct gatccggtgc cggggtgtcg ttggctgtcg tgtgggcgca  21720
gccggtgatg gcggccagag tgatggtgcc gatgacgagg gcggcggcac gccggtgggt  21780
gcgcctcatt ggattctcct gtagttgctc ggtgagccgt agatgggctc gaagttgatg  21840
ccatcaatgt ggttgtcggc gctgaccatc cagccgttgc cggcgtagat ggcgacgtgg  21900
taggccggcg tgccgtagaa gatgaggtcg ccgaccttga gttcgccgcg ctcgatgccg  21960
gtgccgacct gctgctgctg ggcggctgtg cggggcaggc tgatgccgag gcggcggtag  22020
acggcgctgg tgagcccgga gcagtc                                       22046
```

<210> SEQ ID NO 50
<211> LENGTH: 1615

-continued

<212> TYPE: DNA
<213> ORGANISM: Artificial Sequence
<220> FEATURE:
<223> OTHER INFORMATION: pBC1

<400> SEQUENCE: 50
ccccgatggt ttttcccccg acggctcgcc tttgggaagt ttgaagggcg caggttccac 60
acgaaaaacc acaaggcttt ttttgagtaa taaaaaagcg gacggcgagg gcgtgaaaaa 120
aacccgatga acccttgaaa ataaagggcg ggacgggttt tttcttatct tgataatata 180
tagaaacaat gagattttaa aaaaagccct caaacccttg ataatactgg gtttgtggcg 240
ttttttgggg gtggataaat aaaaaccctc tgtgttatgg ttatgttgac tagacaaaac 300
catacagagg gctttacgcc tttctgtatc cagaaaggag ttattaaatt ttatgcacgt 360
taatcatagc attaaaacgt caaatctatc aaatatcgaa tttttgcaag ataaaacgaa 420
aacaggaaaa gagagagatt ggaaaggcaa gaaacaacgg tctttgctga cagcggaaca 480
cttcgaggta gcagggctga ctagcaaagc ggaacagtgc gagagtgtgc tgacacgttg 540
gtgtttaagc gaactgccga agggttaaaa ctatatcaag catggttctg taaagtgagg 600
ttatgcccga tgtgcaattg gcgaagatcg ctgaaaatag cttaccagaa taaaagggtt 660
gtagaggcgg ttaatcaacg tgagaacgtt cagtggctat tcctaaccct taccgtccgc 720
aacacgagcc ctgagagcct tccagagacg atttcagcca tgtttgaggg gtttaatagg 780
ctgacgaagt acaaagcctt taaaacgtct gtaaagggct attttagggc tttagaggtc 840
acaaagaata gagaccctca tagtgaatgg tttggcacgt atcaccctca ttttcacgtt 900
ctgctgtgtg ttccatccag ctatttcaag aaaaaagaat tatacataac cgaacaagaa 960
tggactgacc tttggaaaaa ggctatgaag ttggattaca cgccgattgt ccacgtgcaa 1020
agggtaaaac ccaaagaaca gcttgaggac atggaaacct atgaagaaca gcttaaaaac 1080
gccattaggg aacaaaatgc gattttagaa gtctctaaat atccggtcaa agatacggac 1140
gtcattaaag ggaataaggt cacggccgaa aatgtggaaa ccgttttggc gttagacaac 1200
gccttggcaa ataagcggtt aatcgggtat ggcggtcttt tgaaacaggt tcacaaggaa 1260
ttaaaccttg gagatccgga agatggagat ttagttcatg tttcggaaga ggatgaaatc 1320
gctaatggtg catttgaggt catggcgaaa tggcatatcg gttttagaga ttattggatt 1380
caaaaatagc aggagagaaa actcctgctt ttttattttt tccgaagtta ttggcgaaag 1440
caaacttttt atcgagcgaa gcgaacccta ttgaatacct gcatggcaag gtatgtaaat 1500
gggcactctg tgatttttgg atacaaaata gactctagcg agccgatttt atgacgcagc 1560
aaaaaacgta gtctttttgc gttggagagc ccttcaagta aactgaccaa ggtgg 1615

<210> SEQ ID NO 51
<211> LENGTH: 1854
<212> TYPE: DNA
<213> ORGANISM: Artificial Sequence
<220> FEATURE:
<223> OTHER INFORMATION: pEP2

<400> SEQUENCE: 51
atggtaaatc tgcgcagaca gccctgtgca gctgaaacgc ggttacgtat agcttgccat 60
atgtctagcc atacgtaacc gcaggtaaaa ggcatatttt tcgcgtgtca tggctagtaa 120
ataacaccgg tgtcatttag agtcagggaa agacaatgaa aaacgaagaa agccaccggg 180
cggcaacccg atgactttcg cttatcaccc agcacacacc tgggagaaat cacggtcatg 240

-continued

```
agtttacaga ctcatgcgca gaatgcgcac actaaaacac ctacccgcgt cgagcgcgac    300

cgtggtggac tggacaacac cccagcatct gccagtgacc gcgacctttt acgcgatcat    360

ctaggccgcg atgtactcca cggttcagtc acacgagact ttaaaaaggc ctatcgacgc    420

aacgctgacg gcacgaactc gccgcgtatg tatcgcttcg agactgatgc tttaggacgg    480

tgcgagtacg ccatgctcac caccaagcag tacgccgccg tcctggtcgt agacgttgac    540

caagtaggta ccgcaggcgg tgaccccgca gacttaaacc cgtacgtccg cgacgtggtg    600

cgctcactga ttactcatag cgtcgggcca gcctgggtgg gtattaaccc aactaacggc    660

aaagcccagt tcatatggct tattgaccct gtctacgctg accgtaacgg taaatctgcg    720

cagatgaagc ttcttgcagc aaccacgcgt gtgctgggtg agcttttaga ccatgacccg    780

cacttttccc accgctttag ccgcaacccg ttctacacag gcaaagcccc taccgcttat    840

cgttggtata ggcagcacaa ccgggtgatg cgccttggag acttgataaa gcaggtaagg    900

gatatggcag gacacgacca gttcaacccc accccacgcc agcaattcag ctctggccgc    960

gaacttatca acgcggtcaa gacccgccgt gaagaagccc aagcattcaa agcactcgcc   1020

caggacgtag acgcggaaat cgccggtggt ctcgaccagt atgacccgga acttatcgac   1080

ggtgtgcgtg tgctctggat tgtccaagga accgcagcac gcgacgaaac agcctttaga   1140

catgcgctta agactggcca ccgcttgcgc cagcaaggcc aacgcctgac agacgcagca   1200

atcatcgacg cctatgagca cgcctacaac gtcgcacaca cccacggcgg tgcaggccgc   1260

gacaacgaga tgccacccat gcgcgaccgc caaaccatgg caaggcgcgt gcgcgggtat   1320

gtcgcccaat ccaagagcga gacctacagc ggctctaacg caccaggtaa agccaccagc   1380

agcgagcgga aagccttggc cacgatggga cgcagaggcg gacaaaaagc cgcacaacgc   1440

tggaaaaacag accccgaggg caaatatgcg caagcacaaa ggtcgaagct tgaaaagacg   1500

caccgtaaga aaaaggctca aggacgatct acgaagtccc gtattagcca aatggtgaac   1560

gatcagtatt tccagacagg gacagttccc acgtgggctg aaataggggc agaggtagga   1620

gtctctcgcg ccacggttgc taggcatgtc gcggagctaa agaagagcgg tgactatccg   1680

gacgtttaag ggtctcata ccgtaagcaa tatacggttc ccctgccgtt aggcagttag   1740

ataaaacctc acttgaagaa aaccttgagg ggcagggcag cttatatgct tcaaagcatg   1800

acttcctctg ttctcctaga cctcgcaacc ctccgccata acctcaccga attc         1854
```

<210> SEQ ID NO 52
<211> LENGTH: 2178
<212> TYPE: DNA
<213> ORGANISM: Artificial Sequence
<220> FEATURE:
<223> OTHER INFORMATION: pWVO1

<400> SEQUENCE: 52

```
cgatttttta ttaaaacgtc tcaaaatcgt ttctgagacg ttttagcgtt tatttcgttt     60

agttatcggc ataatcgtta aaacaggcgt tatcgtagcg taaaagccct tgagcgtagc    120

gtggctttgc agcgaagatg ttgtctgtta gattatgaaa gccgatgact gaatgaaata    180

ataagcgcag cgcccttcta tttcggttgg aggaggctca agggagtatg agggaatgaa    240

attccctcat gggtttgatt ttaaaaattg cttgcaattt tgccgagcgg tagcgctgga    300

aaatttttga aaaaaatttg gaatttggaa aaaaatgggg ggaaaggaag cgaattttgc    360

ttccgtacta cgacccccca ttaagtgccg agtgccaatt tttgtgccaa aaacgctcta    420

tcccaactgg ctcaagggtt taaggggttt ttcaatcgcc aacgaatcgc caacgttttc    480
```

```
gccaacgttt tttataaatc tatatttaag tagctttatt gttgttttta tgattacaaa    540

gtgatacact aactttataa aattatttga ttggagtttt ttaaatggtg atttcagaat    600

cgaaaaaaag agttatgatt tctctgacaa aagagcaaga taaaaaatta acagatatgg    660

cgaaacaaaa aggtttttca aaatctgcgg ttgcggcgtt agctatagaa gaatatgcaa    720

gaaaggaatc agaacaaaaa aaataagcga aagctcgcgt ttttagaagg atacgagttt    780

tcgctacttg tttttgataa ggtaattata tcatggctat taaaaatact aaagctagaa    840

attttggatt tttattatat cctgactcaa ttcctaatga ttggaaagaa aaattagaga    900

gtttgggcgt atctatggct gtcagtcctt tacacgatat ggacgaaaaa aaagataaag    960

atacatggaa tagtagtgat gttatacgaa atggaaagca ctataaaaaa ccacactatc   1020

acgttatata tattgcacga aatcctgtaa caatagaaag cgttaggaac aagattaagc   1080

gaaaattggg gaatagttca gttgctcatg ttgagatact tgattatatc aaaggttcat   1140

atgaatattt gactcatgaa tcaaaggacg ctattgctaa gaataaacat atatacgaca   1200

aaaaagatat tttgaacatt aatgattttg atattgaccg ctatataaca cttgatgaaa   1260

gccaaaaaag agaattgaag aatttacttt tagatatagt ggatgactat aatttggtaa   1320

atacaaaaga tttaatggct tttattcgcc ttaggggagc ggagtttgga attttaaata   1380

cgaatgatgt aaaagatatt gtttcaacaa actctagcgc ctttagatta tggtttgagg   1440

gcaattatca gtgtggatat agagcaagtt atgcaaaggt tcttgatgct gaaacggggg   1500

aaataaaatg acaaacaaag aaaaagagtt atttgctgaa aatgaggaat taaaaaaaga   1560

aattaaggac ttaaaagagc gtattgaaag atacagagaa atggaagttg aattaagtac   1620

aacaatagat ttattgagag gagggattat tgaataaata aaagcccccct gacgaaagtc   1680

gaagggggtt tttattttgg tttgatgttg cgattaatag caatacaatt gcaataaaca   1740

aaatgatcga tgctgtttgg caaaaaaaga aaaagtgatt aatttatatt ttatttatgg   1800

cgctaattta ttacggcttt ttttgttgtc ggctagccga ttctgataca tttttttaag   1860

cacaaaaacc acccaatttt ggagtggtgt gtaagtgcgc attgtcatga aaaaatggca   1920

cgcaatttca tcacttttta aagtgatgtg taagtgcgca ttgtcatgaa aaaatggcac   1980

gcaatttcat cactttttaa agtgatgtgt aagtgcgcat tgttcgaaaa atcgaactat   2040

gatttatttt tgctgttgta tttatttttc atcttttggg ttttggtttt gtttttttgtt   2100

gctatcgtag tttatttgct ttttaagggc tctatttttc gttctacggc atttttataa   2160

tttgccaata taatttat                                                 2178
```

<210> SEQ ID NO 53
<211> LENGTH: 2439
<212> TYPE: DNA
<213> ORGANISM: Artificial Sequence
<220> FEATURE:
<223> OTHER INFORMATION: pAP1

<400> SEQUENCE: 53

```
aacaagggtt gttcgcgggg acaaaactag ccccaagctc gcgtttccgc gaacaatccg     60

cgttagtacc ttgacgcggc tttacccagc gcgcctacgc gccgagattt cgcagttcct    120

gcatacttta accagacagt tttaacacta cgagacaaga aagcgccccc ggcagtccgg    180

caagactccg agggcaactg gaagattggt ccttcctcta atgaatagat tatctgaaag    240

aacggcgtta agccttccgg ctcgccagat tcaaaaagtt atccccgccg caggcggaag    300
```

```
gtcgctgaag tccttcgaag ggatgacggc gacgtggtcg gcgcgaggag gagcctccag    360
cgacgaacgc agcagagaca agcgaagcca aatcccttcg aaccggaggg aaggacgctc    420
agcgacccat ccccttggca atacggtatt aacttttcca gtatcaaacg agagcaagaa    480
aacagctaaa tctcgccgtt ctgagagata cgaactcaga gacggattag ccgaaatctc    540
gaccattgag tccgtccgga agtgtggccg cgtgcccgtg gcacctctcg tctcgttgcg    600
agcaaaatct gacggtaaag gcgccggata tggtggtttg cacacttgtg gaagcgtctg    660
ggcgtgccca gtctgtagcg cgaaaatcgc cgctcgccga aaaaccgacc tccaacaggt    720
cgttgaccac gccgtaaaac acggaatgac cgtctcaatg cttacgctca cccagcgtca    780
ccacaaggga caagggctaa aacacctctg ggacgccttg tcgacggcat ggaatcgcgt    840
tacctctggt cgtcgttgga ttgagttcaa ggagcaattt ggtttagtcg gttatgttcg    900
agccaatgaa attactcatg gaaagcacgg ctggcatgtg cattcccatg ttctgattat    960
ttccgagaaa gacccgctga ccagcacgtt tgtctatcaa cgcaaacaag gacgccgccg   1020
ccttccctac cccccagaga tttatatgtc atccgatttc attgctgaac ggtgggaagc   1080
tggccttgcg aagcacggcg ttgattttct ccgcgattcc ggaggcttgg actggaccgt   1140
tgcgaaagac gcgcgagcca tcggcaacta tgtcagcaag atgcagacgt ccacagacgc   1200
gattagctcg gaagtcacgt tgggcggctt caaaaaagcc cgaaacggga acaggacgcc   1260
cttccagata ctcgcggata tcctttcgct cggcgatgtc gacgacctca agctctggaa   1320
agaatatgag aaagcttcgt tcggacgccg tgcacttaca tggtcgaaag ggctcagaga   1380
ttgggcaaat ctcggcgttg aacagtccga cgaagagatt gcctctgagg aaatcgggga   1440
cgaagcaata gcgctattta cgcatgacgc ttggcgtcag gtgcgacgtt ttggagccgc   1500
tgaactactc gatgtgaccg aatccggagg tcgtgcggcc gcttaccgct ggttggattt   1560
tagggaaatt gattggtcat tgcctccgaa aatcgagtga agtcgtcaaa ccatacttta   1620
agtagaggtc gagaagtccg tggaaaagtc gcggcgcctc tactgcgaaa gtaggtattt   1680
atcgatgttt ttcatcggaa aatatagaac taaattccag cccatcgcgc catgcaaacc   1740
ctccccgatt tttgacggca acggcaaacg cacaggtgaa ttttcttcgg agaagatgcg   1800
gactcaagca atcaccgaag acggccgcct cgtcgagctc acctcgattc ctccccagtt   1860
cgtccagttg attgatgacg ctgtgaagag tcgggaactt cttgaattcg agaaggtcaa   1920
tcttgccgta ttgccgcgca acggaggcgg aatttccacc tacctgacac taggggaagc   1980
cgtccacgtc cccgctccgg tcgtcgtgga ggtctcggaa tgatgagcga accctacgga   2040
atcagttcga acgctgaact gcaactcgtt tttagccgtc cagctaaacg agaagcccgt   2100
ctgtatatgt ctcggattct caagaaagaa ctggaatcag ggaagcactc gacgccgacg   2160
gaggccttgg aatcatgcga aaagctctac tggagcgttt ttgaaccgcg acttgttgat   2220
gttgttttgc acgaggtcgg agaatgccgg tgcgcgggta caaattccgc ggttgcccgc   2280
tcgctctcct ctcgcgcatt cattcctgca aggttcgttc aatctcttga aaatggggga   2340
cgcaacccag cccagctcct gacccaagac caagttgcag gtatgcggaa aactttagga   2400
acaaggtgac cacagcgtca cctgaccacc cttttcgtt                          2439
```

<210> SEQ ID NO 54
<211> LENGTH: 2697
<212> TYPE: DNA
<213> ORGANISM: Artificial Sequence
<220> FEATURE:
<223> OTHER INFORMATION: pWKS1

<400> SEQUENCE: 54
gaattcatgg tgttccagga tgatgacgag ttgcgtttcg ggcgcaccat cggcggcagg 60
gtccagaccg ccccaggccg acgctttgca atcctgcgct gcgccaagat caagaccctc 120
ggcaacatgg gcgccagcct tcaacacacc ttccgggaac gcgaaacccc gaacgccgat 180
cctgcccgcc ggaccgacaa cacggttctg atcggcggaa cagacagcgc tgcggtcctc 240
gatgcatggc gcgcccgtgc gccggaaaaa atccgcgcca atgccgtgca tgggctggaa 300
tacttcgttg gcggatcacc cgaggccctg aaggccatga gccgggatca gcaggacgcc 360
tatttccgcg atgccctgaa ctggctcaag acccggcatg gagccgaaaa catcctctca 420
gccgtcatcc accgcgacga gaccaccccg cacatgacgg ttatgaccat cccgctggac 480
caacagggca agctcaatgc ccgcgctttg gtcggcagcc gtcagcagct ctcggctatg 540
cagaccgact tcgcaaaggt tgtgggacag gcgcatggcc ttcagcgcgg tctggaaggc 600
tccagagcca cccacgagcg ggtgaagcgg gtctatgccc atatcagcga cccggaagcc 660
tctgtgagcc tcccagagcg ccgcagaggc ggtttcatgg gtcggggtgg ggaaacggag 720
gcagaatggc gggaaagggc cacagaagcc gtcacagagg cgctggcggg ggtccagcac 780
gccttgcggc gggaacgccg cgacagggct gcagagaccg aggcactgcg tcagcgcctt 840
cagggcagtc cagatcagca gcaggtgaac cagagactgg aacggcaggt tgcccggctg 900
aaggccgaaa cggcccgcct gcacgacagg ctggccaagg tcaaagacga agccgatgca 960
tatcacctca atgcgctcaa gctggacgcg gcccgcgagg ttatcctgac ccatgcgatt 1020
gccttcgtcc gcgatcacgg cctagacgag gccgacatgc tggcgcggat ggaggccggt 1080
ctgaacgaag ctctggcgga gtttaagccg gtgcagcagg agcaggtcgg gacagaacac 1140
gatgccgtgc aaaaaacccg ccagcgcgat gaggggctgg atcacggaga ctaagccgat 1200
ccgccgccag ttcaggccgt ccggccccgg attctgacca taatttcatc gaaaaaaggg 1260
gcgcagccct tcttgttcta atagttctat aagttcaggc gaaaatcgtg cagcaattac 1320
aaaaggttgc gcgtctataa gtggggaatc cagccgcaaa agtggggaat ccagccgcaa 1380
aagtggggaa tccagccgaa atcgcggatt gacgagtggg atttcccgcc caataaatcc 1440
accatgggaa agacactcga cgttgcccgc gaccgggcct ttgaccagac cgcgaccgtg 1500
ctgcccgccg aaatggcgcg gggggtctat atgcgcaacg cccccagcct cgcggccctg 1560
aagctgatgc atctgatgat cgccacggcg ggcgggcgca tggccgatga cgtgcgccac 1620
gaaatgcggc tggccgacat ccgcaagatc gacggtatgg ataaccacac ccgggccagc 1680
ctgaccccgc tctttgcgga actggcggcg gcggtgctga cccacgacga cccggaaaag 1740
cgggtcgtga ccatcggtgg cctgctggac gaagcccgga tcgattaccg gcacgaggtc 1800
agcggcgatc ttctggtgtc gtggaccttc cgcagcatgt tccgccgcat ggcggcggaa 1860
tcgaaccatt gggcgattct cgaccggcag accgtgttcc acctcggcag caagtattcc 1920
gtgctgttgt tccagcacat cgccagcttc aaggaatacg accacattac cggcaagacc 1980
tttaccgtgc cggagttgcg ggctgtgttt ggtatccccg agggcaaaat caagcgtttc 2040
gcagacctca acagagacgt gctgacgccc gccattgccg aaatcaacca gctttcccgc 2100
ctgactctga ccgccacgcc gaacaagatc gggcgcaccg tggccagcgt gacgattgct 2160
tgggaagaaa agcccctcga aggcaagcgc tcgaccaagg ccgaactgga ccgcccgaag 2220
gtgggccgga aggcccggcg cgacggcacc gccgagacgg tggcacgggc cttcccggca 2280

```
tcgggcggga tcgagttcga ccagcattgg cgcgacctca agcgggcggc gggctgcaac   2340

atggacaaca ccatgatcgc cgacaaattc cgggcatggt gcgccgggaa gggcctcgct   2400

ctcgatgccc ggaacatcga acaggcgttc agcagcttct gcaccaaggt gggccgggtc   2460

tgagacccgc cgcgccggtc gctcgatacc tgtggtctcg ctccctctgc ggctaccgtc   2520

agcgcctcgc ctgcatcgcc gccctttccg atcctcatcc cgccccagcc ttatgggggg   2580

atgaggatcg ggccgggact gaaacccgaa gggtaatgaa tgtgtctttc cctgcttggc   2640

agggcgaacg acattcggca gaatgtctag tgagtacaca ttcattaccc ttcaggt      2697
```

```
<210> SEQ ID NO 55
<211> LENGTH: 1952
<212> TYPE: DNA
<213> ORGANISM: Artificial Sequence
<220> FEATURE:
<223> OTHER INFORMATION: pLME108

<400> SEQUENCE: 55

gcagctcaag cgcctggtcg atccgttctc gcacaacgat gaagcgctcg aaaacatctt     60

cttcttcccc cggttctgac atcgctcccc cagtcatcgt gccgtgctag tgctaccggt    120

tcgggtgtgg cgggcgggct gcgccacccc aaggggtccc gcgcctcccc gtccgccgca    180

cccgaaccca tcagcccgag catcgccgca acgtccgcag gaagatcatc aggagtcggg    240

agaccgcaac agcacccacc cgacaaacag acctccacag ccacgagacg gcccccaggg    300

cggccagctg cccgacgatc agccctgttc atccgagacc ccctcagaag accgcagacg    360

cgccgcaacg tccgcacccc agacgtccac gtcctgcccg aacacccgcc gaaactcgtt    420

gacctggcgg tacatcgtgc tctcagccat gaccccggcc cccagcaggc cggagcgtcc    480

gccgtagatg tgccacatca gccagaaccc aagcagccgt tgcaccgtgc tccgagcaac    540

accgagggag agcgccgaca caccggggat catgccgctg atcagcgcca gcacgtccca    600

cggacccaca ttcttttccg acttcttctt cgccatttta gtccacctcc accaattcgt    660

gttcgattcc gtgctcttgc agccaccgcg ccaagccagc ttgaccgccc aattcgcaac    720

ttcgcagaca ctcgtagagc ttctgctgcc cgacgaggcg acgccatccg tcacccgtga    780

tcaaagcgac agtgtcagcg accgagccga cctcctcagc cgcgatcacg tcgtcagatt    840

cctcaaccat gaggccgagg cggtccctca ggcccgcaga ccagccaatc tgtctgcgtc    900

cccggctacc cttctcccac tcgaaccaca ggccaacctc tttcgccaag ccgttggccg    960

cgtcgcccag cacctcccaa gtcgatcgag tcgagagcgc agaacgcgcc gtcttgctct   1020

gggagttcgt caactcgtgg ccgatcttac cttgaaattg tgctttgctc aggtagcgcg   1080

cgaggtggtc gaggccagtt gctgcgctca tctgctgaac gtcttgcgcg cgagcaaggg   1140

gagtcccgag gcccgccgcg agcacgccgc gttcccaacg gccgaacatg gaccggtgca   1200

gcgccagagc gtcgccgaag tcgcccacga ggaacacgag cacatgcaga tgcacatgcc   1260

acccattgcg cccgtgcgta acctcgacca cacgcacgaa gccctcgacc ccgtgacgga   1320

gctggtccga ggtccagccc ttgcccgaag tgactcgccg ccaccccgaa gcgacaccat   1380

cccaaacagc cgtcaaggaa tccttacgag agtgccgaac cgtgaacgtc atgaacgcca   1440

cacgaccacc gtgcttagtc cacgtttcga ccgccgcgcc gagttcaagg ccacgccgag   1500

ccatgatctt cgcgttacac accgggcagg cccagaccga tccgcagctc tgcaacccag   1560

cgaaaccggc ccggccgtcg ctgcaccgca caccaaccga agcgaccgcc gaggcggcaa   1620

cacgaccgca gaacgcaacg cgcttgagcg acgtatgacg ccacaaccaa taacggaccg   1680
```

aaaaccggtg tttgcgcttg tcggcggcca cttcaccagc ggcgggcacg gccgaaggtg 1740
aaacattgtt cgcatgatta tctagggcgc cccctagcgg ggccaccgcc gggctgccgc 1800
ccccacaccc ccggacgcca cgacttcggg cgcgggcatc gaccaccatt ggtcgcgtac 1860
tctgggacaa ggaagacccc ctgctagttg atgctgattc gacaccagac acgctagcag 1920
gggttctctc agttttggga gttctcagtt ct 1952

<210> SEQ ID NO 56
<211> LENGTH: 4408
<212> TYPE: DNA
<213> ORGANISM: Artificial Sequence
<220> FEATURE:
<223> OTHER INFORMATION: pLS1

<400> SEQUENCE: 56
ctgcagaagt agtcgctgat tggctaattc agcgtatcaa agacaaaggc gaccaaaaat 60
agcttgagtt cttttagaac aaaaaagaaa gacagtagtt gcacctactg tctttctttt 120
gcgttgtgct tttagttcct cgaactttta gcgtcaagca tattatatca tggggcgaga 180
aattctgtca aaataatgct ataatgcttt tgaggcacct cagcgatacg gtcggtggtg 240
tgaatctcat ttacgtaggg cgactggaaa cggatagctc aaagggcgcg tttgagtgtc 300
gggtgtggga ctgccttcag cttcgggctg taaagacccc tgatactttt gaatgagatg 360 acccctttggg gtcttttttg ttttttttagg gagatgttgt gggggatttt ttctccgaaa 420
aaatctaaaa tatggggggg ctactacgac ccccccctata gtgccgagtg ccaaaatcaa 480
aaaaaaaacg cctttagcct tagagctgca agggtttgag gctcgtcaaa tctcggcgac 540
ttttcggcga cttttcggcg actttttaga gatttttttgg gaaaaatacg aaaaagattg 600
cattgagtgc acggttatgc tactatagtt ttataaaatt ttgagaggtg acgcatgaaa 660
aaaagattga cgataacatt aagtgaatcg gtacttgaaa atcttgaaaa aatggcaaga 720
gagatggggt tatcaaaatc tgcaatgatt tctgttgcct tggaaaatta caagaaaggt 780
caagaaaaat aaaaaaagcc gtgctggcag gcactggcta aagtcaaaca tttcttgggt 840
atattatact ttatggctaa agaaaaagca agatacttca cttttttact ttatcctgaa 900
tcaattccaa gcgactggga gctgaaactt gaaacgcttg gagtgccgat ggcaattagt 960
ccattgcatg ataaggataa gagtagtatc aaaggacaaa aatataagaa agctcattat 1020
catgtgcttt atatagctaa aaatccagtt actgcagata gtgtacgtaa aaagattaaa 1080
ttattgcttg gtgaaaaaag tcttgcaatg gtgcaggttg ttctcaatgt cgaaaatatg 1140
tatttgtatt taacgcacga gagcaaggac gctattgcta agaagaaaca tgtttatgat 1200
aaggctgata taaagctaat caataatttt gatattgacc gttatgtgac gttagatgtc 1260
gaggaaaaga ccgaactttt caatgtggtt gtatcgctta ttcgtgcgta cactctccaa 1320 aatattttg atttgtatga tttcattgac gaaaatggag aaacttatgg gttgactata 1380
aatttggtta acgaagttat tgcagggaaa actggtttta tgaaattgtt gtttgacgga 1440
gcttatcaac gtagtaagcg tggaacaaag aacgaagaga gataaaaagt tgatctttgt 1500
gaaaactaca gaaagtaaag aatgaaaaga gtaatgctaa catagcatta cggattttat 1560
gaccgatgat gaagaaaaga atttgaaact tagtttatat gtggtaaaat gttttaatca 1620
agtttaggag gaattaatta tgaagtgtaa ttaatgtaac agggttcaat taaaagaggg 1680
aagcgtatca ttaaccctat aaactacgtc tgccctcatt attggagggt gaaatgtgaa 1740

-continued

```
tacatcctat tcacaatcga atttacgaca caaccaaatt ttaatttggc tttgcatttt   1800
atcttttttt agcgtattaa atgaaatggt tttgaacgtc tcattacctg atattgcaaa   1860
tgattttaat aaaccacctg cgagtacaaa ctgggtgaac acagccttta tgttaacctt   1920
ttccattgga acagctgtat atggaaagct atctgatcaa ttaggcatca aaaggttact   1980
cctatttgga attataataa attgtttcgg gtcggtaatt gggtttgttg gccattcttt   2040
cttttcctta cttattatgg ctcgttttat tcaaggggct ggtgcagctg catttccagc   2100
actcgtaatg gttgtagttg cgcgctatat tccaaaggaa aataggggta aagcatttgg   2160
tcttattgga tcgatagtag ccatgggaga aggagtcggt ccagcgattg gtggaatgat   2220
agcccattat attcattggt cctatcttct actcattcct atgataacaa ttatcactgt   2280
tccgtttctt atgaaattat taaagaaaga agtaaggata aaaggtcatt ttgatatcaa   2340
aggaattata ctaatgtctg taggcattgt atttttatg ttgtttacaa catcatatag   2400
catttctttt cttatcgtta gcgtgctgtc attcctgata tttgtaaaac atatcaggaa   2460
agtaacagat ccttttgttg atcccggatt agggaaaaat atacctttta tgattggagt   2520
tctttgtggg ggaattatat ttggaacagt agcagggttt gtctctatgg ttccttatat   2580
gatgaaagat gttcaccagc taagtactgc cgaaatcgga agtgtaatta ttttccctgg   2640
aacaatgagt gtcattattt tcggctacat tggtgggata cttgttgata gaagaggtcc   2700
tttatacgtg ttaaacatcg gagttacatt tctttctgtt agctttttaa ctgcttcctt   2760
tcttttagaa acaacatcat ggttcatgac aattataatc gtatttgttt taggtgggct   2820
ttcgttcacc aaaacagtta tatcaacaat tgtttcaagt agcttgaaac agcaggaagc   2880
tggtgctgga atgagtttgc ttaactttac cagcttttta tcagagggaa caggtattgc   2940
aattgtaggt ggtttattat ccataccctt acttgatcaa aggttgttac ctatggaagt   3000
tgatcagtca acttatctgt atagtaattt gttattactt ttttcaggaa tcattgtcat   3060
tagttggctg gttaccttga atgtatataa acattctcaa agggatttct aaatcgttaa   3120
gggatcaact ttgggagaga gttcaaaatt gatccttttt ttataacagg aattcaagag   3180
ggcaatggct gatatggaac tcaaagagga acttcttgaa aaatatcatg caccgctttt   3240
tgttgatgag agaacaggcg agttgaacaa tgacacggaa gctttttggc atgaaaaaga   3300
gtttgctgat atgtttgaag ttcaatctcc gatacgtgaa acaactaacc aagaaaaaat   3360
ggactggtta agaaaacagt accaagaaga gctgaaaaaa ctagaatcgt ctaaaaagcc   3420
cctagaagac gatttaagcc atttagaaga gttgcttgat aaaaagacca aggaatatat   3480
taaaatcgat tctgaggcct ctgagagggc ctcagagcta tctaaagccg agggatatat   3540
aaatacccta gaaaatcatt cgaagagctt agaagcgaaa atagagtgtt tagagagtga   3600
taatctacaa ttggaaaaac aaaaggcgac aaaactcgaa gcgaaagcgt tgaacgagag   3660
tgagttgcga gaactaaagc ctaagaagaa ttttctagga aaagagcatt atgagttaag   3720
tcctgaacaa tttgaagggt tgaaggcaga agtttatcgt agtagaactc tattgcacca   3780
caaagatatt gaactggagg aagcaaaacg tcaagtatct ctgagagcct ctaaaaacta   3840
ttttacagct agtttagagc gagctaagga aaaagctaaa ggtgagagta tagaccgtct   3900
taaaaagcgaa ataaagcgac taaaaaacga aaattcaatt ttacgtcagc aaaatgacaa   3960
gatgctaggg aaattaagag agttaatgcc tgataaagcc tttaagaatt tgttatcaga   4020
acttaaggcg attaagccaa tcgtgaatat aattaaaaag gctattgaaa agagcttgtt   4080
ctgagcgatt tatgccgtga aagctatttg acaataagca gtgacagagt acgctaggac   4140
```

```
gtgccgagcc gaaaggcttt agcgtttcgg acggacacgg acaaaggacg gcagtcactg   4200

gttacttgtt gtcaaataga ccatggaata aaaagcgtca aaagtcttga gtggatgata   4260

ccctatggta ctctattcgc cttttgactt ttttgctata atttaagtgt cgccagttct   4320

tccgtcaggt aatgcgaact tagactggag gtgagcgttg tgaagacatt cctcgagctt   4380

gtctttgtcc cttttgtggt tggcgttg                                      4408


<210> SEQ ID NO 57
<211> LENGTH: 5804
<212> TYPE: DNA
<213> ORGANISM: Artificial Sequence
<220> FEATURE:
<223> OTHER INFORMATION: pUB6060

<400> SEQUENCE: 57

actgcgatgt acgatagatg ctgtattaag caagtacaca cagcgtcccc tctgcgaggt     60

gccgtctgtg actggttcag gggctcgcc gcccccgaa acccctagca tccactgcga    120

aaattcgcac gttgggtgcg aaactttctc agcggattct catggaaaag cgcaccaaag    180

agatcaaaat cagactcacc gaagcggagc atcagcggtt acttgaacgc tgtgaccgaa    240

cgcatttggc cgagtggtta cgtgccgttg gtttaggcga atcgcggaca gctcgtcgtc    300

gtccgctacc taccgtagac ccgatcttgt tacgtcaggt cagcgggatc ggtaataacc    360

tcaatcaaat agcccgttac ttgaatcagc atggcttacc gccgcaagaa cgggtgtcgt    420

tgttagatgt gctcaatagc attgaccaac atcttgccga actgctggag caacatcatg    480

atcgttaaga ttcatggtcg tggtgccggt ggcgggagtg gccctgtcga ttaccttctg    540

ggccctgatc gtcagcgtga acaagcgacg gtgttacggg gtaaccctga gcacgtcaaa    600

gagctgattg atggctgcga atttgcccga acctatacct ctggcgtgct ctcttttcag    660

gagagcgact tacccgcagg cgaaaaaaca gcgtttgatg gagaatggga gcagacattg    720

atgaccggtc tagataaaga ccagtatgcc tgcctctggg ttcaacatca ggacaaaggg    780

cgtcttgaat tgaattttgt tatcccgaac atcgaattgc agagcggaaa acggctgcaa    840

ccttactttg atcgggctga ccggcctcgc gttaacgcat ggcaaaccct caccaatgac    900

cggcttggat tacgcgaccc gaatgacccc gccaatcgcc gagcattaac cccctcgaat    960

gaccttcctc gcaacaaaca gcaggcagcg gaagccatta ccaaagggct aatcagcttg   1020

attgagcagg gagaaattac ggatcgtaaa ggggtgattt cccaccttac cgatgccgga   1080

ttgtcggtcg tacgggaaac caaatccagt atcagtattg ctgatccggc aggtggcccg   1140

aatattcgct taaaaggagt gctgtatgag cgagatttta aatttagcgc gggagttcga   1200

gagcaaatcg aagcagcaag ccaagactac cgcaacgagc gtcgcgagcg cattcgagaa   1260

gcacgagaaa cgtatcaccg aggccttgaa attaagctca gggaacatac agaccgctat   1320

ccaagaagag aacgacaacc agctaaaaca gatacaccgc ttagtcggaa tgacatggct   1380

gtacagcctg gcattaagcg cgatcctgtt tgcgacattg attggagtag cttggtatct   1440

cgggactatc gtggtcgaac gccagaacga aatcagcgag cagagccaga tcctgcagga   1500

cttaaagagc cagaccggag ccggcgtatc gataattcac gattccaaga acaagagcgt   1560

gtattacctg atccttccgc agggggcgaa gcagatcgac gagtacaaga acgctcaaca   1620

tcgtcaggtc atcaagtaca gcgccaaata acctcatcag acgccacaga atcgattctg   1680

ggcggtttta tctatcaggg tgaagagatt catgccgaaa tggcagcagc agcttctgag   1740
```

```
cgcattagag agcttacaga ggcactacga acaacagcag caagcgtggc aggacagcta   1800
cgccaactta cagcgcatgt tcgaggttac ctcgcaggag ttggcgaaaa acgacagggt   1860
ttgtcaggcc ttgagcatgc aagtcaccgg cttggcgcag caagtcgaga gcttaaacag   1920
aacagtgcgc cgcttgagca attagccaag cggcacgaac agcggcattc tcggcggtca   1980
cggcatgagt ttataagcgt ttatcggcag catcataagc ggcagaacgc tcgcgcttac   2040
cgaccgccac cacgaatacc gtaatggttt gatcgcgaac ctgatagacc aaacgataac   2100
cggatgctcg tagcttgatt ttgtagcaat ccggcagctc tcgcaggcga tttttatcga   2160
tccgcgggtg ctgtagaacc tgctcgagtt ttttcttgaa ctgcagacgg acatcatccc   2220
cgagcttgcg ccattccttc agggctcggg gatcaaactc aaggttatag ctcatccagt   2280
gacaccttta cgcccgcctg tgggttttcc agacgatccc gaacgatagc catcaaatcg   2340
gcatcatcct cggtcagcaa cacctgctgg aacggcaagc gtccgctttg ggccacatac   2400
tccagtgttt ggcgcagaac ctcggacggc gttacgccca gcttttccag tgcggcataa   2460
gagcggcttt tcagctcgtc atcgatccga atattaatcg tggccatcat ctcacctctt   2520
gatgtagtga caagtgtatc tacaagaagt agtatgagcg taaagccgtg cgagaacaag   2580
caggaataac ggattgtcgg ggatgacaaa aaccgttgtt gaggtgtaac ttagcggcag   2640
aaaaaacaaa gccccgaatt catgtgctca acttggcgga agactcatga aattcagggc   2700
taggtcgaaa cctagaaagg atattagcac atgcagcgtg caaaacaaca gccccgccat   2760
aaggctggga gccatggcta atcaggcttt aacgcttttt aacgaccggt taccccacaa   2820
gccgtacttc tccgatgatt tacagtttgg tgtccgcatt gccggtaaag agcgtgctct   2880
cctcgcaaaa tacatccagt ttaaccagcc ccacgccatg tactggcttt gctttgacgt   2940
ggacagggcc ggagccgcga ttgattgggc cgatctgggt gcacctgcgc cgacactcac   3000
catcaaaaac cccgataacg gacatgctca cctgttgtat gccttgaaca ttgcggtacg   3060
caccgcgccg gatggtcgag gccgcctcct caaatatgcc gccgccattg agaatgcgct   3120
gcgtaaaaaa ttgggcgccg atgcggggta ttcagggcta atttgcaaga atccgaacca   3180
cctgcactgg cagatcaccg tctggcagcc tgagctctac accctcgact ggctagccga   3240
ctatctcgac cttggcgctg ccaatgaccg agaaatcctg cccgactacg gtttaggccg   3300
taactgcacc ctattcgata aaacccgcaa gtgggcttac cgcgctatcc gccaaggctg   3360
gccggagtat agccaatggc tacaagcctg cattgaacgc gctaaagcct acaacctgca   3420
gttctccgca cctttagacg agaacgaagt catgggaatt gctaaaagca tttccaagtg   3480
gacaatggtc acttatcgca gtctggggtt tgatgagtat gtgaagttaa ctcattcacc   3540
cgaggtacaa gcatatcgcg gtcggcgaag taaaggcggt ggtagaccta gtattgggga   3600
accatggtta gctttaggta ttagtcgtcg aagttatttt agatggaaaa agctaggtaa   3660
attatgaaaa taattagttt tatcaatatg aaaggtggtg ttggtaagtc tacggttgct   3720
attaatgttg ctcattgctt agcggagcga aatcaaaaaa aggtattgat aattgatatt   3780
gatcctcagt ttaatgcaac tcagtgcgtt atgaaggcag aggattacat agagcatatg   3840
cgtacgggta aggatactat ttgttctttg tttaactctg accgagttgc agctaaaagc   3900
gttagtggac catcttttga aaaatgcaaa gatatcagta gcatatctcc tgttgaaatg   3960
tctgagtatt tgcatatttt acctggtgac cttggtttgc atcgaattga ggttacagct   4020
gggagcgggc aggagttcaa gttaaaacga tacttggatt ctatcagtga caagtatgat   4080
tatgtgattg tggatactcc gccaacacca tcaatatgga tgtctagcgc attgatagct   4140
```

```
tctgactatt atataatacc ggttaaacca gatccgttat caaggacggg gattgattgc   4200

ttgatagtat aatagcagat aaaaaaggaa actttgattt aaaaataaaa tgtgctggag   4260

tggtgtttaa tatggttgaa gaaaactgtg tttagagaga ctaagagttt ttttaataac   4320

agtgatactt ggcgcaatta catttttaga tctttcctgc ctaagaaagt tgcgatagct   4380

aaaaggcaga catcaggaga acatatatta aagacaaaag attcctcttt gcacatgaaa   4440

cttgtcagag tggtcgatga aatcgaagag agaatacagt aataggataa cgtatggata   4500

agttaacaac taaagaaata aagacgttat tgaatttcat tgaagagttc tcttggattt   4560

caaataaata taaaaatttg gataccaata agttatatga ggctcttaat aattgcgagt   4620

ctcgtcgtca aaatgaatat aatgattata tttcgtactc aaaaagtgta ggtaagaata   4680

atcatgtgtc atataggaat agccttaaag ataagacatt tctaattggt aagctcccat   4740

ctcttttgat ggataaagaa ttgttctcta aaaataagga gctatctgac tttgctcgac   4800

tacttggtgt tgaggtcaga ttccctgaga aacgttctag agatgagata atcggcacta   4860

ttatttgctc attacaagag gaaagtagtg ttaaaagaat tcatgagatt ggtgagttta   4920

tctatgcttt aactagcgat gaaaaactaa tgaataacat taaggttgag aagaaaatat   4980

ataatgatga gtatgattgg aataatgtaa ttagactttt atttatgggt aaatgatgtc   5040

tagattgata gggaaagact ttgatttatt tttaggcttc tttttaaatt acagccttaa   5100

agatttggca tctaatggtg attttaaaaa gaagctgcgt gaggcacaca aaaaatacta   5160

tccgttactc actcttagcg ctgagcttga tctcatgttt aggggggatg tgggagagga   5220

ttgtgctgat agggttaaag aaacttgctc tgatataggt tcgtctattt ttttattagc   5280

ccatggaatg tataagcaat ccaacatgtc attgcgtagt tctattgaga actttttaaa   5340

atcaataggt tgcaatcatt gccctgacat attaacagat aagagtgttt tttctgtttt   5400

tgaaaaggct gggcaattag agttattttt agatcctgtg ttcaaatgca agtttgatga   5460

gttgcaatct atttactcat cgttgtgctt atatactcat accgcaagtg ctgaacacat   5520

ggctaaaatt agtgctatgg gcagtattcc aaaacatgat aaagcgaaaa gcgctattct   5580

tgttaatgac ctcactaggc ttgttcgaat ttatcttttc atttacacga agttgtttag   5640

gtgtgaattc ttcaaattta accatgacaa ccgagatgtc attctcagcg cattaaccaa   5700

gtcgcaacga cgttcgttaa tggaaccatc ctgatgtggc actaaacaac ctatatcaga   5760

taacagccct gcttttgcgg ggctttttgt ttgtgcgtga tgtg                    5804
```

<210> SEQ ID NO 58
<211> LENGTH: 1711
<212> TYPE: DNA
<213> ORGANISM: Artificial Sequence
<220> FEATURE:
<223> OTHER INFORMATION: p545

<400> SEQUENCE: 58

```
ggtgccatga gggttctcac tgatacctga atgagtttga cggtggggcc gcatgcacga     60

ctgccatacc gtcaatccga gcgccgcaga ctgggcatgt ccccctgagt aacacttgcc    120

caccgggttc aacgtccgtt gctgatgccc cccattggct gtagccacaa tggccgcagg    180

ataagaacgt ggcgcgcact gtgcaaccgc acgcgaacgt agtgccaagc ggtgcacgat    240

caagaaaatg ctcatcgtgc ggcgttacgg tcatgcgtca gttcgattct tgttcagcgc    300

gtagtgcacg gtgcccacgg aaaccccgac ctcggcagca atcgcacgca tgctctgacc    360
```

-continued

```
ctccgagcgg agctcacgaa tccgcgcgtg gcgtgcggca acgcgggcca cgaactcctc    420

gcgtggctcg gaagtccacc gcttgacggt ggactcggag acaccgagct ttttcgcagc    480

agcggcgatg ctgtagccgt tgcgggggag acgttcacgt gtggtcatga gagaccctcc    540

aagaactgtt gacgggtatg ggcgcgccgt gatgcgccac tggcaatgcc gcctttgtgg    600

ccgccttctt tgccgccttt ggatgctcca cggaggctga tcgctttctg gcgtgcgcgg    660

aaggtttcgg gggtgaagtt gcgccagacc catcgggaaa tggatcgaga taagtgctta    720

agttcgttca agccgagggg gcctgtggcg aattcgtcgg cgatgatcgt ctcgttcagt    780

aggtggatgt gctcgaatac ggtgtgctcc cattcggcga ccgggccgcc ccaggagtgc    840

cggacggccc ggtatgccca catgcgggtg gtgtcgaaca gggtgacgtt gcggccgacc    900

gttgatcggg tgacgttgcg acgcgggttc cctgcctccg gcagtgcgtg gatctcgtcg    960

agggtgtgtg cgagggcgcg cagctcgtag agcgcgtctg cggggcccca gagggtcgca   1020

tgggcggtgc tgagcgggtt ctttgtgatc cggtgcccgt aggatgcatc gccgccgaga   1080

acgtcgcata ggccctgctc gacgcgggcg agcaggttga taggccgtcg ccgcgcggca   1140

tcggtcagac acacagggtt cttcaaggca tagacgatgt gtccggtggt cgtgacacgg   1200

ttcatggaca cgtaggacgg tgaaggcagc ccagcgaggt ctgcggccca gtcagcatcc   1260

gaagcatctc gatcggtgat gaccaaggac tgcatgacca acgggttcgc ttcgatgtaa   1320

ggcagctcca gcgccctctg ccgagtcacg tgccggtacg ccccagactt ctcggctgac   1380

gccagcggct tgcgtggcag ccagctctca gggaacaacg tctcgaacga atccatacat   1440

gcagtgaagc atgcgagtca cgttcagcgt ggtccattcc tcggcgtgtt caaagtgggc   1500

gacgaagacc ccatatcagt tagttacccg gttgagccat gtgagcaaag cgaactctct   1560

ttccacatcc cctgccaaac atcccccgac tcccctgacg ctgccacctg ctccaaggga   1620

tggctggggc gtgttcgggc attgcggcta gttcctcgcg cagctgtgcg atcttcgcct   1680

gaactgctcg ccggctgtca gggtcgacgg c                                  1711
```

<210> SEQ ID NO 59
<211> LENGTH: 7426
<212> TYPE: DNA
<213> ORGANISM: Artificial Sequence
<220> FEATURE:
<223> OTHER INFORMATION: pJD4

<400> SEQUENCE: 59

```
ctgcagcaat ggcaacaacg ttgcgcaaac tattaactgg cgaactactt actctagctt     60

cccggcaaca attaatagac tggatggagg cggataaagt tgcaggacca cttctgcgct    120

cggcccttcc ggctggctgg tttattgctg ataaatctgg agccggtgag cgtgggtctc    180

gcggtatcat tgcagcactg gggccagatg gtaagccctc ccgtatcgta gttatctaca    240

cgacggggag tcaggcaact atggatgaac gaaatagaca gatcgctgag ataggtgcct    300

cactgattaa gcattggtaa ctgtcagacc aagtttactc atatatactt tagattgatt    360

taaaacttca tttttaattt aaaaggatct aggtgaagat cctttttgat aatctcatga    420

ccaaaatccc ttaacgtgag ttttcgttcc actgagcgtc agaccccgtat ctataaactc    480

ttggcttggt tctaatccct ctaaacgatt attatcaata gccgctctaa ccgctttttc    540

tcggcttaat ttttctgtct ctgttataaa attgctattc atcttgttct tcttcaaaaa    600

aaagttaagt aaaataccta cctaaatttt tactagttcg caatctacga gcttataacc    660

tcgttttttc aattcattta aaaaatcaga ttttgagcct aattttgatc tattgctatc    720
```

-continued gttacccgct agaaataccc agtaattacg caaatcttca ttggtaactt tcgtaatatc 780
ggtgtaatga tcttcgagta tttttaagca atctctagcc cataaaccgt actcgtgatt 840
gctcatctta gggttttgct tatcgagttt gacgaacttc ccatacttgt ttttatgtgg 900
aaatactggc cgttttgcaa cttcttcaat tttttgagct gttcgttttt tactaccaat 960
cacaaaattt aaagagtgaa tagtacgccc acgcttgatt tgttcaacct caacgactaa 1020
atcagatttc tcgttaatct cagttattgc aggttccaaa acacgttgat ttaatgaatt 1080
aaatctaggg tatttatttt caacctgaag ccattctttt agtttttcta ctgtaatttc 1140
acgactacca acagagcgat attgtgtaat tagctcataa attcgaattg aatgtacact 1200
gttgaaataa gcgatatgtt tgagttgata ttgcgtgaat tgccctttaa gttgcgttag 1260
gtatggcata acttcatcag tcattgcaat tctaaaacgc ccctctttct tgaaatatgt 1320
tctagaggaa acccaacgaa attcagttac acggtcttta tcttcagttt taacacttcg 1380
gtcataaatc cgttttatag ccgcctgaat ttgcttatag gcgttatctt ggcttatttc 1440
tggaaactca cggacaaaat cagccaccgt aaaatcaaaa atcttttgat tagatttcgg 1500
atccatagtc ccaatagtta aagctaaaat tctgatttca tcaatactca atcggtaatt 1560
ggcttcaata aggctattag cctttacaac aactaaatca tttggcataa gacaacaaat 1620
ttcctgttta aaacaacaag caaaatatac ctgttgttta tatataaaac aacaagtatt 1680
ttcttaaaag ttgtctataa caggaaattt gttgtcttat aacaggaaat ttgttgtcgt 1740
ataacaggaa atttgttgtc gtataacagg aaatttgttg tcgtataagt ttgtaactta 1800
ttgattttac tggttttaaa aacgccgaaa acaagtaaaa aacaaaaata taaaaatata 1860
gggactttcg tcccttttt gggctttcag ccctaatttt ttcttttttc aggattaaaa 1920
attacaaaac ccttacagag caagtaaact tgtttgcttg ttctgcaagg gttcagcaac 1980
cgaagccgtt aggcgtaggc ggtagcctat aaaagccatt taattttatc tttaaatttc 2040
cgtttaaatg ctttgagtgg gtgtctttta tcgtactcat caatcctttt ttgcattctt 2100
tcgtttgctt tgtgatcggc aaatttgaa taagattttt ccatctcatc taacattcta 2160
tcaatccgtt ttttatgttg ccatttcagg taaacataaa cacttatagc aataaaagac 2220
aatatcaata cattgtaaaa aatgattgtt acaatttcgc tcacagttat tttttacctt 2280
tttcaatttc ttcattgata aatgcactca attcatcaaa tttcttgtca tcattgataa 2340
atttacgcaa cttagggaag tttctatcta catctaaaag agggttaaac gattattatc 2400
aatagccgct ctaaccgctt tttctcggct taatttttct gtctctgtta taaaattgct 2460
attcatcttg ttcttctctc acactttaac taattcacag ttcacaatct tataccctcg 2520
attttgcaac tcgtttaaaa aatctgaccg cttaccaagt tttgatctaa aactagcatt 2580
gctagtcaaa aaaacccaat aatgccgtaa atcttctgtt gtaacatcgg caagatcaga 2640
ataaaaatct tcaaggattt ttaggcaatc tctcgcatag tttccatatt cagcattact 2700
cattttggga ttttgagtat ccaatttcac aaacttcccg tacttgtttt tatgcggaaa 2760
tgcagggcgt ttctgttcga tttttaccgc acttttctta ctcttgatcg tgaattttaa 2820
tgctacgatt gttcgcccac gcttgatagg ttcaacatca acaagcagat cggatttagc 2880
attaatttca tttatggatg gagttaatac tcgcttttta aaatccttaa acagtgggta 2940
cttatcagag atacttaacc aacttttaat atcttctacg cttgtttgtc gccaacctgt 3000
atcacgatat tgagaacaca attcataaag gcgaatagcg tgcgtactac ccaaagcccc 3060

-continued

```
aatattgatc aatttatatt ttgtgtagtt atcgtgtaat tcagaaatgt aaggaattag   3120
ctcatcgtgg aactcgatat aaaatcgccc ttcttttta aaataggaac gcttatgaat   3180
taaagctact tctgttaatt cgtgttcgtt atcaaccagt gtaacccaac gctttgagat   3240
ttttaaaacg gcatttctaa cttgtgtgta agctatatca ggatttacat cggggaagct   3300
tttacaaaaa tctgccaccg tgaaatcaaa tccacgctta gacggatttt taggattaaa   3360
aacccccaaa gttaaagcca gaatccgcat ttcatcaagt gtcattgaat agctggcttg   3420
tacaaaattg ttagctttat ggactgttaa atcatttgtc atatcatcaa ggtggacata   3480
aaataaagat tgtcccatta taaccataca gttaaatggt ggtcaataaa aaacaaagac   3540
cactataaca ataaatttgt ccacctataa caataaattt gtccacctat aacaataaat   3600
ttgtccacct ataaatctcg caagccttgt gtaacaaggg gagccagagc ctacaaacaa   3660
gaatacaaac aagaatacaa aaaaatagag cctaaaggct ctttttgggg ctttcagccc   3720
taatttttc ttttttcag gatttaaaat tacaaaaccc ttacagagca agtaaacttg   3780
tttgcttgtt ctgcaagggt tcagcaaccg tagccgtcag gcgtagggcg gtagcctata   3840
aaagccattt aattttatct ttaaacttcc ttttaaatgc tttgagtggg tgtcttttat   3900
cgtactcatc aatccttttt tgcattcttt cgtttgcttt gtgatcggca aattttgaat   3960
aagattttc catctcatct aacattctat caatccgttt tttatgttgc catttcaggt   4020
aaacataaac acttatagca attaaagaca atatcaatac attgtaaaaa atgattgtta   4080
caatttcgct cacagttatt ttttaccttt ttcaatttct tcattgataa atgcactcaa   4140
ttcatcaaat ttcttgtcat cattgataaa tttacgcaac ttagggaagt ttctatctac   4200
atctaaaaga gggttattta ttatttcatt tagccaaaaa gcccctaata aaaccttgta   4260
atgcgtagct ttcttacgct tttctgcttg ttcttttgac ttaatcgcac gaattttcgc   4320
tttgatttcg tcctgcttgc gttgtaaatc tgcttgttgc tgttccaatc ttgtaagttt   4380
ttcgcttgcc atactagccc ctttatatag ttagaaatta tcgttatttt attcagtagg   4440
tgctaggctt gcaagtgttc tgttcattac gttaaaataa cgtaatgccc acttatcagt   4500
ttctcttcga gaaactggtg ggcaagcgta ccgcttgacc gtttcgcaat actcaacact   4560
atggcaatct atcatttaaa cgttcgctat tgcagtaaaa gcaaagggca atcagctcaa   4620
gccaaaaacg actacatcaa ccgcaatgat aaatattcaa agcggttaga tgatttacag   4680
ttttcaggct atggtaatat gccaaaattt gccgaagata atccgcaaga attttggcga   4740
ttgtcagata tttacgagcg agctaatgcc cgagtttgta ctgaaattga atttgcttta   4800
cctagagaat taaccctaga acaacagcaa aaattagtaa gttcgtttat agaaaatacg   4860
gttgatagcg gtagcaataa actaccctac tctttcgcta tccataccga taaaaataat   4920
cataatcccc attgtcattt gatattttca gaacgccaac ttgacggcat agaccgtaca   4980
gccgagcagt tttttaaacg tgctaatact aaatccccag aaaagggcgg agcgatgaaa   5040
acggcagatt ttcgagatcg tgagtttatc caatctgtcc gaaaaacgtg gagagagcaa   5100
gctaatcaag ccttagagca atacggatat gccgcacgaa ttgacgaacg tagctacaag   5160
gaacaaggca tagagcaagc cccaagagca agaattgaca gggtaacgtg gcaagaattg   5220
aaccgattag agcaagaaga acgccaaatc gtgcaagagc ttgcacttaa aggacaagaa   5280
attaacaaag aaaaatccta cttgcagaaa atcgaagaaa aacaggctca aggaatgggc   5340
aaatatgaat ccaaattcgc agctgcgttt tctaaattat cggaaagtgc cctaaaacac   5400
gatttaagca acgaaaaaga aaaagacagt aaaatacaca ctcaagaaga aaaagtgcct   5460
```

caaaatcgca ttcaggggct ttctcaagca gattttgatc agtttttaat tgatgaatgg 5520
ctacctcaaa tagaaaaata cgttaaagcc caagaaaagc gggacggaat ggaagtagag 5580
atcacgcaat acgacaagga tttacagcgt attcagggag actataacaa gctcacagat 5640
aaaaatcagg gttttctcgg tttatgggaa actaaagagc aaaaagcaaa gaaaaaagag 5700
cttgaagatg aatacaaaca tacagcagag caacggaacg ctaaaagcca agaattagcc 5760
gagtatagcc aaaaaataaa agcatacgaa cagaaaacgc tagagccaat caacgagaag 5820
attgccaaat atcaagctga caaccctgaa ataaaaatgc ggagcttagg atttgtgaaa 5880
aaaattaagg ctcaaggggc atataaagcg gctcaagagc gaatggagcg agaaaaacag 5940
caccaacagg aaaaacaaca gagacattta gagcgagaga gtggtttgag cttgtagcta 6000
acgccctacg cctacggctt cggttgttca acccttaaag aactcgcaac aagttgcaaa 6060
ttctttaagg gttcgcaata aaaacaaccg ctaaacattt ctgcccagcg gttgaaaatt 6120
tacctattca ccattacaat gatcaagcag gaaatttttt tgattgccgt aaatgtccgt 6180
atatctagtt gaggcacaac ccgccaaagt cattgcccca accagaacgg cgataaaccg 6240
tatatttacc gataaggcat ccggcagttc aacagaccgg gaagggctgg atttgctgag 6300
gatgaaggtg gaggaaggtg atgtcattct ggttaagaag ctcgaccgtc ttggccgcga 6360
cactgccgat atgatccaac tgataaagga atttgacgct cagggcgtgg cagtccggtt 6420
cattgatgac gggatcagta ccgacggtga tatggggcaa atggtggtca ccatcctgtc 6480
ggctgtggca caggctgaac gccggaggat cctagaacgc acgaatgagg gccgacagga 6540
agcaaagctg aaaggaatca aatttggccg caggcgtacc gtggacagga acgtcgtgct 6600
gacgcttcat cagaagggca ctggtgcaac ggaaattgct catcagctca gtattgcccg 6660
ctccacggtt tataaaattc ttgaagacga aagggcctcg tgatacgctt atttttatag 6720
gttaatgtca tgataataat ggtttcttag acgtcaggtg gcacttttcg gggaaatgtg 6780
cgcggaaccc ctatttgttt atttttctaa atacattcaa atatgtatcc gctcatgaga 6840
caataaccct ggtaaatgct tcaataatat tgaaaaagga agagtatgag tattcaacat 6900
tttcgtgtcg cccttattcc cttttttgcg gcattttgcc ttcctgtttt tgctcaccca 6960
gaaacgctgg tgaaagtaaa agatgctgaa gatcagttgg gtgcacgagt gggttacatc 7020
gaactggatc tcaacagcgg taagatcctt gagagttttc gccccgaaga acgttttcca 7080
atgatgagca cttttaaagt tctgctatgt ggtgcggtat tatcccgtgt tgacgccggg 7140
caagagcaac tcggtcgccg catacactat tctcagaatg acttggttga gtactcacca 7200
gtcacagaaa agcatcttac ggatggcatg acagtaagag aattatgcag tgctgccata 7260
accatgagtg ataacactgc tgccaactta cttctgacaa cgatcggagg accgaaggag 7320
ctaaccgctt ttttgcacaa catgggggat catgtaactc gccttgatcg ttgggaaccg 7380
gagctgaatg aagccatacc aaacgacgag cgtgacacca cgatgc 7426

<210> SEQ ID NO 60
<211> LENGTH: 8830
<212> TYPE: DNA
<213> ORGANISM: Artificial Sequence
<220> FEATURE:
<223> OTHER INFORMATION: pIJ101

<400> SEQUENCE: 60
ggatcctcgt tgccgtcctt gccttcggcg gcccgggtcg cctcgaggtc gagggcgcgg 60

-continued

```
cgggtgaccg cgtgccatcc gtcctcggtc acggcgaccc cggcccgcag ctccccgccg    120
tcggcgtcgg ccgccaggag cagatcgagg tcgtcggcct cggtgtcgcc gccgtcgagc    180
ccgagcatct gccgcaggta gcgggtccat tcgatggccc ggcgtccccg ggttgcccgc    240
tcgtactcgt gccagcgcga gaggttccac tccagcgagc cgaccccggc ggcgtcgtcc    300
tcggtcatgc cgccggtcag gtccccgatc cgtccgagga gttcgaacgg ggcgacgttc    360
ccgccggtcg ccgtcttgag gtcggcgcgg gcgagttcga gggcgggcgc cttcccgtcc    420
tgggtcttgg cgatgtactc ggcgaggtcg ttggcgtcgc gctcggtctc cagccgcttg    480
aagtcgacgc cgtgccggtc gtcgggcgtg aaggcggggt tgaccttgcg cagggcggcg    540
gtccacacgg accgccagtg cccctgccac tcgtcgagcg cggcgccggt cggctcgaag    600
gtggcgacga tctgcttcgc ggaccgctcc ccctcggtcc ggccgccgac caggacgatc    660
gcgtggatgt gcgggtgcca gccgttgatc tgccccacgg tgacttcggt cgcgcggatc    720
atgccgacgt acccgatccg gtctcggatg ccctcgcggt cggcggcccg gtgcccgtcc    780
ttggcccggc gtccggccca cgtgccgccc gtgatcagtc gctggtaggc gcccggccgc    840
cgggggctgt ccggcgtctt ccgggtgccc tggagggcgt ccatgaggtc cgcgagccgg    900
tccgtgtgcc catggcgggc cgtgaaggtg accaggtagg cggtcccccc gcgcttgatc    960
cactcgacca cggcggcggt gatctcctcg gcccgcttgt gccggatcgt ggcggcgcag   1020
accgggcaga gccagatccg cccgcaccgc atcaggccca ggaccacgga cgttccggcc   1080
gccgtctggg cgacgatcac gccggaggca gggtccatca gggcgcggcc gcagcccttg   1140
cacgcggcgt ccccgctgat ccgccacagc gtccggcggc ggctgtaccg ggcggctttc   1200
cgcagtcggg cagcctcggt ccgcgacgtg cttcctactt cccagaggct gtcgcctctc   1260
gggctctccc catccacccc gtccggagaa accgcaggtc ggaggggtgc gggaaactct   1320
gttgtttctt tcccaaggtg ttcgcttttg cctcgggcgg catctcgcgt cacacgcgcg   1380
atcgcccgct tcgctgccat ccggcagcgg tctgagcagt agatacgcgg ccgtttgccc   1440
ggtgtgtggg caattgcggt cccgcagtgg cagcggggcc cggcgggccg atctggcaat   1500
gcctcggcat cgctccgtac tctgggcacg agcaacgttc ctgtctcgcc cggctaaggg   1560
gcgcgagtct gggagcggac gggtcggagg tgcgaagtcc ggcccgttgc tctttggtct   1620
ggtgggaatc ctggcaccaa tcgggccaga ggttccctcc gccactcccg acgccccttg   1680
gggctggtgt gacttggagg gccgaagaga gccccgccgg gtatccggcg gggctttgac   1740
gtgcggtcag tgcgtgtgtc ggcgagcgat ggccacgagg ccctggaagc cgagcggtcc   1800
ggcgaagtcg gcccagtcgc aaccgggctc agcgcagtgg gcggaccagc caccgccgtt   1860
ggggtcctgg accaggttca cggtcccctc ggtcaggcgt ccgtcgaagt cggtcatggt   1920
cggtctcctg gtgggtgggg gcggggcgcc agcacgaagt gccggcgccc cgcgggggtt   1980
ggtcgggtca ggcgccgaac cggcgggcgg cggcggcgac caggccgtcg gcggcggcca   2040
tggcgcggtc gcggtcggtg gtgagggcgg tgcggtcggc ggcggcccgc aggtcgtagg   2100
ccgcttgggc ggcggcggtc gctgcggggg cgagggcggg ggcgagcacc gacacggtgg   2160
tgaggggcgc ggtgatcgcg gagcgggtgg cgtgggactc ggtgcgggcc gcctcgtacg   2220
cctcggggga ggcgccggtc aggcgcaggt cctcgcgcac ccacatggcg cggcggtggt   2280
cggcgagggc ggcggcgagg gcggcgacgg cctggacggc cgcgtcgcgg cgggagtcgt   2340
cgcgggtggt gcgggcggtg cggtgctgga ggagtccggc gaggccggtc ccggcgagcg   2400
tgccgatcac ggcaatgagc gtggtcacca tgtgagcccc ctggcgtcgt gtccgtctgc   2460
```

ctacgtgtat cagtctgaca cgcacgtgtc aggttgcgca atgggtaggc cccgccggtt 2520
tccggcgggg ccatccgtca tgcggcggtg ctgagtcggg cggcgagctg gtgggtggcg 2580
gcgaggatga cgcggatctc cgcgccgccg tcgaccgccg cgagggcggg ggccggggcg 2640
ggtgccggcg gattggtcgg ggtcgggcgg cggcggaggg cgacggccag gaccatggcg 2700
gcgatcgcca cggtggcgag gtaggcgagg gcgatcacgc ggccacctcc ctcgtgacgc 2760
ggcgccagga cgcctgcagc cgtgcctccc cggcggagta gcccatgtcc cggaagcgtc 2820
cggcggcgac ccggtacgac ccggagtcga ccaggccgga catgatcccg tcgatctcct 2880
cgttgctgag cgggaccacg tcggccgacc cctcgatggc ggccgggacg ggctccgtgg 2940
gtccccagac gggcaggcgc caggagggcg gagacgtggg cgtgacacga gaggtgacgc 3000
aggtcagagc gcgtgccgtg ccctcgccct cgcgggcctc ctccagcgtc gaccaggccg 3060
acgccagctc cccggcggtc tcggcctgga cccgggcgac ccgggccccg gcgccggtca 3120
cggcctccag ccgggtgacc tccgtaccgg cctcggcccg gagctgagcg cgggccacgg 3180
ccgccctgtc gcgggcgtcc tgctggatgt cgcggatctg gtccagggcg gtcggggtga 3240
gcgcggtccg ctcccagagc ccgtgcacga gccagagcgc cttggcggcg agggggagcc 3300
aggcgaccgc gagccaggcc ccggccgact cctcacccag cgcgtgcgcg accaggacgc 3360
cggtcgccac ggcgccgaat ccccacccga cgccggtgat cgcgcggctg tggtcgcccc 3420
gcgcggcgag gcgccgctcg tacgcgaggg tggccagcca tccgccgtcg agcccgaggc 3480
cgacgaccaa ggcaacggcc cacggcatgg cctccccgag ccacatcacg atcacgacca 3540
cggtcaggac catggacacc gccgtcatgg cgacggccgg ggcggcggtc atcgaacgct 3600
tcttctccat gatcacttcc ccttccgggc cttgagcgag atggacaggc cgaccccggc 3660
gggggcggcg gcggcgagcg cggtcgccgt ggtggcggcg gtctggagca ggaggcagag 3720
cgtcatgacg acgccgaccg agccgccagc ggcgaccagc gccaggagga tcgggccggt 3780
ccagtcgcgg gcctcggcct ggtggtggac gacgacgacc gtgcgggggt cggtgccgtc 3840
cgggatcagg tgggccggaa tgtgaccggc cctcatctgc gcgtcggggg tgcgcatcag 3900
gccgacacct ccccgacctg cgtcacgacg gacagggagc cgtcctcgga ccgcaggacc 3960
tcgcccgcgt cgagcagctg cttgaccgcc ttcgacacgg agcccttgtt gatgccggtc 4020
acggtggcga cgtcggcgac ggtcgtagcg cccgtgccga tcgcggctgc gaccttctcc 4080
cggttggtcg gcgccttggt cggctgggcc gggacctcag ccgcgggggc ggtctccttc 4140
accagccgga gcggggccgg ggcggaggcg ccggcacttc gtgcaggcga ctcctggcga 4200
cgccagaccg gccggtcggg gagcgcgatc acgtcggccg gggagaacgc gcgggtgttg 4260
atcgggtgag gctgcacctt cggccggac cggagcatcg caaccccggg catgggcagc 4320
tcgtgcgcgt gccagccctt ctccgtcgcg tcctcgccga acaccacgcg ggactccccg 4380
gaggtgctga gcgcgagggc ggcccggtag gtgatctgcg cgctgatctg cgggtcgatg 4440
ccgcccttgg cgtccatggt cggcttctgc gtggcccaga tcaggatgat ctcggccgcc 4500
cgtgccatcc gggccagcgt gctcaggttc tccatgatcc gggaccagtc cgggtcaccc 4560
ggctcttcct tcgacccctt cgcccgggtc ttcttggcca tggcgatgac ctcggcgccc 4620
tcgtcgatga acaccgtgat ccggggccgc tccgggctga tctggatcac gtcctggccg 4680
cgcgggatca gttcaagccg ctcgtgcatc tcctcgacca gctcgtcggt cacgtccagg 4740
acgtcttcga tcgagatggc cgtgcgagcc cggtgctgcc agttgatcgc ctcgacccgc 4800

```
ttggggtcga cgacgaccag gcggtgatcg gcgtactccg agccttccgc cagcagggcg   4860
cgggtggacc aggacttgcc cgagccggac gtaccggcga tcagcatccg gcgcccgagc   4920
ggcacctgca ccggctcgcc ggtcaccgtg tcgactcccc acggggcgcc gggcgtccag   4980
ccggtcaggt cgatcccgtc ggccgcgctg cgggtccgca gcgtgatcac ggcgcggtcg   5040
ccgtgcgatc cggccttgat ctccatgcgg aggtcggtcc gggctccgag cagggcgcgg   5100
atctcctcgt gcttggcctt gaaggcggac ggcttccacc ggccgtccag gcgcaccgtg   5160
gtgaccagcc cggccggggt gacctgaacc ggcgtcgtca ccgtgcctac gaggccgcgc   5220
tcgtcggcgt gctgagccca gtacgacggg tcgagccgct cgaccaggcg ccgctcctcc   5280
gctgacagtt cgtccgcgac cgcgaccgcg accttgcggc ggccgatcac cagcgcggcg   5340
acgttggccg cgatgagtgc gagcgagccc gcgaccggcc aggccccggc ctggtcccag   5400
ccgagagcgg agatgccggc gcccggcacc gcgtgcatgg cgtgcgcctg aacggctcgc   5460
gcccggaggg tcgccgggta gtccttgcgc gcggccttga gcttggtctt cgcctggtcg   5520
cggtgcgtgc gggccgcctt gtccgccgtg cgagccgccc gacgcacggt cgacagcggg   5580
ttcttggacg ccgcccgcgc ggccgtccgc tggctcttgg ccgtggccgc cgtcgaccgc   5640
gcggagttgt agcccttctg ggcgtccatc agcgccttca ggtgctccgg ggtccggagc   5700
gccatgcggc ggtcggcctc ggcgtcccag cgggccgcga acggcgcgag ggtcggggcc   5760
atggcgtcga gcgcgttcgt gatcgctccg gcggcgttct tggagccggt tgcgatcttc   5820
gtagagactg ccttcgggtc cacggtttgt cctttcgcga gggacgtgga tctagggccg   5880
gagaccgttc acgcggtctc cggtccgccc cgtttccggg gctgtgtgtg gcgtcgaaca   5940
aggtccatac tgtggtcgca cagttgctgt gtcaaggcat acactgtgct agacagctac   6000
acaccgcgca ccacactcga aggagtcgtc atgtccctgg agcgcacgcc cccgtacctc   6060
caagtcgtcg ccgcgctgaa ggcaaagatc gtcagcgggg agctgaagca cggggacacg   6120
ctgccgtccg tgcgggacct cgcggcgcag tacgagatct cgaccgccac ggcccagaag   6180
gtccaccgga cgctgaaggc ggaagggctg gcggaggcga agcagggcag cgcgaccacg   6240
gtcagcacgc gacggaccct gcaccggacc gcagccgacc ggctggagtc ggcgctcagc   6300
acgggccgga tctacgcgga cggggagtac gcggtcatca ccagcgccgc ccttgccgag   6360
ccgcccgagt gggtggccga tctcctcggc accgagagcg gccaggccgt gcgacgcgag   6420
cgcgtcaccc actcagccga cgaccagccg gtgagcgcca gcgtgagctg gttctccgca   6480
gacctcgcgg agaccgtgcc cgccctcctg gtccgcgacc ggatcatcgg cggcaccccg   6540
tccgcgatcg aggcagccac cggccgccgg gccgtcgcca ccgaggaagc caccacggcg   6600
gccgccgcga ccgaggacca ggccgcgctt ctgggcgtag ccgcaggcgc cccagtcctg   6660
ctctcacgca acgtctacgt ggacgctcag ggcgacacga tcgaggtcgg ggagtccgtc   6720
gctccggcgg gccgctggcg cgtccaccgg gactgatcac tcgcccattg agaagccccg   6780
tcaggcaccg cccgacgggg cttcttcacg tccagacgac gtggtttccg gggtgtgccc   6840
acccggttga gccgttgcac cccggttgac cccccgcaac cgggtctgac ctgcgaagtt   6900
gcaaggttgc gacggtttcc aggagggggc cctacgcgtg cgcgcgcgag gaagccattt   6960
ttgatctagc ttccggagcc cttctcggcc tccgccttgg cccacgcccg ggccgtgttc   7020
ggagcgaccg ccgtcacctc gttgatgcgg cggtagggga cctccatccg gaccgcctcc   7080
gcgatcagcg ggcgcagctc cttctcaatc tcgtccagct ccgcgaggag cttgatccgc   7140
tgctgcccca acggcttcag cgccgcctct gcctcggccc ggatctcgcc cggtgtcttt   7200
```

tgcgtcatga agtcatcctg accgactgtg tcagtctgcg caactagttc aggctgcgtt 7260
ttttgcggta caactttccc tacgtcatca aggcggcccg cgagcgggcc gcgcggcccg 7320
gcccacggcc cggccgacgc tcctgtcttc gccccgctcc ggcccggccg ccgaccggcc 7380
cgcgcacacg acgggggcgg catcggtggg cggtttacgt ggcgcctgct ccgccgactg 7440
cgggcatcgc cgttgtgctc gccgacaggg cagcggggag gggtggggga ctcgcggccc 7500
tacgcggccg tctgagcgcc tgtcagcctc ccggagcgcc gtacccccgc cgtcgcggtg 7560
ctgagccgcg tgaggcgacc ctgagccccg tcgtgggttg ctggggagca cctgctgccg 7620
cgatgaggtg gcggccgtcg agctggtcag ccgtgcggct ccgtcgtggc cggtcatccg 7680
gctgcccgat cgtggtgggc aagatgccgg cggaaccggc ggacctcgac cgcgacggct 7740
atccggcggg ccgcgggcgg gcctccgtag agggcgaggg cgggcgccat gccgaccgcc 7800
acggcgggcc acaggcccag gagctcccgc acgatcagcg tcccgccgac caggagcagt 7860
gcggccagca ctgccgctaa cgcctggtcc tggtcccggt cctggtggtg catcagtcct 7920
ccccgtgatc acttcggcac ccaccgtagt gatcaccccc gacagcggat caaggggttt 7980
gcgggtcccg gtcggcgccg ggcgggggag gcaggagccg ccgacgctgc ctctgggacg 8040
ggccggacgg caggggggacc ggcggccggg cgagctgcag ccgggggtcc ggcagggccg 8100
gagcgggcgg aaccgtgctc tgacctgcgg cccgagtttc gtcacgtgac ggaatggaag 8160
gctgctgcat ttcgtcacgt gacgtatctc ggcgagcgac tgccgacgcc acggcggaca 8220
cgatcgcctc gcgctggcgc cgggcctcgt acgcccgctg gcggcaggag cggcggcagt 8280
agtcccggct ccggccgacg ccggattgct tgatctccga gccgcaccag gcgcagagct 8340
tcgcgccgtc ggcgtccctg gggtggtggg tgctcatggc cgacgaccgt acgcggcacg 8400
tctcgtagcg aggcgagtcg ggcgcgaggt accgcctgca cgaagtgccg gcggggccga 8460
ccccgggcga gtaatcccag gattactccc gcggcttcga ccccggccgc cgtcgccgcg 8520
tacgtcaccg acccccgccg tacgtcaccg ggatgacgta cggcgggggg gagcgagtta 8580
gtgcgaagtg ggcccacttg cgagccgggc gatgtgccgg gcggcccgct cctggcggtc 8640
gtcggcgtcg tcgtcctggt cgtcgtcctg ctctcgccgt cggcgtgcag ttgcttcctc 8700
gcggcgctgg gcgagggcgg cgagcatgtc ggcgtacgcc tcggccacct cccccgccgt 8760
gagcaccacc actgtgtcgg ccgcgtcggc cagcgccagg acctcccgca cccgttcgcc 8820
cacggccgcc 8830

<210> SEQ ID NO 61
<211> LENGTH: 11046
<212> TYPE: DNA
<213> ORGANISM: Artificial Sequence
<220> FEATURE:
<223> OTHER INFORMATION: pSN22

<400> SEQUENCE: 61
ctgcaggccg gtgactccag agaagggttg aagcggagtt gcggggctag ccccccgagc 60
ctccatcgtt ccgaccgccc ggcctgtccg ggacgggagg acttttcgag cacctggagg 120
agcacgtgac caaccagcag caggaccagg agcagccgca gcgcccggcg gaccgtggcc 180
gccgcgagtt cgcgaagaag ggagccgtga ccgtgctcgc cgctctcgtc tccggagctg 240
ctcgggcggt ggtagcccac ctcctcacgg gaggtggcga gtgacgcggc tcggcagccg 300
ggccggccgc cggacggagg caggagcggc ccggccggaa gccgggccgc cgggcccgct 360

-continued

```
cgcgggccgc cttgatggag tagggaaagt tctaccgcgc ccactcgcca cgccacgaga    420
cgtgccgcgt acggtcgtcg gtcatgagca cagagacacc cacgaacggc gacggcgaga    480
cgctgtgcgc ctggtgcggc cgtggccccg tgccacccag ccggggaacc aagccgcggg    540
cctactgctc gcgcagctgc gtccagcgag cccacgagtc gcgaaagctc cgcaagaagc    600
tgctcggcgc gtacatgaag ggccgggccg aggaggctga gctgcgcgga ggaaagtcac    660
gtgacgatgc aggaaagtca cgtgactttc ccggtcggca ggccccagca aagtcacgtg    720
actttccaaa accccaggtc aaccctgggg ttccgcgtcc cgcggtcccg gtgacgtccg    780
cgccccggtc gaaaggccgg cgcccgctgc tgccccccgc gccgggcgtg acgcgggaga    840
cgctcccgct gttcggcgac gacgacacgc agcccggccc cctcgatggc cgcgccgaca    900
cggagtgacc acgacggccg tcaccccatc gcggcagcag cccgctcccc atcgacccga    960
gacgggcggt gcggtcgcct cacgcagccc agccccgcga cggcgggggt acggggggtc   1020
cggcgactcc tggcccgcca gacggccgca cagagccgcc gacccccac ccctccccgc    1080
cagccgtcgg cgacgcgcac aacgacgatg cccggcggcc gggtgacggc ccgccatgta   1140
aaccgctcag ggatgccgct cgtgggcagc agaaagcccc cgccgggtct cggacggggg   1200
ctcaatgggg aggtagggcg ggggcctggg gtcactcgcc catgggcacc cgggcgccgg   1260
gggcgtagac gtcttcccag tagccgagcg cctgttcgtc gtcgtggaac gtgacggtgg   1320
tgaccatgac ggcgatggct gagtgggccg ggggcgtcga tctcagagcg ttgagttcgt   1380
cctgggacgc ctgccgtgcg tgggcggccc gctgtccctt caccacttcg cgaccggtgc   1440
gctcgctgta gagcttgtcg aactgcttca ccatccgtac gtcctccccc agctcgggga   1500
cggcggccac cgtgtggggc gggtagacgg agacgccgac cgacgtcggc ttgtcgtcct   1560
ggcggaagac gcgaatgcgg atcacggctt cgtcgccggg ctccagggtg agagccgtgc   1620
agatctcggg atcgtggacc gaccgggtca tcacgcggtg gccggaggag gtctcgccgg   1680
gcgcgtagcg catcccgttc ttctccatgc gcttcaagcg gtccgcgcca gtgatgacga   1740
tggggttctt ctccacgacc gtacccagcg ccccgcgcga gctgaccagg ccctcgctct   1800
tcagcacggc caaggcccgg ctcacggtct tggccgccac gccgaactgg gcacggatgt   1860
cagcgacgga cggcagcgtg tcgcccggtg cgagttcccc gctcttgatc agcgtgcgga   1920
agtgggtggc cacgtcggca tagcccttcc cctccggtgc cttgtatggc atggcttctc   1980
cctgtttgtc ggagcgcggt acaccccga aggtacatca atgaccccc caaggtacat      2040
ccttgcttcg aatcggtgct tgatgtacct tcgtggcgtc ggcaaggtac gttaagtacc   2100
tcccgctgac tgatgcgtac cttcggcaag agagggtctg tcgtggccac gaggaacgtt   2160
ccgccccccg gggcgaacaa cagcaggaac aacaagttcg ccgacatggg ggcggcggcc   2220
ggcggtttcg tcggtgcgat gggcggctcg ttcgtcccgc ccgtgaacgt cacggtcaac   2280
cgcacgacca acaagggcgg tggcggacag cagtccggcg gccgccagtc gcatttcatc   2340
ctcggggagc cggagttcaa ctcggctgag gacgtgcgca actactgcaa ccacgtccgc   2400
gccctgatgc tccaggccgc gatcgagctg gccatggccg ccaagatcct ggaggcccgc   2460
ctcgcccagg cgcagacgct gcccggtgac aatccgatcc agggccggat gcgggcgcgg   2520
aaggtcggcc ggagcctcaa gaaggccgcc gacggcgcca cgtccgccgc gaagggcgcg   2580
gtcaccacct acggcgcctt cacccgcgag tacgccgacc tgatgcgccc gcgcccccag   2640
cgtcaggcgc ccaccaaccc cttcaagttc tgagaggcgg taccgagatg ggcaaggacg   2700
ttcagcagca gcaggaagac cgcctcaact ccggcggcac gggaatgggt gcctggctgt   2760
```

-continued ggcaccgggc caagccgtac accccgccgt ggatcgtcac gggcgcggtc ggcgcggcgg 2820
gcgccggcgc ccacgagctg tggggcaact cgccctgggc cggagtcggc ctcaccctcg 2880
cgggggtcgg cctgacggcc gcgacctggt gggcgggcaa gtccaccggg cagcagcgcc 2940
gcctccactc cgccatcacc gtggcggccg gggcgacctg gttcaccgcc tccgccctct 3000
ccggcccgct caccggcccg ctgcccgacc tgtacctgat gggcggcacg agcctcgccc 3060
tgacctggaa catccgccag gtcatgcgct cgtcgacgcc cgagggcgcc ggatccgact 3120
cggacaaggg actcctggag aaggtcgggc tcgcccggac caagctcaag gacgtcaagg 3180
tcgagcccaa ccgcgtcacg gtcccctacg agctgcctgc cggggagctg accaacgacg 3240
acatcaacaa ggccatcccg cgcatcgcgt cggctctcga cgtgccgacc acggccatcc 3300
gtgtccagca cgaccccgac tccgcgagga agggccagtt cgtgatcgtg cccgaggaca 3360
tgctgaagca gcccacgatc tggcccggcc cgttcgcgcc cggcgagtcc gtggccgtgc 3420
gctgcggatc gcgtctacga cgacgcagcg acctggttct cccgctcctc gacgcgatcc 3480
acctgctcgt catggggatg accggctcgg gcaagaccga gggcgccgtg gacctcctgc 3540
tggagatcct gacccgcaac gacgtgaccg tgtggctcgc cgacgcggcc aaggccgggc 3600
aggacttcca gcccctcgtg cccgccctcg actgggcagc cctggacacg gcgtcggccg 3660
gagcgatggt cgacgcggtc caggccgtca tccccgcccg caccgcctgg ctgcgggacc 3720
acagctaccg ggcctgggag cccgcggccg ccaagacgca gaccaacccc gcgcactcct 3780
gcgcgtcggc cggcgcctgc ggctgccccg ggatgccgta cctgctcacc tggttcgagg 3840
aggcggccaa gctcctgcgc gagctgggcg acgacgtgtt caccggcatc gcccaggagg 3900
cccggtcggc gggcgtctcc ctggtcgtct ccatgcagcg cgcctccggc taccagctct 3960
cgacggacac gagggcctcg ctcccggccg ccatgtgctt cggcgtccgg ggcgacgacg 4020
ccgggttcgc cctccccgag gaggtcctgg acgcaggtgc caacccggcc gcgtggggca 4080
acaagcgcaa gggctacgtg tacctggtgt ccgccggggt cgaggaggac ctgtacgcca 4140
accccgcccg gacgttctgg acgggccccc cggccgaggg cagctacgag cggatggccc 4200
gctacgtcgt cgagcacttc gcctcggttc gtgccgagct ggacccggtg accggcgccg 4260
ccgccgagca ggctgccgga ccgctgttca ccaaccgccg tgcccgcgcg ggcgccgcct 4320
ccgccccggc ccgcccggtc caggagcaga tgctcctcga cgacgacggc caggaggacg 4380
gcgacctcgt ggagatggag cacgacggca tcgacctgag cgccgacctc ccgcccgtgg 4440
agaacgacgc ggaactcccg ccggccaagc cgtcgaccga ggaggcccgc gagctcctcg 4500
acgaaatggt cgccacgctc gcctcggtcg gccccggcac ggtcgctgtc cgcgacctca 4560
agccgtacct ggagcagatc ggccgtgacc gctcctgggt ctcccgcgag atgaagcgga 4620
tggccgagga gggccgcctg gccgccacgg gcgaggaggg cgtctaccgc ctcatcccca 4680
cgctcgccgg ggtctgagac ggcccgcaca gccgcacagc cgcacagcgc gaatccccac 4740
gtcacacggc gtgtgaagag ggccgcacac cgcctcgcac accgtgcgca cagccggacc 4800
gcacaccccc cgcacaccga acgacgacgg accgccccgc agcaaccggg gcggcccgcc 4860
cgatgaccac ggaggtagag cccgtgacca ccgacccgaa gcatctcacc gactccgagg 4920
cttccgccga agctgcccgc ctgatccgcg aggcgtacca gccgaccccg gagccgcgcc 4980
ccatgacctt ccgcgacacc acccggtcac agcgttcggc ccgacccgcc cgtgccccag 5040
cccgagaccc ggatcgtccc cgagtgggcc gccggggtcg ccgtcgcctc catcggcatc 5100

-continued

```
ggcgccggcg tcaccggcct cggctgcgga gcctggctca tcttccaggg cctgtcctcc   5160
gtgaccctgc tcggagtcat cgctatcgcc gccccgttcg tcggcgtcgc cacggtggcc   5220
acggccatcg gcgccgccat ctccaaggcc aagcgctcgt cgaccacgaa cgtctaccag   5280
gggaccgtga tcaagcggac cgacatcacg tcgaccgccc gcggcatcgg cgcccgctcc   5340
cggatcgagg gctgagcgcc atgcagatga acactcagga gcaggtcgag caggcggaga   5400
aggtgctccg gctgagctgg atcatcgtct tcggcgtgat cctgttctcc gtcttcacgg   5460
tgacgcccct ggtagagcgg tccactccgg agggctggga gtggtcggcg ccgatcctgc   5520
cgctcgtggt cgacgtcgcc gtcgtcatct cgatccgggt cgacgcgatc gtgtcccggc   5580
tcggagggtc gaccaccggg tggccgctcg ccctgcgggt gctcaccggc ggcgcctccg   5640
tggcgctcaa cgtcgggcac tccgtactcc agggcgacct ggtgggcgcg ctcgtgcaca   5700
cggccgcccc ggcggtgctc atcgtcgtcg ccgaagcgtc gctcaagtgg cgcaaggaga   5760
tcgccgccgc cacggcccgg atcgaggctg agcaccgtga gcgcgaggac gcccgccgcc   5820
gtgagcagcg tgagcgcgag gagaaggcgc gggccgaccg cgagcgtgag caggaggccc   5880
ggcgcctgga gcgtgagcgg caggaggccg ccgaccgtga gcgccgccgc gaggaactcg   5940
ccgaccgtga gcgggagcgt gagcacgccg cccggctcgc ccaacaggag cgtgagacga   6000
ggcccggctg gaggccgagc gcgaggaccg ggccgacgcc cgccgccgcg aggagcagga   6060
ccgccaggag cgtgaacgcg agaaggagcg ggagcgcagg agcaggagcg ccgtgagcag   6120
gaggctgccc gcaaggccaa ggaggccgtg cagaaggccg aacgggaccg gaaggcagcc   6180
gaggcccgca agcccgccct cgcgcccgtg agcgctgctg tgagcacccc ccgcccggcc   6240
gtgagcgccg ccgtgagcac tcccgctcac gagactgctc acgacgccaa gcccgtccag   6300
aagatgagcg aggccgacgc ccgccaggcc gtcgccgacg cggtccgtga gggccgctca   6360
cagcgtcagg tggccacgct caccggctgg tcgaccggct gggtcgccgc ccgcttcaag   6420
gagcttgagg gggccgccgc atgagccgcg ccctgatgta cgcgctcatc ctgccgctgt   6480
tcgcggcgga gtgctgggcc cagttcgtgg tccatgacca gcgctggacg acgctcttcg   6540
ccctcctcgc cggggccgtg ctcgccgtcc gctacgccct cggtccgcgc acggacgacg   6600
aggaatgcct gcccgactgc ccgaagtgcc gcgaatccag gggggacctg tgagcaccac   6660
cgaccagcac ctgaccgcac agcacgccga agtgaaggcc gagatcaccc gcaccgacac   6720
gaagaccgcg ctcttgctcg ccttcgtcgg cgcggtcttg gccggcgcct ggtccctcgc   6780
ccgagacctc cacctcaacc ccgtcgcgta cctggtcggc gtcctcggac tcgccgccct   6840
cctcgccgcg gccggcctcc tgctccggtc ggtccgcccg aacctcaacg gcgggcacgg   6900
cttcccgctg tgggccaccc tcaccccgca gcagctcacc gccgccgccg agacccgcga   6960
cctggccgcc gacgtcgtcg cctgtcccgc ctcgccgttg ccaagttcac ctgcctgcgc   7020
ctggccgtcg acctgacctg cacagggacg gcgtcctcct cgtcctggcc gccgtgatcg   7080
ccctcggagg tgccgcatga cccgcaagcc cgccatccac gacgccgagg cccacgtcgt   7140
cacctcccac ggcagccgac ttcttcaggc gaggaccgcc acccgctcaa ccgggtcgcc   7200
tccctcgccg ggtacgccga gggctgcctg ccgtacgccg aacagccgcc cgctggtcct   7260
gctgctgacc aaccccggcg acggcgggac catgacgctg ctcaggccgg agagatggcc   7320
acgctcctgc ggaagctcgc ccgccaccgg ttcgtcaaga ccagcgccgc cgcccacgcc   7380
cgcgcactgg gcgacgccgc cgcccgcgcc gccgccgacg cgagccctgg gaatggcgga   7440
tcgaagccgc tgcctgaaca ccgaagcccc gccggccttt cggctggcgg ggcttccttc   7500
```

ggcccgtcaa atcacatctg ccccacgggc cgtgtcgcgt gccgggggga acctccggca 7560
caaaaagtgc caggatcacc cccagcaaag cgaaacggcc agggattagg gcccctgacc 7620
gcttctgacg tccgcccgga taccaaccaa gggactcgtc tgttgaacag ggtaagggac 7680
gctgaggcgt ccgcaagagc actcccggct cgcgccgtcc gtccgcgctg ccactgcggc 7740
actgcgatcg agcacacgcc cggcaaacgg ccgcgcgtgt actgctcgaa cgcctgcaag 7800
cagcgggcga agcgcgctct tgccaagatc gcccgggaag ccgccgacgc gcgtccgcga 7860
cccaaaacgt gtcgcgcctt gggaaagaaa caacagagtt tcccgcaccc ctccgacctg 7920
cggaaacgtc ggcgggggca aaaccggtcg cggacagccg ggacgacgcc gcccgcgccc 7980
ggaaggctcg ccggtacgcg aaccgccgga cgctgtggcg gatcaccggg gacgccgcgt 8040
gcaagggctg cggccgggcc ctgatggacc ccgcctccgg cgtgatcgtc gcccagacgg 8100
cggccggaac gtccgtggtc cttgggctga tgcggtgcgg gcggatctgg ctctgcccgg 8160
tctgcgccgc cacgatccgg cacaagcggg ccgaggagat caccgccgcc gtggtcgagt 8220
ggatcaagcg cggggggacc gcctacctgg tcaccttcac cgcccggcac gggcacacgg 8280
accggctcgc ggacctcatg gacgccttgc agggcacgcg gaagacggcc gacgctcccc 8340
ggcggccggg tgcctaccaa cggctgatca cgggcggcac atgggccgga cgccgggcca 8400
aggacgggca ccgggccgct gaccgcgaag gcatccgcga ccggatcggc tacgtcggca 8460
tgatccgcgc gaccgaagtc accgtgggcc agatcaacgg ctggcacccg cacatccacg 8520
cgatcgtcct ggtcggcggc cggaccgagg gcgagaggtc cgcgaagcag atcgtcggca 8580
ccttcgagcc gtccgaggcc gcgctcgacg agtggcaagg ccagtggcga gccgtgtgga 8640
ccgctgccct gcgcaaggtc aacccgcagt tcacgcccga cgaccggcac ggcgttgact 8700
tcaagcggct ggagaccgaa cgcgacgcca acgacctcgc cgagtacatc gccaagaccc 8760
aggacgggaa agcgccggca ctcgaactcg cccgcgccga cctcaagacg gcgaacggcg 8820
ggaacgtcgc cccgttcgaa ctcctcggac ggatcgggga cctgaccggc ggcatgaccg 8880
aggacgacgc cgccggggtc ggctcgctgg aatggaacct ggcccgctgg cacgagtacg 8940
agcgggcgac caaggggcgc cgggccatcg aatggacccg ctacctgcgg cagatgctcg 9000
ggctcgacgg cggcgacacc gaggccgacg acctcgacct gctcctggcg gccgacgccg 9060
acggcggcga actccgcgcc ggggtcgccg tgaccgagga cggatggcac gcggtcaccc 9120
gtcgcgccct cgaccttgcc gccacgcagg ccgccgaggg aaccgacggc aacaccgatc 9180
cggccgccat gggcgagagg gtgcgcgagg tcctggcgca cgccgacgcc gccgacgccg 9240
tggtggtgct cacctccggc gaggtcgccg aggcgtacgc cgacatgctc gccgccctcg 9300
ccctgcgccg cgaggaagca gctgcacgcc gccgccggga gcaggacgac gaccaggacg 9360
acgacgccga cgaccgccag gagcgggccg cccggcacat cgcccgactg cggaactgat 9420
atcgatccgc actaactcgc tgcccgcccc tactcccgcg ccgacctctc cgtgacccgc 9480
acggagaggt gtcggcggcg gtcggaggct tgcccacgag gcgcgacctg cgaggcagcc 9540
gcaggcttgc ccacggggcc tcccaccctc ggtcccaccc tcggtcccac cttcggtccc 9600
acggtggacg cgacggtggg agcaacggcc gagccccctg ctgaagcaac cccgcccggc 9660
gggcgtcact gatatcagtg acccacaact cgctctgcct gtggttactg cctccgaggc 9720
accgccatcg ggtccgccag cccaccgcca tacgcccgcc cacgaccgcc atccgaccgg 9780
aatgcatggc ggtcccatgg cggtcggatc ggaccccatg gcggaccctt ggcggtgcca 9840

```
tggcggaccc agcggagcga gcaagttatc gcgagagcaa tgctctcgcg ggcgctcgtt   9900
ggggcgagca agttatccgc ttggagactc cagcggtgcc ccgaccgagg gcggtcgggg   9960
ttccccgggg aggggaaccc cctttgtcct caccccggtt ttgatcacgt cggcctacgc  10020
cgacggaccc gcgcggcgcg agccgtgcgg aacggaaaac ccggctgccg atcccctcgc  10080
ccgccgcccg cgttcccgcc ccacctccct ctcctcctgg tgctcgtggc ggtcgtgggt  10140
ggcgtagagg ggatgtctgc ccaagcggaa gcccccgacc atgcgcggtg acgtgggacg  10200
ccgcgaagcc cggaaccgga tccccgcaac acccagcgca acccatggcg caacccatgg  10260
cgcaacaccc agcgcaaccc cgaccaagga cggccgggaa cccgctacga cacccccctcg 10320
acgggcagcg cgtcgactcc cggtccgagc gtccgccggc ctttccgggc ggccacgtcc  10380
tggtgctcga tgtcccccag gagtgcgtcc ggctccactc gctcgacggg cagcagccgc  10440
ggactcgcgt ccgccgtcgg cgtgctcctg gtggtgctcg ggccggtgcc gaggtgacgg  10500
cgcggggtgc tcatgacggg agtctcccgt gccgttcccg gagctcccgc agcggccctg  10560
atcgagccgt gcggcttgtg cgttcgtgaa tgcaagaggt gtgaccgttc ttcgcgtgca  10620
cgcgtgtgct cgtgcacctg tgcacgcggt acggcttcgc cgccgacttc gtcgtgaccg  10680
gagcggtcac acctcaggca ttacgaatga cctcggctgg tcgcgccctg cgttgtgccc  10740
tgggtcgcgt cctggattcc ggcctgagtc acgtcctggg tcgcaccgga cgggtccccg  10800
gccgcgcccg gttcggcgcc gtgacctggt ggacaagggg gcggtcggct gccgttccgc  10860
gcgccgactt cttgctggga gcggtgtcgg cgggcgcctt cggatcggaa tgcaagggtg  10920
tgcggcttgc tgctgccgta cgtcatctcg aagacgtacg cgggccgtcg gtgacgtact  10980
cgaggaacga ggccgggctc ggctcggctt ggtcgacccc aggggctttt tcgtctgcgg  11040
tcctgt                                                             11046
```

```
<210> SEQ ID NO 62
<211> LENGTH: 3539
<212> TYPE: DNA
<213> ORGANISM: Artificial Sequence
<220> FEATURE:
<223> OTHER INFORMATION: pGP01

<400> SEQUENCE: 62
```

```
ccacggtgtt ggatgacagt cctttgttgc cactgtcgca gtttttcttt tcgcgaagtg     60
cttgagatcc ttgatgggtg gacagtacgg tatcctcaac cgtggattct acaacggaag    120
ccacaacgaa atcataggag gatatcccat gaacggacga gtgattgttt ggcctgatcc    180
tgcgctcttg tctgccatgc ctttaagttc cggattttcc ccggtcatgt cgtggaaccg    240
cgagctgaag tgtttcaccg atgtgcagac cacgactgac gacggactgc ctgtctgggg    300
ggcagatgcg tggttgagga tgggatggca accgcacgct gacacagtcc aactgcgcat    360
cgctgcacct cgaaagcctg cggtccagcc tgatcctgcg agaatcgctg atttttttgc    420
gcctcgacgt agtgaggctg agcactgatg gcaggcgaac gaacgactgt tctgaccggc    480
gtctactggt ggctccgtat cttgccggtc ttattactcg gcgttgcctt cgcgtgctgg    540
tgtttctcgg tgcatctggt ctacgtgatc ggcttcgctg ttgcggcctt ggcggtggag    600
gcttttccgc cgtctgtatg gcaggtgccc aagaacatgc aggtgccagc acgatacgtc    660
tatcgctggt ggtggtcctt ggcgaaagcg ttcaagccga ttgaatccta tggcggcgac    720
agaatttact atcgacccgg cttgcagtgg atccgctctg accgacatgt actgcatctg    780
gtgcttcgcg ttcctgcagg tcttgccgac tcggcggcat atctggagaa aggtgcagca    840
```

gagatccaac gacagctacg tggcaagaag tcttggagga cctgcatcgt caaacctgcc 900
gagcatggcc tggacatcat tcctcgcgac gcgacagctg gtgatgagtt acttcctgct 960
ccgtccacgt cgtcgtggaa cgtgccagtc ggggttaaac ctgacgggtc cgaggtcgtc 1020
ttggatctct cccatccatc ccacatcctc gtctccggaa agactcgttc cggcaagtca 1080
tcgttcgtct acggcctgct cgatcagatg cgtcatcttc ctgtcactgt ggctggtgtc 1140
gacccgaccg gaatcctctt taatgagctg ggcgacggct ggggcggtga tgctctgcgt 1200
tccaagcgca tcacgaatga cgctgatgct gcagcagttg tccaggtcct ctccatgatc 1260
accgatgaaa tggatcggcg tatctatctt cttaactgtg agcatcgcga caagtggagc 1320
cgcaacgatt tcgagtccga cccgggacgt cgactcatca tcgtcatcct cgaggaatat 1380
ccgggcttga ttgagcggct gcagaacttc gattccgccc gcggcgctcg ctccagtgat 1440
cgttttgcct cgaaggcagc tggcctcgtt ggccgcatcg cgtacgaagg cgccaaggtc 1500
ggggttgtcc tcctccttgt cacacagcga cctgacgcca aaattatcgg cggtccactg 1560
cgagcccagc tcactacgcg ggtgacgttc gcccaagact cagacggatt gcgtatgtcg 1620
catcctgagc tctcatctga gcaggtcaaa cagaattcat gggcctcagg tgtcgggttc 1680
atcgaagcag atggcgtgat tccgctcact cggttccggt cctatcgagc ggaactcacc 1740
gacctgcatc ggcccggggc gtcggtcggc cagatcgatc tgatccagtg aggagctgct 1800
gccgaccgat gccgcggaac tctgagatcg acacgaccac agatgccgta gtcacggaga 1860
cgctcgagga agagatagga ttcagtacca gataaaaaat gcctccccac agcgccaact 1920
gcggggaggc gagtaagacc tttttctccc gggtcatgac cgccaaggag gcgatcggtg 1980
ttaaacatag taacactatc caaggcgcag ccacatgatc ggttgtgctc tgagcatgag 2040
ccgtgtgcgg ctcgccgcag cgagcgtcag cgagcggcgg gcgaccgcct tggtaccacg 2100
cgagcaactt ttccggtatc agattccccc tgtagaaagc cgaatgaggg ccgtcgccat 2160
cgctatgaga tgagggatgg tctacgaaat ccgcaggtca tgccgctgga gcgcgttcgc 2220
aagtgcgggg cagtgccggt ttcgcaacgg atcgcgttga tggcgggtca tggtggtgcc 2280
ggttatgccg gtttggcgac gtgcggaagt gtgtgggctt gccctgtctg tgcggcaaag 2340
atttccgcgc accgtcgtga tgagctggcc cgtgttgtcc aggttgcggt tggactcggc 2400
ttcaaggtgt cgatgctgac gcttactcaa cgtcatcatg ctggtcagga tctcgccgag 2460
ctgtgggcgt cgctccagtc gggttggaat gctgtcacga gtggtcgacg gtggcaggaa 2520
ttttgcgctc agctcggcgt ccagggatgg gtcaaggcag ttgaagtcac ccatgggtcg 2580
catgggtggc acgttcacgt gcacgtgctc gtcatctcta agcaggatcc gactagcgtt 2640
gacactaaga ttcggcatcg ccgcaaacaa ggtcggcgcc ggaccccgta tccagaagag 2700
gtacagaggc ccgaagactt catcgctgaa cggtggtcgc gaggtttgag gaagcgcggc 2760
gtcgacttca tcgccggtag tggtggcctc gattggcaga ctgctgattc tggagacgag 2820
gaagctctcg gtcggtacgt cgcgaagatg aactcgtccg tcgatggcct agcgaacgag 2880
gccacgttgg gcgggttcaa gaaggctcgt agaggtaatc ggacgccgtt ccagatcctc 2940
gaagatttcc tggatacggg ctcggagact gacctgagac tctggcgtac ctatgtttct 3000
gcaagtcatg gccgtaaggc attgacgtgg tccaagggtt tgcgtgactg ggctggcatg 3060
gaatctgaga tgagcgatga gcaggtcgcc gcccaagacc agtgcgggga agcggtcgcc 3120
ctttttgacc atgacgcgtg gcggcagatc cgcactgccg gtgccgcttt cctcctcgac 3180
gagctggagc tccacggatc cgagggcgtc tacgcctggc tgaagaagcg aagaatccat 3240
tatgagatac ctctagttcc ttggagtacg agtacctagg agccagtcgg ggtctgtcaa 3300
ttttttagct cctccatttc atcacactct ttctatgatg aagtcatcac aattcggtat 3360
tctttgactc ccctgagaag ccgataatca ggccagtaga gctatcttat gtgcctaggt 3420
ggatactatt tattcttcac ctatcaggga ctctggtcga tcacagcctc cgtcgacgat 3480
gacacatctg actaggtact atgatgactt catcatagac agaggtggag cacagacga 3539

<210> SEQ ID NO 63
<211> LENGTH: 8136
<212> TYPE: DNA
<213> ORGANISM: Artificial Sequence
<220> FEATURE:
<223> OTHER INFORMATION: pIP501

<400> SEQUENCE: 63
cctgctcggg acccccccta gaatttcgtt attcaccaaa aaaatacgca tggtataaag 60
caccaagcga ttataaaaaa cgtagtcgaa aaaattatga tatggacaca ataaggggaa 120
tgtatggaag ccaaaaaatt aaagaagaaa aagcagaaaa aaaatactta caagcccgat 180
agggtttgta agtttatcag aaaggaagtt ttaaagtgga tattaaaata aaaaaaataa 240
attttgaagg taatatttta aaagttataa aagcgacagt aacagaaatg agaggaataa 300
ataatcatca aaaatatgat tttgatttat atcaaataga agcacgttcg ccaatgtcaa 360
caagagaaat aactttaaca gttgacttta tagaaaaaaa gtatcaggtg atattatcgc 420
ttttggtgat tggtacgatt tggatataga atcagtaaat gaaatattaa agcaattaaa 480
aaaggaagaa caaacattaa gaacaatcaa ttttatttaa aaaagtatca aaaaaaggaa 540
aattattttt ccttttttttg atacttttta ggtttatttg ctttaatata ttcagaaaaa 600
atttttaaaa attcttccgt ttcttctaca gttaaatagt caatttcaaa atacttttct 660
aacaaagcac ctttttcaat tagacgcttt gttcttcttt ttctgttaat attttgctcg 720
ctattcgctc gcaaaatatt tttttgaatt tttagttttt ctattctttt gttgatgtca 780
tttaaatcat tatttgccat aactatttaa gtaattcaga aaaattttga ctattcgcat 840
ttaataaagt ttctaattcg tcatagaata attctttgtt ttcttcaatt gattcaatag 900
aaatattatt ttttgaaagg gtagaaagaa caaagtcacc aatatctgct ttagacttta 960
gaattaattc ttcttttttc ttttgtaatt ctttaatttg aagttcaata tcagaaacag 1020
ttttcttctt tcttttttttt ggcttcgttt tagaattaaa attaccatta attgcattaa 1080
tattttgatc ttgattttcc atgaaatacg cctcctaata tattgtgtaa ctctatcata 1140
ttatattatt tttctaaaat caataaatat aaacggaaat gtcaggttaa acatatttac 1200
ttttataatg ataagtggta aaattaattt attaaggatt cccttagatt atttactaag 1260
ggcgcactta tacgcagtaa cttcgttact tcgtatttat gctataaaac ttaactgtta 1320
gttagtttta tcgtcaagcg tgtttgttaa aattcgctac gctcatgttt gaaaagaaag 1380
agaggtgata caattggcaa tcttccattt atcaatgaca atagcaaaaa gagaaaacgg 1440
aaaaagaagt ttaatcgcaa tggcttctta tcgaagtggt gaaaaattgt atagtgaact 1500
atatgaaaaa actaatctat acaaccatag aactgttaaa ccagaagctt ttattttaaa 1560
acctgattat gtacctaatg agtttttaga tagacagaca ttatggaata aaatggaatt 1620
agcagaaaaa agtccaaacg ctcaactttg tcgagaggta aatgtagcat tgccaattga 1680
attaaataat tcagaccaaa gaatgttgat tgaagatttt gttaaagata attttgtcaa 1740
tgaaggaatg attgcagacg tagccattca tagagatgat gaaaacaatc ctcatgctca 1800
cattatgcta acaatgagag aagtagatag tgaaggcaat atcttaaaca aaagtcatag 1860
aatacctaaa ctagatgaaa atggcaatca gatttttaat gaaaaggggc aaagagtaac 1920
cgtttcaatt aaaacaaatg attggggtag aaaatctctt gtttctgaaa ttcgtaaaga 1980
ttgggcagac aaagttaatc aatatttaaa agatagaaat atcgatcaac aaataacaga 2040
aaaatcgcat gcggaacttg gaaaaaaaga actaccaaca attcatgaag gtttttactc 2100
aaaaaaatta gaagacaaag gagttataag cgagttaaaa agaaaaaatt tagaaattca 2160
aagttacaat gatattctag ccgaacttga taaacttgaa aatcaagaaa aagtattaaa 2220
acaagaccaa aactttactt taaaatttga aaaaactttc tcacctttag aaaaaggaga 2280
actgaaaaat ctttcaaaag aattgaaatt atttattaat gatgaaaaca ttgataaacg 2340
attaggtgaa ttaaaacgat gggaaaattc acttatcttt aataataaaa tggaaattca 2400
aaaacaacgt ttgatgttaa gtaaaattag tagtgaacga gatatgctta caaaggcaaa 2460
tgaaatttta gacaaacaag cagaaagatt cttcaaaaaa tcttatccaa gtttgaatat 2520
tgacaaattt tcaaatcacg aagttagagc aatggttaat gaaaccatat ttagaaaaca 2580
gttattgaat aaagaccagt tagcagaggt catttacaat gaaagagtag tagaaaaaga 2640
agaaagtaaa aagattttta aagaaaaacc atttcaaact agccgttatc ttgattcaaa 2700
aattaaacaa attgaagata gtataacaaa agaaaataac cctgaaagaa aagaaatttt 2760
atcaattaaa aaagaaaaac taataggaat aaaacaagga ttgatagaat atgttcaatc 2820
agaagttgaa agaaaatttg ataaaaatgt ttcaatagat tcagtcatag aaggtgaaat 2880
gttacttgca aaagctgact attacaaaac aactgatttt tctaaagtcg aaggagttgc 2940
tagattcagc agtgaggaaa ttaattccat gttggaacaa tcaaaaggct tcttaactaa 3000
cattcagacg gtgaaaattc ctaatgattg tcaaggtgta ttttttgttc aagatagcat 3060
gaaacatatt gatgaactaa gcccattagc aaaacaaaat ctgaaaaagg ttgttaatcg 3120
caatgcttat ttacctgatt ctgataagat agaattaagt aaagaaattg aaaataccaa 3180
taaagatcaa tcccaagaat tggataaaga cgtaccagaa aaaaatgaag tgactgtaaa 3240
aatgttccaa tttgcgaagt caattaatcg tttgttgagt ggtaaccaac tacagaaaaa 3300
acgaaaccta gacaaattga ttaagcaaac aaaagcaaaa aaaaatcaat cattacaaag 3360
gaatattcct ttgcgataaa ataaaaacaa gaggtgtata aaatgaaaaa atttatcaaa 3420
gatacaaagt ttaagcttgg aagtgcggtt gttgcgttgg gtacattgtt tattactgat 3480
ccagtgtttg cagccactga tccacaagcg aaattagttc aagcgggtaa cactataaaa 3540
ggtgttttaa cagccttaat tgttgtagtt ggtgggattg cttgtgcgaa gattgttatt 3600
aaatacttgc cgtctattga tgacccacaa gaaaaaaata ccatgtataa agccttggga 3660
acagccttgc ttgttacggc attaggtggg gcgttggttt ggttagtacc ttgggcgtat 3720
ggcttacttg cttaatagag aagggagtta gttatgaata gcgatcaagt gaaacaagcc 3780
ctattagatt tgttaaatgc agacactgaa aaagggcgga cttggttttt tccgtctaat 3840
gtatctgatc ggtacacagt cattttaggg ctagatttaa aacaatcagc aaaagcgatc 3900
ggtacggcat taataagcgt gttattgaca attcttattt tccgtagcac agccgttttt 3960
cctttaatta tctatgtcat tgttggtttg gtgtcatttg gtggtgtatg ggcgttttat 4020
acgattaaac caattacaga ccgacctaac atttctatat ctgattttat gaagcaaaga 4080

```
aaagactttt ctaaaagacc aaaagtctat tacaaaaagc caaaagaacg agtgtaaaag   4140
agaggtgatt taattgtttg attttctaaa aaaaagttcc aaaagtaacg ataataaaaa   4200
aagcgatacg atgaaagaaa tgatttattg ggaagatagt tcccgatttc aaggcgtttt   4260
taaagacttt tttgtcgttt atcagccaga aaaaaagcaa ttcagccttg tgagtatgct   4320
aaaagttgac ggcttaaacg ttgatacctt gccagtatca gagcaagaag ggttaaacga   4380
agattttggt gtctttctat ctcaaaacgt tctatatgaa ccgcagatca cttctaagaa   4440
tgtaccagta gaaattgacg attttgtaga agcctggggg attacagtag aaaattatcg   4500
caaaatgcca gggcataacg aagctttatt acaattaaag gctagttact attatcatta   4560
tagaaattta gcaagtaaca tggaaacttc aaagaaacaa cattttgtaa ttaattctga   4620
accaatttca aaggaaacat atgatagttt agaattgtcc tatcaagtgt tacgtgataa   4680
gacaaggaca atcaggacgg ctttaattgc ttttttaagc aagtatgatt gccaagttga   4740
aatgtgtacg attggcgaga tgaaaaaggt tttgaatagt taggagcgtt aaaatggaga   4800
agataccaaa agagaaaatt gtcttgatac ccgaagttga tacggacgtt gtatctgatt   4860
tagcaccatt taactttaca gtagaacgtg acaaattatt gattgatgat tcatacgcag   4920
ttccctatgt cattacaaaa tacaacaata agccacgtgg gaattggttt aatcgtattc   4980
gtaaaatgag tggagatata accatatctc attactacac taaagcaaac ggtaactcat   5040
tgaatgatta ttacaacaga accattaaga acaagcaagc agagatcgat cgttcgcatg   5100
atccgttgac gattatccgt ttagaacgtg aaatgaaaat tgctcaaacg cagttagaac   5160
aagccgttga cgaaaacact tcttatcttt acttgtacac ctatgttttg attaaaagta   5220
agtcagaaga taaattaaaa aaattgtgtg aagattttga aacacgttgt atcgcaagtg   5280
gagtaaaagc gttaattcca tatactatga ttgataaggc gtattggagt tcattaccgt   5340
tacaatctaa tgaagtacct gaatacacct atacaatcgc taattcaatc agtgcaagca   5400
gtatttttcc ttttgatgat aatgaattaa gtgtatttac taaaaatatg attattgagg   5460
gaattaataa agatactgaa aatatcgtta gtattgatta caccaacaga aaattagtag   5520
tcaatcgtaa taaattcgtt tttggtttat ctggtggggg aaagaccact tacttaacgt   5580
cagactattt aaaaaaatat gctttttctg ataactcaac agaattaagg cacagaattg   5640
ttttatttga tcccgaagat gaacaaacag agcgtgtacg ttctctaggg ggcgaaataa   5700
tcaatctatc gtctatgtca gatgttcgta tcaatccatt tcaaatttac tcacgcaata   5760
cgctagatgt tgatttaaaa gaatcattat ccgattttga agaggacgag cttgtagaaa   5820
atattgaaat aaagcataaa gattatgaaa tgactgacaa tgatattgat aaagaaatca   5880
gtaaacgaat gaatatttta acgccttatt tcctaatggt ggatcattct ttgactgata   5940
gtcaattatc cattattaaa atagaagcta aaaaatgcta taccacttta tacgagaaga   6000
aaaacttgtc aaaaatggaa aacaccgatt ttccaacatt ttcagactta gaaaatcgat   6060
tgaaagcctt agaagaaact gatccaaaaa gatacaaacg aattgaagat tttatttatt   6120
cattagaaga ttttacaatc ggaagtcgta ccatttttaa cggtcataca aatatagact   6180
taaacaatcc gttaatttgc ttttctttgc gagatttaca gaccgaagaa gggatcagag   6240
atttagcata cctcaacagc tttagttatc tatttgaaga aataaccaac aatccgcaaa   6300
ttgtaacgtc tgtttatgca gatgaatttc actttttatt gaagaataaa attagtgctg   6360
actttttctt ccaagcatat aaacgcttta gaaaatacaa tgctgattgt accgtatcaa   6420
cccaacagat tgatgatgta ttaaaagcac ctgataatat cggtaaagca attattggga   6480
```

atagctttac aaaagtattc ttcggacttg atgaaacgga agcacaaggt atttcaaatg 6540
agttgaaact taaactcaca aaaaaagaat tatcgttcat tacctcaaaa cgtcaagggg 6600
aagctttgct ttttcatggt acaaagcgag caaagataaa agtagattta acacaggaag 6660
aaatgcgttt gcttaaccca ggcgaatatg aagatattta cggcgttagt ccgaagaaag 6720
agatcaactg gttgttaaga tcgaaaattc aatagaaggg agaaaaaaat gaaatacaaa 6780
atcttgaaaa atttacaatt ctactatcaa gagaatgtca ttgtcgtcca aataaacgaa 6840
aaatatttga cgaatcgaga acatattttt gatgtagaag aaagtgaaca atattttgtt 6900
gatgtcgagg agattttgac caaagacgga aagctagaaa ttgtttataa ccgacctaat 6960
ggctatacac cactactaga tttaaaagaa tatgctgatt tttataaatt ggatatagtg 7020
aatcgattac ttgaaatgaa tgtactagaa aaaacaaaca cctatctagc aatgcaaaat 7080
atcctactca aagatacacg tgacttgctt tttatttata aagcagatca ctttgataat 7140
ttgccttact caactaaaga agaattagag cagtggaaaa attttatttg tagttttttt 7200
ggtaaattca cacttgagaa gtatgagaag aatcgtattg aggttctaac aaaagaaaaa 7260
aattcatttt taaatgatgt agaagcagtt gaaagcttgg aatcattaag agatttaata 7320
aaaaatcgac taaccgaaga acaaaagaat ttcttttctg ctgaattaca ggacaagaaa 7380
gcagacgtcc gaaaaattcg cagaaataaa agcttaaaaa ttgcgttagt tgtaggtgtt 7440
attgcgttat atggcggtac ggttttactt atgaaagtaa atgagaagaa acaagttacg 7500
gctacacagc aaagcgcaga aacagagatc actattttaa ataagattat tgataatgat 7560
agtgagaata tcgaagaaga tatgcaaaag ctcaattatc ctaagaaaaa acaagttgat 7620
atttacgtga aacttggtga ttataccaag gcttatgaac ttgataaaaa gtcagataaa 7680
aaaattattc aaagtctgta caaacaagga gaaaccgaaa aaatagaagc ccttgattta 7740
ccaggaagcg actatttagc agacttcaaa aagattttag cgtatgacaa ttcaacagat 7800
attgagtatc tggttcaaac tagtaccgat acaacaattg ttgaagcttt aatcgataaa 7860
tcagtaaaag aaaaagacat tccaacagtg aaaaatattc gtcaagtatc aattacacaa 7920
aagaaattag caatcgatcc taaacgtcaa atcagtatga ttgacttatt gattgaaaat 7980
aacagtgaag aattagaaaa tatgtataag gataattctt taaatgagga cttgaagaaa 8040
aaacaaacca atgacttgtt agaagaaaac aacacgttgc ttagtgaaaa gattgaatta 8100
acaaacgctg aaaaagatta ggaaggttgg tgattt 8136

<210> SEQ ID NO 64
<211> LENGTH: 2053
<212> TYPE: DNA
<213> ORGANISM: Artificial Sequence
<220> FEATURE:
<223> OTHER INFORMATION: pCU1

<400> SEQUENCE: 64
ctgtttccat tctgtttctg aaattctgtt tttctgagcc atctgtgggc ctccgtagtt 60
ttggttacag aaaggatata ctcagaataa ataggggtca atacaagtac gatttttata 120
aactttattt tatttgaggg tgaggcccgg tgcggcacga gcgcggcgtt gatggtgccg 180
cgaaaggtgc ctggcgccat gcttggatta aaacatgaac cgtgaagaac tgcgaaactt 240
gttttcgcgg ttctgagggg ttgaccgagc cgcgaagtgg taagcgatga tatgcacata 300
tccacaggca tatttttaaa aggtatttta tagatttttt atctttttaa agtcttttag 360

```
agctatataa ctcattgatt taaaatcata aataagtgtt atctctggga atccgcccac    420

cttgttatgg gaattggccc acctatctat gggaaacacc ccaccttact atgggaatta    480

gcccaccttg ttatgggaat tggcccacct tagacgaaac tgtaaaaaat gtatttactt    540

gtttgaactt tgtggtagtg tggagagtaa tttttaaccc acaaaggcaa ggctcatgga    600

taagttgctg aacaaaaaga taaaagttaa gcagtctaac gagcttaccg aagctgctta    660

ctacctctcg ctaaaagcaa agcgcgttct ctggttatgt cttatgcaga cgtatttcac    720

agcttcagta agcgaagatg atgatgagat ggctgtactc ggtgactcta ctttcaaagt    780

aaaggtggct gactatcagc aaatttttca ggtaagccgt aaccaggcta tcaaggatgt    840

taaagaaggc gtgtttgagt taagccgttc tgcggtaatc ttttacccga aagaagggag    900

ttttgactgc gtcgcgcgcc cctggctaac agaggctggc agccgatcag ctcgtggtat    960

ctgggaaatc gaatttaacc ataaactcct gcggtacatt tacggcctga cgaaccagtt   1020

caccacctac tcgctccgcg attgtggcag tcttcgaaat ccacggacga tccgccttta   1080

tgaaagtctt gctcaattca aatcttcagg cttatgggtt actactcatg cttggttaaa   1140

tgaccgtttc cttttgccgg aatcccaaca gaagaacttg gcagagttga aacgatcttt   1200

ccttgatcct gctctcaagc agataaatga gaaaacacct ttacttgcta agtatagtat   1260

tgatgattca ggaaaatttc tgttctcaat aattgataag caaaatcccg tctgacataa   1320

atcagcacac atgagcctgt catttgacaa atttttgtca tgaagatggg cgaatttcca   1380

cacagcaccg gcgcccggca aggtgggcgg attcccacac ggcaccgacg cccggcaagg   1440

tgggcggatt cccacacggc accggcgccc ggcaacggtg ggcggatttc cacacagcac   1500

cggcgcccgg caaggtgggc ggattcccac acggcaccgg cgcccggcaa ggtgggcgga   1560

ttcccacaca gcaccggcgc ccggcaaggt gggcggattt ccacacagca ccggcgcccg   1620

gcaaggtggg cggattccca cacggcaccg gcgcccggca aggtgggcgg attcccacac   1680

ggcaccggcg cccggcaagg tgggcggatt cccacacggc accggcgccc ggcaaggtgg   1740

gcggatttcc acacagcacc ggcgcccggc aaggtgggcg gatttccaca cagcaccggc   1800

gcccggcaag gtgggcggat ttccacacgg caccggcgcc cggcaaggtg ggcggatttc   1860

cataacttta attatacctt tgtgttattt gtggattgtg cagctcagtg gggcgctggc   1920

cgtgacggtg cggtgtcccc cgtaaccggc cgcgcggccg ctaactcgca gtacggcgcc   1980

gcgacccgca gcgggccgcc gtacccgcgc cgcacggcgc ccactgcgca cccccgtgga   2040

ggacgtgcgg cag                                                      2053
```

<210> SEQ ID NO 65
<211> LENGTH: 1540
<212> TYPE: DNA
<213> ORGANISM: Artificial Sequence
<220> FEATURE:
<223> OTHER INFORMATION: pBAV1K-T5

<400> SEQUENCE: 65

```
tccgccgccc tagacctagt gtcattttat ttcccccgtt tcagcatcaa gaacctttgc     60

ataacttgct ctatatccac actgataatt gccctcaaac cataatctaa aggcgctaga    120

gtttgttgaa acaatatctt ttacatcatt cgtatttaaa attccaaact ccgctcccct    180

aaggcgaata aaagccatta aatcttttgt atttaccaaa ttatagtcat ccactatatc    240

taagagtaaa ttcttcaatt ctcttttttg gctttcatca agtgttatat agcggtcaat    300

atcaaaatca ttaatgttca aaatatcttt tttgtcgtat atatgtttat tcttagcaat    360
```

```
agcgtccttt gattcatgag tcaaatattc atatgaacct ttgatataat caagtatctc    420

aacatgagca actgaactat tccccaattt tcgcttaatc ttgttcctaa cgctttctat    480

tgttacagga tttcgtgcaa tatatataac gtgatagtgt ggttttttat agtgctttcc    540

atttcgtata acatcactac tattccatgt atctttatct tttttttcgt ccatatcgtg    600

taaaggactg acagccatag atacgcccaa actctctaat ttttccttcc aatcattagg    660

aattgagtca ggatataata aaaatccaaa atttctagct ttagtatttt taatagccat    720

gatataatta ccttatcaaa aacaagtagc gaaaactcgt atccttctaa aaacgcgagc    780

tttcgcttat tttttttgtt ctgattcctt tcttgcatat tcttctatag ctaacgccgc    840

aaccgcagat tttgaaaaac ctttttgttt cgccatatct gttaattttt tatcttgctc    900

ttttgtcaga gaaatcataa ctcttttttt cgattctgaa atcaccattt aaaaaactcc    960

aatcaaataa ttttataaag ttagtgtatc actttgtaat cataaaaaca acaataaagc   1020

tacttaaata tagatttata aaaaacgttg gcgaaaacgt tggcgattcg ttggcgattg   1080

aaaaaacccct taaacccttg agccagttgg gatagagcgt ttttggcaca aaaattggca   1140

ctcggcactt aatggggggt cgtagtacgg aagcaaaatt cgcttccttt ccccccattt   1200

ttttccaaat tccaaatttt tttcaaaaat tttccagcgc taccgctcgg caaaattgca   1260

agcaattttt aaaatcaaac ccatgaggga atttcattcc ctcatactcc cttgagcctc   1320

ctccaaccga aatagaaggg cgctgcgctt attatttcat tcagtcatcg gctttcataa   1380

tctaacagac aacatcttcg ctgcaaagcc acgctacgct caagggcttt tacgctacga   1440

taacgcctgt tttaacgatt atgccgataa ctaaacgaaa taaacgctaa aacgtctcag   1500

aaacgatttt gagacgtttt aataaaaaat cgcctagtgc                          1540
```

<210> SEQ ID NO 66
<211> LENGTH: 383
<212> TYPE: DNA
<213> ORGANISM: Artificial Sequence
<220> FEATURE:
<223> OTHER INFORMATION: Cos PAC7 383

<400> SEQUENCE: 66

```
gaccacatca cacccgtcag ccggggagga ctcaacaccc tcgacaacgg gcaaatcatc     60

tgcagaacat gcaacagaag caaaggcaac agaacacaac caaacatcaa attccaacaa    120

caaaccacaa aaacattgat tccatggtga aaaacccgcc aacccccacc gggcacaccc    180

cctgcacacc cgtgcaagac ctcgtacggc ttagtgaaat acctcccttt tgttgtttta    240

tcgttttgtc gactttttgt ttggtggtgt gtgtggtgca gcctgagctt cctgatagtc    300

gtgattggtg tggggagacg cgtcggtggt ggtgtgtgtg gggcgaggat ccgcgtgccg    360

ggtttgtgtc tgatgaggag tgg                                            383
```

<210> SEQ ID NO 67
<211> LENGTH: 511
<212> TYPE: DNA
<213> ORGANISM: Artificial Sequence
<220> FEATURE:
<223> OTHER INFORMATION: phage PAC7 origin

<400> SEQUENCE: 67

```
cgacatcagt cttaaagtct taaacacttt aagtaacttt aaagcttcaa ggcttagccc     60

ttaaggatct aagttactat aaaagcttta aacacttaaa gtaactataa agctttaaga    120
```

-continued gcttaacatt taaggatata aataaacatt aaagctttaa agtcttaaag taaatatata 180
accttaacac ttaagttaag tataaaacct taaaggctta gcacttaagg atataaactt 240
aacatcagtg tttaagactt aaagagttaa agtaactatt aagacttaaa ggcttataag 300
ctttaatact ttaagtagct ataagacttt aaaaacctga agtacttaaa gttaaccatc 360
agtcttaaac tttaatatta taagtattaa agcttataag ttataaaagt ttttagaaga 420
gttaaagggt taacttcttt acttctcttc tctctttggt tctttctctc ttctcttctt 480
ttcttcatca ggggagaaga ggaaccttta a 511

<210> SEQ ID NO 68
<211> LENGTH: 29768
<212> TYPE: DNA
<213> ORGANISM: Artificial Sequence
<220> FEATURE:
<223> OTHER INFORMATION: PAC7

<400> SEQUENCE: 68
tgcaggtgct gacggtgtga acggcgttga cggcgctgat ggtcgggatg gttctgccgg 60
tgagcgcggc ccgcaaggcc cttcaggtcc tgccggcccg caaggtgcac agggtgaacg 120
gggtgagcgt ggtcccgccg gtgcgaatgg atcggatggc catgatggta aggatgggcg 180
ctcggtggtg tctgtgtact gttccggggg ccgcctggtt gtgaaatata gtgacggtgt 240
ggcttccacg atatcgggtt cggcggcctg ccagggtgtg aaaccgtcgc ctctagtgac 300
tatatcatcc cacaaataga aaggagtggc tgtgatggtg gtgtttggtg gtggtgtgtt 360
gtgagatata ttcctgcggc gcatcattct gccggctcga atagtccggt gaatagggtt 420
gtgattcatg cgacgtgccc ggatgtgggg tttccgtccg cctcgcgtaa aggacgggct 480
gtgtccacgg caaactattt cgcttcccca tcgtctggtg gttcggcgca ttatgtgtgt 540
gatattgggg agacggtgca atgcttgtcg gagtctacga ttgggtggca tgccccgccg 600
aatccgcata gtttgggtat agagatttgc gcggatgggg gttcgcacgc ctcgttccgg 660
gtgccggggc atgcttacac tcgtgagcag tggctggatc ctcgcgtgtg gcctgcggtt 720
gagcgtgccg ccatcctgtg tagacgtttg tgtgacaagc atggtgttcc gaaaaggaaa 780
ctgtctgtgg ccgatttgaa ggccggtaaa cggggtgttt gcgggcatgt ggatgttacg 840
gatgcgtggc atcagtcgga tcatgacgat ccggggccgt ggtttccgtg ggacaaattt 900
atggctgtgg ttaatggcca cggcggcggt tcaagtagtg aggagttgag tatggctgat 960
gtacaagcgt tacataatca gattaaacag ttgtcggcac aggtggccca gtcggtgaat 1020
aagctgcatc acgatgttgg tgtggttcag gttcagaatg gtgatttggg taaacgtgtt 1080
gatgccttgt cgtgggtgaa gaatcctgtg acggggaagc tgtggcgcac taaggatgct 1140
ttgtggagtg tctggtatta cgtgttggag tgtcgtagcc gtcttgacag gctcgagtct 1200
gctgtcaacg atttgaaaaa gtgatggtgg tttgttgtgg gtaaacagtt ttggttaggt 1260
ttgctggagc gtgccctgaa aacttttgtt caaacgtttg ttgccgtgtt gggggttact 1320
gcgggtgtca cctatactgc ggagtcgttt cgtggtttgc cgtgggaatc cgcgctgatc 1380
acggcaacgg ttgctgctgt cctgtcggtt gctacctcgt ttggtagccc gtcgtttgtg 1440
gccggcaagc ccggcaagca gccccaggtg gatgcgggtt tggttccacc ggatgatggg 1500
ggcttggttg agccgcatat ggtggatgtg tcggatcctg gcatgatcga gccgacggat 1560
gatgcggatc ttgccggcta tgagcctcgg cgtgcagccg agtcggaggt tggcacggta 1620
gagtctactg ttgcataatt gaatatagat gtgtgcccca gcggtgctgc cacgattgtg 1680

-continued

```
tggtggcggc tgctggggca ctatttttgt atatgcggtg tggctatgat tcgttgctgt   1740
cgatggtgtc ttcgagcatc tgatacaggt ggaggcaggt agagatagtt tcgctggcct   1800
gatcgagaac gttccggccg ataacgtttt tgtggttgtc gcggtggcgg atgatagccc   1860
acatgatctc gtcggctgcc gcctgtaata gtttggcctg gtatgcgatt ccggcgagcc   1920
agtctagtgc ttcctggctt gtataggggc tctggtcctc gctgttgccg cgggtgttgc   1980
tgttgtttgt ggggtgtcct gcactgtcgc atagccacag gatttcgctg cactcgtcta   2040
gcgtgtcttg gtcgatagcg agatcgtcga ggctgacatt gttgacggta aggttcacgt   2100
tgtcgaggga gatgggtaca ccgtactggt tttcgacact gtcaacaatg ttttccagct   2160
gttgcatgtt ggtgggctgt tgttggacga tacggtgtat cgctgtgttg agggtggtgt   2220
aggtgatgtt gtgtgtgttg tccatggttt ttatgccatt ccttcgttat cgtctggcat   2280
gtagtatgtg ctgtttgcgt actcggttaa cgtcatcagt gtttggtctg cccactgttt   2340
cacggtttgc cgggtgactc cgagtcgttg ggcggctgtg gcgtaggttt gatcataccc   2400
gtatacttcc cggaatgctg ccaacctagc taggtgtttc ctctgtttgg atggttcaca   2460
ggtgagggtg tagtcgtcga tggctagctg tagatcgatc atggagacga tgttgttgcc   2520
gtggtgttgt ggcgcggttg gtgggggtgg cattcctggc tccacggagg gtttccaggg   2580
gccgccgttc cagatccatt gggcagcttg gatgatgtcg gcggtggtgt aggttcggtt   2640
cactggtcac cccctgaaca ggtcgttggt gttgttggtg tcgaatcgtc cgacgcagtg   2700
gcagtagtcg tacatgagtt taataatgtg ttggtggtct cccaaatagg tgtttccgct   2760
gatgctgtat gtggctgtgc cgtctttcgc gatggtgtat ttggcggtga tggtttcggg   2820
gttttcggtg tcggtgatga ttgctgtggt ggtggcgcct actgtttgga gtatggtggt   2880
ttgggttccg tcgtcgatgg tggttttaac catggtgtgt gttttccctt ttgttagttg   2940
cttgtttggt tgtcggctag atgaataata tcgggtaaag gtttcggctg gtctaggtgt   3000
tgtatggttt tgttggctag ccgtttggct accctgtaac acattttggt gtagtgtttg   3060
ttgtctaggt tgtggtattg ttcccgcacc gcaatatata gcagggagtc ttggtacagg   3120
tcgtctgcac tgattgcggg gtagtgtgcg gctgttttgg tgcatgcccg gttgagtgtg   3180
cgaagatgat ggtctgtggc ccacacccac gatgcggtgg tggccaggtc ggcttttgtt   3240
ggtcgtctgc tcatggcact atttcatctc gctatctgat agttgtttgg tgttttgttg   3300
tggatagtgt agcacactag tcctgggtgg ccggtggtgc ctgtgcggtg acggaaccat   3360
gtggattcgc cttccatgga tgggcattgg atgaaggtgc gttgtccttg ctcggagatt   3420
tctaggtggt gccggtgccc ggccatgaga atattagata cggtgccgtt gtggaattct   3480
tggccgcgcc accaatcata gtgtttaccg gtgcgccatt ggtgcccgtg ggcgtgcagt   3540
atccgtgtgc ctgccacatc aacggtggtg gtcatttcgt ctcggctggg gaagtggaag   3600
tgtaggttgg ggtattggtt attgagctgg taggcttctg cgatggcccg gcagcagtcc   3660
acgtcgaatg agtcatcgta ggtggtgact cctttaccga agcgcacggc ttcaccatgg   3720
ttgccgggga tggatgtgat ggtcacattt ttgcagtggt cgaattggtg gatgagttgc   3780
atcatggcca tgcgggtgag cctgatttgt tcggtgaggg gtgtttgtgt tcgccaggcg   3840
ttgttgcctc cttgtgacac gtatccttcg atcatgtcgc cgaggaaggc gatgtggact   3900
cgttcgggtt tgcctgcttg ttgccagcag tgttttgcga ctatgaggga gtgtaggtag   3960
ttgtcggcga agtgtgctgt ttctccgccg gggatgcctt tgccgatttg gaagtctcct   4020
```

-continued

```
gccccgatga cgaaggctgc ggtgctgtag tcggtgtggg tgtcttgttc gggttttggg   4080
ggtgtccatt cggctagttt atcgacgagt tcgtctaccg ggtaggggtt tgttgcgggt   4140
tggtggtcga tgatttttg tatggatcgg cctgtttctc cgttggggag tgtccattcg   4200
gagatgcgtg tgcggcgcac ggtgccgttg gctagattgt cgtcgatggt gtcgatggcg   4260
ttgtcgtggt tggctagctg tgtgagtagc cggtcaatat tgtctatcac tgggtatcct   4320
cctcttgcgg ggtggtgctg gcttgtttgc ggcgatagtc tttaataacg gtggcggaga   4380
tggggtatcc tgcctgggtg agctgttttg ctagccatga ggcggggata gacctgtcgg   4440
cgagcacgtc ggcggctttg ttgccgtagc gttgaataag ggtttcagtt ttggttgcca   4500
tgatgtccta tcggttgtgt ggtgggctgc catcctgtgc ggcagtcgcc gtcgtgtcct   4560
ggtttgcgtg tgcaccacga tacggttccg tctgtgtggt tgagtgtttt accgcacatg   4620
acgtttcgga gatgctccgg cagctggtca tcctggttgc tggtttgtgt gtcgaagagt   4680
gttttctggt tggtgaaatg ttctgacacg gtgccgttat gcacgggtag tatccatgtt   4740
ttccattgtt gttgtagcct ggtgttccag tggaattgtt tggcggcgtt ttcggcctgt   4800
tttaaggttt tgtggtagcc gactagtatg cgttgatgct gctggtctgg agggtttggg   4860
cctcgccagt attgtgccgc cacggcgtag cggttgctgt ctgtgaaggc gtcccagcag   4920
tattcgataa tgtgttgcaa catactgtct ggcaggctgt cagggttgat gttgatgttt   4980
tgggtgataa tgtcacggat ggcttgccgg tttttggtgg tgggtttgaa cgagatgctc   5040
acgatagtac cggctggtcg tcttgcatga actggttgaa ggtgttgttc ccggcgtgtt   5100
gggcttgtgt tatttgttgg tcggtccagt ctgggtgttg ctgtttcaga tagtgccagt   5160
ggcacgcatt gtaggtttcg tcttgtagcc gtgtgagatg gttttcggtg atgatttgtt   5220
tccacatggc ccatgacacg tcgagccggt cgaggatttc gagggctggg atgttgaatt   5280
ggttcaggaa gaggatttcg tgggtgtagt agtttttctc gtaggcgtcc catccgcttc   5340
ggtgcctgtt gggctggttt ttggggtagg cttcccggca tactttgtgt aaacgcttgg   5400
ccatgtcgtc gggtagttta atgtcggggt tggcgcggat catggatcgc atcccatcat   5460
aggtggtgcc ccaggtgtgc atgatgtagg tggggtcttc tccgtcggcc catttttctg   5520
cacagatggc gaggcggata cgcctcctgg cagcttggct ggtgttgcgc cggttgggga   5580
ttgggcacgt gtcgagggga tccatgatgt tttagtgtac ctttctggtt tcgtgttgtt   5640
gacaggtttt actgtagcac agtgtctagt gcgtgtgtca accctgtttt tccggcttga   5700
aggtaggtgt ctgtgacatc ccctagggtg aggggcacgt gcacagcttg gggagtgcc   5760
gcctggaggg tttgggccat ctggtcgcct gcggggtctg ggtctgacca gatgtagatg   5820
tggtcgtagc cttcaaaaaa tttggtccaa aaaatttgcc acgaggttgc gccgggtagg   5880
gcgacggccg accatccgca ttgttcgagg atcatggagt cgaattcgcc ttcgcaaatg   5940
tgcatttcgg ctgccgggtt ggccatggcg gccatgttgt agatggagcc tgtgtctcct   6000
gccggggtta ggtatttggg gtggttgtgg gttttgcagt cgtgcgggag tgagcagcgg   6060
aaacgcattt ttcttatttc ggctgggccg ccccaaacgg ggtacatgta tgggatggtg   6120
atgcactggt tgtagttttc gtggcctggg atggggtcat tgtcgatgta tccaaggtgg   6180
tggtagcggg ctgtttcttc gctgatgcct cttgctgaga gcaggtcgag tatgttttcg   6240
aggtgggttt cgtagcgggc tgaggctttc tggattcggc ggcgttccgc aatgttgtat   6300
gggcgtatgc tgtcgtacat ttgggttttc ttcttctaat cgttgttgta gcttggcgag   6360
tccgcctccg acaccgcatg tgtggcagta ccagacgccc ttgtcgaggt tgatgctcat   6420
```

ggagggctgg tggtcgtcgt ggaacgggca gagtatgtgt tgctcgttcc tggacggatt 6480
gtaccgtatc tgataatggt cgaggaggcg gcaggtgtca gaggtgtggg aggagctcgt 6540
tgagggttga taccacatag gcttcactcc atggcttgtt gcgctgtttc atcactacga 6600
gtccgatggt ggaattgttt tgtttgtttc ggtgtgtttc gtagttgcgt gcctcccggc 6660
tggcttgttt cacgaattgg gctaggtgtg gttgcccggc tttcgcctcg ataatgtagg 6720
ttttatggcc ggttgtgagg atgaggtcgc cttcgtcttc gcggccgttg aggtggaggc 6780
gttcgatatt gtgtccggtg tcgcgtagct ggtggaggag tcttgtttcc cattcggctc 6840
cggcccgccg gttgcgtgcc tgctgtgtgg ccatagtttt ttagagtcct ttgtgtgttg 6900
tggtcatgtt ccagggctgt ttttcggcga gtggcccgaa gaatgtgtat tcggggtatg 6960
ctctgagtcg ttcgtatcgg gtgccgtcgg ggctggattt gcctgtgcgc tgtttgagta 7020
cggcgatgcg tgcctctgcc ggtatcgata gcccgttgcc gttatcctcg ccaccataca 7080
atgagactcc gaggatgagt tgtggttttt cggagaggcc gtttttgatt tctcgccgtg 7140
ctggcgggtg ttcgatgtcg gttccggttt tgtcggttgc gtggtgtgtg acaataatgg 7200
tggagccagt atccctgccc aatgctgtga tccattgcat ggcttcttgc tgtgcctggt 7260
agtcggattc gcagtcttga atgtccatca ggttgtcgat aacaatgagt ggtgggaagg 7320
tgttccacat ttccatgtag gcttgtaact ccatggtgat gtctgtccat gtgatgggtg 7380
actggaatga gaatgtgatg tgttggccgt ggtggatgct gtctcgatag tattctggcc 7440
cgtagtcgtc gatgttttgt tgtatttgtt gggtggtgtg ttgtgtgttg agggagatga 7500
ttcgtgtgga ggcctcccag ggtgtcatgt cccctgatat gtagagggcg ggctggttga 7560
gcatcgctgt gatgaacatg gctagccctg atttttggct gccggaccgc cccgcgatca 7620
tcaccaagtc gcccttatgg atgtgcaaat cttggttatc atatagtggt gcgagttgtg 7680
gtatgcgggg tagttcggct gcggtttggg aggctctctc gaaggatcgt tgtagagaga 7740
gcatcgggac cttaatctat ctgtctgttg gttgtgtggc tggtcagatg gagtcgatat 7800
cgatatcagc atcagcagag gctgaagtgt catctagctg accattatcg cgcttgtcta 7860
cgtattcggc aaccttatcg tagatggcgt cgtccaatgt tttgagcacg accgcgttga 7920
aaccgttttt ggtgcgcacg gtggctagtt tgaaggcctg ctcctcgcca aggtatgcct 7980
ctagttcgcg gatcatggag tgtgggcggt cgttattgcc gcgggctttc tcaataatag 8040
cgttggggat ggtttctggg gtgccgttgt tgagatcgtc tagggtgtgg aagatggtga 8100
catcagcgta gatgcggtct gcgacctgtc caccgtagcc ttcagtgttg tgctggacgt 8160
cgtgcacttt gaaggcgatg gccgtggcgt cctggtttcg ggaggggttg aagaaggtgc 8220
tgttgctgtt gttgcggtag tttgcgagtc ccataactat tgtttccttt tactgttgtg 8280
tctgtttttg ttggcttata ttggtttatc gggtgaggct gtttcgctta gtgcggaaag 8340
cgtcggaaac atcactgtta ctggtgatga tcttcttgta ctgttttaga aggtctgcta 8400
gctgtgcctt gcttgttgca ttgttgattt tgttgatgac gatggtgttt tctttggatg 8460
cgattttgtt gacgtagtct ttggctgcct ggttgtatcg gtcttggagg atgattgatg 8520
cgctcgctac gagtgttgct agatcccagt ctttggacac gtcatcgttt ttgagtccgc 8580
ctagcaggtc gatgatggcc tgttttgtct gctctgctgt gtctcctcgg atgaccgccc 8640
atggtgcagc atagtctcca ccatatttga gtgtgatcgt gagtcgatca ttgtcgatct 8700
tgtctttatc tgtcatttgg tgtccttttc tttattgtct gtttctggtg gctgtacggt 8760

-continued

```
ggattctacc gggtatctgt acgagttttt gccgttgacg gcccagcagg cgtctcgtac   8820
ggggcatcct ttacagagtg ttgtgacgtg ggggacgaag atgccttcgc tgattccttt   8880
cattgcttga ctgtacatgg atgatacatg ccggtaggtg ttgttgtcaa ggtcgtagag   8940
ttcggtggat gtgccttgtg tcggggactt gtcgtcgttg cggctggtgg ctggcgtcca   9000
aaacatgcct ttcgtgacat ggatgtcgtg ttggttgagc atgtaccggt atgtgtgcag   9060
ctgcatactg tcggcgggta ggcgtccggt tttgaggtcg aggatgaagg tttcgccggt   9120
gtcggtgtcg gtgaaaacac ggtcgatgta gccgactatt tttgtgtcat cgtcgaggat   9180
ggtttctacc gggtattcga tgcctggttt accgtccagg attgcggtga tgtattctgg   9240
gtggttgcgc ctccatgttt tccagcggtc cacaaaggtg gggccgtaaa ccatccacca   9300
gtcgtagtct ttcttgtgtg gtccgcctga ctcgcacatg tttttgcata ttctgccgga   9360
gggtttgatt tctgtgcctt cggattcggc gagggctacc tgggtgtcga aaatgttttt   9420
gaaggatgag agtttgtctg gcagtgcagg gtattcggcg ggattgtaca ggtgtaggtc   9480
gtattgttcg gtgatgtggt gtatggcgct tccggcgatg gtggcgtacc aggtgtggtg   9540
ttgggcgtga tagccgtggg ataggcgcca tttttctccg cattcggccc actgggtgag   9600
tgaactgtag gagatgtgtc ctgggtggct gatggttttc gggtattgtg ctagaggcat   9660
tacttgtcgc ttgtgttcca tgtgttgcgg gtgtcttggc cggcgtggtg ttgctggtag   9720
gcgaggagtg cgaggcagtg ccaggctgcg tgtgctagat ggggtagccc ggattcgtgg   9780
tcgaggttgt tgccttgctg ccatgatagt agatgcctgt agagggcgtc gacactgtgg   9840
ctccacgggt atcctccggt ccagttgttg tcgccatatt tggtggcacc gtatccggct   9900
acttcgccta gggcgtgaag ggatgctggg tcgatgaggg agagcctgca gagtttcaat   9960
tcttttcggg caccgctgtt ggggtcggtg tacatgcggg tgggctcatc catggggtgt  10020
gtgctcctta agggtgggtt actggttgtt gttgtgggct agggcggcgg cgagaataat  10080
gatggcgagg gtttcggcta tcagtatggg tgttgtgatc atttggtgtc tcggggattg  10140
ttggtgagtg ttgaggcacc caggagggtg gcgagggcgc atgcggcaat aatggcgagg  10200
gctgccttgt gtggggtgcc ggttgcgtac atccatgtga tgatggcacc ttggatccag  10260
gctaggctgg tgaagaaggt ttcgtagctg tgcagctcaa tgttgttgtt gggtgtgttc  10320
atgcttgctc ctgaagaatg gtgttgatgg ttttataaat gttgtacagg tcggtttcga  10380
tagataacag ttggttgatt tggtggtcga gatcaatgtc tgggttgagt gtgttgatgc  10440
gggaggcaat atcggtggct gtgcgtagtg tgccgccggt gtggtgaata atgtgtgccg  10500
tgtcggcgag tccggtggtg acggcgtagt gggataggag aggcatagcg gggatgctcc  10560
ttggcgggtt actgttgcgg gttgatgttg aggtcggtga cgtgcggtga gttttctgtt  10620
ccggtgacga ggcagtggac ggtgacgggt agtttggatg ctcccggctg gcggacggtg  10680
gcgccgtaga cgatgctgaa tgtgtcttta ccgatggttt tgtggagttg gaggtcgatg  10740
tcggggttgc cgttccagtt gacaccttgc gctgcggcct gttgttcggc tttgtggttg  10800
caggtgtgtg ctgccgtgat catggtgagt ccggtggcgg tttcttcacc ccttgcttgg  10860
gcttgcttgt gggctttggc ctgctcggct tgtagggatc gggtggcggc tgcctgccgt  10920
gccgctttct cggctttgcg ctgttgggta gtcttggggg tccatgtggt gttggctgtg  10980
gttgcctgtg gggctggctg tgaggtgagt ggcgggttgt cgtctggtgc tggcatgaat  11040
gaggcggcgg caatgatggc ggctgtgatg cctgcgatgg tgtagccgtt tttcttgttc  11100
atgttttgtg tccccttcc ggggtgttgt tcgttgctga catggttaat actttcagcg  11160
```

gctgggccca ctgtcaaggc tgcgctcagt ttgtgtgagc gtttggtgtg tggctagggg 11220
ttttgtcatg taagcgtgac atgtcactac cttgcgtcca gtatccatgg cggttgcgag 11280
ccatcccttt ggcgagcatc tcgtccacag tgaggcacct gcggcgattg gggccttcct 11340
tgaccccgtg atcgcctatg cggtgcatgt ccccggcata agtgccatta aatgtttcgt 11400
ggcagactgt gcagtgttct ggtcggtatc cgatgattgt gctatcgcac ttgtggcatg 11460
tccattgcat gattggtcct tctttcgtgt tttaagcttg tgctctgagg attagagcga 11520
ctttcagccc ttgggggtag gattatatag gtcaggtatt tctaggcgat tctaggctca 11580
ttgtgtgtgg ttggggtttt atcgggcgca tagggttagc aggtggccca cattggtgcg 11640
gctcacattc cagtagagtt gcgtggcttc cttactggtg agcggcttcc actcgtcatg 11700
gctgaacacg gtgccatcgg atgcgatgaa cgtgttgggg cgtagcttgt gaagctcggc 11760
ttccacatgc tgccggtagg cttcggcgag gctctcaaaa tccatgtggt cgcaggagag 11820
gttttcgagg cgtgtcaggt cgaaaggctc cgggcagtcg tagctggctg gagtgtagag 11880
ctgggtgaag tggtcggcga tcttctgcat ggcgggttcc tttctggtgt gtggatggtt 11940
tttatcgtgt ggatgcgaca aggatggcgt ctacgtcgat catgtcgatc atgtcgttga 12000
gttcctcggc ctcattctcg gagaggtggc gccagtcggg tggcccgtat acggcgccgt 12060
cgagggtgac agtccacagg ggccggatga gtcgtatggc ttcttcgact ttggcgtggt 12120
acatgcggcg caccatatcc agatcgatgt cgtctgaatg gtttccggtg aggctgtgga 12180
ggctgagcgg gtcgatttct gtctgcctgt agaggctggt gaatgatggt gtgatgagtg 12240
tgccatccat gagtgtgctc ctttctaggg gttgttgtgg tttctagagt gtgtgggctg 12300
tgaccccaca gtcaaggcta cgctcatttg gattgagcgt ttcatatggg tgtggcatgg 12360
aatctacacc ctcatactgt gtgagatgta tcacatcccc ctggcttggt gtgcacccct 12420
caagactact ctgccgacct ggcgtggagg gtgtagccca gaaatgccgt ttaaagcttc 12480
aggggtacgc ctaggagcgc cttacagggt gggggctagg tatttatacc cccagcatat 12540
tctgatcgat tctagacgac tcccagagcc cgatacacga tcaaccatct cgacatagac 12600
catcagcccc tatcctggtt agctaagcct caactatgtg gacagtgtgg gacactgtgg 12660
gggaagaagg acacggtaca agaaagaggg gggagcatca gccttaaagc cttaagatct 12720
tagcgcttag caccgatggt cttagcagtt agcaccgagc ccttgagggg gctcggcatc 12780
agcctcatcg ggctcagctc atcaggcaca gccctgaaaa gggtacacgc catcagggaa 12840
ggcttgagag tacgaggagc cctagcgacg agtactcgaa agcctgaggg aacaccctca 12900
gtactgatga gcctagcgta ttcggaaagg acgcaagagt aaagtgtgac agctatccgg 12960
gagtgaaacc cgttccgact aggggtttca gccttaacca ccctcaaagg ttacaagact 13020
ctaagaaaat ttaagaaact tcttaggaag aaagttgtgt tcatatcccc ctaaaaacac 13080
ccaaaatagt cctcaaaccc gcctatagag ccaaacagtc aagtttgact cgtctagacg 13140
gcgtatgata ggctggacag gtagccagct ggacgcaagg ccagaaagtg ctgacgcact 13200
tcccgacctc gcttaccatc agtctaccaa acactttaaa gcttcaaggc ttagcgctaa 13260
gcccttaaga tcttaacgct tagcaccgag cccccctcaa gggctcgaca tcagtcttaa 13320
agtcttaaac actttaagta actttaaagc ttcaaggctt agcccttaag gatctaagtt 13380
actataaaag ctttaaacac ttaaagtaac tataaagctt taagagctta acatttaagg 13440
atataaataa acattaaagc tttaaagtct taaagtaaat atataacctt aacacttaag 13500

```
ttaagtataa aaccttaaag gcttagcact taaggatata aacttaacat cagtgtttaa  13560
gacttaaaga gttaaagtaa ctattaagac ttaaaggctt ataagcttta atactttaag  13620
tagctataag actttaaaaa cctgaagtac ttaaagttaa ccatcagtct taaactttaa  13680
tattataagt attaaagctt ataagttata aaagttttta gaagagttaa agggttaact  13740
tctttacttc tcttctctct ttggttcttt ctctcttctc ttcttttctt catcagggga  13800
gaagaggaac ctttaaccgt caacgctgat ggacttttca ccgtgtgact cgtgtgcttc  13860
tggtcgcaag ctcccatcgc acactcccca cactctttca cccgtgcccc tttacggctt  13920
agcgtgttcg tcggaaggcg tacggcgtgt cacgcttaaa cccttaacac caggtaagac  13980
ttaaagtgca tattataagt agaagacttt aaaacctata aggtgttccc gcttagcccg  14040
tgttccttta acgctaggcg ctcagcgcta agatgtgaaa cgtgaacacc catccacccc  14100
catttttctt ccgtgtcctt ctccttttga caccgctggg gggcgatgtg atatttctca  14160
catgccaggg ggtagtggag aaaacaacca ccccggaacg tttaagacac cccctcaaac  14220
gaacaaaaca gggcctagaa tcgatcagca gggcaccggt agggtattcc tacccccaga  14280
cgattcaagg ccattacagg agcaatgaga ggctcacagg ggccatggga gattgggggg  14340
cgtgatggca cacaccaacc gcacagccag ccaagcccac cggcgctggc gggcaaggct  14400
catcacccaa gcccgacaac aaggccaaac cgaatgccca ctctgcggag tcaccatcac  14460
ctggaacacc cacgacctgc caaccagccc cgaagccgac cacatcacac ccgtcagccg  14520
gggaggactc aacaccctcg acaacgggca aatcatctgc agaacatgca acagaagcaa  14580
aggcaacaga acacaaccaa acatcaaatt ccaacaacaa accacaaaaa cattgattcc  14640
atggtgaaaa acccgccaac ccccaccggg cacacccccct gcacacccgt gcaagacctc  14700
gtacggctta gtgaaatacc tcccttttgt tgttttatcg ttttgtcgac tttttgtttg  14760
gtggtgtgtg tggtgcagcc tgagcttcct gatagtcgtg attggtgtgg ggagacgcgt  14820
cggtggtggt gtgtgtgggg cgaggatccg cgtgccgggt ttgtgtctga tgaggagtgg  14880
ttgtttctca tggatgctgc ggtgattcat gatgtggtgt ggcgtgaggg tcgcgcggat  14940
ttggtggctt cgttgcgtgc tcatgtgaag gcttttatgg gtatgttgga taggtattcg  15000
gttgatgtgg cgtctggtgg ccgtggtggg ggttctgcgg tagcgatgat tgaccggtat  15060
aggaagcgta ggggggcttg agtaggtgtc tggtgttgtt gggtctcagg ttcctcgtca  15120
ccgggtggct gtggcgtatt cggtgtctgc tggcggggat gctggggagc ttggtagggc  15180
ttatgggttg acgcctgatc cgtggcagca gcaggtgttg gatgattggc ttgctgtggg  15240
tggtaatggc aggcttgctt cgggtgtgtg tggggtgttt gttccgcggc agaatggcaa  15300
gaatgctatt ttggagattg tggagttgtt taaggcgact attcagggtc gccgtatttt  15360
gcatacggct cacgagttga agtcggctcg taaggcgttt atgcggttgc ggtcgttttt  15420
tgagaatgag cggcagtttc ctgacttgta tcgtatggtg aagtcgattc gtgcgacgaa  15480
tggccaggag gctattgtgt tgcatcatcc ggattgtgcc acgtttgaga agaagtgtgg  15540
ttgtccgggt tggggttcgg ttgagtttgt ggctcgtagc cggggttctg ctcgcgggtt  15600
tacggttgat gatttggtgt gtgatgaggc tcaggagttg tcggatgagc agttggaggc  15660
tttgcttcct accgtgagcg ctgccccgtc tggtgatcct cagcagattt ttttgggtac  15720
gccgccgggg ccgttggctg acgggtctgt ggtgttgcgt cttcgcgggc aggctttgtc  15780
gggtggtaaa cggtttgcgt ggacggagtt ttcgattcct gacgagtctg atccggatga  15840
tgtgtcgcgg cagtggcgga agttggcggg tgacactaat ccggcgttgg ggcgccgcct  15900
```

-continued

```
gaatttcggg acagtctcgg atgagcatga gtcgatgtct gctgccgggt ttgctcggga  15960
gcggcttggc tggtgggatc gtggccagtc tgcttcgtct gtgattccgg cggataagtg  16020
ggttcagtcg gctgtggttg aggcggctct ggttggcggg aaggtttttg gtgtctcgtt  16080
ttctcgctcg ggggatcgtg tcgcgttggc tggtgctggt aaaacggatt ctggtgtgca  16140
tgttgaggtt attgatggcc tgtctgggac gattgttgat ggtgtgggcc agctggctga  16200
ttggttggcg ttgcgttggg gtgacactga aaaggttatg gttgcagggt ctggtgcggt  16260
gttgttgcag aaggctttga cggatcgtgg tgttccgggt cgtggcgtga ttgtggctga  16320
tactggggtg tatgtggagg cgtgtcaagc cttcctggag ggtgtcaggt ctgggagcgt  16380
gtctcatcct cgtgccgatt cgaggcgtga catgttggat attgctgtga ggtcggctgt  16440
gcagaagaag aagggttctg cgtggggttg gggttcctcg tttaaggatg gttctgaggt  16500
tcctttggag gctgtgtctt tggcgtatct tggtgcgaag atggcgaaag cgaagcggcg  16560
tgaacggtct ggtaggaagc gggtgtctgt ggtatgaact cggatgagtt ggctctgatt  16620
gagggcatgt acgatcgtat tcaagggttg tcttcgtggc attgccgtat tgagggctac  16680
tatgagggct ctaatcgggt gcgtgatttg ggggttgcta ttccttcgga gttgcagcgg  16740
gtgcagacgg tggtgtcatg gcctgggatt gcggtggatg ctttggagga gcgtctggat  16800
tggcttggct ggactaatgg tgacggctac ggtttggatg gtgtgtatgc tgcgaatcgg  16860
cttgctacgg cgtcgtgtga tgttcacctt gatgcactga tttttgggtt gtcgtttgtg  16920
gcgatcattc cccaagagga tgggtcggtg ttggttcgtc ctcagtcgcc gaagaattgt  16980
actggccggt tttctgccga tggtcttgt ttggatgctg gccttgtggt gcagcagacg  17040
tgtgatcctg aggttgttga ggcggagttg ttgcttcctg atgtgattgt tcaggtggag  17100
cggcggggtt cgcgtgagtg ggttgagacg ggccgtatcg agaatgtgtt gggtgcggtt  17160
ccgttggtgc ctgttgtgaa tcgtcgccgt acttctagga ttgatggccg ttcggagatt  17220
acgaggtcta ttagggctta cacggatgag gctgttcgca cactgttggg gcagtctgtg  17280
aatcgtgatt tttatgcgta tcctcagcgt tgggtgactg gcgtgagcgc ggatgagttt  17340
tcgcagccgg gttgggttct gtcgatggct tctgtgtggg ctgtggataa ggatgatgat  17400
ggtgacactc cgaatgtggg gtcgtttcct gtgaattctc ctacaccgta ttctgatcag  17460
atgcgtttgt tggcgcagtt gactgcgggt gaggcggctg ttccggaacg ctatttcggg  17520
tttatcactt ctaacccgcc ttctggggag gctttggctg cggaggagtc tcggcttgtg  17580
aagcgtgctg aacgcaggca gacgtcgttt ggtcagggct ggctgtcggt tggtttcctg  17640
gctgcccggg cgttggattc gagtgttgat gaggccgcgt tttttggtga tgttggtttg  17700
cgttggcgtg atgcgtcgac gccgactcgg gcggctacgg ctgatgctgt gacgaagctt  17760
gtgggtgctg gtattttgcc tgctgattct cggacggtgt tggagatgtt gggtttggat  17820
gatgtgcagg ttgaggctgt gatgcgtcat cgtgccgagt cttcggatcc gttggcggca  17880
ctggctgggg ctatttcccg tcaaactaac gaggtttgat aggcgatggc ttcgggtgct  17940
gtgtcgaggc ttgctgcgac tgagtatcag cgtgaggctg tcaggtttgc tgggaagtat  18000
gcgggctatt atgccgagtt gggtcgtttg tggcgtgccg gcaggatgag tgacacgcag  18060
tatgtgcgtt tgtgtgtgga gttggagcgt gccggccatg acggttcagc agctatggcg  18120
ggcaaattcg tttcagattt tcgccggttg aatggtgtcg atcctggttt gatcgtgtat  18180
gacgagtttg atgctgcggc ggctttggct aggtcgtttt cgactatgaa gattatgaat  18240
```

-continued agtgacccgg atagggcgaa tgatacgatt gatgcgatgg ctgcgggtgt taatcgggct 18300
gttatgaatg ctggtcgtga cacggttgag tggtcggcgg gtgcgcaggg taggtcgtgg 18360
cgtcgggtga ctgatggtga tccgtgtgct ttttgtgcca tgttggctac gaggtcggat 18420
tatacgacta aagagcgggc gcttactact ggtcatacgc ggcgtcataa gcgtgccggt 18480
aggcgtccgt ttggttcgaa gtatcatgat cattgtggtt gtacggtggt tgaggttgtt 18540
ggtccttggg aaccgaatag ggctgatgcc gagtatcaga ggacgtatga gaaggctcgt 18600
gagtgggttg atgatcatgg gttgcagcag tcgtctggca atattttgaa ggctatgcgt 18660
actgttggtg gcatgagata atttgatgtg gtttccggtt gtgtgccgcc ggttatcggt 18720
gcacagggtt gtctcccgca cgggggtcaa caatgttgtg ttgttttccg caaggagtgt 18780
agggttaggc tatggccgat cagagtattg aggaacagaa tgttgacaat gatgttgtgg 18840
agtccggaaa ggataacggc attgttgata cagtaaaaga cgatggcggg caggaggtag 18900
ccgacaatca gttgaagaat gaaggcgagg gtaaatcgcc ggggactgat tggaaggcgg 18960
aggcccgtaa gtgggagtct cgtgctaaaa gtaatttcgc cgagttggag aagcttcgta 19020
catcgagtga cgattctgga tctactattg atgagcttcg ccgcaagaat gaggaactcg 19080
aagaccggat taacgggttt gttcttgagg gtgtgaagcg cgaggtggct gccgagtgtg 19140
gcctgtcggg tgatgcgatc gcttttcttc acggtagcga taaggagtcg cttgccgagt 19200
ctgctaaggc tttgaagggt ttgatcgacc atagtagtgg tggtggcgcg ggtgtgcgcc 19260
gtcttgcggg gagtgccccc gttgatgatg ttaaacgacg tgagggtgtc gcgtttgtgg 19320
atgctcttgt caataattct aggagatgat ttatcatggc tgacgatttt ctttctgcag 19380
ggaagcttga gcttcctggt tctatgattg gtgcggttcg tgaccgtgct atcgattctg 19440
gtgttcttgc taaactgtca ccggagcagc cgactatttt cgggcctgtt aagggcgccg 19500
tttttagtgg tgttccgcgc gctaagattg ttggcgaggg cgatgttaag ccttccgcta 19560
gcgttgatgt ttctgcgttt actgcgcagc ctatcaaggt tgtgactcag cagcgtgtct 19620
cggacgagtt tatgtgggct gacgccgatt accgtctggg tgtgcttcag gatctgattt 19680
ccccggccct gggtgcttct attggtcgcg ccgttgatct tattgctttc catggtattg 19740
atcctgctac gggtaagcct gctgcggctg tcaaggtgtc gctggataag acgaataaga 19800
cggttgatgc caccgattcc gctacggctg atcttgttaa ggctgttggt ctgattgctg 19860
gtgctggttt gcaggttcct aacggtgttg ctttggatcc ggcgttctcg tttgctctgt 19920
caactgaggt gtatccgaag ggttcgccgc ttgccggtca gccaatgtat cctgccgccg 19980
ggttcgccgg cctggataat tggcgcggcc taaatgttgg ttcttcttcg actgtttctg 20040
gtgccccgga gatgtcgcct gcttctggtg ttaaggctat tgttggtgat ttctctcgtg 20100
tccattgggg gttccagcgt aacttcccga ttgagctgat cgagtatggt gacccggatc 20160
agacggggcg tgacttgaag ggccataatg aggttatggt tcgtgccgag gctgtgctgt 20220
atgttgcgat tgagtcgctt gattcgtttg ctgtcgtgaa ggagaaggct gccccgaagc 20280
ctaatccgcc ggccggtaac tgattcattt gttgcgataa tgtttatgct gtgtgcaggg 20340
ggtggtgttg atgggtatca ttttgaagcc tgaggatatt gagcctttcg ccgatattcc 20400
tagagagaag cttgaggcga tgattgccga tgtggaggct gtggctgtca gtgtcgcccc 20460
ctgtatcgct aaaccggatt tcaaatatag ggatgccgct aaggctattc tgcgtagggc 20520
tttgttgcgc tggaatgata ctggcgtgtc gggtcaggtg cagtatgagt ctgcgggccc 20580
gtttgctcag actacacggt cgaatactcc tacgaatttg ttgtggcctt ctgagattgc 20640
cgcgttgaag aagttgtgtg agggtgatag tggggctggt aaggcgttca ctattacacc 20700
gaccatgagg agtagtgtga atcattctga ggtgtgttcc acggtgtggg gtgagggttg 20760
ctcgtgcggg tcgaatatta acggctatgc tggcccgttg tgggagatat gatatgaccg 20820
gttttcctta cggtgaaacg gttgtgatgc ttcagccgac tgttcgtgtc gatgatcttg 20880
gtgacaaggt ggaggattgg tctaagcctg tcgagactgt gtaccataac gtggccatct 20940
atgcttccgt ttcgcaggag gatgaggccg cggggcgtga ctcggattat gagcattgga 21000
cactgctgtt caagcagcct gtcaaggctg ctggttatcg gtgtcgttgg cgtattcggg 21060
gtgttgtgtg ggaggctgac gggtctccta tggtgtggca tcatccgatg tctggctggg 21120
atgctggtac gcaggttaat gtgaagcgta agaagggctg atgggttgtg gcacgtgatg 21180
ttgatgtgaa gctgaacttg ccgggtattc gtgaggtgtt gaagtcttct ggggtgcagg 21240
gcatgttggc tgagcgtggt gagcgtgtca agcgtgcggc ctcggcgaat gtgggcggta 21300
acgcttacga tagggcccag tatcgtgccg ggttgtcgtc tgaggtgcag gttcaccgtg 21360
ttgaggctgt ggcgcgtatt ggcaccacct ataagggtgg taaaaggatt gaggctaagc 21420
atggcacgtt ggcgaggtcg attggggctg cgtcgtgatc gtttacggtg atcctcgaat 21480
atgggctaaa cgtgtgttgg cggatgatgg ttggctgtct gatgtaccgt gcacgggtac 21540
tgtgccggat acatttgagg gtgatctgat ttggttggcg ttggatggtg gcccggagtt 21600
gcatgttcgt gagcgtgttt ttttgcgtgt gaatgtgttt tcggatacgc cggatcgtgc 21660
tatgtctttg gctcgccggg ttgaggctgt gctggctgat ggtgtggatg gtgatccggt 21720
ggtgttttgc aggcgttcga ctgggcctga tttgctggtg gatggtgcac gttttgatgt 21780
gtattcgctt tttgagctga tatgtaggcc tgcggagtct gaataagctt attgtttttg 21840
ttttaatgta attgtttgat atttaatggg ggttgtgatg gctgctacac gtaaagcgtc 21900
taatgttcgt tcagcggtta ctggcgacgt ttatattggt gacgcgcacg cgggtgattc 21960
tattaagggt gtggaggcgg ttccttccgg gcttacagct ttggggtatc tgtctgatga 22020
cgggtttaag attaagcctg agcgtaaaac ggatgatttg aaggcttggc agaatgcgga 22080
tgttgttcgc actgtggcta cggagtcgtc tatcgagatt tctttccagc tgattgagtc 22140
gaagaaggag gttatcgaac tgttttggca gtcgaaggtt actgccggat ctgattcggg 22200
ttcgttcgat atttctcctg gtgccacaac aggtgttcac gccctgttga tggatattgt 22260
tgatggcgat caggttattc gctactattt ccctgaggtt gagctcattg atcgtgacga 22320
gattaagggc aagaatggcg aagtgtacgg gtatggtgtg acgttgaagg cgtatcctgc 22380
ccagattaat aagactggta atgcggtgtc gggtcggggg tggatgacgg ctttaaaagc 22440
tgatactcct ccgactcctc cgccggcccc ggttcctccg aagcctcagc cggatccgaa 22500
tccgccgtcc ggtaactgat acacgatttt aggggattgt taatagatga gtgacactgg 22560
tttcacgttg aagattggtg atcgtagctg ggtgttggcg gatgcggagg agacggctca 22620
ggctgttcct gcccgcgttt tccgtcgtgc cgccaggatt gcccagtcgg gggagtctgc 22680
ggatttcgcc caggttgagg tgatgttttc tatgttggag gctgccgccc cagctgacgc 22740
ggtggaggcc ctggaggggc ttcctatggt tcgtgtggcg gaggttttcc gtgagtggat 22800
ggaatacaag cctgacggta agggtgcctc gctgggggaa tagtttggct ccacggcctg 22860
attgatgatt atcgtggggc catcgaatac gatttccgca ccaagtttgg tgtttctgtt 22920
tatagtgttg gtggcccgca gatgtgttgg ggtgaggctg tccggctggc tggcgtgttg 22980

```
tgtaccgata cgtctagcca gttggcggcc caccttaatg gttggcagcg cccgtttgag  23040
tggtgcgagt gggctgtgtt ggacatgttg gatcattaca ggtctgctaa tagtgagggg  23100
cagccggagc ctgtggcgag gccgactgat gagcgtcggg caaggtttac gtctgggcag  23160
gtggacgata ttttggcgcg tgttcgtgcc ggtggcgggg tgtctcgcga gattgatatt  23220
atggggtgaa tagtgtatgt ctggtgagat tgcttccgca tatgtgtcgt tgtatacgaa  23280
gatgcctggc cttaaaagtg atgttggtaa acagttgtcg ggtgttatgc ctgctgaggg  23340
gcagcgttcg ggtagcctgt ttgctaaagg catgaagttg gcgcttggtg gtgcggcgat  23400
gatgggtgcc atcaatgttg ctaagaaggg cctcaagtct atctatgatg tgactattgg  23460
tggcggtatt gctcgcgcta tggctattga tgaggctcag gctaaactga ctggtttggg  23520
tcacacgtct tctgatacgt cttcgattat gaattcggct attgaggctg tgactggtac  23580
gtcgtatgcg ttgggggatg cggcgtctac ggcggcggcg ttgtctgctt cgggtgtgaa  23640
gtctggcggt cagatgacgg atgtgttgaa gactgtcgcg gatgtgtctt atatttcggg  23700
taagtcgttt caggatacgg gcgctatttt tacgtctgtg atggctcgcg gtaagttgca  23760
gggcgatgac atgttgcagc ttacgatggc tggtgttcct gtgctgtctt tgcttgccag  23820
gcagacgggt aaaacctcgg ctgaggtttc gcagatggtg tcgaaggggc agattgattt  23880
tgccacgttt gcggctgcga tgaagcttgg catgggtggt gctgcgcagg cgtctggtaa  23940
gacgtttgag ggcgctatga agaatgttaa gggcgctttg ggctatttgg gtgctacggc  24000
tatggcgccg tttcttaacg gcctgcggca gatttttgtt gcgttgaatc cggttattaa  24060
gtctatcacg gattctgtga agccgatgtt tgctgccgtc gatgctggta tccagcggat  24120
gatgccgtct attttggcgt ggattaaccg tatgccggct atgatcacga gaatgaatgc  24180
acagatgcgc gccaaggtgg agcagttgaa gggcattttt gcgagaatgc atttgcctgt  24240
tcctaaagtg aatttgggtg ccatgtttgc tggcggcacc gcagtgtttg gtattgttgc  24300
tgcgggtgtg gggaagcttg ttgcagggtt tgctccgttg gcggttgcgt tgaagaatct  24360
gttgccgtcg tttggtgctt tgaggggtgc cgccgggggg cttggtggcg tgtttcgcgc  24420
cctgggtggc cctgtcggga ttgtgatcgg cttgtttgcg gcaatgtttg ccacgaacgc  24480
ccagttccgt gccgctgtta tgcagctggt ggctgtggtt ggtcaggcgt tgggccagat  24540
tatggcagct gtgcagccgc tgtttggttt ggttgctggc gtggttgcca ggttggcgcc  24600
ggtgttcggc cagattatcg gtatggttgc tggtttggct gcccggctgg tgcctgttat  24660
tggtatgctt attgcccggc tggttcctgt tatcacccag attattggta tggtaaccca  24720
ggttgctgcc atgttgttgc ctatgctgat gccggttatt caggctgttg ttgctgtgat  24780
acggcaggtt attggtgtca ttatgcagtt gatacctgtt ttgatgccgg ttgtgcagca  24840
gattttgggt gctgtcatgt ctgttttgcc gccgattgtt ggtttgatac ggtcgctgat  24900
accggtgatc atgtcgatta tgcgtgtggt ggtgcaggtt gttggtgctg tgctacaggt  24960
ggtggcccgt attattccgg ttgttatgcc gatttatgtt tcggtgattg gattcattgc  25020
caagatttat gctgcggtta tcgtttttga ggctaaggtt attggcgcta ttcttcgtac  25080
tattacgtgg attgtgaatc attcagtgtc tggcgtgagg tctatgggca cggccatcca  25140
gaatggctgg aatcatatta aatcgtttac gtctgcgttt attaacggtt ttaagtcgat  25200
catttctggc ggcgtgaacg cggttgtggg gtttttttacg cggcttggtt tgtcggttgc  25260
ttcccatgtg aggtccggtt ttaacgctgc gaggggtgct gtttcttccg ccatgaatgc  25320
tattcggagt gttgtgtctt cggtggcgtc tgctgttggc gggtttttca gttcgatggc  25380
```

gtctcgtgtt cggaatggtg ctgtgcgcgg gtttaatggt gcccggagtg cggcttcttc 25440
tgctatgcat gctatggggt ccgctgtgtc tagtggtgtg catggtgtgc tgggtttttt 25500
ccggaatttg cctgacaata ttcggcgtgc gcttggtaat atggggtccc tgttggtgtc 25560
ggctggccgt gatgtggtgt ccggtttagg taatggtatc aagaatgctt tgagtggcct 25620
gttggatacg gtgcgtaata tgggttctca ggttgctaat gcggcgaagt cggtgttggg 25680
tattcattcc ccgtctcggg tgtttcgtga cgaggttggc cggcaggttg ttgccggttt 25740
ggctgagggt attactggta atgctggttt ggcgttggat gcgatgtcgg gtgtggctgg 25800
gaggctgcct gatgcggttg atgcccggtt tggtgtgcga tcgtctgtgg gttcgtttac 25860
cccgtatggc aggtatcagc gcatgaatga taagagtgtt gtggtgaatg tgaatgggcc 25920
tacttatggg gatcctgccg agtttgcgaa gcggattgag cggcagcagc gtgacgcttt 25980
gaacgcgttg gcttacgtgt gattttgggg gtgtggtgca tgtttattcc tgacccgtct 26040
gatcgttctg gtttgactgt gacttggtct atgttgccgt tgattggtaa tgatccggag 26100
cgtgtgcttc atttgacgga ttatacgggg tcgtctccga taatgttgtt gaatgattcg 26160
ttgcgcggtt tgggtgttcc tgaggtggag catttttctc aaactcatgt tggggtgcat 26220
ggctcggagt ggcgcgggtt taatgtgaag cctcgcgagg tgacgctacc ggtgttggtg 26280
tcgggtgttg gcccggatcc ggtgggcggt tttcgtgacg gtttttgaa ggcgtatgac 26340 gagttgtggt ctgcttttcc tcctggcgag gtgggggagt tgtctgtgaa gactcctgcc 26400
ggtcgtgagc gtgtgttgaa gtgccggttt gattcggtgg atgacacgtt tacggtggat 26460
ccggtgaaca ggggttatgc gcgttatctg ttgcatttga cggcttatga cccgttttgg 26520
tatggggatg agcagaagtt tcgtttcagt aacgctaagt tgcaggattg gttgggtggc 26580
ggccctgtcg acggtaaggg taccgcgttt ccggtggtgt tgacgcctgg tgttggttcg 26640
ggttgggata atctgtctaa taagggtgat gtgcctgcgt ggcctgtgat tcgtgttgag 26700
gggccgttgt cgtcgtggtc tgtgcagatt gatggtttgc gtgtgtcctc ggattggccg 26760
gtggaggagt atgattggat cactattgat acggatcctc gtaagcagtc tgcgttgttg 26820
gacgggtttg aggatgtgat ggatcgtttg aaggagtggg agtttgcgcc tatcccgcct 26880
ggcggttctc ggagtgtgaa tattgagatg gttggtttgg gtgccattgt tgtgtcggtg 26940
cagtacaggt tttgagggc ttggtgaata gttgatggct ggttttgttc cgcatgtaac 27000
attgtttaca ccggattatc gccgtgtggc gcctatcaat ttttttgagt cgttgaagtt 27060
gtcgttgaag tggaatggtt tgtccacttt ggagttggtg gtgtctggtg atcattctag 27120
gcttgacggg ttgactaggc cgggtgcgcg gcttgtggtt gattatggtg gtggccagat 27180
tttttctggg cctgtgcgtc gggtgcatgg tgtgggtccg tggcgttctt cgcgtgtgac 27240
tatcacgtgt gaggatgata ttcgtctgtt gtggcgtatg ttgatgtggc ctgtgaatta 27300
tcgtcctggt atggttggta tggagtggcg tgcggatcgg gattatgccc attattcggg 27360
tgcggcggag tcggtggcta agcgggtgtt gggggataat gcttggcgtt ttccgtctgg 27420
tttgtttatg aacgatgatg agagtcgtgg ccgctatatt aaggattttc aggtgcggtt 27480
tcacgtgttt gccgataagt tgttgccggt gttgtcgtgg gctcggatga ctgtcacggt 27540
gaaccagttt gagaatgcga agtttgatca gcgtggtttg gtgtttgatt gtgtgcctgc 27600
tgtgacccgg aaacatgtgt tgactgccga gtcgggttcg attgtgtcgt gggagtatgt 27660
gcgtgacgcc ccgaaggcga catctgtggt ggttggtggc cgtggcgagg gtaaggatcg 27720
gctgttttgt gaggatgttg attcggcggc cgaggatgat tggtttgatc gtgtcgaggt 27780
gtttaaggat gcccgtaaca cggattccga gaaggtgtct ctcttcgatg aggctgagcg 27840
ggtgttgtcc gagtcggggg ctacgtcggg gtttaagatt gagttggctg agtcggatgt 27900
gttgcggttt ggtcccggca atctgatgcc tggggatttg atctatgtgg atgtgggttc 27960
tgggcctatt gcggagattg tgcggcagat tgatgtggag tgtgtatcgc ctggtgatgg 28020
ttggacgaag gtgactccgg ttgcggggga ttatgaggat aatccgtcgg ccctgttggc 28080
tcgccgtgtg gctggtttgg ctgcgggtgt gcgggatttg caaaagtttt agtaagtgat 28140
tggggtttgt tgtgggtatt gtgtgtaaag ggtttgatgg tgtgttgacc gagtatgatt 28200
gggctcaaat gtctggtctg atgggtaata tgccgtctgt gaaggggcct gacgattttc 28260
gtgtcggcac gacgattcag ggttctacgg tgttgtgtga gatcctgccg gggcaggctt 28320
gggctcacgg ggtgatgtgc acgtcgaata gtgttgagac ggtgacgggt cagcttccgg 28380
gcccgggtga gactcgatac gactatgtgg tgttgtctcg ggattggcag gagaatacgg 28440
ccaagttgga gattgttccc ggtgggcgtg cggagcgtgc cagggatgtg ttgagggctg 28500
agcctggcgt gtttcatcag cagctactgg cgactttggt gttgtcgtct aacgggttgc 28560
agcagcagtt ggataggcgt gctgtggcgg ctagggttgc gtttggggag tctgctgcgt 28620
gtgatcctac ccctgtggag ggtgaccgtg tgatggttcc ttcgggggct gtgtgggcta 28680
accatgccgg cgagtggatg ttgttgtctc ccaggattga gacgggttcg aagtcgatca 28740
tgtttggtgg ttctgctgtg tatgcttaca cgatcccgtt tgagcgccag ttcagtagtc 28800
cgcctgttgt ggtggcgtct atggctacgg cggctggggg cacggcacag attgatgtga 28860
aagcctacaa tgtgactgcc caaaatttta gtttggcgtt tattacgaat gatggttcga 28920
agccgaatgg tgtgcctgcg gtggcgaatt ggattgctgt cggcgtgtga ctgcacgggt 28980
gttgtggcgg atggtgtgat gttggggggc tgtggtgtcg tggtttactc ctgcactggt 29040
ggcctctatt tgtaccgcgt tggccacggt tttgggttct gttcaggctg tcacatcccg 29100
gtctaggaag cgtttacgca ggctgtcggc tcaggtggat gcgatggaag agtatacgtg 29160
gggtgtgcgg cgcgaggtgc gaaggtttaa cgccgggctt cctgatgatg tggagccgat 29220
gcatcttcct gatttgcccg agtttttgaa agatactgtt gatggtggag gtgagtaggg 29280
ttgagggagt tggaggagga gaagcggcag cgccgcaatt ttgagaaggc ttcactggtg 29340
ttgttgtttt tgtcgcttgt gttgttggcg gtggttgctg cgggtgcttt gcgtttcggg 29400
gctgtatcct ctgagcggga ttcggagcag gcgagggccc agtcgaatgg tacggctgcc 29460
aggggtttgg ctgcccgtgt gaagcaggcg tgtgcttcgg gtggggtgga gtctgtgcgt 29520
cttcaccgtt ctggtttgtg tgtggatgct gtgcgtgttg agcagcgtgt tcagggtgtg 29580
ccgggtcctg ccggtgagcg cggcccgcaa ggcccttcag gtcctgccgg ccgggatggt 29640
gttaatggtt cggctgggct ggttggccct gttggtccgc aaggttctcc gggtttgaat 29700
ggtgtgaaag gtcctgacgg cttgcctggc gctaacggtt cggatggccg tgatggtgtt 29760
ccaggtcg 29768

<210> SEQ ID NO 69
<211> LENGTH: 29238
<212> TYPE: DNA
<213> ORGANISM: Artificial Sequence
<220> FEATURE:
<223> OTHER INFORMATION: PAC1

<400> SEQUENCE: 69

-continued

```
tagcgtacag ggtgtgccag gtcccgccgg tgagcgcggc ccgcaagggc cggctggtgc     60
tgatggtcgg gatggtgtta atggttcgac tgggctggtt ggccctgtgg gtccgcaggg    120
ttctcctggc ttgaatggtg tggctggccc ggacgggttg cctggtgcga acggatcgga    180
tggccatgat ggtgttccag gtcgtgcagg tgctgacggt gtgaacggcg ctgatggtcg    240
ggatggttcg gccggtgagc gcggtgatgt gggcccttca ggtcctgccg gcccgcaagg    300
tgcacagggt gaacggggtc ctattgggcc tcagggtccg cagggttctg ccggtgctga    360
cggcacgaat ggtaaagacg gtaaagatgg gcgctcggtt gtgtctgtgt actgttccga    420
gggccgcctg gttgtgaaat atagtgacgg tgtggcttct acaatatcga gctcggtggc    480
ctgccagggt gtgaaaccgt cgcctatagt gactatatca tcccacaagt aaaaaagaaa    540
agggaagggt gttactagtg ttgattgtgg tgttaggtgg tgtgtggtga gatacattcc    600
tgcggcgcat cattctgccg gctcgaatag tccggtgaat agggttgtga ttcatgcgac    660
gtgcccggat gtggggtttc cgtctgcctc gcgtaaaggg cgggcggtgt ctacagcaaa    720
ctatttcgcg tccccatcgt cgggtggttc ggcgcattat gtttgcgata ttagtgagac    780
ggtgcagtgc ttgtcggagt ctacgattgg gtggcatgcc ccgccgaatc cgcatagttt    840
gggtatcgag atttgcgcgg atgggggttc gcacgcctcg ttccgtgtgc cggggcatgc    900
ttacactcgg gagcagtggc ttgatcctag ggtgtggcct gcggtggaga aggctgccat    960
cctgtgtaga cgtttgtgtg acaaatataa tgttccgaag aggaagctta gtgcagccga   1020
tttgaaggct ggtaggcggg gcatctgcgg gcatactgat gtgacggatg cgtggcacca   1080
gtcggatcat gacgatcctg ggccgtggtt tccgtgggac aggtttatgg ccgtcgtcaa   1140
cggcaaagat gagagtgggg agttaacggt ggctgatgtg aaagccttgc atgatcagat   1200
taaacaattg tctgcccagc ttactggttc ggtgaataag ctgcaccatg atgttggtgt   1260
ggttcaggtt cagaatggtg atttgggtaa gcgtgttgac gccttgtcgt gggtgaagaa   1320
tccggtgacg gggaagctgt ggcgcacaaa ggatgctttg tggagtgtct ggtattacgt   1380
gctggagtgt cgcagccgca tcagtaggct ggagtctact gtcaacgatt taaagaagtg   1440
atctatggtg ggtaaacagt tttggttggg cttgtttgag cgtgccctga aaacttttat   1500
tcaaacgttt gttgctgtgt tgggtgtgac tgcgggtgtc acttatactg cggagtcgtt   1560
tcgcggtttg ccgtgggagt ctgctctgat tacggccggg gttgctgcaa tactgtcggt   1620
tgctacctcg tttggtagcc cgtcgtttgt ggctggcaaa cctaaaacta cggttgtgga   1680
tgcgggtttg gttccaccgg atgatggggg cttggttgag ccgcacatgg tggatgtgtc   1740
ggatcctggc atgatcgagc ctgcagatga tgcggatctt ggtgtaggct atgtgccgaa   1800
acacgctgcc gagtcggagg ttggcacggt agagtctact gttgcataat tgaatatgtg   1860
tgtgccccag cggtgctgcc acgatcgtgt ggtggttgcc gctggggcac tatttttgta   1920
tattgcggtg tggctatgat tcgttgctgt cgatggtgtc ttcgagcatc tgatacaggt   1980
ggaggcaggt agagatagtt tcgctggcct ggtctagaac gttccggccg ataacatttt   2040
tgtgattgtc gcggtggcgg atgatagccc acatgatctc gtcggctgcc gcttgcaata   2100
gttttgactg gtatgcgatt ccggcgagcc agtctatggc ttccgggctt gccggtgtgt   2160
cgtctggaat gccacaggtg ttgctgttgt ttgtggggta tcctgcactg tcgcaaaacc   2220
acaggatttc gctgcactcg tctagcgtgt cctggtcgat agcaagatcg tcgaggctga   2280
cttcgttgac ggtaaggttc acgttgtcga gggagatggg tacaccgtac tggttttcga   2340
```

-continued

```
cactgtcaac aatgttttcc agctgttgca tgttggtggg ctgttgttgg acgatacggt   2400
gtatcgctgt gttgagggtg gtgtaggtga tattgtgtgt gttgttcatg gttttattcc   2460
atctctgtgc tgtcgtcttg gtcgtatcga ctgtttgcgt agcctgtgag ggtgatgagt   2520
gtttggtctg cccattgttt cactgtttgc cgggtgacac ccaatcgttg ggcggctgtg   2580
gcgtaggttt ggtcgtatcc gtatacttct cggaatgctg ccagccgtgc taaatgtttt   2640
cgctgtttgg atggctggca ggtgagggtg tagtcgtcga tggctagctg tagatcgatc   2700
atggcgacaa tgttgttgcc gtggtgttgt ggcgcggttg gtgggggtgg cattcccggc   2760
tccacggagg gtttccatgg gccgccgttc caaatccatt gggcggcctg aataatatct   2820
gcggtggtgt aggtcctgtt catgtgtcat cccctgaaca ggttgtcgaa gtcgtctgtg   2880
ttgctggtgt tggtggtatc gaatcgtccg acgcagtggc agtagtcgta catgagtttg   2940
ataatgtgtt ggtggtctcc caaataggtg ttgccgctga tgctgtaggt ggctgtgccg   3000
tctttgctga tggtgtattt ggcggtgatg gtttcggggt tttctgtgtt tgtgatgatg   3060
gctgtggtgg tggcgcctac ggtttgtagc ctggtggttt gggttccgtc gtcgagggtg   3120
gtagtaacca tagttggggt tctccttaaa tactggtttg gttgtcggct agatgaataa   3180
tatcggataa aggtttcggc tggtctaggt gttgtatggt tttgttggcg agccgtttgg   3240
ctaccctgta gcacattttg atgtagtgtt tgttgtctag gttgtggtat tgttcccgta   3300
ccgcaatata tagtagggag tcttggtaca ggtcgtctgc gttgattgcg gggtagtgtg   3360
tggctatttt tgtgcatgcc cggttgagtg tgcgtagatg atggtctgtg gcccatcccc   3420
acgatgctgt ggtggccagg tctgatttgg tgggtcgtct gctcatggcg ctatttcatc   3480
tcgctatctg atagttgttt ggtgttttgt tgttgatagt gtagcacact agtccgggat   3540
ggccggtggt gcctgtgcgg tgccggaacc atgtggattc tccttccatg gatgggcatt   3600
ggatgaaggt gcgttgtcct tgctcggaga tttctaggtg gtgccggtgc ccggccatga   3660
gaatattaga tgtggtgccg ttgtggaatt cttggccgcg ccaccattcg tattgtttgc   3720
cggttttcca ttggtgcccg tgtgcgtgca ggatttgtgt gccggctact tcgacggtgg   3780
tggtcatttc gtcccgtgcg gggaagtgga agtgaaggtt gggatattgg ttgtcgagct   3840
ggtaggcttc tgcgatggcg cggcagcagt ccacgtcgaa ggagtcatcg taggtggtga   3900
cgcctttacc gaaacgcacg gcttcaccgt ggttgccggg gatggatgtg atggtcacat   3960
ttttgcagtg gtcgaacatg tggacgagtt gcatcatggc catgcgagtc aaccggattt   4020
gttccgtcaa gggtgtttgt gtgcgccagg cgttgttgcc tccttgtgac acgtatcctt   4080
cgatcatgtc gccgaggaat gcgatgtgga ctcgttgcgg ctgtccggct tgctgccagt   4140
agtgttttgc gactatgagg gagtgcaaat agtcgtctgc gaagtgtgat gtttccccgc   4200
cggggatgcc tttgccgatt tgaaagtctc ccgcccctac cacgaacgca acattgctgt   4260
agtcggtgtg tgtgtcttgg ttgggtttgg ggggtgtcca ttcggctagt ttatcgacga   4320
gttcgtcgac cggatagggg tcggttgcgg gttggtggtc gatgattttt tgtatggatc   4380
ggccggtttc tccgttgggg agtgtccatt cggagatgcg tgtgcgccgt acggtgccgt   4440
ttgcgagatc atcgcggatg gtgtctgctt cgttgtcgtg gttggctagc tgtgtgagga   4500
gccggtctat attgtctatc atcgggtatc ctcctcttgt ggggtggtgt tggcttgttt   4560
gcggcgatag tcttttataa cggtggcgga gatggggtat cctgcctggg tgagctgttt   4620
tgctagccat gaggcgggga tagacctgtc ggcgaggacg tcggcggctt tagccccgta   4680
gcgttgaata agggtttcag ttttggttgc catgatgtcc taggggttgt gtggtgggct   4740
```

gccatcctgt gcggcagtcg ccgtcgtgtc ctggtttgcg ggtgcaccac gatacggttc 4800
cgtctgtgtg gttgagtgtt ttaccgcaca tgacgtcacg taggtgctcg ggaaactcat 4860
cgttgttgtt gtccccgtgc atgtcgatca agtgttgggt tttagtaacc atcatgcctc 4920
ctatgtgtga aagagtgtgc aaatactatg caggtgtcat ggatgtttat gcgggtatgg 4980
ttttcatcac cttgctgaac gttacttggt tactgtacat catctgagtg atttcctgat 5040
cagtcttatc ggggtgctgc tttcgcaggt tcgcccactg gcaggcgttg tcggtctcct 5100
gctgtaaacg tgtcaggtgc tgctcgttga tgatgtgttt ccacattgtc catgacacgt 5160
cgagcctgcg gagcatgttc atggctggca cgttgaagga gttgaggaag agtatttctt 5220
cggtgtagta ctgtttttcg tattggtccc atccgcttcg gtgcctgttg ggctggtttt 5280
tggggtaggc ttcccggcag attttgtgta accgtttggc catgtcgtcg ggtagtttaa 5340
tgtcggggtt ggcgcggatc atggatcgca tcccgtcata ggtggtgccc caggtgtgca 5400
tgatgtggag tgggtcttca ccatcggccc atttttcggc gatgatggcg aggcggatgc 5460
gcctcctggc ggctttactg gtgttgcgcc ggtgggggat ggggcatgtg tcgaggggat 5520
ccatgatatt ttagtgtacc tttccgtgtt gtggttgttt gtctggtttt attgtagcac 5580
tgtgttgagg gcttgtgtca accctgtttt gccggttttc aggtatgtgt ctgtgacatc 5640
ccccagggtg aggggcacgt gggtggcttg ggggagtgct gcctggaggg tttgggccat 5700
ctggtggcct gcctggtctg ggtcggacca gatgtagatg tggtcgtagc cttcgaagaa 5760
tttggtccag aaggtttgcc acgaggttgc gccgggtagg gcgacggctg gccatccgca 5820
ttgttcgagg atcatggagt cgaattcgcc ttcgcaaatg tgcatttcgg ctgccggggt 5880
ggccatggcg gccatgttgt agatggagcc tgtgtctcct gccggggtga ggtatttggg 5940
gtggttgtgg gttttgcagt cgtgtgggag tgagcagcgg aaacgcattt ttcgtatttc 6000
ggctggccgc ccccaaactg ggtacatgta tgggatggtg atgcactggt tgtagttttc 6060
gtggcctggt atggggtcat tgttgatgta tccaaggtgg tggtagcgag ctgtttcttc 6120
gctgatgcct cttgccgaga ggaggtcgag tatgttttcg aggtgggttt cgtagcgggc 6180
tgaggctttc tggattcggc ggcgttccgc aatgttgtat gggcgtatgc tgtcgtacat 6240
tcgggttttc tttctctaat tgttgttgta gtttggcgag tccgcctccg ataccgcatg 6300
tgtggcagta ccagacgccc ttgtcgaggt tgatgctcat ggagggctgg tggtcgtcgt 6360
ggaacgggca gaggatgtgt tgctcgtttt tggacgggtt gtaccgtatc tggtaggtgt 6420
cgaggaggcg gcaggtgtca gaggtgtggg aggagctcgt tgagggttga taccacatag 6480
gcttcgctcc atggcttgtt gcgctgtttc atcactacga gtccgatggt ggactgactt 6540
tcgcggtttc ggtgggtttc gtagttgcgt gcctcccggc tggcttgttt cacgaattcg 6600
gctaggtggg gctggccggc tttcgcctct atcacatagg ttttgtggcc ggttgtgagg 6660
ataaggtcgc cttcgtcttc acggccgttg aggtggaggc gttctatatc atggccggtg 6720
tcgcgtagtt ggtggaggag tcgtgtttcc cattctgcgc cggccctgcg gtttcttgat 6780
tgttgtgtcg acatgatagt cctttgtgtg ttgtggtcat attccagggc tgtttttcgg 6840
cgaggggccc gaagaaggtg tattcggggt aggctcgtag ccgctcgtat cgggtgccgt 6900
cggggctgga tttgcctgtg cgctgtttga ggacggcgat gcgtgcctct gccgggatcg 6960
atagcccgtt gccgttatcc tcgccaccat acaatgagac tccgaggatg agttgtggtt 7020
tttcggagag gccgtttttg atttctcgcc gggcgggcgg gtgttcgatg tcggagccgg 7080

-continued

```
ttttgtcggt tgcgtggtgt gtgacaataa tggtggagcc agtatcgcgg ccgagggctg   7140
tgatccattg catggcttct tgctgggcct gatagtcact ctcgcagtct tggatgtcca   7200
tcaggttgtc gataacgatg atgagtggga aggtgttcca catttccatg taggcttgca   7260
gttccatggt gatatcggtc caggtgatgg gtgactggaa tgagaatgtg atgtgttggc   7320
cgtggtggat gctgtctcga tagtattctg gcccgtaatc gtcgatgttt tgttgtatct   7380
gggcggtggt gtgttgggtg ttgagtgaga tgattcgtgt ggaggcctcc cagggtgtca   7440
tgtcccctga tatgtagagg gctggctggt tgagcatcgc tgtgatgaac atggctagcc   7500
ctgatttttg gctgccggac cgccccgcga tcatgacgag atcccctttg tggatgtgca   7560
tatcctggtt gcggtagagg ggttctagtt gtggtatgcg gggcagctcg gctgcggttt   7620
gggaggccct ctcgaaggat cgttggagag agagcatcgg gaccttatct atctatcggt   7680
tacgatttgt atgaatattg gcggttagat ggagtcgatg tctacatcat cactaccagt   7740
ggtgttgggc tgactgtctc gctggtcaac gtaggctgct acaaggtcgt agatggcgtc   7800
gtccaatggt ttgagcacga ccgcgttgaa gccgtttttg gtgcgcacgg tggcgagttt   7860
gaaggcttgc tcttcgccaa ggtaggtttc gaggtcgcgg atcatggagt gtgggcggtc   7920
gttgctgccg cgtacttttt cgatgatggc gttggggatg gtttctgggg tgctgttgtt   7980
gaggtcgtct agggtgtgga agatggtgac atcagcgtag atgcgatcgg cggtctgtcc   8040
accgtagcct tcagtgttgt gctcgacgtc gtggactttg aaggcgatgg cggtggcgtc   8100
ctggtttcgg gaggggttga agaaggtgct gttgctgttg tttcggtagt ttgcgagtcc   8160
cattgttgtt tcctttacta tttttgttgg tttgtgtcgg tttttatcgg gtgaggctgt   8220
ttcgtttgct gcggaacgcc tcggatacgt cagtgttgct ggtgatgatc ttcttgtact   8280
gtttcagaag gtcggctagc tgtgctttgc ttgttgcatt gttgattttg tcaatgatgg   8340
tgttgtttcc ttcactggca atgttgtcta cgtagtcttt ggcggcctgg ttgtatcggt   8400
cttggaggat gatggatgcg gaggcgatca gtgttgccag gtcccagttc cttgccgccg   8460
aactgttttt gagtccgcct agcaagtcga tgatagtctt ctttacttcg tcggcggtgt   8520
ctccacggat gactgtccat ggggcggcgt agtctccgcc gtatttgagt gtgatggtga   8580
tgcgatcatc agtgctgttg gtgttatcgt tcactggtgc tccttgcttt cttctgttgg   8640
ggctgtgatg gtggtttctg tagggtacct gtaggcgtct ttcccgttga cggcccagca   8700
ggcgtccttg acggggcatc ctttgcagag tgctgtgacg tggggtacga agatgccttg   8760
actgattcct ttcattgctt gactgtacat ggatgataca tgccggtagg tgttgttgtc   8820
aaggtcgtac agttcggtgg atgtgccttg tgtcggggac ttgtcgtcgt tgcggctggt   8880
ggcgggtgtc caaaacatgc ctttcgtcac atgaatgtcg tgttgggcga gcatgtaccg   8940
gtatgtgtgc agctgcatac tgtcggcggg taggcggccg gttttgaggt cgaggatgaa   9000
ggtttcgccg gtgtcggtat ctgtgaaaac acggtcgatg tagccgacaa tctgggtgcc   9060
gtcggggagg gtggtttcta ccgggtattc gatgcctggc tggccgtcaa taacagcggt   9120
gatgtattct gggtggttgc gcctccatgt tttccagcgg tctacaaagg tggggccgta   9180
aaccatccac cagtcgtagt ctttttttgtg tggtccgccc gactcgcaca tgtttttgca   9240
tattctgccg gagggtttga tttctgtgcc ttcggattcg gcgagggcta cttgggtgtc   9300
gaaaatgttt ttgaaggatg cgagtttgtc tggcagtgca gggtattcgg cgggattgta   9360
caggtgtagg tcgtattgtt cggtgatgtg atgtatggcg cttccggcga tggtggcgta   9420
ccaggtgtgg tgttgggcgt ggtagccgtg ggataggcgc catttttctc cgcattcggc   9480
```

-continued

```
ccactgggtg agtgaactgt aggagatgtg gcctggatgg ttgatggttt tcggatattg   9540
tgctaggggc attactggtc gcctttgtgt gtgttccatg ggttgcgggt gtcttggccg   9600
gcgtggtgtt gctggtaggc gaggagtgcg aggcagtgcc aggcagcatg ggctagatgg   9660
ggtagcccgg attcataatc gaggttgttg ccttgctgcc atgatagtag gtgcctgtag   9720
agggcgtcga cgctgtggct ccacgggtag ccgccggtcc agttgttgtc gccgtatttg   9780
gtggcaccgt agcctgccac ggagccgagg gcgtgcaagg ctgtagggtc gatgagggat   9840
agcctgcaaa gtttcaattc tttttggca ccgctgttgg ggtcggtgta catgcgggtt   9900
ggcttatcca tgggggtgtg ctccttaggg gtgggttact ggttggggtt gtgggcgagt   9960
gctacggcga gaataatgat ggcgagggtt tcagcaataa gtatgggtgt tgtgatcatt  10020
tgctgtctcg gggattgttg gtgagtgtgg aggcgcctag gagggtggcg agggcgcatg  10080
cggcaataat ggcgagggct gccttgtgtg gggtgccggt tgcgtacatc catgtgatga  10140
tggcgccttg gatccaggcg aggctggtga agaacgtttc gtagctgtgt agctcaatgt  10200
tgttgggtgt gttcatgctt gctcctgaag aatggtgttg atggttttat aaatgttgta  10260
caggtcggtt tcgatagata acagttggtg gatttcgtgg tcgagatcaa tgtctgggtt  10320
gagggtgttg atgcgggagg caatatcggt ggctgtgcgt agtgtgccgc cggtgtggtg  10380
aataatgtgt gccgtgtcgg cgagtccggt ggtgacagcg tagtgggaga ggagaggcat  10440
agctggggt gctccttggc gggttactgt tgcgggttga tgttgaggtc ggtgacgtgc  10500
ggtgagcttt ctgttccggt gacgaggcag tggacggtga cgggtagttt ggatgctccc  10560
ggctggcgta cggtggcgcc gtaggcgatg gagaaggtgt ctttgccaat aattttgtgg  10620
agttggaggt cgatgtcggg gttgccgttc catttgacac cgtgtgcggc ggcctgttgt  10680
tcggctttgc ggttgcaggt gtgtgctgcc gtgatcatgg tgagtccggt ggcggtttct  10740
tccccccttg cttgggcttg ccggtggttt ttggcctgct cggctcgcag tgactgttct  10800
gcggctgcct ggcgggcttt cttttcggct ttgcgctgtt ggacggtttt gggggtccac  10860
gcggtgttgg ctgtggtggc ctgtggggct ggctgtgagg caagtggcgg attgtcgtct  10920
ggggctggca tgaatgaggc ggcggcaatg atggcgactg tggcgccggc gatggtgtag  10980
cctttttct tgttcatgac tgttgtcccc tttccggggt gttgttcgtt gctgacatga  11040
tcaatacttc cagcgaatga acctcgtgtc aaggctgcgc tcaacgattg tgagcgattc  11100
gtgtgtggct aggggtttta tcggctgtac agggtgagga ggtggcctac gttgatgcgg  11160
gtcacattcc agtagagttg cgtggcttca cccccggtga gtggcttcca ctcgttgtgg  11220
ctgaacacgg tgccgtcggt ggcgatgaat gtgttggggc gtagcttgtg gagttcggct  11280
tccacgctct gccggtaggc ttcggcgagg ccctcaaaat ccatgtggtc gcaggagagg  11340
ttttcgaggc gtgtcaggtc gaagggtgtg ggacagtcgt agctggcggg gctgtagagc  11400
tgggtgaagt ggttggcgat cttctgcatc atgattcctt ttctggtgat ggtgtgttga  11460
tggttttatc gtgtggcttc ggcgatgatg gcgtccacat cgattgtgtc gatcatgtcg  11520
tggagttcct cagcctcatc cgcggtgagt ggctgccagt cctggggtcc gtatatggca  11580
ccgtcgaggg tgacagtcca caggggccgg atgagtcgta cggcttcttc gactttggca  11640
cggtgcaggc ggcagatgat agacgtgtgg gtgttgccta tgtcacatcc tgccaggtgt  11700
gtggggtgga gtgggttgat ttctgtctgc ccgtagaggt tggtgaagga tggtgtgatg  11760
agtgtgccat ccatgagggt gtgctccttt cggtggtgta tgggttgttg tggtttctag  11820
```

agtgtgtagg ttgcgatccc atagtcaagg ctgcactcat tcggattgag cgtttcatgg 11880
gatgtggcag ggatgtggc gtatctcact taagccttta tggcctctct cagtgcctca 11940
aatcctctga gggtaggatt atgcagggtt gaccctgctg atcgattcta ggggccttct 12000
agggcgtctc aggggtatgt ctgggttatg gcgggtgtgg cagatgatct agcgagtcaa 12060
ggtgccgagc tgagacataa gatctatcat ctaggtgtgt gagatgcatc acatcctcct 12120
ggcgtggtgt acacccttaa ggctactcgg tcgatctggc gtggagggtg tagtaaagaa 12180
atgccgttta aagccttcgc acggcgccta ggagcgcctt acggggtggg ggctaggtat 12240
ttataccccc agcacattct gatcgattct agacgcctcc aggatcctga tacacgatca 12300
gctatccaga cgcagatcac cagtccctat cctggttagc taagcctcaa ctatgtggac 12360
agtgtgggat actgtggggg aagaaggaca cggtaaaaag aagagggggg agcatcagcc 12420
ttcacacctt caagccttaa ggttttagcg cttagcaccg atggtcttag cagttagcac 12480 cgagcccccct cacgggctcg gcatcagccc gaacaggcac agccctgaaa ggagtacacg 12540
ccatcaggga aggcttgaga gtacgaggag ccctagcgac gagtactcga aagcctgagg 12600
gaacaccctc agcactgatg ggcctagcgt gttcggaaag gacacaagag tgaagtgtga 12660
cagctatccg ggagtgaaac ccgttctgac taggggtttc agccttaacc acctgtaaag 12720
gttacaagac tctaagaaaa tttaaggaaa agtttaggtt taatttttgg acctttacta 12780
ccaaaaacac ccgtttacac ccctcaaacc cgcctataga gccaaatcca ccagtttgac 12840
tcatcccagg tggggtatga taggctggac aggtagccag ctggacgcaa ggccgaaatc 12900
cgctgacgcg gctttcaccc ttacatccat cagtctacca aagacttaaa gacctaaggg 12960
cttagcgcta aggtgctgat agcttagcac cgagcccctc aagggctcgg catcagtctt 13020
aaagctttaa acactttaag taaacttaag agcttagcac ttaaagttaa ttaataacct 13080
taaaggctta cacacttagc actgagccct ttaaggctca gcatcagtat aaagatctta 13140
acacctaagt taagtataaa accttaaagg cttagcactt aaggatataa acttaacatc 13200
agtgtttaag actttaaaac ttaaaataac tattaagact taaagactta taagctttaa 13260
acacttaaag taactataag actttaaaga ccttaagtat ttaaagttaa ccatcagtct 13320
taaactttaa tattataacc tataagtctt aaagcttata ggtataataa tataatataa 13380
gttataaaag ttttagaaga gctaaggggt taacttcttt acttctctac tctctttggt 13440
actttctctc ttctcttctt ttcttcatca ggggagaaga ggaaccttta accgtcaacg 13500
ctgatggact tttcaccgtg tgactcgtgt gcttctggtc gcacgctccc atcgcacact 13560
ccccacactc tgacacccgt gcccctttca ggcttgacgt gttcggctga aggcgtacgg 13620
cgtgtcacgc ttaaaccctt aacaccaggt aagacttaaa gtgtatatta taagtagaag 13680
actttaaaac cttaaggtgt tcccgcttag cctgtgtcct ttagcgctag gcgccaagcg 13740
ctaagctgtg aaacgcgaac acccatccac ccccattttt cttccgtgtc cttcttcttt 13800
tgacaccgct ggggggcgat gtgatatttc tcacatgcca gggggtagtg gagaaaacaa 13860
acaccccggc acaaacagaa caccccctca aacgaacaaa acaccccccca gaatcgatca 13920 gcagggcaag ggcaaggtat tcataccccc aacacctttc aggccgttac aggagcaatg 13980
agaggctcac aggggcaagg ggagatcagg ggacgcgatg gcacacacca accgcaccgc 14040
atcatcagcc caccggcgtt ggcggcaacg actcatcacc caagcccaac aacaaggcca 14100
aaccgaatgc ccactctgcg gagcccagat agcctgggac acccatgacc taccaaccag 14160
ccccgaagcc gaccacatca cacccgtcag cagaggagga ctcaacaccc tcgacaacgg 14220
gcaaatcatc tgcagaacat gcaacagaag caaaggcaat cgcagcgaac caaacatcaa 14280
attccaacaa caaaccacaa aaacattgat tccatggtga aaaacctgtc aacccccacc 14340
ggggacaccc cctgcacagg cgtgcaagac ctcgtacggc ttagtgaaat acctcccttt 14400
tgtggatttg tctgtttgtc gactttttgt gttggtggtg agtgttgtgc agcctgagct 14460
tcctgatggt cgtgattggt gtggggagac gcgtcgttgg tggcgtgtgt ggggtgagga 14520
ttcgcgtgcc gggttggtgt ctgatgagga gtggctgttt ctcatggatg ctgcggtgat 14580
tcatgatgtg gtgtggcgtg agggtcgcgc ggatttggtg gcttcgcttc gtgctcatgt 14640
gaaggcgttt atgggcatgc tggaggctca ttctggggat gctggcacta ctgtgggtgg 14700
tgggggttct gcggtggcga tgattgaccg gtataggaag cgcaaggggg cctgattagg 14760
tgtctggtgt tgtgggttct caggttcctc gtcaccgtgt ggctgcggcg tatcaggtga 14820
ctgccggcaa tgatgctggt gctcttgggg ctgcgtatgg gttgactccg gatccgtggc 14880
agcagcaggt gttggatgat tggctggctg tcggtggtaa tggcaggctt gctgcgggtg 14940
tgtgtggggt gtttgtgcct cgccagaacg gcaaaaacgc gatccttgag gttgttgagc 15000
tttttaagat ggtggttcag ggtcggcgta ttttgcatac ggctcacgag ttgaagtcgg 15060
ctcgtaaggc gtttatgcgg ttgagatcgt tttttgagaa tgagcgccgc tatccggatt 15120
tggctcgtat ggtgaaggcg attcgggcga cgaatggtca ggagtcgatc attttgcatc 15180
atcctgattg cagtgtgggt ggtaagaagt gtggctgccc tggttggggt tcggttgagt 15240
ttgtggctcg tagccggggt tcggctcgcg ggtttacggt tgatgatttg gtgtgtgatg 15300
aggctcagga gttgtcggat gagcagttgg aggctttgct tcctacggtg tctgcggctc 15360
cttcgggtga tccgcagcag attttccttg gtaccccgcc ggggcctttg gctgatggtt 15420
ctgtggtgtt gcgtttgcgt gggcaggctt tgtcgggtgg taaaaggttt gcgtggacgg 15480
agttttcgat tcctgacgag tctgatccgg atgatgtgtc gcggcagtgg cggaagttgg 15540
cgggtgacac taatccagcc ttgggtaggc gtctgaattt tgggactgtg tcggatgagc 15600
atgaatcgat gtctgctgcc gggtttgctc gggagcggct tggctggtgg gatcgtggcc 15660
agtctgctac gtctgttgtt ccggcggata agtgggctca gtctgctgtg gatgaggcgg 15720
ctctggttgg cggcaaggtg tttggtgtct cgttttctcg ttctggggat cgggttgctt 15780
tggcgggtgc cggccggact gatgctgggg ttcatgttga ggttattgat gggctgtcgg 15840
ggacgattgt tgatggtgtg ggccggttgg ctgactggtt ggcggttcgt tggggtgata 15900
ctgaccggat catggttgcc gggtctggtg cggtgttgtt gcagaaggcg ttgacggatc 15960
gtggtgttcc gggccgtggc gtggtggttg ctgatactgg cacctatgtg gaggcgtgtc 16020
aggcgttttt ggagggtgtg aggtctggga atgtttctca tcctcgtgct gattctcgcc 16080
gtgacatgtt ggatattgct gtgaggtcgg cggttcagaa gaagaagggt tctgcgtggg 16140
gttggggttc ctcgtttaag gatggttctg aggttccttt ggaggctgtg tctttggcgt 16200
atcttggtgt gaagatggcg aaggctaggc ggcgtgagag gtctggtagg aagcgggtgt 16260
ctgtggtatg aactcggatg agttggcttt gattgagggc atgtacgatc gtatccaaag 16320
gttgtcttcg tggcattgtc gtattgaggg ctactatgag ggttctagcc gggtgcgtga 16380
tttgggggtg gctattcctc cggagttgca gcgtgtgcag acggtggtgt cgtggcctgg 16440
tatagctgtg gatgctttgg aggagcgtct ggattggctt ggctggacta atggtgacgg 16500
ctacggcctg gatggtgtgt atgctgcgaa tcggcttgct acggcgtcgt gtgatgtgca 16560

-continued

```
tttggatgcg ctgatttttg gtttgtcgtt tgtggctgtt atccctcagg gggatgggtc  16620
ggtgttggtt cgtccgcagt caccaaagaa ttgtactggc cggttttcgg ctgacgggtc  16680
tcgtttggat gctggccttg tggtgcagca gacgtgtgat cctgaggttg ttgaggcgga  16740
gttgttgctg cctgatgtga ttgttcaggt ggagcggcgt gggtctcgtg agtgggttga  16800
gacgggccgt atcgtgaata gtcttggtgc ggttccgttg gtgccgattg tgaatcgtcg  16860
ccgtacgtct aggattgatg gccgttcgga gatcactcgg tcgattaggg cttacacgga  16920
tgaggctgtg cgcacactgt tggggcagtc tgtgaatcgt gacttctatg cctaccctca  16980
gcgttgggtg actggcgtgt cggctgacga gttttcgcag cctggctggg tcctgtcgat  17040
ggcttctgtg tgggctgttg ataaggatga tgacggtgac accccgaatg tggggtcgtt  17100
tcctgtgaat tcgcctacac cgtattcaga tcagatgcgg ctgttggcgc agttgactgc  17160
gggtgaggct gcggttcctg aacgctattt cgggtttatc acgtctaacc cacctagtgg  17220
ggaggctttg gctgcggagg agtctcggct tgtgaagcgt gctgaacgca ggcagacgtc  17280
gtttggtcag ggctggttgt cggttggttt cctggctgcc agggcgcttg attcgagtgt  17340
tgatgaggcc gcgtttttcg gtgatgtggg tttgaggtgg cgtgatgctt cgacgccgac  17400
tcgggcggct acggcggatg ctgtgacgaa gcttgttggt gccggtattt tgcccgcgga  17460
ttctcggacg gtgttggaga tgttggggct tgatgatgtg caggttgagg ctgtgatgcg  17520
gcatcgtgcc gagtcgtcgg atccgttggc tgcgcttgct ggggctatat cgcgtcaaac  17580
taacgaggtt tgataggcga tggcttcggg ggttgcgtcg aggttggctg ctgccgggta  17640
tcagcggcag gcgattcgtt ttgccgggaa gtatgcgggc tattatgccg agttggggcg  17700
tttgtggcat tccgggaaga tgacagatgc gcagtatgtg cgtttgtgtg tggagttgga  17760
gcgtgccggc catgacggtt ccgcggcgct ggcgggcaag ttcgtgtcgg attttcggaa  17820
gcttaacggt gtggatcctg gtttgatcgt gtatgacgag tttgatgctg ccgccgcgtt  17880
ggctaggtcg ttttcgacta tgaagattat gaatagtgac ccggataggg cgaatgatac  17940
gattgatgct atggcggcgg gtgttaatcg ggctgtcatg aatgctggcc gtgacacggt  18000
tgagtggtct gctggcgcgc agggtaggtc gtggcgcagg gtgactgatg gtgatccgtg  18060
cgcgttttgt gccatgttgg ctacgaggtc ggattatacg accaaagagc gggcgcttac  18120
tactggtcat acgcggcgtc ataagcgtgc cggtaggcgt ccgtttggtt cgaagtatca  18180
tgatcattgt gggtgtacgg tggttgaggt tgttgggcgt tgggagccaa atagggctga  18240
tgccgagtat cagaggacgt atgagaaggc ccgtgagtgg gttgatgatc atggtttgca  18300
gcagtcgcct ggcaatattt tgaaggctat gcgtactgtt ggcggcatga gataatttga  18360
tgtggtttcc ggttgtgcgc cgccggttat cggtgcacag ggttgtctcc cgcacggggg  18420
tcaacaatgt tgtgttgttt tccgcaagga gtgtaaggtt aggctatggc cgatcagagt  18480
gttgaggaac agaatgtcga caatgatgct gttgagcccg gaaagggtgg agacattgtt  18540
gatgttgtga aggatgggcg ggctgccggc gatgatcatg ccggtgatgt ttccgtgaag  18600
ggtgaggctt ctgggtcttc gggcacggat tggaaggctg aggctcgtaa gtgggagtct  18660
cgtgctaaaa gtaatttcgc cgagttggag aagcttcgta catcgagtga cgattctgga  18720
tctactattg atgagcttcg ccgcaagaat gaggaactcg aagacaggat caacgggttt  18780
gttcttgagg gtgtgaagcg tgaggtggct gccgagtgtg gcctgtcggg tgatgcggtc  18840
gctttcttgc acggtagcga tcgtgaagca ctggtggagt ctgctaaggc tttgaagggt  18900
ttgattgacc atagtagtgg tggcgcgggt gtgcgccgtc ttgcggggag tgccccccgtt  18960
```

-continued

```
gatgatgtta aacgacgtga gggtgtcgcg tttgtggatg ctcttgtcaa taattctagg  19020
agatgatttg tgatggctga cgattttctt tctgcaggga agcttgagct tcctggttct  19080
atgattggtg cggttcgtga ccgtgctatc gattctggtg ttttggcgaa gctttcgccg  19140
gagcagccga ctatttttgg ccctgttaag ggtgccgtgt ttagtggtgt tcctcgcgcc  19200
aagattgttg gtgagggtga ggttaagcct tctgcgtctg ttgatgtttc ggcgtttact  19260
gcgcagccta tcaaggttgt gactcagcag cgtgtctcgg acgagtttat gtgggctgat  19320
gctgattacc gtctgggtgt tttgcaggat ctgatttcgc ctgctcttgg cgcttcgatt  19380
ggtcgcgctg ttgatctgat tgctttccac ggtattgatc cggctacggg taagcctgct  19440
gcggctgtca agtcttcgct ggataagacg aagaatattg ttgatgcaac cgatagtgct  19500
acggctgatc tgattaaggc ggttgggctg attgctggtg ccggtttgca ggttcctaac  19560
ggggttgctt tggatccggc gttctcgttt gccctgtcta ctgaggtgta tccgaagggg  19620
tctccgcttg ccggccagcc tatgtatcct gccgccgggt tcgccggttt ggataattgg  19680
cgtggcttga atgttggtgc ttcttcgact gtttctggcg ccccggagat gtcgcctgcc  19740
tctggtgtta aggctattgt tggtgatttc tctcgtgttc attggggttt ccagcgtaac  19800
ttcccgatcg agcttatcga gtatggtgac ccggatcaga ctgggcgtga cctgaagggc  19860
cataatgagg ttatggttcg cgccgaggcg gtgctgtatg tggctatcga gtcgcttgat  19920
tcgtttgctg ttgtgaagga gaaggctgcc ccgaagccta atcctccggc cgagaactga  19980
tttattgttg cggtgatgtg tcaatgtgca gggggtggtg ttgatgggta tcattttgaa  20040
gcctgaggat attgagcctt tcgccgatat tcctagagag aagcttgagg cgatgattgc  20100
cgatgtggag gctgtggctg tcagtgtcgc cccctgtatc gctaaaccgg atttcaaata  20160
caaggatgcc gctaaggcta ttctgcgcag ggctttgttg cgctggaatg ataccggggt  20220
ttctggtcag gtgcagtatg agtctgcggg tcctttcgct cagactacac ggtctaatac  20280
tcccacgaat ttgttgtggc cttctgagat tgccgcgttg aagaagctgt gtgagggtga  20340
tggtggggct ggtaaagcgt tcactatcac tccaactatt aattgtcgat atgcacattc  20400
tgaggtgtgt tccacggtgt ggggtgaggg ttgctcgtgc gggtcgaata ttaacggcta  20460
cgctggccct ttgtgggaga tatgatatga ccagttttcc ttatggtgaa acgattgtga  20520
tgcttcagcc gactgttcgt gtcgatgatc ttggtgacaa ggtggaagac tggtctaagc  20580
ctgtcgagac tgtgttccat aacgtggcca tctatgcttc gttgtcgcag gaggatgagg  20640
ccgcggggcg tgactcggat tatgagcatt ggtcgatgct tttcaagcag cctattgtgg  20700
gtgctgatta tcgttgcagg tggcgtatcc ggggtgttgt gtgggaggct gacgggtctc  20760
ctatcgtgtg gcatcatccg atgtctggct gggatgcggg cacgcaggtt aatgtgaagc  20820
gcaagaaggg ctgataggtt gtggctcagg atgtgaatgt gaagctgaac ttgccgggta  20880
ttcgtgaggt gttgaagtct tctggggtgc agtctatgtt ggctgagcgt ggcgaaaggg  20940
ttaggcgtgc ggcctcggcg aatgttggcg gtaacgcttt cgatagggcc caatacagta  21000
atggtttgtc gtcggaggtg caggttcacc gggttgaggc tgtggcgagg attggtacca  21060
cctataaggg tggtaaaagg attgaggcga agcatggcac gttggcgagg tcgattgggg  21120
ctgcgtcgtg atcgtttacg gtgatccgcg cgtgtgggct aaacgcgtac tcaaggatga  21180
tggctggctg tctgatatac catgtaccgg gacagtgccg gatagctttg agggtgacct  21240
tatttggttg gctcttgatg gtggcccaca gttgcatgtg cgtgagcagg ttttttgcg   21300
```

```
cgtgaatgtg ttttcggata cgccggatcg tgctatgtcg ttggcgcgtc gtgttgaggc  21360
tgtgctggct gatggtgtgg acggtgaccc tgtggtgtac tgtaaacggt ctactggccc  21420
tgatttgctg gttgacggtg cacgttttga tgtgtattcg ctttttgagc tgatatgtag  21480
gcctgcggag tctgaataag cttattgttt ttgttttaat gtaattgttt gatatttaat  21540
gggggttgtg atggctgcaa cacgtaaagc gtctaatgtt cgctctgctg ttacgggtga  21600
cgtttatatt ggtgccgctc atgctggtga cgctattgat ggtgtgaaga cggttcctga  21660
cggtcttacc gctttagggt acctgtctga tgacgggttt aagattaagc ctgagcgtaa  21720
aacggatgat ttgaaggctt ggcagaatgc ggatgttgtt cgcacggttg ctactgagtc  21780
gtctatcgag atttcttttc agctgatcga gtctaagaag gaggttatcg aactgttttg  21840
gcagtcgaag gttactgccg gatccgattc gggttcgttt gatatttctc cgggtgccac  21900
gacgggtgtt cacgccctgt tgatggatat tgtggatggc gatcaggtta tccgttacta  21960
tttccctgag gttgagcttg tcgatcgtga cgagattaag ggtaagaatg gcgaggtgta  22020
cgggtatggt gtgacgttga aggcgtatcc tgcccagatt aataagaagg gtgatgcggt  22080
gtctggtcgg gggtggatga cggctttaaa agctgatact cctccggttc cgccttctcc  22140
gaagcctcag ccggatccga atccgccgtc cgataattga tacacgagtt tgagggattg  22200
ttgatagatg agtgacacag gttacacgtt gaagatcggt gaccgtagtt gggtgttggc  22260
ggatgcggag gagacggctc aggctgttcc tgcccgcgtg tttcgtcgtg cagctaagat  22320
tgcccagtcg gggga gtctg cggatttcgc ccaggttgag gtgatgtttt ctatgttgga  22380
ggctgccgcc ccggctgacg cggtggaggc tctggagggg cttcctatgg ttcgtgttgc  22440
cgagattttc cgccagtgga tggagtggaa gcctgaaggt aagggtgcct ctttggggga  22500
atagtttggc tccacggcct gattgatgag tatcgtgggg ccatcgaata tgattggcgc  22560
acaaggtttg gtgtgtgcat atacgatata ggtggtcctg caatggggtg gggtgaggct  22620
gtccggctgg ctggcgtgtt gtgtaccgat acgtctagcc agttggcggc ccacctgaat  22680
ggttggcagc gcccgtttga gtggtgcgag tgggctgtgt tggacatgct ggatcattac  22740
aggtctgcta atagtgaggg gcagccggag cctgtggcga ggcctacgga tgagcgtagg  22800
gcccggttta cgtctgggca ggtggacgat attttggcgc gtgttcgtgc cggtggcggg  22860
gtgtctcgcg agattaatat tttggggtga atagtgtatg tctggtgaga ttgcttccgc  22920
atatgtgtcg ttgtatacga agatgccggg tttgaaatca gatgttggta aacagctttc  22980
tggggtgatg ccggctgagg gtcagcgttc gggtagcttg tttgctaaag gcatgaagct  23040
ggctttgggt ggcgccgcaa tggtgggcgc cattaatgtt gctaagaagg gcctcaagtc  23100
gatttatgat gtgactattg gtggcggtat tgctcgcgct atggctattg atgaggctca  23160
ggctaagttg actggtttgg gtcatacgtc ttctgatacg tcttcgatta tgaattcggc  23220
tattgaggct gtgactggta cgtcgtatgc gttgggggat gcggcttcta ctgcggcggc  23280
gttgtctgct tcgggtgtga agtctggcgg gcagatgacg gatgtgttga agactgtcgc  23340
cgatgtgtct tatatttcgg gtaagtcgtt tcaggatacg ggcgctattt ttacgtctgt  23400
gatggctcgc ggtaagttgc agggcgatga catgttgcag cttactatgg cgggtgttcc  23460
tgtcctgtct ttgcttgcca ggcagacggg taaaacgtct gctgaggtgt cgcagatggt  23520
gtcgaagggg cagattgatt ttgccacgtt tgcggctgcg atgaagcttg gcatgggtgg  23580
tgctgcgcag gcgtctggta agacgtttga gggcgctatg aagaatgtta agggtgccct  23640
gggctatctt ggtgctacgg ctatggcgcc gtttcttaac gggttgcggc agatttttgt  23700
```

```
tgcgttgaat ccggttatca agtcggtgac ggattctgtg aagccgatgt ttgctgccgt  23760
cgatgctggt attcagcgta tgatgccgtc tattttggcg tggattaacc gtatgccggg  23820
catgatcact cgaatgaatg cacagatgcg cgccaaggtg gagcagttga agagtatttt  23880
tgcaaggttg catttgcctg ttcctaaagt gaatttgggt gccatgtttg cgggtggcac  23940
agccgtgttc ggtattgtgg ctgccggtgt ggggaagctt gttgcagggt ttgccccgtt  24000
ggcggtgtcg ttgaagaatc tgttgccgtc gtttggtgct ttgaagggtg ccgctggtgg  24060
gcttggcggc gtgtttcgcg ccctgggtgg ccctgttggt attgtgatcg gcttgtttgc  24120
ggccatgttt gctacgaacg cccagttccg tgccgctgtt atgcagcttg tggctgtggt  24180
tggccaggcg ttgggccaga ttatggccgc tgtgcagccg ctgttgggtt tggttgctgg  24240
gctggtggca cggttggctc ccgtttttgg ccagattgtt ggtttggtgg ctggtttggc  24300
tgcgcagctt gttcctttga ttagtatgct ggttgcccgg ctagttcctg tgatcaccca  24360
gattattggt gcagtgacgc aggtggcggc catgttgttg ccggcgttga tgccggtgct  24420
tcaggcgatt gttgctgtga tacggcaggt tgttggtgtt gtgatgcaac tggtgcctgt  24480
tttgatgcct gtgattcagc agattttggg tgctgtcatg tctgtgctgc cgcctatcat  24540
cggcctgatc cggtcgttga taccagtcat catgtcggtt atgcgtgtgg tggttcaggt  24600
tgttgcggtt gtgatacagg tggtggcccg tattcttgct gttgtggctc cgatggtggc  24660
tgctgtggtg ggttttgttg cccgtattgt tggtgctgtc gtgtcggctg tggcccgtgt  24720
gattgcggct gtggcccgtg tgatcggatg ggttgtggcc cattttgtgt ctggtttggc  24780
acgcatgggt tcggttattc aggctggctg gaatcatatt agagcgttta cgtcggcgtt  24840
tatgagcggt ttcaagtcga tcatttctgg cggcgtgaac gctgttgtgg ggtttttttac  24900
gcggcttggt tcttcggttg cttcccatgt gaggtctggt tttaacgcgg ctcgtggcgc  24960
tgtttcttct gcgatgaatg ctatccggag tgttgtgtct tcggtggcgt ctgctgttgg  25020
cgggtttttc agttcgatgg cgtctagggt tcgtagtggt gctgtgcgcg ggtttaatgg  25080
tgcccggagt gcggcttctt ctgctatgca tgctatgggg tccgctgtat ctagcggggt  25140
gcatggtgtg ctgggttttt tccggaattt gcctggtaat attcggcgtg cgcttggtaa  25200
tatggggtcc ttgttggtgt ctgcgggccg tgatgtggtg tctggtttgg gtaatggtat  25260
ccggaatgct atgagtggct tgttggatac ggtgcgtaat atgggttctc aggttgcgaa  25320
tgcggcgaag tcggtgttgg gtattcattc accgtctagg gtgtttcgtg accaggttgg  25380
ccggcaggtt gttgccggtt tggctgaggg gatcacaggg aatgctggtt tggcgttgga  25440
tgcgatgtcg ggtgtggctg gaaggctgcc ggatgctgtt gatgcccggt ttggtgtgcg  25500
atcgtctgtg ggctcgttta ccccgtacga ccggtatcgg cgtgcgagcg agaagagtgt  25560
tgtggtgaat gtgaatgggc ctacttatgg ggatccgaac gagtttgcga agcggattga  25620
gcggcagcag cgtgacgctt tgaacgcgtt ggcttacatg tgatcgaggg ggtgttgtgc  25680
atgtttattc ctgacccgtc tgatcgttct ggtttgactg ttacctggtc tatgttgccg  25740
ttgattggta atgatccgga gcgtgtgctt catttgacgg attatacggg tgcgtcgcct  25800
gtcatgttgt tgaatgattc gttgcgcggt ttgggtgttc ctgaggttga gcatttttct  25860
caaactcatg ttggggtgca cggctcggag tggcgcgggt ttaatgtgaa gcctcgcgag  25920
gtgacattac ctgtcctggt gtcgggtgtg gatccggatc cggtgggcgg gtttcgtgac  25980
ggtttcatga aagcctatga cgagttgtgg tcggcgtttc ccccgggcgg ggtgggggag  26040
```

ttgtctgtga agactcctgc tggtcgtgag cgtgtgttga agtgccggtt tgattcggtg 26100
gatgatacgt ttacggttga tccggtgaat cgtggctatg ctcgctatct gttgcatttg 26160
acagcttatg acccgttttg gtatggggat gagcagaggt ttcgttttag taacgcgaag 26220
ttgcaggatt ggttgggtgg cggccctgtc ggtaaggatg gcacggcgtt tcctgtggtg 26280
ttgacgcctg gtgttggttc gggttgggat aatctgtcga ataagggtga tgtgcctgcg 26340
tggcctgtga ttcgtgttga ggggcctttg gagtcgtggt ctgtgcagat tgatggtttg 26400
cgtgtgtctt cggattatcc tgttgaggag tatgattgga tcactattga tacggatcct 26460
cgtaagcagt ctgcgttgtt ggatgggttt gaggatgtga tggatcgttt gacagagtgg 26520
gagtttgcgc ctatcccgcc tggcggttct cggagtgtga atattgagat ggttggtttg 26580
ggtgccattg ttgtgtcggt gcagtacagg tttttgaggg cttggtgaat agttgatggc 26640
tggtcttgtc ccgcatgtaa cgttgtttac gccggattat cgtcgtgtgg cgcctatcaa 26700
ttttttgag tcgttgaagt tgtcgttgaa gtggaatggt ttgtctacgc tggagttggt 26760
ggtgtctggg gatcattcta ggcttgacgg gttgactagg ccgggtgcgc ggctggttgt 26820
tgattatggt ggtggccaga ttttttctgg gcctgtgcgt aaggttcatg gtgtgggtcc 26880
gtggcgttct tcgcgggtga ctatcacgtg tgaggatgat atccgcctgt tgtggcgtat 26940
gctaatgtgg cctgtgaatt atcgtcccgg catggttggt tcggagtggc gtgccgacag 27000
ggattatgct cactattcgg gtgcggcgga gtcggtggct aagcaggtgt tgggggataa 27060
tgcttggcgt tttccgcctg gtttgtttat gaacgatgat gagagtcgtg gccgctatat 27120
taaggatttt caggcccggt tccatgtgtt tgccgataag ttgttgccgg tgttgtcgtg 27180
ggctcggatg actgtttcgg tgaaccagtt tgagaatgcg cagtttgatc agcggggttt 27240
gctgtttgat tgtgtgcctg ctgtgacccg gaagcatgtg ttgactgccg agtctggttc 27300
gattgtgtcg tgggagtatg tgcgtgacgc cccgaaggct acgtctgtgg tggttggtgg 27360
ccgcggcgag ggcaaagatc ggctgttttg tgaggatgtt gattcgatgg ccgaggggga 27420
ttggtttgat cgtgtcgagg tgtttaagga tgcccgtaac acggattctg aacatgtgca 27480
tctcatcgat gaggctgagc aggtgctgtc cgagttaggg gccacgtcgg ggtttaagat 27540
cgagttggct gagtcggatg tgttgcggtt tgggccaggc aatctgatgc cgggtgatct 27600
tatctatgtg gatgtgggtt ctggccctat tgcggagatt gtgcggcaga ttgatgtgga 27660
gtgtgattcg cctggtgatg gttggacgaa ggtgactcct gttgcggggg attatgagga 27720
taatccgtcg gcgttgttgg ctcgccgtgt ggctggtttg gctgcgggtg tgcgggattt 27780
gcaaaagttt tagtaagtga ttggggtttg ttgtgggtat tgtgtgtaaa gggtttgatg 27840
gtgtgttgac cgagtatgat tggctcaaa tgtctggtct gatgggtaat atgccgtctg 27900
tgaagggccc ggatgatttt cgtgtcggta cgacggttca gggtgccaca gtgttgtgta 27960
gtgttttgcc ggggcaggcg tgggctcacg gggtgatgtg cacgtcgaat agtgttgaga 28020
cggtgacggg gcagcttccg ggccctggcg agactagata cgactatgtt gtcctgtctc 28080
gggattggga gcagaacacg gccaagttgg agattgttcc tggggggcgt gcggagcgtg 28140
ccagggatgt gttgcgcgcc gagcctggcg tgtttcatca gcaactgttg gcgactttgg 28200
tggtgtcgtc taacgggttg cagcagcagt tggataggcg tgctatagcg gctagggtgg 28260
cgtttggcga gtctgctgcg tgtgatccta cccctgtgga gggtgaccgg gtgatggttc 28320
cttcgggggc tgtgtgggct aatcatgcta acgagtggat gctactgtct ccgaggattg 28380
agacgggttc taagtcgatc atgtttggcg ggtctgctgt gtatgcttac acgatcccgt 28440
ttgcccgccc gtttagtagt ccgcctgttg tggtggcgtc tatggctacg gcggctgggg 28500
gcacgcagca gattgatgtg aaagcctaca atgtgactgc caaggatttt ggtttagcgt 28560
ttattacgaa tgacgggtct aagccttctg gtgtgcctgc ggtagctaac tggattgctg 28620
tcggcgtgta atgcgctgct tgtgtgtgcg ggatatgttg tggtggttgt agtggtaggg 28680
ggctgtagtg tcatggttta cacccacact tgtagcctct atttgtaccg ctatcgctac 28740
tgtccttggt tcgattcagg cggttactta caggtcgaag aagaggctta ggcagttgtc 28800
tgcacaggtt gatgcgatgg aagaatacac atggaatatt cgccatattg ttcatcgcta 28860
taacgcgaat ttgcctgaga atgttgagcc tgtaaaaatg cctgatttgc ccgagttttt 28920
gaaggatact gttgatagtg gtggggggtg aattgtgagg gagttggagg aagagaaacg 28980
gcagcgccgc aattttgaga aggcttcact ggtgttgttg tttttgtcgc ttgtgttgtt 29040
ggctgtggtt gctgtgggtg ctttgcgttt cggggctgta tcctctgagc gggattcgga 29100
gcaggctagg gcccagtcga atggtacggc cgctaagggg ttggctgcga gtgtaaggcg 29160
ggcgtgcgtc tctggtgggc aggagtcggt gcgtcttcac cagtctggct tgtgtgtgga 29220
tgctcagcgt gttgagcg 29238

<210> SEQ ID NO 70
<211> LENGTH: 29699
<212> TYPE: DNA
<213> ORGANISM: Artificial Sequence
<220> FEATURE:
<223> OTHER INFORMATION: PAC9

<400> SEQUENCE: 70
tgatggtcgg gatggttcgg ccggtgagcg cggtgatgtg ggcccttcag gtcctgccgg 60
cccgcaaggt gcacagggtg aacggggtga gcgcggcccc gccggtgcga acggatccga 120
tggtaaagac ggtaaggatg gtgctgatgg ccgtgatggg cgttcggtga tatcggtgta 180
ctgttccggg ggccgcctgg ttgtgaaata tagtgacggt acggcctcta ccgtgtcggg 240
ttctgcggcc tgcgagagtg tgaaaccatc acctgtggtt actgtatcat cccataggtg 300
aacaagaaga gggaagggtg ttactagtgt tgattgtggt gtttgggggt ggtgtgtggt 360
gagatacatt ccagcggcgc atcactctgc cggttcgaat agtccggtga acagggttgt 420
gattcatgca acatgcccgg atgtggggtt tccgtccgct tcgcgtaagg gtcgggctgt 480
gtctacagcg aactatttcg cttccccatc atcggggggt tcggcgcatt atgtttgtga 540
tattggggag acggtgcagt gcctgtcaga ggggactata gggtggcatg ccccgccgaa 600
tccgcattct ttgggtatag agatttgcgc ggatgggggt tcgcatgcct cgttccgtgt 660
accggggcat gcttacacga gggagcagtg gcttgatccg caggtgtggc ccgcagtgga 720
gagggccgct atcctgtgtc ggcagttgtg tgacaagcat ggtgttccga aaaggaaact 780
gtctgtggcc gatttgaagg ccggtaaacg gggtgtgtgc gggcatgtgg atgttacgga 840
tgcgtggcat cagtcggatc atgacgatcc ggggccgtgg tttccgtggg acaaatttat 900
ggctgtggtg aatggccacg gcggcggttc aagtagtgag gagttgagta tggctgatgt 960
acaagcgtta cataatcaga ttaaacagtt gtcggcacag gtggcccagt cggtgaataa 1020
gctgcatcac gatgttggtg tggttcaggt tcagaatggt gatttgggta aacgtgttga 1080
tgccctgtcg tgggtgaaga atccggtgac cgggaagctg tggcgcacca aagacgccct 1140
gtggagcatc tggtattacg tgttggagtg tcgcagccgc atagacaggc ttgagtctgc 1200

-continued

```
tgttaatggt ttgaaaaagt gatggtggtt tgttgtgggt aaacagtttt ggttgggctt   1260
gtttgagcgt gccctgaaaa cttttattca aacgtttgtt gctgtgcttg gggtgacggc   1320
gggtgttact tatactgcgg agtcgtttcg cggtttgccg tgggagtctg ccctgataac   1380
agcaacggtt gctgcggtgc tgtctgttgc tacatcgttt ggtagcccgt catttgtggc   1440
cggcaaacct aaaaccacgg ttgtggatgc tgggcttgtt ccacccgacg atgggggcat   1500
ggttgagccg cactcggtgg atgtgtcgga tcctggcatg atcgagccga cagatgatgt   1560
ggatggtttt gctggctatg tgccgaagcg tgcagccgag tcggaggtta gcacggtgga   1620
gtctactgtt gcataattga acatagatgt gtgccccagc ggtgctgcca cgatcgtgtg   1680
gtggttgccg ctggggcact ctttttgtgt ctataggagt tttacaggtt gtcgtctagt   1740
gtgtcttcga gcatctggtc caggtagagg caggcggaga tagtatcgtt ggcctggtct   1800
agaacgttct ggccgataac atttttatga ttgtcgcggt ggctgatgat agaccgcatg   1860
atatcgtcgg ccgccgcctg caatagtttg gcctggtatg cgattcctgc gagccagtct   1920
agtgcttcct ggcttgccag tgtgtcgtct ggaatgccac gggtgttgct gttgtttgtg   1980
gggtgtcctg cactgtcgca gcaccacaag atttcgctgc actcgtctag cgtgtcctgg   2040
tcgatagcaa gatcgtcgag gctgacttct ttgacggtaa ggttcacatt gtcgagggag   2100
atgggtacac cgtattggtt ttcgacactg tcaacaatgt tttccaactg ttgcatgttg   2160
gtgggctgtt gttggatgat acggtgtact actgttttga tggcggtgta ggggatattg   2220
tgtgtgttgt tcatggtttt tatcccaccc ctgtgttgtc gtcgttattg tctggatagt   2280
atctactgtt tgcgtagcct gtgagggtga tgagtgtttg gtctgcccac tgtttcactg   2340
tctgccgggt gacacccaat cgttgggcgg ctgtggcgta ggtttgatca tacccgtata   2400
cttcacggaa tgcggctagc ctggctaggt gttttcgctg tttggagggt tcacatgata   2460
gggtgtagtc gtcgatggcg agctgtagat cgatcatggt ggcaatgttg ttgccgtgat   2520
gctgggggc ggttggtggg ggtggcattc ctggctccac actgggtttc catgggccgc   2580
cgttccagat ccattgggcg gcttggatga tgtcggcggt ggtgtaggtt cggttcatgt   2640
gtcacccccct gaacaggtcg ttgctggtgc tggtgttggt ggtgtcgaat cgtccgacgc   2700
agtggcagta gtcgtacatg agtttgataa tgtgttggtg gtctcccaaa taggtgtttc   2760
cgctgatact gtaggtggct gtgccgtctt tactgatggt gtatttggcg gtgatggttt   2820
cggggttttc ggtgtcggtg atgattgctg tggtggtggt gcctactgtt tgtagcacgg   2880
tggtttgggt tccgtcgtcg atagtggttt taaccatggt gtgtgttctc cctttttaga   2940
tgctggtttg gttgtcggct agatgaatga tgtcgggtaa gggtttcggc tggtctaggt   3000
gttgtatggt tttgttggct agccgtttgg ctaccctgta acacattttg gtgtagtgtt   3060
tgttgtctag gttgtggtat tgttcccgca ccgcaatata tagtagagag tcttggtaca   3120
ggtcgtctgc actgattgcg gggtagtgtg cggctgtttt ggtgcatgcc cggttgagtg   3180
tgcgtagatg atggtctgtg gcccacaccc acgatgcggt ggtggctagg tcggcttttg   3240
ttggtcgtct gctcatggca tttctttcat cgggctatct ggtagttgtt tggtgttttg   3300
ttgttgatag tgtagcacac gagtccgggg tttccggtgg tgccagtctt gtgccggtac   3360
catgtggatt cgccttccat ggatgggcat tggatgaagg tgcgttgtcc ttgttcggag   3420
atttctaggt ggtgccggtg cccggccatg aggatgtggg atgtggtgcc gttgtggaat   3480
tcttggccgc gccaccaatc atagtgtttg ccggtgcgcc attggtgtcc gtgggcgtgc   3540
aggatttgtg tgccggccac gtcgacggtg gtggtcattt cgtcccgttg ggggaagtgg   3600
```

-continued

```
aagtgaaggt tggggtattg gttgttgagc tggtaagctt ctgcgatggc gcggcagcag   3660
tccacgtcaa aggagtcgtc gtaggtggtg actcctttgc cgaagcgcac ggcttcgccg   3720
tggttgccgg ggatggatgt gatggtcaca tttttgcagt ggtcgaacat gtggacgagt   3780
tgcatcatgg ccatgcgggt gagcctgatt tgttcggtga ggggtgtttg tgtgcgccag   3840
gcgttgttgc ctccttgtga cacgtatcct tcgatcatgt cgccgaggaa tgcgatgtgg   3900
actcgttcgg gtttgcctgc ctgttgccag tagtgttttg cgactatgag ggagtgcaaa   3960
tagtcgtctg cgaatcggct ggtttctccg ccggggatgc ctttgccgat ttggaagtcg   4020
cctgccccga taacgaaggc tgtctcgtca ctgctttggg tgtcttgttc gggtttgggt   4080
ggctgccatt cggctagttt gttgacgagt tcgtcgacgg ggtaggggtc ggttgcgggt   4140
tggtggtcga tgatttttg tatggatcgg cctgtttctc cgttggggag tgtccattcg   4200
gagatgcgtg tgcggcgtac agtaccgttg gctagattgt cgtcgatggt gtcgatggcg   4260
ttgtcgtggt tggctagctg tgtgagtagc cggtctatat tgtctatcac tggttttcct   4320
cctctggcgg ggtggtgttg gcttgtttgc ggcggtagtc ttttataacg gtggcggaga   4380
tggggtatcc tgcctgggtg agctgttttg ctagccacga ggcgggtata gacctgtcgg   4440
cgaggacgtc tgcagccttg ttgccgtagc gttgaataag ggtttcagtt ttggttgcca   4500
tgatgtccta tcggttgtgt ggcgggctgc catcctgtgc ggcagtcgcc gtcgtggcct   4560
ggtttgcgtg tgcaccacga tacggttccg tctgtgtggt tgagtgtttt gccgcacatg   4620
acgttttgta gatgctcggg cagggcgccg tcaccctggt tgctggtttg tgtgtcgaag   4680
agtgttttct ggttggtgaa atgctctgac acggtgccgt tgtgtacggg tagtatccat   4740
gttttccatt gttgttgtag ccgggtgttc cagtggaatt gtttggccgc gttcgtggct   4800
tgtttgatgg ttttgtagta gccgacgagg atgcgctggt gttcactgtc gggtgggttt   4860
tggcctcgcc agtattgtgc cgcgacggca tacctgttgt tgtctgtgaa ggcgtcccag   4920
cagtattcga taatgtgttg tagtacacta tcgggaatgt ctcgtacttg gttttcgtcg   4980
agccacgcgt cgacaatgat gttgcgtatg gcgtgtttgt ctttggtggt gggtttgaac   5040
gagatactca ccatgctggc ctgtcgtctt gcatgaaatc gttaaaggat gattcgcttg   5100
tgcggcgtgc ctgggtgatt tgctggtcag tccagtcggg gtgttgctgt ttcagatagt   5160
accagcggca ggcatcatat gtttcgttct gcaagcgggt gagatggttt tcggtgatga   5220
tttgtttcca cattgtccac gaaacgtcga gcctgcggag catgtccatg gccggcacat   5280
taaacgagtc aaggaagagt atttcgtggg tgtagtagtt tttctcgtag gcgtaccatc   5340
cgcttcggtg cctgtggggc tggtttttgg ggtaggcttc ccggcatact ttgtgtaaac   5400
gtttggccat gtcgtcgggt agttcaatgt cggggttggc gcggatcatg gatcgcatcc   5460
cgtcgtaggt ggtgccccag gtgtgcatga tgtgtagtgg gttgtctcca tcggcccatt   5520
tttctgcaca gatggcgagg cggatgcgcc tcctggctgt ttggctggtg ttgcgccggt   5580
tggggattgg gcacgtgtcg aggggatcca ttatgtttta gtgtaccttt ctggtttcgt   5640
gttgttgacg tgttttactg tagcacagtg tctagtgctt gtgtcaaccc tgtttttccg   5700
gcctgcaggt aggtgtctgt gacatctccg accgtgaggg gcacatgggt ggcttggggg   5760
agtgctgcct ggatggtttg tgccatctgg tcgcctgcgg ggtctgggtc tgaccagatg   5820
tagatgtggt cgtagccttc gaagaatttg gtccagaagt tttgccacga ggttgcgccg   5880
ggtagggcta cggccggcca tccgcattgt tcgaggatca tggagtcgaa ttcgccttcg   5940
```

-continued

```
caaatgtgca tttcggctgc cgggttggcc atggcggcca tgttgtagat ggagcctgtg   6000
tccccggctg gggtcaagta tttggggtgg ttgtgggttt tgcagtcgtg tgggagtgag   6060
cagcggaaac gcatttttcg tatttcggct ggccgctccc aaacggggta catgtatggg   6120
atggtgatgc actggttgta gttttcgtgg cctggtatgg ggtcattgtc gatgtatcca   6180
aggtggtggt agcgggctgt ttcttcgctg atgcctcttg ctgagagcag gtcgagtatg   6240
ttttcgaggt gggtttcgta gcgggctgag gctttctgga ttcggcggcg ttccgcaatg   6300
ttgtagggtt gtatgctgtc gtacattcgg gttttcttct tctagtcgtt gttgtagttt   6360
gtggagtcct cctccgacac cgcatgtgtg gcagtaccag acgcccttgt cgaggttgat   6420
gctcatggag ggctggtggt cgtcgtggag cgggcagagt atgtgttgct cgtttttgga   6480
cgggttgtag cgtatctggt agatgtcgag gatgcggcgg gtgtcagagg tgtgggagga   6540
gctcgttgag ggttgatacc acataggctt cgctccaggg tttgttgcgt tgtttcatca   6600
ctacgagtcc gatggtggaa ttgttttcgc ggtttcggtg tgtttcgtag ttgcgtgcct   6660
cccggctggc ttgtttcacg aattcggcta ggtggggctg gccggctttc gcctcgataa   6720
tgtaggtttt gttgctggtt gtgaggatga ggtcgccttc gtcttcgcgg ccgttgaggt   6780
ggaggcgttc gatatcgtgt ccggtgtcgc gtagctggtg caataatcgt gtttcccatt   6840
cggctccggc ccgccggttg cgtgcctgct gtgtggccat agtttttaga gtcctttgtg   6900
tgttgtggtc atgttccagg gctgtttttc ggcgaggggc ccgaagaatg tgtattcggg   6960
gtaggctcgt agtcgttcat atcgggtgcc gtcggggctg gatttgccgg tgcgctgttt   7020
caatactgcg atgcgtgcct cggccggtat cgtgagaccg ttgccgttat cctcgccacc   7080
atacaatgag actcccaata tgagttgtgg tttttcggag aggccgtttt tgatttctcg   7140
ccgtgccggg gggtgttcga tgtcggttcc ggttttgtcg gtggcgtggt gtgtgacaat   7200
aatggtggat ccggtgtcgc ggcctaatgc tgtgatccat tgcatggctt cttgctgtgc   7260
ctgatagtca ctctcgcagt cttggatgtc catcaggttg tcgataacaa tgagtggcgg   7320
gaaggtgttc cacatttcca tgtaggcttg cagctccatg gtgatgtctg tccatgtgat   7380
gggtgactgg aatgagaatg tgatgtgttg gccgtggtgg atgctgtctc gatagtattc   7440
tggtccgtag tcgtcgatgt tttgttgtat ctgtgtggtg gtgtgttggg tgttgagtga   7500
gatgattcgt gtggaggcct cccagggtgt catgtcccct gatatgtaga gggcgggctg   7560
gttgagcatg gcggtgatga acatggctag cccggatttt tggctgcctg agcgccccgc   7620
aatcatgacg agatcccctt tgtggatgtg catgtcctgg ttgcggtaga ggggttctag   7680
ttgtggtatg cggggcagct cggctgcggt ttgggaggct ctctcgaagg atcgttggag   7740
agagagcatc gggaccttat ctatctatcg gttgggtgtg ttttggtggt cagatggagt   7800
cgatgtcgat gtcagcatcg gcgggggctg tggtgtcgtc tagctggccg ttatcgcgct   7860
tgtctacgta ttcggcaacc ttatcgtaga tggcgtcatc gagggggtgg tgtcgtctag   7920
ctggccgtta tcgcgcttgt ctacgtattc ggcaacctta tcgtagatgg cgtcatcgag   7980
gggtttgagc acgaccgcat tgaacccgtt tttggtgcgc acggtggcga gtttgaaggc   8040
ctgctcctcg ccaaggtagg cttcgaggtc gcggatcatg gaatgtgggc ggtcgttgtt   8100
gccgcgcgct ttctcaataa tagcgttggg aatgatttct ggggtgccgt tgttgagatc   8160
gtctagggtg tggaagattg tgacatcagc gtagatgcga tcggctgtct gtccaccgta   8220
gccttcggtg ttgtgttcta cgtcgcggat tttgaaggcg atggcggtgg cgtcctggtt   8280
tcgggagggg ttgaagaagg tgctgttgct gttgttgcgg tagttggcga gtcccatggt   8340
```

```
tgtttccttt actgtttgtg ttggtttgtg tcggttttat cgggtgaggc tgtttcgttt   8400
gctgcggaaa gcctcggaca cgtcactgtt actggtgatg attttcttgt actgtttcag   8460
aaggtcggct agctgtgcct tgcttgttgc attgttgatt ttgtcgatga taatctcgtt   8520
ttcgtttgat gcgatgttgt ctacgtagtc tttggctgcc tggttgtagc ggtcttggag   8580
gatgatggat gcgcttgcta cgagtgttgc tagatcccag tctttggaca cgtcaccgtt   8640
tttgaggccg cctagcagat caataatgga ttgtttgatg tcttctgcgg tgtctccgcg   8700
gatgactgtc catggggctg cgtagtctcc accgtatttg agtgtgatag ttagctttcc   8760
gctgtctgtg gtgtgctcgt cggtcacgtg ttttcctttt cgttgttttc ggcttctggt   8820
ggctgtacgg tggtttctac cgggtatctg tacgagtttt tcccgttgac ggcccagcag   8880
gcgtccttga cggggcatcc tttgcagagt gctgtgacgt ggggtacgaa gatgccttgg   8940
ctgattcctt tcattgcttg actgtacatg gatgatacat gccggtaggt gttgttgtca   9000
agatcaatga gttcggtgga tgtgccctgc tcaaccgatt gctcgtctcc cttggtggta   9060
gcgggtgtcc aaaacattcc tttcgtcaca tggatgccgt gttggttgag catgtaacgg   9120
taggtgtgca gctgcatact gtcggcgggt aggcgtccgg ttttgaggtc caaaatgaag   9180
gtttcacccg tattcgtatc tgtgaatacc cggtcgatgt agccaacgat ctgggtgccg   9240
tcggggaggg tggtttctac cgggtattcg atgcccggct cgccgtcaat aacagcggta   9300
gcatattctg ggtggttgcg cctccatgtt ttccaccggt ccacaaaggt ggggccgtaa   9360
atcatccacc aattgtagtc tttcttgtgt gtcccgcccg actcgcacat gtttttgcat   9420
attctgccgg agggtttgat ttctgtgcct tcggattcgg cgagggcgac ttgggtgtcg   9480
aaaatgtttt tgaaggatga gagtttgtct ggcagtgcag ggtattcggc gggattgtac   9540
aggtgtaggt cgtattgttc ggtgatgtgg tgtatggcgc ttccggcgat ggtggcatac   9600
caggtgtggt gttgggcgtg gtagccgtgg gataggcgcc atttttcacc gcattcggcc   9660
cactgtgaca gtgatgagta ggagatgtgg cctggatggt caatggtgga cggtttttgt   9720
gctaggggca ttacttgtcg cttttgtggg tgttccatgg gtttcgggtg tcttggccgg   9780
cattgtgttg ctggtatgcg aggagtgcga ggcagtgcca ggcagcatgg gccagatggg   9840
gtagcccgga ttcatcatcg aggttgttgc cttgctgcca tgataacagg tgccggtaga   9900
gggcgtcaac actgtggctc cacggatagc cgccggtcca gttgttgtcg ccgtatttgg   9960
tggcgccgta tccggccaca gagccgaggg cgtgtaaggc tgtagggtcg atgagggata  10020
gcctgcaaag tttcaattct ttcttggcgc cagtatcagg gtcggtgtac atgctggtgg  10080
gctcatccat ggtgtgtgtg ctccttaagt atggggttac tggttggggt tgtgggcgag  10140
tgctacggcg agaataatga tggcgagggt ttcagcgatc agtatgggtg ttgtgatcat  10200
ttgtggtcgc ggggattgtt ggtgagggtt gaggcgccca ggaggatagt gagggcgcat  10260
gcggcgatga tggcgagggc tgccttgtgt ggggtgccgg tggcgtacat ccatgtgatg  10320
atgccgcctt ggatccaggc gaggctggtg aagaacgttt cgtagctgtg tagctcaatg  10380
ttgttgttgg gtgtgttcat gcttgctcct gaagaatggt gttgatggtt gtgtaaatgt  10440
tgtacaggtc ggtttcgata gataacagtt ggtggatttg gtggtcgaga tcaatgtcgg  10500
ggttgagggt gttgatgcgg gaggcgatgt cggtggctgt gcgtagtgtg ccgccggtgt  10560
ggtgaatgat gtgtgccgtg tcggcgagtc cggtggtgac agtgtagtgg gagaggagag  10620
gcatagctgg gggtgctcct tgacggggtt actgttgcgg gttgatgttg aggtcggtga  10680
```

cgttggggtg gtcttctgtt ccggtgacga ggcagtggac ggtgactggg agtttggatg 10740
cgccgggctg tttcgcggtt gcgccgtaga cgatggagaa ggtgtctttg ccaataattt 10800
tgtggagttg gaggtcgatg tcggggttgc cgttccattt gacgccttgt gtggcggcct 10860
gttgttcggc tttgcggttg caggtgtgtg ctgcggtgat catggtgagt ccggtggcgg 10920
tttcttcacc ccttgcttgg gcttgcttgt gggttttctg ctgttcggct cgcagtgact 10980
gttctgctgc tgcctgccgt gctttctttt cggctttgcg ctgttgggta gtcttggggg 11040
tccattcggt gttggctgtg gtggcttgcg gtgcgggttg tgatgcgagt ggcggattgt 11100
cgtctggggc tggcatgaag gatgctgcgg cgatgatggc ggctgtgatt ccggcgatgg 11160
tgtagccgtt tttcttgttc atgattttgt gttccccttt ccggggtgtt gttcgttgct 11220
gacatgatta atactttcag cggctgggcc cactgtcaag gctgcgctca acgattgtga 11280
gcgatacttg tgtggctagg ggttttgtcc ttgaggtggg agatgtcttt cccttgcgtc 11340
cagtatccat ggcggttgcg agtcatccct ttggcgagca tctcgtccac ggtgagacac 11400
ctgcgacgat ctggaccctc cttgactccc tgatcgcctg tgcggtgcat gtcaccggca 11460
caagtaccat taaatgtctc gtggcagatt gtgcaatgct ctggtcggta tccgatgatt 11520
gtgctatcgc acttgtggca tgtccattgc atgattggtc cttctttcgt gttttaagct 11580
tgtactctga ggattagagc gactttcagc ccttgggggg tatgattata taggtcaggt 11640
atttctaggc gattctaggc tcattgtgtg tggctggggg ttatcgggca cacagggtga 11700
ggagttggcc aacattgatg cgggtcacat tccagtagag ttgcgtggct tccccaccgg 11760
tgagtggctt ccactcgtca tggctgaaca cggtgccgtc ggttgcgatg aatgtgttgg 11820
ggcgtagctt gtgaagctca gtctctacac gctgccggta ggcttcggcg aggccctcga 11880
aatccatgtg gtcgcagggg aggttttcga ggcgtgtcag gtcgaagggt gtggggcagt 11940
cgtagctggc ggggctgtag agctgggtga aatggttggc gatcttctgc atgacgggtt 12000
ccttttctcg tatggtgagt tgatagtttt atcgggtgga tgcgacaagg atggcgtcta 12060
catcgatcat gtcgatgaga tcgtggagtt cctcggcctc attctcggag aggtggcgcc 12120
agccatagtc gccgtatacg gcgccgtcga gggtgacagt ccacaggggc cggatgagtc 12180
gtatggcttc ttgtacttta gcgtggtaca tgcggcgcac catatccaga tcgatgtcgt 12240
ctgaatggtt tccagtgagg ctgtagaggc tgagcgggtc gatttctgtc tgcctgtaga 12300
gggatgtgaa tgatggtgtg atgagtgtgc catccatgag agtgtgctcc tttcggtggt 12360
ggaggggttg ttgtggtttc tagagtgtgt aggctgcgac ccatagtcaa ggctgcgctc 12420
attcggattg agcgtttcat atgggtgtgg catggaatct acacccccat actgtgtgag 12480
ataggccaca tcctcctggc ttggtgtgaa ccctcgagac tactctgcct atctggcgtg 12540
gagggtgtag cccagaaata ccgtttaaag ccttcatacg gcgcctagga gcgccttaca 12600
gggtgggggc taggtattta tacccccaag caattctgat cgattctaga cgcctcccag 12660
gagcccgata cacgatccgc tatccagaca cagatcatca gcccctatcc tggttagcta 12720
agcctcaact atgtggacag tgttgattac tgtggggtaa gaaggacacg gtaaaagaaa 12780
gaggggggag catcggcttt caagccttaa ggtcttagca gttagcaccg agcccctcaa 12840
gggctcgtcg tcagcccatc aggcacggcc ctgaacgggg tacacgccat cagggaaggc 12900
ttgagagtac gaggagcctt agcgacgagt actcgaaagc ctgagggaac accctcagca 12960
ctgatgggtc tagcgtgttc ggaaaggaca caggagtaaa gcgtgacagc tgtccgggag 13020
tgaaacccgt tctgactagg ggtttcagcc ttaaccaccc tcaaaggtta caagactcta 13080
agaaaattta aggaaaagtt taggtttaat ttttggacct ttactaccaa aaacacccgt 13140
ttacacccct caaacccgcc tatagagcca aatccaccag tttgactcat cccaggtggc 13200
atatgatagg ctggacaggt agccagctgg acgcaaggcc gaaatccgct gacgcggctt 13260
tcacccttac atccatcagt ctaccaaaga cttaaagacc taagggctta gcgctaaggt 13320
gctgatagct tagcaccgag cccttgaggg gctcggcatc agccctaaag ccttaaacac 13380
ttaaagtaca tataaaactt taaaagctta acacttaagg ttataaataa acattaaagc 13440
tttaaagtct taaagtacat atataacctt aacacctaag ttaagtataa aaccttaaag 13500
gcttagcact gaaggatata aacttcacat cagtttttaa gactttaaaa cttaaaataa 13560
ctattaagac ttaaagactt ataagtttta aacacttaaa gtaactataa gactttaaag 13620
accttaagta cttaaagtta accatcagtc ttaaacttta atattataac ctataagtct 13680
taaagcttat aagttataaa agttttagaa gagctaagag gttaacttct ttacttctct 13740
tctctctttg gttctttctc tcttctcttc ttttcttcat caggggagaa gaggaacctt 13800
ttaccatcag cgccgatgga ctgtcaccgt gtgactcgtg taccaccggt cgcacgctcc 13860
cggtttcaca ctccccacac tctgacaccc gtgtcccttt caggcttagc gtgttcggct 13920
gaaggcgtac ggcgtgtcgc gccaacaccc ttaacaccag gtaagactta aagtgtatat 13980
tatatgtaga agactttaaa acctataagg tgttcccgct tagcctgtgt cctacaccgc 14040
taggcgccaa gcgttaagtc ttgaaacgcg aacacacacc cacccccatt tttctttcgt 14100
gtccttctct tttgacaccg ctggggggcg atgtgatctt tctcactacc catgggggta 14160
gtggagaaca cacccacccc accatcaaca gaacaccccc tcaaacgaac aaaacagggc 14220
ctagaatcga tcggcagggc aagggcaagg tattcatacc cccaacacat tccaggccgt 14280
cagagaggca aataagaccc gtacagggct agtcgaggat cggagacgtg atggcacaca 14340
ccaatcgcac cgcatccgcc gcacaccgac actggcggca acgactcatc acccaagccc 14400
gacagcaagg ccaaaccgaa tgcccactct gcggagcaac catcacctgg gacacctacc 14460
agctgccaac tagccccgaa gccgaccaca tcacacccgt cagcagggga ggactcaaca 14520
ccctcgacaa cgggcaaatc atctgcagaa catgcaacag aagcaaaggc aacagaacac 14580
aaccaaacat caaattccaa caacaaacca caaaaaacct tgttccatgg tgacaaaacc 14640
cgccaacccc caccggggac accccctgca cacccgtgca agacctcgta cggcttagtg 14700
aaatacctcc cttttgtgga tttgtctgtt tgtcgacttt ttgtgttggt ggtgagtgtt 14760
gtgcagcctg agcttcctga gggacacgag tggtgtgggg agacgcgtcg ttggtggcgt 14820
gtgtggggtg aggatagccg cgcgcagtac gtgtctgatg aggagtggct gtttcttatg 14880
gatgctgcgg tgattcatga ttgtgtgtgg cgtgagggtc gcgcggattt ggtggcttcg 14940
cttcgtgctc atgtgaaggc ttttatgggt atgttggatc gttattcggt tgatgtggcg 15000
tctggtggcc gtggtggggg ttctgcggtg gcgatgattg accggtatag gaagcgtagg 15060
ggggcctgat taggtgtctg gtgttgttgg gtctcaggtt cctcgtcatc gtgtggctgc 15120
ggcgtattcg gtgtctgctg gcggtgatgc tggggagttg ggtcgtgcgt atgggttgac 15180
gcctgatccg tggcagcagc aggtgttgga tgattggcta gctgtgggtg gtaatggcag 15240
gcttgcttcg ggtgtgtgtg gggtgtttgt gcctcgccag aatggcaaga atgctatttt 15300
ggaggttgtg gagttgttta aggcgactat tcagggtcgc cgtattttgc atacggctca 15360
cgagttgaag tcggctcgta aggcgtttat gcggttgagg tcgttttttg agaatgagcg 15420
gcagtttcct gacttgtatc gtatggtgaa gtcgattcgt gcgacgaatg gccaggaggc 15480
tattgtgttg catcatccgg attgtgccac gtttgagcgt aagtgtggtt gtccgggttg 15540
gggttcggtt gagtttgtgg cccgttctcg tggttctgct cgcgggttta cggttgatga 15600
tttggtgtgt gatgaggctc aggagttgtc ggatgagcag ttggaggcgt tgcttcctac 15660
ggtgtctgcg gctccttcgg gtgatcctca gcagattttc ttgggtacgc cgcctgggcc 15720
gttggctgac gggtctgtgg tgttgcgttt gcgcgggcag gctttgtcgg gtggtaaaag 15780
gtttgcgtgg acggagtttt ctatcccgga tgagtctgat ccggatgatg tgtcgcggca 15840
gtggcggaag cttgctggtg agacgaatcc tgcgctgggt aggcgtctga atttcgggac 15900
ggtgagcgat gagcatgagt cgatgtctgc tgccgggttt gctcgggagc ggcttggctg 15960
gtgggatcgt ggccagtctg cttcttcggt gattccggcg gataagtggg ttcagtcggc 16020
tgtggatgag gcggctctgg ttggcgggaa agtgtttggt gtctcgtttt ctcgttcggg 16080
ggatcgtgtc gctttggctg gtgctggccg gactgatgct ggtgttcatg ttgaggtgat 16140
tgatgggctg tcggggacga ttgttgatgg tgtgggccgg ttggctgact ggttggcggt 16200
tcgttggggt gatactgacc ggatcatggt tgccgggtct ggtgcggtgt tgttgcagaa 16260
ggcgttgacg gatcgtggtg ttccgggccg tggcgtgatt gtggctgata ctggggtgta 16320
tgtggaggcg tgtcaggcgt tttggagggg tgtcaggtcg ggtgtggttt ctcatcctcg 16380
tgccgattcg aggcgtgaca tgttggatat tgctgtgagg tcggctgtgc agaagaagaa 16440
gggttctgcg tggggttggg gttcctcgtt taaggatggt tctgaggttc ctttggaggc 16500
tgtgtctttg gcgtatcttg gtgcgaagat ggcgaaggct aggcggcgtg aacggtctgg 16560
taggaagcgg gtgtctgtgg tatgaattcg gatgagttgg ctctgattga gggcatgtac 16620
gatcgtatcc gaaggttgtc ttcgtggcat tgccgtattg agggctacta tgagggctct 16680
agccgggtgc gtgatttggg ggttgctatt cctccggagt tgcagcgtgt gcagacggtg 16740
gtgtcgtggc ctggtattgc ggtggatgct ttggaggagc gtctggattg gcttggctgg 16800
actaatggtg acggctacgg tctggatggt gtgtatgctg cgaatcggct tgctacggcg 16860
tcgtgtgatg tgcatttgga tgcgctgatt tttgggttgt cgtttgtggc tgttattccc 16920
cagggtgatg ggtcggtgtt ggttcgtccg cagtcgccga agaattgcac gggccggttt 16980
tcggctgacg ggtctcgtct ggatgctggc cttgtggtgc agcagacgtg tgatcctgag 17040
gttgttgagg ctgagctttt gttgcctgat gtgattgttc aggtggagcg gcgaggtagc 17100
cgtgagtggg ttgagacggg ccgtataccg aatgtgcttg ggctgttcc gttggtgcct 17160
gttgtgaatc gtcgccgtac gtctaggatt gatgggcgtt cggagatcac tcggtcgatt 17220
agggcttaca cggatgaggc tgttcgcaca ctgttggggc agtctgtgaa tcgtgacttt 17280
tatgcctatc ctcagcgttg ggtgacgggt gtgtcggctg acgagttttc gcagcctggc 17340
tgggtcctgt cgatggcttc tgtgtgggct gtggataagg atgacgacgg tgacactccg 17400
aatgtggggt cgtttcctgt gaattctcct acaccgtatt cggatcagat gcgtttgttg 17460
gctcagctga cggcgggtga ggctgcggtt ccggagcgct atttcgggtt tatcacgtct 17520
aacccgcctt ctggggaggc tttggctgcg gaggagtcga ggcttgtgaa gcgtgccgag 17580
cggcgtcaga cgtcgtttgg tcagggctgg ctgtcggttg gtttcctggc tgccagggcg 17640
cttgattcga gtgttgatga ggccgcgttt ttcggcgatg tgggtttgcg ttggcgtgac 17700
gcttcaaccc cgactcgggc ggctacggct gatgctgtga cgaagcttgt gggtgccggt 17760
attcttccgg cggattctcg tacggtgttg gagatgctgg ggcttgatga tgtgcaggtt 17820

```
gaggctgtga tgcgtcatcg tgccgagtct tcggatccgt tggcggcact ggctggggct  17880
atatcgcgtc aaactagcga ggtttgatag gcgatggctt cgggtgttgc gtcaaggttg  17940
gctgctgccg ggtatcagcg tgaggcggtc aggtttgccg ggaagtatgc gggctattat  18000
gccgagcttg gtcgtttgtg gcattccggg aagatgacag atgcgcagta tgtgcgtttg  18060
tgtgtggagt tggagcgtgc cggccatgac ggttcagcgg cgttggcggg taagttcgtg  18120
tcggattttc ggaagcttaa cggtgtggat cctggtttga tcgtgtatga cgagtttgat  18180
gctgccgccg cgttggctag gtcgttttcg actattaaga tgatgaatag tgacccggat  18240
agggctaagg atacggttga tgcgatggcg gcgggtgtta atcgggctgt catgaatgct  18300
ggccgtgaca cggttgagtg gtctgcgggt gcgcagggta ggtcgtggcg ccgggtgacg  18360
gatggtgatc cgtgcgcgtt ttgtgccatg ttggctacga ggtcggatta tacgaccaaa  18420
gagcgggcgc ttactactgg tcatactcgg cgtcataagc gtggcggtag gcgtccgttt  18480
ggttcgaagt atcatgatca ttgtggttgt acggtggttg aggttgttgg cccttgggag  18540
ccaaataggg ctgatgccgc atatcagagg acgtatgaga aggctcgtga gtgggttgat  18600
gatcatgggt tgcagcagtc gcctggcaat attttgaagg ctatgcgtac tgttggtggc  18660
atgagataat ttgatgtggt ttccggttgt gtgccgccgg ttatcggtgc acagggttgt  18720
ctcccgcacg gggtcaaca atgttgtgtt gttttccgca aggagtatag ggttaggcta  18780
tggccgatca aaaagttgaa gaacagaatg ttgacaatga tgctgttgag cccggaaagg  18840
gtggagacgt tgttgatgtt gtgaaggatg ggcaggctgc cggcgatgat catgccggtg  18900
atgtttccgt gaaggaggag tcttcttctg gcacggattg gaaggctgag gctcgtaagt  18960
gggagtctcg tgctaaaagt aatttcgccg agttggagaa gcttcgcgcc tcggatggtg  19020
atgcggggtc tgtgattgat gagcttcgcc gcaagaatga ggaactcgaa gaccggatta  19080
atgggtttgt tcttgagggt gtgaagcgcg aggtggctgc cgagtgtggc ctgtcgggtg  19140
atgctgtcgc ttttttgcac ggtggcgatc gtgaagcact ggtggagtct gctaaggctt  19200
tgaagggttt gatcgaccat agtagtggtg gcgcgggtgt gcgccgtctt gcggggagtg  19260
cccccgttga tgatgttaaa cgacgtgagg gtgtcgcgtt tgtggatgct cttgtcaata  19320
attctaggag atgatttgtg atggctgacg attttctttc tgcagggaag cttgagcttc  19380
ctggttctat gattggtgcg gttcgtgacc gtgctatcga ttctggtgtt ttggcgaagc  19440
tttcgccgga gcagccgact atttttggcc ctgttaaggg tgccgtgttt agtggtgttc  19500
ctcgcgctaa gattgttggt gagggcgagg ttaagccttc cgcgtctgtt gatgtttcgg  19560
cgtttactgc gcagcctatc aaggttgtga ctcagcagcg tgtctcggac gagtttatgt  19620
gggctgatgc tgattaccgt ctgggtgttt tgcaggatct gatttccccg gctcttggtg  19680
cttcgattgg tcgcgccgtg gatctgattg ctttccatgg tattgatcct gccactggta  19740
aagcggctgc cgctgtgcat acttcgctgg ataagacgac gcatattgtt gatgccacgg  19800
attctgctac ggctgatctt gttaaggctg tcggcctgat tgctggtgct ggtttgcagg  19860
ttcctaacgg ggttgctttg gatcccgcgt tctcgtttgc cctgtctact gaggtgtatc  19920
cgaaggggtc tccgcttgcc ggccagccta tgtatcctgc cgccgggttt gccggtttgg  19980
ataattggcg cggcctgaat gttggtgctt cttcgactgt ttctggcgcc ccggagatgt  20040
cgcctgactc gggtgttaag gctattgtgg gtgatttctc tcgtgttcat tggggtttcc  20100
agcgtaactt cccgatcgag cttatcgagt atggcgatcc ggatcagact ggccgcgatt  20160
```

tgaagggcca taatgaggtt atggttcgtg ccgaggctgt gctgtatgtg gctatcgagt 20220
cgcttgattc gtttgctgtt gtgaaggaga aggctgcccc gaagcctaat ccgccggccg 20280
agaactgatt tattgttgcg gtgatgtgtc aatgtgcagg gggtggtgtt gatgggtatc 20340
attttgaagc ctgaggatat tgagcctttc gccgatattc ctagagagaa gcttgaggcg 20400
atgattgccg atgtggaggc tgtggctgtc agtgtcgccc cctgtatcgc taaaccggat 20460
ttcaaataca aggatgccgc taaggctatt ctgcgcaggg ctttgttgcg ctggaatgat 20520
actggcgtgt cgggtcaggt gcagtacgag tctgcgggtc ctttcgctca gactacacgg 20580
tctagtactc ccacgaattt gttgtggcct tctgagattg tcgcgttgaa gaagctgtgt 20640
gagggtgatg gtggggctgg taaagcgttc actattacac cgaccatgag gagtagtgtg 20700
aatcattctg aggtgtgttc cacggtgtgg ggtgagggtt gctcgtgcgg gtcgaatatt 20760
aacggctacg ctggcccctt gtgggagata tgatatgacc agttttcctt atggtgaaac 20820
ggttgtgatg cttcaaccga ctgttcgtgt cgatgatctt ggcgacaagg tggaagactg 20880
gtctaagcct gtcgagactg tgtaccataa cgtggccata tatgcttccg tttcgcagga 20940
ggatgaggct gcggggcgtg actcggatta tgagcattgg tcgatgctgt tcaagcagcc 21000
tgttgtgggc gctgattatc gttgtaggtg gcgtattcgg ggtgttgtgt gggaggctga 21060
cgggtctcct atggtgtggc atcaccccat gtccggttgg gatgctggta cgcaggttaa 21120
tgtgaagcgt aagaagggct gatgggtagt ggctcaggat gtgaatgtga agctgaactt 21180
gccgggtatt cgtgaggtgt tgaagtcttc tggagtgcat ggcatgttgg ctgagcgtgg 21240
cgagcgtgtc aagcgtgccg cagcggcgaa tgtgggtggt aacgcgtttg atagggccca 21300
ataccgtaat ggtttgtcgt cggaggtgca ggttcaccgt gttgaggctg tggcgaggat 21360
tggcaccacc tataagggtg ggaagcgtat tgaggcgaag catggcacgt tggcgaggtc 21420
gattggggct gcgtcgtgat cgtttacggt gatccgcgtg tgtgggctaa acgcgtgctc 21480
aaggatgatg gctggctgtc tgggataccg tgtacgggga cggtgcctga ggatttcagc 21540
ggtgacctga tctggttggc gttggatggt ggcccacagt tgcatgttcg tgagcgtgtt 21600
tttttgcgcg tgaacgtgtt ttcggatacg ccggatcgtg ctatgtcgtt ggcgcgtcgt 21660
gtcgaggctg tgctggctga tagtgtggac ggtgaccctg tggtgtactg taaacggtct 21720
actggccctg atttgctggt tgatggtgca cgttttgatg tgtattcgct ttttgagctg 21780
atatgtaggc ctgcggagtc tgaataagct tattgttttt gttttaatgt aattgtttga 21840
tatttaatgg gggttatgat ggctgcaaca cgtaaagcgt ctaatgttcg ctcagcggtt 21900
actggcgacg tttatattgg tgacgcgcac gcgggtgata ctattaaggg tgtggaggcg 21960
gttccttccg ggcttaccgc tttagggtat ctgtctgatg acgggtttaa gattaagcct 22020
gagcgtaaaa cggatgattt gaaggcttgg cagaatgcgg atgttgttcg cactgtggct 22080
acggagtctt ctatcgagat ttctttccag ctgatcgaat ccaaaaaaga ggttatcgaa 22140
ctgttttggc agtcgaaggt tactgccgga tccgattcgg gttcttttga tatttctcct 22200
ggtgccacga cgggtgttca cgctctgttg atggatattg ttgatggtga tcaggttatt 22260
cgctactatt tccctgaggt tgagctcatt gatcgtgacg agatcaaggg taagaatggt 22320
gaagtgtacg ggtatggtgt gacgttgaag gcgtatcctg cccagattgg taagactggt 22380
aatgcggtgt ctggtcgggg gtggatgacg gctttaaaag ctgatactcc tccttctccg 22440
aagcctcagc cggatccgaa tccgccggcc gagaactgat acacgatttt aggggattgt 22500
tgatagatga gtgacactgg tttcacgttg aagattggtg atcgtagctg ggtgttggcg 22560

-continued

```
gatgctgagg agacggcgca ggctgttcct gcccgcgttt tccgtcgtgc cgccaggatt  22620
gcccagtcgg gggagtctgc ggatttcgcc caggttgagg tgatgttttc tatgttggag  22680
gctgccgccc cggctgacgc tgtggaggcc ctggaggggc ttcctatggt tcgtgtggcg  22740
gaggttttcc gtgagtggat ggaatataag cctgacggta agggtgcctc gctgggggaa  22800
tagtttggct ccacggcctg attgatgatt atcgtggggc catcgaatac gatttccgca  22860
ctaaatttgg tgtttctgtt tatagtgttg gtggcccgca gatgtgttgg ggtgaggctg  22920
tccggctggc tggcgtgttg tgtactgata cgtctagcca gttggcggcc cacctgaatg  22980
gttggcagcg cccgtttgag tggtgtgagt gggctgtgtt ggacatgttg gatcattaca  23040
ggtctgctaa tagtgagggg cagccggagc ctgtggcgag gccgacggat gagcgtaggg  23100
cccggtttac gtctgggcag gtggacgata ttttggcgcg tgttcgtgcc ggtggcgggg  23160
tgtctcgcga gattaatatt atggggtgaa tagtgtatgt ctggtgagat tgcttccgcg  23220
tatgtgtcgt tgtatacgaa gatgcctggc cttaaaagtg atgttggtaa acagctttct  23280
ggggtgatgc ctgcggaggg tcagcgttcg ggtagcttgt ttgctagcgg gatgaagttg  23340
gcgcttggtg gtgcggcgat gatgggtgcc atcaatgttg ctaagaaggg cctcaagtct  23400
atctatgatg tgactattgg tggcggtatt gctagggcga tggctattga tgaggctcag  23460
gctaaactga ctggtttggg tcatacgtcg tctgacacgt cttcgattat gaattcggct  23520
attgaggctg ttactggtac gtcgtacgcg ttgggggatg cggcgtctac ggctgcggcg  23580
ttgtctgctt cgggtgtgaa gtctggcggg cagatgacgg atgtgttgaa gactgtcgcc  23640
gatgtgtctt atatttcggg taagtcgttt caggatacgg gcgctatttt tacgtccgtg  23700
atggctcgcg gtaagttgca gggcgatgac atgttgcagc ttactatggc gggtgttcct  23760
gtgctgtctt tgcttgccag gcagacgggt aaaacgtctg ctgaggtgtc gcagatggtg  23820
tcgaaggggc agattgattt tgccacgttt gcggctgcga tgaagcttgg catgggtggt  23880
gctgcgcagg cgtctggtaa gacgtttgag ggcgctatga agaatgttaa gggtgccctg  23940
ggttatttgg gtgctacggc tatggcgccg tttcttaacg ggttgcggca gatttttgtt  24000
gcgttgaatc cggttattaa gtctatcacg gattctgtga agcctatgtt tgcgtcggtg  24060
gatcagggga ttcagcgggt gatgccgtct attttggcgt ggattaaccg tatgccgggc  24120
atgattacga gaatgaatgc acagatgcgc gccaaggttg agcagttgaa gggcgttttt  24180
gcgaggctgc atttgcctgt tcctaaggtg aattttggtg ccatgtttgc tggcggcacc  24240
gcagtgttcg gtattgttgc tgcgggtgtt gggaagcttg ttgcggggtt tgccccgttg  24300
gcggtgtctt tgaagaatct gttgccgtcg tttggtgctt tgaggggtgc cgctgggggg  24360
cttggtggcg tgtttcgcgc cctgggtggc cctgttggta ttgtgatcgg gctgtttgct  24420
gccatgtttg ctacgaacgc ccagttccgt gccgctgtta tgcagcttgt gggggttgtt  24480
ggccgggctt tggggcagat tatggtcgct gtgcagccac tgttcgggat tgttgctggc  24540
gtggttgcca ggttggcgcc agtgttcggc cagattatcg gtatggttgc tggtttggct  24600
gcccggctgg tgcctgttat tggtatgctt attgcccggc tggttcctgt tatcacccag  24660
attattggta tggtaaccca ggttgctgcc atgttgttgc ctatgctgat gccggttatt  24720
caggctgttg ttgctgtgat acggcaggtt attggtgtga tcatgcagtt gatacctgtt  24780
ttgatgccgg ttgtgcagca gattttgggt gctgtcatgt ctgttttgcc gccgattgtt  24840
ggtttgatac ggtcgctgat accggtgatc atgtcgatta tgcgtgtggt ggtgcaggtt  24900
```

-continued

```
gttggtgccg tgttgcaggt ggtggcccgt attattccgg ttgttatgcc gatttatgtt  24960
tcggtgattg gattcattgc caagatttat gctgcggtta tcgtttttga ggctaaggtt  25020
attggcgcta ttcttcgtac tattacgtgg attgtgaatc attcagtgtc tggcgtgagg  25080
tctatgggca cggccatcca gaatggctgg aatcatatca aatcgtttac gtcggcgttt  25140
attaacggtt tcaagtcgat catttctgcc ggtgttgccg cggttgtggg gtttttttacg  25200
cggcttggtt tgtcggttgc ttctcatgtt cggtctgggt ttaacgcggc ccgtggcgct  25260
gtttcggctg cgatgaatgc tattcggagt gttgtgtctt cggtggcgtc tgctgttggc  25320
gggtttttcg ggtcgatggc gtctagggtt cgtagtggtg ctgtgcgcgg gtttaatggt  25380
gcccggagtg cggcttcttc tgctatgcat gctatgggct cggctgtgtc tagtggtgtg  25440
catggtgtgc taggattttt ccggaatttg cctggcaata ttcggcatgc tctcggcaat  25500
atggggttct tgttggtgtc ggctggccgt gatgtggtgt ctggtttggg taacggtatt  25560
aagaatgcta tgagtggcct gttggatacg gtgcgtaaca tgggttctca ggttgctaat  25620
gcggctaagt ctgtgttggg tattcattcc ccgtctcgag tgtttcgtga ccaggttggc  25680
cggcaggttg ttgccggttt ggccgagggg atcaccggga atgcgggttt ggcgttggat  25740
gcgatgtcgg gtgtggctgg acggctgcct gatgcggttg atgcccggtt tggtgtgcga  25800
tcatcggtgg gctcgtttac cccgtatgac aggtatcggc ggatgggcga gaagagtgtt  25860
gtggtgaatg tgaatgggcc tacttatggt gatcctaacg agtttgcgaa gcggattgag  25920
cggcagcagc gtgacgcttt gaacgcgttg gcttacgtgt gattgggggt gttgtgcatg  25980
tttattcctg acccgtctga tcgtgccggt ttgactgtta cctggtctat gttgccgttg  26040
attggtaatg atccggagcg tgtgcttcat ttgacggatt atacgggtgc gtctcctgtc  26100
atgttgttga atgattcgtt gcgcggtttg ggtgttcctg aggtggagca tttttctcaa  26160
actcatgttg gggtgcacgg ctcggagtgg cgcgggttta atgtgaagcc tcgcgaggtg  26220
acattacctg tcctggtgtc gggtgttggt gtggatccgg ttggcgggtt tcgtgacggt  26280
tttttgaagg cgtatgacga gttgtggtct gcttttcctc cgggcgagga gggggagttg  26340
tctgtgaaga ccccgtctgg ccgtgagcgt gtgctaaaat gccggtttga ttcggtggat  26400
gacacgttta ctgtggatcc ggtgaacagg ggttatgcgc gctatctgtt gcatttgaca  26460
gcttatgacc cgttttggta tggggatgag cagaagtttc gttttagtaa tgcgaagttg  26520
caggattggt taggtggcgg ccctgtcggc aagaagggta ccgcttttcc ggtggtgttg  26580
acgcctggtg ttggttcggg ttgggataat ctgtctaata ggggtgatgt gcctgcgtgg  26640
cctgtgattc gtgtggaggg cccgttggag tcgtggtctg tgcagattga tggtttgcgt  26700
gtgtcttcgg attacccggt ggaggagttt gattggatca ctattgatac ggatcctcgc  26760
aaacagtctg cattgttgaa cgggtttgag gatgtgatgg atcgtttgac agagtgggag  26820
tttgccccta tcccgcctgg cggttctaag agtgtgaata ttgagatggt tggtttgggt  26880
gccattgttg tgtcggtgca gtacaggttt ttgagggctt ggtgaatagt tgatggctgg  26940
tcttgttccg catgtaacat tgtttacacc tgattatcgc cgtgtggcgc ctatcaattt  27000
ttttgagtcg ttgaagttgt cgttaaagtg gaatggtttg tccactttgg agttggtggt  27060
gtctggtgat cattctaggc ttgacgggtt gactaggccg ggtgcacggc tggttgttga  27120
ttatggtggt ggccagattt tttctgggcc tgtgcgtcgg gttcatggtg tgggtccgtg  27180
gcgttcttcc catgtgacta tcacgtgtga ggatgatatt cgtctgttgt ggcgtatgtt  27240
gatgtggcct gtggattatc gtcctggttt ggttggtatg gagtggcgtg ctgaccggga  27300
```

-continued

```
ttatgcccac tattcgggtg cggctgagtc ggtggctaag caggtgttgg gggataatgc  27360
ttggcgtttt ccgcctggtt tgtttatgaa cgatgatgag agtcgtggac ggttcattaa  27420
ggattttcag gtgcggtttc acgtgtttgc cgataagttg ttgccggtgt tgtcgtgggc  27480
tcggatgact gtcacggtga accagtttga gaatgcgaag tttgatcagc gtggtttggt  27540
gtttgattgt gtgcctgctg tgacgcgtaa gcatgtgttg actgccgagt ctggttcgat  27600
tgtgtcgtgg gagtatgtgc gtgacgcccc gaaggcgaca tcggtggtgg ttggtggccg  27660
cggcgagggc aaagatcggc tgttttgtga ggatgttgat tcgatggccg aggatgactg  27720
gtttgatcgt gtcgaggtgt ttaaggatgc ccgtaacacg gattctgagc atgtgcatct  27780
cattgatgag gctgagcagg tgttgtccga gttgggggcc acgtcggggt ttaagatcga  27840
gttggctgag tcggatgtgt tgcggtttgg gcccggcaat ctgatgcccg gggatttgat  27900
ctatgtggat gtgggttctg gccctatcgc agagattgtg cggcagattg atgtggagtg  27960
tgagtcgccg ggtgacgggt ggacgaaggt gactcctgtt gcaggggatt atgagaataa  28020
tccgtcggcc ctgttggcgc ggcgtgttgc tggtttggct gcgggtgtgc gggatttgca  28080
aaaattctag aaaagattag gggtttgttg tgggtattgt gtgtaaaggg tttgatggtg  28140
tgttgaccga gtatgattgg gctcaaatgt ctggtctgat gggtaatatg ccgtccgtga  28200
aagggccgga cgattttcgt gtcggcacta ctgttcaggg tgccacagtg ttgtgtgagg  28260
tcctgccggg gcaggcttgg gcccacgggg tgatgtgcac gtcgaatagt gttgagacgg  28320
tgaccggcca gcttccgggc ccgggtgaga cccgatacga ctatgtggtg ttgtctcggg  28380
attgggaggc gaatacggcc aagttggaga ttgttcctgg ggggcgtgcg gagcgtgccc  28440
gtgacgtgtt gagggccgag cctggcgtgt accatcagca gttgttggct actttggtgg  28500
tgtcgtctaa cgggttgcag cagcagctgg ataggcgtgc tatagcggct agggtggcgt  28560
ttggcgagtc tgctgcgtgt gatcctaccc cagtggaggg tgaccgtgtg atggttccct  28620
ctggggctgt gtgggctaat catgccggcg agtggatgct gttgtccccc aggattgaga  28680
cgggttctaa gtcgatcatg tttggcgggt ctgctgtgta tgcttacacg attccgtttg  28740
agcggccgtt tagtagtgcg cctgttgtgg tggcgtctat ggctacggcg gctgggggca  28800
cgcagcagat caatgtgaaa gcctacaatg tgactgtcca aaattttagt ttggcgttta  28860
ttacgaatga tggttcgaag ccgaatggtg tgcctgcggc ggctaattgg attgctgtcg  28920
gcgtgtgact gtacaggtgt tgtggcggat ggtgtgatgt tggggggctg tggtgtcgtg  28980
gtttactcct gcactggtgg cctctatttg taccgcgttg gccacggttt tgggttctgt  29040
tcaggctgtc acatcccggt ctaggcggcg tttacgcagg ctgtctgcgc aggtggatgc  29100
gatggaagag tatacgtggg gtgtgcggcg cgaggtgcga aggtttaacg ccgggcttcc  29160
tgatgatgtg gagccgatgc atcttcctga tgtgcccgag tttttgaagg atactgttga  29220
tggtggaggt gagtagggtt gagggagttg gaggaggaga agcggcagcg ccgcaatttt  29280
gagaaggctt ccctgatact gttatttttg tcgcttgtgt tgttggcggt ggttgccggg  29340
ggtgctttgc ggtacgggtc tgtggcttct caaagggatt cggagcaggc gagggcccag  29400
tcgaatggta cagccgctaa agggttggct gcccgtgtga agcaggcgtg tacccagggt  29460
ggcgtggagt ctgtgaagct gcacaggtct ggtttgtgtg tggatgctgt gcgtgttgag  29520
cagcgtgttc agggtgtgca gggtcctgcc ggtgagcgtg gcccgcaagg gcccgctggt  29580
gttgatggcc gggatggtag caatggttct gctgggctgg ttggccctgt tgggccgcag  29640
```

ggttcccctg gtttgaatgg tgttccaggt cgtgcaggtg tcgatggtgt gaacggcgc 29699

<210> SEQ ID NO 71
<211> LENGTH: 29596
<212> TYPE: DNA
<213> ORGANISM: Artificial Sequence
<220> FEATURE:
<223> OTHER INFORMATION: PAC2

<400> SEQUENCE: 71
ctggtttgaa tggtgtgaaa ggtcctgacg ggttgcctgg cgctaacggt tcggatggcc 60
gtgatggtgt tccaggtcgt gcaggtgtcg atggtgtgaa cggcgctgat ggtcgggatg 120
gttcggccgg tgagcgcggt gatgtgggcc cttcaggtcc tgccggcccg caaggtgcac 180
agggtgaacg gggtgagcgc ggccccgccg gtgcgaacgg atccgatggt aaagacggta 240
aggatggtgc tgatggccgt gatgggcgtt cggtgatatc ggtgtactgt tccgggggcc 300
gcctggttgt gaaatatagt gacggtacgg cctctaccgt gtcgggttct gcggcctgcg 360
agagtgtgaa accatcacct gtggttactg tatcatccca taggtgaaca agaagaggga 420
agggtgttac tagtgttgat tgtggtgttt gggggtggtg tgtggtgaga tacattccag 480
cggcgcatca ctctgccggt tcgaatagtc cggtgaacag ggttgtgatt catgcaacat 540
gcccggatgt ggggtttccg tccgcttcgc gtaagggtcg ggctgtgtct acagcgaact 600
atttcgcttc cccatcatcg gggggttcgg cgcattatgt ttgtgatatt ggggagacgg 660
tgcagtgcct gtcagagggg actatagggt ggcatgcccc gccgaatccg cattctttgg 720
gtatagagat ttgcgcggat gggggttcgc atgcctcgtt ccgtgtaccg gggcatgctt 780
acacgaggga gcagtggctt gatccgcagg tgtggcccgc agtggagagg gccgctatcc 840
tgtgtcggca gttgtgtgac aagcatggtg ttccgaaaag gaaactgtct gtggccgatt 900
tgaaggccgg taaacggggt gtgtgcgggc atgtggatgt tacggatgcg tggcatcagt 960
cggatcatga cgatccgggg ccgtggtttc cgtgggacaa atttatggct gtggtgaatg 1020
gccacggcgg cggttcaagt agtgaggagt tgagtatggc tgatgtacaa gcgttacata 1080
atcagattaa acagttgtcg gcacaggtgg cccagtcggt gaataagctg catcacgatg 1140
ttggtgtggt tcaggttcag aatggtgatt tgggtaaacg tgttgatgcc ctgtcgtggg 1200
tgaagaatcc ggtgaccggg aagctgtggc gcaccaaaga cgccctgtgg agcatctggt 1260
attacgtgtt ggagtgtcgc agccgcatag acaggcttga gtctgctgtt aatggtttga 1320
aaaagtgatg gtggtttgtt gtgggtaaac agttttggtt gggcttgttt gagcgtgccc 1380
tgaaaacttt tattcaaacg tttgttgctg tgcttggggt gacggcgggt gttacttata 1440
ctgcggagtc gtttcgcggt ttgccgtggg agtctgccct gataacagca acggttgctg 1500
cggtgctgtc tgttgctaca tcgtttggta gcccgtcatt tgtggccggc aaacctaaaa 1560
ccacggttgt ggatgctggg cttgttccac ccgacgatgg gggcatggtt gagccgcact 1620
cggtggatgt gtcggatcct ggcatgatcg agccgacaga tgatgtggat ggttttgctg 1680
gctatgtgcc gaagcgtgca gccgagtcgg aggttagcac ggtggagtct actgttgcat 1740
aattgaacat agatgtgtgc cccagcggtg ctgccacgat cgtgtggtgg ttgccgctgg 1800
ggcacacttt ttgtgtctat aggagtttta caggttgtcg tctagtgtgt cttcgagcat 1860
ctggtccagg tagaggcagg cggagatagt atcgttggcc tggtctagaa cgttctggcc 1920
gataacattt ttatgattgt cgcggtggct gatgatagac cgcatgatat cgtcggccgc 1980
cgcctgcaat agtttggcct ggtatgcgat tcctgcgagc cagtctagtg cttcctggct 2040

-continued

```
tgccagtgtg tcgtctggaa tgccacgggt gttgctgttg tttgtggggt gtcctgcact   2100
gtcgcagcac cacaagattt cgctgcactc gtctagcgtg tcctggtcga tagcaagatc   2160
gtcgaggctg acttctttga cggtaaggtt cacattgtcg agggagatgg gtacaccgta   2220
ttggttttcg acactgtcaa caatgttttc caactgttgc atgttggtgg gctgttgttg   2280
gatgatacgg tgtactactg ttttgatggc ggtgtagggg atattgtgtg tgttgttcat   2340
ggtttttatc ccacccctgt gttgtcgtcg ttattgtctg gatagtatct actgtttgcg   2400
tagcctgtga gggtgatgag tgtttggtct gcccactgtt tcactgtctg ccgggtgaca   2460
cccaatcgtt gggcggctgt ggcgtaggtt tgatcatacc cgtatacttc acggaatgcg   2520
gctagcctgg ctaggtgttt tcgctgtttg gagggttcac atgatagggt gtagtcgtcg   2580
atggcgagct gtagatcgat catggtggca atgttgttgc cgtgatgctg gggggcggtt   2640
ggtgggggtg gcattcctgg ctccacactg ggtttccatg ggccgccgtt ccagatccat   2700
tgggcggctt ggatgatgtc ggcggtggtg taggttcggt tcatgtgtca ccccctgaac   2760
aggtcgttgc tggtgctggt gttggtggtg tcgaatcgtc cgacgcagtg gcagtagtcg   2820
tacatgagtt tgataatgtg ttggtggtct cccaaatagg tgtttccgct gatactgtag   2880
gtggctgtgc cgtctttact gatggtgtat ttggcggtga tggtttcggg gttttcggtg   2940
tcggtgatga ttgctgtggt ggtggtgcct actgtttgta gcacggtggt ttgggttccg   3000
tcgtcgatag tggttttaac catggtgtgt gttctccctt tttagatgct ggtttggttg   3060
tcggctagat gaatgatgtc gggtaagggt ttcggctggt ctaggtgttg tatggttttg   3120
ttggctagcc gtttggctac cctgtaacac attttggtgt agtgtttgtt gtctaggttg   3180
tggtattgtt cccgcaccgc aatatatagt agagagtctt ggtacaggtc gtctgcactg   3240
attgcggggt agtgtgcggc tgttttggtg catgcccggt tgagtgtgcg tagatgatgg   3300
tctgtggccc acacccacga tgcggtggtg gctaggtcgg cttttgttgg tcgtctgctc   3360
atggcatttc tttcatcggg ctatctggta gttgtttggt gttttgttgt tgatagtgta   3420
gcacacgagt ccggggtttc cggtggtgcc agtcttgtgc cggtaccatg tggattcgcc   3480
ttccatggat gggcattgga tgaaggtgcg ttgtccttgt tcggagattt ctaggtggtg   3540
ccggtgcccg gccatgagga tgtgggatgt ggtgccgttg tggaattctt ggccgcgcca   3600
ccaatcatag tgtttgccgg tgcgccattg gtgtccgtgg gcgtgcagga tttgtgtgcc   3660
ggccacgtcg acggtggtgg tcatttcgtc ccgttggggg aagtggaagt gaaggttggg   3720
gtattggttg ttgagctggt aagcttctgc gatggcgcgg cagcagtcca cgtcgaagga   3780
gtcgtcgtag gtggtgactc ctttgccgaa gcgcacggct tcgccgtggt tgccggggat   3840
ggatgtgatg gtcacatttt tgcagtggtc gaacatgtgg acgagttgca tcatggccat   3900
gcgggtgagc ctgatttgtt cggtgagggg tgtttgtgtg cgccaggcgt tgttgcctcc   3960
ttgtgacacg tatccttcga tcatgtcgcc gaggaatgcg atgtggactc gttcgggttt   4020
gcctgcctgt tgccagtagt gttttgcgac tatgagggag tgcaaatagt cgtctgcgaa   4080
tcggctggtt tctccgccgg ggatgccttt gccgatttgg aagtcgcctg ccccgataac   4140
gaaggctgtc tcgtcactgc tttgggtgtc ttgttcgggt ttgggtggct gccattcggc   4200
tagtttgttg acgagttcgt cgacggggta ggggtcggtt gcgggttggt ggtcgatgat   4260
tttttgtatg gatcggcctg tttctccgtt ggggagtgtc cattcggaga tgcgtgtgcg   4320
gcgtacagta ccgttggcta gattgtcgtc gatggtgtcg atggcgttgt cgtggttggc   4380
```

-continued

```
tagctgtgtg agtagccggt ctatattgtc tatcactggt tttcctcctc tggcggggtg   4440
gtgttggctt gtttgcggcg gtagtctttt ataacggtgg cggagatggg gtatcctgcc   4500
tgggtgagct gttttgctag ccacgaggcg ggtatagacc tgtcggcgag gacgtctgca   4560
gccttgttgc cgtagcgttg aataagggtt tcagttttgg ttgccatgat gtcctatcgg   4620
ttgtgtggcg ggctgccatc ctgtgcggca gtcgccgtcg tggcctggtt tgcgtgtgca   4680
ccacgatacg gttccgtctg tgtggttgag tgttttgccg cacatgacgt tttgtagatg   4740
ctcgggcagg gcgccgtcac cctggttgct ggtttgtgtg tcgaagagtg ttttctggtt   4800
ggtgaaatgc tctgacacgg tgccgttgtg tacgggtagt atccatgttt tccattgttg   4860
ttgtagccgg gtgttccagt ggaattgttt ggccgcgttc gtggcttgtt tgatggtttt   4920
gtagtagccg acgaggatgc gctggtgttc actgtcgggt gggttttggc ctcgccagta   4980
ttgtgccgcg acggcatacc tgttgttgtc tgtgaaggcg tcccagcagt attcgataat   5040
gtgttgtagt acactatcgg gaatgtctcg tacttggttt tcgtcgagcc acgcgtcgac   5100
aatgatgttg cgtatggcgt gtttgtcttt ggtggtgggt ttgaacgaga tactcaccat   5160
gctggcctgt cgtcttgcat gaaatcgtta aaggatgatt cgcttgtgcg gcgtgcctgg   5220
gtgatttgct ggtcagtcca gtcggggtgt tgctgtttca gatagtacca gcggcaggca   5280
tcatatgttt cgttctgcaa gcgggtgaga tggttttcgg tgatgatttg tttccacatt   5340
gtccacgaga cgtcgagcct gcggagcatg tccatggccg gcacattaaa cgagtcaagg   5400
aagagtattt cgtgggtgta gtagtttttc tcgtaggcgt accatccgct tcggtgcctg   5460
tggggctggt ttttggggta ggcttcccgg catactttgt gtaaacgttt ggccatgtcg   5520
tcgggtagtt caatgtcggg gttggcgcgg atcatggatc gcatcccgtc gtaggtggtg   5580
ccccaggtgt gcatgatgtg tagtgggttg tctccatcgg cccatttttc tgcacagatg   5640
gcgaggcgga tgcgcctcct ggctgtttgg ctggtgttgc gccggttggg gattgggcac   5700
gtgtcgaggg gatccattat gttttagtgt acctttctgg tttcgtgttg ttgacgtgtt   5760
ttactgtagc acagtgtcta gtgcttgtgt caaccctgtt tttccggcct gcaggtaggt   5820
gtctgtgaca tctccgaccg tgaggggcac atgggtggct tgggggagtg ctgcctggat   5880
ggtttgtgcc atctggtcgc ctgcggggtc tgggtctgac cagatgtaga tgtggtcgta   5940
gccttcgaag aatttggtcc agaagttttg ccacgaggtt gcgccgggta gggctacggc   6000
cggccatccg cattgttcga ggatcatgga gtcgaattcg ccttcgcaaa tgtgcatttc   6060
ggctgccggg ttggccatgg cggccatgtt gtagatggag cctgtgtccc cggctggggt   6120
caagtatttg ggtggttgt gggttttgca gtcgtgtggg agtgagcagc ggaaacgcat   6180
ttttcgtatt tcggctggcc gctcccaaac ggggtacatg tatgggatgg tgatgcactg   6240
gttgtagttt tcgtggcctg gtatggggtc attgtcgatg tatccaaggt ggtggtagcg   6300
ggctgtttct tcgctgatgc ctcttgctga gagcaggtcg agtatgtttt cgaggtgggt   6360
ttcgtagcgg gctgaggctt tctggattcg gcggcgttcc gcaatgttgt agggttgtat   6420
gctgtcgtac attcgggttt tcttcttcta gtcgttgttg tagtttgtgg agtcctcctc   6480
cgacaccgca tgtgtggcag taccagacgc ccttgtcgag gttgatgctc atggagggct   6540
ggtggtcgtc gtggagcggg cagagtatgt gttgctcgtt tttggacggg ttgtagcgta   6600
tctggtagat gtcgaggatg cggcgggtgt cagaggtgtg ggaggagctc gttgagggtt   6660
gataccacat aggcttcgct ccagggtttg ttgcgttgtt tcatcactac gagtccgatg   6720
gtggaattgt tttcgcggtt tcggtgtgtt tcgtagttgc gtgcctcccg gctggcttgt   6780
```

```
ttcacgaatt cggctaggtg gggctggccg gctttcgcct cgataatgta ggttttgttg   6840
ctggttgtga ggatgaggtc gccttcgtct tcgcggccgt tgaggtggag gcgttcgata   6900
tcgtgtccgg tgtcgcgtag ctggtgcaat aatcgtgttt cccattcggc tccggcccgc   6960
cggttgcgtg cctgctgtgt ggccatagtt tttagagtcc tttgtgtgtt gtggtcatgt   7020
tccagggctg tttttcggcg aggggcccga agaatgtgta ttcggggtag gctcgtagtc   7080
gttcatatcg ggtgccgtcg gggctggatt tgccggtgcg ctgtttcaat actgcgatgc   7140
gtgcctcggc cggtatcgtg agaccgttgc cgttatcctc gccaccatac aatgagactc   7200
ccaatatgag ttgtggtttt tcggagaggc cgtttttgat ttctcgccgt gccgggggggt   7260
gttcgatgtc ggttccggtt ttgtcggtgg cgtggtgtgt gacaataatg gtggatccgg   7320
tgtcgcggcc taatgctgtg atccattgca tggcttcttg ctgtgcctga tagtcactct   7380
cgcagtcttg gatgtccatc aggttgtcga taacaatgag tggcgggaag gtgttccaca   7440
tttccatgta ggcttgcagc tccatggtga tgtctgtcca tgtgatgggt gactggaatg   7500
agaatgtgat gtgttggccg tggtggatgc tgtctcgata gtattctggt ccgtagtcgt   7560
cgatgttttg ttgtatctgt gtggtggtgt gttgggtgtt gagtgagatg attcgtgtgg   7620
aggcctccca gggtgtcatg tcccctgata tgtagagggc gggctggttg agcatggcgg   7680
tgatgaacat ggctagcccg gatttttggc tgcctgagcg ccccgcaatc atgacgagat   7740
ccccttttgtg gatgtgcatg tcctggttgc ggtagagggg ttctagttgt ggtatgcggg   7800
gcagctcggc tgcggtttgg gaggctctct cgaaggatcg ttggagagag agcatcggga   7860
ccttatctat ctatcggttg ggtgtgtttt ggtggtcaga tggagtcgat gtcgatgtca   7920
gcatcggcgg gggttgagca cgaccgcatt gaacccgttt ttggtgcgca cggtggcgag   7980
tttgaaggcc tgctcctcgc caaggtaggc ttcgaggtcg cggatcatgg aatgtgggcg   8040
gtcgttgttg ccgcgcgctt tctcaataat agcgttggga atgatttctg ggtgccgtt   8100
gttgagatcg tctagggtgt ggaagattgt gacatcagcg tagatgcgat cggctgtctg   8160
tccaccgtag ccttcggtgt tgtgttctac gtcgcggatt ttgaaggcga tggcggtggc   8220
gtcctggttt cgggaggggt tgaagaaggt gctgttgctg ttgttgcggt agttggcgag   8280
tcccatggtt gtttccttta ctgtttgtgt tggtttgtgt cggttttatc gggtgaggct   8340
gtttcgtttg ctgcggaaag cctcggacac gtcactgtta ctggtgatga ttttcttgta   8400
ctgtttcaga aggtcggcta gctgtgcctt gcttgttgca ttgttgattt tgtcgatgat   8460
aatctcgttt tcgtttgatg cgatgttgtc tacgtagtct ttggctgcct ggttgtagcg   8520
gtcttggagg atgatggatg cgcttgctac gagtgttgct agatcccagt ctttggacac   8580
gtcaccgttt ttgaggccgc ctagcagatc aataatggat tgtttgatgt cttctgcggt   8640
gtctccgcgg atgactgtcc atggggctgc gtagtctcca ccgtatttga gtgtgatagt   8700
tagctttccg ctgtctgtgg tgtgctcgtc ggtcacgtgt tttcctttttc gttgttttcg   8760
gcttctggtg gctgtacggt ggtttctacc gggtatctgt acgagttttt cccgttgacg   8820
gcccagcagg cgtccttgac ggggcatcct ttgcagagtg ctgtgacgtg gggtacgaag   8880
atgccttggc tgattccttt cattgcttga ctgtacatgg atgatacatg ccggtaggtg   8940
ttgttgtcaa gatcaatgag ttcggtggat gtgccctgct caaccgattg ctcgtctccc   9000
ttggtggtag cgggtgtcca aaacattcct ttcgtcacat ggatgccgtg ttggttgagc   9060
atgtaacggt aggtgtgcag ctgcatactg tcggcgggta ggcgtccggt tttgaggtcc   9120
```

-continued

```
aaaatgaagg tttcacccgt attcgtatct gtgaataccc ggtcgatgta gccaacgatc   9180
tgggtgccgt cggggagggt ggtttctacc gggtattcga tgcccggctc gccgtcaata   9240
acagcggtag catattctgg gtggttgcgc ctccatgttt tccaccggtc cacaaaggtg   9300
gggccgtaaa tcatccacca attgtagtct ttcttgtgtg tcccgcccga ctcgcacatg   9360
tttttgcata ttctgccgga gggtttgatt tctgtgcctt cggattcggc gagggcgact   9420
tgggtgtcga aaatgttttt gaaggatgag agtttgtctg gcagtgcagg gtattcggcg   9480
ggattgtaca ggtgtaggtc gtattgttcg gtgatgtggt gtatggcgct tccggcgatg   9540
gtggcatacc aggtgtggtg ttgggcgtgg tagccgtggg ataggcgcca tttttcaccg   9600
cattcggccc actgtgacag tgatgagtag gagatgtggc ctggatggtc aatggtggac   9660
ggtttttgtg ctaggggcat tacttgtcgc ttttgtgggt gttccatggg tttcgggtgt   9720
cttggccggc attgtgttgc tggtatgcga ggagtgcgag gcagtgccag gcagcatggg   9780
ccagatgggg tagcccggat tcatcatcga ggttgttgcc ttgctgccat gataacaggt   9840
gccggtagag ggcgtcaaca ctgtggctcc acggatagcc gccggtccag ttgttgtcgc   9900
cgtatttggt ggcgccgtat ccggccacag agccgagggc gtgtaaggct gtagggtcga   9960
tgagggatag cctgcaaagt ttcaattctt tcttggcgcc agtatcaggg tcggtgtaca  10020
tgctggtggg ctcatccatg gtgtgtgtgc tccttaagta tggggttact ggttggggtt  10080
gtgggcgagt gctacggcaa gaataatgat ggcgagggtt tcagcgatca gtatgggtgt  10140
tgtgatcatt tgtggtcgcg gggattgttg gtgagggttg aggcgcccag gaggatagtg  10200
agggcgcatg cggcgatgat ggcgagggct gccttgtgtg gggtgccggt ggcgtacatc  10260
catgtgatga tgccgccttg gatccaggcg aggctggtga agaacgtttc gtagctgtgt  10320
agctcaatgt tgttgttggg tgtgttcatg cttgctcctg aagaatggtg ttgatggttg  10380
tgtaaatgtt gtacaggtcg gtttcgatag ataacagttg gtggatttgg tggtcgagat  10440
caatgtcggg gttgagggtg ttgatgcggg aggcgatgtc ggtggctgtg cgtagtgtgc  10500
cgccggtgtg gtgaatgatg tgtgccgtgt cggcgagtcc ggtggtgaca gtgtagtggg  10560
agaggagagg catagctggg ggtgctcctt gacggggtta ctgttgcggg ttgatgttga  10620
ggtcggtgac gttggggtgg tcttctgttc cggtgacaag gcagtggacg gtgactggga  10680
gtttggatgc gccgggctgt ttcgcggttg cgccgtagac gatggagaag gtgtctttgc  10740
caataatttt gtggagttgg aggtcgatgt cggggttgcc gttccatttg acgccttgtg  10800
tggcggcctg ttgttcggct ttgcggttgc aggtgtgtgc tgcggtgatc atggtgagtc  10860
cggtggcggt ttcttcaccc cttgcttggg cttgcttgtg ggttttctgc tgttcggctc  10920
gcagtgactg ttctgctgct gcctgccgtg ctttcttttc ggctttgcgc tgttgggtag  10980
tcttgggggt ccattcggtg ttggctgtgg tggcttgcgg tgcgggttgt gatgcgagtg  11040
gcggattgtc gtctggggct ggcatgaagg atgctgcggc gatgatggcg gctgtgattc  11100
cggcgatggt gtagccgttt ttcttgttca tgattttgtg ttcccctttc cggggtgttg  11160
ttcgttgctg acatgattaa tactttcagc ggctgggccc actgtcaagg ctgcgctcaa  11220
cgattgtgag cgatacttgt gtggctaggg gttttgtcct tgaggtggga gatgtctttc  11280
ccttgcgtcc agtatccatg gcggttgcga gtcatccctt tggcgagcat ctcgtccacg  11340
gtgagacacc tgcgacgatc tggaccctcc ttgactccct gatcgcctgt gcggtgcatg  11400
tcaccggcac aagtaccatt aaatgtctcg tggcggatgg tgtgatgctc tggtcggtat  11460
ccgatgattg tgctatcgca cttgtggcat gtccattgca tgattggtcc ttctttcgtg  11520
```

```
ttttaagctt gtactctgag gattagagcg actttcagcc cttgggggt atgattatat  11580
aggtcaggta tttctaggcg attctaggct cattgtgtgt ggctgggggt tatcgggcac  11640
acagggtgag gagttggcca acattgatgc gggtcacatt ccagtagagt tgcgtggctt  11700
ccccaccggt gagtggcttc cactcgtcat ggctgaacac ggtgccgtcg gttgcgatga  11760
atgtgttggg gcgtagcttg tgaagctcag tctctacacg ctgccggtag gcttcggcga  11820
ggccctcgaa atccatgtgg tcgcagggga ggttttcgag gcgtgtcagg tcgaagggtg  11880
tggggcagtc gtagctggcg gggctgtaga gctgggtgaa atggttggcg atcttctgca  11940
tgacgggttc cttttctcgt atggtgagtt gatagtttta tcgggtggat gcgacaagga  12000
tggcgtctac atcgatcatg tcgatgagat cgtggagttc ctcggcctca ttctcggaga  12060
ggtggcgcca gccatagtcg ccgtatacgg cgccgtcgag ggtgacagtc cacaggggcc  12120
ggatgagtcg tatggcttct tgtactttag cgtggtacat gcggcgcacc atatccagat  12180
cgatgtcgtc tgaatggttt ccggtgaggc tgtagaggct gagcgggtcg atttctgtct  12240
gcctgtagag ggatgtgaat gatggtgtga tgagtgtgcc atccatgaga gtgtgctcct  12300
ttcggtggtg gaggggttgt tgtggtttct agagtgtgta ggctgcgacc catagtcaag  12360
gctgcgctca ttcggattga gcgtttcata tgggtgtggc atggaatcta cacccccata  12420
ctgtgtgaga taggccacat cctcctggct tggtgtgaac cctcgagact actctgccta  12480
tctggcgtgg agggtgtagc ccagaaatac cgtttaaagc cttcatacgg cgcctaggag  12540
cgccttacag ggtgggggct aggtatttat acccccaagc aattctgatc gattctagac  12600
gcctcccagg agcccgatac acgatccgct atccagacac agatcatcag cccctatcct  12660
ggttagctaa gcctcaacta tgtggacagt gttgattact gtggggtaag aaggacacgg  12720
taaaagaaag agggggggagc atcggccttc aagccttaag gtcttagcag ttagcaccga  12780
gcccctcaag ggctcgtcgt cagcccatca ggcacggccc tgaacggggt acacgccatc  12840
agggaaggct tgagagtacg aggagcctta gcgacgagta ctcgaaagcc tgagggaaca  12900
ccctcagcac tgatgggtct agcgtgttcg gaaaggacac aggagtaaag cgtgacagct  12960
gtccgggagt gaaacccgtt ctgactaggg gtttcagcct taaccaccct caaaggttac  13020
aagactctaa gaaaatttaa ggaaaagttt aggtttaatt tttggacctt tactaccaaa  13080
aacacccgtt tacacccctc aaacccgcct atagagccaa atccaccagt ttgactcatc  13140
ccaggtggca tatgataggc tggacaggta gccagctgga cgcaaggccg aaatccgctg  13200
acgcggcttt caccettaca tccatcagtc taccaaagac ttaaagacct aagggcttag  13260
cgctaaggtg ctgatagctt agcaccgagc ccttgagggg ctcggcatca gccctaaagc  13320
cttaaacact taaagtacat ataaaacttt aaaagcttaa cacttaaggt tataaataaa  13380
cattaaagct ttaaagtctt aaagtacata tataacctta acacctaagt taagtataaa  13440
accttaaagg cttagcactg aaggatataa acttcacatc agtttttaag actttaaaac  13500
ttaaaataac tattaagact taaagactta taagttttaa acacttaaag taactataag  13560
actttaaaga ccttaagtac ttaaagttaa ccatcagtct taaactttaa tattataacc  13620
tataagtctt aaagcttata agttataaaa gttttagaag agctaagagg ttaacttctt  13680
tacttctctt ctctctttgg ttctttctct cttctcttct tttcttcatc aggggagaag  13740
aggaaccttt taccatcagc gccgatggac tgtcaccgtg tgactcgtgt accaccggtc  13800
gcacgctccc ggtttcacac tccccacact ctgacacccg tgtccctttc aggcttagcg  13860
```

tgttcggctg aaggcgtacg gcgtgtcgcg ccaacaccct taacaccagg taagacttaa 13920
agtgtatatt atatgtagaa gactttaaaa cctataaggt gttcccgctt agcctgtgtc 13980
ctacaccgct aggcgccaag cgttaagtct tgaaacgcga acacacaccc acccccattt 14040
ttctttcgtg tccttctctt ttgacaccgc tggggggcga tgtgatcttt ctcactaccc 14100
ccatgggtag tggagaacac acccacccca ccatcaacag aacacccccct caaacgaaca 14160
aaacagggcc tagaatcgat cggcagggca agggcaaggt attcataccc ccaacacatt 14220
ccaggccgtc agagaggcaa ataagacccg tacagggcta gtcgaggatc ggagacgtga 14280
tggcacacac caatcgcacc gcatccgccg cacaccgaca ctggcggcaa cgactcatca 14340
cccaagcccg acagcaaggc caaaccgaat gcccactctg cggagcaacc atcacctggg 14400
acacctacca gctgccaact agccccgaag ccgaccacat cacacccgtc agcaggggag 14460
gactcaacac cctcgacaac gggcaaatca tctgcagaac atgcaacaga agcaaaggca 14520
acagaacaca accaaacatc aaattccaac aacaaaccac aaaaaacctt gttccatggt 14580
gacaaaaccc gccaaccccc accggggaca ccccctgcac acccgtgcaa gacctcgtac 14640
ggcttagtga aatacctccc ttttgtggat ttgtctgttt gtcgactttt tgtgttggtg 14700
gtgagtgttg tgcagcctga gcttcctgag ggacacgagt ggtgtgggga gacgcgtcgt 14760
tggtggcgtg tgtggggtga ggatagccgc gcgcagtacg tgtctgatga ggagtggctg 14820
tttcttatgg atgctgcggt gattcatgat tgtgtgtggc gtgagggtcg cgcggatttg 14880
gtggcttcgc ttcgtgctca tgtgaaggct tttatgggta tgttggatcg ttattcggtt 14940
gatgtggcgt ctggtggccg tggtgggggt tctgcggtgg cgatgattga ccggtatagg 15000
aagcgtaggg gggcctgatt aggtgtctgg tgttgttggg tctcaggttc ctcgtcatcg 15060
tgtggctgcg gcgtattcgg tgtctgctgg cggtgatgct ggggagttgg gtcgtgcgta 15120
tgggttgacg cctgatccgt ggcagcagca ggtgttggat gattggctag ctgtgggtgg 15180
taatggcagg cttgcttcgg gtgtgtgtgg ggtgtttgtg cctcgccaga atggcaagaa 15240
tgctattttg gaggttgtgg agttgtttaa ggcgactatt cagggtcgcc gtattttgca 15300
tacggctcac gagttgaagt cggctcgtaa ggcgtttatg cggttgaggt cgttttttga 15360
gaatgagcgg cagtttcctg acttgtatcg tatggtgaag tcgattcgtg cgacgaatgg 15420
ccaggaggct attgtgttgc atcatccgga ttgtgccacg tttgagcgta agtgtggttg 15480
tccgggttgg ggttcggttg agtttgtggc ccgttctcgt ggttctgctc gcgggtttac 15540
ggttgatgat ttggtgtgtg atgaggctca ggagttgtcg gatgagcagt tggaggcgtt 15600
gcttcctacg gtgtctgcgg ctccttcggg tgatcctcag cagattttct tgggtacgcc 15660
gcctgggccg ttggctgacg ggtctgtggt gttgcgtttg cgcgggcagg ctttgtcggg 15720
tggtaaaagg tttgcgtgga cggagttttc tatcccggat gagtctgatc cggatgatgt 15780
gtcgcggcag tggcggaagc ttgctggtga gacgaatcct gcgctgggta ggcgtctgaa 15840
tttcgggacg gtgagcgatg agcatgagtc gatgtctgct gccgggtttg ctcgggagcg 15900
gcttggctgg tgggatcgtg gccagtctgc ttcttcggtg attccggcgg ataagtgggt 15960
tcagtcggct gtggatgagg cggctctggt tggcgggaaa gtgtttggtg tctcgttttc 16020
tcgttcgggg gatcgtgtcg ctttggctgg tgctggccgg actgatgctg gtgttcatgt 16080
tgaggtgatt gatgggctgt cggggacgat tgttgatggt gtgggccggt tggctgactg 16140
gttggcggtt cgttggggtg atactgaccg gatcatggtt gccgggtctg gtgcggtgtt 16200
gttgcagaag gcgttgacgg atcgtggtgt tccgggccgt ggcgtgattg tggctgatac 16260

```
tggggtgtat gtggaggcgt gtcaggcgtt tttggagggt gtcaggtcgg gtgtggtttc  16320
tcatcctcgt gccgattcga ggcgtgacat gttggatatt gctgtgaggt cggctgtgca  16380
gaagaagaag ggttctgcgt ggggttgggg ttcctcgttt aaggatggtt ctgaggttcc  16440
tttggaggct gtgtctttgg cgtatcttgg tgcgaagatg gcgaaggcta ggcggcgtga  16500
acggtctggt aggaagcggg tgtctgtggt atgaattcgg atgagttggc tctgattgag  16560
ggcatgtacg atcgtatccg aaggttgtct tcgtggcatt gccgtattga gggctactat  16620
gagggctcta gccgggtgcg tgatttgggg gttgctattc ctccggagtt gcagcgtgtg  16680
cagacggtgg tgtcgtggcc tggtattgcg gtggatgctt tggaggagcg tctggattgg  16740
cttggctgga ctaatggtga cggctacggt ctggatggtg tgtatgctgc gaatcggctt  16800
gctacggcgt cgtgtgatgt gcatttggat gcgctgattt ttgggttgtc gtttgtggct  16860
gttattcccc agggtgatgg gtcggtgttg gttcgtccgc agtcgccgaa gaattgcacg  16920
ggccggtttt cggctgacgg gtctcgtctg gatgctggcc ttgtggtgca gcagacgtgt  16980
gatcctgagg ttgttgaggc tgagcttttg ttgcctgatg tgattgttca ggtggagcgg  17040
cgaggtagcc gtgagtgggt tgagacgggc cgtataccga atgtgcttgg ggctgttccg  17100
ttggtgcctg ttgtgaatcg tcgccgtacg tctaggattg atgggcgttc ggagatcact  17160
cggtcgatta gggcttacac ggatgaggct gttcgcacac tgttggggca gtctgtgaat  17220
cgtgactttt atgcctatcc tcagcgttgg gtgacgggtg tgtcggctga cgagttttcg  17280
cagcctggct gggtcctgtc gatggcttct gtgtgggctg tggataagga tgacgacggt  17340
gacactccga atgtggggtc gtttcctgtg aattctccta caccgtattc ggatcagatg  17400
cgtttgttgg ctcagctgac ggcgggtgag gctgcggttc cggagcgcta tttcgggttt  17460
atcacgtcta acccgccttc tggggaggct ttggctgcgg aggagtcgag gcttgtgaag  17520
cgtgccgagc ggcgtcagac gtcgtttggt cagggctggc tgtcggttgg tttcctggct  17580
gccagggcgc ttgattcgag tgttgatgag gccgcgtttt tcggcgatgt gggtttgcgt  17640
tggcgtgacg cttcaacccc gactcgggcg gctacggctg atgctgtgac gaagcttgtg  17700
ggtgccggta ttcttccggc ggattctcgt acggtgttgg agatgctggg gcttgatgat  17760
gtgcaggttg aggctgtgat gcgtcatcgt gccgagtctt cggatccgtt ggcggcactg  17820
gctggggcta tatcgcgtca aactagcgag gtttgatagg cgatggcttc gggtgttgcg  17880
tcaaggttgg ctgctgccgg gtatcagcgt gaggcggtca ggtttgccgg gaagtatgcg  17940
ggctattatg ccgagcttgg tcgtttgtgg cattccggga agatgacaga tgcgcagtat  18000
gtgcgtttgt gtgtggagtt ggagcgtgcc ggccatgacg gttcagcggc gttggcgggt  18060
aagttcgtgt cggattttcg gaagcttaac ggtgtggatc ctggtttgat cgtgtatgac  18120
gagtttgatg ctgccgccgc gttggctagg tcgttttcga ctattaagat gatgaatagt  18180
gacccggata gggctaagga tacggttgat gcgatggcgg cgggtgttaa tcgggctgtc  18240
atgaatgctg gccgtgacac ggttgagtgg tctgcgggtg cgcagggtag gtcgtggcgc  18300
cgggtgacgg atggtgatcc gtgcgcgttt tgtgccatgt tggctacgag gtcggattat  18360
acgaccaaag agcgggcgct tactactggt catactcggc gtcataagcg tggcggtagg  18420
cgtccgtttg gttcgaagta tcatgatcat tgtggttgta cggtggttga ggttgttggc  18480
ccttgggagc caaatagggc tgatgccgca tatcagagga cgtatgagaa ggctcgtgag  18540
tgggttgatg atcatgggtt gcagcagtcg cctggcaata ttttgaaggc tatgcgtact  18600
```

gttggtggca tgagataatt tgatgtggtt tccggttgtg tgccgccggt tatcggtgca 18660
cagggttgtc tcccgcacgg gggtcaacaa tgttgtgttg ttttccgcaa ggagtatagg 18720
gttaggctat ggccgatcaa aaagttgaag aacagaatgt tgacaatgat gctgttgagc 18780
ccggaaaggg tggagacgtt gttgatgttg tgaaggatgg gcaggctgcc ggcgatgatc 18840
atgccggtga tgtttccgtg aaggaggagt cttcttctgg cacggattgg aaggctgagg 18900
ctcgtaagtg ggagtctcgt gctaaaagta atttcgccga gttggagaag cttcgcgcct 18960
cggatggtga tgcggggtct gtgattgatg agcttcgccg caagaatgag gaactcgaag 19020
accggattaa tgggtttgtt cttgagggtg tgaagcgcga ggtggctgcc gagtgtggcc 19080
tgtcgggtga tgctgtcgct tttttgcacg gtggcgatcg tgaagcactg gtggagtctg 19140
ctaaggcttt gaagggtttg atcgaccata gtagtggtgg cgcgggtgtg cgccgtcttg 19200
cggggagtgc ccccgttgat gatgttaaac gacgtgaggg tgtcgcgttt gtggatgctc 19260
ttgtcaataa ttctaggaga tgatttgtga tggctgacga ttttctttct gcagggaagc 19320
ttgagcttcc tggttctatg attggtgcgg ttcgtgaccg tgctatcgat tctggtgttt 19380
tggcgaagct ttcgccggag cagccgacta tttttggccc tgttaagggt gccgtgttta 19440
gtggtgttcc tcgcgctaag attgttggtg agggcgaggt taagccttcc gcgtctgttg 19500
atgtttcggc gtttactgcg cagcctatca aggttgtgac tcagcagcgt gtctcggacg 19560
agtttatgtg ggctgatgct gattaccgtc tgggtgtttt gcaggatctg atttccccgg 19620
ctcttggtgc ttcgattggt cgcgccgtgg atctgattgc tttccatggt attgatcctg 19680
ccactggtaa agcggctgcc gctgtgcata cttcgctgga taagacgacg catattgttg 19740
atgccacgga ttctgctacg gctgatcttg ttaaggctgt cggcctgatt gctggtgctg 19800
gtttgcaggt tcctaacggg gttgctttgg atcccgcgtt ctcgtttgcc ctgtctactg 19860
aggtgtatcc gaaggggtct ccgcttgccg gccagcctat gtatcctgcc gccgggtttg 19920
ccggtttgga taattggcgc ggcctgaatg ttggtgcttc ttcgactgtt tctggcgccc 19980
cggagatgtc gcctgactcg ggtgttaagg ctattgtggg tgatttctct cgtgttcatt 20040
ggggtttcca gcgtaacttc ccgatcgagc ttatcgagta tggcgatccg gatcagactg 20100
gccgcgattt gaagggccat aatgaggtta tggttcgtgc cgaggctgtg ctgtatgtgg 20160
ctatcgagtc gcttgattcg tttgctgttg tgaaggagaa ggctgccccg aagcctaatc 20220
cgccggccga gaactgattt attgttgcgg tgatgtgtca atgtgcaggg ggtggtgttg 20280
atgggtatca ttttgaagcc tgaggatatt gagcctttcg ccgatattcc tagagagaag 20340
cttgaggcga tgattgccga tgtggaggct gtggctgtca gtgtcgcccc ctgtatcgct 20400
aaaccggatt tcaaatacaa ggatgccgct aaggctattc tgcgcagggc tttgttgcgc 20460
tggaatgata ctggcgtgtc gggtcaggtg cagtacgagt ctgcgggtcc tttcgctcag 20520
actacacggt ctagtactcc cacgaatttg ttgtggcctt ctgagattgt cgcgttgaag 20580
aagctgtgtg agggtgatgg tggggctggt aaagcgttca ctattacacc gaccatgagg 20640
agtagtgtga atcattctga ggtgtgttcc acggtgtggg gtgagggttg ctcgtgcggg 20700
tcgaatatta acggctacgc tggccccttg tgggagatat gatatgacca gttttcctta 20760
tggtgaaacg gttgtgatgc ttcaaccgac tgttcgtgtc gatgatcttg gcgacaaggt 20820
ggaagactgg tctaagcctg tcgagactgt gtaccataac gtggccatat atgcttccgt 20880
ttcgcaggag gatgaggctg cggggcgtga ctcggattat gagcattggt cgatgctgtt 20940
caagcagcct gttgtgggcg ctgattatcg ttgtaggtgg cgtattcggg gtgttgtgtg 21000

```
ggaggctgac gggtctccta tggtgtggca tcaccccatg tccggttggg atgctggtac  21060
gcaggttaat gtgaagcgta agaagggctg atgggtagtg gctcaggatg tgaatgtgaa  21120
gctgaacttg ccgggtattc gtgaggtgtt gaagtcttct ggagtgcatg gcatgttggc  21180
tgagcgtggc gagcgtgtca agcgtgccgc agcggcgaat gtgggtggta acgcgtttga  21240
tagggcccaa taccgtaatg gtttgtcgtc ggaggtgcag gttcaccgtg ttgaggctgt  21300
ggcgaggatt ggcaccacct ataagggtgg gaagcgtatt gaggcgaagc atggcacgtt  21360
ggcgaggtcg attggggctg cgtcgtgatc gtttacggtg atccgcgtgt gtgggctaaa  21420
cgcgtgctca aggatgatgg ctggctgtct gggataccgt gtacggggac ggtgcctgag  21480
gatttcagcg gtgacctgat ctggttggcg ttggatggtg gcccacagtt gcatgttcgt  21540
gagcgtgttt ttttgcgcgt gaacgtgttt tcggatacgc cggatcgtgc tatgtcgttg  21600
gcgcgtcgtg tcgaggctgt gctggctgat agtgtggacg gtgaccctgt ggtgtactgt  21660
aaacggtcta ctggccctga tttgctggtt gatggtgcac gttttgatgt gtattcgctt  21720
tttgagctga tatgtaggcc tgcggagtct gaataagctt attgtttttg ttttaatgta  21780
attgtttgat atttaatggg ggttatgatg gctgcaacac gtaaagcgtc taatgttcgc  21840
tcagcggtta ctggcgacgt ttatattggt gacgcgcacg cgggtgatac tattaagggt  21900
gtggaggcgg ttccttccgg gcttaccgct ttagggtatc tgtctgatga cgggtttaag  21960
attaagcctg agcgtaaaac ggatgatttg aaggcttggc agaatgcgga tgttgttcgc  22020
actgtggcta cggagtcttc tatcgagatt tctttccagc tgatcgaatc caaaaaagag  22080
gttatcgaac tgttttggca gtcgaaggtt actgccggat ccgattcggg ttcttttgat  22140
atttctcctg gtgccacgac gggtgttcac gctctgttga tggatattgt tgatggtgat  22200
caggttattc gctactattt ccctgaggtt gagctcattg atcgtgacga gatcaagggt  22260
aagaatggtg aagtgtacgg gtatggtgtg acgttgaagg cgtatcctgc ccagattggt  22320
aagactggta atgcggtgtc tggtcggggg tggatgacgg ctttaaaagc tgatactcct  22380
ccttctccga agcctcagcc ggatccgaat ccgccggccg agaactgata cacgatttta  22440
ggggattgtt gatagatgag tgacactggt ttcacgttga agattggtga tcgtagctgg  22500
gtgttggcgg atgctgagga gacggcgcag gctgttcctg cccgcgtttt ccgtcgtgcc  22560
gccaggattg cccagtcggg ggagtctgcg gatttcgccc aggttgaggt gatgttttct  22620
atgttggagg ctgccgcccc ggctgacgct gtggaggccc tggaggggct tcctatggtt  22680
cgtgtggcgg aggttttccg tgagtggatg gaatataagc ctgacggtaa gggtgcctcg  22740
ctgggggaat agtttggctc cacggcctga ttgatgatta tcgtggggcc atcgaatacg  22800
atttccgcac taaatttggt gtttctgttt atagtgttgg tggcccgcag atgtgttggg  22860
gtgaggctgt ccggctggct ggcgtgttgt gtactgatac gtctagccag ttggcggccc  22920
acctgaatgg ttggcagcgc ccgtttgagt ggtgtgagtg ggctgtgttg gacatgttgg  22980
atcattacag gtctgctaat agtgaggggc agccggagcc tgtggcgagg ccgacggatg  23040
agcgtagggc ccggtttacg tctgggcagg tggacgatat tttggcgcgt gttcgtgccg  23100
gtggcggggt gtctcgcgag attaatatta tggggtgaat agtgtatgtc tggtgagatt  23160
gcttccgcgt atgtgtcgtt gtatacgaag atgcctggcc ttaaaagtga tgttggtaaa  23220
cagctttctg gggtgatgcc tgcggagggt cagcgttcgg gtagcttgtt tgctagcggg  23280
atgaagttgg cgcttggtgg tgcggcgatg atgggtgcca tcaatgttgc taagaagggc  23340
```

```
ctcaagtcta tctatgatgt gactattggt ggcggtattg ctagggcgat ggctattgat  23400
gaggctcagg ctaaactgac tggtttgggt catacgtcgt ctgacacgtc ttcgattatg  23460
aattcggcta ttgaggctgt tactggtacg tcgtacgcgt tgggggatgc ggcgtctacg  23520
gctgcggcgt tgtctgcttc gggtgtgaag tctggcgggc agatgacgga tgtgttgaag  23580
actgtcgccg atgtgtctta tatttcgggt aagtcgtttc aggatacggg cgctattttt  23640
acgtccgtga tggctcgcgg taagttgcag ggcgatgaca tgttgcagct tactatggcg  23700
ggtgttcctg tgctgtcttt gcttgccagg cagacgggta aaacgtctgc tgaggtgtcg  23760
cagatggtgt cgaaggggca gattgatttt gccacgtttg cggctgcgat gaagcttggc  23820
atgggtggtg ctgcgcaggc gtctggtaag acgtttgagg gcgctatgaa gaatgttaag  23880
ggtgccctgg gttatttggg tgctacggct atggcgccgt ttcttaacgg gttgcggcag  23940
atttttgttg cgttgaatcc ggttattaag tctatcacgg attctgtgaa gcctatgttt  24000
gcgtcggtgg atcaggggat tcagcgggtg atgccgtcta ttttggcgtg gattaaccgt  24060
atgccgggca tgattacgag aatgaatgca cagatgcgcg ccaaggttga gcagttgaag  24120
ggcgtttttg cgaggctgca tttgcctgtt cctaaggtga attttggtgc catgtttgct  24180
ggcggcaccg cagtgttcgg tattgttgct gcgggtgttg ggaagcttgt tgcggggttt  24240
gccccgttgg cggtgtcttt gaagaatctg ttgccgtcgt ttggtgcttt gaggggtgcc  24300
gctgggggc ttggtggcgt gtttcgcgcc ctgggtggcc ctgttggtat tgtgatcggg  24360
ctgtttgctg ccatgtttgc tacgaacgcc cagttccgtg ccgctgttat gcagcttgtg  24420
gggttgttg gccgggcttt ggggcagatt atggtcgctg tgcagccact gttcgggatt  24480
gttgctggcg tggttgccag gttggcgcca gtgttcggcc agattatcgg tatggttgct  24540
ggtttggctg cccggctggt gcctgttatt ggtatgctta ttgcccggct ggttcctgtt  24600
atcacccaga ttattggtat ggtaacccag gttgctgcca tgttgttgcc tatgctgatg  24660
ccggttattc aggctgttgt tgctgtgata cggcaggtta ttggtgtgat catgcagttg  24720
atacctgttt tgatgccggt tgtgcagcag attttgggtg ctgtcatgtc tgttttgccg  24780
ccgattgttg gtttgatacg gtcgctgata ccggtgatca tgtcgattat gcgtgtggtg  24840
gtgcaggttg ttggtgccgt gttgcaggtg gtggcccgta ttattccggt tgttatgccg  24900
atttatgttt cggtgattgg attcattgcc aagatttatg ctgcggttat cgtttttgag  24960
gctaaggtta ttggcgctat tcttcgtact attacgtgga ttgtgaatca ttcagtgtct  25020
ggcgtgaggt ctatgggcac ggccatccag aatggctgga atcatatcaa atcgtttacg  25080
tcggcgttta ttaacggttt caagtcgatc atttctgccg gtgttgccgc ggttgtgggg  25140
ttttttacgc ggcttggttt gtcggttgct tctcatgttc ggtctgggtt taacgcggcc  25200
cgtggcgctg tttcggctgc gatgaatgct attcggagtg ttgtgtcttc ggtggcgtct  25260
gctgttggcg ggtttttcgg gtcgatggcg tctagggttc gtagtggtgc tgtgcgcggg  25320
tttaatggtg cccggagtgc ggcttcttct gctatgcatg ctatgggctc ggctgtgtct  25380
agtggtgtgc atggtgtgct agggtttttc cggaatttgc ctggcaatat tcggcatgct  25440
ctcggcaata tggggttctt gttggtgtcg gctggccgtg atgtggtgtc tggtttgggt  25500
aacggtatta agaatgctat gagtggcctg ttggatacgg tgcgtaacat gggttctcag  25560
gttgctaatg cggctaagtc tgtgttgggt attcattccc cgtctcgagt gtttcgtgac  25620
caggttggcc ggcaggttgt tgccggtttg gccgagggga tcaccgggaa tgcgggtttg  25680
gcgttggatg cgatgtcggg tgtggctgga cggctgcctg atgcggttga tgcccggttt  25740
```

```
ggtgtgcgat catcggtggg ctcgtttacc ccgtatgaca ggtatcggcg gatgggcgag  25800
aagagtgttg tggtgaatgt gaatgggcct acttatggtg atcctaacga gtttgcgaag  25860
cggattgagc ggcagcagcg tgacgctttg aacgcgttgg cttacgtgtg attgggggtg  25920
ttgtgcatgt ttattcctga cccgtctgat cgtgccggtt tgactgttac ctggtctatg  25980
ttgccgttga ttggtaatga tccggagcgt gtgcttcatt tgacggatta tacgggtgcg  26040
tctcctgtca tgttgttgaa tgattcgttg cgcggtttgg gtgttcctga ggtggagcat  26100
ttttctcaaa ctcatgttgg ggtgcacggc tcggagtggc gcgggtttaa tgtgaagcct  26160
cgcgaggtga cattacctgt cctggtgtcg ggtgttggtg tggatccggt tggcgggttt  26220
cgtgacggtt ttttgaaggc gtatgacgag ttgtggtctg cttttcctcc gggcgaggag  26280
ggggagttgt ctgtgaagac cccgtctggc cgtgagcgtg tgctaaaatg ccggtttgat  26340
tcggtggatg acacgtttac tgtggatccg gtgaacaggg gttatgcgcg ctatctgttg  26400
catttgacag cttatgaccc gttttggtat ggggatgagc agaagtttcg ttttagtaat  26460
gcgaagttgc aggattggtt aggtggcggc cctgtcggca agaagggtac cgcttttccg  26520
gtggtgttga cgcctggtgt tggttcgggt tgggataatc tgtctaatag gggtgatgtg  26580
cctgcgtggc ctgtgattcg tgtggagggc ccgttggagt cgtggtctgt gcagattgat  26640
ggtttgcgtg tgtcttcgga ttacccggtg gaggagtttg attggatcac tattgatacg  26700
gatcctcgca aacagtctgc attgttgaac gggtttgagg atgtgatgga tcgtttgaca  26760
gagtgggagt ttgcccctat cccgcctggc ggttctaaga gtgtgaatat tgagatggtt  26820
ggtttgggtg ccattgttgt gtcggtgcag tacaggtttt tgagggcttg gtgaatagtt  26880
gatggctggt cttgttccgc atgtaacatt gtttacacct gattatcgcc gtgtggcgcc  26940
tatcaatttt tttgagtcgt tgaagttgtc gttaaagtgg aatggtttgt ccactttgga  27000
gttggtggtg tctggtgatc attctaggct tgacgggttg actaggccgg gtgcacggct  27060
ggttgttgat tatggtggtg gccagatttt ttctgggcct gtgcgtcggg ttcatggtgt  27120
gggtccgtgg cgttcttccc atgtgactat cacgtgtgag gatgatattc gtctgttgtg  27180
gcgtatgttg atgtggcctg tggattatcg tcctggtttg gttggtatgg agtggcgtgc  27240
tgaccgggat tatgcccact attcgggtgc ggctgagtcg gtggctaagc aggtgttggg  27300
ggataatgct tggcgttttc cgcctggttt gtttatgaac gatgatgaga gtcgtggacg  27360
gttcattaag gattttcagg tgcggtttca cgtgtttgcc gataagttgt tgccggtgtt  27420
gtcgtgggct cggatgactg tcacggtgaa ccagtttgag aatgcgaagt ttgatcagcg  27480
tggtttggtg tttgattgtg tgcctgctgt gacgcgtaag catgtgttga ctgccgagtc  27540
tggttcgatt gtgtcgtggg agtatgtgcg tgacgccccg aaggcgacat cggtggtggt  27600
tggtggccgc ggcgagggca aagatcggct gttttgtgag gatgttgatt cgatggccga  27660
ggatgactgg tttgatcgtg tcgaggtgtt taaggatgcc cgtaacacgg attctgagca  27720
tgtgcatctc attgatgagg ctgagcaggt gttgtccgag ttgggggcca cgtcggggtt  27780
taagatcgag ttggctgagt cggatgtgtt gcggtttggg cccggcaatc tgatgcccgg  27840
ggatttgatc tatgtggatg tgggttctgg ccctatcgca gagattgtgc ggcagattga  27900
tgtggagtgt gagtcgccgg gtgacgggtg gacgaaggtg actcctgttg caggggatta  27960
tgagaataat ccgtcggccc tgttggcgcg gcgtgttgct ggtttggctg cgggtgtgcg  28020
ggatttgcaa aaattctaga aaagattagg ggtttgttgt gggtattgtg tgtaaagggt  28080
```

ttgatggtgt gttgaccgag tatgattggg ctcaaatgtc tggtctgatg ggtaatatgc 28140
cgtccgtgaa agggccggac gattttcgtg tcggcactac tgttcagggt gccacagtgt 28200
tgtgtgaggt cctgccgggg caggcttggg cccacggggt gatgtgcacg tcgaatagtg 28260
ttgagacggt gaccggccag cttccgggcc cgggtgagac ccgatacgac tatgtggtgt 28320
tgtctcggga ttgggaggcg aatacggcca agttggagat tgttcctggg gggcgtgcgg 28380
agcgtgcccg tgacgtgttg agggccgagc ctggcgtgta ccatcagcag ttgttggcta 28440
ctttggtggt gtcgtctaac gggttgcagc agcagctgga taggcgtgct atagcggcta 28500
gggtggcgtt tggcgagtct gctgcgtgtg atcctacccc agtggagggt gaccgtgtga 28560
tggttccctc tggggctgtg tgggctaatc atgccggcga gtggatgctg ttgtccccca 28620
ggattgagac gggttctaag tcgatcatgt ttggcgggtc tgctgtgtat gcttacacga 28680
ttccgtttga gcggccgttt agtagtgcgc ctgttgtggt ggcgtctatg gctacggcgg 28740
ctgggggcac gcagcagatc aatgtgaaag cctacaatgt gactgtccaa aattttagtt 28800
tggcgtttat tacgaatgat ggttcgaagc cgaatggtgt gcctgcggcg gctaattgga 28860
ttgctgtcgg cgtgtgactg tacaggtgtt gtggcggatg gtgtgatgtt ggggggctgt 28920
ggtgtcgtgg tttactcctg cactggtggc ctctatttgt accgcgttgg ccacggtttt 28980
gggttctgtt caggctgtca catcccggtc taggcggcgt ttacgcaggc tgtctgcgca 29040
ggtggatgcg atggaagagt atacgtgggg tgtgcggcgc gaggtgcgaa ggtttaacgc 29100
cgggcttcct gatgatgtgg agccgatgca tcttcctgat gtgcccgagt tttgaaggga 29160
tactgttgat ggtggaggtg agtagggttg agggagttgg aggaggagaa gcggcagcgc 29220
cgcaattttg agaaggcttc cctgatactg ttgtttttgt cgcttgtgtt gttggcggtg 29280
gttgccgggg gtgctttgcg gtacgggtct gtggcttctc aaagggattc ggagcaggcg 29340
agggcccagt cgaatggtac agccgctaaa gggttggctg cccgtgtgaa gcaggcgtgt 29400
acccagggtg gcgtggagtc tgtgaagctg cacaggtctg gtttgtgtgt ggatgctgtg 29460
cgtgttgagc agcgtgttca gggtgtgcag ggtcctgccg gtgagcgtgg cccgcaaggg 29520
cccgctggtg ttgatggccg ggatggtagc aatggttctg ctgggctggt tggccctgtt 29580
gggccgcagg gttccc 29596

<210> SEQ ID NO 72
<211> LENGTH: 29124
<212> TYPE: DNA
<213> ORGANISM: Artificial Sequence
<220> FEATURE:
<223> OTHER INFORMATION: PAC10

<400> SEQUENCE: 72
gggtttagcc agccgtgtgc ggcaggcgtg tgcttcgggt ggggtggagt ctgcgcggct 60
tcaccggtct ggtttgtgtg tggatgctgt gcgtgttgag cgtagcgtgc agggtgtgcc 120
gggtcctgcc ggtgtacggg gcccgcaagg ccctgcaggt gctgacggca gggatggtgt 180
taatggttcg gctgggctgg ttggccctgt tggtccgcaa ggttcccctg gcttgaatgg 240
tgtgaaaggt cctgacgggt tgcctggtgc gaatggatcg gatggccatg atggtgttcc 300
aggtcgtgca ggtgctgacg gtatgaacgg cgttgacggc agggatggtg ttaatggttc 360
ggctggtgag cgcggtgatg tgggcccttc aggtcctgcc ggcccgcaag gtgcacaggg 420
tgaacggggt gagcgcggcc ccgccggtac gaacggatac gatggtaagg atggtaagga 480
tggccgttct gttgtgtccg tgtactgttc cgggggcagc ctggttgtga aatatagtga 540

-continued

```
cggtgtggtt tctaccgtat cggactcggc ggcctgccag ggtgtgaaac cgtcgcctat    600
agtgactata tcatcccaca aatagaaagg agtggctgtg atggtagtgt ttggtggtgt    660
gtggtgaggt ttattcctgc ggcgcatcac tcaagcggtt cgaatagtcc ggtgaatagg    720
gttgtgattc atgcgacatg cccggatgtg gggtttccgt ctgcctcgcg taaggggcgg    780
gcggtgtcta cagcaaacta ttttgcttcc ccgtcttcgg gtggttcggc gcattatgtg    840
tgtgatattg gggagacggt gcagtgcttg tctgagtcta cgattgggtg gcatgccccg    900
ccgaatccgc atagtttggg tatagagatt tgcgcggatg gggggttcgca cgcctcattc    960
cgggtgccgg ggcatgctta cactcgtgag cagtggctgg atcctagggt gtggcctgcg   1020
gtggagaagg ctgccatcct gtgtagacgt ttgtgtgaca aatataatgt tccgaaaagg   1080
aagcttagtg cagccgattt gaaggctggt aaacgtggtg tttgcgggca tgtggatgtt   1140
acggatgcgt ggcatcagtc ggatcatgat gatcctgggc cgtggtttcc gtgggacagg   1200
tttatggccg tcgtcaacgg cggcagtgga gatagtgggg agttaactgt ggctgatgtg   1260
aaagccttgc atgatcagat taaacaattg tctgctcagc ttactggttc ggtgaataag   1320
ctgcaccacg atgtgggtgt ggttcaggtt cagaatggtg atttgggtaa acgtgttgat   1380
gccctgtcgt gggtgaagaa tccggtgacg gggaagctgt ggcgcgccaa ggatgctttg   1440
tggagtgtct ggtattacgt gctggagtgt cgtagccgta ttgacaggct tgagtcgact   1500
gttaatggtt tgaaaaagtg atggtggtgt gttgtgggta aacagttttg gttgggcctg   1560
ttggagcgtg ccctgaaaac ttttattcaa acgtttgttg ctgtgcttgg ggtgacggcg   1620
ggtgtcacgt atactgcgga gtcgtttcgc ggtttgccgt gggagtctgc actgattacg   1680
gctacggttg ctgctgtgtt gtcggtggct acttcgtttg gtagcccgtc gtttgtggcc   1740
ggcaagccta aaaccacggt tgtggatgcg ggtttggttc caccggatga tgggggcttg   1800
gttgagccgc atatggttga tgtgtcggat cctggcatga tcgagcctgc agatgatgcg   1860
gatcttggtg taggctatgt gccgaaacac gctgccgagt cggaggttgg gacggtagag   1920
tctactgttg cataattgaa catagatgcg tgccccagcg gtgctgccac gatcgtgtgg   1980
tggttgccgc tggggcacta tttctgttta tgcggtgtgg ctatgattcg ttgcggtcga   2040
tggtgtcttc gagcatctga tacaggtgga ggcaggtaga gatcgtatcg ctggcctggt   2100
ctagaacgtt ccggccgata acgtttttgt ggttgtcgcg gtggcggatg atagcccaca   2160
tgatctcgtc ggcctccgct tgtaatagtt ttgcctggta tgcgattccg gcgagccagt   2220
ctagtgcttc ctggcttgca taggggctct ggtcctcgct gttgtcacgg gtgttgctgt   2280
tgtttgtggg gtgtcctgca ctgtcgcata accacaggat ttcgctgcac tcgtctagcg   2340
tgtcctggtc gatagcgaga tcgtcgaggc tgacttcgtt gacggtaagg ttcacgttgt   2400
cgagtgagat gggtacaccg tactggtttt cgacactgtc aacaatgttt tccagctgtt   2460
gcatgttggt gggctgttgt tggacgatac ggtgtatcgc tgtgttgagg gtggtgtagg   2520
tgatattgtg tgtgttgttc atggttttat cccatccctg tgctgtcgtc gttttcgtct   2580
ggatagtatc tactgtttgc gtagcctgtt agggtgatga gtgtttggtc tgcccactgt   2640
ttcacggttt gtcttgtcac cccgagtcgt tgggctgcca ccgaataggt ttgatcatac   2700
ccgtatactt ctctgaatgc tgccagccgt gccaaatgtt ttcgctgttt ggatggctgg   2760
caggtgaggg tgtagtcgtc gatggctagc tgcaaatcga tcatggtgac aatgttgttg   2820
ccgtggtgtt gtggcgcggt tggtggtggt ggcattcctg gttcgacact cggtttccat   2880
```

-continued

```
gggcctccgt tccagatcca ttgggcggct tggatgatgt cggcggtggt gtaggttcgg   2940
ttcactggta atccttaaac aagtcgttca tgttgctggt gttgctggtg ttgctggtgt   3000
cgaatcgtcc cacacagtgg cagtagtcgt acatgagttt aataatgtgt tggtggtctc   3060
ccaaataggt gttgccgctg atgctgtagg tggctgtgcc gtctttactg atggtgtatt   3120
tggcggtgat ggtttcgggg ttttcggtgt cggtgatgat ggctgtggtg gtggtgccta   3180
cggtttgtag cacggtggtt tgggttccgt cgtcgatggt ggttttaacc atgaggggtt   3240
ctccttttaa atgcttgttt ggttgtcggc tagatgaata atatcggata aaggtttcgg   3300
ctggtctagg tgttgtatgg ttttgttggc tagccgtttg gctaccctgt agcacatttt   3360
ggtatagtgt ttgttgtcta ggttgtggta ttgttcccgc accgcaatat atagtaggga   3420
gtcttgatag aggtcgtctg cactgattgc ggggtagtgt gtggctgttt tggtgcatgc   3480
ccggttgagt gtgcgtagat gatggtttgt ggcccatccc cacgatgcgg tggtggctat   3540
gtctgctttt gttggtcgtc tgctcatggc atctctttca tctggctatc tggtagttgt   3600
ttggtgtttt gttgttgata gtgtagcaca cgagtccggg gtttccggtg gcgcctgtgc   3660
ggtgccggaa ccatgtggat tcgccttcca tggatgggca ttggatgaag gtgcgttggc   3720
cttgctcgga gatttctagg tggtgccggt gcccggccat gaggatgtgg gatgtggtgc   3780
cgttgtggaa ttcttggccg cgccaccatt cgtagtgttg gttgttgcgc cattggtggc   3840
cgtgggcgtg caggatttgt gtgccggcca ccccaacggt ggtggtcatt tcgtcccggc   3900
tggggaagtg gaagtgaaga ttggggtagt tgttgttgag ctggtaggct tctgcgatgg   3960
cccggcagca gtccacgtcg aaggagtcgt cgtaggtggt gactcctttg ccgaagcgta   4020
cggcttctcc gtggttgccg gggattgagg tgatggtgac gttttggcag tggtcgaaca   4080
tgtggatgag ttgcatcatg gccatgcggg tgagcctgat ttgttccgtc aagggtgttt   4140
gggtgcgcca ggcgttgttg cctccttgtg acacgtatcc ttcgatcatg tcgccgagga   4200
aggcgatgtg gactcgttgc ggctgtcctg cctgttgcca gtagtgtttt gctgctgtga   4260
gggagtgcaa atagtcgtcg gcgaagtgtg ctgtttctcc gttggggatg cctttgccga   4320
tttggaagtc tcccgcccct accacgaacg caaccttgtt gttgctgcgg gtgtgggtgt   4380
ctggttttgg gggtgtccat tcggctagtt tatcaacgag ttcgtccacg gggtaggggt   4440
ctgttgcggg ttggtggtcg atgatttttt gtatggatcg gcctgtttct ccgttgggga   4500
gtgtccattc ggagatgcgt gtgcggcgta cggtgccgtt ggctagattg tcgcagatgg   4560
tgtctgcttc gctatcgtgg ttggctagct gtgtgaggag ccggtctata ttgtctatca   4620
ctggttttcc tcctcttgcg gggtggtgtt ggcttgtttg cggcgatagt ctttaataac   4680
ggtggcggag atggggtatc ctgcctgggt gagctgtttt gctagccatg aggcggggat   4740
ggttttgtcg gcgagcacgt ctgcagcttt gttgccgtag cgttgaataa gggtttcagt   4800
tttggttgcc atgatgtggt tttgtcggcg agcacgtctg cagctttgtt gccgtagcgt   4860
tgaataaggg tttcagtttt ggttgccatg atgtcctagg ggttgtgtgg tgggctgcca   4920
tcctgtgcgg cagtcgccgt cgtgtcctgg tttgcgtgtg caccacgata cgttgccggc   4980
attgtggatg atggcacggc cgcatatgac gtcacgtaga tgctcgggaa acttgtcgtt   5040
gttgtttccg ttcgtgtcga tcaagtgttg ggttttagta accatcatgt ctcctatgtg   5100
tgaaagagtg tgcaaatact atgcaggtgt catggatgtt tatgcgggta tggttttcat   5160
caccttgctg aatgtgactt ggttactgta catcatctgg gtgatttcct gatcggtctt   5220
gtcggggtgc tgctttcgca ggttcgccca ttggcaggcg ttgtcggtct cttgctggag   5280
```

-continued

```
ccgggtcagg tgctgctcgt tgatgatgtg tttccacatt gtccacgaca cgtcgagcct   5340
gcggagcatg ttcatggctg gcacgttaaa cgagtcgagg aagagtattt cttcggtgta   5400
gtactgtttt tcgtattggt cccatccgct tcggtgcctg ttgggctggt ttttggggta   5460
ggcttcccgg catactttgt gtaaccgttt ggccatgtcg tcgggtagtt taatgtcggg   5520
gttggcgcgg atcatggatc gcatcccatc gtaggtggtg ccccagcggt gcatgatgct   5580
gagtgggtct tcaccatcgg cccatttttc tgcacagatg gcgaggcgta tgcgcctcct   5640
ggcggctttg ctggtgtcgc ggcggccggg gatggggcac gtgtcgagag gatccatgat   5700
gttttatatg cctttctttg tttggtttgc ttgtgtggtt ttattgtagc actgtgtcta   5760
gtgcttgtgt caaccctgtt tttccggcct gcaggtaggt gtctgtgaca tcgcccaggg   5820
tgaggggcac gtgtatggct tgggggagtg ctgcctggag ggtttgtgcc atctggtggc   5880
ctgccttgtc tgggtcggac cagatgtaga tgtggtcgta gccttcgaag aatttggtcc   5940
aaaagttttg ccacgaggtt gcgccgggta gggcgacggc cgaccatccg cattgttcga   6000
ggatcatgga gtcgaattca ccttcgcaaa tgtgcatttc tgctgccggg ttggccatgg   6060
cggccatgtt gtagatggag cctgtgtcac cggccggggt taggtatttg gggtggttgt   6120
gggttttgca gtcgtgcggg agtgagcagc ggaaacgcat ttttcttatt tcggctggcc   6180
gcccccaaac ggggtacatg tatgggatgg tgatgcactg gttgtagttt tcgtggccgg   6240
gtatggggtc attgtcgatg tatccaaggt ggtggttgcg ggctgtttct tcgctgatgc   6300
ctcttgctga gagcaggtcg agtatgtttt cgaggtgggt ttcgtagagg gccgaggctt   6360
tctggattcg gcggcgttcc gcaatgttgt atgggcgtat gctgtcgtac attcgggttt   6420
tctttctcta gttgttgttt cagttgggcg agtccgcctc cgataccgca tgtgtggcag   6480
taccagacgc ccttgtcgag gttgatgctc atggagggct ggtggtcgtc gtggaatggg   6540
cagaggatgt gttgctcgtt cctggatggg ttgtaacgga tgcggtaggt gtcgaggagg   6600
cggcaggtgt cagaggtgtg ggaggagctc gttgagggtt gataccacat aggcttcgct   6660
ccagggtttg ttgcgctgtt tcatcactac gagtccgatg gtggactggc tttctcggtt   6720
tcggtgggtt tcgtagttgc gtgcctccag gctggcttgt ttcacgaatt cggctaggtg   6780
gggctgcccg gctttcgcct cgataatgta ggttttatgg ccggttgtga ggatgaggtc   6840
gccttcatcc tctttaccgt tgaggtggag gcgttctata tcatagccgg tgtcgcgtag   6900
ctggtggagg agtcttgttt cccattcggc cccggcccgc cggttgcgtg cctgctgtgt   6960
aaccatcata gtcctttgtg tgttgtggtc atgttccagg gatgtttttc ggcgagtggc   7020
ccgaagaatg tgtattcggg gtaggctcgt agccgctcat attttgttcc gtctgggctg   7080
gatttgccgg tgcgctgttt caacactgcg atgcgcgcct cggctggtat cgtgagcccg   7140
ttgccgttat cctcgccacc ataaagtgag actcccaata tgagttgtgg tttttcggag   7200
aggccgtttt taatttcccg tctagctggc gggtgttcga tgtcggagcc ggttttgtcg   7260
gttgcgtggt gtgtgacaat aatggtggag ccagtatccc tgcccaatgc tgtgatccat   7320
tgcatggctt cttgctgtgc ctggtagtcg gattcgcagt cttgaatgtc catcaggttg   7380
tcgataacaa tgagtggtgg gaaagtgttc cacatttcca tgtaggcttg tagctccatg   7440
gtgatgtcgg tccaggtgat gggtgactgg aatgagaagg tgatgtgttg gccgtggtgg   7500
atgctgtctc gatagtattc tggcccgtag tcgtcgatgt tgtgttgtat ctgtgtggtg   7560
gtgtgttggg tgttgagtga gatgattcgt gtggaggcct cccagggtgt catgtcccct   7620
```

gatatgtaga gggcgggctg gttgagcatg gcggtgatga acatggctag cccggatttt 7680
tggctgccgg agcgccccgc gatcatgacc aaatcccctt tgtggatgtg catgtcctgg 7740
ttgcggtaga ggggttctag ttggggtatg cggggcagct cggctgcggt ttgggaggct 7800
ctcgcaaagg atctttggag agagagcatc ggagccttta tctatcgatc ggttggatgt 7860
gttgtggtgg tcagatggag tcgatgtcta catcatcact atcagtggtg ttgggctggc 7920
tgtctcgccg atcaacgtag gctgctacaa ggtcgtagat ggcgtcgtcc aatggtttga 7980
gcacgaccgc gttgaacccg tttttagtgc gcacctgatc gagtttgaag gcctgctcct 8040
cgccaagata tgcctctaaa tcgcggatca tggagtgtgg gcggtcgttg ttgcctcgca 8100
ctttttcgat aatggcgttg gggatggttt ctggggtgcc gttgttgagg tcgtctaggg 8160
tgtggaagat ggtgacatca gcgtagatac gatcggcgac ctgtccaccg tagccttcag 8220
tgttgtgctg aacgtcgtgg actttgaagg cgatggcggt ggcgtcctgg tttcgggagg 8280
ggttgaagaa ggtgctgttg ctgttgttgc ggtagtttgc gagtcccatt attgtttcct 8340
ttactgtttt gttggtttgt gtcggttttt atcgggtgag gctgtttcgt ttgctgcgga 8400
aagcctcgga aacgtcactg ttactagtga tgatcttttt gtactgtttc agtagatcgg 8460
ctagctgtgc tttgcttgtt gcattgttga ttttgtcgat gatggtgttg tttccttctg 8520
aggcgatgtt gtctacgtag tctttggcgg cctggttgta tcggtcttgg aggatgatgg 8580
atgctgtggc gatcagtgtt gccaggtccc agttccttgc cgcggagctg tttttgagtc 8640
cgcctaacag gtcgatgatg gctttcttta cctggtcggc ggtgtctcct cggatgacgg 8700
tccatggggc ggcgtagtct ccgccgtatt tgagggtgac ggtgaatcgg tcgtcgtctg 8760
tgttgtcggt cactggtgct ccttgtcttc ttgtgttggg gctgtgatgg tggtttctat 8820
agggtacctg taggcgtctt tcccgttgac ggcccagcag gcgtctctga cggggcatcc 8880
tttacagagt gctgtgacgt gtgggacgaa gatgccttgg ctgattcctt tcattgcttg 8940
actgtacatg gatgatacat gccggtaggt gttgttgtca aggtcgtaca gttcggtggc 9000
cgttccctgc ttggcggact gtttgtctgt tttggttgat gcgggtgtcc aaaacatgcc 9060
ttttgtcaca tcgttgccgt gttgggcgag catgtaccgg taggtgtgca gctgcatgct 9120
gtctgctggt aggcggccgg ttttgaggtc gaggatgaag gtttcgccgg tgtcggtgtc 9180
ggtgaagata cggtcgatgt agccaacgat ctgggtgccg tcctggaggg tggtttctac 9240
cgggtattcg atgcctggct ggccgtctag gactgctgtg tggtattgcg gattgtttgt 9300
gcgccagtgt ttccaccggt cgacgaaggt ttgcccgtaa accatccacc agtcgtagtc 9360 tttttgtgt ggcccgcccg actcgcacat gtttttgcac accctgccgg agggtttaat 9420
ctccataccc tctgatcggg tgagggcgac ttgggtgtcg aaaatgtttt tgaaggatga 9480
gagtttgtct ggcagtgcag ggtattcggc ggggttgtac aggtgtaggt cgtattgttc 9540
ggtgatgtgg tgtatggcgc ttccggcgat ggtggcgtac caggtgtggt gttgggcgtg 9600
gtagccgtgg gataggcgcc atttttctcc gcattcggcc cactgtgaca gtgatgagta 9660
ggagatgtgg cctggatggt ggatggtttt cggatattgt gctagaggca ttacttgtcg 9720
cttttgttcc atgggttgcg ggtgtctacc ccggcattgt gttgctggta tgcgaggagt 9780
gctaggcagt gccaggcagc atgtgccagg tggggtagcc cggattcata atcgaggttg 9840
tttccttgct gccaggatag cacatggcgg tagagggcgt caacgctgtg gctccacgga 9900
tagccgccgg tccagttgtt gtcgccgtat ttggtggcac cgtagcctgc aacctcgccg 9960
agggcgtgta aggctgcggg gtcgatgagg gagagcctgc aaagtttgag ttctttcttg 10020

```
gcgccagtat cagggtcggt gtacatgcgg gtgggctcat ccatggggtg tgtgctcctt  10080
aagggtgggt tactggttgg ggttgtgggc gagtgctact gcgagaataa tgatggcgag  10140
ggtttctgcg atgaggatgg gtgttgtgat catttgttgt ctcggggatt gctggtgagt  10200
gtggaggcgc ctaggagggt ggtgagggcg catgcggcga tgatggcgag ggctgccttg  10260
tgtggggtgc cggtggcgta catccatgtg atgatggcgc cttggatcca ggcgaggctg  10320
gtgaagaacg tttcgtagct gtgtagctcg ctgttgttgc tggtgatgtc attcatggta  10380
gttttctgct ttgtgtgcga tggttgtgta catgtcgttg agtgtggttt cgatggtgat  10440
gagagtgttg atttcttggt tgaggtcgat gttgtctttg agggtgtcga tgcgggcggc  10500
gatgtcggtg gcggtgcgta ggcttactgc tgcaccgtgg atgatgtggc acatgtcggt  10560
gaggccgacc ttggcgatat agtgtgacat gagaggcatg atgggtgtgt cgtctttctg  10620
gtcagcgtga cgggttgatg gacatgtctt ctacctgtgg cttgtcttcg gtgcctgata  10680
cttggcaaaa gactttcacg tgcgccttgg atgctccggg ttgcttggcg gtggcaccgt  10740
aggcgatagt aaaggcgtct ttgtgggcgc cgatgacttt gtgtaggaag aggtcgatgt  10800
cggggtttcc gttccatttg acaccgtttt ctgcggctgc ctgggtggct ttctggttgc  10860
aggcgtgtgc tgccgtaatc atggtgagtc cggtggcggt ttcttcaccc cttgcttggg  10920
cttgcttgtg ggtttttgct tgttcggctt gtagggagcg gactgcggct gcctgccgtg  10980
ctttcttttc ggctttgcgc tgctgggtag tcttgggggt ccattcggtg ttggctgtgg  11040
tggcctgtgg ggctggctgt gaggcgagtg gcggattgtc gtctggggct ggcatgaatg  11100
aggcggcggc aatgatggcg gctgtgattc cggcgatggt gtagccgttt ttcttgttca  11160
tgactgttgt cccctttccg gggtgttgtt cgttgctgac atgattaatc atggtgtgga  11220
cggttcccca tgtcaaggct gcgctcaacg attgtgagcg tttggtgtgt ggctaggggt  11280
tttatcgggc acacagggtg agtagatggc caacattgat gcggctcaca ttccagtaga  11340
gttgtgtggc ttcaccgccg gtgagcggct tccactcgtt gtggctgaac acggtgccat  11400
cggatgcgat gaatgtgtcg gggcgtagct tgtgaagctc ggcttccacg ctctgccggt  11460
aggtttcggc gaggccctca aaatccatgt ggtcgcagga gaggttttcg aggcgtgtca  11520
ggtcgaaggg tgtggggcag tcgtagctgg cgggggtgta gagctgggtg aagtggttgg  11580
cgatcttctg catgatgatg tccttttggt tgctgataac cttgttgagg gtttatcggg  11640
tggatgtgat aaggatggcg tccacgtcga tcatgtcgat gagatcgtgg agttcctcgg  11700
cctcgttttc ggtgagtggc tgccagttgt tgtcgccgta cacggcgccg tcgagggtga  11760
cagtccacag tggccggatg aggcgtacgg cttcttgtac tttagcgtgg tacatgcggc  11820
gcaccatatc cagatccatg tcgtctgaat ggtttccgat gaggttgtgg aggctgagcg  11880
ggtcgatttc tgtctgcctg tagagggatg tgaaggatgg ggtgatgagt gtgccatcca  11940
tgggtgatgt tcctttctgg attgtcttgg ttggttgttg tggtttctag agtgtgcggg  12000
ttgcaaccgg gagtcaaggc tgcgctcatt cggattgagt gtttcatgct ggagtgtcgg  12060
gtgtgacaga tgtcacttaa gcctttattg cctctctcgg cgtctcacat catctggggg  12120
taagattatg cagggttgac cctgctgatc gattctaggg cccttctagg gcgtctcagg  12180
ggtacgtctg ggtgatagcg ggtgtggcag atgatctagc gagtcaaggt accgagctta  12240
gacgtaagat ctatcatcta ggcgtgtgag atgtatcaca tcctcctggc tgggtgtgca  12300
ccctcaaggc tactctgccg atctggcgtg gagggtgtag cccagaaatg ccgtttaaag  12360
```

-continued

```
ccttcacatg gcgcctagaa gcgccttgca gggtgggggc taggtattta tacccccaac  12420
acattctgat cgattctaga cgcctatagg agcctgatac acgatcaacc atctcggcat  12480
agatcatcag cccctatcct agttagctaa gcctgaacta tgtggacagt gtaggatgct  12540
aagagggaag aaggacacgg taaaagaaag aggggggggc atcaaccttc acgcccgagg  12600
tacttaagtt aaccttaggg tcttagcacc gagcccctca agggctcggc atcagcatca  12660
tcgggatcag ccgatccggc acagccttag caagtacaca ccatcaggga aggcttgaga  12720
gtacgaggag ccctagcgac gagtactcga aagcctgagg gaacaccctc agcactgatg  12780
ggcctagcgt gttcggaaag tacacagggg tacagtgtga gagctgttcg ggagctaaac  12840
cccttccggc tagggcaaac accagtccta gactatccca caccctcatc tgttaacctt  12900
ccgttcatta aacgttaagg aaacttttag gtttgatttt tggaccttaa ccaccaaaaa  12960
cacccattta cacccctcaa acccgccaat agagccaaac gccggtgttg agggtatctc  13020
tacctagtgt gataggctgg acaggtagcc agctggacgc aaggccagaa agtgctgacg  13080
cacttcccga cctcgcttac catcagtcta ccaaacactt aaaagcttaa cagctaagcg  13140
ctaagccctt aagacctcaa cgcttagcac cgagcccttg aggggctcgg catcagtctt  13200
aggtacttaa agtaacttta aaccttaaag gcttagcact taaggatata aacttaacat  13260
cagtgtttaa gactttaata ctttaagtaa ctataagacc ttaaagcttt aaacacttaa  13320
agttaaccat cagtcttaaa ctttaatatt ataacttata agctttaata cttatattat  13380
attataacct ataagtctta aagcttatag gttataaaag ttttagaaga gctaagaggt  13440
taacttcttt acttctctac tctctttggt tctttctctc ttctcttctt ttcttcatca  13500
ggggagaaga ggaatcttta ccatcagcgc cgatgacctt tcaccgtgtg gatcgtgtgc  13560
ttctggtcgc aagctcccat cgcacactcc ccacactctt acacccgtgt ccctttcggg  13620
cttggcgtgt tcggctaaag gcgtacggcg tgtcacgcta acacccttaa caccgggtaa  13680
gacttaaagt gtatattata tgtagaagac tttaaaacct ataaggtgtt cccgcttagc  13740
ccgtgtccta caccgctagg cgccaagcgc taagccttga aacgcgaaca cacacccacc  13800
ccctttttc ttccgtgtcc ttctcttttg acaccgctgg ggggcgatgt gatctttctc  13860
acacccatgg gggtagtgga gaaaacaaac accccggcac aaacagaaca ccccctcaaa  13920
cgaacaaaac agccccccag aatcgaccag cagggcaagg gtagagtatc catacccccca  13980
acggtttcca ggccgttaca gaggcaaata agacccgtac agggctaggc gaggaacaga  14040
cacatcatgg cacgcaccaa ccgcacagcc gccacggcac accgacgctg gcggcaacga  14100
ctcatcaccc aagcccaaca gcaaggccaa accacctgcc cactctgcgg agtcaccatc  14160
acctgggaca cccaccagct accaaccagc cccgaagccg accacatcac acccgtcagc  14220
cggggaggac tcaacaccct agacaacggg caaatcatct gcagaacatg caacagaagc  14280
aaaggcaatc gcagcgaacc aaacatcaaa ttccaacaac aaaccacaaa aaaccttgtt  14340
tcatggtaga aaacctgcca gcccccaccg gggacacccc ctgcacaggc gtgcaagacc  14400
tcgtacggct tagtgaaata cctccctttt gtggatttgt ctgtttgtcg actttttgtg  14460
ttggtggtga gtgttgtgca gcctgagctt cctgatagtc gtgattggtg tggggagacg  14520
cgtcgttggt ggcgtgtgtg gggtgaggat agccgtgcat cgtacgtgtc tgatgaggag  14580
tggttgtttc tccttgatgc ggctgtgatt catgatgtgg tgtggcgtga gggtcgcgcg  14640
gatttggtgg cttcgcttcg tgctcatgtg aaggctttta tgggtatgtt ggatcggtat  14700
tcggttgatg tggtgtctgg tggccgtgcc ggtggttctg cggtggcgat gattgatcgg  14760
```

```
tataggaagc gtaaaggggc ctaatgtcga gtgttgttgg ttctcaggtt cctcgtcatc  14820
gtgtggctgc ggcgtattcg gtgtctgctg gtggtgatgc tggggagttg ggtcgtgcgt  14880
atgggttgac gcctgatccg tggcagcagc aggtgttgga tgattggctg gctgtcggta  14940
gcaatggcag gcttgcttcg ggtgtgtgtg gggtgtttgt gcctcgccag aatggcaaga  15000
atgctatttt ggaggttgtg gagttgttta aggcgactat tcagggtcgc cgtattttgc  15060
atacggctca cgagttgaag tcggctcgta aggcgtttat gcggttgagg tcgttttttg  15120
agaatgagcg gcagtttcct gacttgtatc gtatggtgaa gtcgattcgg gcgacgaatg  15180
gtcaggaggc tattgtgttg catcacccgg attgtccgac ttttgagaag aagtgtggct  15240
gcagcggttg gggttcggtt gagtttgtgg cccgttctcg gggttctgct cgcgggttta  15300
cggttgatga tttggtgtgt gatgaggctc aggagttgtc ggatgagcag ttggaggcgt  15360
tgcttcctac ggtaagtgct gccccgtctg gtgatccgca gcagattttc cttggtacgc  15420
cgcctgggcc gttggctgat ggttctgtgg tgttgcgttt gcgtgggcag gcgcttggtg  15480
gcggtaaaag gtttgcgtgg acggagtttt cgattcctga cgagtctgat ccggatgatg  15540
tgtcgcggca gtggcggaag ttggcggggg atacgaatcc ggcgttgggg cgtcgcctga  15600
attttgggac cgtaagcgat gagcatgagt cgatgtctgc tgccggtttt gctcgggagc  15660
ggcttggctg gtgggatcgt ggccagtctg ctgtgtctgt ggttcctgct gataagtggg  15720
ctcagtctgc ggtggatgag gcgagtctgg ttggcgggaa agtgtttggt gtctcgtttt  15780
ctcgttctgg ggatcgggtt gctttggcgg gtgccggcaa gactgatgct ggggttcatg  15840
ttgaggttat tgatgggctg tcgggaacga ttgttgatgg tgtgggccgg ttggcggact  15900
ggttggcggt tcgttggggt gatactgacc ggatcatggt tgccgggtct ggtgcggtgt  15960
tgttgcagaa ggcgttgacg gatcgtggta ttccgggccg tggcgtggtg gttgctgata  16020
ctggcgttta tgtggaggct tgtcaggcgt ttcttgaggg tgtcaggtcg ggtgtgatca  16080
gtcatcctcg tgctgattct cgccgtgaca tgttggatat tgctgtgagg tcggctgtgc  16140
agaagcgtaa ggggtctgcg tggggttggg gttcctcgtt taaggatggt tctgaggttc  16200
ctttggaggc tgtgtctttg gcgtttttgg gggctaaacg tgttcgtcgt ggccgtcggg  16260
agcgtagtgg taggaagcgg gtgtctgtgg tatgaactcg gatgagttgg ctctgattga  16320
gggcatgtac gatcgtatcc aaaggttgtc ttcgtggcat tgtcgtattg agggctacta  16380
tgagggctct aatcgggtgc gtgatttggg ggtggctatt cctccggagt tgcagcgtgt  16440
gcagacggtg gtgtcgtggc ctggtatagc tgtggatgct ttggaggagc gtctggattg  16500
gcttggctgg atgaatggtg acggctacgg cctggatggt gtgtatgctg cgaatcggct  16560
tgctacggcg tcgtgtgatg tgcatttgga tgcgctgatt tttgggttgt cgtttgttgc  16620
gataattcct catggtgatg gtacggtgtc ggttcgtccg cagtcaccaa agaattgtac  16680
gggcaagttt tcggctgacg ggtctcgttt ggatgctggt ttggtggtgc agcagacgtg  16740
tgatcctgag gttgttgagg ctgagctttt gcttcctgat gtgattgttc aggtggagcg  16800
gcgtggttcg cgtgaatggg ttgaggtgga tcgtataccg aatgtgttgg gtgcggttcc  16860
gttggtgcct attgtgaatc gtcgccgtac ttctaggatt gatggccgtt cggagattac  16920
gaggtctatt agggcttaca cggatgaggc tgtgcgcaca ctgttggggc agtctgtgaa  16980
tcgtgatttt tatgcgtatc ctcagcgttg ggtgactggc gtgagcgcgg atgagttttc  17040
gcagcctggc tgggtcctgt cgatggcttc tgtgtgggct gtggataagg atgatgacgg  17100
```

-continued

```
tgacactccg aatgtggggt cgtttcctgt caatagtcct acaccgtatt cggatcagat  17160
gagactgttg gcgcagttga ctgcgggtga ggcggctgtt ccggaacgct atttcgggtt  17220
tatcacgtct aacccaccta gtggggaggc tttggctgcc gaggaatctc ggcttgtgaa  17280
gcgtgctgag cggcgtcaaa cgtcgtttgg tcagggttgg ctgtcggttg gtttttggc  17340
tgccaaggcg ttggattctc gtgttgatga ggccgatttt tttggtgatg ttggtttgcg  17400
ttggcgtgat gcttcgacgc ctacccgggc ggctacagct gatgctgtga cgaagcttgt  17460
tggtgccggt attttgcctg ctgattctcg tacggtgttg gagatgttgg ggcttgatga  17520
tgtgcaggtt gaggctgtga tgcgtcatcg tgctgagtcg tctgacccgt tggcggtgct  17580
tgctggggct atatcgcgtc aaactaacga ggtatgatag gcgatggctt cgggggttga  17640
ggcgaggctt gcggcgactg agtatcagcg tgaggcggtc aggtttgctg ggaagtatgc  17700
gggctattat tctgagcttg gtcgtttgtg gcgtgccggc aggatgagtg acacgcagta  17760
tgtgcgtttg tgtgtggagt tggagcgtgc cggccatgat ggttcggcat cgttggctgc  17820
caggtttgtg tcggattttc gccggttgaa tggtgtggat ccgggtttga ttgtgtatga  17880
cgagtttgat gctgcggcgg ctttggctag gtctatttcg accacgaaga ttcttgagag  17940
tgacccggat agggcgaatg acacgattga tgcgatggcg gcgggttttg atcgggctgt  18000
tatgaatgct ggtcgtgaca cggttgagtg gtctgcgggt gcgcagggta ggtcgtggcg  18060
tcgtgtgacg gatggtgatc cgtgtgcttt ttgtgccatg ttggctacga ggtcggatta  18120
tacgacaaaa gagagggcac ttactactgg acatactcgg cgtcataagc gtggtggtaa  18180
gcgtccgttt ggttcgaagt atcatgatca ttgtggttgt acggtggttg aggttgttgg  18240
cccttgggaa ccaaataggg ctgatgccga gtatcagagg acgtatgaga aggcccgtga  18300
gtgggttgat gatcatgggt tgcagcagtc gcctggcaat attttgaagg ctatgcgtac  18360
tgttggcggc atgagataat ttgatgtggt ttccggttgt gcgccgccgg ttattggtgc  18420
acagggttgt ctcccgcacg gggtcaaca atgttgtgtt gttttccgca aggagtgtag  18480
ggttaggcta tggccgatca gagtgttgag gaacagaatg ttgacaatga tgttgtggag  18540
tccggaaagg ataacggcat tgttgataca gtaaaagacg atggcggaca ggaggtggcc  18600
gacaatcagt tgaagaatga aggcgagggt aaatcgccgg ggactgattg gaaggcggag  18660
gcccgtaagt gggagtctcg tgctaaaagt aatttcgctg agttggagaa gcttcgcgcc  18720
tcggatggtg atgcggggtc tgtgattgat gatcttcgcc gcaagaatga ggaactcgaa  18780
gaccggatta acgggtttgt tcttgagggt gtgaagcgcg aggtggcttc agagtgtggc  18840
ctgtcgggtg atgctgtcgc tttcttgcac ggtagcgatc gtgaagcgct ggtggagtct  18900
gcgaaagctt tgaagggttt gatcgaccat agtagtggtg gcgcgggtgt gcgccgtctt  18960
gcggggagtg cccccgttga tgatgttaaa cgacgtgagg gtgtcgcgtt tgtggatgct  19020
cttgtcaata attctaggag atgatttgtg atggctgacg attttctttc tgcagggaag  19080
cttgagcttc ctggttctat gattggtgcg gttcgtgacc gtgctatcga ttctggtgtt  19140
ttggcgaagc tttcgccgga gcagccgact atttttggcc ctgttaaggg tgccgtgttt  19200
agtggtgttc ctcgcgctaa gattgttggt gagggcgagg ttaagccttc cgcgtctgtt  19260
gatgtttcgg cgtttactgc gcagcctatc aaggttgtga ctcagcagcg tgtctcggac  19320
gagtttatgt gggctgatgc tgattaccgt ctgggtgttt tgcaggatct gatttccccg  19380
gctcttggtg cttcgattgg tcgcgccgtg gatctgattg ctttccatgg tattgatcct  19440
gccactggta aagcggctgc cgctgtgcat acttcgctgg ataagacgaa gcatattgtt  19500
```

-continued

```
gatgccacgg attctgctac gaccgatctg gtcaaggctg tcggtcttat cgctggtgct  19560
ggtttgcagg ttcctaacgg ggttgctttg gatccggcgt tctcgtttgc tttgtctact  19620
gaggtgtatc ctaagggttc gcctcttgct ggccagccga tgtatcctgc cgccgggttt  19680
gccggtttgg ataattggcg tggcttgaat gttggttctt cttcgactgt ttctggcgcc  19740
ccggagatgt cgcctgcctc tggtgttaag gctattgtgg gtgatttctc tcgtgttcat  19800
tggggtttcc agcgtaactt cccgatcgag cttatcgagt atggtgaccc ggatcagact  19860
gggcgtgacc tgaagggcca taatgaggtt atggttcgtg ctgaggctgt gctgtatgtg  19920
gctatcgagt cgcttgattc gtttgctgtt gtgaaggaga aggctgcccc gaagcctaat  19980
ccgccggccg agaactgatt tattgttgcg gtgatgtgtc aatgtgcagg gggtggtgtt  20040
gatgggtatc attttgaagc ctgaggatat tgagcctttc gccgatattc ctagagagaa  20100
gcttgaggcg atgattgccg atgtggaggc tgtggctgtc agtgtcgccc cctgtatcgc  20160
taaaccggat ttcaaataca aggatgctgc taaggctatt ctgcgtaggg ctttgttgcg  20220
ctggaatgat actggcgtgt cgggtcaggt gcagtatgag tctgcgggtc ctttcgctca  20280
gactacacgg tctagtactc ccacgaattt gttgtggcct tctgagattg ccgcgttgaa  20340
gaagctgtgt gagggtgatg gtggggctgg taaagcgttc actattacac cgaccatgag  20400
gagtagggtg aatcattctg aggtgtgttc cacggtgtgg ggtgagggtt gctcgtgtgg  20460
gtcgaatatt aacggctacg ctggcccttt gtgggagata tgatatgacc agttttcctt  20520
atggtgaaac ggttgtgatg cttcaaccga ctgttcgtgt cgatgatctt ggtgacaagg  20580
ttgaggattg ggggcatctt gtagaaacag tgtaccataa cgtggccatc tatgcttccg  20640
tttcgcagga ggatgaggcc gcggggcgtg actctgacta tgagcattgg tcgatgcttt  20700
tcaagcagtc tgttgttggt gctgattatc gttgcaggtg gcgtatccgg ggtgttgtgt  20760
gggaggctga cgggtctcct atggtgtggc atcatccgat gtctggctgg gatgcgggca  20820
cgcagatcaa tgtgaagcgt aagaagggct gatgggtagt ggctcaggat gtgaatgtga  20880
agctgaactt gccgggtatt cgtgaggtgt tgaagtcttc tggggtgcag gctatgttgg  20940
ctgagcgtgg cgagcgtgtc aagcgtgcgg cctcggcgaa tgtgggcggg aacgctttcg  21000
ataaggccca ataccgtaat ggtttgtcgt cggaggtgca ggttcaccgt gttgaggctg  21060
tcgctcgtat aggcaccaca tataagggtg ggaagcgtat tgaggcgaag catggcacgc  21120
tggctcgttc gattggggct gcgtcgtgat cgtctacgat gaccccagga agtgggctaa  21180
acgcgtgctc aaggatgatg gctggctgtc tgatataccc tgtgtgggga cggtgcccga  21240
tgattttatg ggtgacctgg tttggttggc gttggatggt ggcccgcagt tgcatgttcg  21300
tgagcgtgtt tttttgcgcg tgaatgtgtt ttctgatacg cctgatcggg ctatgtcttt  21360
ggcgcgtcgt gttgaggctg tgctggctga cggggttgat ggtgatccgg tggtgtactg  21420
taaacggtct actggtcctg atttgctggt tgatggtgca cgttttgatg tgtattcgct  21480
gttcgagctg atatgtaggc ctgtcgaatc cgagtaaacg tatttgtttt tgttttaatg  21540
taattgtttg atatttaatg ggggttgtga tggctgcaac acgtaaagcg tctaatgttc  21600
gttcagcggt tactggcgac gtttatattg gtgacgcgca cgcgggtgat actattaagg  21660
gtgtggaggc ggttccttcc gggcttacag ctttagggta tctgtcggat gacgggttta  21720
agattaagcc tgagcgtaaa acggatgatt tgaaggcttg gcagaatgcg gatgttgttc  21780
gcacggttgc taccgagtct tctatcgaga tttcttttca gctgatcgag tctaagaagg  21840
```

```
aggttatcga actgttttgg cagtcgaagg ttactgccgg agccgattcg ggttcgttcg  21900
atatttctcc tggtgccacc actggcgtgc acgctttact gatggatatt gttgatgggg  21960
atcaggttat tcgctactat ttccctgagg ttgagcttat cgatcgtgac gagattaagg  22020
gtaagaatgg cgaagtgtac gggtatggtg tgacgttgaa ggcttaccct gctcagatta  22080
ataagactgg taatgcggtg tcgggtcgag ggtggatgac ggctttaaaa gctgatactc  22140
cccettctcc gaagcctcag ccggatccga atccgccgtc tgagaactga tacacgattt  22200
tagggattgt tgatagatga gtgacacagg ttacacgttg aagattggtg accgtagctg  22260
ggtgttggcg gatgcggagg agacggctca ggctgttcct gctcgcgttt ttcgtcgtgc  22320
agctaagatt gcccagtctg gggagtctgc ggatttcgct caggttgagg tgatgttttc  22380
tatgttggag gctgcagccc cggctgacgc ggtggaggcc ctggaggggc ttcctatggt  22440
tcgtgttgcc gagattttcc gccagtggat ggagtggaag cctgaaggta agggtgcctc  22500
tttgggggaa tagtttggct ccacggcctg attgatgagt atcgtggggc catcgaatat  22560
gattggcgca caaggtttgg tgtgtgcata tacgatatag gtggtcctgc gatggggtgg  22620
ggtgaggctg tccggctggc tggcgtgttg tgtggtgata cgtcgagcca gttggcggcc  22680
cacctgaatg gttggcagcg cccgtttgag tggtgcgagt gggctgtgtt ggacatgctg  22740
gatcattaca ggtctgctaa tagtgagggg cagccggagc ctgtggcgag gcctacggat  22800
gagcgtaggg gccggtttac gtctgggcag gtggatgata ttttggcgcg tgttcgtgct  22860
ggtggcgggg tgtctcgcga gattaatatt atggggtgaa tagtgtatgt ctggtgagat  22920
tgcttccgca tatgtgtctt tgtatacgaa gatgcctggt ttgaaggcgg atgttggtaa  22980
acagctttct ggtgtgatgc ctgctgaggg tcagcgttcg ggtagtcttt ttgctaaggg  23040
catgaagttg gcgcttggtg gtgccgcaat ggtgggtgcc atcaatgttg ctaagaaggg  23100
cctcaagtcg atttatgatg tgactattgg tggtggtatt gctagggcga tggctattga  23160
tgaggctcag gctaaactga ctggtttggg tcatacgtct tctgacacgt cttcgattat  23220
gaattcggct attgaggctg tgactggtac gtcgtatgcg ttgggtgatg cggcttctac  23280
tgcggcggcg ttgtctgctt cgggtgtgaa gtctggcggg cagatgacgg atgtgttgaa  23340
gactgtcgcc gatgtgtctt atatttcggg taagtcgttt caggatacgg gcgctatttt  23400
tacgtctgtg atggcccgcg gtaagttgca gggcgatgac atgttgcagc ttacgatggc  23460
gggtgttcct gtgttgtctt tgcttgccag gcagacgggt aaaacgtcgg ctgaggtgtc  23520
gcagatggtg tcgaaggggc agattgattt tgccacgttt gcggctgcga tgaagcttgg  23580
catgggtggt gctgcgcagg cgtctggtaa gacgtttgag ggcgctatga agaatgtgaa  23640
gggcgccctg ggttatttgg gtgctacggc tatggccccg tttcttaatg ggttgcggca  23700
gatttttgtt gcgttgaatc cggttatcaa gtcggtgacg gattctgtga agccgatgtt  23760
tgctgccgtc gatgctggta ttcagcgtat gatgccgtct attttggcgt ggattaatcg  23820
tatgccgggc atgatcactc gaatgaatgc acagatgcgc gccaaggttg agcagttgaa  23880
gggcattttt gcgagaatgc atttgcctgt tcctaaagtg aatttgggtg ccatgtttgc  23940
tggcggcacc gcagtgtttg gtgttgttgc tgccggtgta gggaagcttg ttgcagggtt  24000
tgccccgttg gcggtgtcgt tgaagaatct gttgccgtcg tttggtgctt tgaagggtgt  24060
cgctggcggg cttggtggcg tgtttcgcgc cctgggtggc cctgttggta ttgtgatcgg  24120
cttgtttgct gccatgtttg ctacgaacgc ccagttccgt ggcgcggtga tgcagcttgt  24180
gggggttgtt ggccaggctt tggggcagat tatggccgct gtgcagcctg tgtttggttt  24240
```

```
ggttgccggt ttggtggccc ggttggcgcc agtgtttgcc cagattatcg gtttggttgc  24300
aggtttggct gcccagctta tgccggtgat tagtatgctt gttgcccggc tggttcctgt  24360
gatcacccag attattggtg cggtgacaca ggttgctgca atgttgttgc ctgcgttgat  24420
gccggtgttg caggctgttg tggctgtgat tcggcaggtt gttggcgtga tcatgcagtt  24480
ggtgcctgtt ttgatgcctg tgattcaaca gattttgggt gctgtcatgt ctgtgctgcc  24540
acccattatt ggtcttatcc ggtcgttgat gcctgtgatt gcggcggtta tgcgtgtggt  24600
ggtgcaggtt gttgcggttg tgatacaggt ggtggcccgt attcttgcgg ttgtggctcc  24660
gatggtggcg gctgtggtag ggtttgtggc ccgtattgtt ggtgctgtcg tgtcggctgt  24720
tgcccgtgtt attgctgctg ttgcccgtgt catcgggtgg attgtggccc attttgtgtc  24780
tggtttggca cgtatgggtt cggtggttca ggctggctgg aatcggatta gggcgtttac  24840
gtcagcgttt attaacggtt tcaagtcggt gatttctggc ggcgtgaacg cggttgtggg  24900
gttttttgcc cggctgggtt cttctgttgc ttctcatgtg aggtctggtt ttaacgcggc  24960
ccgtggcgct gtttcttctg cgatgaatgc tatccggagt gtggtgtctt cggtggcgtc  25020
tgctgttggc gggtttttca gttcgatggc gtctagggtt cgtagtggtg ctgtgcgcgg  25080
gtttaatggt gcccggagtg cggcatcttc tgctatgcat gctatggggt ccgctgtgtc  25140
taacggtgtg catggtgtgc tgggtttttt ccggaatttg cctggcaata ttcggcgtgc  25200
gcttggtaat atggggtccc tgttggtgtc ggctggccgt gatgtggtgt ctggtttggg  25260
taatggtatc cggaatgcta tgagtggcct gttggatacg gtgcgtaata tgggttctca  25320
ggttgctaat gcggcgaagt cggtgttggg tattcattcc ccgtctcggg tgtttcgtga  25380
ccaggttggc cgtcaggttg ttgctggttt ggctgagggt attactggta atgctggttt  25440
ggcgttggat gcgatgtcgg gtgtggcggg acggctgcct gatgcggttg atgcccggtt  25500
tggtgtgcga tcgtctgtgg gctcgtttac cccgtatggc aggtatcagc gtatgaatga  25560
taagagtgtt gtggtgaatg tgaatgggcc tacttatggt gatcctaacg agtttgcgaa  25620
gcggattgag cggcagcagc gtgacgcgtt gaatgcgttg gcttacgtgt gattgggggt  25680
gttgtgcatg tttattcctg acccgtctga tcgttcgggt ttgactgtga catggtcgat  25740
ggatccgctg tttggtgggg ggcgtgtgct tcatttgacg gattatacgg gtgcgtctcc  25800
tgctatgttg ttgaatgatt cgttgcgcgg tttgggtgtt cccgaggttg agcatttttc  25860
tcaaacacat gttggggtgc acggctcgga gtggcgcggg tttaatgtga agcctcgcga  25920
ggtgacgcta ccggtgttgg tgtcgggtgt tgactcggat ccggatggcg ggtttcgtga  25980
cggttttttg aaagcctatg gcgagttgtg gtctgctttt cctcctggcg aggaggggga  26040
gttgtcggtg aagactcctg caggtcgtga gcgtgtgttg aagtgtcggt ttgattcggt  26100
ggatgacacg tttacggttg atcctgtgaa tcgtggctat gcgcgttatg tgattcattt  26160
gacagcttat gacccgtttt ggtatgggga ggagcagaag tttcgtttta gtaacgcgaa  26220
gttgcaggat tggttgggtg gcggccctgt cggcaaggat ggcacggcgt ttcctgtggt  26280
gttgacgcct ggtgttggtt ctggttggga taatctgtct aataagggtg atgtgcctgt  26340
gtggcctgtg attcgtgttg aggggccttt ggagtcgtgg tctgtgcaga ttgatggttt  26400
gcgtgtgtct tcggattatc ctgtcgagga gtttgattgg atcactattg atacggatcc  26460
tcgtaaacag tctgcgttgt tgaatgggtt tgaggatgtg atggatcgtt tgacagagtg  26520
ggagtttgcc ccgattccgc ctggcggttc gaagagtgtg aatattgaga tggttggttt  26580
```

```
gggtgccatt gttgtgtcgg tgcagtacag gtttttgagg gcttggtgaa tagttgatgg  26640
ctggtctggt tccgcagata acattgttta cgccggatta tcgccgggtt gcgcctatca  26700
attttttga gtcgttgaag ttgtcgttga agtggaatgg tttgtcgacg ctggagttgg  26760
tggtgtcggg ggatcattct aggcttgacg ggttgactag gccgggtgca cggctggtgg  26820
ttgattatgg tggtggccag attttttctg ggcctgtgcg tcgggtgcat ggtgtgggtc  26880
cgtggcgttc ttcgcgggtg actatcacgt gtgaggatga tattcgcctg ttgtggcgta  26940
tgttgatgtg gcctgtgaat tatcgtcctg gtttggttgg tatggagtgg cgtgccgaca  27000
gggattatgc tcactattct ggtgcggcgg agtcggttgc taagcaggtg ttgggggata  27060
atgcttggcg ttttccgcct ggtttgttta tgaacgatga tgagagtcgt ggccgctata  27120
ttaaggattt tcaggtgcgg tttcacgtgt ttgccgataa gttgttgccg gtgttgtcgt  27180
gggctcggat gactgtttcg gtgaaccagt ttgagaatgc gaagtttgat cagcggggtt  27240
tgctgtttga ttgtgtgcct gctgtgacgc gtagtcatgt gttgactgcc gagtctgggt  27300
ctattgtgtc gtgggagtat gtgcgtgacg ccccgaaggc tacttcggtg gtggttggtg  27360
gccgtggcga gggtaaggat cggctgtttt gtgaggatgt tgattcgatg gccgaggggg  27420
attggtttga tcgtgtagag gtgtttaagg atgcccgtaa cacggattct gaacatgtgc  27480
atctcatcga tgaggctgag caggtgctgt ccgagttagg ggccacgtcg gggtttaaga  27540
tcgagttggc tgagtcggat gtgttgcggt ttgggccagg ccgcctgatg cccggggatt  27600
tgatctatgt ggatgtgggc tcggggccta ttgcggagat tgttcggcag attgatgtgg  27660
agtgtgattc gcctggtgat ggttggacga aggtgacacc ggttgcgggg gattatgagg  27720
ataatccgtc ggcactgttg gctcgccgtg tggctggttt ggctgccggt gtgcgggatt  27780
tgcaaaaatt ttagtaagtg attggggttt gttgtgggta ttgtgtgtaa agggtttgat  27840
ggtgtgttga ccgagtatga ttgggctcaa atgtctggtc tgatgggtaa tatgccgtct  27900
gtgaaagggc cggacgattt tcgtgtcggc acgacgattc agggtgccac agtgttgtgt  27960
gaggtcctgc cggggcaggc ttgggctcac ggggtgatgt gcacgtcgaa tagtgttgag  28020
acggtgacgg ggcagctgcc tggtcctggt gagacccgct acgactatgt ggtgttgtcg  28080
cgggattggg agcagaacac agccaagttg gagattgttc agggtggccg tgcggagcgt  28140
gcccgggatg tgttgcgtgc cgagcctggc gtgtttcatc agcagctact ggcgactttg  28200
gtgttgtcgt ctaacgggtt gcagcagcag ctggataggc gtgctgttgc ggctagggtt  28260
gcgtttggcg agtctgcggc ttgcgatccc accccctgtgg agggtgaccg tataatggtg  28320
ccttcggggg ctgtgtgggc taaccatgcc ggcgagtgga tgctgttgtc acccagaatt  28380
gagacgggtt cgaagtcgat catgtttggt ggttctgctg tgtatgctta cacgatcccg  28440
tttgagcgcc agttcagtag tccgcctatt gtggtggcgt ctatggctac ggcggctggg  28500
ggcacgcagc agatcgatgt gaaagcctac aatgtgactg cccaaaattt tagtttggcg  28560
tttattacga atgatggttc gaagccgaat ggtgtgcctg cggttgcgaa ttggattgct  28620
gtcggagtgt gactgcacgg gtgttgtggc ggatggtgtg atgttggggg gctgtagtgt  28680
cgtggtttac tcctgcactg gtggcctcta tctgtaccgc gttggccacg gttttgggtt  28740
ctgttcaggc tgtcacatcc cggtctagga agcgtttacg caggctgtcg gctcaggtgg  28800
atgcgatgga agagtatacg tggggtgtgc ggcgcgaggt gcgaaggttt aacgccgggc  28860
ttcctgacga tgtggagccg atgcatcttc ctgatttgcc cgagtttttg aaagatactg  28920
ttgatggtgg aggtgagtag ggttgaggga gttggaggaa gagaaacggc agcgccgcaa  28980
```

```
ttttgagaaa gcttcactgt tgctgttgtt tttgtcgctt gtactgttgg cggtggttgc  29040

tgcgggtgct ttgcgtttcg gggctgtatc ctctgagcgg gattcggagc aggcgagggc  29100

ccagtcgaat ggtacggctg ccag                                         29124
```

<210> SEQ ID NO 73
<211> LENGTH: 30016
<212> TYPE: DNA
<213> ORGANISM: Artificial Sequence
<220> FEATURE:
<223> OTHER INFORMATION: PAC22

<400> SEQUENCE: 73

```
gcgcagggtg agcgtggccc cgccggtgtg aacggatccg atggtaaaga cggtaaagat     60

ggtaaggatg gcgctgatgg gcgttcggtg atatcggtgt actgttccgg gggccgcctg    120

gttgtgaaat atagtgacgg tacagcctcc accgtgtcgg gttctgcggc ctgtgagagt    180

gtgaaaccgt cacctgtggt taccgtatca tcccacaaat agaatatgaa gagggaaggg    240

tgttactagt gttgattgtg gtgtttggtg gtggtgtgtt gtgagataca ttccagcggc    300

gcatcactcg gccggttcga atagtccggt gaacagggtt gtgattcatg cgacatgccc    360

ggatgtgggg tttccgtctg cttcgcgtaa ggggcgggcg gtgtctacgg cgaactattt    420

tgcttcccca tcgtctggtg gttcggcgca ttatgtgtgt gatgttgggg agactgtgca    480

gtgcctgtcg gagtctacga ttggttggca tgccccgccg aatccgcatt ctttgggtat    540

agagatttgc gcggatggcg gttcgcacgc ctcgtttcgt gtgccagggc atgcttacac    600

tcgtgagcag tggcttgatc cgcaggtgtg gcccgcggtg gagagggcgg ctgtcctgtg    660

tcggcagttg tgtgacaagc atggtgttcc gaaaagaaaa ctgtctgtgg ccgatttgaa    720

ggccggtaaa cggggcatct gcgggcacac tgatgtgacg gatgcgtggc atcagtcgga    780

tcatgacgat ccggggccgt ggtttccgtg ggacaaattt atggctgtgg tgaatggcca    840

cggctgcggt tcaagtagtg aggagttaac ggtggctgat gtgaaagcgt tacatgatca    900

gattaaacaa ttgtctgccc agcttactgg ttcggtgaat aagctgcatc acgatgttgg    960

tgtggttcag gttcagaatg gtgacctggc gcgccgcgtg gaggctttgt cgtgggtgaa   1020

gaatccggtg acggggaagc tgtggcgcag caaggatgcc ctgtggagtg tctggtatta   1080

cgtgttggag tgtcgtagcc gtattgacag gcttgagtct gctgtcaacg atttgaaaaa   1140

gtgatggtgg tttgttgtgg gtaaacagtt ttggttgggc ctgctggagc gggcgttgaa   1200

gacttttgtg caaacgtttg ttgctgtgtt gggggtgacg gcgggtgtca cgtatactgc   1260

ggagtcgttt cgtggtttgc cgtgggagtc ggcgctgatt acggctacgg ttgctgcggt   1320

tttgtcggtt gctacctcgt ttggtagccc gtcgtttgtg gctggtaagc caagcaagcc   1380

tcaggtggat gcgggtttgg ttgagcctca catggtggat gtgtcggatc ctggcatgat   1440

cgagccgacg gatgatgctg atcttggtgt gggctatgtg ccgaaacacg ctgccgagtc   1500

ggaggttggc acggtagagt cgactgttgc ataagtgaat atagatgtgt gccccagcgg   1560

tgctgccacg gttgtgtggt ggttgccgct ggggcactat ttttgtgtct atagtatttt   1620

atgattcgtt gctgtcgatg gtgtcttcga gcatctggta caggtggagg caggtgcaga   1680

tggtttcgct ggcctggtct agaacggttc ggccgataac gtttttgtgg ttgtcgcggt   1740

ggcggatgat agcccacatg atctcgtcgg ctgccgcctg taatagtttt gcctggtatg   1800

cgattccggc gagccagtct agtgcttcct ggcttgcgta ggggctctgg tcctcgctgt   1860
```

-continued

```
tgccgcgggt gttgctgttg tttgtggggt gtccttcact gtcgcatagc cataggattt   1920
cgctgcactc gtctagcgtg tcttggtcga tagcgagatc gtcgaggctg acattgttga   1980
cggtaaggtt cacgttgtcg atggagatgg gtacaccgta ctggttttca acactgtcaa   2040
caatgttttg tagttgttgc atgttggtgg gctgttgttg gacgatgcgg tgtatcgctg   2100
tgttgagggt ggtgtaagtg atgttgtgtg tgttgttcat ggtttttatg ccattccttc   2160
gttatcgtct ggcatgtagt atgtgctgtt tgcgtactcg gtgagggtga tgagtgtttg   2220
gtctgcccac tgtttcacgg tttgccgggt gactccgagt agttgggcgg ctgtggcgta   2280
ggtttggtcg tatccgtata cttcccggaa tgctgccaac ctagctaaat gttttcgctg   2340
tttggagggt tcacaggcga gggtgtagtc gtcgatggcg agttgtagat cgatcatggt   2400
aacaaggttg ttgccgtgat gctgggggc ggttggtggg ggtggcatgc ccggctccac   2460
actgggtttc catggtccgc cgttccagat ccattgtgcg gcttggatga tgtcggcggt   2520
agtgtaggtt cggttcatgt gtcacccccct gaacaggtcg ttggtgttgc tggtgcgggt   2580
ggtgtcgaat cgtccgacgc agtggcagta gtcgtacatg agtttgataa tgtgttggtg   2640
gtctcccaaa taggtgttgc cgctgatgct gtaggtggct gtgccgtctt tgctgatggt   2700
gtatttggcg gtgatggttt cggggttttc ggtgtcggtg atgattgctg tggtggtggt   2760
gcctactgtt tggagcacgg tggtttgggt tccgtcgtcg atggtggttt taaccatggt   2820
gtgtgttctc ccctttgtgt tagttgctgg tttggttgtc ggctagatga atgatgtcgg   2880
gtaagggttt cggctggtct aggtgttgtg tggttttgtt ggctaaacgt ttggctaccc   2940
tgtagcacat tttggtgtag tgtttgttgt cgaggttgtg gtattgttcc cgcaccgcaa   3000
tatatagcag ggagtcttgg tataggtcgt ctgcactgat tgcggggtag tgtgcggctg   3060
ttttggtgca tgcccggttg agtgtgcgta gatgatggtt tgtggcccac acccacgatg   3120
cggtggtggc taggtcggct tttgttggtc gtcggctcat ggcatctctt tcatctggct   3180
atctggtagt tgtttggtgt tttgttgttg atagtgtagc acacgagtcc ggggttgccg   3240
gtggtgcctg ttttgtgccg gaaccatgtg gattctcctt ccatggaggg gcattggatg   3300
aaggtgcgtt gtccttgctc ggagatttct aggtggtgcc ggtgcccggc catgagaatg   3360
tgggatgtgg tgccgttgtg gaattcttgt ccgcgccacc attcgtagtg tttgccggtg   3420
cgccattggt ggccgtgggc gtgcagtatc cgtgtgcctg ccacatcaac ggtggtggtc   3480
atttcgtcgc gttgggggaa gtggaagtgt aggttggggt attggttgtt gagctggtag   3540
gcttctgcga tggcgcggca gcagtccacg tcgaaggagt cgtcgtaggt ggtgactcct   3600
ttgccgaagc gtacggcttc tccgtggttg ccggggatgg atgtgatggt gacgtttttg   3660
cagtggtcga attggtggat gagttgcatc atggccatgc gtgtcaaccg gatttgttcc   3720
gtcaaggggg tttgtgtgcg ccaggcgttg ttgccgcctt gtgacacgta tccttcgatc   3780
atgtcgccga ggaatgcgat gtggactcgt tgcggttttc cggcttgttg ccagtagtgt   3840
ttagctgatg tgagggtgtg taggtagtcg tcggcgaagt gtgatgtttc tcctccgggg   3900
atgcctttgc cgatttggaa gtctcctgcc ccgatgacga aggccgcggt gctgtagtcg   3960
gtgcgggtgt cttgttcggg ttttgggggt gtccattcgg ctagcttgtc gacgagttcg   4020
tctaccgggt aggggttggt tgcgggttgg tggtcaataa ttttttgtat ggatcggcct   4080
gtttctccgt tcggtaaggt ccattcggag atgcgtgtgc ggcgcacggt gccgttggct   4140
agattgtcgt cgatggtgtc gatggcgttg tcgtggttgg cgagctgtgt gaggagccgg   4200
tctatgttgt ctatcatcgg gtatcctcct cttctgtttg tggtgtggtg gcttgtttgc   4260
```

```
ggcggtagtc tttgatgacg gtggcggaga tggggggta tcctcctctt ctgtttgtgg   4320
tgtggtggct tgtttgcggc ggtagtcttt gatgacggtg gcggagatgg ggtatccggc   4380
ttcagtgagc attcgggcta gctgtgtggc ggggatcgtc ttgtcggcga ggacgtctgc   4440
agccttatca ccgtagcgtt ggatgagggt ttcagttttg gttgccatgg tgtcctatcg   4500
gttgtgtggt gggctgccat cctgtgcggc agtcgccgtc gtgtcctggt ttgcgtgtgc   4560
accacgatac ggttccgtct gtgtggttga gtgttttgcc gcacatgacg ttttgtagat   4620
gctcgggcag tgcgccgtta ctctggttgc tggtttgtgt gtcgaagagt gttttctggt   4680
tggtgaaatg ctcggatacg gtgccgttgt ggactgggag tatccatgtt ttccattgtt   4740
gttgcatccg ggtgttccag tggaattgtt tagccgcgtt ttctgcctgt ttggcggttt   4800
tgtagtagcc tacaatgatt cgctggtggt tgttgtctgg ctggtgtggc cctttccagt   4860
attgtgccgc cacggcgtag cggttgctgg ctgtgaagcg ctcccagcag tattcaataa   4920
tgtgttgcag tacactatcg ggaatgtctt gtgcttggtt ttcgttaagc cattcttcaa   4980
caatgatgtc gcgtatggcg cgtttgtctt tagtggtggg tttgaacgag atgctcacga   5040
tagcaccggc tggtcgtctt gcatgaactg gttgaaggtg ttgttcccgg cgtgttgggc   5100
ttgtgtgatt tgctggtcgg tccagtctgg gtgttgctgt ttcagatagt gccagtggca   5160
cgcattgtag gtttcgtctt gtagccgtgt gagatggttt tcggtgatga tttgtttcca   5220
catagtccac gagacgtcga gcctgttgag gatttcgagg gctgggatgt tgaattggtt   5280
gaggaacagg atttcgtggg tgtagtattc cttctcgtag gcgtcccatc cgcttcggtg   5340
cctgttgggc tggtttttgg ggtaggcttc ccggcagatt ttgtgcaaat gtttggccat   5400
gtcgtcgggt agtttaatgt cagggttggc gcggatcatg gatcgcatcc catcataggt   5460
ggtgccccag gtgtgcatga tgtaggtggg gtcttcacca tcagtccatt tttctgcaca   5520
gatggcgagg cggatacgcc tcctggcggc ttggctggtg ttgcgccggt tggggattgg   5580
gcacgtgtcg aggggatcca tgatgctttt tatgcctttc tttgtttggg ttgtttgtct   5640
agttttactg tagcacagtg tctagtgctt gtgtcaaccc tgtttttccg gcctgcaggt   5700
aggtgtctgt gacgtcgccg agggtgaggg gcacatgggt ggcttggggg agtgctgcct   5760
ggagggtgtg ggccatctgg tcgcctgctt tgtctgggtc tgaccatatg tagatgtggt   5820
cgtagccttc aaaaaatttg gtccaaaagt tttgccacga ggtggcgccg ggtagggcga   5880
cggccgacca tccgcattgt tcgaggatca tggagtcgaa ttcgccttcg caaatgtgca   5940
tttcggctgc ctggttggcc atggcggcca tgttgtagat ggagcctgtg tcccctgccg   6000
gtgtcaagta tttggggtgg ttgtgggttt tgcaatcatg ggggagtgag cagcggaaac   6060
gcatttttcg tatttcggct ggcccttccc agacggggta catgtagggg atggtgatgc   6120
actggttgta gttttcgtgg cctgggatgg ggtcattgtc gatgtatcca aggtggtggt   6180
agcgggctgt ttcttcgctg attcctcttg ccgagagcag gtcgagtatg ttttcgaggt   6240
gggtttcgta tagggccgag gctttctgga ttcggcggcg ttccgcaatg ttgtaggggc   6300
gtatgctgtc gtacattcgg gttttcttcc tctaatcgtt gtttcagttt gtggagtcca   6360
cctccgatac cgcatgtgtg gcagtaccag acgcccttgt cgaggttgat gctcatggag   6420
ggctggtggt cgtcgtggaa cgggcagagg atgtgttgct cgttcctgga cgggttgtag   6480
cgtatctggt gggcgtcgag gaggcggcag gtgtcagagg tgtgggagga gctcgttgag   6540
ggttgatacc acataggctt cgctccaggg tttgttgcgc tgtttcatga tgacgagtcc   6600
```

-continued

```
gatggtggac tggttttctc ggtttcggtg ggtttcatag ttgcgtgcct cccggctggc   6660
ttgtttcacg aattcggcga gatgtggttg cccggctttc gcctcgataa tgtaggtttt   6720
gtggccggtt gtgaggatga ggtcgccttc gtcttcgcgg ccgttgaggt ggaggcgttc   6780
gatatcatgt ccgatgtcgc gtagctggtg gaggagtctt gtttcccatt cggccccagc   6840
tcgcctattc ctggattgct gtgtagccat catagtcctt tgtgtgttgg ggtcatgttc   6900
cagggctgtt tttctactag gggtccgaag aatgtgtatt cggggtaggc tcgtagtcgt   6960
tcgtatcggg tgccgtctgg gctggatttg ccggttctct gtttgagtac ggcgatgcgc   7020
gcctcggcgg ggatggtgag cccgttgccg ttgtcttcgc caccgtagag tgagactccc   7080
aggattagtt gtggtttttc ggagaggccg tttttgattt cccgcctagc tggggggtgt   7140
tcgatgtcgg tgccggtttt gtcggttgcg tggtgggtga caataatggt ggagccagtg   7200
tcgcggccta gtgctgtgat ccattgcatg gcttcttgct gtgcctgata gtcactttcg   7260
cagtcttgga tgtccatcag gttgtcgatg acgatgatgg gtgggaaggt gttccacatt   7320
tccatgtagg cttggagttc catggtgatg tctgtccatg tgatgggtga ctggaatgag   7380
aatgtgatgt gtccgccgtg gtggatgctg tctcgatagt attctggccc gtagttgtcg   7440
atgttgtgtt gtatctgttg ggtggtgtgt tgggtgttga gtgagatgat tcgtgtggag   7500
gcctcccagg gtgtcatgtc ccctgatatg tagagggctg gctggttgag catcgcggtg   7560
atgaacattg ctagccctga tttttggctg ccggaccgcc ccgcgatcat gactaggtcc   7620
cctttgtgga tgtgcatgtc ctggttgtca tacaagggtg ctagttgggg tatgcggggc   7680
agttcggcgg cggtttggga ggccctctcg aaggatcttt ggagagagag catcggagcc   7740
ttaatctatc tgtctgttgg ttgggtgttg gtggtcagat ggagtcgatg tcgatgtcag   7800
catcggcggg ggctgtggtg tcgtctagct ggccggtgtc gcgcttgtct acgtattcgg   7860
caaccttatc gtagatggcg tcgtccaatg gtttgaggac gaccgcgttg aacccgtttt   7920
tggtgcgaac ggtggcgagt ttgaaggcct gctcttcgcc gagataggct tctaggtcgc   7980
ggatcatgga gtgtgggcgg tcgttgttgc ctcgcgcttt ctcgatgata gcgttgggga   8040
tagtttctgg ggtgccattg ttgagatcct ggagtgtgtg gaagatggtg acatcggcgt   8100
aaatacggtc ggcgacctgt ccgccgtagc cttcggtgtt gtgctggacg tcgcggattt   8160
tgaaggcgat ggcggtggcg tcctggtttc gggaggggtt gaagaaggtg ctgttgctgt   8220
tgttgcggta gttggcgagt cccattgttg tttcctttac tatttgtgtt ggtttttgtt   8280
gtcttatatt ggtttatcgg gtgaggctgt ttcgtttact gcggaacgcc tcagacacgt   8340
cactgttact ggtgatgatc ttcttgtact gtttgaggag gtctgctagt tgtgtcttgc   8400
tggtggcttt gttgatccgg tcgatgatga tgtcgttttc ctggttggcg attttgttga   8460
cgtagtcttt ggcggcttta tcgtatcgat cttgaagcag gattgctgcg ctagcgatca   8520
aggtggctaa atcccagtct ttggatacgg tttcgtcttt caatcctcct agcaggtcaa   8580
tgatggattg tttgatgtct tctgcggtgt ctccgcggat gactgtccat ggggcggcat   8640
agtctccacc gtatttgagt gtgatagtta gttttccgtt gtctgtggtg tgctcgtcgg   8700
tcacgtgttt tccttttcgt tactgtcggt ttggggtggc tgtacggtgg tttctatcgg   8760
gtatctgtac gagtttttgc cgttgacggc ccagcaggcg tccttgacgg ggcatccttt   8820
gcagagtgct gtgacgtggg gtacgaagat gccttggctg attcctttca ttgcttgact   8880
gtacatggat gatacatgcc ggtaggtgtt gttgtcaagg tcgtagagtt cggttgctgt   8940
gccctgctcg actgattgct cgtctccctt ggtggtggcg ggtgtccaaa acatgccttt   9000
```

cgtcacatgg atgccgtgtt ggttgagcat gtaccggtat gtgtgcagct gcatactgtc 9060
ggcgggtagg cggccggttt tgaggtcgag gatgaaggtt tcgccggtgt tggtgtcggt 9120
gaatacccgg tcaatatatc cgacaatctg ggtgccgtct tggagggtgg tttctaccgg 9180
gtattcgatg cctggctggc cgtcaataac agcggtagcg tattctgggt ggttgcgcct 9240
ccatgttttc caccggtcca caaaggtggg gccgtatatc atccaccaat tgtagtcttt 9300
cttgttgggg cccccgcttt cgcacatgtt tttgcacact cggccggagg gtttgatgtt 9360
tgtgccttcg gattcggcga gggcgatttg ggtgtcgaaa atgtttgtga aggatgcgag 9420
tttgtctggt agtgcagggt attcggcggg attgtacagg tgtaagtcgt attgttcggt 9480
gatgtggtgt atggcgcttc cggcgatggt ggcgtaccag gtgtggtgtt gggtgtggta 9540
gccgtgggat aggcgccatt tttctccgca ttcggcccac tgtgacagtg aactgtagga 9600
gatgtggcct ggatggtgga tggttttcgg gtattgtgct aggggcatta cttgtcgcct 9660
ttgtgggtgt tccatgggtt gcgggtgtct accccggcat cgtgttgctg gtaggcgagg 9720
agtgccaagc agtgccaggc agcatgtgcc agatgcggca aatgtgattc gtggtcgagg 9780
ttgtttcctt gctgccatga tagcaggtgc ctgtagaggg cgtcgacact gtggctccac 9840
gggtagccgc cggtccagtt gttgtcgccg tatttggtgg caccgtagcc tgccacttcg 9900
ccgagggcgt gcaaggcggt agggtcgatg agggatagcc tgcaaagttt caattctttc 9960
ttggcacccg tatcagggtc ggtgtacatg ctggttggct catccatggt gtgtgtgctc 10020
cttacgtgtg gggttactgg ttggggttgt gggcgagtgc tacggcgaga ataatgatgg 10080
cgagggtttc tgcgatcagt attggtgttg tgatcatttg ctgtcgcggg gattgttggt 10140
gagggtggat gcgcctagca gggtggtgag ggcgcatgcg gcgatgatgg cgagggcggc 10200
tttgtggctg gtgccggtgg cgtacatcca tgtgatgatg gcgccctgta tccatgccag 10260
tgtggtgaag aacgtttcgt agctgtgcag ctcgatactg ttgggtgtgt tcatgcttgc 10320
tcctgaagaa tggtgttgat ggttgtgtaa atgttgtaca ggtcggcttc gatggtttgt 10380
agctgtttga tttggtggtc gaggtcaatg tttgggttga gggtgttgat gcgggatgcg 10440
atgtcggtgg ctgtgcgtag tgtgccgccg gtgtggtgaa tgatgtgtgc cgtgtcggcg 10500
agtccggtgg tgacagcgta gcgggagagg agaggcatga ctggggggtg ctccttgacg 10560
gggttactgt tgcgggttga tgttgaggtc ggtgacgtgc ggtgagcttt ctgttcctgt 10620
gacgaggcag tggacggtga cggggagttt ggatgctccc ggctggcgga cggtggcgcc 10680
gtagacgatg ctgaacgtgt ctttgccaat aattttgtgg agttggaggt cgatgtcggg 10740
gttgccgttc catttgacac cctgtgctgc agctgcctgt tcagccttgt cattgcaggc 10800
gtgtgccgcg gtgatcatgg tgagacctgt ggaggtttct tcaccccgtg tttgggcttg 10860
ccggtgggcg cgctgctgtt cggcttggag ggagcggact gctgcagcct gcttggcggc 10920
tttctcggct ttgcgctgtt ggacggtttc aggtgtccat tcggtgttgg ctgtggtggc 10980
ttgtggggct ggctgtgagg cgagtggcgg attatcatcg ggtgccggga ggaaggatgc 11040
tgcggcgatg atggcgatgg tggcgccggc gatggtgtag cctgttttct tgttcatgat 11100
tttgtgttcc cctttccggg gtgttgttcg ttgctgacat gatcaatact ttcagcggct 11160
ggaccctgtg tcaaggtgtc gctcagtatt cttgagcgaa tgtggtttga ctgggggtga 11220
tggcttcttt cgcccaatag gatgtgccac cgctggtcca gtatccgagt ttgttgcgct 11280
gcatgccctt ggcttccatc tcatccacgg tgaggcacct gcggcgattg gggccttcct 11340

-continued

```
tgaccccgtg gtcgcctacc cggtgcatgt cgcctgaggt ggtactcgtg aatgtttcgt  11400
ggcagattgt gcagtgctct ggtcggtatc cgatgattgt gctatcgcac ttgtggcatg  11460
tccattgcat gattgctcct attttccatt ataagacttc ctgtagtgcc attttagcgc  11520
cttgcgggtc ttgggggtac aactatatag gtcaggtatt tctaggcgat tctaggctca  11580
ttgtgtgcga ctggtggtta tcgggcgcac agagtgagca ggtggccaac attgatgcgg  11640
gtcacattcc agtagagttg cgtggcttcc tcactggtga gcggcttcca ctcgttgtgg  11700
ctgaacacgg tgccatcgga tgctatgaac gtgttggggc gtagcttgtg gagttcagtc  11760
tctacatgcc gacggtaggt ttcggcgagg ccctcgaaat cgaggtggtc gcaggagagg  11820
ttttcgaggc gtgtcaggtc gaaaggctca gggcagtcgt agctggcggg gctgtagagc  11880
tgggtgaagt ggttggcaat cttctgcatc atgattcctt ttctggtgat ggtgtgttga  11940
tggttttatc gggtggatgc tttgaggatg gcgtctacat cgatcatgtc gatcatgtcg  12000
ttgagttcct cggcctcatt ctcggagagg tggcgccagc cgggtggccc gtatagggcg  12060
ccgtcgaggg tgacagtcca caggggccgg atgagtcgta tggcttcttc gactttggcg  12120
tggtacatgc ggcgcaccat atccagatcg atgtcgtctg aatggtttcc ggtgaggctg  12180
tggaggctga gtgggtcgat ttctgtctgc ccgtagaggc tggtgaatga tggtgtgatg  12240
agtgtgccat ccatgagggt gctcccttct gaactgtttg ggttggttgt tgtggtttct  12300
agagtgtgta ggttgcaacc ccatagtcaa ggctacgctc attcggattg agcgtttcat  12360
gctggagtgt gtcgggtgtg acagatgtca ctgaatcctt gatggcctct ctcagcgcct  12420
gaaatatgtc cggggtggga ttatgcaggg ttgaccctgc tgatcgattc taggcccccct  12480
acagggcgtc tcaggggtat gtctgggtga tagcaggttc ggtagatgat ctagcgagtc  12540
aaggtgccaa gctgagacag aagatctacc atctaggtgt gtgagatgta tcacactcgc  12600
ctggcttagt gtgcaccctc aagaccacct agtcgatctg gcgtggaggg tgcagcccag  12660
aaataccgtt taaagccttc gcgcggagcc taggagcgcc ttacagggtg ggggctaggt  12720
attcataccc ccaagcaatt ctgatcgatt ctagacgcct ccaggggccc gatacacgat  12780
cagtagtcca gacacagatc atcaacccct atcctggtta gctaagcctc aactatgtgg  12840
acagtgtggg atgctaagag ggaagaagga cacggtaaaa gaaagagggg ggagcatcag  12900
ccttcaagcc tgaaggtctt agcgcttagc accgagcccc ctcaagggct cggcatcagc  12960
ccgaacaggc tcagctcatc aggcacagcc ctgaaaaggg tacacgccat cagggaaggc  13020
ttgagagtac gaggagccct agcgacgagt actcgaaagc ctgaggaaac accctcagca  13080
ctgatgggcc tagcgtgttc ggaaaggaca caagagtaaa gtgtgacagc tgtccgggag  13140
tgaaacccgt tccggctagg ggtttcagcc ttaaccaccc tcaaaggtta caagactcta  13200
agaaaattta agaaaactct taggaagaaa gttgtgttca tatcccccta aaaacaccca  13260
aaatagccct caaacccgcc tatagagcca aaaccaccag tttgactcat cccaggtggg  13320
gtatgatagg ctggacaggt agccagctgg acgcgaggcc agaaagtgct gacgcacttc  13380
ccgacctcgc ttaccatcag tctaccaaac actttaaagc ttcaaggctt agcgctaagc  13440
ccttaagacc ttaacactga acaccgagcc ccctcaaggg ctcggcatca gccttaaagc  13500
cttaaacact ttaagtaact ttaaaacctt aacagcttaa cacttaaggt tataaataaa  13560
cattaaagct ttaaagtctt aaagtaaata tataacctta acacttaagt taagtataaa  13620
accttaaaag ctaagcactt aaagatataa acttaacatc agtgtttaag acttaaagag  13680
ttaaagtaac tattaagact taaaggctta taagctttaa acacttaaag taactataag  13740
```

actttaaaaa ccttaagtac ttaaagttaa ccatcagtct taaactttaa tactataacc 13800
tataagtctt aaagcttata ggtataataa tataatataa gtattaaagc ttataagtta 13860
taaaagtttt agaagagtta aagggttaac ttctttactt ctcttctctc tttggttctt 13920
tctctcttct cttcttttct tcatcagggg agaagaggaa cctttaaccg tcaacgctga 13980
tggactttca accgtgtgac tcgtgtacca ccggtcgcac gctcccgatg gcacactccc 14040
cacatgctac ctgtgtccct ttcaggctta gcgtgttcgg ctgaaggcgt acggcgtgtc 14100
acgcttaaac ccttaacacc aggtaagact taaagtgtat attataagta gaagacttta 14160
aaacctttaa ggtgttcccg ctgagcctgt gttcttcacc gctaggcgct aagcgctaag 14220
ccttgaaacg cgaacaccca tccacccttt tcttttaccg tgtccttctt cttttgacac 14280
cgctgggggg cgatgtgatc tttttcacat gccagggggt aggagaagaa aacaaccacc 14340
ccggcacaaa cagaacaccc ccctaaacga acaaaacagg gcccaggatc gaacagcagg 14400
gcaccggtag agtattccta cccccagaca attccaggcc gttacaggag caatgagagg 14460
ctcacagggg ccataggaga tcaggggacg tgatggcaca caccaaccgc acagccagcc 14520
aagcccaccg gcgctggcgg caacgactca tcacccaagc caaacagcaa ggccaaaccg 14580
aatgcccact ctgcggagcc accatcacct ggggcacaca tgacctgcca accagccccg 14640
aagccgacca catcacaccc gtcagcaggg gaggactcaa caccctcgac aacgggcaaa 14700
tcatctgcag aacatgcaac agaagcaaag gcaatcgcag cgaaccaaac attcaattcc 14760
aacaacaaac cacaaaaacg ttgatcccat ggtgaaaaaa cagccaaccc ccacgggaac 14820
caccccctgc acacccgtgc aagacctcgt acggcttagt gaaatacctc ccttttgtgg 14880
ttttgtctgt ctgtcgactt tttgtgttgg tggtgagtgt tgtgcagcct gagcttcctg 14940
atagtcgtgg atggtgtggg gagacgcgtc gttggtggcg tgtgtggggt gaggatagtc 15000
gcgcgcagta cgtgtctgat gaggagtggc tgtttctcat ggatgctgcg gtgattcatg 15060
attgtgtgtg gcgtgagggt cgcgcggatt tggtggcttc gcttcgtgct catgtgaagg 15120
cttttatggg catgttggat cggtattcgg ttgatgtggt gtctggtggc cgtggtgggg 15180
gttctgctgt ggcgatgatt gaccggtatc ggaagcgtaa aggggcctaa tgtcgagcgt 15240
tgttggttct caggttcctc gtcaccgggt ggctgcggct tattcggtgt ctgctggcgg 15300
tgatgcgggt gagcttggta gggcttacgg gttgacgcct gatccgtggc agcagcaggt 15360
gttggatgat tggctggctg tgggtggtaa tggcaggctt gcttcgggtg tgtgtggggt 15420
gtttgtgcct cgccagaatg gcaagaatgc tattttggag attgtggagt tgtttaaggc 15480
gactattcag ggtcgccgta ttttgcatac ggctcacgag ttgaagtcgg ctcgtaaggc 15540
gtttatgcgg ttgaggtcgt tttttgagaa tgagcggcag tttcctgact tgtatcgtat 15600
ggtgaagtcg attcgggcga cgaatggcca ggaggctatt gtgttgcatc atccggattg 15660
tgccacgttt gagaagaagt gtggctgtcc gggttggggt tcggttgagt ttgtggcccg 15720
tagccggggt tcggctcgcg ggtttactgt tgatgatttg gtgtgtgatg aggctcagga 15780
gttgtcggat gagcagttgg aggctttgct tcctacagtg agcgctgccc cgtctggtga 15840
tccgcagcag attttccttg gcacgccgcc tgggccgttg gctgacgggt ctgtggtgtt 15900
gcgtcttcgc gggcaggcgc ttggtggcgg taagcggatt gcgtggacgg agttttcgat 15960
tcctgacgag tctgatccgg atgatgtgtc gcggcagtgg cggaagcttg ctggtgacac 16020
taatccggcg ttgggtcgtc gtctgaattt tgggactgtg tcggatgagc atgagtcgat 16080
gtctgctgcc ggttttgctc gggagcggct tggctggtgg gatcgtggcc agtctgcttc 16140
gtcggtgatt ccggcggata agtgggttca gtctgctgtg ggtgaggcga gtcttgttgg 16200
cggtaaagtg tttggtgtct cgttttctcg ctcgggggat cgtgtcgcgt tggcgggtgc 16260
tggccggact gatgctgggg ttcatgttga ggttattgat ggcctgtctg gcacgattgt 16320
tgatggtgtg ggccagctgg ctgactggtt ggcgttgcgt tggggtgaca ctgaaaagat 16380
tatggttgcc gggtcgggtg cggtgttgtt gcagaaggcg ttgacggatc gtggtgttcc 16440
gggccgtggc gtgattgtgg ccgatactgg ggtgtatgtg gaggcgtgtc aagccttcct 16500
ggagggtgtc aggtcgggtg tgatcagtca ccctagggct gattcgaggc gtgacatgtt 16560
ggatattgct gtgaggtcgg ctgtgcagaa gaagaagggt tctgcgtggg gttggggttc 16620
ctcgtttaag gatggttctg aggttccttt ggaggctgtg tctttggcgt atcttggtgc 16680
gaagatggcg aaagcgaagc ggcgtgaacg gtctggtagg aagcgggtgt ctgtggtatg 16740
aactcggatg agttggctct gattgagggc atgtttgatc gtatccgaag gttgtcttcg 16800
tggcattgtc gtattgaggg ctactatgag ggttctgccc gggtgcgtga tttgggggtg 16860
gctattcctc cggagttgca gcgtgtgcag acggtggtgt cgtggcctgg gattgcggtg 16920
gatgctttgg aggagcgtct ggattggctt ggctggacga atggtgacgg ctacggcctg 16980
gatggtgtgt atgctgcgaa tcggcttgct acggcgtcgt gtgatgtcca ccttgatgcg 17040
ctgatttttg ggttgtcgtt tgttgcgatc attccccaag aggatgggtc ggtgttggtt 17100
cgtccgcagt cgccgaagaa ttgtacgggc cggttttctg ccgatgggtc tcgtttggat 17160
gctggccttg tggtgcagca gacgtgtgat cctgaggttg ttgaggcgga gttgttgctt 17220
cctgatgtga ttgttcaggt ggagcggcga ggtagccgtg agtgggttga gacgggccgt 17280
atcgagaatg tgttgggtgc ggttccgttg gtgcctgttg tgaatcgtcg ccgtacttcg 17340
aggattgatg gccgttcgga gatcactcgg tcgattcgtg cttacacgga tgaggctgtt 17400
cgcacactgt tggggcagtc tgtgaatcgt gatttttatg cctatccgca aaggtgggtt 17460
acgggtgtgt cggctgacga gttttcgcag cctggctggg ttctgtcgat ggcttctgtg 17520
tgggctgttg ataaggatga tgacggcgat accccgaatg tggggtcgtt tcctgtgaat 17580
tctcctacac cgtattcgga tcagatgcgt ttgttggcgc agttgactgc gggtgaggcg 17640
gctgttccgg aacgctattt cgggtttatc acgtctaacc cgccttcggg tgaggctttg 17700
gctgcggagg agtctcggct tgtgaagcgt gctgagcgga ggcagacgtc gtttggtcag 17760
ggctggttgt cggttggttt cttggctgcc agggcgttgg attcgagtgt tgatgaggcc 17820
gcgtttttttg gtgatgtggg tttgcgttgg cgtgatgctt cgacgccgac tcgggcggct 17880
acggcggatg ctgtgacgaa gcttgtgggt gtcggtattt tgccggcgga ttctcggacg 17940
gtgttggaga tgttggggct tgatgatgtg caggttgagg ctgtgatgcg gcatcgtgcc 18000
gagtcgtcgg atccgttggc ggcgctggct ggggctattt ctcgtcaaac taacgaggtt 18060
tgataggcga tggcttcggg ggttgtgtcg aggcttgctg cgactgagta tcagcgtgag 18120
gcggtcaggt ttgccgggaa gtatgcgggc tattatgccg agctgggtcg tttgtggcat 18180
tccgggaaga tgacagatgc gcagtatgtg cgtttgtgtg tggagttgga gcgtgccggc 18240
catgacggtt ccgcggcgtt ggcgggcaaa ttcgtgtccg attttcgccg gttgaatggt 18300
gtggatccgg gtttgatcgt gtatgacgag tttgatgctg cggcggcgtt ggctaggtcg 18360
ttttcgacta tgaagattct taagagtgac ccggataggg cgaatgatac gattggtgcg 18420
atggctgcgg gttttgatcg ggctgtgatg aatgctggcc gtgacacggt tgagtggtct 18480

-continued gcgggtgtgc agggtaggtc gtggcgcagg gtgactgatg gtgatccgtg tgctttttgt 18540
gccatgttgg ctacgaggtc ggattatacg actaaagagc gggcgcttac tacgggtcat 18600
actcggcgtc ataagcgtgc cggtaggcgt ccgtttggtt cgaagtatca tgatcattgt 18660
ggttgtacgg tggttgaggt tgttggccct tgggagccga atagggctga tgccgcatat 18720
cagaggacgt atgagaaggc tcgtgagtgg gttgatgatc atgggttgca gcagtcgcct 18780
ggcaatattt tgaaggctat gcgtactgtt ggcgatatga gatgatggtt tccggttgtg 18840
tgccgccggt tattggtgca cagggttgtc tcccgcacgg gggtcaacaa tgttgtgttg 18900
ttttccgcaa ggagtgtagg ttaggctatg gccgatcaga gtgttgaaga acagaatgtt 18960
gacaatgatg ctgttgagcc cggaaagggt ggagacgttg ttgatgttgt gaaggatggg 19020
caggctgccg gcgatgatca tgccggtgat gtttccgtga aggaggagtc ttcttctggc 19080
acggattgga aggctgaggc ccgtaagtgg gagtctcgtg ctaaaagtaa ttttgccgag 19140
ttggagaagc ttcgcgcctc ggatggtgat gcggggtctg tgattgatga gcttcgccgc 19200
aagaatgagg aactcgaaga ccggattaat gggtttgttc ttgagggtgt gaagcgtgag 19260
gtggctgccg agtgtggcct gtcgggtgat gcggtcgctt tcttgcacgg tggcgatcgt 19320
gaagcactgg tggagtctgc taaggctttg aagggtttga tcgaccagag tggtggtggc 19380
gcgggtgtgc gccgtcttgc ggggagtgcc cccgttgatg atgttaaacg acgtgagggt 19440
gtcgcgtttg tggatgctct tgtcaataat tctaggagat gatttataat ggctgacgat 19500
tttctttctg cagggaagct tgagcttcct ggttctatga ttggtgcggt tcgtgaccgt 19560
gctatcgatt ctggtgtttt ggcgaagctt tcgccggagc agccgactat tttcggcccg 19620
gtgaagggtg ccgtgtttag tggtgttcct cgcgcgaaga ttgttggtga gggcgaggtt 19680
aagccttccg cgtctgttga tgtttcggcg tttactgcgc agcctatcaa ggttgtgact 19740
cagcagcgtg tgagcgacga gtttatgtgg gctgacgcgg attaccgtct gggtgttttg 19800
caggatctga tttcgcctgc tctgggtgcc tcgattggtc gcgccgtgga tttgattgct 19860
ttccacggta ttgatcctgc cactggtaag cctgccgcgg ctgtcaaggt gtcgctggat 19920
aagacgaagc atattgttga tgccacggat tccgctacga ctgatcttgt gaaggctgtc 19980
ggcctgatcg ctggtgctgg tttgcaggtt cctagcgggg ttgctttgga tccggcgttc 20040
tcgtttgctc tgtctactga ggtgtatccg aaggggtctc cgcttgccgg tcagccgatg 20100
tatcctgccg ccgggtttgc cggtttggat aattggcgtg ggctgaatgt tggtgcttct 20160
tcgactgttt cgggtgcccc ggagatgtcg cctgcctctg gtgttaaggc tattgttggt 20220
gatttctctc gtgttcattg gggcttccag cgtaacttcc cgatcgagct gatcgagtat 20280
ggtgacccgg atcagactgg gcgtgatctg aagggccata atgaggttat ggttcgtgcc 20340
gaggctgtgc tgtatgtggc tatcgagtcg cttgattcgt ttgctgttgt gaaggagaag 20400
gctgcaccga ctcctcctcc ggctggtaac tgatacaaga taagcgaatg tgtactatgt 20460
gcagggggtg gtgttgatgg gtatcatttt gaagcctgag gatattgagc ctttcgctga 20520
tattcctaga gagaagcttg aggcgatgat cgctgatgtg gaggctgtgg ctgtcagtgt 20580
cgccccctgt atcgctaaac cggatttcaa atacaaggat gccgctaagg ctattctgcg 20640
cagggctttg ttgcgctgga atgataccgg ggtttcgggt caggtgcagt atgagtctgc 20700
gggcccgttt gctcagacta cacggtctaa tactcccacg aatttgttgt ggccttccga 20760
gattgctgcg ttgaagaagt tgtgtgaggg tgatggtggg gctggtaaag cgttcactat 20820

-continued

```
cacacccact attaatagta gatatgcaca ttctgaggtg tgttccacgg tgtggggtga  20880
gggttgctcg tgcgggtcga atattaacgg ctacgctggc cctttgtggg agatatgata  20940
tgaccagttt tccttatggt gaaacggttg tgatgcttca gccgactgtt cgtgtcgatg  21000
atcttggcga caaggtggaa gactggtcta agcctgtcga gactgtgtac cataacgtgg  21060
ccatttatgt ctctgtttcg caggaggatg aggctgccgg ccgtgactct gattatgagc  21120
attggtcgat gcttttcaag cagcctgttg tgggtgccgg ttatcgttgc cggtggcgta  21180
ttcggggtgt tgtgtgggag gctgacgggt ctcctatcgt gtggcatcac cccatgtccg  21240
gttgggatgc tggtacgcag gttaatgtga agcgtaagaa gggctgatgg gttgtggctc  21300
aggatgtgaa tgtgaagctg aacttgccgg gtattcgtga ggtgttgaag tcttctgggg  21360
tgcagtcgat gttggctgag cgtggcgagc gtgtcaagcg tgcggcctcg gcgaatgtgg  21420
gcggtaatgc ttttgataag gcccaatacc gtagcggttt gtcgtcggag gtgcaggttc  21480
accgtgttga ggctgtggcc cgtattggca ccacctataa gggtgggaag cgtattgagg  21540
cgaagcatgg cacgctggcc cggtcgattg ggctgcgtc gtgatcgttt atggtgatcc  21600
gcgtgtgtgg gctaaacgtg tgctcaagga tgatggctgg ctgtccgata taccttgtgt  21660
ggggacggtg cctgaggatt ttagcggtga cttgatttgg ttggctcttg atggtggccc  21720
gcagttgcat gttcgtgagc gtgttttttt gcgtgtgaat gtgttttctg atatgccgga  21780
tcgtgctatg tcgttagcta ggcgtgttga ggctgtgctg gctgatggtg tggacggtga  21840
cccggtggtg ttttgtcggc gttctactgg ccctgatttg ctggttgatg gtgcacgttt  21900
tgatgtgtat tcgctttttg agctggtgtg tcggcctgtc gaatccgagt aagcgtatcg  21960
ttgtttttta gtttgattgt tttgtagttt gattgttttt tgggggttat gatggctgaa  22020
acacgtaaag cgtctaatgt tcgctctgct gttactggcg acgtttatat tggtaaagcg  22080
cacgcgggtg attctattaa gggtgtggag gcggttcctt ccgggcttac agctttaggg  22140
tatctgtctg atgacgggtt taagattaag cctgagcgta aaacggatga tttgaaggct  22200
tggcagaatg cggatgttgt tcgcactgta gctacggagt cgtctatcga gatttctttc  22260
cagctgatcg agtctaagaa agaggttatc gaactgtttt ggcagtcgaa ggttactgcc  22320
ggatccgatt cgggttcgtt cgatatttca ccaggcgcca ccactggcgt gcatgcttta  22380
ctgatggata ttgttgatgg tgatcaggtt attcgctact atttccctga ggtcgagttg  22440
atcgatcgtg acgagattaa gggcaagaat ggcgaggtgt atgggtatgg tgtgacgttg  22500
aaggcgtatc ctgcccagat taataagact ggtgatgcgg tgtctggtcg ggggtggatg  22560
acggctttaa aagctgatac tcctccgact cctcctccag ccccggttcc tccgaagcct  22620
cagccggatc cgaatccgcc gtccgataac tgatacacga ttttagggga ttgttgatag  22680
atgagtgaca ctggttacac gttgaagatt ggtgaccgta gctgggtgtt ggcggatgcg  22740
gaggagacgg ctcaggctgt tcctgcccgc gtgtttcgcc gtgccgccag gattgcccag  22800
tcgggtgagt ctgcggattt cgcccaggtt gaggtgatgt tttcgatgtt ggaggctgcc  22860
gcaccggctg acgcggtgga tgctttggag gggcttccta tggttcgtgt tgccgagatt  22920
ttccgcgagt ggatggaata taagcctgac ggtaagggtg cctcgctggg ggaatagttt  22980
ggctccacgg cctgattgat gattatcgtg gggccatcga atacgatttc cgcaccaagt  23040
ttggtgtttc tgtttatagt gttggtggcc cgcagatgtg ttggggtgag gctgtccggc  23100
tggctggcgt gttgtgtacc gatacgtcta gccagttggc ggcccatctg aatggttggc  23160
agcgcccgtt tgagtggtgt gagtgggctg tgttggacat gttggatcat tacaggtctg  23220
```

```
ctaatagtga ggggcagccg gagcctgtgg tgaggccgac ggatgagcgt agggcccggt  23280
ttacgtctgg gcaggtggac gatattttgg cgcgtgttcg tgctggtggc ggggtgtctc  23340
gcgagattaa tattatgggg tgaatagtgt atgtctggtg agattgcttc cgcgtatgtg  23400
tcgttgtata cgaagatgcc tggccttaaa agtgatgttg gtaaacagct ttctggggtg  23460
atgcctgcgg agggtcagcg ttcgggtagc ttgtttgctg gcgggatgaa gttggcgctt  23520
ggtggtgcgg cgatgatggg tgccatcaat gttgctaaga agggcctcaa gtcgatttat  23580
gatgtgacta ttggtggcgg tatagctagg gctatggcta ttgatgaggc tcaggctaaa  23640
ctgactggtt tgggtcatac gtcgtctgac acgtcttcga ttatgaattc ggctattgag  23700
gctgtgactg gtacgtcgta tgcgttgggt gatgcggcgt ctacggcggc ggcgttgtct  23760
gcttcgggtg tgaagtctgg cgggcagatg acggatgtgt tgaagactgt cgccgatgtg  23820
tcttatattt cgggtaagtc gtttcaggat acgggtgcta tttttacgtc tgtgatggct  23880
cgcggtaagt tgcagggcga tgacatgttg cagcttacga tggcgggtgt tcctgtgctg  23940
tctttgcttg ccaggcagac tggtaaaacg tctgctgagg tgtcgcagat ggtgtcgaag  24000
gggcagattg attttaacac gtttgcggct gcgatgaagc ttggcatggg tggtgctgcg  24060
caggcgtctg gtaagacgtt tgagggcgct atgaagaatg ttaagggtgc cctgggttat  24120
cttggtgcta cggctatggc gccgtttctt aacgggttgc ggcagatttt tgttgcgttg  24180
aatccggtta tcaagtcggt gacggattct gtgaagcccc tgtttgcatc ggtggatcag  24240
gggattcagc ggatgatgcc gtctattttg gcgtggatta accggatgcc gggcatgatc  24300
actcgaatga atgcacagat gcgcgccaag gtggagcagt tgaagggcgt tttgcgagg   24360
ctgcatttgc ctgtccctaa agtgaatttg ggtgccatgt ttgctggcgg caccgcagtg  24420
tttggtattg ttgccgccgg tgtggggaag cttgttgcag ggtttgcccc gttggcggtg  24480
tcgttgaaga atttgttgcc gtcttttggt gctttgaggg gtgccgctgg ggggcttggt  24540
ggcgtgtttc gcgccttggg tggccctgtt ggtattgtga tcggcttgtt tgctgccatg  24600
tttgctacga atgcccagtt ccgtgccgct gttatgcagc ttgtgggggt tgttggccgg  24660
gctttggggc agattatggt cgccttgcag ccactgttcg ggattgttgc tggcgtggtt  24720
gccaggttgg ctcccgtttt tggccagatt attggtatgg ttgctggttt ggcggcccgg  24780
ctggtgcctg ttattggtat gcttattgcc aggctggttc ctgttatcac ccagattatt  24840
ggtatggtaa cccaggttgc tgccatgttg ttgcctatgc tgatgccggt tattcaggct  24900
gttgttgctg tgatacggca ggttattggt gtggtcatgc agttgatacc tgttttgatg  24960
ccggttgtgc agcagatttt gggtgctgtc atgtctgttt tgccgccgat tgttggtttg  25020
atacggtcgc tgataccggt gatcatgtcg attatgcgtg tggtggtgca ggttgttggt  25080
gccgtgctac aggtggtggc ccgtattatt ccggttatta tgccgattta tgtttcggtg  25140
attggattca ttgccaagat ttatgctgcg gttatcgttt ttgaggctaa ggttattggc  25200
gctattcttc gtactattac gtggattgtg aatcattcag tgtctggcgt gaggtctatg  25260
ggcacggcca tccagaatgg ctggaatcat atcaaatcgt ttacgtctgc gtttattaac  25320
ggtttcaagt cgatcatttc tgccggtgtt gccgcggttg tggggttttt tacgcggctt  25380
ggtttgtcgg ttgcctccca tgtgaggtct ggttttaatg cggcccgtgg agctgtttct  25440
tccgctatgg gtgcgattcg gagtgttgtg tcttcggtgg cgtctgctgt tggcgggttt  25500
ttcgggtcga tggcttctcg ggtccggaat ggtgctgtgc gcgggtttaa cggggccagg  25560
```

```
agtgcggctt cttctgctat gcatgctatg gggtccgcgg tgtctaacgg tgtgcatagt  25620
gtgctggggt ttttccggaa tctgcccagc aatattaggg gcgccttggg tagtatgggg  25680
tctttgttgg tgtctgctgg ccgtgatgtg gtggccggtt tgggtaacgg tattaagaat  25740
gctttgagtg gcctgttgga tacggtgcgt aatatgggtt ctcaggttgc gaacgcggcg  25800
aagtctgtgt tgggtattca ttctccgtct cgggtgtttc gtgacgaggt tggccgtcag  25860
gttgttgccg gtttggctga gggtattact gggaatgctg gtttggcgtt ggatgctatg  25920
tcgggtgtgg ctggtcggct gccggatgtt gtggatgccc ggtttggtgt gcgatcgtct  25980
gtgggctcgt ttaccccgta tgaccggtat cggagtgcga gcgagaagag tgttgtggtg  26040
aatgtgaatg ggcctactta tggtgatcct aatgagtttg cgaagcggat tgagcggcag  26100
cagcgtgacg ctttgaacgc gttggcttac gtgtgattgg gggtgttgtg catgtttatt  26160
cctgaccctt ctgatcgtgc cggtttgact gttacttggt ctatgttgcc gttgattggt  26220
aatgatcctg agcgtgtgct tcatttgacg gattatacgg gtgcgtctcc tgtcatgttg  26280
ttgaatgatt cgttgcgtgg ccttggtgtt cctgaggttg agcatttttc tcaaactcat  26340
gttggggtgc atggctcgga gtggcgcggg tttaatgtga agcctcgcga ggtgacgttg  26400
ccggtgttgg tgtcgggtgt cgacgaggat ccggtgggcg ggtttcgtga cggtttttttg  26460
aaagcctatg atgcgttgtg gtctgctttt cctcccggcg aggaggggga actgtcggtg  26520
aagactcctg ccggcaaaga gcgtgtgttg aagtgccggt ttgattcggc tgatgacacg  26580
tttacggtgg atccggtgaa caggggttat gcccgctatc tgttgcattt gacagcttat  26640
gacccgtttt ggtatgggga tgagcaaaag tttcgtttca gtaacgcgaa gttgcaggat  26700
tggttgggtg gcggccctgt cggcaagaag ggtaccgcgt ttcctgtggt gttaacaccg  26760
ggtgtgggct ctggctggga taacctgtct aacaggggtg atgtgccggc gtggcctgtg  26820
attcgtgttg agggccccct ggagtcgtgg tctgtgcaga ttgatggttt gcgtgtgtct  26880
tcggactatc cggtggagga gtatgattgg attactattg atacggatcc tcgtaagcag  26940
tctgcgttgt tggacgggtt tgaggatgtg atggatcgtt tgacggagtg ggagtttgct  27000
cctattcctc cgggtggttc gaagagtgtg aatattgaga tggttggttt gggtgccatt  27060
gttgtgtcgg tgcagtacag gtttttgagg gcttggtgaa tggttgatgg ctggtcttgt  27120
tccgcatgtc acattgttta cacctgatta tcgccgggta gcccctatca attttttga  27180
gtcgctaaaa ctgtcgttga agtggaatgg tttgtccact ttggagttgg tggtgtcggg  27240
ggatcattcc aggcttgacg ggttgacgaa gcctggggct cggctggttg ttgattatgg  27300
tggtggccag attttttctg ggcctgtgcg taaagtgcat ggtgtgggtc cttggcgttc  27360
ttcccgtgtg actatcacgt gtgaggatga tatccgcctg ttgtggcgta tgctgatgtg  27420
gcctgtgaat tatcgtcctg gtttggtggg ttcggagtgg cgtgcggacc gggattatgc  27480
ccactattcg ggtgcggctg agtcggttgc taagcaggtg ttgggggata atgcttggcg  27540
ttttccgcct ggtttgttta tgaacgatga tgagagtcgt ggccgctata ttaaggattt  27600
tcaggcccgg tttcacttgt ttgccgataa actgttgccg gtgttgtcgt gggctcggat  27660
gactgtcacg gtgaaccagt ttgaggatgc gaagtttgat cagcgtggtt tgctgtttga  27720
ttgtgttccg gctgtgactc gtgagcatgt gttgactgcc gagtcgggtt cgattgtgtc  27780
gtgggagtat gtgcgtgacg caccgaaggc tacgtcggtg gttgtgggtg gccgcggcga  27840
gggccgggac aggctgtttt gtgaggatgt tgattcggcg gccgaggagg actggtttga  27900
tcgtgtagag gtgtttaagg atgcccgtaa cacggattct gagaaggtgt ctctcttcga  27960
```

```
tgaggctgag caggtgctgc aagagtcggg ggccacgtcg gggtttaaga tcgagttggc  28020
cgagtcggat gtgttacggt ttgggcccgg caatctgatg cccggtgatc ttatctatgt  28080
ggatgtgggc tcggggccta ttgcggagat tgttcggcag attgatgtgg agtgcgattc  28140
gccgggtgac gggtggacga aggtgactcc tgttgctggg gattatgagg ataatccgtc  28200
ggcgctgttg gctcgccgtg tggctggttt ggctgcgggt gtgcgggatt tacaaaaatt  28260
ctaattgttg ggggtttgtt gtgggtattg tgtgtaaagg gtttgatggt gtgttgaccg  28320
agtatgattg ggctcaaatg tctggtctga tgggtaatat gccgtccgtt catggcccgg  28380
atgattttcg tgtcggcacg acgattcagg gttccacggt gttgtgtgag gtcctgccgg  28440
ggcaggcttg ggctcacggg gtgatgtgca cgtcgaatgc tgttgagacg gtgacaggtc  28500
agcttccggg cccgggtgag acccgctatg actatgtggt gttgtcgcgg gattgggagc  28560
agaatacggc gaagttggag attgttcctg gtgggcgtgc tgagcgtgct agggatgtgt  28620
tgcgtgcgga gcctggcgtg ttccatcagc agttgttggc tactttggtg gtgtcgtcta  28680
acgggttgca gcagcagctt gacaggcgtg ctatagctgc ccgtgtggcg tttggggagt  28740
ctgctgcgtg tgaccctacc cctgtggagg gtgaccgtgt gatggttcct tcgggggctg  28800
tgtgggctaa ccatgctaac gagtggatgc tcctgtctcc tcgggttgag acgggttcta  28860
agcagatcca gtttggcggg tctgctgtgt atgcttacac gatcccgttt gcccggccgt  28920
ttagtagccc gcctatcgtg gtggcgtcta tggctacggc ggctgggggc acgacacaga  28980
ttgatgtgaa agcctacaat attactagca aggattttag tttggcgttt attacgaatg  29040
atggttcgaa gccgaatggt gtgcctgcgg cggctaattg gattgctgtc ggcgtgtaat  29100
gtacggcttg cgtgtgcggg acgtgttgtg gtggttgtag tggtaggggg ctgtagtgtc  29160
atggtttaca cctacgcttg tggcctctct ttgtaccgct atcgctactg ttcttggttc  29220
gattcaggcg gctatgtaca ggtcgaagaa gaggcttagg cagttgtctg cgcaggttga  29280
tgcgatggaa gagtacacgt ggaatattcg ccatattgtt caccgctata acgcgaattt  29340
gccggatgat gttgagccgg tgaagatgcc tgatttgccc gagtttttga aggatactgt  29400
tgatggtggt ggggggtgaa ttgtgaggga gttagaggag gagaagcggc agcgccgctc  29460
gtttgagaag gcttccctga tattgttgtt cttgtcgctt gtcctgttgg cggtggttgc  29520
cgggggtgct ttacgtttcg ggctgtatc ctctgagcgg gattcggagc aggctaaagc  29580
ccagtctaat ggtacagccg ccaggggttt ggctgcccgt gtgtggcagg tgtgtgcttc  29640
tggtggatgg gagtctgtgc ggcttcacca gtctggtttg tgtgtggatg ctgtgcgtgt  29700
tgagcggagt gtgcagggtg ttccgggtcc ggctggtgtg cgtggcccgc aggggccggc  29760
tggtgttgat ggccgggatg gtagcaatgg ttctgctggg ctggttgggc ctgttggtcc  29820
gcagggttcc cctggcttga atggcgtgaa gggtcctgac gggctgcccg gcagtgacgg  29880
ccaggatggc cgtgatggtg ttccgggccg tgcaggagtg gacggtgtga acggatccga  29940
tggcaaggat ggtcgtgatg gttcggctgg tgagcgcggc gatgtggggc cttcgggtcc  30000
tgccggaccc cctggc                                                  30016
```

<210> SEQ ID NO 74
<211> LENGTH: 29913
<212> TYPE: DNA
<213> ORGANISM: Artificial Sequence
<220> FEATURE:
<223> OTHER INFORMATION: PAC13

<400> SEQUENCE: 74

```
tgagcgtggc cccgccggtg tgaatggatc cgatggtaaa gatggtaagg atggccgctc     60
ggtggtgtct gtgtactgtt ctgatggtcg cctggttgtg aaatatagtg acggtgtggc    120
ttctaccata tcgggttcgg tggcctgcca gggtgtgaaa ccgtcgccta tagtgactat    180
atcatcccaa aaatagaaag gagtggctgt gatggtagtg tttggtggtg gtgtgtggtg    240
agatacattc ctgcagcgca tcactcggcc ggttcgaata gtccggtgaa caggggttgtg    300
attcatgcga catgcccgga tgtggggttt ccgtccgcct cgcgtaaggg tcgggcggtg    360
tctacagcaa actattttgc ttccccatcg tcgggtggtt ctgctcatta tgtttgcgat    420
attagtgaga cagtgcaatg tttgagtgag tctacgattg gttggcatgc cccgccgaat    480
ccgcattctt tgggtataga gatttgcggc gatgggggtt cgcacgcctc gttccgtgtg    540
ccggggcatg cttacacgag ggagcagtgg ctggatccta gggtgtggcc tgcggtggag    600
aaggctgcca tcctgtgtag acgtttgtgt gacaaatata atgttccgaa aaggaaactg    660
tcggctgccg atttgaaggc cggtaaacgt ggtgtttgcg ggcatgtgga tgttacggat    720
gcgtggcatc agtcggatca tgacgatccg gggccgtggt ttccgtggga caaatttatg    780
gctgtggtga atggccacgg cggcggttca agtagtgagg agttgagtat ggctgatgta    840
caagcgttac atgatcagat taaacagttg tcggcacagg tggcccagtc ggtgaataag    900
ctgcatcacg atgttggtgt ggttcaggtt cagaatggtg atttgggtaa gcgtgttgat    960
gccttgtcgt gggtgaagaa tcctgtgacg gggaagctgt ggcgcactaa ggatgctttg   1020
tggagtgtct ggtattacgt gttggagtgt cgtagccgta ttgacaggct cgagtctgct   1080
gtcaacgatg tgaaaaagtg atggtggttt gtggtgggta aacagttttg gttgggcctg   1140
ctggagcggg cgttaaagac ttttgtgcaa acgtttgtgg ctgtgttggg ggtgacggcg   1200
ggtgtcacgt atacggcgga gtcgtttcgt ggtttgccgt gggaatcggc cctgatcaca   1260
gccggggttg ctgcggtttt gtcggttgct acctcgtttg gtagcccgtc gtttgtggcc   1320
ggcaaacctg gcaagcagcc cctggtggat gagggtttgg ttccaccgga tgatcctgga   1380
atagtggagt ctcactcggt ggatgtgtcg gatcctggca tgatcgagcc gacggatgat   1440
gcggatcttg gtgtaggcta tgtgccgaaa catgctgccg agtcggaggt tggcatgata   1500
gagtctactg ttgcataagt gaatatagat gtgtgcccca gcggtgctgc cacggttgtg   1560
tggtggttgc cgctggggca ctctttttat gttctatagt attctatgat tcgttgctgt   1620
cgatggtgtc ttcgagcatc tggtacaggt ggaggcaggt agagatagtt tcgctggcct   1680
ggtcgagaac ggttcggccg ataacgtttt tgtgattgtc gcggtggcgg atgatagccc   1740
acatgatctc gtcggccgcc gcctgcaata gtttggcctg gtatgcgatc ccggcgagcc   1800
agtctagtgc ttccgggctt gcatgggggc tctggtcctc gctgttgccg cgggtgttgc   1860
tgttgtttgt ggggtgtcct gcactgtcgc ataaccacag gatttcgctg cactcgtcta   1920
gcgtgtcctg gtcgatagcg agatcgtcga ggctgacatt gttgacggta aggttcacgt   1980
tgtcgaggga gatgggtaca ccgtactggt tttcgacact gtcaacaatg ttttgtagtt   2040
gttgcatgtt ggtgggctgt tgttggacga tgcggtgtat cgctgtgttg agggtggtgt   2100
aggtgatgtt gtgtgtgttg tccatggttt ttatgccatt ccttcgttat cgtctggcat   2160
gtagtatgtg ctgtttgcgt actcggttaa cgtcatcagt gtttggtctg cccactgttt   2220
cacagtctgc cttgtcactc cgagtcgttg ggcggcagac gcatatgttt ggtcataccc   2280
gtatacttcc ctgaatgctg ccaaccgtgc caaatgtttt cgctgtttgg atggctggca   2340
```

-continued

```
ggtgagggtg tagtcgtcga tggctagctg tagatcgatc atggtaacga tgttgttgcc   2400
gtggtgttgt ggcgcggttg gtgggggtgg catgcctggc tccacactgg gtttccatgg   2460
tccgccgttc cagatccatt gggcggcttg aataatgtcg gcggtagtat aggttcggct   2520
cacttggtca ccccctgaac aggtcgttgc tggtggtggt gtcgaatcgt ccgacgcagt   2580
ggcagtagtc gtacatgagt ttaataatgt gttggtggtc tcccaaatag gtgtttccgc   2640
tgatactgta ggtggctgtg ccgtctttac tgatggtgta tttggcggtg atggtttcgg   2700
ggttttcggt gtcggtgatg atggctgtgg tggtggcacc tactgtttgg agcacggtgg   2760
tttgggttcc gtcgtcgatg gtggttttaa ccatgaggtg ttctcccttt gtgttagttg   2820
ctggtttggt tgtcggctag atgaatgatg tcgggtaagg gtttcggctg gtcgaggtgt   2880
tgtatggttt tgttggctag ccgtttggct accctgtaac acattttggt gtagtgtttg   2940
ttgtctaggt tgtggtattg ttcccgcacc gcaatatata gcagggagtc ttggtatagg   3000
tcgtctgcac tgattgcggg gtagtgtgcg gctactttgg tacatgcccg gttgagtgtg   3060
cgtagatgat ggtctgtggc ccacacccac gatgcggtgg tggctaggtc ggcttttgtt   3120
ggtcgtctac tcatggcatc tctttcatct ggctatctgg tagttgtttg gtgttttgtt   3180
gttgatagtg tagcacacga gcccggggtt tccggtggtg cccgtcttgt gccggtacca   3240
tgtggattcg ccttccatgg atgggcattg gatgaaggtg cgttgtcctt gctcggagat   3300
ttctaggtgg tgccggtgcc ctgccatgag aatatgggat gtggtgccgt tgtggaattc   3360
ttggccgcgc caccaatcat agtgtttgcc ggtgcgccat tggtggccgt gggcgtgcag   3420
tatccgtgtg cctgccacat caacggtggt ggtcatttcg tctcggctgg ggaaatggaa   3480
gtgtaggttg gggtattggt tgttgagctg gtaggcttct gcgatggcgc ggcagcagtc   3540
tacgtcgaag gagtcgtcgt aggtggtgac gcctttgccg aagcgtacgg cttctccgtg   3600
gttgccgggg atggatgtga tggtgacgtt tttgcagtgg tcgaattggt ggatgagttg   3660
catcatggcc atgcgggtga gcctgatttg ttctgtcagg ggtgtttggg tgcgccaggc   3720
gttgttgcct ccttgtgaca cgtatccttc gatcatgtcg ccgaggaagg cgatgtggac   3780
tcgttgcggt ttgcctgcct gttgccagta gtgttttgcg actatgaggg agcgtaggta   3840
gttgtcggcg aagtgtgctg tttctcctcc ggggatgcct ttgccgattt ggaagtctcc   3900
cgccccgatg acgaaggccg cggtgctgta gtcggtgtgg gtgtcttgtt cgggttttgg   3960
gggtgtccat tcggctagtt tatcaacgag ttcgtctacc gggtaggggt tggttgctgg   4020
ttggtggtca ataatttttt gtatggatcg gccggtttct ccgttcggta aggtccattc   4080
ggagatgcgt gtgcggcgca cggtgccgtt ggctagattg tcgtcgatgg tgtcgatggc   4140
gttgtcgtgg ttggctagct gtgtgagtag ccggtctatg ttgtctatca ctgggtatcc   4200
tcctcgtgtg tggtggtggc ttgtttgcgg cggtagtctt tgataacggt ggcggagatg   4260
gggtatccgg cttgggtgag ttgttttgct agccacgagg cggggatggt tttgtcggcg   4320
agcacgtctg cagccttatc accgtagcgt tggatcaatg tttcagtttt ggttgccatg   4380
atgtcctatc ggctgtgtgg cgggctgcca tcctgtgcgg cagtcgccgt cgtgtcctgg   4440
tttgcgggtg caccacgata cggttccgtc tgtgtggtgg agtgttttgc cgcacaggac   4500
gttttggaga tgctccggca gctggtcatt ctggttgctg gtttgtgtgt cgaagagtgt   4560
tttctggttg gtgaaatgct cggacacggt gccattatgc acgggtagta tccatgtttt   4620
ccattgttgt tgcatccggg tgttccagtg gaattgtttg gcagctgtct cggcttgttt   4680
```

ggcggttttg tagtagccga ctagtatgcg ctggtgttca ctgtcgggcg ggttttggcc 4740
tcgccagtat tgtgccgcaa ccgcgtacct gttgttgtcg gtgaagcgct gccagcagta 4800
ttcgatgatg tgttgcagta cactatcggg aattttttgt gtttggtttt cgttgagcca 4860
ttcggcttcg atgatgccgt gtatggcgcg tttgtctttg gtggtgggtt tgaacgagat 4920
gctcacgata gtaccggctg atcgtcttgc atgaactggt tgaaggtgtt gttcccggcg 4980
tgttgggctt gtgtgatttg ctggtcggtc cagtctgggt gttgctgttt cagatagtgc 5040
cagtggcacg cattgtaggt ttcgtcttgt agccgtgtga gatggttttc ggtgatgatt 5100
tgtttccaca tagtccatga cacgtcgagc ctgttgagga tttctatggc tgggatgttg 5160
aattggtcga ggaagaggat ttcgtgggtg tagtagtttt tctcgtaggc gtcccatccg 5220
cttcggtgcc tgttgggctg gtttttgggg taggcttccc ggcatacttt gtgtaaccgt 5280
ttggccatgt cgtcgggtag tttaatgtcg gggttggcgc ggatcatgga tcgcatccca 5340
tcataggtgg tgccccaggt gtgcatgatg taggtggggt cttcaccatc ggcccatttt 5400
tctgcacaga tggcgaggcg gatgcgcctc ctggctgttt ggctgatgtt gcgccggttg 5460
gggatggggc acgtgtcgag gggatccatg atgtttttta tgcctttctt ggtttcgtgt 5520
tgttgacggg ttttactgta gcacagtgtc tagtgcttgt gtcaaccctg tttttccggc 5580
ctgcaggtag gtgtctgtga catcccccag ggtgaggggc acgtgggtgg cttgggggag 5640
tgctgcctgg agggtttgtg ccatctggtc gcctgctttg tctgggtcgg accagatgta 5700
gatgtggtcg tagccttcga agaatttggt ccaaaagttt tgccacgagg tggcgccggg 5760
tagtgctacg gccgaccatc cgcattgttc gaggatcatg gagtcgaatt cgccttcgca 5820
aatgtgcatt tcggctgccg ggttggccat ggcggccatg ttgtagatgg agcctgtgtc 5880
ccctgccggg gtcaaatatt tggggtggtt gtgggttttg cagtcgtgcg ggagtgagca 5940
gcggaaacgc atttttcgta tttcggctgg ctgtccccaa acggggtaca tgtatgggat 6000
ggtgatgcac tggttgtagt tttcgtggcc tgggatgggg tcattgtcga tgtatccaag 6060
gtggtggtag cgggctgttt cttcgctgat gcctcttgcc gagagcaggt cgagtatgtt 6120
ttcgaggtgg gtttcgtagc gggctgaggc tttctggatt cggcggcgtt ccgcaatgtt 6180
gtaggggcgt atgctgtcgt acattcgggt tttttttctc tagtcgttgt tgtagtttgg 6240
cgagtcctcc tccgataccg catgtgtggc agtaccagac gcccttgtcg aggttgatgc 6300
tcatggaggg ctggtggtcg tcgtggaacg ggcagaggat gtgttgctca ttcctagacg 6360
gattgtaccg tatctggtag gtgtcgagga ggcggcaggt gtcagaggtg tgggaggagc 6420
tcgttgaggg ttgataccac ataggcttcg ctccatggct tgttgcgttg tttcatgacg 6480
acgagtccga tggtggactg gttttcgcgg tttcggtgtg tttcgtagtt gcgtgcctcc 6540
cggctggctt gtttcacgaa ttgggctagg tggggttgtc ctgctttcgc ctcgataatg 6600
taggttttat ggccggttgt gaggatgagg tcgccttcgt cctctttacc gttgaggtgg 6660
aggcgttcta tatcatggcc ggtgtcgcgt agctggtgca ataatcgtgt ttcccattct 6720
gcgcctgccc tgcggttgcg tgactgttgt gtcgacatga tagtcctttg tgtgttgtgg 6780
tcatgttcca tggctgtttt tcggcgagtg gcccgaagaa tgtgtattcc gggtatgccc 6840
tgagccgctc atattttgtt ccgtctgggc tggatttgcc tgtgcgctgt ttcaacactg 6900
agatgcgtgc ctcggcgggg atcgtgagcc cgttgccgtt atcctcgcca ccataaagtg 6960
agactcccaa tatgagttgt ggtttttcgg agaggccgtt tttgatttcc cgcctagccg 7020
gggggtgttc gatgtcggtg ccggttttgt cggtggcgtg gtgggtgaca atgatggtgg 7080

-continued

```
agccagtatc tctacctaat gctgtgatcc attgcatggc ttcctgctgg gcctggtagt   7140
cgctctcgca gtcttggatg tccatcaggt tgtcgataac gatgatgggt gggaaggtgt   7200
tccacatttc catgtaggct tgcagttcca tggtgatgtc tgtccatgtg atgggtgact   7260
ggaatgagaa tgtgatgtgt tggccgtggt ggatgctgtc tcgatagtat tctggcccgt   7320
agtcgtcgat gttttgttgt atctgtgtgg tggtgtgttg ggtgttgagt gagatgattc   7380
gcgtggaggc ctcccagggt gtcatgtccc ctgatatgta gagggcgggc tggttgagca   7440
tggcggtgat gaacattgct agcccggatt tttggctgcc ggaccgcccc gcgatcatga   7500
ctaggtcccc tttgtggatg tgcatgtcca ggttgtcata caagggtgct agttgtggta   7560
tgcggggcag ttcggcggct gtttgggagg ctctctcgaa ggatcgttgg agagagagca   7620
tcggagcctt aatctatctg tctatcggtt ggatgatgtt ttggtggtca gatggagtcg   7680
atgtcgatgt cagcatcagc aggggctgtg gtgtcgtcta gctgaccgtt atcgcgtttg   7740
tctacgtatt cggcaacctt atcgtagatg gcgtcatcga ggggtttgag cacgaccgcg   7800
ttgaagccgt tttggtgcg cacggtggcg agtttgaagg cctgctcctc gccaaggtag   7860
gcttcgaggt cgcggatcat ggagtgtggg cggtcgttgt tgccgcgggc tttctcaatg   7920
atagcgttgg ggatggtttc tggggtgccg ttgttgagat cctcgagggt gtggaagata   7980
gtcacatcag cgtaaatacg atcggcggtc tgtccaccgt agccttcggt gttgtgttcc   8040
acgtcgcgga ttttgaaggc gatggcggtg gcgtcctggt ttcgggaggg gttgaagaag   8100
gtgctgttgc tgttgttgcg gtagtttgcg agtcccattg ttgtttcctt tactgtttgt   8160
gttgttttgt ttgttggttt gtgtcggttt ttatcgggtg aggctgtttc gtttgctgcg   8220
gaaagcctca gacacgtcac tgttactagt gatggtcttc ttgtactgtt tgaggaggtc   8280
ggctagctgt gccttgcttg ttgcattgtt gattttgtcg atgacgatgc tgttttcttt   8340
ggatgcgatg ttgtccacgt agtctttggc ggcctggttg tatcggtctt ggaggatgat   8400
ggatgctgtg gcgatcaggg ttgccaggtc ccagttcctt gccgcggagc tgtttttgag   8460
tccgcctagc aggtcgatga tagtcttctt tacctggtcg gcggtgtctc cgcggatgac   8520
ggtccatggg gcggcgtagt cgcctccgta tttgagtgtg acggtgaatc ggtcgtcgtc   8580
tgtgttgtcg gtcactggtg ctccttgcct tcttttgttg gggctgtgat ggtggtttct   8640
atagggtacc tgtaggcgtc tttcccgtta acagcccagc aggcgtcctt gacggggcat   8700
cctttacaga gtgctgtgac gtggggtacg aagatgcctt gactgattcc tttcattgct   8760
tgactgtaca tggatgatac atgccggtag gtgttgttgt caagatcgta cagttcggtg   8820
gatgtgccct gttcgaccga ttgctcgtcc cccttggtgg tggcgggtgt ccaaaacatg   8880
cctttcgtca catcgttgcc gtgttgggcg agcatgtacc ggtaggtgtg cagctgcata   8940
ctgtcggcgg gtaggcgtcc tgttttgagg tcgagaatga aggtttcgcc agtgtcggtg   9000
tcggtgaaaa cgcggtcgat gtagccaacg atctgggtgc cgtcctggag ggtggtttct   9060
accgggtatt cgatgcctgg ctggccgtct aggattgcgg tgatgtattc tgggtggttg   9120
cgcctccatg ttttccagcg gtccacaaag gtggggccgt acatcatcca ccagtcgtag   9180
tctttcttgt gtggcccgcc cgactcgcac atgtttttgc atattctgcc ggagggtttg   9240
atttctgtgc cttcggattc ggcgagggcg acttgggtgt cgaaaatgtt tttgaaggat   9300
gagagtttgt ttggtagtgc agggtattcg gtggggttgt acaggtgtag gtcgtattgt   9360
tcggtgatgt ggtgtatggc gcttccggcg atggtggcat accaggtgtg gtgttgggca   9420
```

-continued

```
tggtagccgt gggataggcg ccatttttca ccacattcgg cccactgtga cagtgatgag   9480
taggagatgt ggcctggatg gtggatggtt ttcgggtatt gtgctagggg cattactggt   9540
cgcctttgtg ggtgttccat gggtttcggg tgtcttggcc ggcattgtgt tgctggtagg   9600
cgaggagtgc gaggcagtgc caggcagcat gggctagatg gggtagcccg gattcgtggt   9660
cgaggttgtt gccttgctgc catgatagta ggtgcctgta gagggcgtcg acgctgtggc   9720
tccacgggta tccgccggtc cagttgttgt cgccgtattt ggtggcaccg tagcctgcga   9780
cttcgccgag ggcgtgtaag gctgcggggt cgatgaggga gagtcggcat agtttgagtt   9840
ctttttggc gcctgtgtct gggttggtgt acatgcgggt gggcttatcc atggggtgtg   9900
tgctccttag gggtgggtta ctggttgggg ttgtgggcga gtgctacggc gaggatgatg   9960
atggcgaggg tttctgcgat gatgatgggt gttgtgatca tttggtgtct cggggattgt  10020
tggtgagggt tgaggcgcct aggagggtgg tgagggcgca tgcggcgatg atggcgaggg  10080
ctgccttgtg tggggtgccg gttgcgtaca tccatgtgat gatggcgcct tggatccatg  10140
ccagtgtggt gaagaatgtt tcgtagctgt gtagctcgct tttgttgctg gtgatgtcat  10200
tcatggtagt tttctgcttt gtgtgcgatg gttgtgtaca tgtcgttgag tgtggtttcg  10260
atggtgatga gagtgttgat ttcttggttg aggtcgatgt tgtctttgag ggtgtcgatg  10320
cgggcggcga tgtcggtggc ggtgcgtagg cttactgctg caccgtggat gatgtggcat  10380
atgtcggtga ggccgacttt ggcgatgtag tgtgacatga gaggcatagc ggggatgctc  10440
cttggcgggt tactgttgcg ggttgatgtt gaggtcggtg acgttggggt ggtcttctgt  10500
tccggtgacg aggcagtgga cggtgactgg gagtttggat gcgccgggct gtttcgcggt  10560
tgcgccgtag acgatggaga aggtgtcttt accaataatt ttgtggagtt ggaggtcgat  10620
gtcggggttg ccgttccagt tgacaccgtg tgctgcggcc tgctgttcgg ctttgcggtt  10680
gcaggtgtgt gctgcggtga tcatggtgag accctgtgag gtttcttcac cccttgcttg  10740
ggcttgccgg tgggttttct gctgttcggc tcgcagtgac tgttctgcgg cggcctggcg  10800
tgctttcttt tcggctttgc gctgttggat agtcttgggt gtccattcgg tgttggctgt  10860
ggtggcttgc ggtgcgggct gtgatgcgag tggcggattg tcgtcgggtg ctggcaggaa  10920
ggatgctgcg gcgatgatgg cggctgtgat tccggcgatg gtgtagcctg ttttcttgtt  10980
catggctttg tgttcccctt tccggggtgt tgttcgttgc tgacatgatt aatactttca  11040
gcggctgggc ccactgtcaa ggctgcgctc agtttgcgtg agcgatactt gtgtggctag  11100
gggtgatggc ttctttcgcc caataggatg tgccaccgct ggtccagtat ccgagtttgt  11160
tgcgctgcat gcccttggcg tccatctcgt cgatcgtgag gcacctgcga cgactggggc  11220
ctgtcttgac tccatggtcg cctacccggt gcatgtcgcc tgaggtggta ctcgtgaatg  11280
tttcgtggca gattgtgcag tgctctggct tgtatccgat gatggtgcta tcgcacttgt  11340
ggcatgtcca ttgcatgatt gctcctattt tccattataa gacttcctgt agtgccattt  11400
tagcgccttg cgagtcttgg gggtacaact atataggtcg ggtatttcta ggcgattcta  11460
ggctcgttgt gtgtggttgg gggtttatcg ggcgcacagg gtgagcaggc ttccgatgtt  11520
gatgcgtatc acattccagt agagttgtgt ggcttcaccg tcggtgagtg gcttccactc  11580
gtcatggctg aacacggtgc catcggatgc gatgaacgtg ttggggcgta gcttgtggag  11640
ttcagtctct acacgctgcc ggtaggcttc ggcgaggccc tcaaaatcca tgtggtcgca  11700
ggagaggttt tcgaagcgtg tcaagtcgat gggtgtgggg cagtcgtcgt tggtgggggt  11760
gtagagctgg gtgaagtggt tggcgatctt ctgcatgacg ggttcctttt ctcgtgtgat  11820
```

-continued

```
gggttgatag ttttatcggg ttgcggcggc aataatggca tccacgtcga tcatgtcgat  11880
catgtcgttg agttcctcgg cctcattctc ggagaggtgg cgccagccat agtcgccgta  11940
tacggcgccg tcgagggtga cagtccacag gggccggatg agtcgtacgg cttcttcgac  12000
tttggcgtgg tacatgcggc gcaccatatc cagatcgatg tcgtctgaat ggtttccggt  12060
gaggctgtgg aagctgagcg ggtcgatttc tgtctgcctg tcgaggctgg tgaatgatgg  12120
tgtgatgagt gtgccatcca tagggtgtgt gctcctttcg gtggtggagg ggttgttgtg  12180
gtttctagag tgtgtaggtt gcgaccccac agtcaaggtg gcgctcattc ggattgagcg  12240
tttcatggaa ggtgacggat gtcactgaag ccttgatggc ctctctcatc gcctgaaatc  12300
ttctagaggt aggattatgc agggtttacc ctgctgatcg attctagggg ccttctaggg  12360
cgtctcaggg gtgtatctgg gtgatagcag gtccggtaga tctatcttgg ctttcatgac  12420
gggggtcgag gtgccagatc tggtcatgga atccacaccc tcatactgtg tgagatgtat  12480
cacatcctcc tggcttggtg tgccctctcg aggctactct gccgatctgg cgtgaagggt  12540
gtagcccaga aatgccgttt aaagcctccc tatggcgcct aggagcgcct tacagagtgg  12600
gggctaggta ttcatacccc caagcaattc tgatcgattc tagacgcctc ccagagcctg  12660
atacacgatc aaccatctcg gcatagacca gcagccccta tcctggttag ctaagcctca  12720
actatgtgga cagtgtggga tactaagggg gaagaaggac acggtaaaag aaagaggggg  12780
agcatcagcc ttagggtctt agcacttagc gcttagcacc gagcccctca agggctcggc  12840
atcagcccga cagcccgagc aggctcagcc gatcaggcac agccctgaaa ggggtacacg  12900
ccatcaggga aggcttgaga gtacgaggag ccctagcgac gagtactcga aagcctgagg  12960
gaacacccat cagcactgat gggcctagcg tgttcggaaa ggacacaaga gtacagtgtg  13020
acagctgttc gggagtgaaa cctgttctga ctaggggttt cagccttaac caccctcaaa  13080
ggttacaaga ctctaagaaa atttaaggaa aagtttaggt ttaatttttg gacctttact  13140
accaaaaaca cccgtttaca cccctcaaac ccgcctatag agccaaaacc accagtttga  13200
ctcatcccag gtggggtatg ataggctgga caggtagcca gctggacgca aggccgaaat  13260
ccgctgacgc ggctttcacc cttacatcca tcagtctacc aaagacttaa aagcttaaca  13320
gctaagcgct aagcccttaa gaccttaaca cttagcaccg agcccctcaa gggctcggca  13380
tcagtcttaa agccttaaac acttaaagtt ataaataaac attaaagctt taaagtctta  13440
aagtaaatat ataaccttaa cagttaaacg tttaaagctt taaaccttaa cacctaagtt  13500
aagtataaaa ccttaaaggc ttagcactta aggatataaa cttaacatca gtgtttaaga  13560
ctttaagact ttaaaactta aaataactat taatacttaa aagcttataa gtattaaaca  13620
cttaaagtaa ctataagact ttaaaaacct taagtactta aagttaacca tcagtcttaa  13680
actttaatat tataacctat aagtcttaaa gcttataggt gtaataatat aatataagta  13740
ttaaagctta taagttataa aagttttaga agagttaaag ggttaacttc tttacttctc  13800
tactctcttt ggtactttct ctcttctctt cttttcttca tcaggggaga agaggaacct  13860
ttaccatcag cgccgatgga cttttcgccg tgtgtctcgt gtaccaccgg tcgcacgctc  13920
ccggtttgta cactccccac actctgacac ctgtgtccct ttacggcttg gcgtgttcgg  13980
ctgaaggcgt acggcgtgtc acgctcacac ccttaacacc aggtaagact taaagtgtat  14040
attataagta gaagacttta aaacctgtaa ggtgttcccg cttagcccgt gtccttccac  14100
gctaggcgcc aagcgctaag ctgtgaaacg cgaacacaca cccaccccct tttttcttc  14160
```

```
gtgtccttct cttttgaca cagctggggg gcgatgtgat ctttttcaca tgccaggggg  14220
tagtggagaa aacaagcacc ccggaatgtt caagacaccc cctcaaacga acaaaacgcc  14280
ccccataatc gatgagcagg gcaagggcaa ggtattcata cccccaacgg ttcccaggct  14340
gttagagagg caaataagac ccctgcaagg gtaggcgagg aacagacaca tcatggcacg  14400
caccaaccgc accgcatcat cagcccaccg ccgctggcgg gcaagactca tcacccaagc  14460
acgcaagcaa ggccaaaccg aatgcccact ctgcggagcc accatcacct ggaacacaca  14520
tgacctgcca accagccccg aagccgacca catcacaccc gtcagcaggg gaggactcaa  14580
caccctcgac aacgggcaaa tcatctgcag aacatgcaac agaagcaaag gcaatcgcag  14640
cgaaccaaac atccaattcc aacaacaaac cacaaaaacg ctgatcccat ggtgaaaaaa  14700
ctgtcaaccc ccaccgggac cccccctgca cacccgtgca agacctcgta cggcttagtg  14760
aaatacctcc cttttgtggt tttgtctgtt tgtcgacttt ttgtgttggt ggtgagtgtt  14820
gtgcagcctg agcttcctgg tggtcgtgag tggtgtgggg agacgcgtcg ttggtggcgt  14880
gtgtggggtg aggatagccg cgcatcgtat gtgtctgatg aggagtggtt gtttcttatg  14940
gatgctgcgg tgattcatga ttgtgtgtgg cgtgagggca gggcggattt ggtggcttcg  15000
cttcgtgctc atgtgaaggc gtttatgggc atgttggatc gttattcggt tgatgtggtg  15060
tctggtggcc gtggtggggg ttctgcggtg gcgatgattg accggtatag gaagcgcagg  15120
ggggcttgag taggtgtctg gtgttgtggg ttctcaggtt cctcgtcatc gtgtggctgc  15180
ggcgtattcg gtgtctgctg ggggtgatgc tggggagttg ggtcgtgcgt atgggttgac  15240
gcctgatccg tggcagcagc aggtgttgga tgattggctt gctgtgggtg gtaatggtag  15300
gcttgcttcg ggtgtgtgtg gggtgtttgt tccgcggcag aatggcaaga atgctatttt  15360
ggagattgtg gagttgttta aggcgactat tcagggtcgt cgtattttgc atacggctca  15420
cgagttgaag tcggctcgta aggcgtttat gcggttgagg tcgttttttg agaatgagcg  15480
gcagtttcct gatttgtatc gtatggtgaa gtcgattcgt gcgacgaatg gccaggaggc  15540
tattgtgttg catcatccgg attgtgccac gtttgagcgt aagtgtggtt gtccgggttg  15600
gggttcggtt gagtttgtgg ctcgtagccg gggttctgct cgcgggttta cggttgatga  15660
tttggtgtgt gatgaggctc aggagttgtc ggatgagcag ttggaggctt tgcttcctac  15720
ggtgagcgct gccccgtctg gtgatccgca gcagattttt ttgggtacgc cgcctggccc  15780
gttggctgac gggtctgtgg tgttgcgttt gcgcgggcaa gccctcggtg gggggaaacg  15840
tatcgcgtgg actgagtttt cgattcctga cgagtctgat ccggatgatg tgtcgcggca  15900
gtggcggaag cttgctggtg atactaatcc ggcgttgggg cgtcgtctga attttgggac  15960
cgtaagcgat gagcatgagt cgatgtctgc tgccggtttt gctcgggagc ggcttggctg  16020
gtgggatcgt ggccagtctg ctgcgtctgt gataccggct gataagtggg ctcattctgc  16080
ggtggatgag gcggctctgg ttggcgggaa ggtttttggt gtctcgtttt ctcgttcggg  16140
ggatcgtgtc gcgttggcgg gtgctggccg gactgatgct ggtgtgcatg ttgaggtgat  16200
tgatggcctg tcggggacga ttgttgatgg tgtgggccag ttggctgatt ggttggcgtt  16260
gcgttggggt gacactgaaa agatcatggt tgccgggtct ggtgcggtgt tgttgcagaa  16320
ggcgttgacg gatcgtggtg ttccgggtcg tggcgtgatt gtggctgata ctggggtgta  16380
tgtggaggcg tgtcaggctt ttctggaggg tgttcgttcg ggtgtgatca gtcatccgcg  16440
tgccgattcg aggcgtgaca tgttggatat tgctgtgagg tcggctgtgc agaagaagaa  16500
gggttctgcg tggggttggg gttcctcgtt taaggatggt tctgaggttc ctttggaggc  16560
```

tgtgtctttg gcgtatcttg gtgcgaagat ggcgaaggct aggcggcgtg aacggtctgg 16620
taggaagcgg gtgtctgtgg tatgaactcg gatgagttgg ctctgattga gggcatgtac 16680
gatcgtattc aaaggttgtc ttcgtggcat tgtcgcattg agggctacta tgagggttct 16740
gcccgggtgc gtgatttggg ggttgctatt cctccggagt tgcagcgtgt gcagacggtg 16800
gtgtcgtggc ctggtattgc tgtggatgct ttggaggagc gtctggattg gcttggctgg 16860
actaatggtg acggctacgg cctggatggt gtgtatgctg cgaatcgtct atcaaccgcg 16920
tcatgcgacg tccaccttga tgcactgatt tttgggttgt cgtttgttgc gatcattccc 16980 caggggggatg gttcggtgtc tgttcgtccg cagtcgccca agaattgtac tggccggttt 17040
tcggctgacg ggtctcgttt ggatgcgggt ttggtggttc agcagacgtg tgatcctgag 17100
gtggttgagg ctgagttgtt gcttcctgat gtgattgttc aggtggagcg gcgtgggtct 17160
cgtgagtggg ttgagacggg ccgtatcgag aatagtcttg gtgcggttcc gttggtgcct 17220
attgtgaatc gtcgccgtac ttctaggatt gatggccgtt cggagattac gaggtctatt 17280
agggcttaca cggatgaggc tgtgcgcaca ttgttgggcc agtctgtgaa tcgtgacttc 17340
tacgcctacc cgcaaaggtg ggttacgggt gtgtcggctg acgagttttc gcagcctggc 17400
tgggtcctgt cgatggcttc tgtgtgggct gtggataagg atgatgacgg cgacacaccg 17460
aatgtgggat cgtttcctgt gaattctcct acaccgtatt cggatcagat gcgtttgttg 17520
gcgcagttga ctgcgggtga ggcggctgtt ccggaacgct atttcgggtt tatcacgtct 17580
aacccgcctt ctggggaggc tttggctgcg gaggagtctc ggcttgtgaa gcgtgctgaa 17640
cgccggcaga cgtcgtttgg tcagggctgg ttgtcggttg gtttttggc tgcccgggcg 17700 ttggattcga gtgttgatga ggctgcgttt tttggtgatg tgggtttgcg ttggcgtgat 17760
gcttcgacgc cgactcgggc ggctacggcg gatgctgtga cgaagcttgt tggtgccggt 17820
attttgcccg cggattctcg gacggtgttg gagatgttgg gtttggatga tgtgcaggtt 17880
gaggctgtga tgcgtcatcg tgctgagtct tcggatccgt tggcggcgct ggctggggct 17940
atatcgcgtc aaactaacga ggtttgatag gcgatggctt cgggtgctat gtcgaggctt 18000
gctgcgactg agtatcagcg tgaggcggtc aggtttgctg ggaagtatgc gggctattat 18060
gccgagcttg gtcgtttgtg gcattccggg aagatgacag atgcgcagta tgtgcgtttg 18120
tgtgtggagt tggagcgtgc cggccatgat ggttcggcat cgttggcggg caggtttgtg 18180
tcggattttc gccggttgaa tggtgtggat cctggtttga ttgtgtatga cgagtttgat 18240
gctgccgccg cgttggctag gtcgttttcg actattaaga ttcttaagag tgatccggat 18300
agggtgaatg acacgattga tgcgatggct gcgggtgtta atcgggctgt catgaatgct 18360
ggccgtgaca cggttgagtg gtctgcgggt gcgcagggta ggtcgtggcg cagggtgacg 18420
gatggtgatc cgtgcgcgtt ttgtgccatg ttggctacga ggtcggatta tacgaccaaa 18480
gaaagggcac tcactactgg tcatacgcgg cgtcataagc gtggtggtaa gcgtccgttt 18540
ggttcgaagt atcatgatca ttgtgggtgt acggtggttg aggttgttgg cccttgggaa 18600
ccaaataggg ctgatgccgc atatcagagg acgtacgaga aggcccgtga gtgggttgat 18660
gatcatgggt tgcagcagtc gcctggcaat attttgaagg ctatgcgtac tgttggcgac 18720
atgagatgat ggtttccggt tgtgtgccgc cggttatcgg tgcacagggt tgtctcccgc 18780
acgggggtca acaatgttgt gttgttttcc gcaaggagta taggttaggc tatggccgat 18840
cagagtgttg aagaacagaa tgtcgacaat gatgctgttg agcccggaaa gggcgaggac 18900

-continued

```
attgttgctg ttgtgaagga tgggcaggct gccggcgatg atcatgccgg tgatgtttcc  18960
gtgaaggagg agtcttcttc tggcacggat tggaaggctg aggcccgtaa gtgggagtct  19020
cgtgctaaaa gtaatttcgc cgagttggag aagcttcgcg cctcggatgg tgatgcggga  19080
tctactattg atgagcttcg ccgcaagaat gaggaactcg aagacaggat caacgggttt  19140
gttcttgagg gtgtgaagcg cgaggtggct gccgagtgtg gcctgtcggg tgatgcggtc  19200
gctttcttgc acggcgacga tcgtgaagca ctggtggagt ctgctaaggc tttgaagggt  19260
ttgatcgacc atagcagtgg tggcgcgggt gtgcgccgtc ttgcggggag tgcccccgtt  19320
gatgatgtta aacgacgtga gggtgtcgcg tttgtggatg ctcttgtcaa taattctagg  19380
agatgatttg tgatggctga cgattttctt tctgcaggga agcttgagct tcctggttct  19440
atgattggtg cggttcgtga ccgtgctatc gattctggtg ttttggcgaa gctgtcgccg  19500
gagcagccga ctattttcgg cccggtgaag ggtgccgtgt ttagtggtgt tcctcgcgct  19560
aagattgttg gtgagggtga ggttaagcct tccgcgtctg ttgatgtttc ggcgtttact  19620
gcgcagccta tcaaggttgt gactcagcag cgtgtctcgg acgagtttat gtgggctgac  19680
gctgattacc gtttgggtgt tttgcaggat ctgatttccc ctgctcttgg tgcttcgatt  19740
ggtcgcgctg tggatctgat tgctttccat ggtattgatc ctgctacggg taagcctgct  19800
gcggctgtca aggtgtcgct ggataagact tcgaagacgg ttgatgcaac cgattccgct  19860
acggctgatc ttgttaaggc tgtcggcctg attgctgggg ctggtttgca ggttcctaat  19920
ggtgttgctt tggatccggc gttctcgttt gctctgtcga ctgaggtgta tccgaagggg  19980
tctccgcttg ccggtcagcc gatgtatcct gcggccgggt ttgccggttt ggataattgg  20040
cgtgggctga atgttggtgc ttcttcgact gtttctggtg ccccggagat gtcgcctgcc  20100
tctggtgtta aggctattgt tggtgatttc tctcgtgttc attggggttt ccagcgtaac  20160
ttcccgatcg agcttatcga gtatggtgac ccggatcaga ctgggcgtga cctgaagggc  20220
cataacgagg ttatggttcg tgccgaggct gtgctgtatg tggctatcga gtcgcttgat  20280
tcgtttgctg ttgtgaagga gaaggctgcc ccgaagccta atccgccggc cgagaactga  20340
tttattgttg cggtgatgtg tcaatgtgca gggggtggtg ttgatgggta tcattttgaa  20400
gcctgaggat attgagcctt tcgccgatat ccctgagggg aagcttgagg cgatgattgc  20460
tgatgtggag gctgtggctg tcagtgtcgc cccctgtatc gctaaaccgg atttcaaata  20520
caaggatgcc gctaaggcta ttctgcgtag ggctttgttg cgctggaatg ataccggggt  20580
ttcgggtcag gtgcagtatg agtctgcggg cccgtttgct cagactacac ggtcgaatac  20640
tcctacgaat ttgttgtggc cttctgagat tgctgcgttg aagaagttgt gtgaggggga  20700
tggtggggct ggtaaagcgt tcactatcac cccaacgatt aatggtcgat atgcacattc  20760
tgaggtgtgt tccacggtgt ggggtgaggg ttgctcgtgc ggatctgata ttaacggcta  20820
cgctggccct ttgtgggaga tatgatatga ccggttttcc ttacggtgaa acggttgtga  20880
tgcttcagcc gactgttcgt gtcgatgatc ttggtgacaa ggtggaagac tggtctaagc  20940
ctgtcgagac tgtgtactat aacgtggcca tctatgcttc cgtttcgcag gaggatgagg  21000
ccgcgggccg tgactctgac tatgagcatt ggtcgatgct tttcaagcag cctgttgtgg  21060
gtgccggtta tcgttgccgg tggcgtattc gtggtgttgt gtgggaggct gacgggtctc  21120
ctatcgtgtg gcatcacccc atgtccggtt gggatgctgg cacgcaggtt aatgtgaagc  21180
gtaagaaggg ctgataggtt gtggctcagg atgtgaatgt gaagctgaac ttgtctggta  21240
ttcgtgaggt gttgaagtct tctggggtgc agggcatgtt ggctgagcgt ggcgagaggg  21300
```

tgaggcgtgc ggcctcggcg aatgtgggcg gtaatgcttt cgatagggcc cagtatcgtg 21360
ccgggttgtc gtcggaggtg caggttcacc gtgttgaggc tgtggcccgt attggcacca 21420
cctataaggg tgggaagcgt attgaggcga agcatggcac gctggcccgg tcgattgggg 21480
cggcgtcgtg atcgtctacg gtgaccccag gaaatgggct aaacgcgtgc tcaaggatga 21540
tggctggctg tctgatatac cctgtgtggg gacggtgcct gatgatttca gcggtgatct 21600
gatttggttg gctcttgatg gtggcccgca gttgcatgtt cgtgagcgtg tttttttgcg 21660
ggtgaatgtg ttttctgata tgccggatcg tgctatgtcg ttggcgcgtc gtgttgaggc 21720
tgtgctggct gatggtgtgg acggtgaccc tgtggtgtac tgtaggcgtt ctactggccc 21780
tgatttgctg gttgatggtg cacgttttga tgtgtattcg ctttttgagc ttatatgtag 21840
gcctgcggag tctgaataag cttattgttt ttgttttaat gtaattgttt gatatttaat 21900
gggggttatg atggctgcaa cacgtaaagc gtctaatgtt cgctctgctg ttactggcga 21960
cgtttatatt ggtgacgcgc acgcgggtga tactattaag ggtgtggagg cggttccttc 22020
cgggcttaca gctttagggt atctgtcgga tgacgggttt aagattaagc ctgagcgtaa 22080
aacggatgat ttgaaggctt ggcagaatgc ggatgttgtt cgcacggttg ctaccgagtc 22140
gtctatcgag atttcttttc agctgatcga gtctaagaag gaggttatcg agctgttttg 22200
gcagtcgaag gttactgctg gcgccgattc gggttcgttt gatatttctc caggcgccac 22260
cactggcgtg cacgctttac tgatggatat tgttgatggg gatcaggtta ttcgctacta 22320
tttccctgag gttgagttga tcgatcgtga cgagattaag ggtaagaatg gcgaggtgta 22380
tgggtatggt gtgacgttga aggcgtatcc tgcccagatt aataagaagg gtgatgcggt 22440
gtctggtcgg gggtggatga cggctttaaa agctgatact cctccgacgc ctcctccggc 22500
cccggttcct ccgaagcctc agccggatcc gaatcctccg gctggtaact gatacacgat 22560
tttagggatt gttgatagat gagtgacacg ggtttcacgt tgaagattgg tgaccgtagc 22620
tgggtgttgg cggatgcgga ggagacggcg caggctgttc ctgcccgtgt ttttcgccgt 22680
gccgccagga ttgcccagtc gggggagtct gcggatttcg cccaggttga ggtgatgttt 22740
tctatgttgg aggctgccgc cccggctgat gctgtggagg ccttggaggg gcttcctatg 22800
gttcgtgtgg cggaggtttt ccgtcagtgg atggaataca agcctgacgg taagggtgcc 22860
tcgctggggg aatagtttgg ctccacggcc tgattgatga ttatcgtggg gccatcgaat 22920
atgattggag gacccggttc ggttgctcgg tttatgatgt tggtggcccg gtgatgtgtt 22980
ggggtgaggc tgtccggctg gctggcgtgt tgtgtaccga tacgtctagc cagttggcgg 23040
cccacctgaa tggttggcag cgcccgtttg agtggtgtga gtgggcggtg ttggacatgt 23100
tggatcatta caggtctgct aatagtgagg ggcagccgga gcctgtggcg aggcctacgg 23160
atgagcgtag ggcccggttt acgtctgggc aggtggacga tattttggcg cgtgttcgtg 23220
ccggtggcgg ggtgtctcgc gagattaata ttatggggtg aatagtgtat gtctggtgag 23280
attgcttccg catatgtgtc gttgtatacg aagatgcctg gtttgaaggc tgatgttggt 23340
aaacatttgt cgggtgtgat gcctgctgag ggtcagcgtt ctggtagcct gtttgctaag 23400
ggcatgaagt tggctcttgg tggtgcggcg atgatgggcg ctatcaatgt tgctaagaag 23460
ggcctcaagt ctatctatga tgtgactatt ggtggcggta ttgctagggc gatggctatt 23520
gatgaggctc aggctaagtt gactggtttg ggtcatacgt cttctgatac gtcttcgatt 23580
atgaattcgg ctattgaggc tgtgactggt acgtcgtatg cgttgggtga tgcggcgtct 23640
acggctgcgg cgttgtctgc ttcgggtgtg aagtctggcg ggcagatgac ggatgtgttg 23700
aagactgtcg ccgatgtgtc ttatatttcg ggtaagtcgt ttcaggatac gggtgctatt 23760
tttacgtcgg ttatggcgcg cggtaagttg cagggcgatg acatgttgca gcttacgatg 23820
gcgggtgttc ctgtgctgtc tttgcttgcc aggcagactg gtaaaacgtc tgctgaggtg 23880
tcgcagatgg tgtcgaaggg gcagattgat tttaacacgt ttgcggctgc gatgaagctt 23940
ggcatgggtg gtgctgcgca ggcgtctggt aagacgtttg agggcgctat gaagaatgtt 24000
aagggcgccc tgggttattt gggtgctacg gctatggccc cgtttttgaa cggtctgcgg 24060
cagattttg ttgcgttgaa tccggttatc aagtctatca cggattctgt gaagcccctg 24120
tttgcgtcgg tggatcaggg gattcagcgg gtgatgccgt ctattttggc gtggattaat 24180
cgtatgccgg ctatgatcac gagaatgaat gcacagatgc gcgccaaggt ggagcagttg 24240
aagggcgttt ttgcgaggct gcatttgcct gttcctaagg tgaatttggg tgccatgttt 24300
gctggcggca ccgcggtgtt tggtattgtt gctgcgggtg ttgggaagct tgttgcgggg 24360
tttgccccgt tggcggtgtc gttgaagaat ctgttgccgt cgtttggtgc tttgaggggt 24420
gccgccgggg ggcttggtgg cgtgtttcgc gccctgggtg gccctgttgg tattgtgatc 24480
ggcttgtttg ctgccatgtt tgctacgaat gcccagttcc gtgccgctgt tatgcagctt 24540
gtgggggttg ttggccgggc tttggggcag atcatggtcg ctattcagcc actgttcggg 24600
attgttgctg gcgtggttgc caggttggcg ccagtgttcg gccagattat cggtatggtt 24660
gctggtttgg ctgcccaatt ggtgcctgtt attggtatgc ttattgcccg gctggttcct 24720
gttatcaccc agattattgg tatggtaacc caggttgctg cgatgatttt gcctatgctg 24780
atgccggtta ttcaggctgt tgttgctgtg atacggcagg ttattggtgt gatcatgcag 24840
ttggtgcctg ttttgatgcc ggttgtgcag cagattttgg gtgctgtcat gtctgttttg 24900
ccgccgattg ttggtttgat acggtcgctg ataccggtga tcatgtcgat tatgcgtgtg 24960
gtggtgcagg ttgttggtgc cgtgctacag gtggtggccc gtattattcc ggttgttatg 25020
ccgatttatg tttcggtgat tggattcatt gccaagattt atgctgcggt tatcgttttt 25080
gaggctaagg ttattggcgc tattcttcgt actattacgt ggattgtgaa tcattcggtg 25140
tctggcgtga ggtctatggg cacagccatc cagaatggct ggaatcatat caaatcgttt 25200
acgtctgcgt ttattaacgg tttcaagtcg atcatttctg gcggcgttgc cgcggttgtg 25260
gggtttttta cgcggcttgg tttgtcggtt gcctcccatg tgaggtccgg ttttaacgcg 25320
gctcgtggcg ctgtttcttc tgcgatgggt gctatccgga gtgttgtgtc ttcggtggcg 25380
tctgctgttg gcgggttttt cgggtcgatg gcttctcggg ttcgtagtgg tgctgtgcgc 25440
gggtttaatg gcgcccggag tgcggcttct tctgctatgc atgctatggg gtccgcggtg 25500
tctaacggcg tgcatggtgt gctagggttt ttccggaatc tgccgggcaa tattcggcgt 25560
gctctcggta atatggggtc cttgttggtg tctgctggcc gtgatgtggt gtctggtttg 25620
ggtaatggta tccggaatgc tatgagtggc ctgttggata cggtgcgtaa tatgggttct 25680
caggttgcta atgcggcgaa gtcggtgttg ggtattcatt cgccgtcgag ggtgtttcgt 25740
gacgaggttg gccgtcaggt tgttgctggt ttggctgagg gtattactgg taatgctggt 25800
ttggcgttgg atgcgatgtc gggtgttgct tcgcagcttc cggatgctgt tgatgcccgg 25860
tttggtgtgc gatcgtctgt gggctcgttt accccgtacg accggtatcg gcgtgcgagc 25920
gagaagagtg ttgtggtgaa tgttaacggg ccgacgtatg gggatccgaa cgagtttgcg 25980
aagcggattg agcggcagca gcgtgacgct ttgaacgcgt tggcttacgt gtgatagggg 26040

-continued

```
ggtgtggttc atgtttattc ctgacccgtc tgatcgtgcc ggtttgactg tgacctggtc  26100
tatgttgccg ttgattggtg atgctccgga gcgtgtgctt catttgacgg attatacggg  26160
gtcgtctccg gtgatgttgt tgaatgattc gttgcgcggt ttgggtgttc ctgaggttga  26220
gcatttttct cagactcatg ttggggtgca cggctcggag tggcgcgggt ttaatgtgaa  26280
gcctcgcgag gtgactttgc cggtgttggt gtcgggtgtt gaccctgatc cggtgggcgg  26340
gtttcgtgac ggtttttga aagcctatga cgagttgtgg tctgcgtttc ctcctggcga  26400
ggtgggggag ttgtcggtga agaccccgtc tggtcgtgag cgtgtgctgc ggtgccggtt  26460
tgattcggtg gatgacactt ttacggtgga tccggtgaac aggggttatg cgcgttatct  26520
gttgcatttg acggcttatg acccgttttg gtatggggat gagcaaaagt ttcgttttag  26580
taacgcgaag ttgcaggatt ggttgggtgg cggccctgtt aataagaagg gtaccgcgtt  26640
tcctgtggtg ttaacaccgg gtgtgggctc gggctgggat aacctgtcta ataagggtga  26700
tgtgcctgcg tggcctgtga ttcgtgttga gggtcctttg gagtcgtggt ctgtgcagat  26760
tgatggtttg cgtgtgtctt cggattggcc tgtcgaggag tatgattgga tcactattga  26820
tacggatcct cgtaagcagt ctgcgttgtt ggacgggttt gaggatgtga tggatcgttt  26880
gacggagtgg gagtttgcgc ctattcctcc tggcggttct cggagtgtga atattgagat  26940
ggttggtttg ggtgccattg ttgtgtcggt gcagtacagg tttttgaggg cttggtgaat  27000
agttgatggc tggtcttgtt ccgcatgtaa cattgtttac gccggattat cgccgtgtgg  27060
cgcctatcaa ttttttgag tcgttgaaac tgtcgttgaa gtggaatggt ttgtccactt  27120
tggagttggt ggtgtcgggg gatcattcta ggcttgacgg gttgacgagg ccgggtgcgc  27180
ggctggttgt tgattatggt ggtggccaga tttttctgg gcctgtgcgt agggtgcatg  27240
gtgtgggtcc gtggcggtct tcccgtgtga ctatcacgtg tgaggatgat attcgtctgt  27300
tgtggcgtat gttgatgtgg cctgtgaatt atcgtcctgg tttggtgggt atggagtggc  27360
gtgcggatag ggattatgct cactattcgg gtgcggcgga gtcggtggct aagcaggtgt  27420
tgggggataa tgcttggcgt tttcctcctg gtttgtttat gaacgatgat gagagtcgtg  27480
gccgctatat taaggatttt caggtgcggt ttcacgtgtt tgccgataaa ttgttgccgg  27540
tgttgtcgtg ggctcggatg actgtcacgg tgaaccagtt tgagaatgcg aagtttgatc  27600
agcgtggttt ggtgtttgat tgtgtgccgg ctgtgacccg gaagcatgtg ttgactgccg  27660
agtcgggttc gattgtgtcg tgggagtatg tgcgtgacgc cccgaaggct acttcggtgg  27720
tggttggtgg ccgcggcgag ggcaaggatc ggctgttttg cgaggatgtt gattcgatgg  27780
ccgaggatga gtggtttgat cgtgtcgagg tgtttaagga tgcccgtaac acggattcag  27840
agcatgtgca tcttattgat gaggctgagc aggtgttgtc cgagttaggg gctacgtcgg  27900
ggtttaagat cgagttggct gagtcggatg tgttgcgttt tgggccaggc aatctgatgc  27960
cgggtgattt gatctatgtg gatgtgggct cggggcctat tgcggagatt gtgcggcaga  28020
ttgatgtgga gtgtgattcg cctggtgatg ggtggacgaa ggtgacacct gttgcggggg  28080
attatgagga taatccgtcg gccctgttgg cgcggcgtgt tgccggtttg gctgcgggtg  28140
tgcgggattt gcaaaaattc tagaaaagat gaggggtttg ttgtgggtat tgtgtgtaaa  28200
gggtttgatg gtgtgttgac cgagtatgat tgggctcaaa tgtctggtct gatgggtaat  28260
atgccgtctg tgaagggccc ggatgatttt cgtgtgggca cgactgttca gggtgccaca  28320
gtgttgtgtg aggttttgcc ggggcaggct tgggctcacg ggtgatgtg cacgttgaat  28380
```

agtgttgaga cggtgacagg gcagctgccg ggccctgggg gggcccgcta cgactatgtg 28440
gtcctgtctc gggattggca ggagaatacg gccaagttgg agattgttcc tggggggcgt 28500
gcggagcgtg cccgtgacgt gttgagggct gagcctggcg tgtttcatca gcagttgttg 28560
gcgactttgg tgttgtcgtc tgacgggttg cagcagcagc tggataggag ggctatagcg 28620
gctagggttg cgtttggcga gtctgctgcg tgtgacccga ccccggtgga gggtgaccgt 28680
gtgatggttc cttcgggggc tgtgtgggct aatcatgcta acgagtggat gttgttgtct 28740
ccgaggattg agacgggttc gaagtcgatc atgtttggcg gttctgctgt gtatgcttac 28800
acgatcccgt ttgatcgcca gtttgctagt ccgccggttg tggtggcgtc tatggctacg 28860
gcggctgggg gcacggcaca gattgatgtg aaagcctaca atattactgc caaagatttt 28920
agtttggcgt ttattacgaa tgatggttcg aagccgaatg gtgtgcctgc ggttgcgaat 28980
tggattgctg tcggcgtgtg accgggttgt tgttgtggcg gatggtgtga tgttgggggg 29040
ctgtggtgtc gtggtttact cctgcactgg tggcctctat ttgtaccgcg ttggccacgg 29100
ttttgggttc tgttcaggcg gtcacgtcta aatctcggag gcgtttgcgg cggctgtcgg 29160
cgcaggtgga tgcgatggaa gagtatacgt ggggtgtgcg gcgtgaggtt cgccggttta 29220
acgctgggct tccggatggg gtggagccga tgcatcttcc tgatgtgcct gagtttttga 29280
aggatactgt tgatggtgga ggtgagtagg gttgagggag ttggaggagg agaagcggca 29340
gcgccgcaat tttgagaagg cttcactggt gttgttgttt ttgtcgcttg tgttgttggc 29400
ggtggttgct gtgggtgctt tgcgtttcgg ggcggtatcc tctgagcggg attcggagca 29460
ggcgagggcc cagtcgaatg gtacagcggc tcggggttta gccagcagtg tgaagcaggc 29520
gtgtgcttcg agtggggtgg agtcggtgcg gcttcaccgg tctggtttgt gtgtggatgc 29580
tgtgcgtgtt gagcggagtg tgcagggtgt gccgggtcct gccggtgagc gcggcccgca 29640
aggccctgca ggggttgacg gccgggatgg tgttaatggt tcggctgggc tggttggccc 29700
tgttggtccg cagggttctc ctggtttgaa tggtgtgaag ggtcctgacg ggttgcctgg 29760
tgtgaatgga tcggatggcc atgatggtgt tccaggtcgt gcaggtgctg acggtgtgaa 29820
cggcgctgat ggtcgggatg gttcgggcgg tgagcgcggc gatgtgggcc cttcaggtcc 29880
tgtcggaccc cctggtgcgc agggtgaacg ggg 29913

<210> SEQ ID NO 75
<211> LENGTH: 29562
<212> TYPE: DNA
<213> ORGANISM: Artificial Sequence
<220> FEATURE:
<223> OTHER INFORMATION: PAC263

<400> SEQUENCE: 75
aatggtgtga agggtcctga cgggttgcct ggcgttaacg gttcggatgg ccgtgatggt 60
gttccgggtc gtgcaggtgc tgacggtgtg aacggcgttg acggccggga tggtgttaat 120
ggttcggctg gtgagcgcgg cgaacagggc ccttcaggtc ctgccggccc ccaaggcgaa 180
cggggtgagc gcggccccgc cggtgctaac ggatccgatg gtaaagatgg taaagatggt 240
aaagatggcc gttctgtggt gtctgtgtac tgttctgatg gtcgcctggt tgtgaaatat 300
agtgacggtg tggcttccac gatatcgggc tcggtagcct gccagggtgt gaaaccgtcg 360
cctatagtga ctatatcatc ccacaaataa aagaggaagg gtgttactgt gattgtcatg 420
ttttggggtg gtgtgtggtg aggtttattc ctgcggcgca tcattcttcc ggttcgaata 480
gtccggtgaa tagggttgtg attcacgcga catgcccgga tgtggggttt ccgtccgcgt 540
cccgtaaagg gcgggcggtg tccacggcaa actatttcgc gtccccatcg gcgggtgggt 600
ggggtttccg tccgcgtccc gtaaagggcg ggcggtgtcc acggcaaact atttcgcgtc 660
cccatcggcg ggtggttcgg cgcattatgt gtgtgatatt tcggagactg tgcagtgctt 720
gtcggagtct acgattgggt ggcatgcccc gccgaatccg catagtttgg gtatagagat 780
ttgcgcggat gggggttcgc atgcctcgtt ccgggtgcca ggccatgctt acacgaggga 840
gcagtggctt gatccgcggg tgtggcccgc ggttgagaag gcggctgtcc tgtgccggcg 900
tttgtgtgac aaatataatg ttccgaagag gaaactgtct gtggccgatt tgaaggccgg 960
taaacggggt gtgtgtggcc atgtggatgt gacggatgcg tggcatcagt cggatcatga 1020
cgatccgggg ccgtggtttc cgtgggacaa gtttatggcc gtagtcaacg gcaaagatga 1080
gagtggggag ttaactgtgg ctgatgtgaa agccttgcat gatcagatta aacaattgtc 1140
tgctcagctt agtggttcgg tgaataagct gcatcacgat gttggtgtgg ttcaggttca 1200
gaatggtgat ttgggtaaac gtgttgatgc cttgtcgtgg gtgaagaatc ctgtgacggg 1260
gaagctgtgg cgcagcaagg atgctttgtg gagtgtctgg tattacgtgt tggagtgtcg 1320
tagccgtctt gacaggctcg agtctgctgt caacgatttg aaaaagtgat ggtggtttgt 1380
tgtgggtaaa cagttttggt taggtgtgct ggagcgggcg gctaagactt ttgtgcaaac 1440
gtttgttgcg gtgttggggg tgacggcggg tgtcacctat acggcggagt cgtttcgcgg 1500
tttgccgtgg gagtctgccc tgatcacggc tacggtggct gcggtgctgt cggttgctac 1560
atcgtttggt agcccagcgt ttgtggccgg taaacctaaa accacgcctg tggatgcggg 1620
tttggttcca ccggatgatg ggggcttggt tgagccgcac tcggtggatg tgtcggatcc 1680
tggcatgatt gagcctgcag atgatgtgga tcttggtgta ggctatgagc ctcggcgtgc 1740
tgccgagtcg gaggttggca cggtagagtc tactgttgca taagtgaata tatgtgtgtg 1800
ccccagcggt gctgccacga tcgtgtggtg gttgccgctg gggcactatt tttgtatatt 1860
gcggtgtggc tatgattcgt tgctgtcgat ggtgtcttcg agcatctgat acaggtggag 1920
gcaggtagag atcgtttcgc tggcctggtc gagaacgttc cggccgataa cgtttttgtg 1980
gttgtcgcgg tggcggatga tagaccacat gatctcgtcg gctgccgcct gcaatagttt 2040
tgcctgatat gcgatcccgg cgagccagtc tagtgcttcc tggcttgcat aggggctctg 2100
gtcctcgctg ttgccgcggg tgttgctgtt gtttgtgggg tgtcctgcac tgtcgcagaa 2160
ccataggatt tcgctgcact cgtctagcgt gtcttggtcg atagcgagat cgtcgaggct 2220
gacattgttg acggtaaggt tcacgttgtc gagggagatg ggtacaccgt actggttttc 2280
gacactgtca acaatgtttt gcagctggtt catgttggtg ggctgttgtt ggatgattcg 2340
gtgtaccgct gttttgaggg cggtgtaggg gatattggtt atgttgttca tggttttatc 2400
ccatccctgc gctgtcgtct tggtagtatc gactgtttgc gtaacctgtg agggtgatga 2460
gtgtttggtc tgcccactgt ttcacggttt gccgggtgac tccgagtcgt tgggctgcca 2520
ccgaataggt ttggtcatac ccgtatactt ccctgaaggc tgccaggcgt gctagccgtt 2580
tccgctgttt ggatggctgg caggtgaggg tgtagtcgtc tatcgctaat tgtaggtcga 2640
tcatggtgac gatgttgttg ccgtggtgtt ggggggcggt tggtgggggt ggcatgcctg 2700
gctccacact gggtttccat gggcctccgt tccagatcca ttgggcggct tggatgatgt 2760
cggcggtggt gtaggttcgg ttcactggtc atcccctgaa taggttgtcg aggttgtctg 2820
ggttgctggt gttggtggtg tcgaatcgtc ccacacagtg gcagtagtcg tacatgagtt 2880
taataatgtg ttggtggtct cccaaatagg tgtttccgct gatactgtag gtggctgtgc 2940
cgtctttact aatagtgtat ttggcggtga tggtttcggg tgtttctgtg ttggtgatga 3000
ttgctgtggt ggtggcgcct acggtttgta gcctggtggt ttgggttccg tcgtcgagga 3060
tggtagtaac catgagggtt gtcctttagt tgctggtttg gttgtcggct agatgaatga 3120
tatcgggtaa aggtttcggc tggtcgaggt gttgtatggt tttgttggct agccgtttgg 3180
ctaccctgta gcacattttg gtgtagtgtt tgttgtctag gttgtggtat tgttcccgca 3240
ccgcaatata tagtagggag tcttggtata ggtcgtctgc actgattgcg gggtagtgtg 3300
tggctgtttt ggtgcatgcc cggttgagtg tgcgtagatg atggtctgtg gcccacaccc 3360
acgatgcggt ggtggctagg tcggcttttg ttggtcgtct gctcatggca ctattacctg 3420
gctatctggt agttgtttgg tgttttgttg ttgatagtgt agcacacgag tccggggttg 3480
ccggtggtgc ctgtgcggtg cctataccag acggattctc cttccatgga tgggcattgg 3540
atgaaggtgc gttgtccttg ctcggagatt tcgaggtggt gccggtgtcc ggccatgagg 3600
atgtgggatg tggtgccgtt gtggaattct tggccgcgcc accattcgta gtgttggttg 3660
ttgcgccatt ggtgtccgtg ggcgtgcagt atttgtgtgc cggccacatc aacggtggtg 3720
gtcatttcgt ctcgtctggg gaagtggaag tgaaggttgg ggtagttgtt ggtgagttgg 3780
taggcttcgg cgatggcgcg gcagcagtct acatcgaagg agtcgtcgta ggtggtgact 3840
cctttgccga atcgtacggc ttcaccgtgg ttgccgggga tggaggtgat ggtgacgttg 3900
gcgcagtggt cgaacatgtg gacgagttgc atcatggcca tgcgggtgag cctgatttgt 3960
tccgtcaagg gtgtttgtgt gcgccacgcg ttagagccgc cttgtgacac gtatccttcg 4020
atcatgtcgc cgaggaatgc gatgtggacc cgttgcggct ggcctgcctg ttgccagtag 4080
tgttttgcga ctatgaggga gtgcaaatag tcgtcggcga agtgtgctgt ttctccgccg 4140
gggatgcctt tgccgatttg gaagtcgcct gccccgatga cgaaggccgc agtgctgtag 4200
tcggtgtggg tgtcttgttc gggtttgggt ggctgccatt cggctagctt gtcgacgagt 4260
tcgtctatag ggtaggggtt tgttgcgggt tggtggtcga tgattttttg tatggatcgg 4320
cctgtttctc cgttggggag tgtccattcg gagatgcgtg tgcggcgtac ggtgccgttg 4380
gctaggttgt cgtcgatggt gtcgatggcg ttgtcgtggt tggctagttg tgtgagtagc 4440
cggtctatat tgtctatcac tgggtatcct cctcttcctc gtgtgtggtg gtggcttgtt 4500
tgcggcggta gtctttaatg acggtggcgg agatggggta tcctgcctgg gtgagcattt 4560
gggctagctg tgtggcgggg atagacctgt cggcgagcac gtctgcagcc ttgcggccgt 4620
agcgttggat gagggtttca gttttggttg ccatgatgtc ccatcggttg tgtggtgggc 4680
tgccatcctg tgcggcagtc gccgtcgtgt cctggtttgc gtgtgcacca cgatacggtt 4740
ccgtctgtgt ggttgagtgt tttaccgcac atgacgtttt gtagatgctc cggcagctcg 4800
ctattgctat cgtcttgctc gtctagcaaa gttttttgtt gggtgaaaaa ctcggacacg 4860
gtgccgttgt ggactgggag tatccatgtt ttccattgtt gttgtagccg ggtgttccag 4920
tggaattgtt ttgctgcgtt cgtggcttgt ttgatggttt tgaagtagcc tacaatgatc 4980
cgttgatggt cactatcggg cttgtgtggc cctttccaat attgggcagc tacagcgtac 5040
ctgttgttgt ctgtgaagcg cccccagcag tattccacca tgtgtgatag taccttgtcg 5100
ggcatgtctc gtacttggtt ttcgtcgagc catgcgtcga caataatgtt gcgtatggct 5160
cgcttgtctt tggtggtggg tttgaatgcg atgctcacaa tgcgggcctg tcgtcttgca 5220
tgaactggtt gaaggtgttg ttcccggcgt gttgggcttg tgtgatttgc tggtcggtcc 5280

-continued agtcggggtg ttgctgtttc agatagtgcc agtggcacgc attgtaggtt tcgtcttgga 5340
gccgtgtgag atggttttcg gtgatgattt gtttccacat ggcccatgac acgtcgagcc 5400
ggttgaggat ttcgagggct gggatgttga attggttcag gaagaggatt tcatgggtgt 5460
agtagttttt ctcgtaggcg tcccatccgc ttcggtgcct gttgggctgg tttttggggt 5520
aggcttcccg gcagattttg tgtaaccgtt tggccatgtc tttgggtagt ttaatgtcgg 5580
ggttggcgcg gatcatggat cgcatcccat cataggtggt gccccaggtg tgcatgatgc 5640
ggagtgggtc ttcaccatcg gcccattttt ctgcacagat ggcgaggcgt atgcgtctcc 5700
tggcggcttt actggtgtcg cggcggccgg ggatggggca ggtgtcgagg ggatccatga 5760
tgttttagtg tacctttccg tgttgtggtt gtttgtctgg ttttattgta gcactgtgtt 5820
gagggcttgt gtcaaccctg tttttccgac ctgaaggtag gtgtctgtga catcccccag 5880
ggtgaggggc acatgggtgg cttgggggag tgccgtctgg aaggtttggg ccatctggtc 5940
tcctgctttg tctgggtcgg accagatgta gatgtggtcg tagccttcga agaatttggt 6000
ccaaaagttt tgccacgagg ttgcgccggg tagggcgacg gccgaccatc cgcattgttc 6060
gaggatcatg gagtcgaatt cgccttcgca aatgtgtatt tcggctgccg ggttggccat 6120
ggcggccatg ttgtagatgg agcctgtgtc tcctgccggg gttaggtatt tggggtggtt 6180
gtgggttttg cagtcgtgct ggagtgagca gcggaaacgc atttttctta tttcggctgg 6240
cccttcccaa acggggtaca tgtatgggat ggtgatgcac tggttgtagt tttcgtggcc 6300
tgggatgggg tcattgtcga tgtatccaag gtggtggtag cgggctgttt cttcgctgat 6360
gcctcttgct gagaggaggt cgagtatgtt ttcgaggtgg gtttcgtaga gggccgaggc 6420
tttctggatt cggcggcgtt ccgcaatgtt gtatgggcgt atgctgtcgt acattcgggt 6480
tttcttcttc taattgttgt tgtagtttgg cgaggcctcc tccgataccg catgtgtggc 6540
agtaccagac gcccttgtcg aggttgatgc tcatggaggg ctggtggtcg tcgtggaacg 6600
ggcagaggat gtgttgctcg ttcttggacg ggttgtaccg tatgtggtag gtgtcgagga 6660
ggcggcgggt gtcagaggtg tgggaggagc tcgttgaggg ttgataccac ataggcttcg 6720
ctccagggtt tgttgcgctg tttcatcact acgagtccga tagtggactg gttttcgcgg 6780
tttcggtggg tttcgtagtt gcgtgcctcc cggctggctt gtttcacgaa ttcggcgagg 6840
tggggctgcc cggctttggc ttcgataatg taggttttgt tgccggtggt gaggatgagg 6900
tcgccttcat cctctttacc gttgaggtgg aggcgttcta tatcatggcc ggtgtcgcgt 6960
agctggtgga ggagtcgtgt ttcccattcg gctccggctc ggcggtttct tgattgttgt 7020
gtcgacatga tagtcctttg tggtgttcgg tcatgttcca tggctgtttt tcggcgagtg 7080
gcccgaagaa tgtgtattcg ggtaggctc tgagtctttc gtatcgggtt ccgtctgggc 7140
tggatttgcc tgtgcgctgt ttgagtacag cgatgcgtgc ctctgccggt atcgataggc 7200
cgttgccgtt gtcttcgcca ccatacaggg agactcccaa tatgagttgt ggtttttcgg 7260
agaggccgtt tttgatttcc cgcctagccg gggggtgttc gatgtcggag ccggttttgt 7320
cggttgcgtg gtgtgtgaca ataatggtgg agcccgtgtc cctacctaat gctgtgatcc 7380
attgcatggc ttcttgctgg gcctgatagt cactctcgca gtcttgtatg tccatcaggt 7440
tgtcgataac gatgatgggt gggaaggtgt tccacatttc catgtaggct tgcagttcca 7500
tggtgatgtc tgtccatgtg atgggtgact ggaatgagaa tgtgatgtgt ccgccgtggt 7560
ggatgctgtc tcgatagtat tctggcccgt agtcgtcgat gttgtgttgt atctgggcgg 7620

-continued

```
tggtgtgttg ggtgttgagt gagatgattc gtgtggaggc ctcccagggg gtcatgtccc   7680
ctgatatgta gagggctggc tggttgagca ttgctgtgat gaacatggct agcccggatt   7740
tttggctgcc ggagcgcccc gcgatcatga cgagatcccc tttgtggatg tgcatgtcca   7800
ggttgcggta gaggggttct agctggggga tgcggggcag ctcggctgcg gtttgggagg   7860
ctctctcgaa ggatcgttgg agagagagca tcgggacctt atctatctgt ctatcggttg   7920
gatgatgttt tggtggtcag atggagtcga tgtcgatgtc agcatcagca ggggctgtgg   7980
tgtcgtctag ctggccgtta tcgcgtttgt ctacgtattc ggcaacctta tcgtagatgg   8040
cgtcgtcgag ggtttgagc acgaccgcgt tgaagccgtt tttggtgcgt acggtggcga   8100
gtttgaaggc ttgttcttcg ccaaggtagg cttcgaggtc gcggatcatg gagtgtgggc   8160
ggtcgttgct gccgcgtact ttttcgatga tggcgttggg gatggtttct ggggtgccgt   8220
tgttgaggtc gtctagggtg tggaagatgg tgacatcagc gtagatgcga tcggcggtct   8280
gtccaccgta gccttcggtg ttgtgttcta cgtcgtggat tttgaaggcg atggcggtgg   8340
cgtcctggtt tcgggagggg ttgaagaagg tgctgttgct gttgtttcgg tagtttgcga   8400
gtcccattgt tgtatccttt actgttttgt tggtttgtgt aggttttatc gggtgaggct   8460
gtttcgtttg ctgcggaaag cctcggaaac gtcactgtta ctggtgatga tctttttgta   8520
ctgtttgaga aggtcggcta gctgtgcttt gctggttgca ttgttgattt tgtcgatgat   8580
ggtgttgttt ccttctgagg cgatgttgtc tacgtagtct ttggcggcct ggttgtagcg   8640
atcttggagg atgatggatg ctgtggcgat cagtgttgcc aggtcccagt tccgtgccgc   8700
cgaactgttt ttgagtccgc ctaacaggtc gatgatggcc tgttttgtct gctctgctgt   8760
gtctcctcgg atgaccgccc atggtgcagc atagtctcca ccgtatttga gtgtgatcgt   8820
gagtcgatca ttgtcgatct tgtctttatc ggtcatttgg tgtccttttc tttattgtct   8880
gtttctggtg gctgtacggt agattctacc gggtacctgt aggcgtcttt cccgttgacg   8940
gcccagcagg cgtcttgtac ggggcagcct ttacagagtg ttgtgacgtg tgggacgaag   9000
atgcctgcgc tgattccttt cattgcttga ctgtacatgg atgatacatg ccggtaggtg   9060
ttgttgtcaa ggtcgtacag ttcggtggat gtgccttgtg tcggggactt gtcgtcgttg   9120
cggctggtgg ccggcgtcca aaacatgcct tttgttacat cgttgccgtg ttggttgagc   9180
atgtaccggt aggtgtgcag ctgcatactg tcggcgggta ggcgtccggt tttgagatcg   9240
aggatgaagg tttcgccggt gtcggtgtcg gtgaagatac ggtcgatgta gccaacgatc   9300
tgggtgccgt cggggagggt ggtttctacc gggtattcga tgcctggttt accgtccagg   9360
attgcggtga tgtattctgg gtggttgcgt ctccatgttt tccagcggtc cacaaaggtg   9420
gggccgtaca tcatccacca attgtagtct tttttgtgtg gcccgcccga ttcgcacatg   9480
tttttgcata ttctgccgga gggtttgatt tctgtgcctt cggattcggc gagggctact   9540
tgtgtggcga aaatgttttt gaaggatgcg agtttgtctg gtagcgcagg gtattcggcg   9600
gggttgtata ggtgtaggtc gtattgttcg gtgatgtggt gtatggcgct tccggcgatg   9660
gtggcgtacc aggtgtggtg ttgggtgtgg tatccgtgtt ggagacgcca tttttcgccg   9720
cattcggccc attgtgacag tgatgagtag gagatgtggc ctggatggtt gatggttttc   9780
gggtattgtg ctagaggcat tacttgtcgc ttttgttcca tgggtttcgg gtgtcttggc   9840
cggcatcgtg ttgctggtat gcgaggagtg cgaggcagtg ccaggcagca tgggctagat   9900
gcggtagccc ggattcataa tcgaggttgt tgccttgctg ccatgataac aggtgccggt   9960
agagggcatc aacgctgtgg ctccacgggt atcctccggt ccagttgttg tcgccgtatt  10020
```

tggtggcacc gtagcctgct acgtcgccga gagcgtgaag ggatgctggg tcgatgaggg 10080
agagcctgca aagtttgagt tcttttcggg caccgctgtt ggggtcggtg tacatgcggg 10140
ttggctcatc catgagatat gtgctcctta agcgtgggtt actggttagg gttgtgggcg 10200
agtgctacgg cgagaataat gatggcgagg gtttcagcga tgatgatggg tgttgtgatc 10260
atttgctgtc tcggggattg ttggtgagtg ttgatgcgcc taggagggtg gtgagggcgc 10320
atgcggcaat gatggcgagg gctgccttgt gtggggtgcc ggttgcgtac atccatgtga 10380
tgatgccgcc ttggatccag gctaggctgg tgaagaacgt ttcgtagctg tgtagctcaa 10440
tgttgttgtt gggtgtgttc atgcttgctc ctgaagaatg gtgttgatgg ttttataaat 10500
gttgtacagg tcggcttcga tggtttgtag ctgtttgatt tggtggtcga gattaatgtc 10560
tgggttgagg gtgttgatgc gggaggcaat atctgtggct gtgcgtagtg ttccgccggt 10620
gtggtgaata atgtgtgccg tgtcggcgag tccggtgatg acagcgtagt gggataggag 10680
aggcatagct ggggggtgct ccttggcggg ttactgttgc gggttgatgt tgaggtcggt 10740
gacgtgcggg tggtcttctg ttccggtgac gaggcagtgg acggtgacgg gtagtttgga 10800
tgcgccggga tgtttcgcgg ttgcgccgta gacgatggag aaggtgtctt taccaataat 10860
tttgtggagt tggaggtcga tgtcggggtt gccgttccag ttgaggccgt gtgcggcggc 10920
ctgttgttcg gctttgcggt tgcaggtgtg tgctgccgtg atcatggtga gtccggtggc 10980
ggtttcttca ccccgtgttt gggcttgctt gtgggctttc tgctgttctg cttgtaggga 11040
gcggactgcg gctgcctgct tggctgtttt ctcggctttg cgctgttgga cggttttggg 11100
ggtccattcg gtgttggctg tggtggcttg tggggctggt tgtgaggcga gtggcggatt 11160
gtcgtcgggt gctgggagga aagagcatgc ggcgatgatg gcggctgtga ttccggcgat 11220
ggtgtagccg tttttcttgt tcatggctgt tgtccccttt ccggggtgtt gttcgttgct 11280
gacatgatca atacttccag cgaatggacc tcgtgtcaag actgcgctca aatgttctga 11340
gcgatccttg tgtggctagg ggttttatcg ggcgcatagg gtgagtaggt ggcctacgtt 11400
gatgcggctc acattccagt agagttgtgt ggcttcaccg ccggtgagcg gcttccactc 11460
gtcgtggctg aacacggtgc catcggatgc gatgaacgtg tcggggcgta gcttgtgaag 11520
ttcggcttcc acgctctgcc ggtaggtttc ggcgaggccc tcaaaatcca tgtggtcgca 11580
ggagaggttt tcgaggcgtg tcaggtcgaa gggtgtgggg cagtcgtagc tggcgggggt 11640
gtagagctgg gtgaagtggt cggcgatctt ctgcatgacg ggttcctttt ctcgtgtggt 11700
gggttgatgg tttttatcgt gtggcttcgg cgatgatggc gtctacatag atcatgtcga 11760
tgagatcgtg gagttcctcg gcctcattct cggagaggtg gcgccagtcg ggtggcccat 11820
atactgcgcc gtcgagggtg acagtccaca gtggccggat gagtcgtatg gcttcttgta 11880
ctttagcgtg gtacatgcgg cgcaccatat cgagatcgat gtcgtctgaa tggtttccgg 11940
tgaggctgtg gaggctaagc gggtcgattt ctgtctgcct gtagagggat gtgaaggatg 12000
gtgtgatgag tgtgccatcc atgatgggtg tgctcctttc ggtggtgtag gggttgttgt 12060
ggtttttatg gtgtgagggt tgtgatccat agtcaaggct gcgctcaatc ggattgagcg 12120
tttcatggag tgtgtcgggt gtgacagatg tcactgaagc ctttattgcc tctctcagcg 12180
tctcaaatct tctaggggta gaaatatact agggcagccc tataaatcga ttctaggccc 12240
ctttctgtga ctctgagggg catatgtgag tggagggtgg tatgacaggt ggcatggact 12300
tggaggaagg tgtccagtcg ggagcgctcg atgatccggc tgcacgggtg tctggaaggc 12360
ttatggtctg cgtgagatat gtcacatcac ctagactcta ggaacactac ccacacctgt 12420
agagtctatt ctgcagatgg caccagagcc aagaatgcct ctctaaggca cgtaaaggcc 12480
cctctgaggc tcttacaccc tcaactctag gtatttgtac ccccagcata ttctgatcga 12540
ttctagggcc ctttttgagg cttacgcgag aacagcaccc aaagactagc ccatcaaccc 12600
ttactctggt tagctaagcc tgcactatgt ggacagtgtg ggatgctaag agggaagaag 12660
gacacggtaa aagaaaaaag ggggagtacc agccttcacg ccttcaagcc ttaaggtctt 12720
agcactaagc acttagcacc gagccccctc aagggctcgg catcagcccg agcaggctca 12780
gccctgaaag gggtacacgc catcagggaa ggcttgagag tacgaggagc cttagcgacg 12840
agtactcgaa agcctgagga aacaccatca gcactgatgg gcctagcgcg ttcggaaagg 12900
acacaagagt aaagtgtgac agctatccgg gagtgaaacc cgttctggct aggggtttca 12960
gccttaacca cctgtaaagg ttacaagact ctaagaaaat ttaagaaact tcttaggaag 13020
aaagttgtgt tgatgtcacc ccaaaaacac ctaaaatagc cctcaaaccc gcctatagag 13080
ccaaacagtc aagtttgact cgtcttgacg gcgtatgcta ggctggacag gtagccagct 13140
ggacgcaagg ccagaaagtg ctgacgcact tcccgacctt gcttaccatc agtctaccaa 13200
agacttaaaa gtttaacagc taagcgctaa gcccttaaga cctaaacgct tagcaccgag 13260
ccccctcaag ggctcggcat cagtcctaag agcttagccc ttaaggatct aaggttacta 13320
taaagcttta aacactttaa gtaaacttaa gagcttagca cttaaagtta attaataacc 13380
ttaaaggctt acacacttag cactgagccc ttcaaggctc agcatcagta taaagacctt 13440
aacacctaag ttaagtataa aactttaaag gcttagcgct taaggatata aacttaacat 13500
cagtgtttaa gacttaaaga gttaaacact taaagtaact ataatacttt aaaaatctta 13560
agtacttaaa gttaaccatc agtcttaaac tttaatatta taacctataa gtattaaagc 13620
ttataagtta taaaagtttt agaagagcta aggggttaac ttctttactt ctcttctctc 13680
tttggttctt tctctcttct ctccttttct tcatcagggg agaagaggaa cctttaccat 13740
cagcgccgat gggcttttca tcgtgtgact cgtgtgcttc tggtcgcaag ctcccatcgc 13800
acactcccca cactcttaca cccgtgcccc tttcaggctt agcgtgttcg gctgaaggcg 13860
tacggcgtgt cacgctcaca cccttaacac cgggtgagac ttaaagtgta tattatatgt 13920
agaagacttt aaaacctata gagtgtttct gctgagcctg tgtcctacac cgctaggcgc 13980
caagcgctaa gccttgaaac gcgaacacac acccaccccc ttttctcttt cgtgtccttc 14040
tcttttgaca ccgctggggg gcgatgtgat ctttctcaca tgccaggggg tagtggagaa 14100
aacaaacacc ccggcacaaa cagaacaccc cctcaaacga acaaaacagc ccccaggatc 14160
gactagcagg gcaagggtag agtattcata cccccagacg attccaggcc gttagagagg 14220
caatgagagg ctcacagggg tcatgggaga tcggggaacg cgatggcaca caccaaccgc 14280
acagccagcc aagcccaccg acgctggcgg caacgactca tcacccaagc ccgacaacaa 14340
ggccaaaccg aatgcccact ctgcggagca accatcacct gggacacaca ccagctgcca 14400
accagccccg aagccgacca catcacaccc gtcagcaggg gaggactcaa caccctcgac 14460
aacgggcaaa tcatctgcag aacatgcaac agaagcaaag gcaatcgcag cgaaccaaac 14520
atcaaattcc aacaacaaac cacaaaaaca cttgtttcat ggtgacaaac ccgccaaccc 14580
ccaccgggca cacccccctgc acacccgtgc aagacctcgt acggcttagt gaaatacctc 14640
ccttttgtgg atttgtctgt ttgtcgactt tttgtgttgg tggtgagtgt ggtgcagcct 14700
gagcttcctg atggtcgtga gtggtgtggg gagacgcgtc gttggtggcg tgtgtggggt 14760

```
gaggatagtc gcgcgcagta cgtgtctgat gaggagtggc tgtttctcat ggatgctgcg  14820
gtgattcatg attgtgtgtg gcgtgagggt cgcgcggatt tggtggcttc gcttcgtgct  14880
catgtgaagg cttttatggg tatgttggat cggtattcgg ttgatgtggc gtctggtggc  14940
cgtggtgggg gttctgcggt ggcgatgatt gaccggtata ggaagcgcaa gggggcctga  15000
ttaggtgtct ggtgttgttg ggtctcaggt tcctcgtcat cgtgtggctg cggcgtattc  15060
ggtgtctgct ggcggtgatg cgggtgagct tggtagggcg tatgggttga cgcctgatcc  15120
gtggcagcag caggtgttgg atgattggct ggctgtcggt ggtaatggca ggcttgcttc  15180
gggtgtgtgt ggtgtgtttg tgcctcgcca gaatggcaag aatgcgatcc ttgaggttgt  15240
ggagttgttt aaggcgacta ttcagggtcg ccgtattttg catacggctc acgagttgaa  15300
gtcggctcgt aaggcgttta tgcggttgag gtcgtttttt gagaatgagc ggcagtttcc  15360
tgacttgtat cgtatggtga agtcgattcg tgcgacgaat ggtcaggagg ctattgtgtt  15420
gcatcatccg gattgtgcca cttttgagaa gaagtgtggc tgtccgggtt ggggttcggt  15480
tgagtttgtg gcccgttctc gtggttctgc tcgcgggttt acggttgatg atttggtgtg  15540
tgatgaggct caggagttgt cggatgagca gttggaggct ttgcttccta cggtgagcgc  15600
tgccccgtct ggtgatccgc agcagatttt cctgggtacg ccgcctgggc cgttggcgga  15660
cgggtctgtg gtgttgcgtt tgcgtggtca ggctttgtcg ggtggtaaaa ggtttgcgtg  15720
gacggagttt tcgattcctg acgagtctga tccggatgat gtgtcgcggc agtggcggaa  15780
gttggcgggg gatacgaatc ctgcgttggg tcgtcgcctg aatttcggga ccgtaagcga  15840
tgagcatgag tcgatgtctg ctgccggttt tgctcgggag cggcttggct ggtgggatcg  15900
tggccagtct gctacgtcgg tgattccggc tgataagtgg gctcagtcgg ctgtggatga  15960
ggcgagtctg gttggcggga aagtgtttgg tgtctcgttt tctcgttctg ggatcgggt   16020
tgctttggct ggtgccggcc ggactgatgc tggggttcat gttgaggtta ttgatgggct  16080
gtctggcacg attgttgatg gtgtgggccg gttggctgac tggttggcgg ttcgttgggg  16140
tgatactgac cggatcatgg ttgccgggtc tggtgcggtg ttgttgcaga aggcgttgac  16200
ggatcgtggt attccgggcc gtggcgtggt ggttgccgat actggcgtgt atgtggaggc  16260
gtgtcaagcc ttcctggaag gtgtaaggtc tgggaatgtt tctcatcctc gtgctgattc  16320
tcgccgtgac atgttggata ttgctgtgag gtcggctgtg cagaagcgta aggggtctgc  16380
gtggggttgg ggttcctcgt ttaaggatgg cagtgaggtg cctttggagg ctgtgtcttt  16440
ggcgtatctt ggtgcgaaga tggcgaaagc gaagcggcgt gaacggtctg gtaggaagcg  16500
ggtgtctgtg gtatgaactc ggatgagttg gctctaattg agggcatgta cgatcgtatc  16560
caaaggttgt cttcgtggca ttgtcgcatt gagggctact atgagggctc gaatcgggtg  16620
cgtgaccttg gtgtggctat tccgccggag ttgcagcgtg tgcagactgt ggtgtcgtgg  16680
cctggtatag ccgtggatgc tttggaggag cgtctggatt ggcttggctg gactaatggt  16740
gacggctacg gcctggatgg tgtgtatgct gcgaatcggc ttgctacggc gtcgtgtgat  16800
gtgcatttgg atgcactaat ttttgggttg tcgtttgttg cgattattcc tcatggtgat  16860
gggtcggttt tggttcgtcc gcagtcacca aagaattgca caggtaagtt ttcggctgac  16920
ggttctcgtc tggaggctgg ccttgtggtg cagcagacgt gtgatcctga ggtggttgag  16980
gctgagcttt tgttgcctga tgtgattgtt caggtggagc ggcggggttc gcgtgaatgg  17040
gtcgagacgg gccgtattga gaatgtgttg ggtgcggttc cgttggtgcc tattgtgaat  17100
```

cgtcgtcgta cttctaggat tgatggccgt tctgagatta cgaggtctat tagggcttac 17160
acggatgagg ctgttcgcac actgttgggg cagtctgtga atcgtgattt ttatgcgtat 17220
cctcaacgtt gggtgactgg cgtgtcggct gacgagtttt cgcagccggg ttgggtcctg 17280
tcgatggctt ctgtgtgggc tgtggataag gatgatgacg gtgacactcc gaatgtgggg 17340
tcgtttcctg tcaattcgcc tacaccgtat tcggatcaga tgagactgtt ggcgcagttg 17400
actgcgggtg aggcggctgt tccggaacgc tatttcgggt ttatcacgtc taacccacct 17460
agtggggagg ctttggctgc cgaggaatct cggcttgtga agcgtgctga acgcaggcag 17520
acgtcgtttg gtcagggctg gttgtcggtt ggttttttgg ctgccaaggc gttggattct 17580
cgtgttgatg aggccgattt ttttggtgat gttggtttgc gttggcgtga tgcttcaacc 17640
ccgactcggg cggctacggc tgatgctgtg acgaagcttg ttggtgccgg tattttgcct 17700
gctgattctc gtacggtgtt ggagatgctg gggcttgatg atgtgcaggt tgaggctgtg 17760
atgcgtcatc gtgccgaatc tgcggatccg ttggcggcac tggctggggc tatatcgcgt 17820
caaactaacg aggcatgata ggcgatggct tcgggtgcta tgtcgaggct tgctgcgact 17880
gagtatcagc gtgaggcggt caggtttgct gggaagtatg cgggctatta tgccgagctg 17940
ggtcgtttgt ggcgtgccgg gaagatgaca gacgcgcagt atgtgcgttt gtgtgtggag 18000
ttggagcgtg ccggccatga tggttcggca tcgttggctg ccaggtttgt gtcggatttt 18060
cgccggttga atggtgtgga tccgggtttg attgtgtatg acgagtttga tgctgccgcc 18120
gcgttggcta ggtcgttttc gactatgaag attcttgaga gtgacccgga tagggcgaat 18180
gacacgattg atgcgatggc tgcgggtgtt aatcgggctg tcatgaatgc tggccgtgac 18240
acggttgagt ggtctgcggg tgcgcagggt aggtcgtggc gtagggttac tgatggtgat 18300
ccgtgtgctt tttgtgccat gttggctacg aggtcggatt atacgacaaa agaaagggca 18360
ctcactaccg gtcatacgcg gcgtcataag cgtggtggta agcgtccgtt tggttcgaag 18420
tatcatgatc attgtggttg tacggtggtt gaggttgttg gcccttggga gccaaatagg 18480
gctgatgtcg agtatcagag gacgtatgag aaggcccgtg agtgggttga tgatcatggg 18540
ttgcagcagt cgcctggcaa tattttgaag gctatgcgta ctgttggcga tatgagataa 18600
tttgatgtgg tttccggttg tgcgccgccg gttattggtg cacagggttg tctcccgcac 18660
gggggtcaac aatgttgtgt tgttttccgc aaggagtgta gggttaggct atggccgatc 18720
agagtgttga ggaacagaat gttgacaatg atgttgtgga gtccggaaag gataacggca 18780
ttgttgatac agtaaaagac gatggcgggc aggaggtagc cgacaatcag ttgaagaatg 18840
aaggcgaggg taaatcgccg gggactgatt ggaaggcgga ggcccgtaag tgggagtctc 18900
gtgctaaaag taatttcgcc gagttggaga agcttcgcgc ctcggatggt gattctggat 18960
ctactattgc tgagcttcgc cgcaagaatg aggaactcga agacaggatc aacgggtttg 19020
ttcttgaggg tgtgaagcgc gagatggctt cagagtatgg tttgtccagt gatgcgatcg 19080
ttttcttgtc gggtggcgat aaggagtcgc ttgccgagtc tgcgaaagct ttgaagggtt 19140
tgatcgacca tagtagtggt ggcgcgggtg tgcgccgtct tgcggggagt gcccccgttg 19200
atgatgttaa acgacgtgag ggtgtcgcgt ttgtggatgc tcttgtcaat aattctagga 19260
gatgatttgt gatggttgac gattttcttt ctgcagggaa gctggagctt cctggttcta 19320
tgattggtgc ggttcgtgac cgtgctatcg attctggtgt tttggcgaag ctttcgccgg 19380
agcagccgac tatttttggc cctgttaagg gtgccgtgtt tagtggtgtt cctcgtgcta 19440
agattgttgg tgagggcgag gttaagcctt ccgctagcgt tgatgtttcg gcgtttactg 19500
cgcagcctat caaggttgtg actcagcagc gtgtctcgga cgagtttatg tgggctgatg 19560
ctgattaccg tctgggtgtt ttgcaggatc tgatttcccc ggctcttggt gcttcgattg 19620
gtcgcgccgt ggatctgatt gctttccatg gtattgatcc tgccactggt aaagcggctg 19680
ccgctgtgca tacttcgctg gataagacga agcatattgt tgatgccacg gattctgcta 19740
cgaccgatct ggtcaaggct gtcggtctta tcgctggtgc tggtttgcag gttcctaacg 19800
gggttgcttt ggatccggcg ttctcgtttg ccctgtctac tgaggtgtat ccgaaggggt 19860
ctccgcttgc cggccagcct atgtatcctg ccgccgggtt tgctggtttg gataattggc 19920
gtggcttgaa tgttggttct tcttcgactg tttctggcgc cccggagatg tcgcctgcct 19980
ctggtgttaa ggctattgtt ggtgatttct cgcgtgttca ttggggtttc cagcgtaact 20040
tcccgatcga gcttatcgag tatggtgacc cggatcagac tgggcgtgac ctgaagggcc 20100
ataatgaggt tatggttcgt gccgaggctg tgctgtatgt ggctatcgag tcgcttgatt 20160
cgtttgctgt tgtgaaggag aaggctgccc cgaagcctaa tccgccggcc gagaactgat 20220
ttattgttgc ggtgatgtgt caatgtgcag gggtggtgt tgatgggtat catttgaag 20280
cctgaggata ttgagccttt tgccgatatt cctagagaga agcttgaggc gatgattgcc 20340
gatgtggagg ctgtggctgt cagtgtcgcc ccctgtatcg ctaaaccgga tttcaaatac 20400
aaggatgccg ctaaggctat tctgcgcagg gctttgttgc gctggaatga tactggcgtg 20460
tcgggtcagg tgcagtatga gtctgcgggt cctttcgctc agactacacg gtctagtact 20520
cccacgaatt tgttgtggcc ttctgagatt gccgcgttga agaagctgtg tgagggtgat 20580
ggtggggctg gtaaagcgtt cactattaca ccgaccatga ggagtagtgt gaatcattct 20640
gaggtgtgtt ccacggtgtg gggtgagggt tgctcatgcg ggtcgaatat taacggctac 20700
gctggccctt tgtgggagat atgatatgac cagttttcct tatggtgaaa cggttgtgat 20760
gcttcaaccg actgttcgtg tcgatgatct tggtgacaag gttgaggatt gggggcatcc 20820
tgtagaaacc gtgtaccata acgtggccat ctatgcttcc gtttcgcagg aggatgaggc 20880
cgcggggcgt gactctgact atgagcattg gtcgatgctt ttcaagcagt ctgttgttgg 20940
tgctgattat cgttgccggt ggcgtattcg gggtgttgtg tggggggctg acgggtctcc 21000
tatggtgtgg catcacccca tgtccggttg ggatgcgggc acgcagatca atgtgaagcg 21060
caagaagggc tgatagattg tggctcagga tgtgaatgtg aagctgaact tgccgggtat 21120
tcgtgaggtg ttgaagtctt ctggggtgca ggctatgttg gctgagcgtg gcgagcgtgt 21180
caagcgtgcg gcctcggcga atgtgggcgg taacgctttc gataaggccc aataccgtaa 21240
tggtttgtcg tcggaggtgc aggttcaccg tgttgaggct gtcgctcgta taggtaccac 21300
atataagggt gggaagcgta ttgaggcgaa gcatggcacg ctggctaggt cgattggggc 21360
ggcgtcgtga tcatctacga tgaccccagg aagtgggcta aacgcgtgct caaggatgat 21420
ggctggctgt ctgggatacc atgcaccggg acagtgcccg atgattttac gggtgacctg 21480
atttggttgg cgttggatgg tggcccacag ttgcatgttc gcgagcaagt ttttttgcgc 21540
gtgaatgtgt tttctgatac gccggatcgt gctatgtcgc tagccaggcg ggtggaggct 21600
gtccttgcgg atggggttga tggcaaccct gtggtgtact gtaaacggtc tactggtcct 21660
gatttgctgg ttgatggtgc acgttttgat gtgtattcgc tgttcgagct gatatgtagg 21720
cctgtcgagt ctgagtaaac gtatttgttt ttgttttaat gtaattgttt gatatttaat 21780
gggggttgtg atggctgcaa cacgtaaagc gtctaatgtt cgttcagcgg ttactggcga 21840

```
cgtttatatt ggtgacgcgc acgcgggtga tactattaag ggtgtggagg cggttcctga  21900
cggtcttacc gctttagggt atctgtcgga tgacgggttt aagattaagc ctgagcgtaa  21960
aacggatgat ttgaaggctt ggcagaatgc ggatgttgtt cgcacggttg ctaccgagtc  22020
ttctatcgag atttctttcc agctgatcga gtctaagaag gaggttatcg agctgttttg  22080
gcagtcgaag gttactgccg gatccgattc aggttcgttc gatatttctc cgggtgccac  22140
gacgggtgtt cacgccctgt tgatggatat tgtggatggt gatcaggtta ttcgctacta  22200
tttccctgag gttgagttga tcgatcgtga cgagatcaag ggcaagaatg gcgaggtgta  22260
cgggtatggt gtgacgttga aggcgtatcc tgcccagatt aataagaagg gtgatgcggt  22320
gtcgggtcgg gggtggatga cggctttaaa agctgatact cctccggttc cgccttctcc  22380
gaagccgaag ccggatccta atccgccgtc tgagaactga tacacgattt taggggattg  22440
ttgatagatg agtgacacgg gttacacgtt gaagattggt gaccgtagct gggtgttggc  22500
ggatgcggag gagacggctc aagctgtgcc tgcccgcgtg tttcgccgtg cagctaagat  22560
tgcccagtcg gggagtctg cggatttcgc ccaggttgag gtgatgtttt ctatgttgga  22620
ggctgccgcc ccagtggatg ctgtggaggc cctggagggg cttcctatgg ttcgtgtggc  22680
cgagatttc cgtgagtgga tggaatataa gcctgacggt aagggtgcct cgctgggga  22740
atagtttggc tccacggcct gattgatgat tatcgtgggg ccatcgaata tgattggagg  22800
acccggttcg gttgctcggt ttatgatgtt ggtggcccga taatgtgttg gggtgaggct  22860
gttcggctgg ctggcgtgtt gtgtaccgat acgtctagcc agttggcggc ccacctgaat  22920
ggttggcagc gcccgtttga gtggtctgag tgggcggtgt tggacatgtt ggatcattac  22980
aggtctgcta atagtgaggg gcagccggag cctgtggcga ggcctacgga tgagcgtagg  23040
gcccggttta cgtttgggca ggtggacgat attttggcgc gtgttcgtgc cggtggcggg  23100
gtgtctcgcg agattaatat tatggggtga atagtgtatg tctggtgaga ttgcttccgc  23160
atatgtgtcg ttgtatacga agatgcctgg tttgaaggct gatgttggta aacagttgtc  23220
gggtgttatg cctgctgagg gtcagcgttc gggtagtctt tttgctaagg gtatgaagtt  23280
ggcgcttggt ggtgccgcaa tggtgggtgc catcaatgtt gctaagaagg gcctcaagtc  23340
gatttatgat gtgactattg gtggcggtat tgctcgcgct atggctattg atgaggctca  23400
ggctaagttg actggtttgg gtcatacgtc gtctgacacg tcttcgatta tgaattcggc  23460
tattgaggct gtgactggta cgtcgtatgc gttgggggat gcggcttcta ctgcggcggc  23520
gttgtctgct tcgggtgtga agtctggcgg gcagatgacg gatgtgttga agactgtcgc  23580
cgatgtgtct tatatttcgg gtaagtcgtt tcaggatacg ggcgctattt ttacgtctgt  23640
gatggcccgc ggtaagttgc agggtgatga catgttgcag cttacgatgg cgggtgttcc  23700
tgtactgtct ttgcttgcca ggcagacggg taaaacgtcg gctgaggtgt cgcagatggt  23760
gtcgaagggg cagattgatt ttgccacgtt tgcggctgcg atgaagcttg gcatgggtgg  23820
tgctgcgcag gcgtctggta agacgtttga gggcgctatg aagaatgtta agggcgcttt  23880
gggctatctt ggtgctacgg ctatggcgcc gtttcttaac gggttgcggc agatttttgt  23940
tgcgttgaat ccggttatca agtctatcac ggattctgtg aagccgatgt ttgctgccgt  24000
cgatgctggt attcagcgta tgatgccgtc tattttggcg tggattaacc gtatgccggg  24060
catgatcact cgaatgaatg cacagatgcg cgccaaggtg gagcagttga agggcatttt  24120
tgcaaggttg catttgcctg tccctaaagt gaatttgggt gccatgtttg ctggcggcac  24180
cgcagtgttt ggtattgttg ctgccggtgt ggggaagctt gtcgcggggt ttgccccgtt  24240
```

-continued ggcggtgtcg gtgaagaatc tactgccgtc gtttggtgct ttgaagggtg ccgccggcgg 24300
gcttggcggc gtgtttcgcg ccctgggtgg ccctgtcggg attgtgatcg gcttgtttgc 24360
tgccatgttt gctacgaacg cccagttccg tgccgctgtt atgcagcttg tggctgtggt 24420
tggtcaagcc ctggggcaga ttatggccgc tgtgcagcct gtgtttggtt tggttgcggg 24480
tctggtggcc cggttggcgc cagtgtttgc ccagattatt ggtttggttg ccgggctggc 24540
tgcccagttg atgcctgtga ttggtatgct tgttgcccgg ctggttcctg tgatcaccca 24600
gattattggt gcggtgacgc aggtggcggc catgttgctg ccggcgttga tgccggtgtt 24660
gcaggctgtt gttgctgtga tacggcaggt tgttggcgtg atcatgcagt tggtgccggt 24720
gttgatgccg gtgattcagc agattttggg tgcggtcatg tctgtgctgc cgccgattat 24780
tggtttgatc cggtcgttga tgcctgtgat tgcggcggtt atgcgtgtgg tggtgcaggt 24840
tgtttcggtt gtgatacagg tggtggcccg tattcttgct gttgtggctc cgatggtggc 24900
tgccgtggta gggtttgttg cccgtattgt tggtgctgtc gtgtcggctg ttgcccgtgt 24960
tattgctgct gttgcccgtg ttatcgggtg gattgttgct cattttgtgt cgggtttggc 25020
gcgtatgggt tcggttattc aggctggctg gaatcatatt agggcgttta cgtctgcgtt 25080
tattaacggt tttaagtcgg tgatttctgg cggcgtgaac gctgttgtgg ggttttttac 25140
gcggcttggt ttgtcggttg cttctcatgt tcggtctggt tttaacgcgg ctcgtggtgc 25200
tgtttcttct gcgatgaatg ctattcggag tgttgtgtct tcggtggcgt ctgctgttgg 25260
cgggtttttc agttcgatgg cgtctagggt tcgtagtggt gttgtgcgcg ggtttaatgg 25320
ggccaggaat gcggcatctt ccgctatgca tgctatgggg tccgctgtgt ctagcggcgt 25380
gcatagtgtg ctagggtttt tccggaatct gcctggcaat attcggcatg ctctcggtaa 25440
tatggggtct ttgttggtgt ctgctggccg tgatgtggtg gccggtttgg gtaacggtat 25500
taagaatgct ttgagtggcc tgttggatac ggtgcgtaat atgggttctc aggttgctaa 25560
tgctgcgaag tcggtgttgg gtattcattc cccgtcgagg gtgtttcgtg acgaggttgg 25620
ccgtcaggtt gttgccggtt tggctgaggg tattactggt aatgcgggtt tggcgttgga 25680
tgcgatgtct ggtgtggctg gtcggctgcc tgatgtggtg gatgcccggt ttggtgtgcg 25740
atcgtctgtg ggctcgttta ccccgtacga ccggtatcgg cgtgcgagtg agaagagtgt 25800
tgtggtgaat gttaacgggc ccacgtatgg tgatcctaac gagtttgcga agcggattga 25860
gcgtcagcag cgtgacgctt tgaacgcttt ggcttacgtg tgatagggggg tgtggttcat 25920 gtttcttcct gacccgtctg atcgttctgg tttgactgtt acctggtcta tggatccgct 25980
gtttggcgat gagcgtgtgc ttcatttgac ggattatacg gggtcgtctc cggtgatgtt 26040
gttgaatgat tcgttgcgcg gtttgggtgt tcctgaggtg gagcattttt ctcaaactca 26100
tgttggggtg catggctcgg agtggcgcgg gtttaatgtg aagcctcgcg aggtgacgct 26160
gcctgtcctg gtgtcgggtg ttggtgtgga tcctgtgggc gggtttcgtg acggtttttt 26220
gaaagcctat gacgcgttgt ggtctgcttt tcctcccggg gaggagggtg aactgtcggt 26280
gaagactcct gccggcaaag agcgtgtgct gaagtgccgg tttgattcgg ctgatgacac 26340
gtttacggtg gatccggtga acaggggtta tgcgcgttat ctgttgcatt tgacggctta 26400
tgacccgttt tggtatgggg atgagcagaa gtttcgtttc agtaacgcga agttgcagga 26460
ttggttgggt ggcggccctg tcggcaagaa gggtacagcg tttcctgtgg tgttgacgcc 26520
tggtgttggt tcgggttggg ataacttgtc taataggggt gatgtgccgg cgtggcctgt 26580
gattcgtgtg gagggccccc tggagtcgtg gtctgtgcag attgatggtt tgcgtgtgtc 26640
ttcggattgg cctgtcgagg agtatgattg gatcactatt gatacggatc ctcgtaaaca 26700
gtctgcgttg ttgaacgggt ttgaggatgt gatggatcgt ttgaaggagt gggagtttgc 26760
gcctatcccg cctggcggtt ctaagagtgt gaatattgag atggttggtt tgggtgccat 26820
tgttgtgtcg gtgcagtaca ggtttttgag ggcttggtga atagttgatg gctggtcttg 26880
ttccgcggat aacattgttt acaccggatt atcaccgtgt ggcgcctatc aattttttg 26940 aatcgttgaa actgtcgttg aagtggaatg gtttgtccac tttggagttg gtggtgtctg 27000
gtgatcattc taggcttgac gggttgacta agccgggtgc acggctggtt gttgattatg 27060
gtggtggcca gatttttct gggcctgtgc gtaaggttca tggtgtgggt ccgtggcgtt 27120
cttcgcgggt gactatcacg tgtgaagatg atattcgtct gttgtggcgt atgttgatgt 27180
ggcctgtgaa ttatcgtcct ggtatggttg gtatggagtg gcgtgccgac agggattatg 27240
cccactattc gggtgcggct gagtcggtgg ctaagcaggt gttgggggat aatgcttggc 27300
gttttccgcc tgatatattt atggtggatg ataagagtcg tggccgctat attaaggatt 27360
ttcaggcgcg gtttcacgtg tttgccgata agttgttgcc ggtgttgtcg tgggctcgga 27420
tgactgtcac ggtgaaccag tttgagaatg cgaagcagga tcagcggggt ttgctgtttg 27480
attgtgtgcc tgccgtgacc cgtaagcatg tgttgactgc cgagtctggg tctattgtgt 27540
cgtgggagta tgtgagggat gccccgaagg cgacatctgt ggtggttggt ggccgcggcg 27600
agggtaagga tcggctgttt tgtgaggatg ttgattcggc ggccgaggat gactggtttg 27660
atcgtgtcga ggtgtttaag gatgcccgta acacggattc tgaacatgtg catcttattg 27720
atgaggcgga gcaggtgctg caggagtctg ggccacgtc ggggtttaag atcgagttgg 27780
ccgagtcgga tgtgttgcgg tttgggccag gcaatctgat gccgggtgat ttgatctatg 27840
tggatgtggg ctcgggctct atcgcggaga ttgttcggca gattgatgtg gagtgtgatt 27900
cgccgggtga tggttggacg aaagtgactc ctgttgcggg ggattatgag gataatccgt 27960
cagcattgtt ggctcgccgt gttgccggtt tggctgcggg tgtgcgggat ttgcaaaagt 28020
tttagaagga ttggggtttg ttgtgggtat tgtgtgtaaa gggtttgatg gtgtgttgac 28080
cgagtatgat tgggctcaaa tgtctggtct gatgggtaat atgccgtcgg tgaaagggcc 28140
ggatgatttt cgtgtcggta cgactattca gggtgccaca gtgttgtgtg aggtcctgcc 28200
ggggcaggct tgggctcacg gggtgatgtg cacgtcgaat agtgttgaga cggtgacggg 28260
gccgcttccg ggccctggcg agacccgata cgactatgtg gtgttgtctc gggattggga 28320
gcagaatacg gccaagttgg agattgtttc tggggggcgt gcggagcgtg ccagggatgt 28380
gttgcgtgcc gagcctggcg tgtttcatca gcagttgttg gcgactttgg tgttgtcgtc 28440
taacgggttg cagcagcagt tggataggcg tgctatagcg gctagggttg cgtttggcga 28500
gtctgctgcg tgtgatccta ccccggtgga gggtgaccgg gtgatggttc cttcgggggc 28560
tgtgtgggct aatcatgcta acgagtggat gctactgtct ccgaggattg agacgggttc 28620
taagcagatc cagtttggcg ggtctgccgt gtatgcttac acgatcccgt ttgatcgcca 28680
gttcactagt gcgcctgtcg tggtggcgtc tatggctacg gcggctgggg gcacggcaca 28740
gatcgatgtg aaagcctaca atgttactgc caaggatttt cggttggcgt ttatcacgaa 28800
tgacgggtct aagccgaatg gtgtgcctgc ggtggctaac tggattgctg tcggcgtgtg 28860
actgtacagg tgttgtggcg gatggtgtga tgttgggggg ctgtggtgtc gtggtttact 28920
cctgcactgg tggcctctat ctgtacggcg ttggccacgg ttttgggttc tgttcaggct 28980
gtcacatccc ggtctaggaa gcgtttacgc aggctgtctg cgcaggtgga tgcgatggaa 29040
gagtatacgt ggggtgtgcg gcgcgaggtt cgaaggttta acgccgggct tcctgacgag 29100
gtggagccta tgcatcttcc tgatttgccc gagtttttga aagatactgt tgatggtggt 29160
ggggggtgaa ttgtgaggga gttggaggaa gaaaaaaggc agcgccgctc gtttgagaag 29220
gcttccctga tactgttgtt cctgtcgctt gtgctgttgg cggtggttgc tgcgggtgct 29280
ttacggtacg ggtctgtggc ttcccagcgg gattcggagc aggcgagggc ccagtctaat 29340
ggtacagccg ctaaagggtt ggccagccgt gtgaagcggg tgtgtgcttc gggtgggcag 29400
gagtcggtgc ggcttcacca gtctggcttg tgtgtggatg ctcggcgtgt tgagcggagt 29460
gtgcagggtg tgccgggtcc tgcaggtgct gatggccggg atggtgttaa tggttcggct 29520
gggctggttg gccctgttgg tccgcagggt tctcctggtt tg 29562

<210> SEQ ID NO 76
<211> LENGTH: 83
<212> TYPE: DNA
<213> ORGANISM: Artificial Sequence
<220> FEATURE:
<223> OTHER INFORMATION: Cos PAC7 83bp

<400> SEQUENCE: 76
aaaacccgcc aacccccacc gggcacaccc cctgcacacc cgtgcaagac ctcgtacggc 60
ttagtgaaat acctcccttt tgt 83

<210> SEQ ID NO 77
<211> LENGTH: 816
<212> TYPE: DNA
<213> ORGANISM: Artificial Sequence
<220> FEATURE:
<223> OTHER INFORMATION: endolysin gene

<400> SEQUENCE: 77
gtgaataggg ttgtgattca tgcgacgtgc ccggatgtgg ggtttccgtc cgcctcgcgt 60
aaaggacggg ctgtgtccac ggcaaactat ttcgcttccc catcgtctgg tggttcggcg 120
cattatgtgt gtgatattgg ggagacggtg caatgcttgt cggagtctac gattgggtgg 180
catgccccgc cgaatccgca tagtttgggt atagagattt gcgcggatgg ggggttcgcac 240 gcctcgttcc gggtgccggg gcatgcttac actcgtgagc agtggctgga tcctcgcgtg 300
tggcctgcgg ttgagcgtgc cgccatcctg tgtagacgtt tgtgtgacaa gcatggtgtt 360
ccgaaaagga aactgtctgt ggccgatttg aaggccggta aacggggtgt ttgcgggcat 420
gtggatgtta cggatgcgtg gcatcagtcg gatcatgacg atccggggcc gtggtttccg 480
tgggacaaat ttatggctgt ggttaatggc cacggcggcg gttcaagtag tgaggagttg 540
agtatggctg atgtacaagc gttacataat cagattaaac agttgtcggc acaggtggcc 600
cagtcggtga ataagctgca tcacgatgtt ggtgtggttc aggttcagaa tggtgatttg 660
ggtaaacgtg ttgatgcctt gtcgtgggtg aagaatcctg tgacggggaa gctgtggcgc 720
actaaggatg ctttgtggag tgtctggtat tacgtgttgg agtgtcgtag ccgtcttgac 780
aggctcgagt ctgctgtcaa cgatttgaaa aagtga 816

<210> SEQ ID NO 78
<211> LENGTH: 249
<212> TYPE: DNA
<213> ORGANISM: Artificial Sequence
<220> FEATURE:

<223> OTHER INFORMATION: PAC7-m28-gp45 plaque n:1 from alignment figure
18

<400> SEQUENCE: 78
tagtggagaa aacaaccacc ccggaacgtt taagacaccc cctcaaacga acaaaacagg 60
gcctagaatc gatcagcagg gcaccggtag ggtattccta cccccagacg attcaaggcc 120
aaaccgaatg cccactctgc ggagtcacca tcacctggaa cacccacgac ctgccaacca 180
gccccgaagc cgaccacatc acacccgtca gccggggagg actcaacacc ctcgacaacg 240
ggcaaatca 249

<210> SEQ ID NO 79
<211> LENGTH: 20
<212> TYPE: DNA
<213> ORGANISM: Artificial Sequence
<220> FEATURE:
<223> OTHER INFORMATION: endolysin target

<400> SEQUENCE: 79
atgcgacgtg cccggatgtg 20

<210> SEQ ID NO 80
<211> LENGTH: 20
<212> TYPE: DNA
<213> ORGANISM: Artificial Sequence
<220> FEATURE:
<223> OTHER INFORMATION: Cos target

<400> SEQUENCE: 80
aaaacccgcc aacccccacc 20

<210> SEQ ID NO 81
<211> LENGTH: 1673
<212> TYPE: DNA
<213> ORGANISM: Artificial Sequence
<220> FEATURE:
<223> OTHER INFORMATION: editing template endolysin

<400> SEQUENCE: 81
tcacctgtca agacggctac gacactccaa cacgtaatac cagacactcc acaaagcatc 60
cttagtgcgc cacagcttcc ccgtcacagg attcttcacc cacgacaagg catcaacacg 120
tttacccaaa tcaccattct gaacctgaac cacaccaaca tcgtgatgca gcttattcac 180
cgactgggcc acctgtgccg acaactgttt aatctgatta tgtaacgctt gtacatcagc 240
catactcaac tcctcactac ttgaaccgcc gccgtggcca ttaaccacag ccataaattt 300
gtcccacgga aaccacggcc ccggatcgtc atgatccgac tgatgccacg catccgtaac 360
atccacatgc ccgcaaacac cccgtttacc ggccttcaaa tcggccacag acagtttcct 420
tttcggaaca ccatgcttgt cacacaaacg tctacacagg atggcggcac gctcaaccgc 480
aggccacacg cgaggatcca gccactgctc acgagtgtaa gcatgccccg gcacccggaa 540
cgaggcgtgc gaacccccat ccgcgcaaat ctctataccc aaactatgcg gattcggcgg 600
ggcatgccac ccaatcgtag actccgacaa gcattgcacc gtctccccaa tatcacacac 660
ataatgcgcc gaaccaccag acgatgggga agcgaaatag tttgccgtgg acacagcccg 720
tcctttacgc gaggcggacg gaaatcccac atccgggcac gtcgcatgaa tcacaaccct 780
attcaccgga ctattcgagc cggcagaatg atgcgccgca ggaatatatc tcacaacaca 840
ccaccaccaa acaccaccat cacagccact cctttctatt tgtgggatga tatagtcact 900

-continued agaggcgacg gtttcacacc ctggcaggcc gccgaacccg atatcgtgga agccacaccg 960
tcactatatt tcacaaccag gcggcccccg gaacagtaca cagacaccac cgagcgccca 1020
tccttaccat catggccatc cgatccattc gcaccggcgg gaccacgctc accccgttca 1080
ccctgtgcac cttgcgggcc ggcaggacct gaagggcctt gcgggccgcg ctcaccggca 1140
gaaccatccc gaccatcagc gccgtcaacg ccgttcacac cgtcagcacc tgcacgacct 1200
ggaacaccat cacggccatc cgaaccgtta gcgccaggca agccgtcagg acctttcaca 1260
ccattcaaac ccggagaacc ttgcggacca acagggccaa ccagcccagc cgaaccatta 1320
acaccatccc ggccggcagg acctgaaggg ccttgcgggc cgcgctcacc ggcaggaccc 1380
ggcacaccct gaacacgctg ctcaacacgc acagcatcca cacacaaacc agaacggtga 1440
agacgcacag actccacccc acccgaagca cacgcctgct tcacacgggc agccaaaccc 1500
ctggcagccg taccattcga ctgggccctc gcctgctccg aatcccgctc agaggataca 1560
gccccgaaac gcaaagcacc cgcagcaacc accgccaaca acacaagcga caaaaacaac 1620
aacaccagtg aagccttctc aaaattgcgg cgctgccgct tctcctcctc caa 1673

<210> SEQ ID NO 82
<211> LENGTH: 1908
<212> TYPE: DNA
<213> ORGANISM: Artificial Sequence
<220> FEATURE:
<223> OTHER INFORMATION: editing template cos

<400> SEQUENCE: 82
acgagccaca aactcaaccg aaccccaacc cggacaacca cacttcttct caaacgtggc 60
acaatccgga tgatgcaaca caatagcctc ctggccattc gtcgcacgaa tcgacttcac 120
catacgatac aagtcaggaa actgccgctc attctcaaaa aacgaccgca accgcataaa 180
cgccttacga gccgacttca actcgtgagc cgtatgcaaa atacggcgac cctgaatagt 240
cgccttaaac aactccacaa tctccaaaat agcattcttg ccattctgcc gcggaacaaa 300
caccccacac acacccgaag caagcctgcc attaccaccc acagcaagcc aatcatccaa 360
cacctgctgc tgccacggat caggcgtcaa cccataagcc ctaccaagct ccccagcatc 420
cccgccagca gacaccgaat acgccacagc cacccggtga cgaggaacct gagacccaac 480
aacaccagac acctactcaa gcccccctac gcttcctata ccggtcaatc atcgctaccg 540
cagaaccccc accacggcca ccagacgcca catcaaccga atacctatcc aacataccca 600
taaaagcctt cacatgagca cgcaacgaag ccaccaaatc cgcgcgaccc tcacgccaca 660
ccacatcatg aatcaccgca gcatccatga gaaacaacca ctcctcatca gacacaaacc 720
cggcacgcgg atcctcgccc cacacacacc accaccgacg cgtctcccca caccaatcac 780
gactatcagg aagctcaggc tgcaccacac acaccaccaa acaaaaagtc gacaaaacga 840
taaaacaaca aaagggaggt atttcactaa gccgtacgag gtcttgcacg ggtgtgcagg 900
gggtgtgtcc ggtgggggtt ggcgggtttt tcaccatgga atcaatgttt ttgtggtttg 960
ttgttggaat ttgatgtttg gttgtgttct gttgcctttg cttctgttgc atgttctgca 1020
gatgatttgc ccgttgtcga gggtgttgag tcctccccgg ctgacgggtg tgatgtggtc 1080
ggcttcgggg ctggttggca ggtcgtgggt gttccaggtg atggtgactc cgcagagtgg 1140
gcattcggtt tggccttgtt gtcgggcttg ggtgatgagc cttgcccgcc agcgccggtg 1200
ggcttggctg gctgtgcggt tggtgtgtgc catcacgccc cccaatctcc catggcccct 1260
gtgagcctct cattgctcct gtaatggcct tgaatcgtct gggggtagga ataccctacc 1320
ggtgccctgc tgatcgattc taggccctgt tttgttcgtt tgagggggtg tcttaaacgt 1380
tccggggtgg ttgttttctc cactaccccc tggcatgtga gaaatatcac atcgcccccc 1440
agcggtgtca aaaggagaag gacacggaag aaaaatgggg gtggatgggt gttcacgttt 1500
cacatcttag cgctgagcgc ctagcgttaa aggaacacgg gctaagcggg aacaccttat 1560
aggttttaaa gtcttctact tataatatgc actttaagtc ttacctggtg ttaagggttt 1620
aagcgtgaca cgccgtacgc cttccgacga acacgctaag ccgtaaaggg gcacgggtga 1680
aagagtgtgg ggagtgtgcg atgggagctt gcgaccagaa gcacacgagt cacacggtga 1740
aaagtccatc agcgttgacg gttaaaggtt cctcttctcc cctgatgaag aaaagaagag 1800
aagagagaaa gaaccaaaga gagaagagaa gtaaagaagt taacccttta actcttctaa 1860
aaacttttat aacttataag ctttaatact tataatatta aagtttaa 1908

<210> SEQ ID NO 83
<211> LENGTH: 1705
<212> TYPE: DNA
<213> ORGANISM: Artificial Sequence
<220> FEATURE:
<223> OTHER INFORMATION: editing template endonuclease

<400> SEQUENCE: 83
actataaaag ctttaaacac ttaaagtaac tataaagctt taagagctta acatttaagg 60
atataaataa acattaaagc tttaaagtct taaagtaaat atataacctt aacacttaag 120
ttaagtataa aaccttaaag gcttagcact taaggatata aacttaacat cagtgtttaa 180
gacttaaaga gttaaagtaa ctattaagac ttaaaggctt ataagcttta atactttaag 240
tagctataag actttaaaaa cctgaagtac ttaaagttaa ccatcagtct taaactttaa 300
tattataagt attaaagctt ataagttata aaagttttta gaagagttaa agggttaact 360
tctttacttc tcttctctct ttggttcttt ctctcttctc ttcttttctt catcagggga 420
gaagaggaac ctttaaccgt caacgctgat ggacttttca ccgtgtgact cgtgtgcttc 480
tggtcgcaag ctcccatcgc acactcccca cactctttca cccgtgcccc tttacggctt 540
agcgtgttcg tcggaaggcg tacggcgtgt cacgcttaaa cccttaacac caggtaagac 600
ttaaagtgca tattataagt agaagacttt aaaacctata aggtgttccc gcttagcccg 660
tgttccttta acgctaggcg ctcagcgcta agatgtgaaa cgtgaacacc catccacccc 720
catttttctt ccgtgtcctt ctccttttga caccgctggg gggcgatgtg atatttctca 780
catgccaggg ggtagtggag aaaacaacca ccccggaacg tttaagacac cccctcaaac 840
gaacaaaaca gggcctagaa tcgatcagca gggcaccggt agggtattcc tacccccaga 900
cgattcaagg ccattacagg agcaatgaga ggctcacagg ggccatggga gattgggggg 960
cgtgatggca cacaccaacc gcacagccag ccaagcccac cgtcgctggc gggcaaggct 1020
catcacccaa gcccgacaac aaggccaaac cgaatgccca ctctgcggag tcaccatcac 1080
ctggaacacc cacgacctgc caaccagccc cgaagccgac cacatcacac ccgtcagccg 1140
gggaggactc aacaccctcg acaacgggca aatcatctgc agaacatgca acagaagcaa 1200
aggcaacaga acacaaccaa acatcaaatt ccaacaacaa accacaaaaa cattgattcc 1260
atggtgaaaa acccgccaac ccccaccggg cacacccccct gcacacccgt gcaagacctc 1320
gtacggctta gtgaaatacc tcccttttgt tgttttatcg ttttgtcgac tttttgtttg 1380
gtggtgtgtg tggtgcagcc tgagcttcct gatagtcgtg attggtgtgg ggagacgcgt 1440

-continued cggtggtggt gtgtgtgggg cgaggatccg cgtgccgggt ttgtgtctga tgaggagtgg 1500
ttgtttctca tggatgctgc ggtgattcat gatgtggtgt ggcgtgaggg tcgcgcggat 1560
ttggtggctt cgttgcgtgc tcatgtgaag gcttttatgg gtatgttgga taggtattcg 1620
gttgatgtgg cgtctggtgg ccgtggtggg ggttctgcgg tagcgatgat tgaccggtat 1680
aggaagcgta ggggggcttg agtag 1705

<210> SEQ ID NO 84
<211> LENGTH: 420
<212> TYPE: DNA
<213> ORGANISM: Artificial Sequence
<220> FEATURE:
<223> OTHER INFORMATION: UnaG cds

<400> SEQUENCE: 84
atggtggaga agttcgtcgg tacatggaag atcgccgact cgcacaactt tggcgagtac 60
ctgaaggcca ttggtgctcc caaggagctg tcggacggcg gcgatgccac caccccgacc 120
ctgtacatct cgcagaagga cggcgataag atgacggtga agattgaaaa cggcccgccc 180
accttcctcg atactcaagt gaagttcaag ttgggtgagg agttcgatga attcccgtcg 240
gaccgtcgta agggcgtcaa gagcgtcgtc aatctcgtcg gagagaagct ggtctacgtt 300
cagaagtggg acggcaagga gactacctac gtgcgtgaga tcaaggacgg taagctggtg 360
gtgaccctca ccatgggaga tgtcgtcgcc gtccgcagct accggcgcgc caccgagtga 420

<210> SEQ ID NO 85
<211> LENGTH: 249
<212> TYPE: DNA
<213> ORGANISM: Artificial Sequence
<220> FEATURE:
<223> OTHER INFORMATION: PAC7-m28-gp45 plaque n:2 from alignment figure
18

<400> SEQUENCE: 85
tagtggagaa aacaaccacc ccggaacgtt taagacaccc cctcaaacga acaaaacagg 60
gcctagaatc gatcagcagg gcaccggtag ggtattccta cccccagacg attcaaggcc 120
aaaccgaatg cccactctgc ggagtcacca tcacctggaa cacccacgac ctgccaacca 180
gccccgaagc cgaccacatc acacccgtca gccggggagg actcaacacc ctcgacaacg 240
ggcaaatca 249

<210> SEQ ID NO 86
<211> LENGTH: 300
<212> TYPE: DNA
<213> ORGANISM: Artificial Sequence
<220> FEATURE:
<223> OTHER INFORMATION: Cos PAC7 pIC400

<400> SEQUENCE: 86
aggcaacaga acacaaccaa acatcaaatt ccaacaacaa accacaaaaa cattgattcc 60
atggtgaaaa acccgccaac ccccaccggg cacaccccct gcacacccgt gcaagacctc 120
gtacggctta gtgaaatacc tcccttttgt tgttttatcg ttttgtcgac tttttgtttg 180
gtggtgtgtg tggtgcagcc tgagcttcct gatagtcgtg attggtgtgg ggagacgcgt 240
cggtggtggt gtgtgtgggg cgaggatccg cgtgccgggt ttgtgtctga tgaggagtgg 300

<210> SEQ ID NO 87
<211> LENGTH: 300
<212> TYPE: DNA

<213> ORGANISM: Artificial Sequence
<220> FEATURE:
<223> OTHER INFORMATION: Cos PAC7 pIC401

<400> SEQUENCE: 87
gaccacatca cacccgtcag ccggggagga ctcaacaccc tcgacaacgg gcaaatcatc 60
tgcagaacat gcaacagaag caaaggcaac agaacacaac caaacatcaa attccaacaa 120
caaaccacaa aaacattgat tccatggtga aaaacccgcc aaccccccacc gggcacaccc 180 cctgcacacc cgtgcaagac ctcgtacggc ttagtgaaat acctcccttt tgttgtttta 240
tcgttttgtc gactttttgt ttggtggtgt gtgtggtgca gcctgagctt cctgatagtc 300

<210> SEQ ID NO 88
<211> LENGTH: 217
<212> TYPE: DNA
<213> ORGANISM: Artificial Sequence
<220> FEATURE:
<223> OTHER INFORMATION: Cos PAC7 pIC402

<400> SEQUENCE: 88
aggcaacaga acacaaccaa acatcaaatt ccaacaacaa accacaaaaa cattgattcc 60
atggtgaaaa acccgccaac cccccaccggg cacaccccct gcacacccgt gcaagacctc 120
gtacggctta gtgaaatacc tcccttttgt tgttttatcg ttttgtcgac tttttgtttg 180
gtggtgtgtg tggtgcagcc tgagcttcct gatagtc 217

<210> SEQ ID NO 89
<211> LENGTH: 150
<212> TYPE: DNA
<213> ORGANISM: Artificial Sequence
<220> FEATURE:
<223> OTHER INFORMATION: Cos PAC7 pIC403

<400> SEQUENCE: 89
aaaacccgcc aaccccccacc gggcacaccc cctgcacacc cgtgcaagac ctcgtacggc 60
ttagtgaaat acctcccttt tgttgtttta tcgttttgtc gactttttgt ttggtggtgt 120
gtgtggtgca gcctgagctt cctgatagtc 150

<210> SEQ ID NO 90
<211> LENGTH: 150
<212> TYPE: DNA
<213> ORGANISM: Artificial Sequence
<220> FEATURE:
<223> OTHER INFORMATION: Cos PAC7 pIC404

<400> SEQUENCE: 90
aggcaacaga acacaaccaa acatcaaatt ccaacaacaa accacaaaaa cattgattcc 60
atggtgaaaa acccgccaac cccccaccggg cacaccccct gcacacccgt gcaagacctc 120
gtacggctta gtgaaatacc tcccttttgt 150

<210> SEQ ID NO 91
<211> LENGTH: 35
<212> TYPE: DNA
<213> ORGANISM: Artificial Sequence
<220> FEATURE:
<223> OTHER INFORMATION: AD1541 primer

<400> SEQUENCE: 91
gttccagctc ttccgaggac cacatcacac ccgtc 35

<210> SEQ ID NO 92
<211> LENGTH: 35
<212> TYPE: DNA
<213> ORGANISM: Artificial Sequence
<220> FEATURE:
<223> OTHER INFORMATION: AD1542 primer

<400> SEQUENCE: 92
gttccagctc ttcctgccca ctcctcatca gacac 35

<210> SEQ ID NO 93
<211> LENGTH: 38
<212> TYPE: DNA
<213> ORGANISM: Artificial Sequence
<220> FEATURE:
<223> OTHER INFORMATION: IC511 primer

<400> SEQUENCE: 93
gttccagctc ttccgagagg caacagaaca caaccaaa 38

<210> SEQ ID NO 94
<211> LENGTH: 37
<212> TYPE: DNA
<213> ORGANISM: Artificial Sequence
<220> FEATURE:
<223> OTHER INFORMATION: IC512 primer

<400> SEQUENCE: 94
gttccagctc ttcctgcgac tatcaggaag ctcaggc 37

<210> SEQ ID NO 95
<211> LENGTH: 37
<212> TYPE: DNA
<213> ORGANISM: Artificial Sequence
<220> FEATURE:
<223> OTHER INFORMATION: IC513 primer

<400> SEQUENCE: 95
gttccagctc ttccgagaaa acccgccaac ccccacc 37

<210> SEQ ID NO 96
<211> LENGTH: 38
<212> TYPE: DNA
<213> ORGANISM: Artificial Sequence
<220> FEATURE:
<223> OTHER INFORMATION: IC514 primer

<400> SEQUENCE: 96
gttccagctc ttcctgcaca aaagggaggt atttcact 38

<210> SEQ ID NO 97
<211> LENGTH: 21
<212> TYPE: DNA
<213> ORGANISM: Artificial Sequence
<220> FEATURE:
<223> OTHER INFORMATION: AD1261 primer

<400> SEQUENCE: 97
cagcggcgct gctaagaact t 21

<210> SEQ ID NO 98
<211> LENGTH: 20
<212> TYPE: DNA
<213> ORGANISM: Artificial Sequence
<220> FEATURE:
<223> OTHER INFORMATION: AD1262 primer

<400> SEQUENCE: 98
ccggctggca aatgaggcat 20

<210> SEQ ID NO 99
<211> LENGTH: 25
<212> TYPE: DNA
<213> ORGANISM: Artificial Sequence
<220> FEATURE:
<223> OTHER INFORMATION: IC208 primer

<400> SEQUENCE: 99
gcttccttag cttgcgaaat ctcga 25

<210> SEQ ID NO 100
<211> LENGTH: 26
<212> TYPE: DNA
<213> ORGANISM: Artificial Sequence
<220> FEATURE:
<223> OTHER INFORMATION: IC310 primer

<400> SEQUENCE: 100
gttcggctaa acccaaaagt aaaaac 26

<210> SEQ ID NO 101
<211> LENGTH: 25
<212> TYPE: DNA
<213> ORGANISM: Artificial Sequence
<220> FEATURE:
<223> OTHER INFORMATION: IC443 primer

<400> SEQUENCE: 101
ccagggtgtg aaaccgtcgc ctcta 25

<210> SEQ ID NO 102
<211> LENGTH: 25
<212> TYPE: DNA
<213> ORGANISM: Artificial Sequence
<220> FEATURE:
<223> OTHER INFORMATION: IC444 primer

<400> SEQUENCE: 102
cgcaaacacc ccgtttaccg gcctt 25

<210> SEQ ID NO 103
<211> LENGTH: 25
<212> TYPE: DNA
<213> ORGANISM: Artificial Sequence
<220> FEATURE:
<223> OTHER INFORMATION: IC446 primer

<400> SEQUENCE: 103
agggtattcc tacccccaga cgatt 25

<210> SEQ ID NO 104
<211> LENGTH: 22
<212> TYPE: DNA
<213> ORGANISM: Artificial Sequence
<220> FEATURE:
<223> OTHER INFORMATION: AD1289 primer

<400> SEQUENCE: 104
ccaatcatcc aacacctgct gc 22

<210> SEQ ID NO 105
<211> LENGTH: 29768

-continued

<212> TYPE: DNA
<213> ORGANISM: Artificial Sequence
<220> FEATURE:
<223> OTHER INFORMATION: PAC7_1.1

<400> SEQUENCE: 105
tcgtacggct tagtgaaata cctccctttt gttgttttat cgttttgtcg actttttgtt 60
tggtggtgtg tgtggtgcag cctgagcttc ctgatagtcg tgattggtgt ggggagacgc 120
gtcggtggtg gtgtgtgtgg ggcgaggatc cgcgtgccgg gtttgtgtct gatgaggagt 180
ggttgtttct catggatgct gcggtgattc atgatgtggt gtggcgtgag ggtcgcgcgg 240
atttggtggc ttcgttgcgt gctcatgtga aggcttttat gggtatgttg gataggtatt 300
cggttgatgt ggcgtctggt ggccgtggtg ggggttctgc ggtagcgatg attgaccggt 360
ataggaagcg tagggggggct tgagtaggtg tctggtgttg ttgggtctca ggttcctcgt 420
caccgggtgg ctgtggcgta ttcggtgtct gctggcgggg atgctgggga gcttggtagg 480
gcttatgggt tgacgcctga tccgtggcag cagcaggtgt tggatgattg gcttgctgtg 540
ggtggtaatg gcaggcttgc ttcgggtgtg tgtggggtgt ttgttccgcg gcagaatggc 600
aagaatgcta ttttggagat tgtggagttg tttaaggcga ctattcaggg tcgccgtatt 660
ttgcatacgg ctcacgagtt gaagtcggct cgtaaggcgt ttatgcggtt gcggtcgttt 720
tttgagaatg agcggcagtt tcctgacttg tatcgtatgg tgaagtcgat tcgtgcgacg 780
aatggccagg aggctattgt gttgcatcat ccggattgtg ccacgtttga gaagaagtgt 840
ggttgtccgg gttggggttc ggttgagttt gtggctcgta gccggggttc tgctcgcggg 900
tttacggttg atgatttggt gtgtgatgag gctcaggagt tgtcggatga gcagttggag 960
gctttgcttc ctaccgtgag cgctgccccg tctggtgatc ctcagcagat ttttttgggt 1020
acgccgccgg ggccgttggc tgacgggtct gtggtgttgc gtcttcgcgg gcaggctttg 1080
tcgggtggta aacggtttgc gtggacggag ttttcgattc ctgacgagtc tgatccggat 1140
gatgtgtcgc ggcagtggcg gaagttggcg ggtgacacta atccggcgtt ggggcgccgc 1200
ctgaatttcg ggacagtctc ggatgagcat gagtcgatgt ctgctgccgg gtttgctcgg 1260
gagcggcttg gctggtggga tcgtggccag tctgcttcgt ctgtgattcc ggcggataag 1320
tgggttcagt cggctgtggt tgaggcggct ctggttggcg ggaaggtttt tggtgtctcg 1380
ttttctcgct cgggggatcg tgtcgcgttg gctggtgctg gtaaaacgga ttctggtgtg 1440
catgttgagg ttattgatgg cctgtctggg acgattgttg atggtgtggg ccagctggct 1500
gattggttgg cgttgcgttg ggtgacact gaaaaggtta tggttgcagg gtctggtgcg 1560
gtgttgttgc agaaggcttt gacggatcgt ggtgttccgg gtcgtggcgt gattgtggct 1620
gatactgggg tgtatgtgga ggcgtgtcaa gccttcctgg agggtgtcag gtctgggagc 1680
gtgtctcatc ctcgtgccga ttcgaggcgt gacatgttgg atattgctgt gaggtcggct 1740
gtgcagaaga agaagggttc tgcgtggggt tggggttcct cgtttaagga tggttctgag 1800
gttcctttgg aggctgtgtc tttggcgtat cttggtgcga agatggcgaa agcgaagcgg 1860
cgtgaacggt ctggtaggaa gcgggtgtct gtggtatgaa ctcggatgag ttggctctga 1920
ttgagggcat gtacgatcgt attcaagggt tgtcttcgtg gcattgccgt attgagggct 1980
actatgaggg ctctaatcgg gtgcgtgatt tgggggttgc tattccttcg gagttgcagc 2040
gggtgcagac ggtggtgtca tggcctggga ttgcggtgga tgctttggag gagcgtctgg 2100
attggcttgg ctggactaat ggtgacggct acggtttgga tggtgtgtat gctgcgaatc 2160

```
ggcttgctac ggcgtcgtgt gatgttcacc ttgatgcact gatttttggg ttgtcgtttg   2220
tggcgatcat tccccaagag gatgggtcgg tgttggttcg tcctcagtcg ccgaagaatt   2280
gtactggccg gttttctgcc gatgggtctt gtttggatgc tggccttgtg gtgcagcaga   2340
cgtgtgatcc tgaggttgtt gaggcggagt tgttgcttcc tgatgtgatt gttcaggtgg   2400
agcggcgggg ttcgcgtgag tgggttgaga cgggccgtat cgagaatgtg ttgggtgcgg   2460
ttccgttggt gcctgttgtg aatcgtcgcc gtacttctag gattgatggc cgttcggaga   2520
ttacgaggtc tattagggct tacacggatg aggctgttcg cacactgttg gggcagtctg   2580
tgaatcgtga tttttatgcg tatcctcagc gttgggtgac tggcgtgagc gcggatgagt   2640
tttcgcagcc gggttgggtt ctgtcgatgg cttctgtgtg ggctgtggat aaggatgatg   2700
atggtgacac tccgaatgtg gggtcgtttc ctgtgaattc tcctacaccg tattctgatc   2760
agatgcgttt gttggcgcag ttgactgcgg gtgaggcggc tgttccggaa cgctatttcg   2820
ggtttatcac ttctaacccg ccttctgggg aggctttggc tgcggaggag tctcggcttg   2880
tgaagcgtgc tgaacgcagg cagacgtcgt ttggtcaggg ctggctgtcg gttggtttcc   2940
tggctgcccg ggcgttggat tcgagtgttg atgaggccgc gttttttggt gatgttggtt   3000
tgcgttggcg tgatgcgtcg acgccgactc gggcggctac ggctgatgct gtgacgaagc   3060
ttgtgggtgc tggtattttg cctgctgatt ctcggacggt gttggagatg ttgggtttgg   3120
atgatgtgca ggttgaggct gtgatgcgtc atcgtgccga gtcttcggat ccgttggcgg   3180
cactggctgg ggctatttcc cgtcaaacta acgaggtttg ataggcgatg gcttcgggtg   3240
ctgtgtcgag gcttgctgcg actgagtatc agcgtgaggc tgtcaggttt gctgggaagt   3300
atgcgggcta ttatgccgag ttgggtcgtt tgtggcgtgc cggcaggatg agtgacacgc   3360
agtatgtgcg tttgtgtgtg gagttggagc gtgccggcca tgacggttca gcagctatgg   3420
cgggcaaatt cgtttcagat tttcgccggt tgaatggtgt cgatcctggt ttgatcgtgt   3480
atgacgagtt tgatgctgcg gcggctttgg ctaggtcgtt ttcgactatg aagattatga   3540
atagtgaccc ggatagggcg aatgatacga ttgatgcgat ggctgcgggt gttaatcggg   3600
ctgttatgaa tgctggtcgt gacacggttg agtggtcggc gggtgcgcag ggtaggtcgt   3660
ggcgtcgggt gactgatggt gatccgtgtg ctttttgtgc catgttggct acgaggtcgg   3720
attatacgac taaagagcgg gcgcttacta ctggtcatac gcggcgtcat aagcgtgccg   3780
gtaggcgtcc gtttggttcg aagtatcatg atcattgtgg ttgtacggtg gttgaggttg   3840
ttggtccttg ggaaccgaat agggctgatg ccgagtatca gaggacgtat gagaaggctc   3900
gtgagtgggt tgatgatcat gggttgcagc agtcgtctgg caatattttg aaggctatgc   3960
gtactgttgg tggcatgaga taatttgatg tggtttccgg ttgtgtgccg ccggttatcg   4020
gtgcacaggg ttgtctcccg cacgggggtc aacaatgttg tgttgttttc cgcaaggagt   4080
gtagggttag gctatggccg atcagagtat tgaggaacag aatgttgaca atgatgttgt   4140
ggagtccgga aaggataacg gcattgttga tacagtaaaa gacgatggcg ggcaggaggt   4200
agccgacaat cagttgaaga atgaaggcga gggtaaatcg ccggggactg attggaaggc   4260
ggaggcccgt aagtgggagt ctcgtgctaa aagtaatttc gccgagttgg agaagcttcg   4320
tacatcgagt gacgattctg gatctactat tgatgagctt cgccgcaaga atgaggaact   4380
cgaagaccgg attaacgggt ttgttcttga gggtgtgaag cgcgaggtgg ctgccgagtg   4440
tggcctgtcg ggtgatgcga tcgcttttct tcacggtagc gataaggagt cgcttgccga   4500
gtctgctaag gctttgaagg gtttgatcga ccatagtagt ggtggtggcg cgggtgtgcg   4560
```

-continued

```
ccgtcttgcg gggagtgccc ccgttgatga tgttaaacga cgtgagggtg tcgcgtttgt   4620
ggatgctctt gtcaataatt ctaggagatg atttatcatg gctgacgatt ttctttctgc   4680
agggaagctt gagcttcctg gttctatgat tggtgcggtt cgtgaccgtg ctatcgattc   4740
tggtgttctt gctaaactgt caccggagca gccgactatt ttcgggcctg ttaagggcgc   4800
cgtttttagt ggtgttccgc gcgctaagat tgttggcgag ggcgatgtta agccttccgc   4860
tagcgttgat gtttctgcgt ttactgcgca gcctatcaag gttgtgactc agcagcgtgt   4920
ctcggacgag tttatgtggg ctgacgccga ttaccgtctg ggtgtgcttc aggatctgat   4980
ttcccggcc ctgggtgctt ctattggtcg cgccgttgat cttattgctt tccatggtat   5040
tgatcctgct acgggtaagc ctgctgcggc tgtcaaggtg tcgctggata agacgaataa   5100
gacggttgat gccaccgatt ccgctacggc tgatcttgtt aaggctgttg gtctgattgc   5160
tggtgctggt ttgcaggttc ctaacggtgt tgctttggat ccggcgttct cgtttgctct   5220
gtcaactgag gtgtatccga agggttcgcc gcttgccggt cagccaatgt atcctgccgc   5280
cgggttcgcc ggcctggata attggcgcgg cctaaatgtt ggttcttctt cgactgtttc   5340
tggtgccccg gagatgtcgc ctgcttctgg tgttaaggct attgttggtg atttctctcg   5400
tgtccattgg gggttccagc gtaacttccc gattgagctg atcgagtatg gtgacccgga   5460
tcagacgggg cgtgacttga agggccataa tgaggttatg gttcgtgccg aggctgtgct   5520
gtatgttgcg attgagtcgc ttgattcgtt tgctgtcgtg aaggagaagg ctgccccgaa   5580
gcctaatccg ccggccggta actgattcat ttgttgcgat aatgtttatg ctgtgtgcag   5640
ggggtggtgt tgatgggtat cattttgaag cctgaggata ttgagccttt cgccgatatt   5700
cctagagaga agcttgaggc gatgattgcc gatgtggagg ctgtggctgt cagtgtcgcc   5760
ccctgtatcg ctaaaccgga tttcaaatat agggatgccg ctaaggctat tctgcgtagg   5820
gctttgttgc gctggaatga tactggcgtg tcgggtcagg tgcagtatga gtctgcgggc   5880
ccgtttgctc agactacacg gtcgaatact cctacgaatt tgttgtggcc ttctgagatt   5940
gccgcgttga agaagttgtg tgagggtgat agtggggctg gtaaggcgtt cactattaca   6000
ccgaccatga ggagtagtgt gaatcattct gaggtgtgtt ccacggtgtg gggtgagggt   6060
tgctcgtgcg ggtcgaatat taacggctat gctggcccgt tgtgggagat atgatatgac   6120
cggttttcct tacggtgaaa cggttgtgat gcttcagccg actgttcgtg tcgatgatct   6180
tggtgacaag gtggaggatt ggtctaagcc tgtcgagact gtgtaccata acgtggccat   6240
ctatgcttcc gtttcgcagg aggatgaggc cgcggggcgt gactcggatt atgagcattg   6300
gacactgctg ttcaagcagc ctgtcaaggc tgctggttat cggtgtcgtt ggcgtattcg   6360
gggtgttgtg tgggaggctg acgggtctcc tatggtgtgg catcatccga tgtctggctg   6420
ggatgctggt acgcaggtta atgtgaagcg taagaagggc tgatgggttg tggcacgtga   6480
tgttgatgtg aagctgaact tgccgggtat tcgtgaggtg ttgaagtctt ctggggtgca   6540
gggcatgttg gctgagcgtg gtgagcgtgt caagcgtgcg gcctcggcga atgtgggcgg   6600
taacgcttac gatagggccc agtatcgtgc cgggttgtcg tctgaggtgc aggttcaccg   6660
tgttgaggct gtggcgcgta ttggcaccac ctataagggt ggtaaaagga ttgaggctaa   6720
gcatggcacg ttggcgaggt cgattggggc tgcgtcgtga tcgtttacgg tgatcctcga   6780
atatgggcta aacgtgtgtt ggcggatgat ggttggctgt ctgatgtacc gtgcacgggt   6840
actgtgccgg atacatttga gggtgatctg atttggttgg cgttggatgg tggcccggag   6900
```

ttgcatgttc gtgagcgtgt ttttttgcgt gtgaatgtgt tttcggatac gccggatcgt 6960
gctatgtctt tggctcgccg ggttgaggct gtgctggctg atggtgtgga tggtgatccg 7020
gtggtgtttt gcaggcgttc gactgggcct gatttgctgg tggatggtgc acgttttgat 7080
gtgtattcgc tttttgagct gatatgtagg cctgcggagt ctgaataagc ttattgtttt 7140
tgttttaatg taattgtttg atatttaatg gggttgtga tggctgctac acgtaaagcg 7200
tctaatgttc gttcagcggt tactggcgac gtttatattg gtgacgcgca cgcgggtgat 7260
tctattaagg gtgtggaggc ggttccttcc gggcttacag ctttggggta tctgtctgat 7320
gacgggttta agattaagcc tgagcgtaaa acggatgatt tgaaggcttg gcagaatgcg 7380
gatgttgttc gcactgtggc tacggagtcg tctatcgaga tttctttcca gctgattgag 7440
tcgaagaagg aggttatcga actgttttgg cagtcgaagg ttactgccgg atctgattcg 7500
ggttcgttcg atatttctcc tggtgccaca acaggtgttc acgccctgtt gatggatatt 7560
gttgatggcg atcaggttat tcgctactat ttccctgagg ttgagctcat tgatcgtgac 7620
gagattaagg gcaagaatgg cgaagtgtac gggtatggtg tgacgttgaa ggcgtatcct 7680
gcccagatta ataagactgg taatgcggtg tcgggtcggg ggtggatgac ggctttaaaa 7740
gctgatactc ctccgactcc tccgccggcc ccggttcctc cgaagcctca gccggatccg 7800
aatccgccgt ccggtaactg atacacgatt ttaggggatt gttaatagat gagtgacact 7860
ggtttcacgt tgaagattgg tgatcgtagc tgggtgttgg cggatgcgga ggagacggct 7920
caggctgttc ctgcccgcgt tttccgtcgt gccgccagga ttgcccagtc gggggagtct 7980
gcggatttcg cccaggttga ggtgatgttt tctatgttgg aggctgccgc cccagctgac 8040
gcggtggagg ccctggaggg gcttcctatg gttcgtgtgg cggaggtttt ccgtgagtgg 8100
atggaataca agcctgacgg taagggtgcc tcgctggggg aatagtttgg ctccacggcc 8160
tgattgatga ttatcgtggg gccatcgaat acgatttccg caccaagttt ggtgtttctg 8220
tttatagtgt tggtggcccg cagatgtgtt ggggtgaggc tgtccggctg gctggcgtgt 8280
tgtgtaccga tacgtctagc cagttggcgg cccaccttaa tggttggcag cgcccgtttg 8340
agtggtgcga gtgggctgtg ttggacatgt tggatcatta caggtctgct aatagtgagg 8400
ggcagccgga gcctgtggcg aggccgactg atgagcgtcg ggcaaggttt acgtctgggc 8460
aggtggacga tattttggcg cgtgttcgtg ccggtggcgg ggtgtctcgc gagattgata 8520
ttatggggtg aatagtgtat gtctggtgag attgcttccg catatgtgtc gttgtatacg 8580
aagatgcctg gccttaaaag tgatgttggt aaacagttgt cgggtgttat gcctgctgag 8640
gggcagcgtt cgggtagcct gtttgctaaa ggcatgaagt tggcgcttgg tggtgcggcg 8700
atgatgggtg ccatcaatgt tgctaagaag ggcctcaagt ctatctatga tgtgactatt 8760
ggtggcggta ttgctcgcgc tatggctatt gatgaggctc aggctaaact gactggtttg 8820
ggtcacacgt cttctgatac gtcttcgatt atgaattcgg ctattgaggc tgtgactggt 8880
acgtcgtatg cgttgggggga tgcggcgtct acggcggcgg cgttgtctgc ttcgggtgtg 8940
aagtctggcg gtcagatgac ggatgtgttg aagactgtcg cggatgtgtc ttatatttcg 9000
ggtaagtcgt ttcaggatac gggcgctatt tttacgtctg tgatggctcg cggtaagttg 9060
cagggcgatg acatgttgca gcttacgatg gctggtgttc ctgtgctgtc tttgcttgcc 9120
aggcagacgg gtaaaacctc ggctgaggtt tcgcagatgg tgtcgaaggg gcagattgat 9180
tttgccacgt ttgcggctgc gatgaagctt ggcatgggtg gtgctgcgca ggcgtctggt 9240
aagacgtttg agggcgctat gaagaatgtt aagggcgctt tgggctattt gggtgctacg 9300

```
gctatggcgc cgtttcttaa cggcctgcgg cagatttttg ttgcgttgaa tccggttatt   9360
aagtctatca cggattctgt gaagccgatg tttgctgccg tcgatgctgg tatccagcgg   9420
atgatgccgt ctattttggc gtggattaac cgtatgccgg ctatgatcac gagaatgaat   9480
gcacagatgc gcgccaaggt ggagcagttg aagggcattt ttgcgagaat gcatttgcct   9540
gttcctaaag tgaatttggg tgccatgttt gctggcggca ccgcagtgtt tggtattgtt   9600
gctgcgggtg tggggaagct tgttgcaggg tttgctccgt tggcggttgc gttgaagaat   9660
ctgttgccgt cgtttggtgc tttgaggggt gccgccgggg ggcttggtgg cgtgtttcgc   9720
gccctgggtg gccctgtcgg gattgtgatc ggcttgtttg cggcaatgtt tgccacgaac   9780
gcccagttcc gtgccgctgt tatgcagctg gtggctgtgg ttggtcaggc gttgggccag   9840
attatggcag ctgtgcagcc gctgtttggt ttggttgctg gcgtggttgc caggttggcg   9900
ccggtgttcg gccagattat cggtatggtt gctggtttgg ctgcccggct ggtgcctgtt   9960
attggtatgc ttattgcccg gctggttcct gttatcaccc agattattgg tatggtaacc  10020
caggttgctg ccatgttgtt gcctatgctg atgccggtta ttcaggctgt tgttgctgtg  10080
atacggcagg ttattggtgt cattatgcag ttgatacctg ttttgatgcc ggttgtgcag  10140
cagattttgg gtgctgtcat gtctgttttg ccgccgattg ttggtttgat acggtcgctg  10200
ataccggtga tcatgtcgat tatgcgtgtg gtggtgcagg ttgttggtgc tgtgctacag  10260
gtggtggccc gtattattcc ggttgttatg ccgatttatg tttcggtgat tggattcatt  10320
gccaagattt atgctgcggt tatcgttttt gaggctaagg ttattggcgc tattcttcgt  10380
actattacgt ggattgtgaa tcattcagtg tctggcgtga ggtctatggg cacggccatc  10440
cagaatggct ggaatcatat taaatcgttt acgtctgcgt ttattaacgg ttttaagtcg  10500
atcatttctg gcggcgtgaa cgcggttgtg gggtttttta cgcggcttgg tttgtcggtt  10560
gcttcccatg tgaggtccgg ttttaacgct gcgagggggtg ctgtttcttc cgccatgaat  10620
gctattcgga gtgttgtgtc ttcggtggcg tctgctgttg gcgggttttt cagttcgatg  10680
gcgtctcgtg ttcggaatgg tgctgtgcgc gggtttaatg gtgcccggag tgcggcttct  10740
tctgctatgc atgctatggg gtccgctgtg tctagtggtg tgcatggtgt gctgggtttt  10800
ttccggaatt tgcctgacaa tattcggcgt gcgcttggta atatggggtc cctgttggtg  10860
tcggctggcc gtgatgtggt gtccggttta ggtaatggta tcaagaatgc tttgagtggc  10920
ctgttggata cggtgcgtaa tatgggttct caggttgcta atgcggcgaa gtcggtgttg  10980
ggtattcatt ccccgtctcg ggtgtttcgt gacgaggttg gccggcaggt tgttgccggt  11040
ttggctgagg gtattactgg taatgctggt ttggcgttgg atgcgatgtc gggtgtggct  11100
gggaggctgc ctgatgcggt tgatgcccgg tttggtgtgc gatcgtctgt gggttcgttt  11160
accccgtatg gcaggtatca gcgcatgaat gataagagtg ttgtggtgaa tgtgaatggg  11220
cctacttatg gggatcctgc cgagtttgcg aagcggattg agcggcagca gcgtgacgct  11280
ttgaacgcgt tggcttacgt gtgattttgg gggtgtggtg catgtttatt cctgacccgt  11340
ctgatcgttc tggtttgact gtgacttggt ctatgttgcc gttgattggt aatgatccgg  11400
agcgtgtgct tcatttgacg gattatacgg ggtcgtctcc gataatgttg ttgaatgatt  11460
cgttgcgcgg tttgggtgtt cctgaggtgg agcatttttc tcaaactcat gttggggtgc  11520
atggctcgga gtggcgcggg tttaatgtga agcctcgcga ggtgacgcta ccggtgttgg  11580
tgtcgggtgt tggcccggat ccggtgggcg gttttcgtga cggttttttg aaggcgtatg  11640
```

acgagttgtg gtctgctttt cctcctggcg aggtggggga gttgtctgtg aagactcctg 11700
ccggtcgtga gcgtgtgttg aagtgccggt ttgattcggt ggatgacacg tttacggtgg 11760
atccggtgaa caggggttat gcgcgttatc tgttgcattt gacggcttat gacccgtttt 11820
ggtatgggga tgagcagaag tttcgtttca gtaacgctaa gttgcaggat tggttgggtg 11880
gcggccctgt cgacggtaag ggtaccgcgt ttccggtggt gttgacgcct ggtgttggtt 11940
cgggttggga taatctgtct aataagggtg atgtgcctgc gtggcctgtg attcgtgttg 12000
aggggccgtt gtcgtcgtgg tctgtgcaga ttgatggttt gcgtgtgtcc tcggattggc 12060
cggtggagga gtatgattgg atcactattg atacggatcc tcgtaagcag tctgcgttgt 12120
tggacgggtt tgaggatgtg atggatcgtt tgaaggagtg ggagtttgcg cctatcccgc 12180
ctggcggttc tcggagtgtg aatattgaga tggttggttt gggtgccatt gttgtgtcgg 12240
tgcagtacag gtttttgagg gcttggtgaa tagttgatgg ctggttttgt tccgcatgta 12300
acattgttta caccggatta tcgccgtgtg gcgcctatca attttttga gtcgttgaag 12360
ttgtcgttga agtggaatgg tttgtccact ttggagttgg tggtgtctgg tgatcattct 12420
aggcttgacg ggttgactag gccgggtgcg cggcttgtgg ttgattatgg tggtggccag 12480
atttttctg ggcctgtgcg tcgggtgcat ggtgtgggtc cgtggcgttc ttcgcgtgtg 12540
actatcacgt gtgaggatga tattcgtctg ttgtggcgta tgttgatgtg gcctgtgaat 12600
tatcgtcctg gtatggttgg tatggagtgg cgtgcggatc gggattatgc ccattattcg 12660
ggtgcggcgg agtcggtggc taagcgggtg ttgggggata atgcttggcg ttttccgtct 12720
ggtttgttta tgaacgatga tgagagtcgt ggccgctata ttaaggattt tcaggtgcgg 12780
tttcacgtgt ttgccgataa gttgttgccg gtgttgtcgt gggctcggat gactgtcacg 12840
gtgaaccagt ttgagaatgc gaagtttgat cagcgtggtt tggtgtttga ttgtgtgcct 12900
gctgtgaccc ggaaacatgt gttgactgcc gagtcgggtt cgattgtgtc gtgggagtat 12960
gtgcgtgacg ccccgaaggc gacatctgtg gtggttggtg gccgtggcga gggtaaggat 13020
cggctgtttt gtgaggatgt tgattcggcg gccgaggatg attggtttga tcgtgtcgag 13080
gtgtttaagg atgcccgtaa cacggattcc gagaaggtgt ctctcttcga tgaggctgag 13140
cgggtgttgt ccgagtcggg ggctacgtcg gggtttaaga ttgagttggc tgagtcggat 13200
gtgttgcggt ttggtcccgg caatctgatg cctggggatt tgatctatgt ggatgtgggt 13260
tctgggccta ttgcggagat tgtgcggcag attgatgtgg agtgtgtatc gcctggtgat 13320
ggttggacga aggtgactcc ggttgcgggg gattatgagg ataatccgtc ggccctgttg 13380
gctcgccgtg tggctggttt ggctgcgggt gtgcgggatt tgcaaaagtt ttagtaagtg 13440
attggggttt gttgtgggta ttgtgtgtaa agggtttgat ggtgtgttga ccgagtatga 13500
ttgggctcaa atgtctggtc tgatgggtaa tatgccgtct gtgaaggggc ctgacgattt 13560
tcgtgtcggc acgacgattc agggttctac ggtgttgtgt gagatcctgc cggggcaggc 13620
ttgggctcac ggggtgatgt gcacgtcgaa tagtgttgag acggtgacgg gtcagcttcc 13680
gggcccgggt gagactcgat acgactatgt ggtgttgtct cgggattggc aggagaatac 13740
ggccaagttg gagattgttc ccggtgggcg tgcggagcgt gccagggatg tgttgagggc 13800
tgagcctggc gtgtttcatc agcagctact ggcgactttg gtgttgtcgt ctaacgggtt 13860
gcagcagcag ttggataggc gtgctgtggc ggctagggtt gcgtttgggg agtctgctgc 13920
gtgtgatcct acccctgtgg agggtgaccg tgtgatggtt ccttcggggg ctgtgtgggc 13980
taaccatgcc ggcgagtgga tgttgttgtc tcccaggatt gagacgggtt cgaagtcgat 14040

-continued catgtttggt ggttctgctg tgtatgctta cacgatcccg tttgagcgcc agttcagtag 14100
tccgcctgtt gtggtggcgt ctatggctac ggcggctggg ggcacggcac agattgatgt 14160
gaaagcctac aatgtgactg cccaaaattt tagtttggcg tttattacga atgatggttc 14220
gaagccgaat ggtgtgcctg cggtggcgaa ttggattgct gtcggcgtgt gactgcacgg 14280
gtgttgtggc ggatggtgtg atgttggggg gctgtggtgt cgtggtttac tcctgcactg 14340
gtggcctcta tttgtaccgc gttggccacg gttttgggtt ctgttcaggc tgtcacatcc 14400
cggtctagga agcgtttacg caggctgtcg gctcaggtgg atgcgatgga agagtatacg 14460
tggggtgtgc ggcgcgaggt gcgaaggttt aacgccgggc ttcctgatga tgtggagccg 14520
atgcatcttc ctgatttgcc cgagtttttg aaagatactg ttgatggtgg aggtgagtag 14580
ggttgaggga gttggaggag gagaagcggc agcgccgcaa ttttgagaag gcttcactgg 14640
tgttgttgtt tttgtcgctt gtgttgttgg cggtggttgc tgcgggtgct ttgcgtttcg 14700
gggctgtatc ctctgagcgg gattcggagc aggcgagggc ccagtcgaat ggtacggctg 14760
ccaggggttt ggctgcccgt gtgaagcagg cgtgtgcttc gggtggggtg gagtctgtgc 14820
gtcttcaccg ttctggtttg tgtgtggatg ctgtgcgtgt tgagcagcgt gttcagggtg 14880
tgccgggtcc tgccggtgag cgcggcccgc aaggcccttc aggtcctgcc ggccgggatg 14940
gtgttaatgg ttcggctggg ctggttggcc ctgttggtcc gcaaggttct ccgggtttga 15000
atggtgtgaa aggtcctgac ggcttgcctg gcgctaacgg ttcggatggc cgtgatggtg 15060
ttccaggtcg tgcaggtgct gacggtgtga acggcgttga cggcgctgat ggtcgggatg 15120
gttctgccgg tgagcgcggc ccgcaaggcc cttcaggtcc tgccggcccg caaggtgcac 15180
agggtgaacg gggtgagcgt ggtcccgccg gtgcgaatgg atcggatggc catgatggta 15240
aggatgggcg ctcggtggtg tctgtgtact gttccggggg ccgcctggtt gtgaaatata 15300
gtgacggtgt ggcttccacg atatcgggtt cggcggcctg ccagggtgtg aaaccgtcgc 15360
ctctagtgac tatatcatcc cacaaataga aaggagtggc tgtgatggtg gtgtttggtg 15420
gtggtgtgtt gtgagatata ttcctgcggc gcatcattct gccggctcga atagtccggt 15480
gaatagggtt gtgattcatg cgacgtgccc ggatgtgggg tttccgtccg cctcgcgtaa 15540
aggacgggct gtgtccacgg caaactattt cgcttcccca tcgtctggtg gttcggcgca 15600
ttatgtgtgt gatattgggg agacggtgca atgcttgtcg gagtctacga ttgggtggca 15660
tgccccgccg aatccgcata gtttgggtat agagatttgc gcggatgggg gttcgcacgc 15720
ctcgttccgg gtgccggggc atgcttacac tcgtgagcag tggctggatc ctcgcgtgtg 15780
gcctgcggtt gagcgtgccg ccatcctgtg tagacgtttg tgtgacaagc atggtgttcc 15840
gaaaaggaaa ctgtctgtgg ccgatttgaa ggccggtaaa cggggtgttt gcgggcatgt 15900
ggatgttacg gatgcgtggc atcagtcgga tcatgacgat ccggggccgt ggtttccgtg 15960
ggacaaattt atggctgtgg ttaatggcca cggcggcggt tcaagtagtg aggagttgag 16020
tatggctgat gtacaagcgt tacataatca gattaaacag ttgtcggcac aggtggccca 16080
gtcggtgaat aagctgcatc acgatgttgg tgtggttcag gttcagaatg gtgatttggg 16140
taaacgtgtt gatgccttgt cgtgggtgaa gaatcctgtg acggggaagc tgtggcgcac 16200
taaggatgct ttgtggagtg tctggtatta cgtgttggag tgtcgtagcc gtcttgacag 16260
gctcgagtct gctgtcaacg atttgaaaaa gtgatggtgg tttgttgtgg gtaaacagtt 16320
ttggttaggt ttgctggagc gtgccctgaa aacttttgtt caaacgtttg ttgccgtgtt 16380

```
gggggttact gcgggtgtca cctatactgc ggagtcgttt cgtggtttgc cgtgggaatc  16440
cgcgctgatc acggcaacgg ttgctgctgt cctgtcggtt gctacctcgt ttggtagccc  16500
gtcgtttgtg gccggcaagc ccggcaagca gccccaggtg gatgcgggtt tggttccacc  16560
ggatgatggg ggcttggttg agccgcatat ggtggatgtg tcggatcctg gcatgatcga  16620
gccgacggat gatgcggatc ttgccggcta tgagcctcgg cgtgcagccg agtcggaggt  16680
tggcacggta gagtctactg ttgcataatt gaatatagat gtgtgcccca gcggtgctgc  16740
cacgattgtg tggtggcggc tgctggggca ctatttttgt atatgcggtg tggctatgat  16800
tcgttgctgt cgatggtgtc ttcgagcatc tgatacaggt ggaggcaggt agagatagtt  16860
tcgctggcct gatcgagaac gttccggccg ataacgtttt tgtggttgtc gcggtggcgg  16920
atgatagccc acatgatctc gtcggctgcc gcctgtaata gtttggcctg gtatgcgatt  16980
ccggcgagcc agtctagtgc ttcctggctt gtatagggcc tctggtcctc gctgttgccg  17040
cgggtgttgc tgttgtttgt ggggtgtcct gcactgtcgc atagccacag gatttcgctg  17100
cactcgtcta gcgtgtcttg gtcgatagcg agatcgtcga ggctgacatt gttgacggta  17160
aggttcacgt tgtcgaggga gatgggtaca ccgtactggt tttcgacact gtcaacaatg  17220
ttttccagct gttgcatgtt ggtgggctgt tgttggacga tacggtgtat cgctgtgttg  17280
agggtggtgt aggtgatgtt gtgtgtgttg tccatggttt ttatgccatt ccttcgttat  17340
cgtctggcat gtagtatgtg ctgtttgcgt actcggttaa cgtcatcagt gtttggtctg  17400
cccactgttt cacggtttgc cgggtgactc cgagtcgttg ggcggctgtg gcgtaggttt  17460
gatcataccc gtatacttcc cggaatgctg ccaacctagc taggtgtttc ctctgtttgg  17520
atggttcaca ggtgagggtg tagtcgtcga tggctagctg tagatcgatc atggagacga  17580
tgttgttgcc gtggtgttgt ggcgcggttg gtgggggtgg cattcctggc tccacggagg  17640
gtttccaggg gccgccgttc cagatccatt gggcagcttg gatgatgtcg gcggtggtgt  17700
aggttcggtt cactggtcac cccctgaaca ggtcgttggt gttgttggtg tcgaatcgtc  17760
cgacgcagtg gcagtagtcg tacatgagtt taataatgtg ttggtggtct cccaaatagg  17820
tgtttccgct gatgctgtat gtggctgtgc cgtctttcgc gatggtgtat ttggcggtga  17880
tggtttcggg gttttcggtg tcggtgatga ttgctgtggt ggtggcgcct actgtttgga  17940
gtatggtggt ttgggttccg tcgtcgatgg tggttttaac catggtgtgt gttttccctt  18000
ttgttagttg cttgtttggt tgtcggctag atgaataata tcgggtaaag gtttcggctg  18060
gtctaggtgt tgtatggttt tgttggctag ccgtttggct accctgtaac acattttggt  18120
gtagtgtttg ttgtctaggt tgtggtattg ttcccgcacc gcaatatata gcagggagtc  18180
ttggtacagg tcgtctgcac tgattgcggg gtagtgtgcg gctgttttgg tgcatgcccg  18240
gttgagtgtg cgaagatgat ggtctgtggc ccacacccac gatgcggtgg tggccaggtc  18300
ggcttttgtt ggtcgtctgc tcatggcact atttcatctc gctatctgat agttgtttgg  18360
tgttttgttg tggatagtgt agcacactag tcctgggtgg ccggtggtgc ctgtgcggtg  18420
acggaaccat gtggattcgc cttccatgga tgggcattgg atgaaggtgc gttgtccttg  18480
ctcggagatt tctaggtggt gccggtgccc ggccatgaga atattagata cggtgccgtt  18540
gtggaattct tggccgcgcc accaatcata gtgtttaccg gtgcgccatt ggtgcccgtg  18600
ggcgtgcagt atccgtgtgc ctgccacatc aacggtggtg gtcatttcgt ctcggctggg  18660
gaagtggaag tgtaggttgg ggtattggtt attgagctgg taggcttctg cgatggcccg  18720
gcagcagtcc acgtcgaatg agtcatcgta ggtggtgact cctttaccga agcgcacggc  18780
```

```
ttcaccatgg ttgccgggga tggatgtgat ggtcacattt ttgcagtggt cgaattggtg  18840
gatgagttgc atcatggcca tgcgggtgag cctgatttgt tcggtgaggg gtgtttgtgt  18900
tcgccaggcg ttgttgcctc cttgtgacac gtatccttcg atcatgtcgc cgaggaaggc  18960
gatgtggact cgttcgggtt tgcctgcttg ttgccagcag tgttttgcga ctatgaggga  19020
gtgtaggtag ttgtcggcga agtgtgctgt ttctccgccg gggatgcctt tgccgatttg  19080
gaagtctcct gccccgatga cgaaggctgc ggtgctgtag tcggtgtggg tgtcttgttc  19140
gggttttggg ggtgtccatt cggctagttt atcgacgagt tcgtctaccg ggtaggggtt  19200
tgttgcgggt tggtggtcga tgattttttg tatggatcgg cctgtttctc cgttggggag  19260
tgtccattcg gagatgcgtg tgcggcgcac ggtgccgttg gctagattgt cgtcgatggt  19320
gtcgatggcg ttgtcgtggt tggctagctg tgtgagtagc cggtcaatat tgtctatcac  19380
tgggtatcct cctcttgcgg ggtggtgctg gcttgtttgc ggcgatagtc tttaataacg  19440
gtggcggaga tggggtatcc tgcctgggtg agctgttttg ctagccatga ggcggggata  19500
gacctgtcgg cgagcacgtc ggcggctttg ttgccgtagc gttgaataag ggtttcagtt  19560
ttggttgcca tgatgtccta tcggttgtgt ggtgggctgc catcctgtgc ggcagtcgcc  19620
gtcgtgtcct ggtttgcgtg tgcaccacga tacggttccg tctgtgtggt tgagtgtttt  19680
accgcacatg acgtttcgga gatgctccgg cagctggtca tcctggttgc tggtttgtgt  19740
gtcgaagagt gttttctggt tggtgaaatg ttctgacacg gtgccgttat gcacgggtag  19800
tatccatgtt ttccattgtt gttgtagcct ggtgttccag tggaattgtt tggcggcgtt  19860
ttcggcctgt tttaaggttt tgtggtagcc gactagtatg cgttgatgct gctggtctgg  19920
agggtttggg cctcgccagt attgtgccgc cacggcgtag cggttgctgt ctgtgaaggc  19980
gtcccagcag tattcgataa tgtgttgcaa catactgtct ggcaggctgt cagggttgat  20040
gttgatgttt tgggtgataa tgtcacggat ggcttgccgg tttttggtgg tgggtttgaa  20100
cgagatgctc acgatagtac cggctggtcg tcttgcatga actggttgaa ggtgttgttc  20160
ccggcgtgtt gggcttgtgt tatttgttgg tcggtccagt ctgggtgttg ctgtttcaga  20220
tagtgccagt ggcacgcatt gtaggtttcg tcttgtagcc gtgtgagatg gttttcggtg  20280
atgatttgtt tccacatggc ccatgacacg tcgagccggt cgaggatttc gagggctggg  20340
atgttgaatt ggttcaggaa gaggatttcg tgggtgtagt agtttttctc gtaggcgtcc  20400
catccgcttc ggtgcctgtt gggctggttt ttggggtagg cttcccggca tactttgtgt  20460
aaacgcttgg ccatgtcgtc gggtagttta atgtcggggt tggcgcggat catggatcgc  20520
atcccatcat aggtggtgcc ccaggtgtgc atgatgtagg tggggtcttc tccgtcggcc  20580
catttttctg cacagatggc gaggcggata cgcctcctgg cagcttggct ggtgttgcgc  20640
cggttgggga ttgggcacgt gtcgagggga tccatgatgt tttagtgtac ctttctggtt  20700
tcgtgttgtt gacaggtttt actgtagcac agtgtctagt gcgtgtgtca accctgtttt  20760
tccggcttga aggtaggtgt ctgtgacatc ccctagggtg aggggcacgt gcacagcttg  20820
ggggagtgcc gcctggaggg tttgggccat ctggtcgcct gcggggtctg ggtctgacca  20880
gatgtagatg tggtcgtagc cttcaaaaaa tttggtccaa aaaatttgcc acgaggttgc  20940
gccgggtagg gcgacggccg accatccgca ttgttcgagg atcatggagt cgaattcgcc  21000
ttcgcaaatg tgcatttcgg ctgccgggtt ggccatggcg gccatgttgt agatggagcc  21060
tgtgtctcct gccggggtta ggtatttggg gtggttgtgg gttttgcagt cgtgcgggag  21120
```

```
tgagcagcgg aaacgcattt ttcttatttc ggctgggccg ccccaaacgg ggtacatgta  21180
tgggatggtg atgcactggt tgtagttttc gtggcctggg atggggtcat tgtcgatgta  21240
tccaaggtgg tggtagcggg ctgtttcttc gctgatgcct cttgctgaga gcaggtcgag  21300
tatgttttcg aggtgggttt cgtagcgggc tgaggctttc tggattcggc ggcgttccgc  21360
aatgttgtat gggcgtatgc tgtcgtacat ttgggttttc ttcttctaat cgttgttgta  21420
gcttggcgag tccgcctccg acaccgcatg tgtggcagta ccagacgccc ttgtcgaggt  21480
tgatgctcat ggagggctgg tggtcgtcgt ggaacgggca gagtatgtgt tgctcgttcc  21540
tggacggatt gtaccgtatc tgataatggt cgaggaggcg gcaggtgtca gaggtgtggg  21600
aggagctcgt tgagggttga taccacatag gcttcactcc atggcttgtt gcgctgtttc  21660
atcactacga gtccgatggt ggaattgttt tgtttgtttc ggtgtgtttc gtagttgcgt  21720
gcctcccggc tggcttgttt cacgaattgg gctaggtgtg gttgcccggc tttcgcctcg  21780
ataatgtagg ttttatggcc ggttgtgagg atgaggtcgc cttcgtcttc gcggccgttg  21840
aggtggaggc gttcgatatt gtgtccggtg tcgcgtagct ggtggaggag tcttgtttcc  21900
cattcggctc cggcccgccg gttgcgtgcc tgctgtgtgg ccatagtttt ttagagtcct  21960
ttgtgtgttg tggtcatgtt ccagggctgt ttttcggcga gtggcccgaa gaatgtgtat  22020
tcggggtatg ctctgagtcg ttcgtatcgg gtgccgtcgg ggctggattt gcctgtgcgc  22080
tgtttgagta cggcgatgcg tgcctctgcc ggtatcgata gcccgttgcc gttatcctcg  22140
ccaccataca atgagactcc gaggatgagt tgtggttttt cggagaggcc gtttttgatt  22200
tctcgccgtg ctggcgggtg ttcgatgtcg gttccggttt tgtcggttgc gtggtgtgtg  22260
acaataatgg tggagccagt atccctgccc aatgctgtga tccattgcat ggcttcttgc  22320
tgtgcctggt agtcggattc gcagtcttga atgtccatca ggttgtcgat aacaatgagt  22380
ggtgggaagg tgttccacat ttccatgtag gcttgtaact ccatggtgat gtctgtccat  22440
gtgatgggtg actggaatga gaatgtgatg tgttggccgt ggtggatgct gtctcgatag  22500
tattctggcc cgtagtcgtc gatgttttgt tgtatttgtt gggtggtgtg ttgtgtgttg  22560
agggagatga ttcgtgtgga ggcctcccag ggtgtcatgt cccctgatat gtagagggcg  22620
ggctggttga gcatcgctgt gatgaacatg gctagccctg atttttggct gccggaccgc  22680
cccgcgatca tcaccaagtc gcccttatgg atgtgcaaat cttggttatc atatagtggt  22740
gcgagttgtg gtatgcgggg tagttcggct gcggtttggg aggctctctc gaaggatcgt  22800
tgtagagaga gcatcgggac cttaatctat ctgtctgttg gttgtgtggc tggtcagatg  22860
gagtcgatat cgatatcagc atcagcagag gctgaagtgt catctagctg accattatcg  22920
cgcttgtcta cgtattcggc aaccttatcg tagatggcgt cgtccaatgt tttgagcacg  22980
accgcgttga aaccgttttt ggtgcgcacg gtggctagtt tgaaggcctg ctcctcgcca  23040
aggtatgcct ctagttcgcg gatcatggag tgtgggcggt cgttattgcc gcgggctttc  23100
tcaataatag cgttggggat ggtttctggg gtgccgttgt tgagatcgtc tagggtgtgg  23160
aagatggtga catcagcgta gatgcggtct gcgacctgtc caccgtagcc ttcagtgttg  23220
tgctggacgt cgtgcacttt gaaggcgatg gccgtggcgt cctggtttcg ggaggggttg  23280
aagaaggtgc tgttgctgtt gttgcggtag tttgcgagtc ccataactat tgtttccttt  23340
tactgttgtg tctgtttttg ttggcttata ttggtttatc gggtgaggct gtttcgctta  23400
gtgcggaaag cgtcggaaac atcactgtta ctggtgatga tcttcttgta ctgttttaga  23460
aggtctgcta gctgtgcctt gcttgttgca ttgttgattt tgttgatgac gatggtgttt  23520
```

```
tctttggatg cgattttgtt gacgtagtct ttggctgcct ggttgtatcg gtcttggagg  23580
atgattgatg cgctcgctac gagtgttgct agatcccagt ctttggacac gtcatcgttt  23640
ttgagtccgc ctagcaggtc gatgatggcc tgttttgtct gctctgctgt gtctcctcgg  23700
atgaccgccc atggtgcagc atagtctcca ccatatttga gtgtgatcgt gagtcgatca  23760
ttgtcgatct tgtctttatc tgtcatttgg tgtccttttc tttattgtct gtttctggtg  23820
gctgtacggt ggattctacc gggtatctgt acgagttttt gccgttgacg gcccagcagg  23880
cgtctcgtac ggggcatcct ttacagagtg ttgtgacgtg ggggacgaag atgccttcgc  23940
tgattccttt cattgcttga ctgtacatgg atgatacatg ccggtaggtg ttgttgtcaa  24000
ggtcgtagag ttcggtggat gtgccttgtg tcggggactt gtcgtcgttg cggctggtgg  24060
ctggcgtcca aaacatgcct ttcgtgacat ggatgtcgtg ttggttgagc atgtaccggt  24120
atgtgtgcag ctgcatactg tcggcgggta ggcgtccggt tttgaggtcg aggatgaagg  24180
tttcgccggt gtcggtgtcg gtgaaaacac ggtcgatgta gccgactatt tttgtgtcat  24240
cgtcgaggat ggtttctacc gggtattcga tgcctggttt accgtccagg attgcggtga  24300
tgtattctgg gtggttgcgc ctccatgttt tccagcggtc cacaaaggtg gggccgtaaa  24360
ccatccacca gtcgtagtct ttcttgtgtg gtccgcctga ctcgcacatg tttttgcata  24420
ttctgccgga gggtttgatt tctgtgcctt cggattcggc gagggctacc tgggtgtcga  24480
aaatgttttt gaaggatgag agtttgtctg gcagtgcagg gtattcggcg ggattgtaca  24540
ggtgtaggtc gtattgttcg gtgatgtggt gtatggcgct tccggcgatg gtggcgtacc  24600
aggtgtggtg ttgggcgtga tagccgtggg ataggcgcca tttttctccg cattcggccc  24660
actgggtgag tgaactgtag gagatgtgtc ctgggtggct gatggttttc gggtattgtg  24720
ctagaggcat tacttgtcgc ttgtgttcca tgtgttgcgg gtgtcttggc cggcgtggtg  24780
ttgctggtag gcgaggagtg cgaggcagtg ccaggctgcg tgtgctagat ggggtagccc  24840
ggattcgtgg tcgaggttgt tgccttgctg ccatgatagt agatgcctgt agagggcgtc  24900
gacactgtgg ctccacgggt atcctccggt ccagttgttg tcgccatatt tggtggcacc  24960
gtatccggct acttcgccta gggcgtgaag ggatgctggg tcgatgaggg agagcctgca  25020
gagtttcaat tcttttcggg caccgctgtt ggggtcggtg tacatgcggg tgggctcatc  25080
catggggtgt gtgctcctta agggtgggtt actggttgtt gttgtgggct agggcggcgg  25140
cgagaataat gatggcgagg gtttcggcta tcagtatggg tgttgtgatc atttggtgtc  25200
tcggggattg ttggtgagtg ttgaggcacc caggagggtg gcgagggcgc atgcggcaat  25260
aatggcgagg gctgccttgt gtggggtgcc ggttgcgtac atccatgtga tgatggcacc  25320
ttggatccag gctaggctgg tgaagaaggt ttcgtagctg tgcagctcaa tgttgttgtt  25380
gggtgtgttc atgcttgctc ctgaagaatg gtgttgatgg ttttataaat gttgtacagg  25440
tcggtttcga tagataacag ttggttgatt tggtggtcga gatcaatgtc tgggttgagt  25500
gtgttgatgc gggaggcaat atcggtggct gtgcgtagtg tgccgccggt gtggtgaata  25560
atgtgtgccg tgtcggcgag tccggtggtg acggcgtagt gggataggag aggcatagcg  25620
gggatgctcc ttggcgggtt actgttgcgg gttgatgttg aggtcggtga cgtgcggtga  25680
gttttctgtt ccggtgacga ggcagtggac ggtgacgggt agtttggatg ctcccggctg  25740
gcggacggtg gcgccgtaga cgatgctgaa tgtgtcttta ccgatggttt tgtggagttg  25800
gaggtcgatg tcggggttgc cgttccagtt gacaccttgc gctgcggcct gttgttcggc  25860
```

tttgtggttg caggtgtgtg ctgccgtgat catggtgagt ccggtggcgg tttcttcacc 25920
ccttgcttgg gcttgcttgt gggctttggc ctgctcggct tgtagggatc gggtggcggc 25980
tgcctgccgt gccgctttct cggctttgcg ctgttgggta gtcttggggg tccatgtggt 26040
gttggctgtg gttgcctgtg gggctggctg tgaggtgagt ggcgggttgt cgtctggtgc 26100
tggcatgaat gaggcggcgg caatgatggc ggctgtgatg cctgcgatgg tgtagccgtt 26160
tttcttgttc atgttttgtg tcccctttcc ggggtgttgt tcgttgctga catggttaat 26220
actttcagcg gctgggccca ctgtcaaggc tgcgctcagt ttgtgtgagc gtttggtgtg 26280
tggctagggg ttttgtcatg taagcgtgac atgtcactac cttgcgtcca gtatccatgg 26340
cggttgcgag ccatcccttt ggcgagcatc tcgtccacag tgaggcacct gcggcgattg 26400
gggccttcct tgaccccgtg atcgcctatg cggtgcatgt ccccggcata agtgccatta 26460
aatgtttcgt ggcagactgt gcagtgttct ggtcggtatc cgatgattgt gctatcgcac 26520
ttgtggcatg tccattgcat gattggtcct tctttcgtgt tttaagcttg tgctctgagg 26580
attagagcga ctttcagccc ttgggggtag gattatatag gtcaggtatt tctaggcgat 26640
tctaggctca ttgtgtgtgg ttggggtttt atcgggcgca tagggttagc aggtggccca 26700
cattggtgcg gctcacattc cagtagagtt gcgtggcttc cttactggtg agcggcttcc 26760
actcgtcatg gctgaacacg gtgccatcgg atgcgatgaa cgtgttgggg cgtagcttgt 26820
gaagctcggc ttccacatgc tgccggtagg cttcggcgag gctctcaaaa tccatgtggt 26880
cgcaggagag gttttcgagg cgtgtcaggt cgaaaggctc cgggcagtcg tagctggctg 26940
gagtgtagag ctgggtgaag tggtcggcga tcttctgcat ggcgggttcc tttctggtgt 27000
gtggatggtt tttatcgtgt ggatgcgaca aggatggcgt ctacgtcgat catgtcgatc 27060
atgtcgttga gttcctcggc ctcattctcg gagaggtggc gccagtcggg tggcccgtat 27120
acggcgccgt cgagggtgac agtccacagg ggccggatga gtcgtatggc ttcttcgact 27180
ttggcgtggt acatgcggcg caccatatcc agatcgatgt cgtctgaatg gtttccggtg 27240
aggctgtgga ggctgagcgg gtcgatttct gtctgcctgt agaggctggt gaatgatggt 27300
gtgatgagtg tgccatccat gagtgtgctc ctttctaggg gttgttgtgg tttctagagt 27360
gtgtgggctg tgaccccaca gtcaaggcta cgctcatttg gattgagcgt ttcatatggg 27420
tgtggcatgg aatctacacc ctcatactgt gtgagatgta tcacatcccc ctggcttggt 27480
gtgcacccct caagactact ctgccgacct ggcgtggagg gtgtagccca gaaatgccgt 27540
ttaaagcttc aggggtacgc ctaggagcgc cttacagggt gggggctagg tatttatacc 27600
cccagcatat tctgatcgat tctagacgac tcccagagcc cgatacacga tcaaccatct 27660
cgacatagac catcagcccc tatcctggtt agctaagcct caactatgtg gacagtgtgg 27720
gacactgtgg gggaagaagg acacggtaca agaaagaggg gggagcatca gccttaaagc 27780
cttaagatct tagcgcttag caccgatggt cttagcagtt agcaccgagc ccttgagggg 27840
gctcggcatc agcctcatcg ggctcagctc atcaggcaca gccctgaaaa gggtacacgc 27900
catcagggaa ggcttgagag tacgaggagc cctagcgacg agtactcgaa agcctgaggg 27960
aacaccctca gtactgatga gcctagcgta ttcggaaagg acgcaagagt aaagtgtgac 28020
agctatccgg gagtgaaacc cgttccgact aggggtttca gccttaacca ccctcaaagg 28080
ttacaagact ctaagaaaat ttaagaaact tcttaggaag aaagttgtgt tcatatcccc 28140
ctaaaaacac ccaaaatagt cctcaaaccc gcctatagag ccaaacagtc aagtttgact 28200
cgtctagacg gcgtatgata ggctggacag gtagccagct ggacgcaagg ccagaaagtg 28260
ctgacgcact tcccgacctc gcttaccatc agtctaccaa acactttaaa gcttcaaggc 28320
ttagcgctaa gcccttaaga tcttaacgct tagcaccgag cccccctcaa gggctcgaca 28380
tcagtcttaa agtcttaaac actttaagta actttaaagc ttcaaggctt agcccttaag 28440
gatctaagtt actataaaag ctttaaacac ttaaagtaac tataaagctt taagagctta 28500
acatttaagg atataaataa acattaaagc tttaaagtct taaagtaaat atataacctt 28560
aacacttaag ttaagtataa aaccttaaag gcttagcact taaggatata aacttaacat 28620
cagtgtttaa gacttaaaga gttaaagtaa ctattaagac ttaaaggctt ataagcttta 28680
atactttaag tagctataag actttaaaaa cctgaagtac ttaaagttaa ccatcagtct 28740
taaactttaa tattataagt attaaagctt ataagttata aaagttttta gaagagttaa 28800
agggttaact tctttacttc tcttctctct ttggttcttt ctctcttctc ttcttttctt 28860
catcagggga gaagaggaac ctttaaccgt caacgctgat ggacttttca ccgtgtgact 28920
cgtgtgcttc tggtcgcaag ctcccatcgc acactcccca cactctttca cccgtgcccc 28980
tttacggctt agcgtgttcg tcggaaggcg tacggcgtgt cacgcttaaa cccttaacac 29040
caggtaagac ttaaagtgca tattataagt agaagacttt aaaacctata aggtgttccc 29100
gcttagcccg tgttccttta acgctaggcg ctcagcgcta agatgtgaaa cgtgaacacc 29160
catccacccc catttttctt ccgtgtcctt ctccttttga caccgctggg gggcgatgtg 29220
atatttctca catgccaggg ggtagtggag aaaacaacca ccccggaacg tttaagacac 29280
cccctcaaac gaacaaaaca gggcctagaa tcgatcagca gggcaccggt agggtattcc 29340
tacccccaga cgattcaagg ccattacagg agcaatgaga ggctcacagg ggccatggga 29400
gattgggggg cgtgatggca cacaccaacc gcacagccag ccaagcccac cggcgctggc 29460
gggcaaggct catcacccaa gcccgacaac aaggccaaac cgaatgccca ctctgcggag 29520
tcaccatcac ctggaacacc cacgacctgc caaccagccc cgaagccgac cacatcacac 29580
ccgtcagccg gggaggactc aacaccctcg acaacgggca aatcatctgc agaacatgca 29640
acagaagcaa aggcaacaga acacaaccaa acatcaaatt ccaacaacaa accacaaaaa 29700
cattgattcc atggtgaaaa acccgccaac ccccaccggg cacaccccct gcacacccgt 29760
gcaagacc 29768

<210> SEQ ID NO 106
<211> LENGTH: 23
<212> TYPE: DNA
<213> ORGANISM: Artificial Sequence
<220> FEATURE:
<223> OTHER INFORMATION: primer IC290

<400> SEQUENCE: 106
gatggagacc accaacacat tat 23

<210> SEQ ID NO 107
<211> LENGTH: 303
<212> TYPE: DNA
<213> ORGANISM: Artificial Sequence
<220> FEATURE:
<223> OTHER INFORMATION: PAC7 endonuclease

<400> SEQUENCE: 107
atggcacaca ccaaccgcac agccagccaa gcccaccggc gctggcgggc aaggctcatc 60
acccaagccc gacaacaagg ccaaaccgaa tgcccactct gcggagtcac catcacctgg 120
aacacccacg acctgccaac cagccccgaa gccgaccaca tcacacccgt cagccgggga 180
ggactcaaca ccctcgacaa cgggcaaatc atctgcagaa catgcaacag aagcaaaggc 240
aacagaacac aaccaaacat caaattccaa caacaaacca caaaaacatt gattccatgg 300
tga 303

<210> SEQ ID NO 108
<211> LENGTH: 20
<212> TYPE: DNA
<213> ORGANISM: Artificial Sequence
<220> FEATURE:
<223> OTHER INFORMATION: sgRNA target in PAC7 wt endonuclease region

<400> SEQUENCE: 108
gccattacag gagcaatgag 20

<210> SEQ ID NO 109
<211> LENGTH: 22
<212> TYPE: DNA
<213> ORGANISM: Artificial Sequence
<220> FEATURE:
<223> OTHER INFORMATION: primer AL97

<400> SEQUENCE: 109
ggtcttgcac gggtgtgcag gg 22

<210> SEQ ID NO 110
<211> LENGTH: 30
<212> TYPE: DNA
<213> ORGANISM: Artificial Sequence
<220> FEATURE:
<223> OTHER INFORMATION: primer IC619

<400> SEQUENCE: 110
aggcttataa gctttaatac tttaagtagc 30

<210> SEQ ID NO 111
<211> LENGTH: 21
<212> TYPE: DNA
<213> ORGANISM: Artificial Sequence
<220> FEATURE:
<223> OTHER INFORMATION: primer AL219

<400> SEQUENCE: 111
acaaacaccc cacacacacc c 21

<210> SEQ ID NO 112
<211> LENGTH: 2999
<212> TYPE: DNA
<213> ORGANISM: Artificial Sequence
<220> FEATURE:
<223> OTHER INFORMATION: template for homologous recombination to
introduce 908bp in locus 1

<400> SEQUENCE: 112
gggtttccgt ccgcctcgcg taaaggacgg gctgtgtcca cggcaaacta tttcgcttcc 60
ccatcgtctg gtggttcggc gcattatgtg tgtgatattg gggagacggt gcaatgcttg 120
tcggagtcta cgattgggtg gcatgccccg ccgaatccgc atagtttggg tatagagatt 180
tgcgcggatg ggggttcgca cgcctcgttc cgggtgccgg ggcatgctta cactcgtgag 240
cagtggctgg atcctcgcgt gtggcctgcg gttgagcgtg ccgccatcct gtgtagacgt 300
ttgtgtgaca agcatggtgt tccgaaaagg aaactgtctg tggccgattt gaaggccggt 360

-continued

```
aaacggggtg tttgcgggca tgtggatgtt acggatgcgt ggcatcagtc ggatcatgac    420
gatccggggc cgtggtttcc gtgggacaaa tttatggctg tggttaatgg ccacggcggc    480
ggttcaagta gtgaggagtt gagtatggct gatgtacaag cgttacataa tcagattaaa    540
cagttgtcgg cacaggtggc ccagtcggtg aataagctgc atcacgatgt tggtgtggtt    600
caggttcaga atggtgattt gggtaaacgt gttgatgcct tgtcgtgggt gaagaatcct    660
gtgacgggga agctgtggcg cactaaggat gctttgtgga gtgtctggta ttacgtgttg    720
gagtgtcgta gccgtcttga caggctcgag tctgctgtca acgatttgaa aaagtgatgg    780
tggtttgttg tgggtaaaca gttttggtta ggtttgctgg agcgtgctct gaaaactttt    840
gttcaaacgt ttgttgccgt gttgggggtt actgcgggtg tcacctatac tgcggagtcg    900
tttcgtggtt tgccgtggga atccgcgctg atcacggcaa cggttgctgc tgtcctgtcg    960
gttgctacct cgtttggtag cccgtcgttt gtggccggca agcccggcaa gcagccccag   1020
gtggatgcgg gtttggttcc accggatgat gggggcttgg ttgagccgca tatggtggat   1080
gtgtcggatc ctggcatgat cgagccgacg gatgatgcgg atcttgccgg ctatgagcct   1140
cggcgtgcag ccgagtcgga ggttggcacg gtagagtcta ctgttgcata attgaatata   1200
gatgtgtgcc ccagcggtgc tgccacgatt gtgtggtggc ggctgctggg gcactatttt   1260
tgtatatgcg gtgtggtcat catcagagcc aggcagggtc ggcgaggagg gtttgcagtt   1320
cgtcagtcag acgggcggtg tggaacccgt cggccgccgc gtggtggatc tggaccgaaa   1380
gtggcagcag gaggcgagcg tcacgctctg tgtaacggcc gagagtgaag atcggtgcca   1440
ggtgatccca accgtcacgg atatcaagag tgaatccggt gaaggaggcc cacggcaggg   1500
aggacacatc gaaagcgtta ggggggggt ttccctgcgg gaagaagtcg gtggcgcggg   1560
agtgctcggc cagcaacggg gcagcggtat cgtggaaggt gccgaagtct gggtcgtacg   1620
gagcccacac acaggcgaag gtctctcgtt ccggattgaa aacggtgaag gctgggtgga   1680
cgaccggcca gacagcgggg tcgccggagg ccgtcaggca catacggaac tcctcgtgtc   1740
ggttgacgac ggtggccaaa gcccacacct gggccaagta cgatttgcgc ggggagcggc   1800
gcagggcggc cgcgaaggcg gtcacgtcca cctcgacggt catggcgtaa gtgcagggca   1860
cgcgacgacg gtagtggtcg aagtgctgcc ggcgcggcca cgtgtccagg tcgattgggg   1920
ccggggtcgg gatcggggcg tccatctcag taggtccctt tctgtccgtt gcgcggcgtc   1980
cccgacgctc ttactgcagg agactcttcc aaggccgcgg ccgttctgac ggcaactggg   2040
agagaatatc aactctgccc attaggcgcg aatcctgatg cgagatgaga tattgccgac   2100
cgaggagaag cccccaaaga aattccacgc tcagcgggct caactgacgc cccaagagaa   2160
ccggacccgc ccaggccgca ccccctatga ttcgttgctg tcgatggtgt cttcgagcat   2220
ctgatacagg tggaggcagg tagagatagt ttcgctggcc tgatcgagaa cgttccggcc   2280
gataacgttt ttgtggttgt cgcggtggcg gatgatagcc cacatgatct cgtcggctgc   2340
cgcctgtaat agtttggcct ggtatgcgat tccggcgagc cagtctagtg cttcctggct   2400
tgtatagggg ctctggtcct cgctgttgcc gcgggtgttg ctgttgtttg tggggtgtcc   2460
tgcactgtcg catagccaca ggatttcgct gcactcgtct agcgtgtctt ggtcgatagc   2520
gagatcgtcg aggctgacat tgttgacggt aaggttcacg ttgtcgaggg agatgggtac   2580
accgtactgg ttttcgacac tgtcaacaat gttttccagc tgttgcatgt tggtgggctg   2640
ttgttggacg atacggtgta tcgctgtgtt gagggtggtg taggtgatgt tgtgtgtgtt   2700
gtccatggtt tttatgccat tccttcgtta tcgtctggca tgtagtatgt gctgtttgcg   2760
```

-continued

```
tactcggtta acgtcatcag tgtttggtct gcccactgtt tcacggtttg ccgggtgact   2820

ccgagtcgtt gggcggctgt ggcgtaggtt tgatcatacc cgtatacttc ccggaatgct   2880

gccaacctag ctaggtgttt cctctgtttg gatggttcac aggtgagggt gtagtcgtcg   2940

atggctagct gtagatcgat catggagacg atgttgttgc cgtggtgttg tggcgcggt    2999


<210> SEQ ID NO 113
<211> LENGTH: 383
<212> TYPE: DNA
<213> ORGANISM: Artificial Sequence
<220> FEATURE:
<223> OTHER INFORMATION: PAC7 wt from alignment figure 18

<400> SEQUENCE: 113

tagtggagaa aacaaccacc ccggaacgtt taagacaccc cctcaaacga acaaaacagg     60

gcctagaatc gatcagcagg gcaccggtag ggtattccta cccccagacg attcaaggcc    120

attacaggag caatgagagg ctcacagggg ccatgggaga ttggggggcg tgatggcaca    180

caccaaccgc acagccagcc aagcccaccg gcgctggcgg gcaaggctca tcacccaagc    240

ccgacaacaa ggccaaaccg aatgcccact ctgcggagtc accatcacct ggaacaccca    300

cgacctgcca accagccccg aagccgacca catcacaccc gtcagccggg gaggactcaa    360

caccctcgac aacgggcaaa tca                                            383


<210> SEQ ID NO 114
<211> LENGTH: 249
<212> TYPE: DNA
<213> ORGANISM: Artificial Sequence
<220> FEATURE:
<223> OTHER INFORMATION: PAC7-m28-gp45 plaque n:3 from alignment figure
      18

<400> SEQUENCE: 114

tagtggagaa aacaaccacc ccggaacgtt taagacaccc cctcaaacga acaaaacagg     60

gcctagaatc gatcagcagg gcaccggtag ggtattccta cccccagacg attcaaggcc    120

aaaccgaatg cccactctgc ggagtcacca tcacctggaa cacccacgac ctgccaacca    180

gccccgaagc cgaccacatc acacccgtca gccggggagg actcaacacc ctcgacaacg    240

ggcaaatca                                                            249
```